US012137611B2

(12) United States Patent
Yoon et al.

(10) Patent No.: US 12,137,611 B2
(45) Date of Patent: Nov. 5, 2024

(54) COMPOUND, AND ORGANIC LIGHT EMITTING DEVICE AND ORGANIC LIGHT EMITTING DISPLAY DEVICE INCLUDING THE SAME

(71) Applicants: LG Display Co., Ltd., Seoul (KR); DONGJIN SEMICHEM CO., LTD., Incheon (KR)

(72) Inventors: Kyung-Jin Yoon, Paju-si (KR); Yu-Jin Bae, Paju-si (KR); Bo-Min Seo, Paju-si (KR); Jeong-Eun Baek, Paju-si (KR); Joong-Hwan Yang, Paju-si (KR); Chun-Ki Kim, Paju-si (KR); Jung-Hyun Yoon, Paju-si (KR); Hyung-Won Cho, Paju-si (KR); Kyu-Soon Shin, Paju-si (KR); Jeong-A Seo, Paju-si (KR); Hyung-Jin Lee, Paju-si (KR); Young-Sam Jin, Paju-si (KR); Dong-Hyun Lee, Paju-si (KR)

(73) Assignee: LG Display Co., Ltd., Seoul (KR)

( * ) Notice: Subject to any disclaimer, the term of this patent is extended or adjusted under 35 U.S.C. 154(b) by 580 days.

(21) Appl. No.: 16/702,269

(22) Filed: Dec. 3, 2019

(65) Prior Publication Data

US 2020/0185622 A1 Jun. 11, 2020

(30) Foreign Application Priority Data

Dec. 7, 2018 (KR) ........................ 10-2018-0157114

(51) Int. Cl.
*H01L 51/50* (2006.01)
*C07D 491/20* (2006.01)
(Continued)

(52) U.S. Cl.
CPC ....... *H10K 85/6572* (2023.02); *C07D 491/20* (2013.01); *C07D 519/00* (2013.01);
(Continued)

(58) Field of Classification Search
None
See application file for complete search history.

(56) References Cited

U.S. PATENT DOCUMENTS 9,978,949 B2 5/2018 Mujica-Fernaud et al.
10,957,860 B2 3/2021 Mujica-Fernaud et al.
(Continued)

FOREIGN PATENT DOCUMENTS

CN 108864139 * 11/2018 .......... H01L 1151/50
CN 108864139 A 11/2018
(Continued)

OTHER PUBLICATIONS

China National Intellectual Property Administration, Office Action, CN Patent Application No. 201911234392.7, Jan. 28, 2022, 15 pages.
Korean Intellectual Property Office, Office Action, Korean Patent Application No. 10-2018-0157114, Sep. 15, 2023, 42 pages.

*Primary Examiner* — Gregory D Clark
(74) *Attorney, Agent, or Firm* — Fenwick & West LLP

(57) ABSTRACT

The present disclosure provides a compound of following formula and an organic light emitting device and an organic light emitting display device including the compound. The compound of the present disclosure serves as a host or a dopant in an emitting material layer.

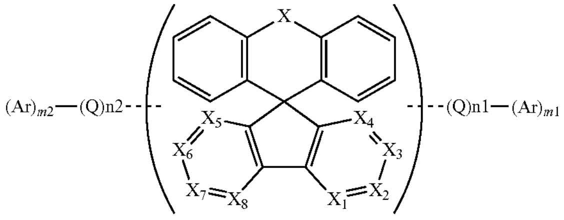

8 Claims, 2 Drawing Sheets

100

(51) Int. Cl.

| | |
|---|---|
| ***C07D 519/00*** | (2006.01) |
| ***C09K 11/06*** | (2006.01) |
| ***H10K 85/60*** | (2023.01) |
| *H10K 50/11* | (2023.01) |
| *H10K 50/13* | (2023.01) |
| *H10K 50/15* | (2023.01) |
| *H10K 50/16* | (2023.01) |
| *H10K 50/17* | (2023.01) |
| *H10K 50/844* | (2023.01) |
| *H10K 101/10* | (2023.01) |
| *H10K 101/30* | (2023.01) |
| *H10K 101/40* | (2023.01) |

(52) U.S. Cl.

CPC ...... *C09K 11/06* (2013.01); *C09K 2211/1018* (2013.01); *H10K 50/11* (2023.02); *H10K 50/13* (2023.02); *H10K 50/15* (2023.02); *H10K 50/16* (2023.02); *H10K 50/17* (2023.02); *H10K 50/844* (2023.02); *H10K 2101/10* (2023.02); *H10K 2101/30* (2023.02); *H10K 2101/40* (2023.02)

(56) References Cited

U.S. PATENT DOCUMENTS

2007/0012915 A1* 1/2007 Lee .................... H01L 51/0059 257/40
2015/0295181 A1* 10/2015 Mujica-Fernaud .. C07D 409/12 252/500
2017/0018720 A1 1/2017 Adachi et al.
2018/0248124 A1 8/2018 Mujica-Fernaud et al.
2019/0378995 A1* 12/2019 Noh .................. H10K 85/6574

FOREIGN PATENT DOCUMENTS

CN 109956964 A 7/2019
CN 110590755 A 12/2019
CN 110734448 A 1/2020
CN 110759939 A 2/2020
KR 10-2015-0083917 A 7/2015
KR 2017136836 * 12/2017 ............. H01L 51/50
KR 10-2019-0140686 A 12/2019

* cited by examiner

COMPOUND, AND ORGANIC LIGHT EMITTING DEVICE AND ORGANIC LIGHT EMITTING DISPLAY DEVICE INCLUDING THE SAME

CROSS-REFERENCE TO RELATED APPLICATIONS

This application claims priority to and the benefit of Republic of Korea Patent Application No. 10-2018-0157114 filed on Dec. 7, 2018, which is hereby incorporated by reference in its entirety.

BACKGROUND

Technical Field

The present disclosure relates to a novel compound, and an organic light emitting device (OLED), and an organic light emitting display device including the compound.

Description of the Related Art

The material used in an organic layer of the OLED (organic light emitting diode) may be classified into an emitting material, a hole injection material, a hole transporting material, an electron transporting material, an electron injection material, and so on depending on their function. The emitting material may be classified into a high molecular weight material and a low molecular weight material depending on their molecular weight. The emitting material may be classified into a phosphorescent material and a fluorescent material depending on their emission mechanism. The emission of the fluorescent material is derived from a singlet excited state, while the emission of the phosphorescent is derived from a triplet excited state. In addition, the emitting material may be classified into a blue emitting material, a green emitting material and a red emitting material depending on their emission color. To provide excellent natural color, the emitting material may be further classified into a yellow emitting material and an orange emitting material.

To improve the color purity and the emission efficiency by the energy transfer, the host-guest system, i.e., host and dopant system, may be used. Namely, when the dopant, which has smaller energy band gap and higher emission efficiency than the host and higher, is doped into an emitting material layer, the exciton, which is generated in the host, is transferred into the dopant such that the light with high emission efficiency is provided.

However, the OLED using the related art emitting material has high driving voltage, low emission efficiency, and short lifespan. Accordingly, development of novel emitting material is required.

SUMMARY

Accordingly, the embodiment of the present disclosure is directed to a novel compound and an OLED and an organic light emitting display device using the same that substantially obviate one or more of the problems due to limitations and disadvantages of the related art.

Additional features and advantages of the disclosure will be set forth in the description which follows, and in part will be apparent from the description, or may be learned by practice of the disclosure. The objectives and other advantages of the disclosure will be realized and attained by the structure particularly pointed out in the written description and claims hereof as well as the appended drawings.

To achieve these and other advantages and in accordance with the purpose of the embodiments of the disclosure, as embodied and broadly described herein, embodiments relate to a compound of

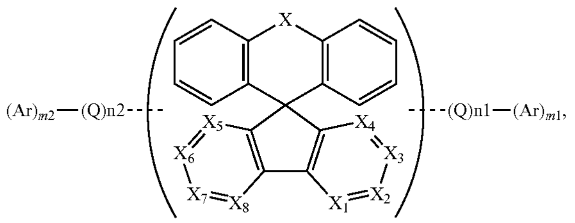

wherein Y is $CR_1R_2$, O or S, and each of $R_1$ and $R_2$ is independently selected from the group consisting of hydrogen, substituted or non-substituted $C_6$-$C_{24}$ aryl group and substituted or non-substituted $C_5$-$C_{24}$ heteroaryl group, wherein each of $X_1$ to $X_8$ is independently selected from C or N, and at least one of $X_1$ to $X_8$ is N, wherein Q is independently selected from the group consisting of substituted or non-substituted $C_6$-$C_{60}$ aryl group, substituted or non-substituted $C_5$-$C_{60}$ heteroaryl group, CN and $NR_3R_4$, and each of $R_3$ and $R_4$ is independently selected from the group consisting of hydrogen, substituted or non-substituted $C_6$-$C_{60}$ aryl group and substituted or non-substituted $C_5$-$C_{60}$ heteroaryl group, wherein Ar is independently selected from the group consisting of substituted or non-substituted $C_1$-$C_{20}$ alkyl group, substituted or non-substituted $C_6$-$C_{24}$ aryl group, substituted or non-substituted $C_5$-$C_{24}$ heteroaryl group, CN and $NR_5R_6$, and each of $R_5$ and $R_6$ is independently selected from the group consisting of hydrogen, substituted or non-substituted $C_6$-$C_{24}$ aryl group and substituted or non-substituted $C_5$-$C_{24}$ heteroaryl group, and wherein n1, n2, m1 and m2 is one of 0, 1 and 2, and at least one of n1 and n2 is 1 or more.

Embodiments also relate to an organic light emitting device including a first electrode, a second electrode facing the first electrode, and a first emitting material layer between the first and second electrodes and including a compound.

Embodiments also relate to an organic light emitting display device including a substrate, an organic light emitting device on the substrate, and an encapsulation film covering the organic light emitting diode.

It is to be understood that both the foregoing general description and the following detailed description are by example and explanatory and are intended to provide further explanation of the disclosure as claimed.

BRIEF DESCRIPTION OF THE DRAWINGS

The accompanying drawings, which are included to provide a further understanding of the disclosure and are incorporated in and constitute a part of this specification, illustrate embodiments of the disclosure and together with the description serve to explain the principles of the disclosure.

DETAILED DESCRIPTION

Figure 1:
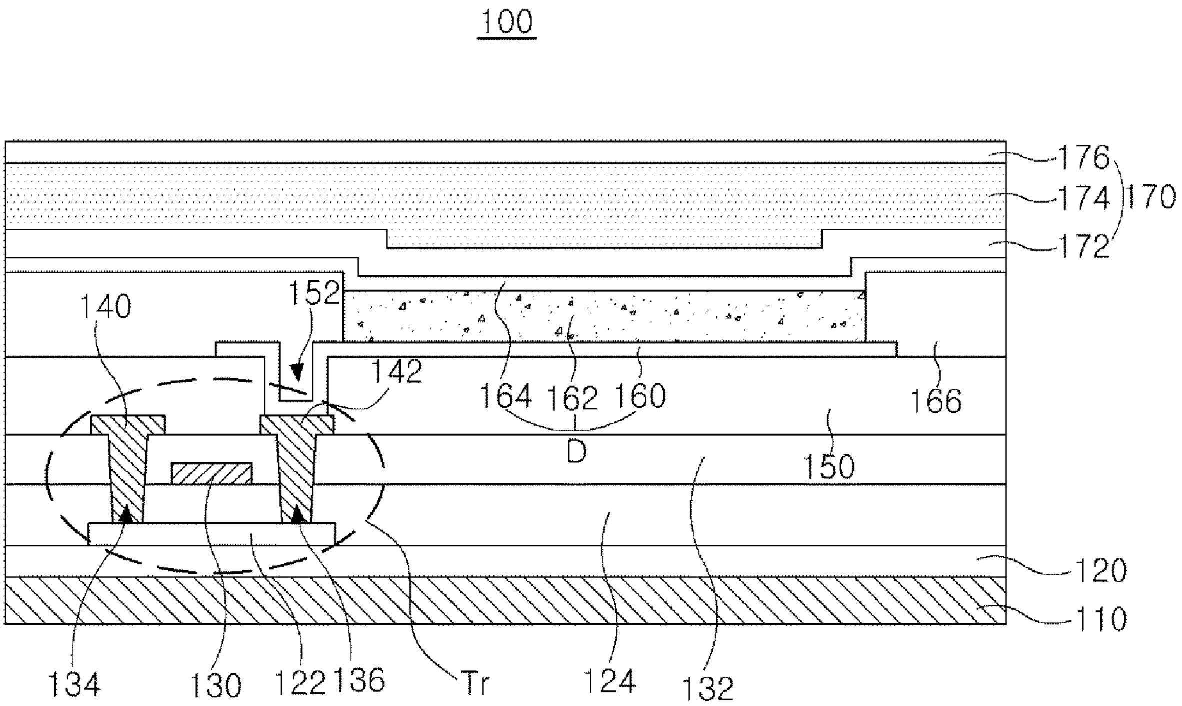
FIG. 1 is a schematic cross-sectional view of an organic light emitting display device according to the present disclosure.

Reference will now be made in detail to example embodiments, examples of which are illustrated in the accompanying drawings.

In the description, the term of "aryl" may be a $C_5$-$C_{30}$ aromatic hydrocarbon ring, e.g., phenyl, benzyl, naphthyl, biphenyl, terphenyl, fluorenyl, phenanthrenyl, triphenylenyl, perylenyl, chrysenyl, fluoranthenyl, benzofluorenyl, benzotriphenylenyl, benzochrysenyl, anthracenyl, stilbenyl or pyrenyl, and the term of "heteroaryl" may be a $C_3$-$C_{30}$ aromatic ring including at least one hetero-atom, e.g., pyrrolyl, pyrazinyl, pyridinyl, indolyl, isoindoleyl, furyl, benzofuranyl, isobenzofuranyl, dibenzofuranyl, benzothiophenyl, dibenzothiophenyl, quinolyl, isoquinolyl, quinoxalinyl, carbazolyl, phenanthridinyl, acridinyl, phenanthrolinyl, thienyl, pyridine ring, pyrazine ring, pyrimidine ring, pyridazine ring, triazine ring, indole ring, quinoline ring, acridine ring, pyrrolidine ring, dioxane ring, piperidine ring, morpholine ring, piperazine ring, carbazole ring, furan ring, thiophene ring, oxazole ring, oxadiazole ring, benzoxazole ring, thiazol ring, thiadiazole ring, benzothiazole ring, triazole ring, imidazole ring, benzoimidazole ring, pyran ring or dibenzofuran ring.

When a compound and/or a moiety is referred to as being "substituted", the compound and/or the moiety may be substituted by at least one selected from the group consisting of deuterium, halogen, amino group, nitrile group, nitro group, $C_1$-$C_{20}$ alkyl group, $C_2$-$C_{20}$ alkenyl group, $C_1$-$C_{20}$ alkoxy group, $C_3$-$C_{20}$ cycloalkyl group, $C_3$-$C_{20}$ heterocycloalkyl group, $C_6$-$C_{30}$ aryl group and $C_3$-$C_{30}$ heteroaryl group.

The present disclosure provides a compound represented by Formula 1.

Formula 1

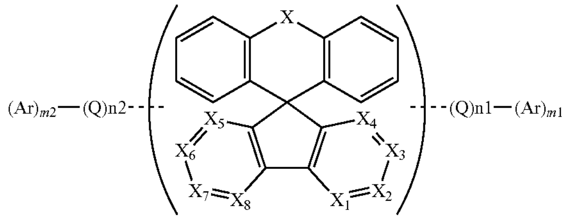

In Formula 1, Y is $CR_1R_2$, O or S, and each of $R_1$ and $R_2$ is independently selected from the group consisting of hydrogen, substituted or non-substituted $C_6$-$C_{24}$ aryl group and substituted or non-substituted $C_5$-$C_{24}$ heteroaryl group. Each of $X_1$ to $X_8$ is independently selected from C or N, and at least one of $X_1$ to $X_8$ is N.

Q is independently selected from the group consisting of substituted or non-substituted $C_6$-$C_{60}$ aryl group, substituted or non-substituted $C_5$-$C_{60}$ heteroaryl group, CN and $NR_3R_4$, and each of $R_3$ and $R_4$ is independently selected from the group consisting of hydrogen, substituted or non-substituted $C_6$-$C_{60}$ aryl group and substituted or non-substituted $C_5$-$C_{60}$ heteroaryl group.

Ar is independently selected from the group consisting of substituted or non-substituted $C_1$-$C_{20}$ alkyl group, substituted or non-substituted $C_6$-$C_{24}$ aryl group, substituted or non-substituted $C_5$-$C_{24}$ heteroaryl group, CN and $NR_5R_6$, and each of $R_5$ and $R_6$ is independently selected from the group consisting of hydrogen, substituted or non-substituted $C_6$-$C_{24}$ aryl group and substituted or non-substituted $C_5$-$C_{24}$ heteroaryl group.

Each of n1, n2, m1 and m2 is one of 0, 1 and 2, and at least one of n1 and n2 is 1 or more.

For example, Ar may independently be a t-butyl group, a carbazole group, a cyano group (CN), a phenoxazine group, a carbonyl group.

Since the compound of the present disclosure may provide fluorescent emission or delayed fluorescent emission, the compound may be used as an organic emitting material.

According to an embodiment of the present disclosure, the compound may be used alone or in combination with a known compound in an emitting layer of the organic light emitting device. The compound according to the present disclosure may be used as a dopant of a known host material. In addition, known materials can be used as dopants, and the compounds of the present disclosure may be used as an assist dopant.

The compound of the present disclosure has a triplet energy suitable for a blue fluorescent host by introducing diazafluorene having a spiro-structure such that deep blue emission of high color purity can be provided.

In addition, the HOMO and LUMO molecular orbital function can be separated by the structural characteristics of spiro-diazafluorene, and the charge balance in the emitting layer can be controlled by the bipolar characteristics. Accordingly, high emitting efficiency is provided.

In addition, the compound according to an embodiment of the present disclosure can be used as a thermally activated delayed fluorescence host material to minimize the difference between the excited singlet energy and the excited triplet energy ($\Delta E_{ST}$) such that high emitting efficiency is provided.

In an embodiment of the present disclosure, the compound may be represented by Formula 2.

Formula 2

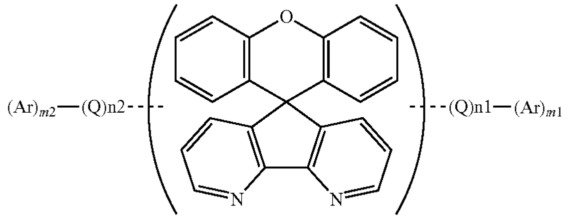

In Formula 2, the definition of Ar, Q, n1, n2, m1 and m2 is the same as in Formula 1.

Since Y is fixed to oxygen atom in Formula 2, the energy level of HOMO and LUMO of the compound is adjusted. In addition, the diazafluorene core has a high triplet (T1) energy level. Accordingly, the compound provides properties of high efficiency, long lifespan and low driving voltage.

Q in Formula 1 and/or Formula 2 may be represented by Formula 3-1.

Formula 3-1

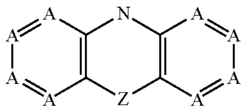

In Formula 3-1, Z is a single bond, S, O or $CR_7R_8$, and each of $R_7$ and $R_8$ is independently selected from the group consisting of hydrogen and $C_1$-$C_{24}$ alkyl group. A is C or N.

When Q has a structure of Formula 3-1, electrons may be provided such that the HOMO energy level of the compound may be controlled.

Alternatively, Q in Formula 1 and/or Formula 2 may be represented by Formula 3-2.

Formula 3-2

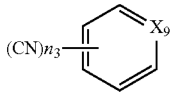

In Formula 3-2, $X_9$ is carbon or nitrogen, and n3 is 0 or 1.

Alternatively, Q in Formula 1 and/or Formula 2 may be one of Formula 4.

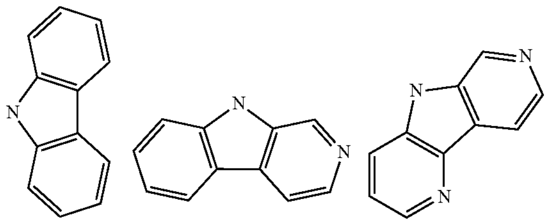

-continued

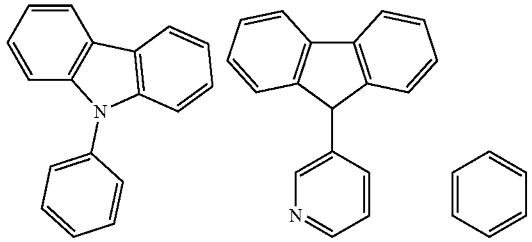

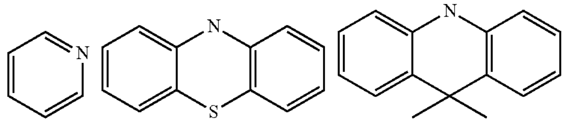

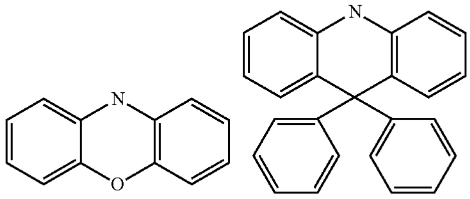

When Q has a structure of Formula 4, electrons may be provided such that the HOMO energy level of the compound may be controlled.

In an embodiment of the present disclosure, the compound may be represented by one of Formulas 5 to 22.

Formula 5

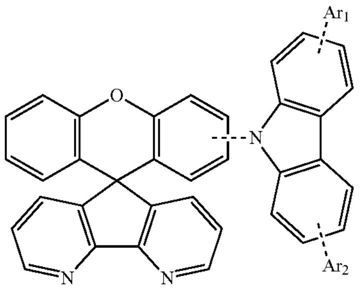

Formula 6

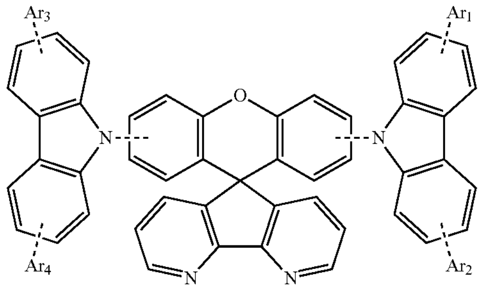

Formula 7

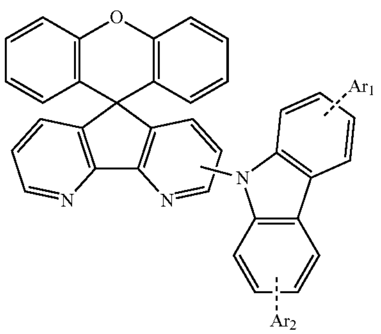

Formula 8

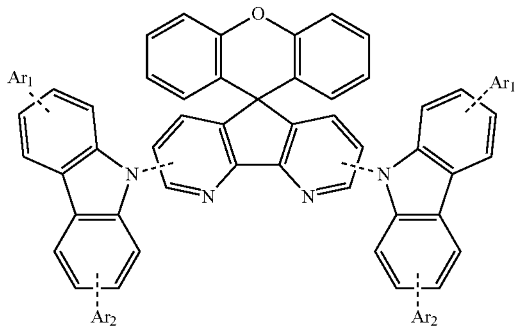

-continued
Formula 9
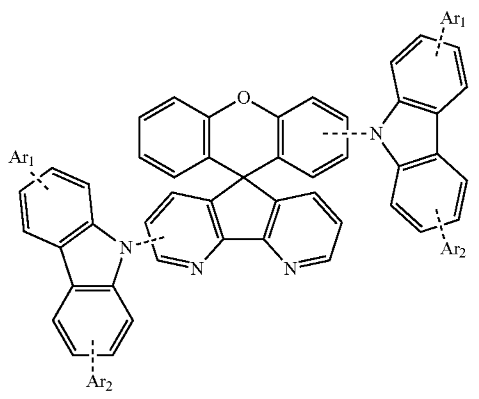
Formula 10
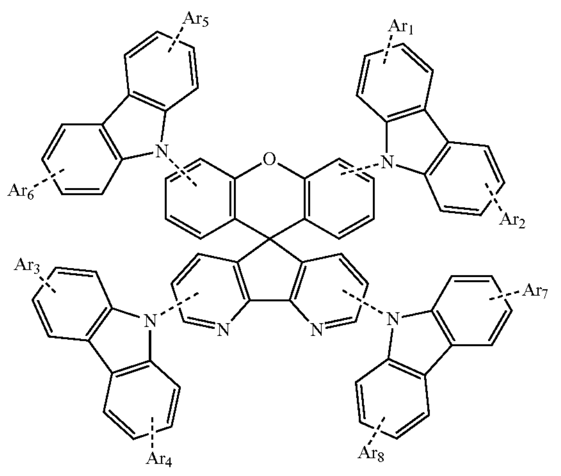
Formula 11
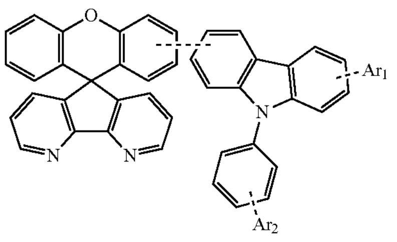
Formula 12
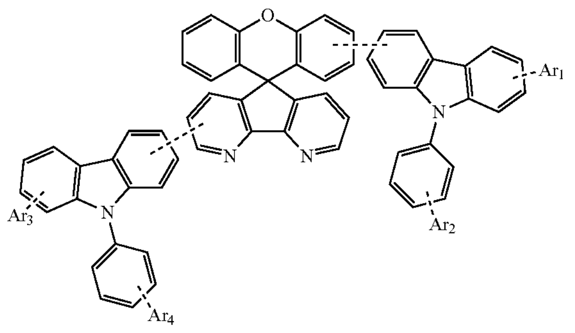
Formula 13
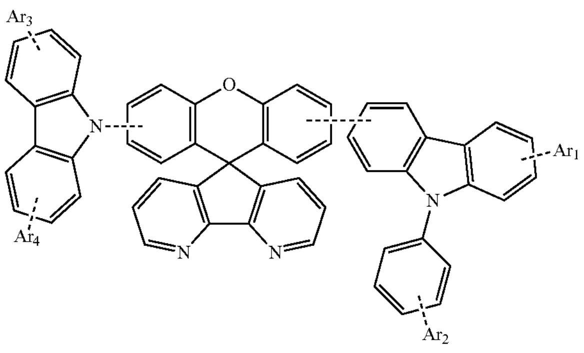
Formula 14
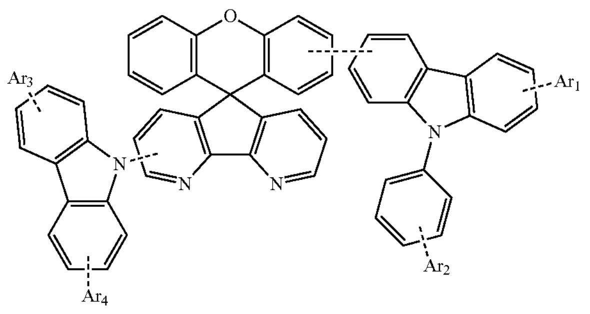
Formula 15
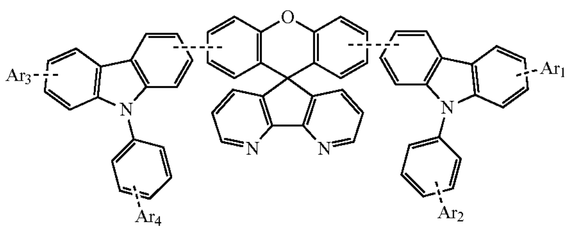
Formula 16
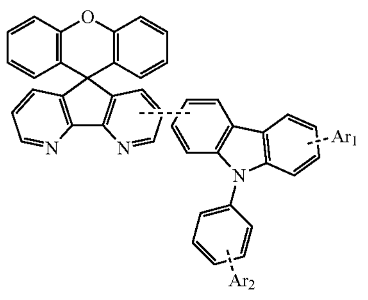

-continued
Formula 17
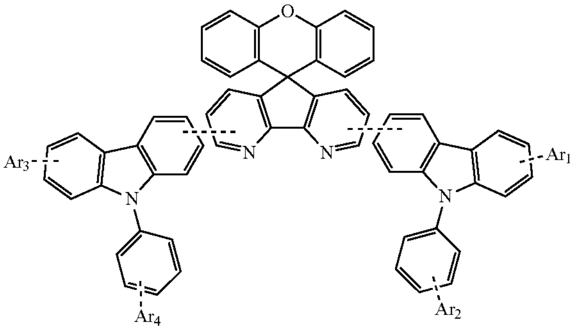
Formula 18
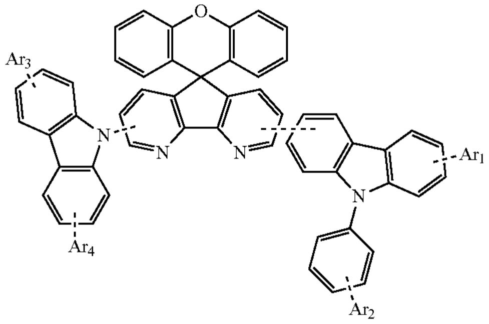
Formula 19
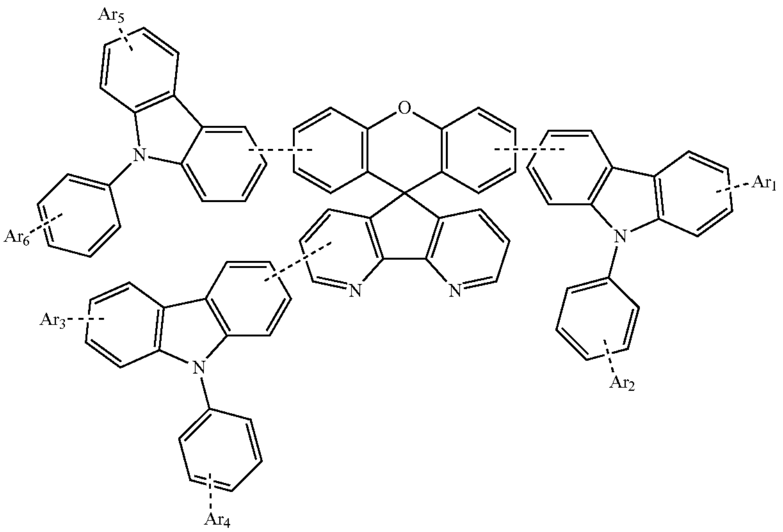
Formula 20
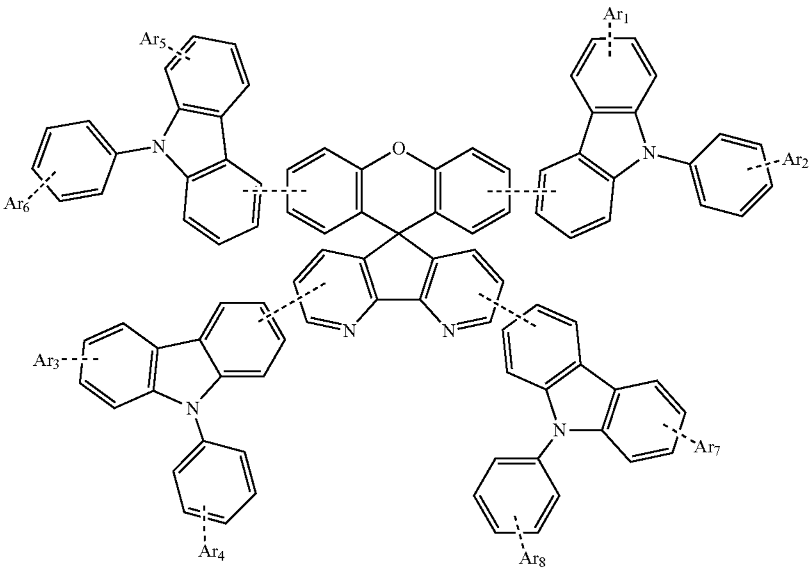

-continued

Formula 21

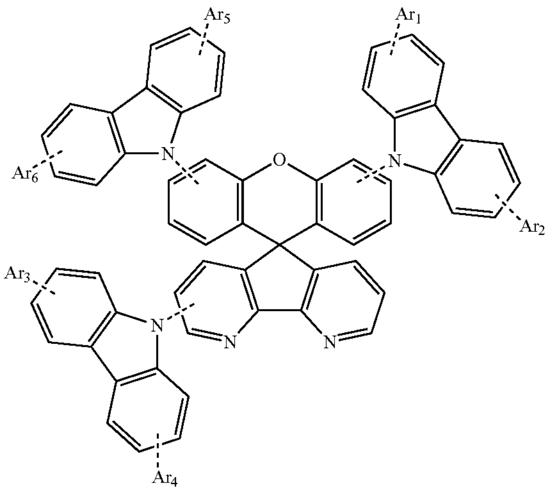

Formula 22

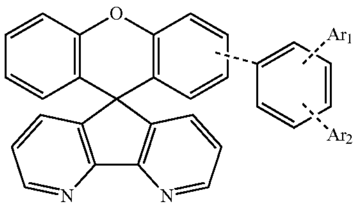

In formulas 5 to 22, each of $Ar_1$ to $Ar_8$ may independently be hydrogen, a substituted or non-substituted $C_6$-$C_{24}$ aryl group, a substituted or non-substituted $C_5$-$C_{24}$ heteroaryl group, or CN. For example, each of $Ar_1$ to $Ar_8$ may independently be a t-butyl group, a carbazole group, a cyano group (CN), a phenoxazine group, or a carbonyl group.

The compound of the present disclosure may be one of following.

1

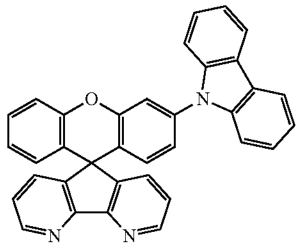

2

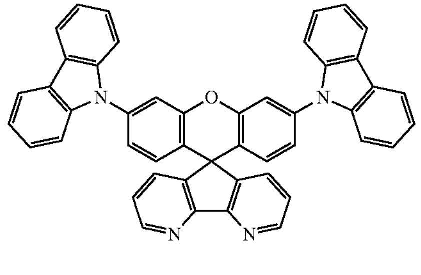

3

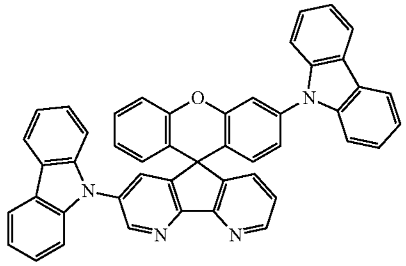

-continued

4

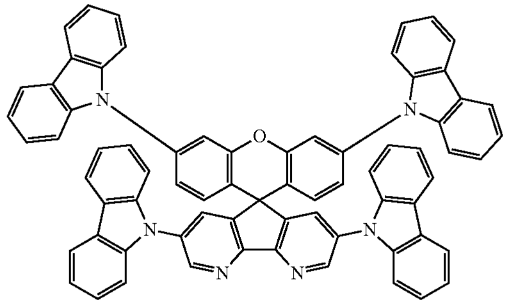

5

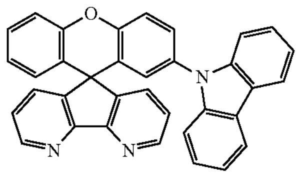

6

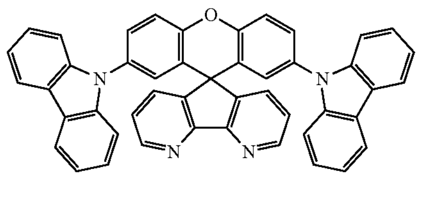

7

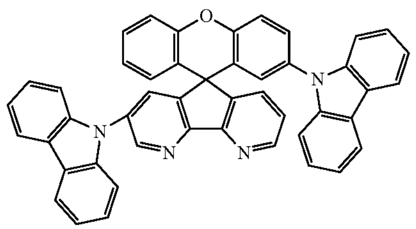

-continued
8
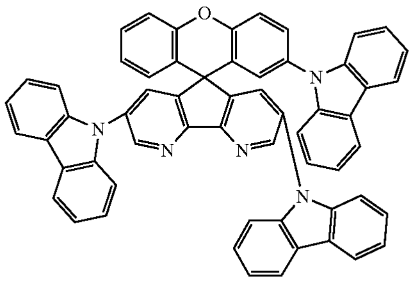
9
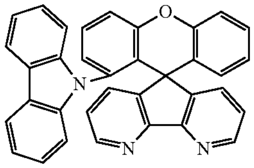
10
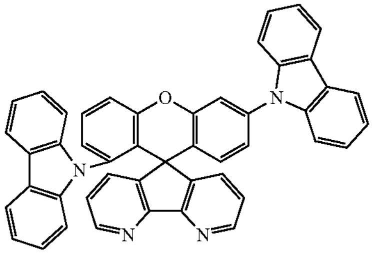
11
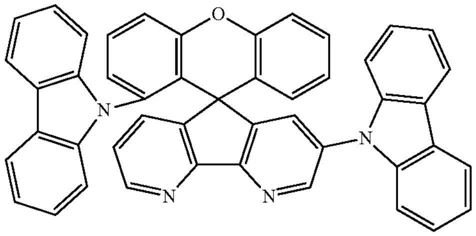
12
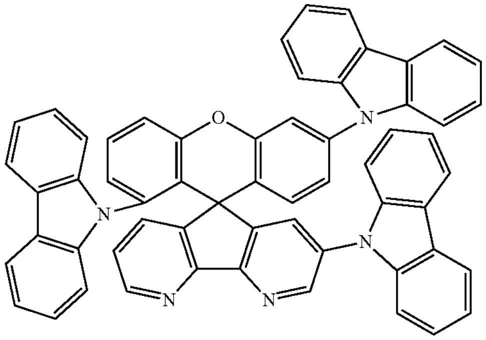
-continued
13
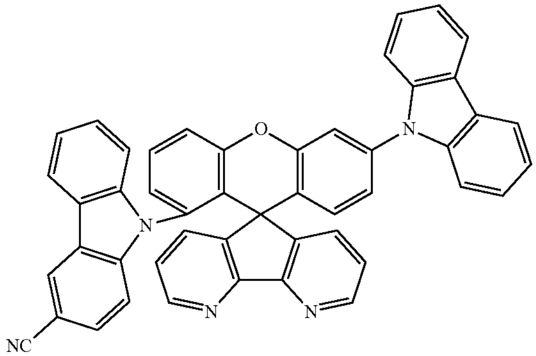
14
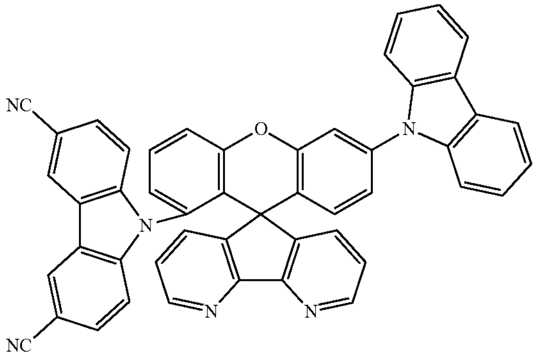
15
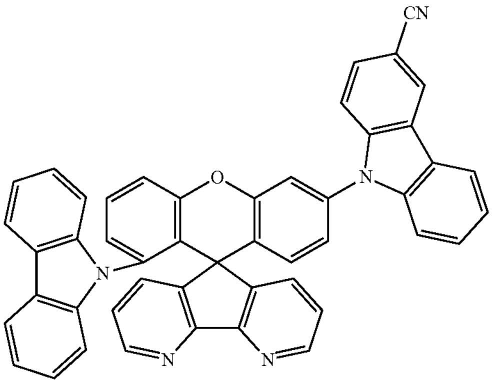
16
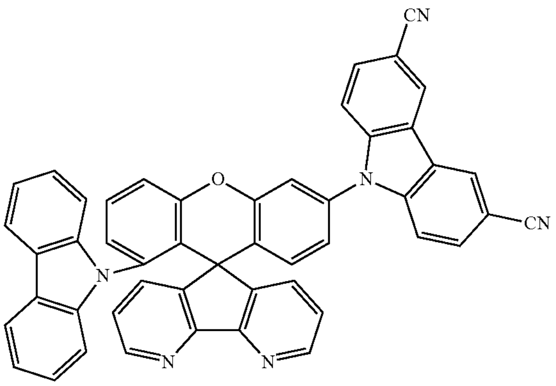

17
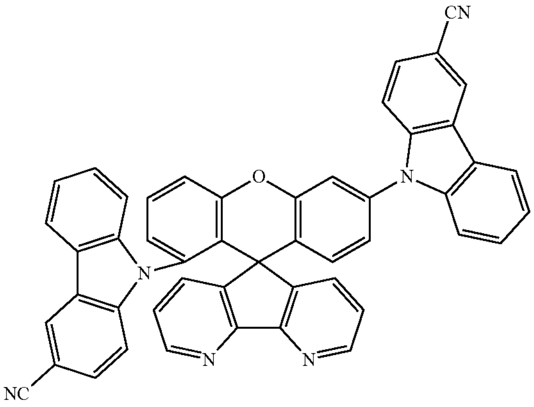
18
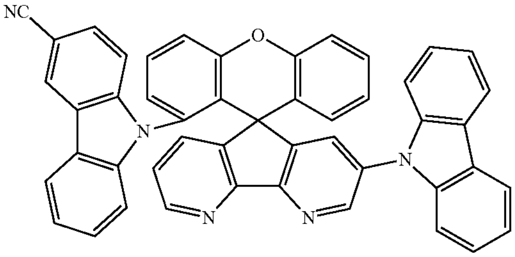
19
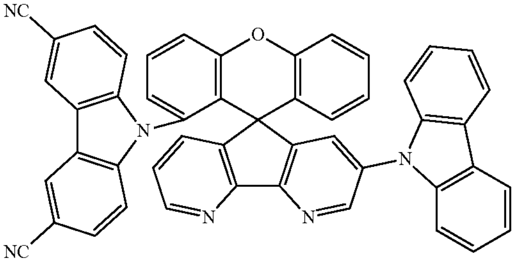
20
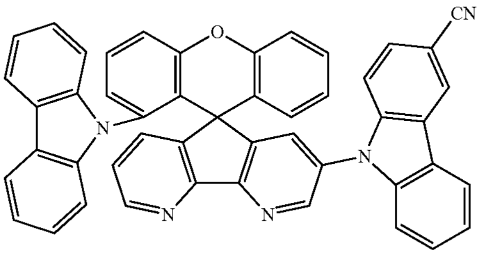
21
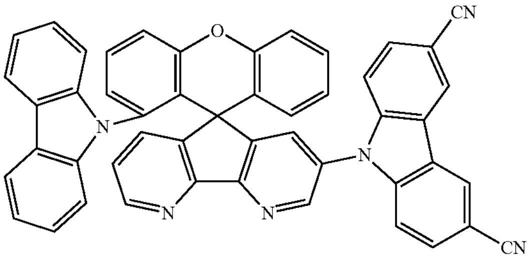
22
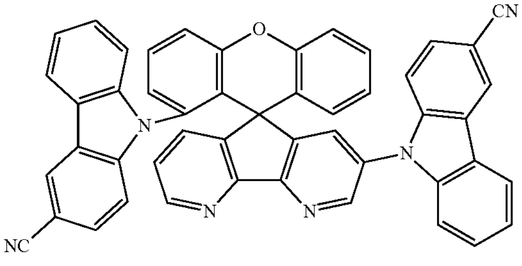
23
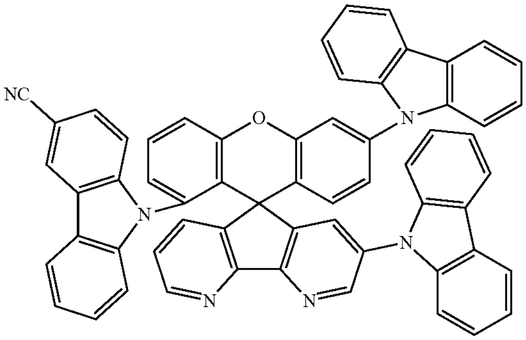
24
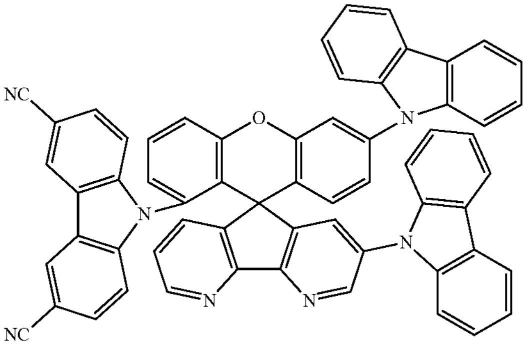
25
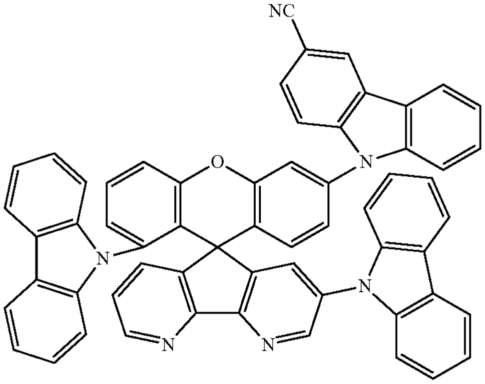

-continued
26
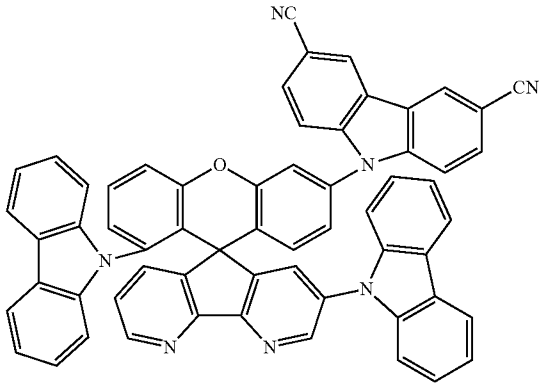
27
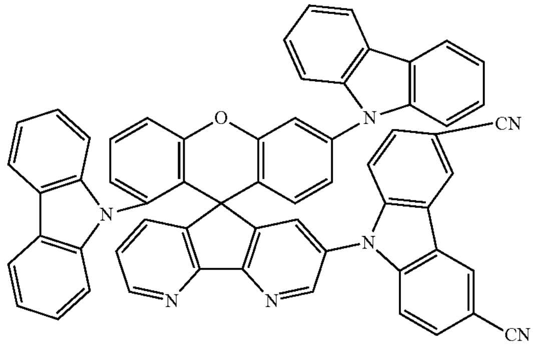
28
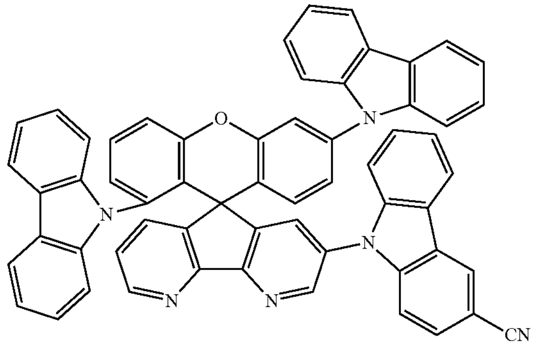
29
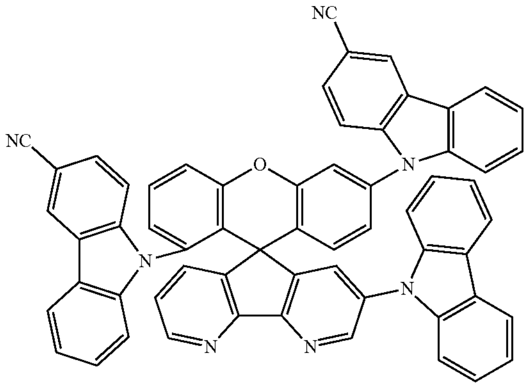
-continued
30
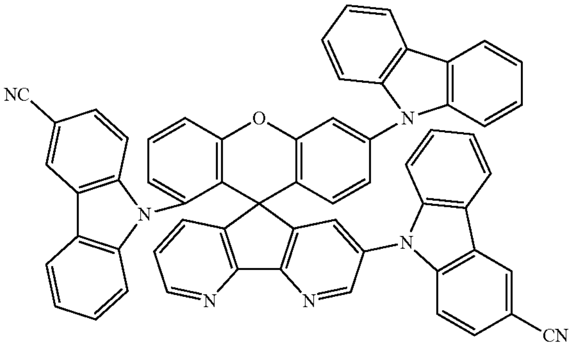
31
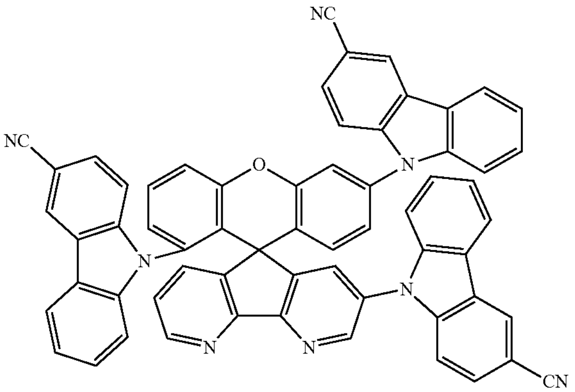
32
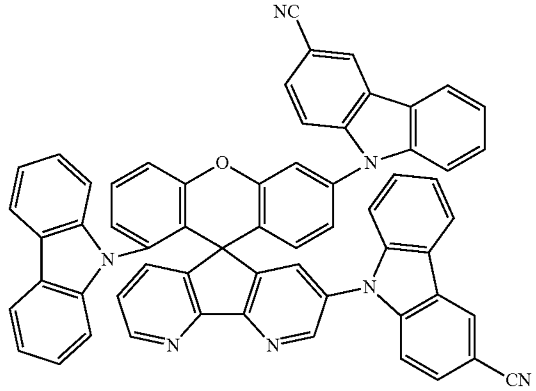
33
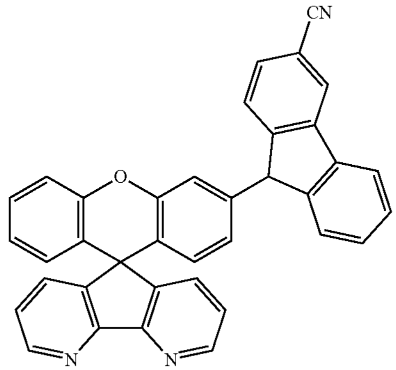

-continued
34
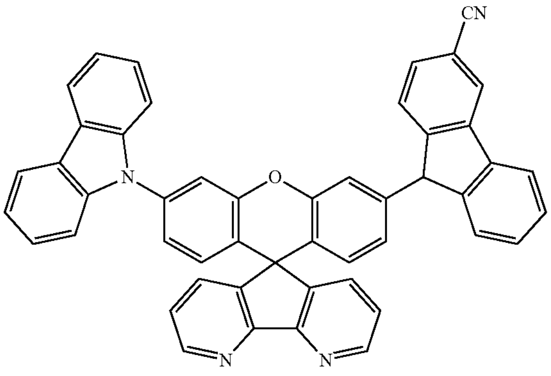
35
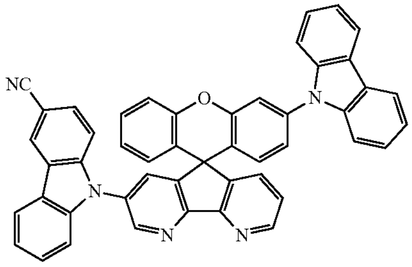
36
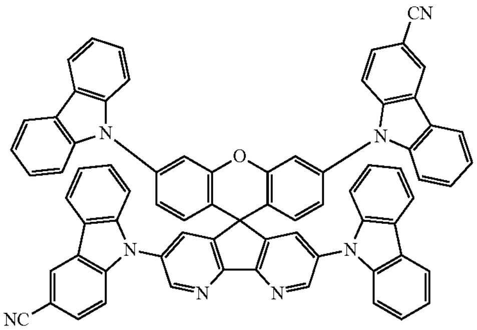
37
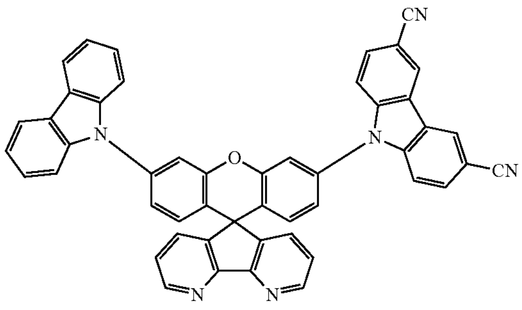
38
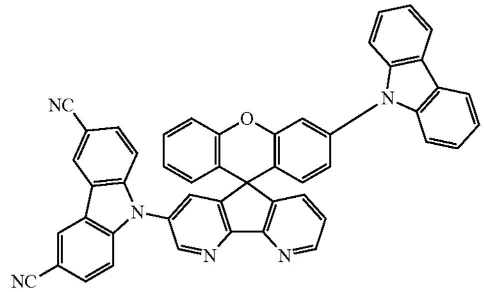
-continued
39
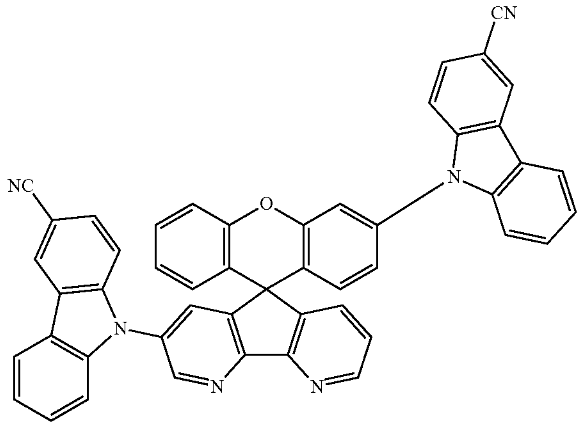
40
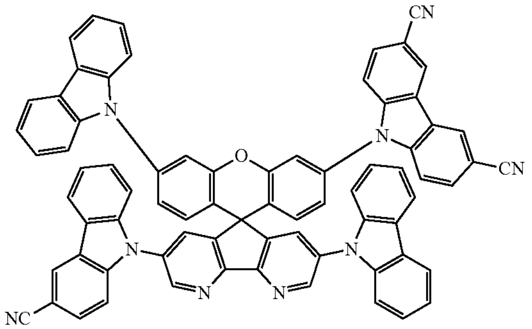
41
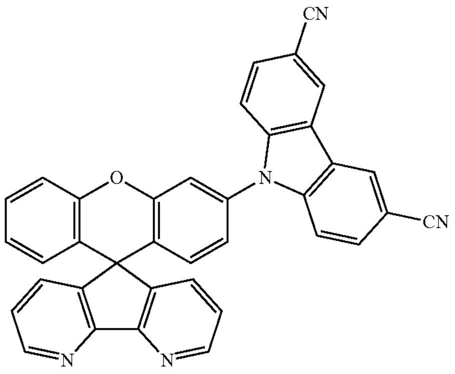
42
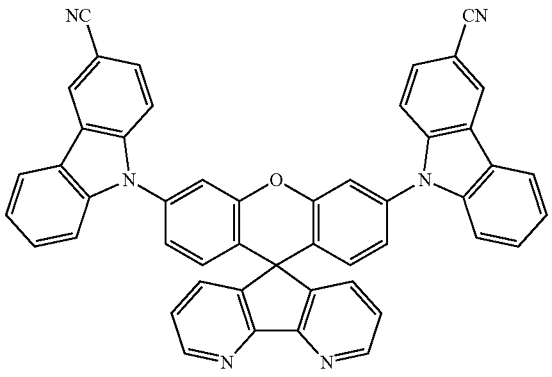

-continued
43
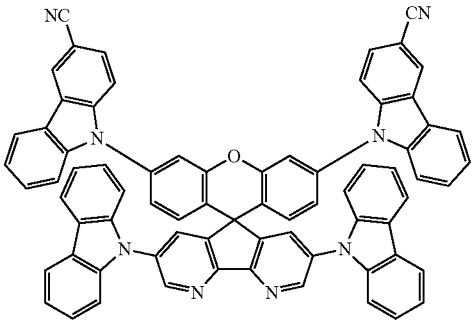
44
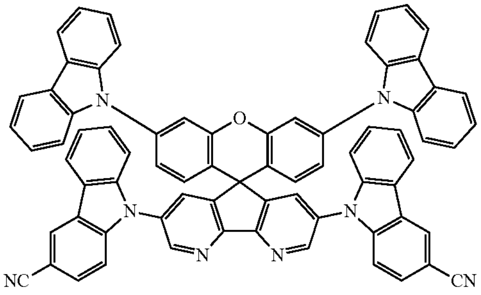
45
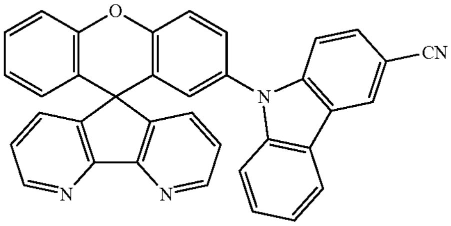
46
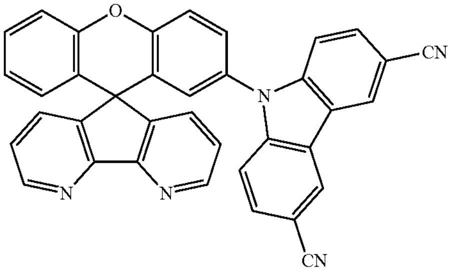
47
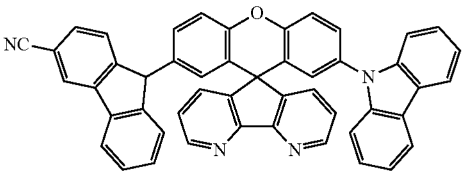
48
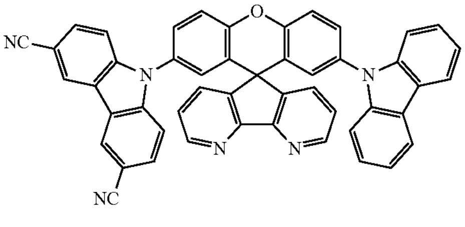
-continued
49
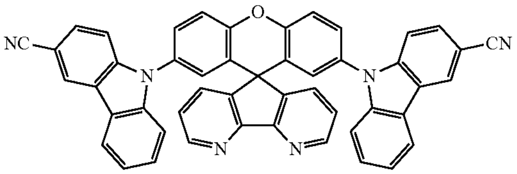
50
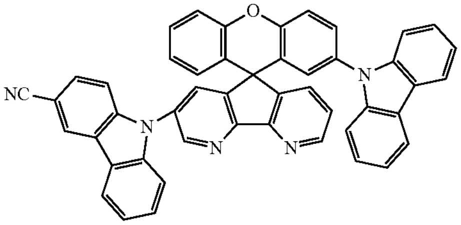
51
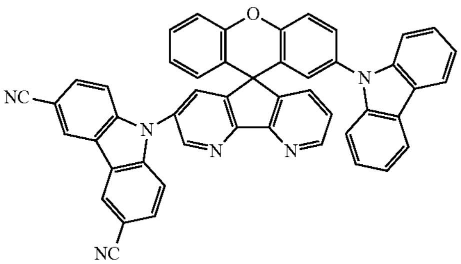
52
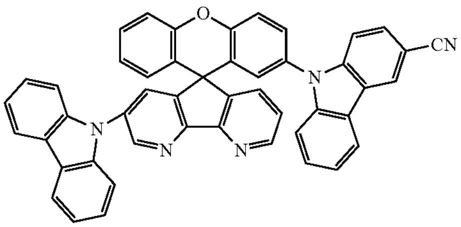
53
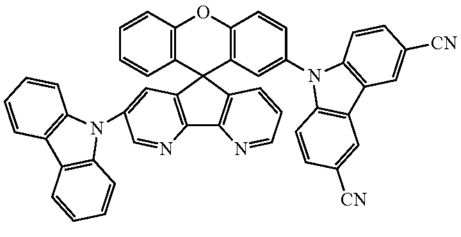
54
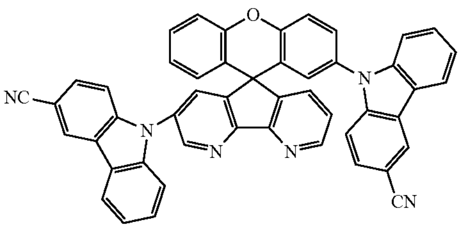

55
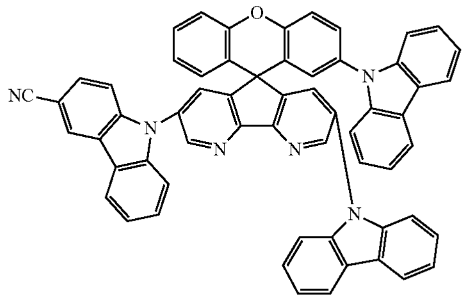
56
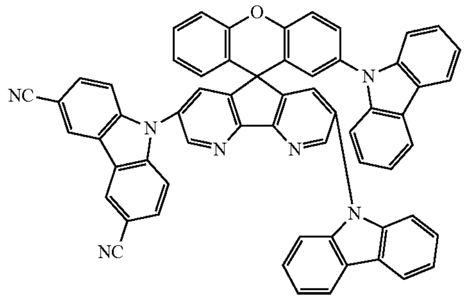
57
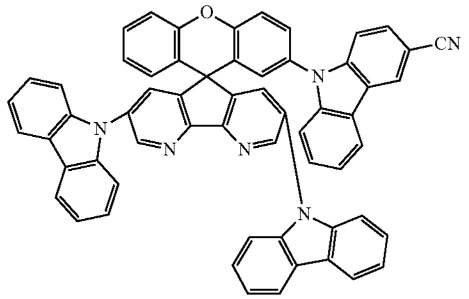
58
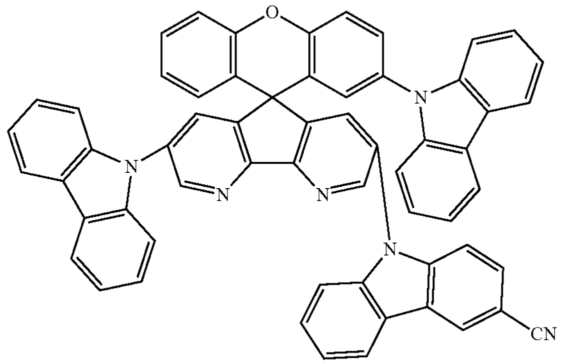
59
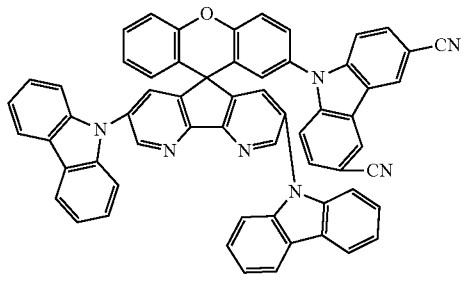
60
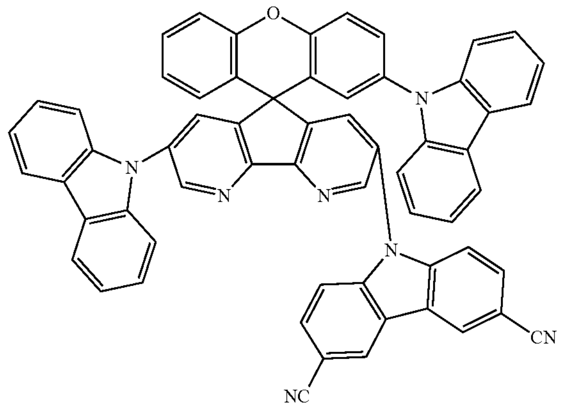
61
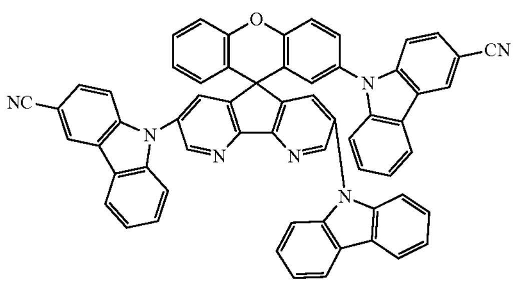
62
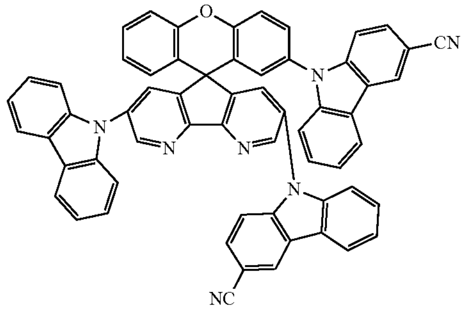
63
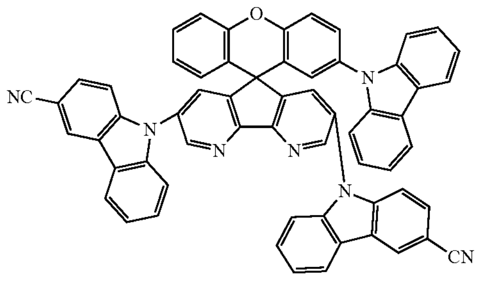

-continued
64
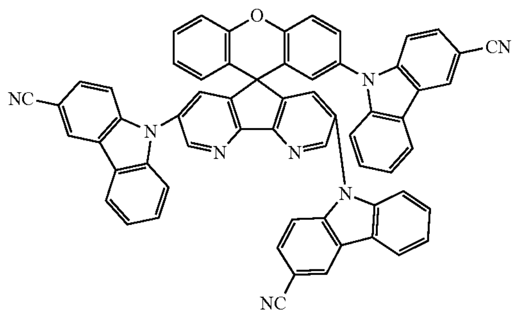
65
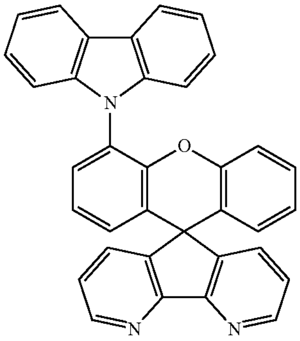
66
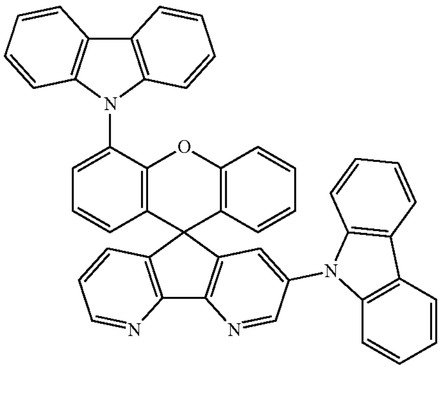
67
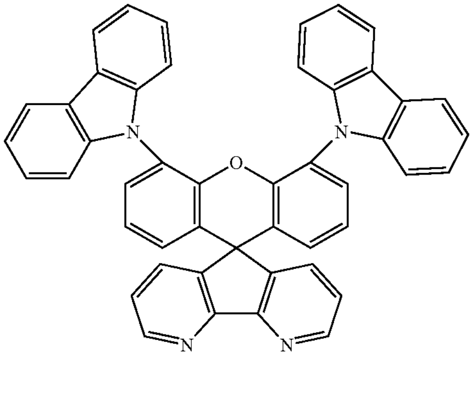
-continued
68
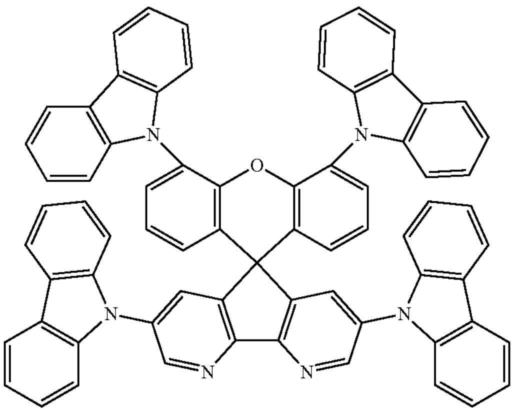
69
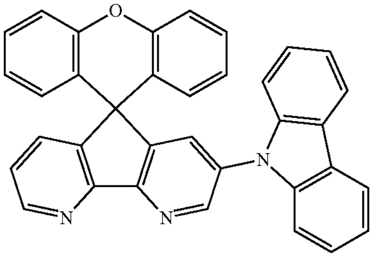
70
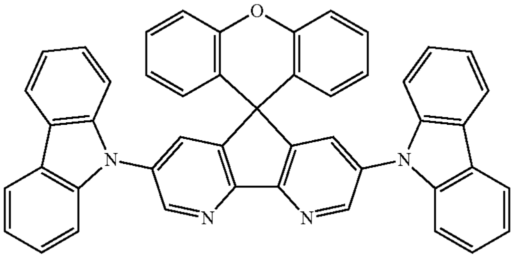
71
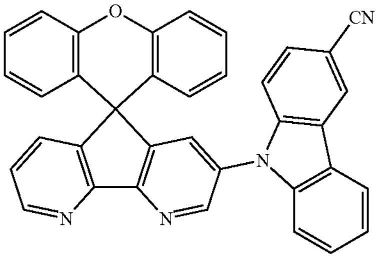
72
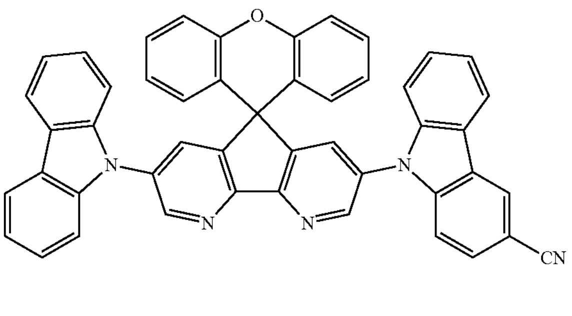

-continued
73
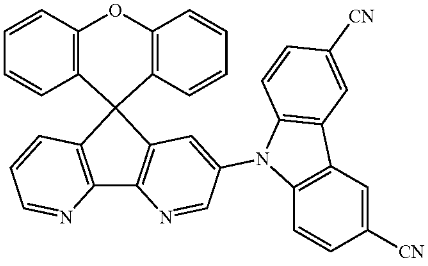
74
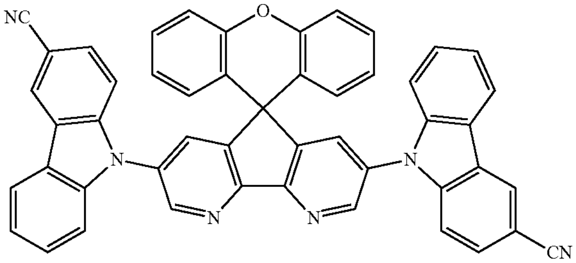
75
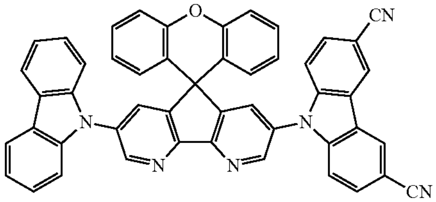
76
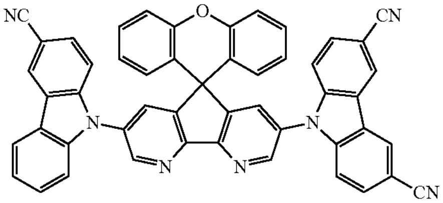
77
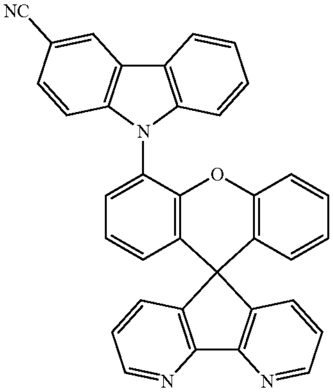
-continued
78
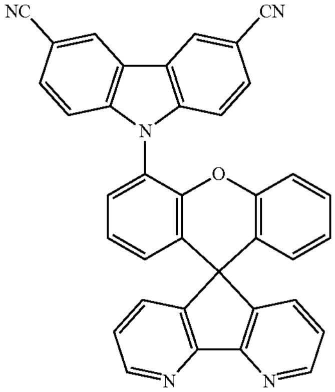
79
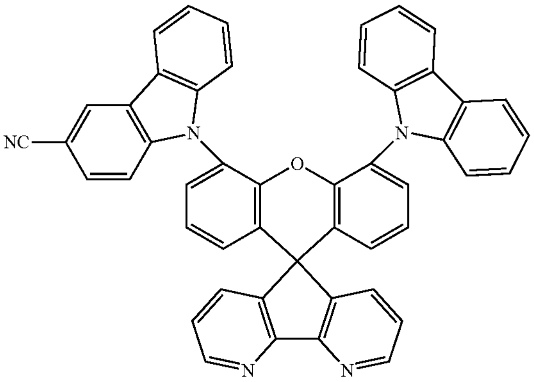
80
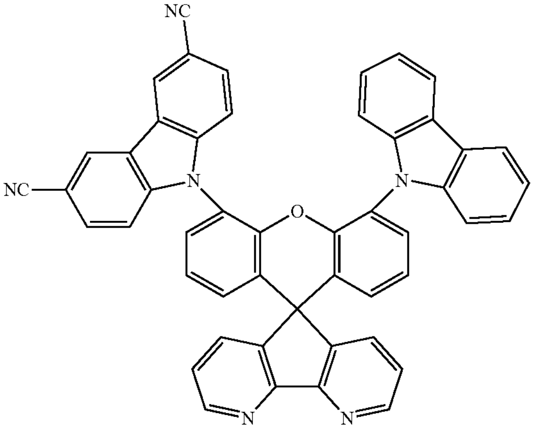
81
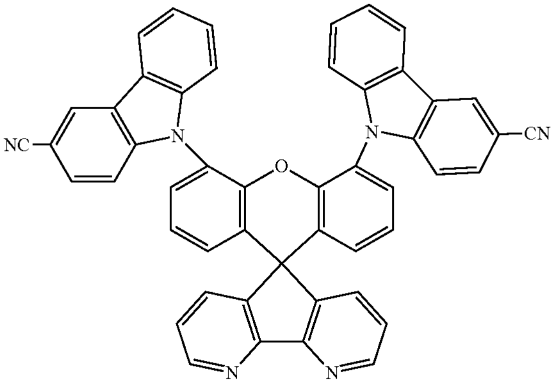

-continued
82
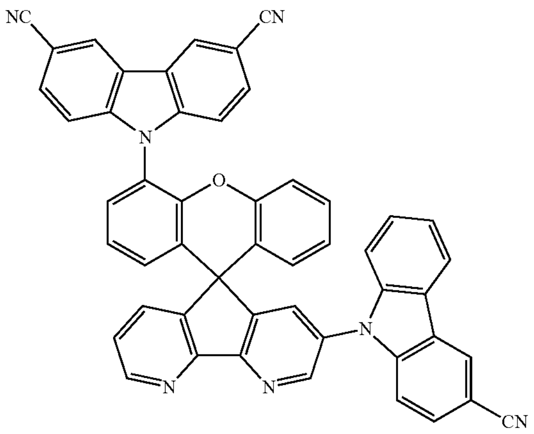
83
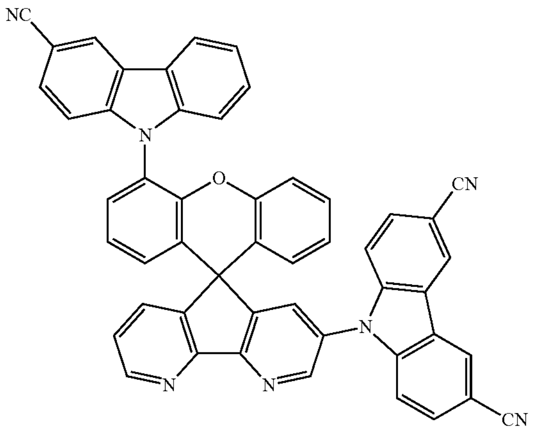
84
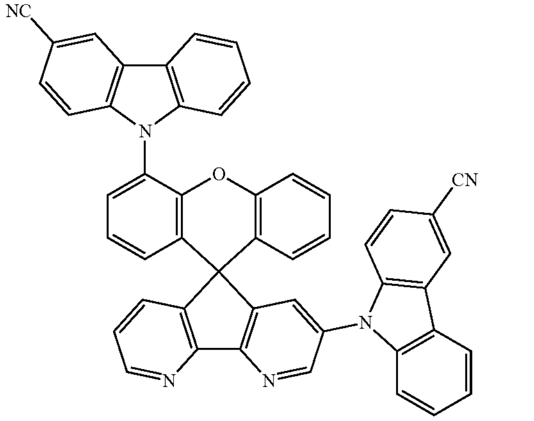
-continued
85
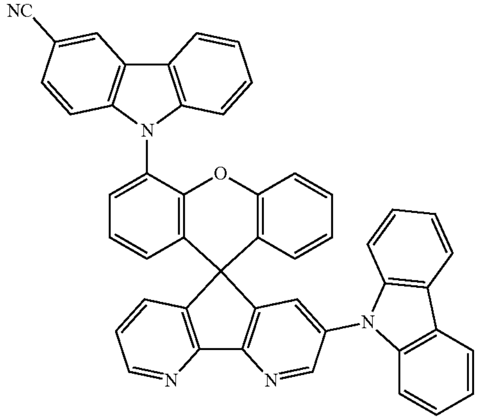
86
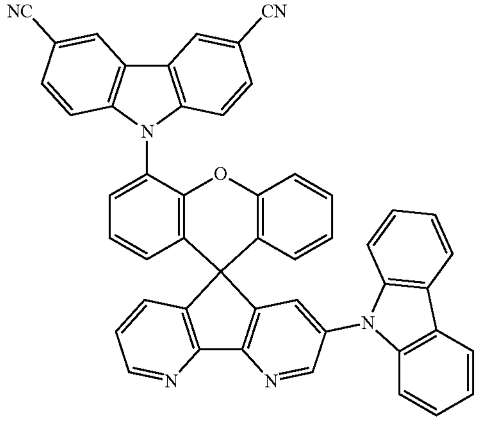
87
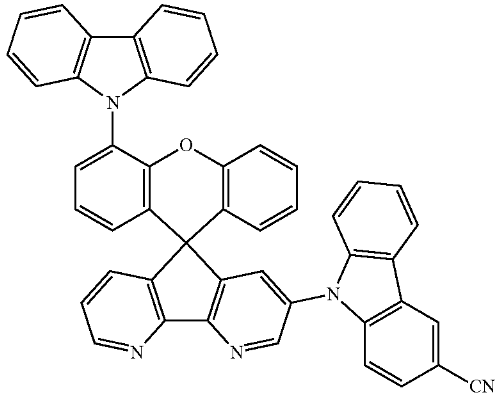
88
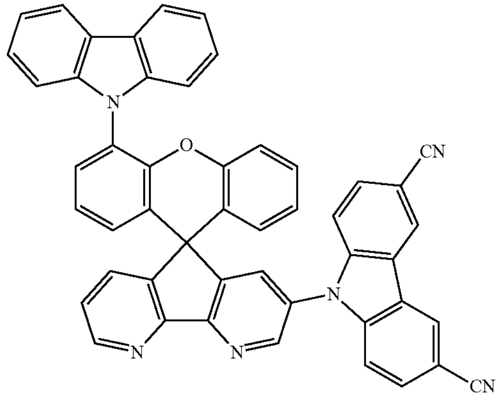

-continued
89
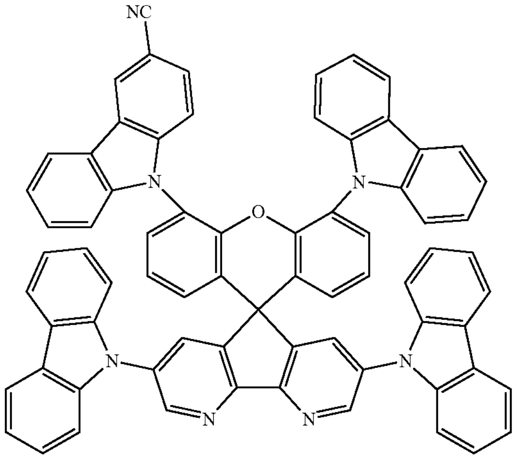
90
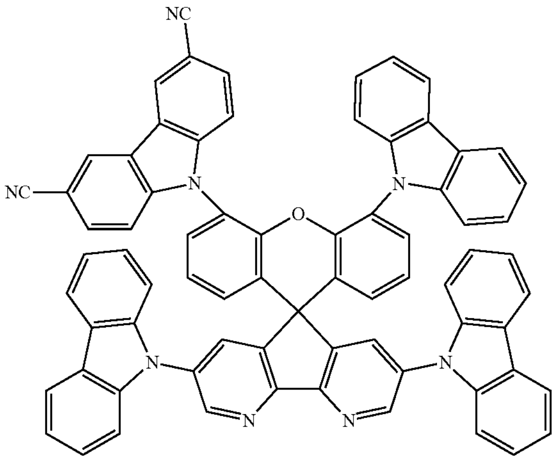
91
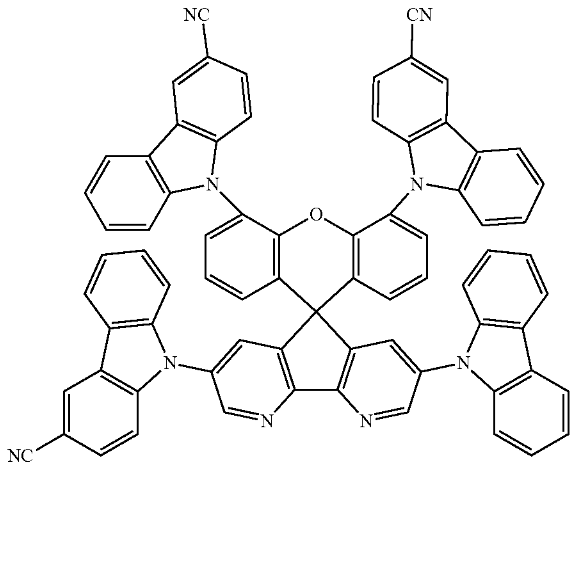
-continued
92
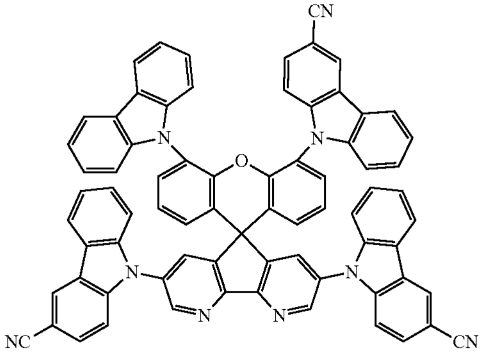
93
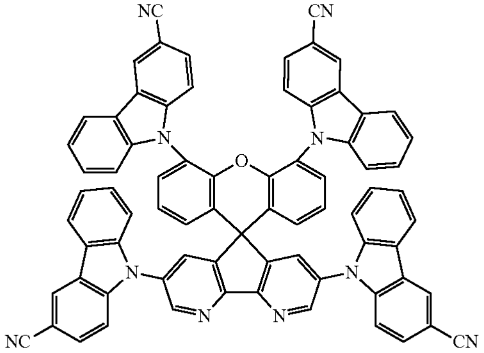
94
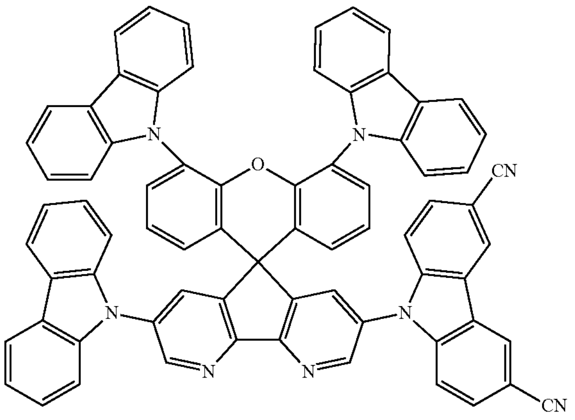
95
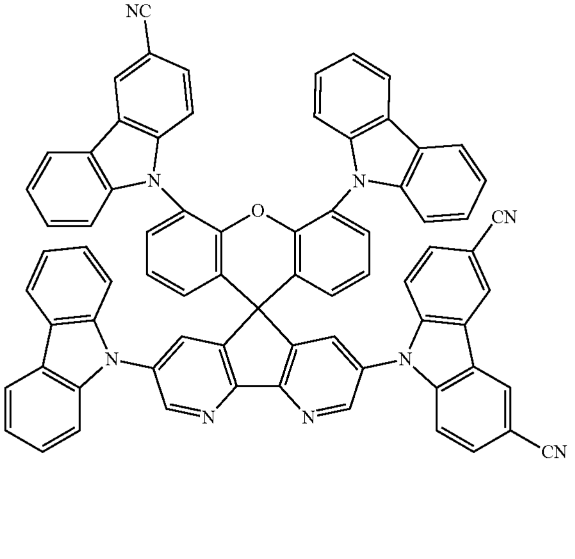

-continued
96
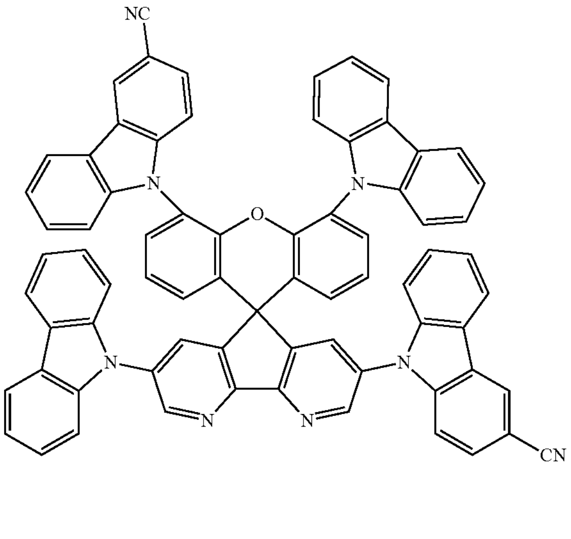
97
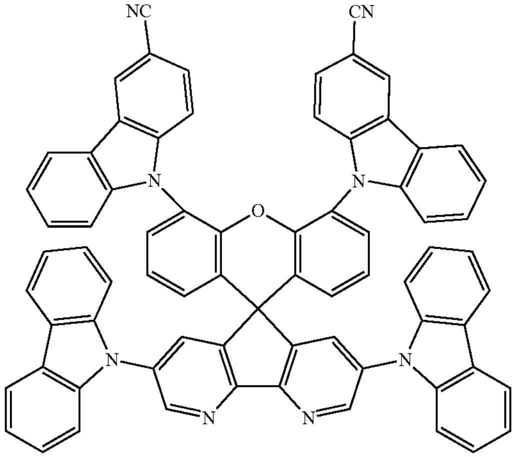
98
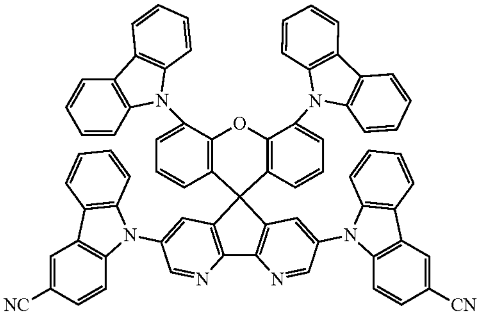
-continued
99
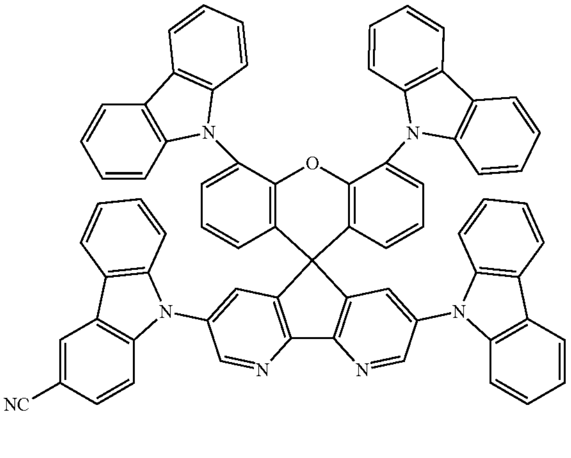
100
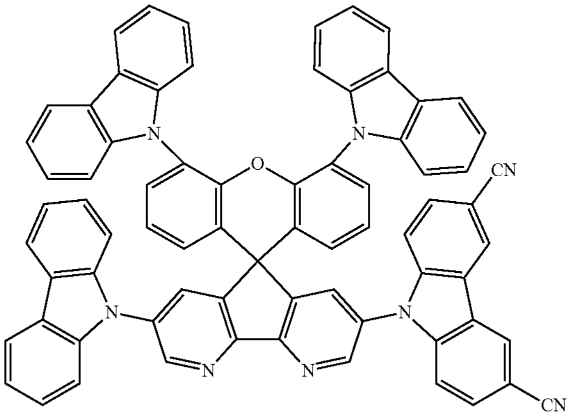
101
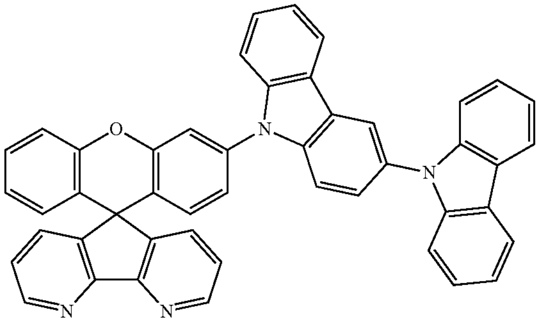
102
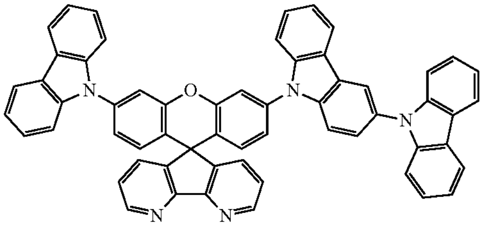

-continued
103
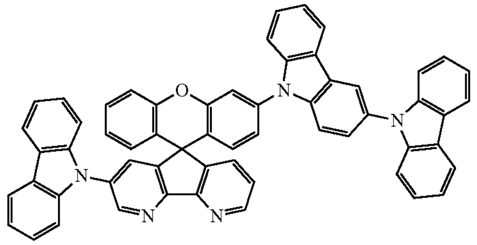
104
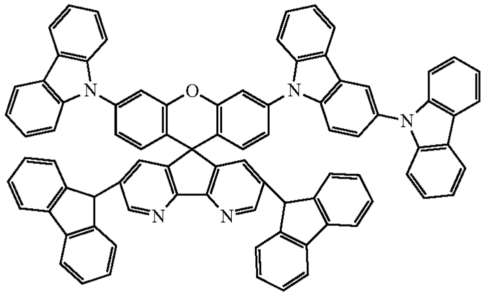
105
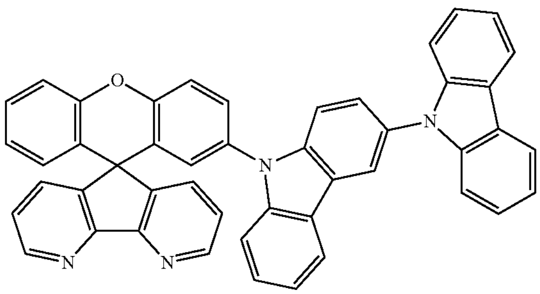
106
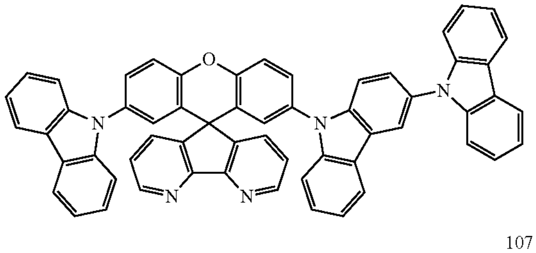
107
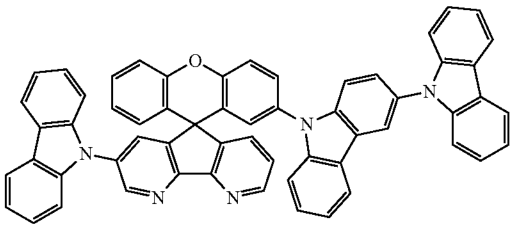
-continued
108
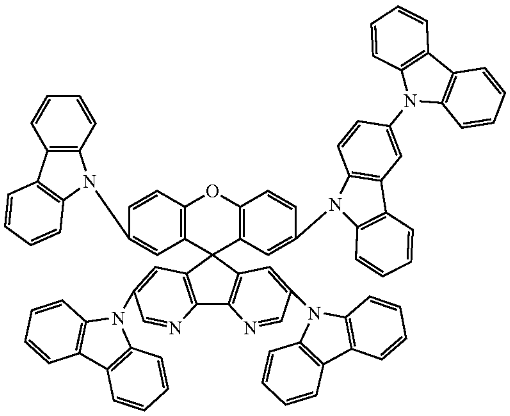
109
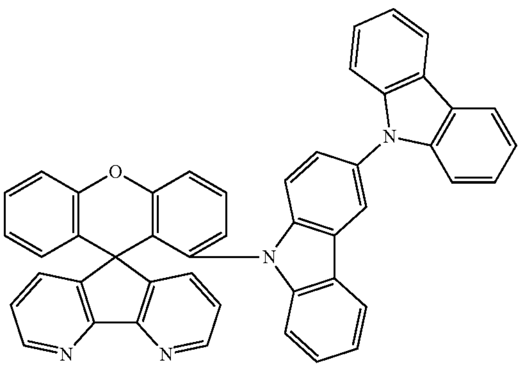
110
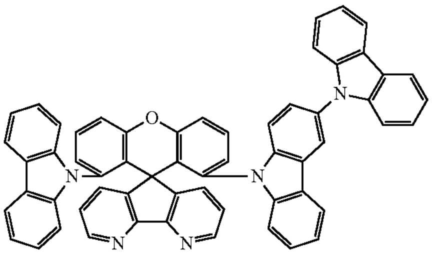
111
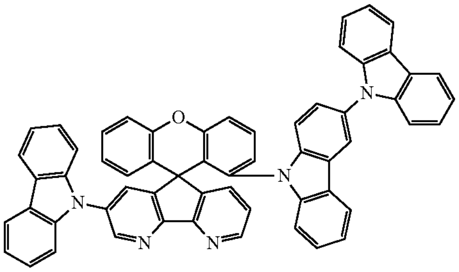

-continued
112
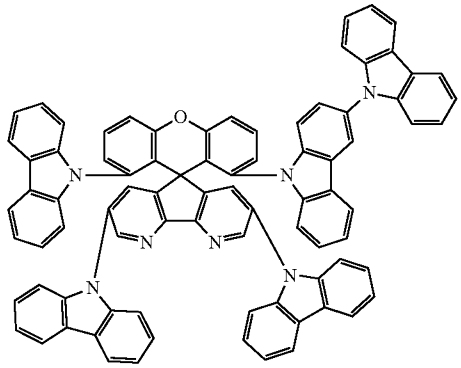
113
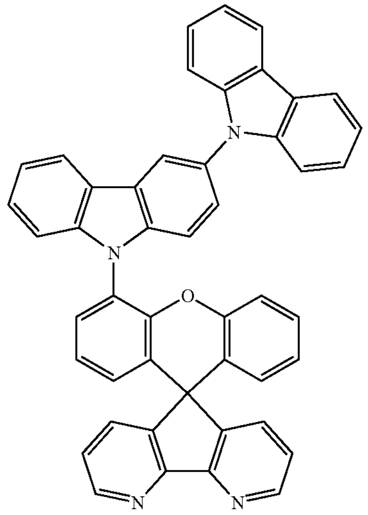
114
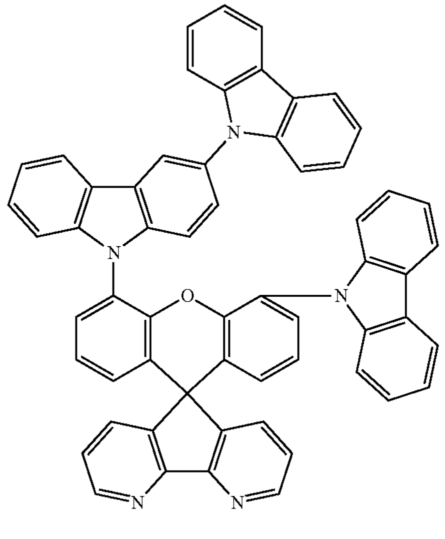
-continued
115
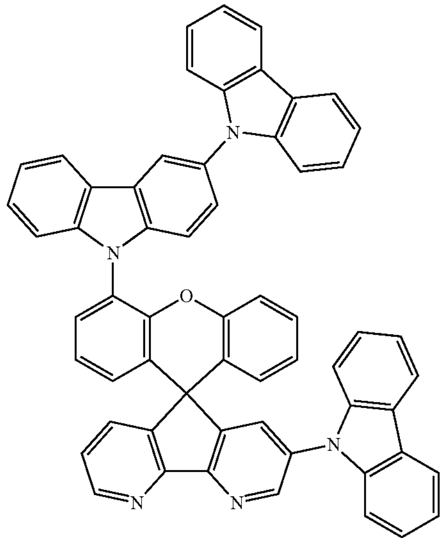
116
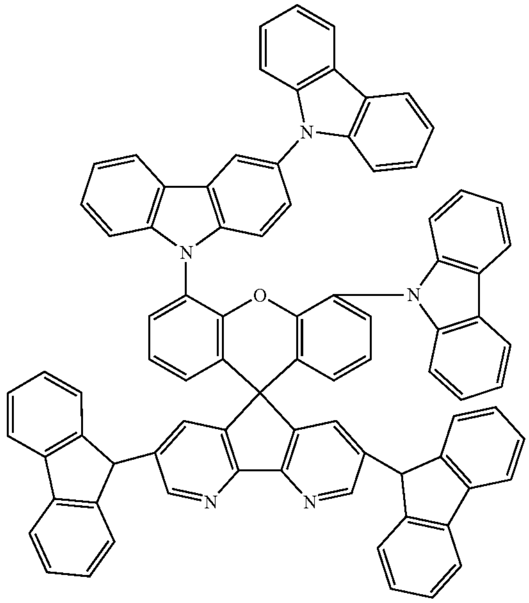
117
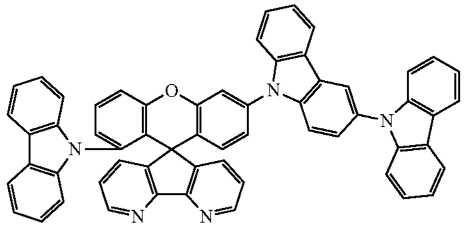
118
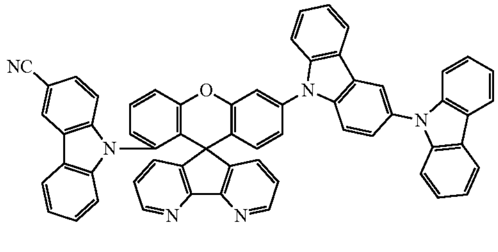

-continued
119
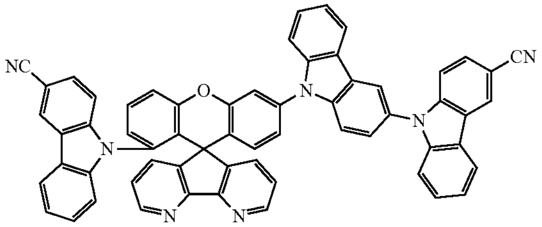
120
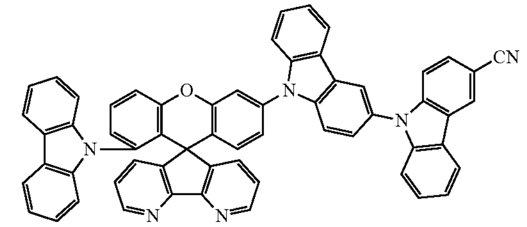
121
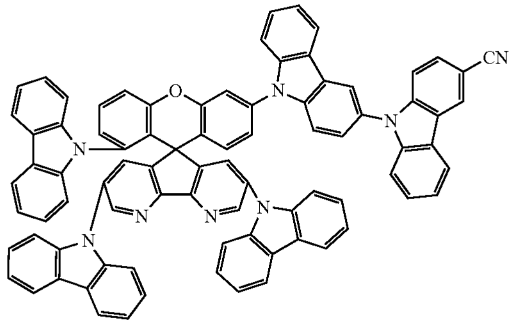
122
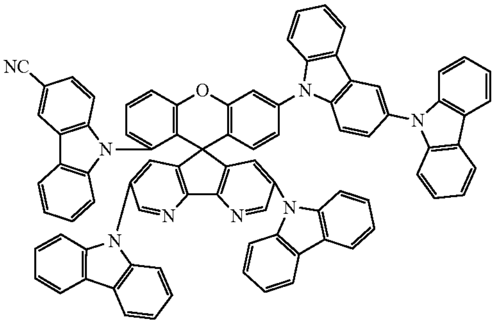
123
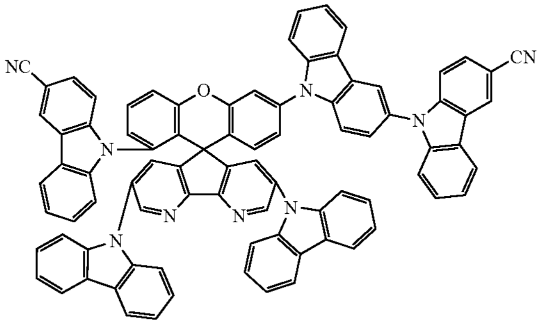
-continued
124
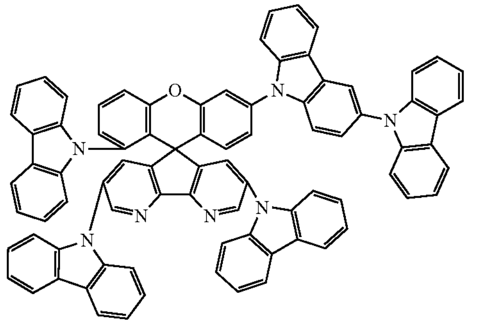
125
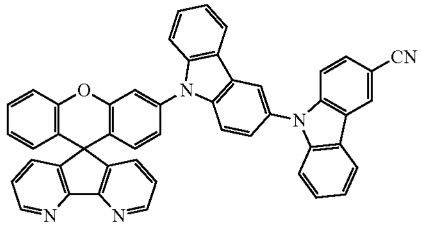
126
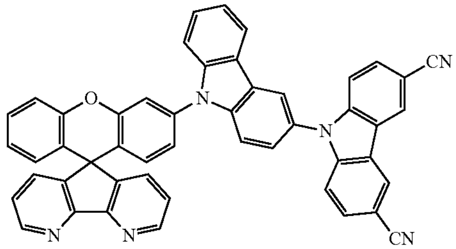
127
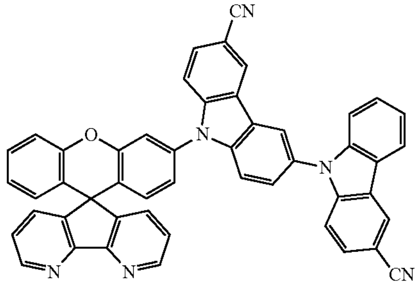
128
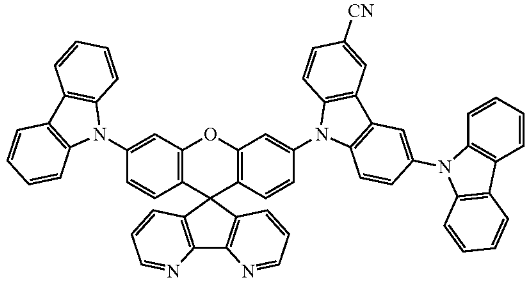

-continued
129
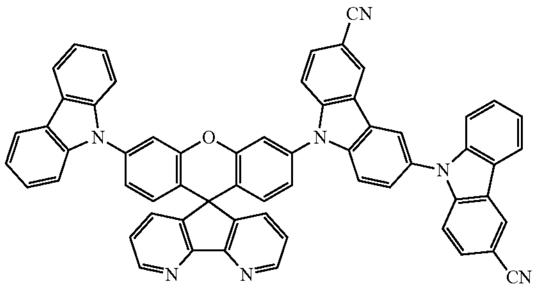
130
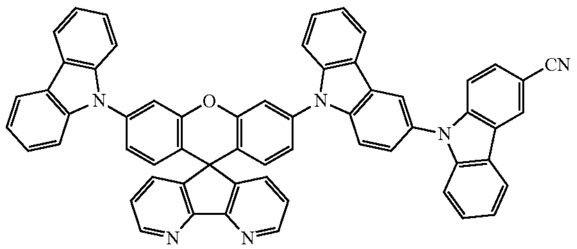
131
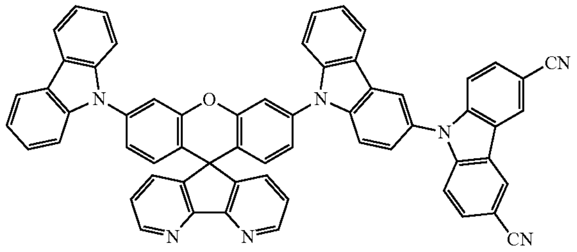
132
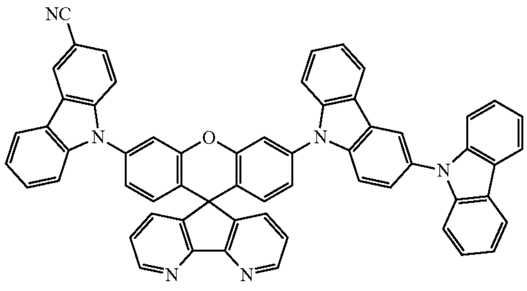
133
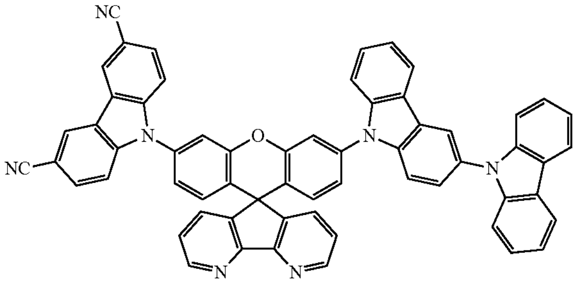
-continued
134
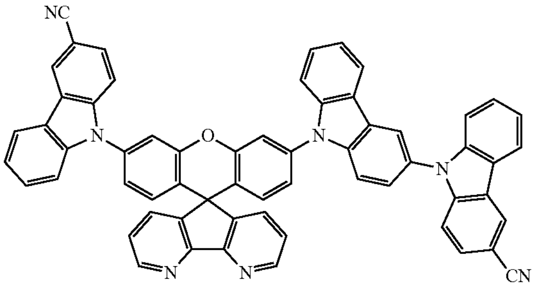
135
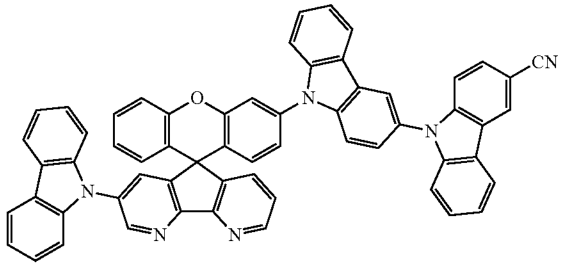
136
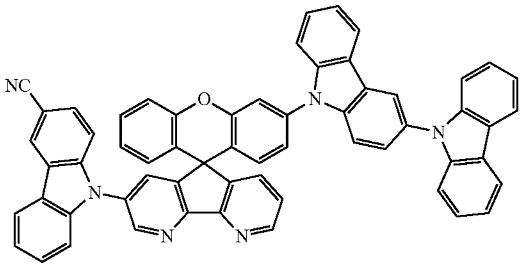
137
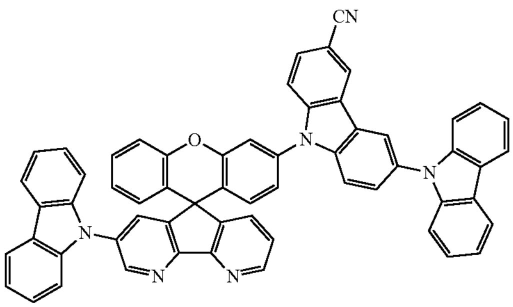
138
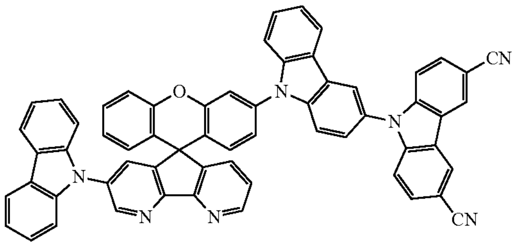

-continued
139
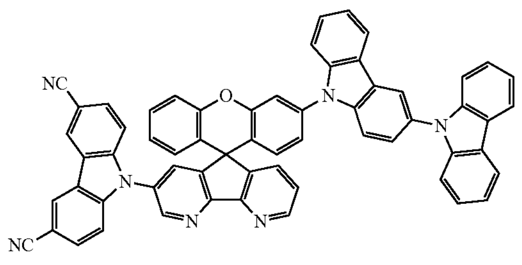
140
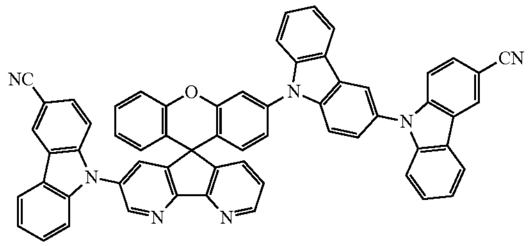
141
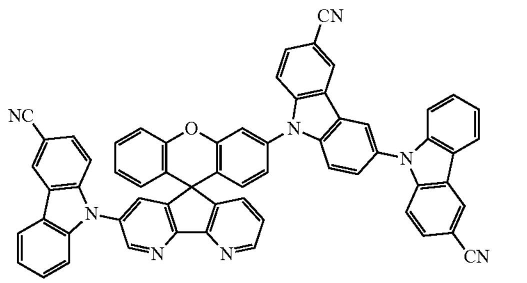
142
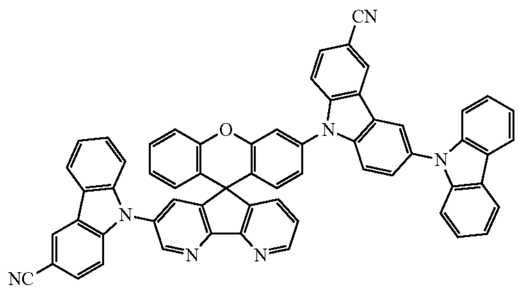
143
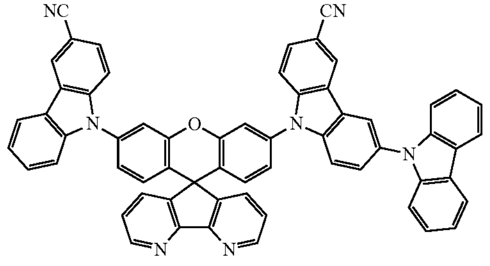
-continued
144
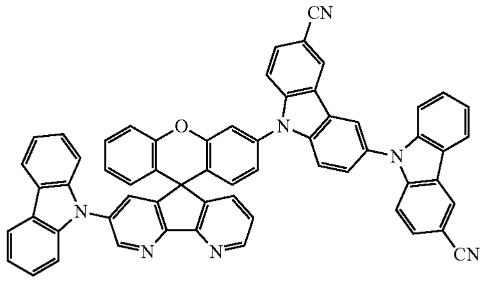
145
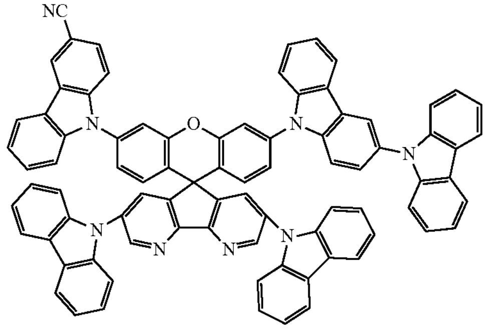
146
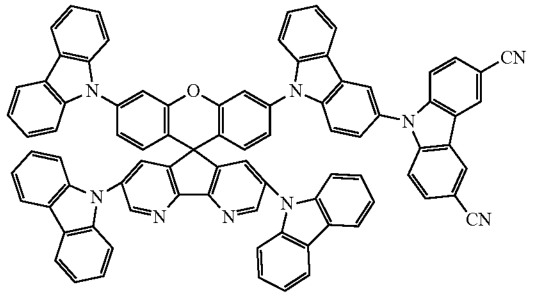
147
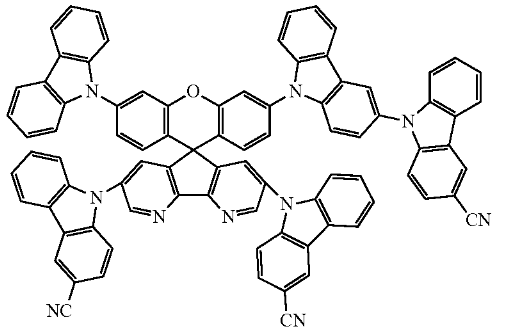
148
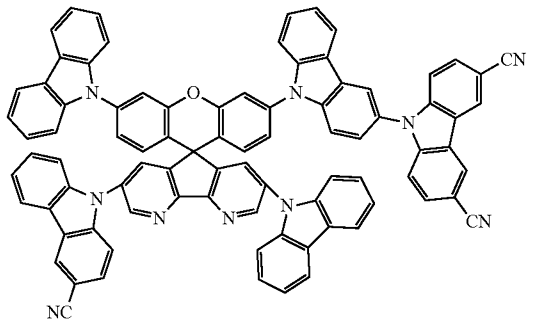

-continued
149
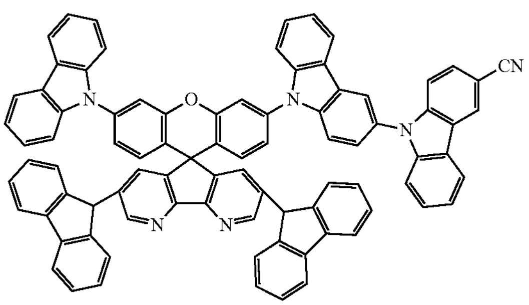
150
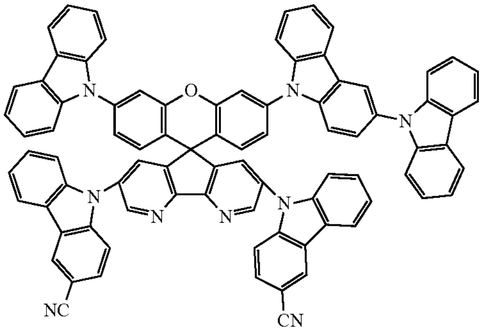
151
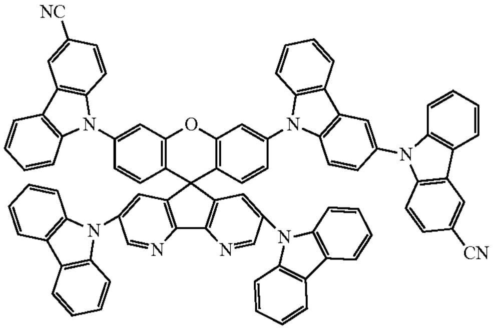
152
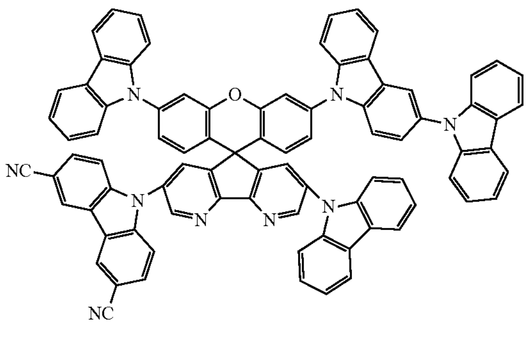
-continued
153
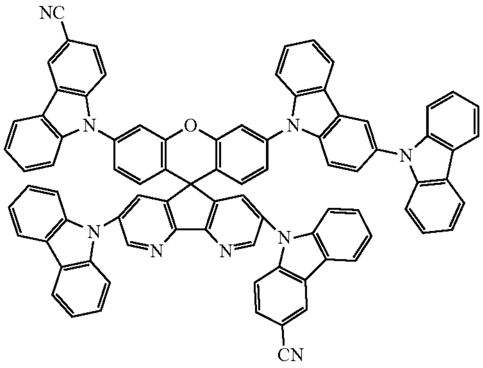
154
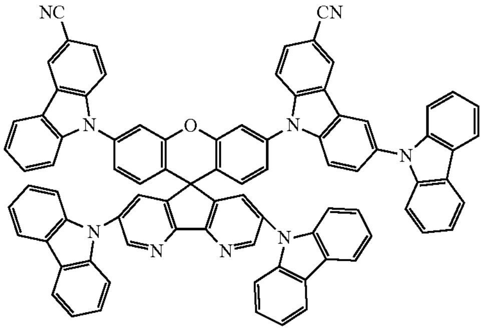
155
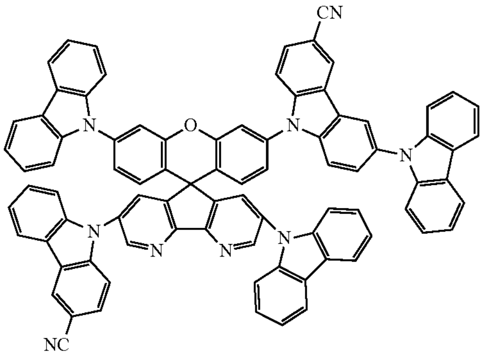
156
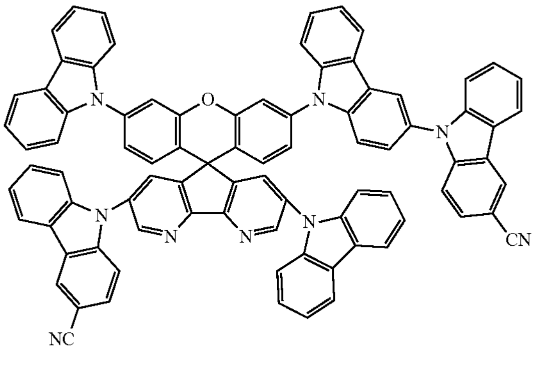

-continued
157
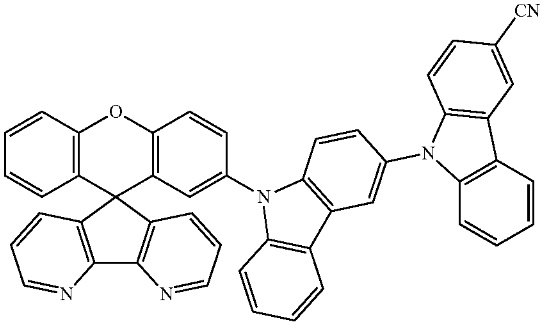
158
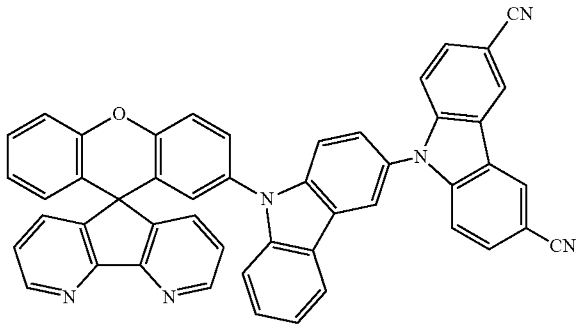
159
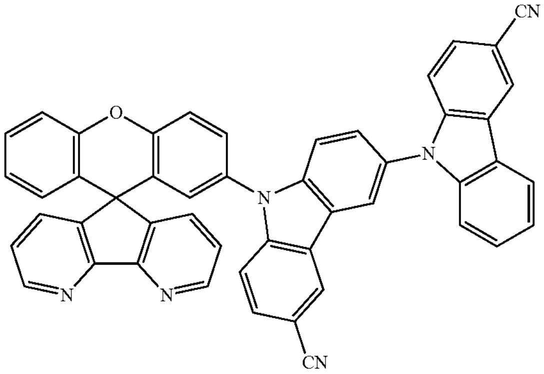
160
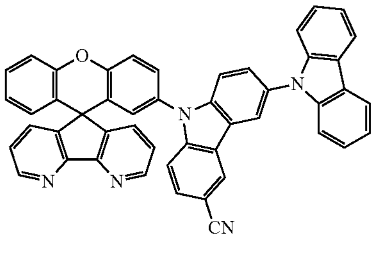
161
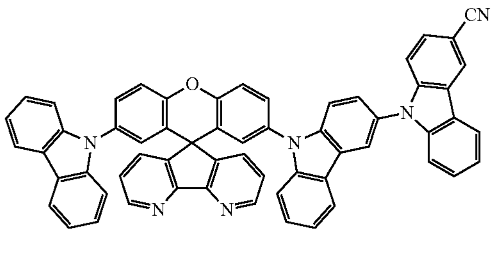
-continued
162
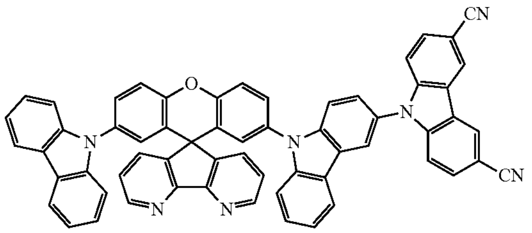
163
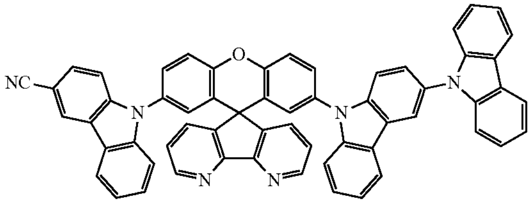
164
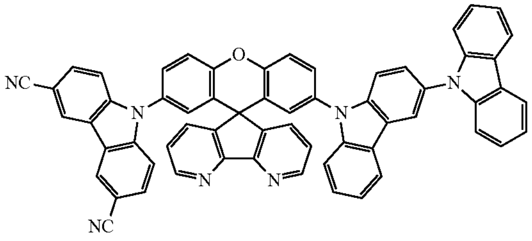
165
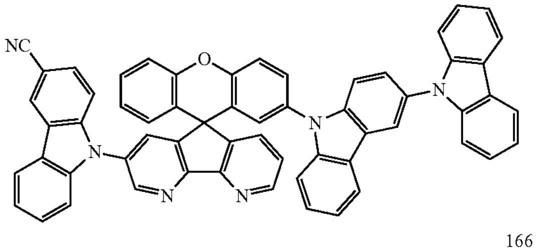
166
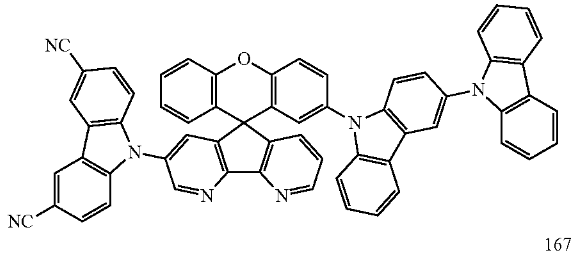
167
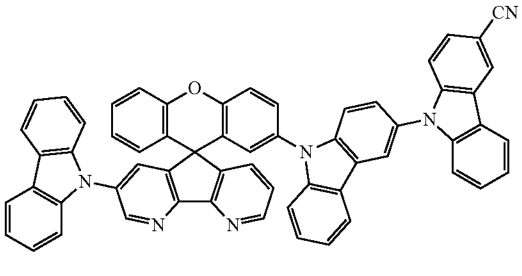

-continued
168
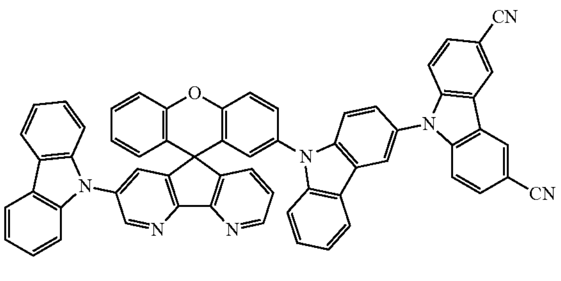
169
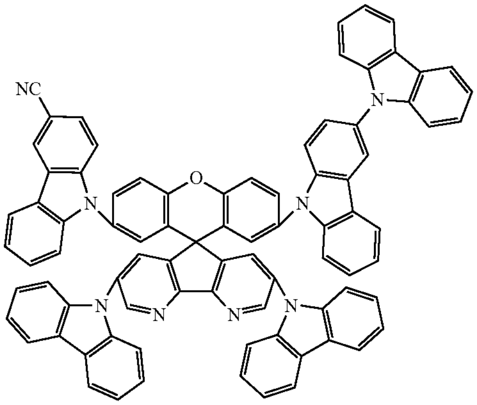
170
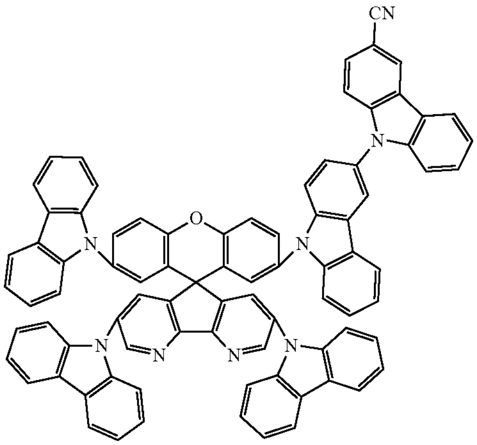
171
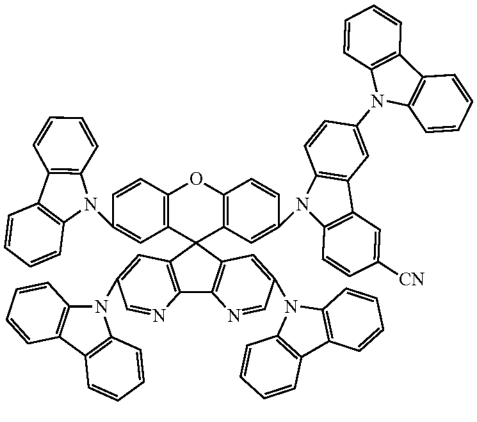
-continued
172
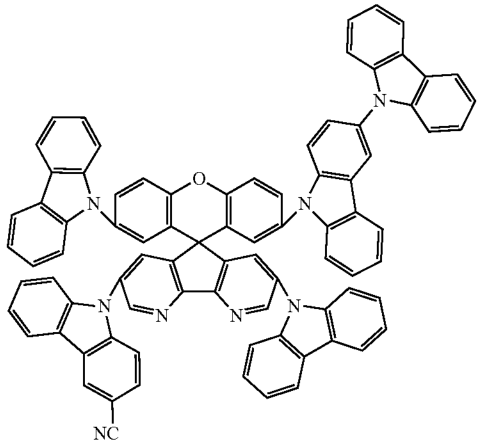
173
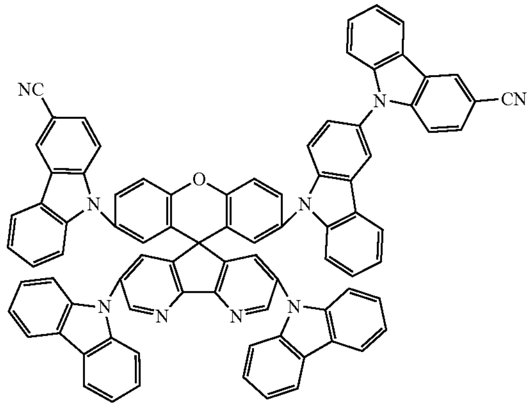
174
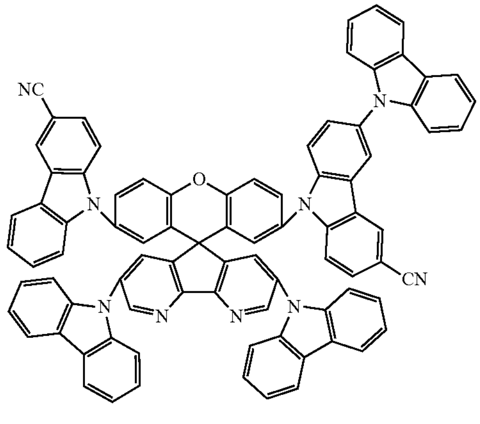

-continued
175
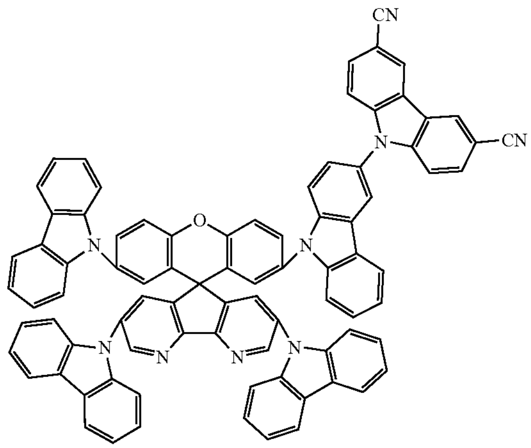
176
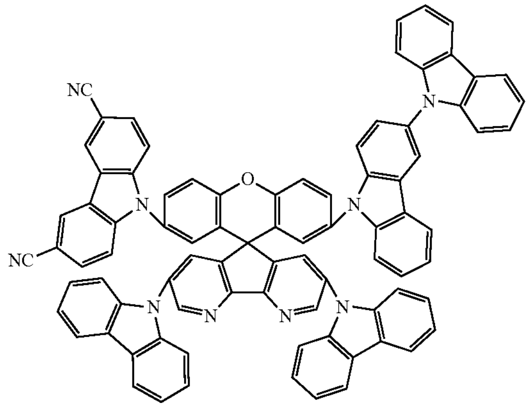
177
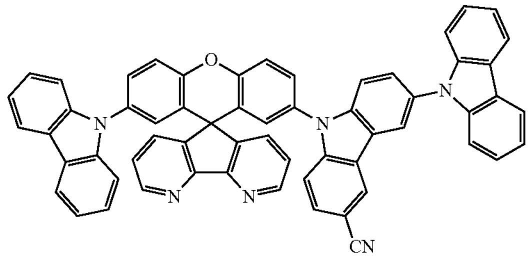
178
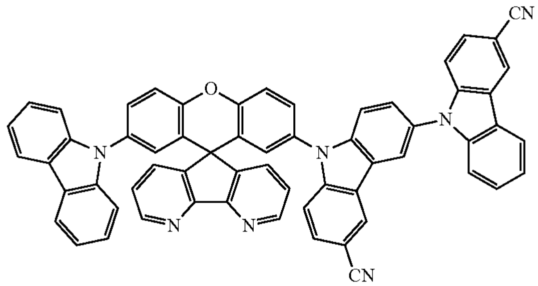
-continued
179
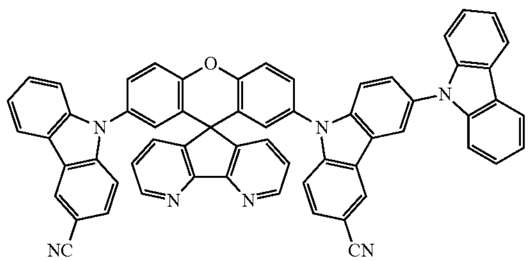
180
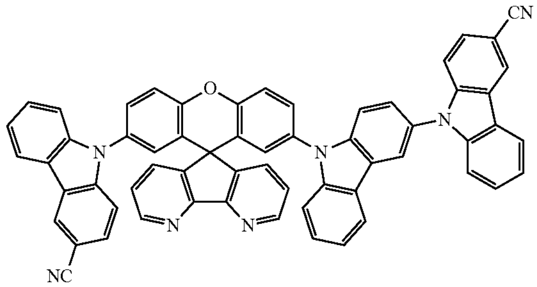
181
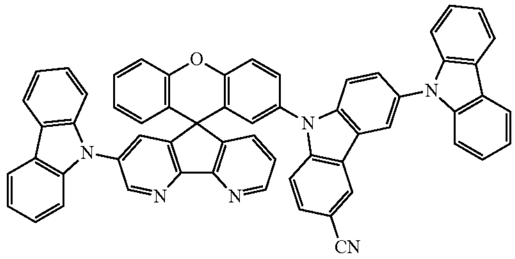
182
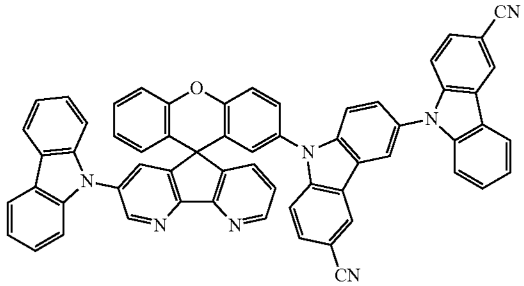
183
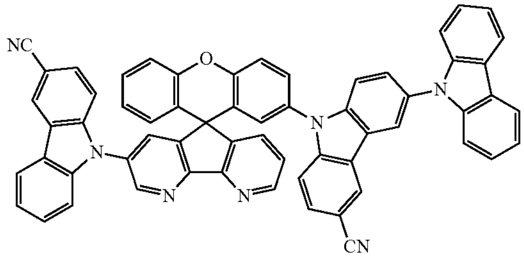

-continued
184
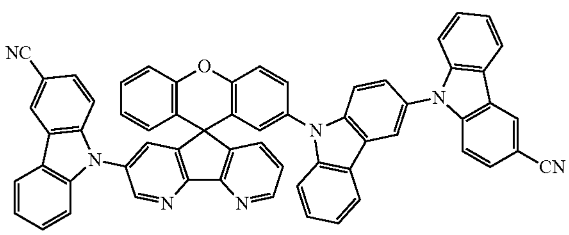
185
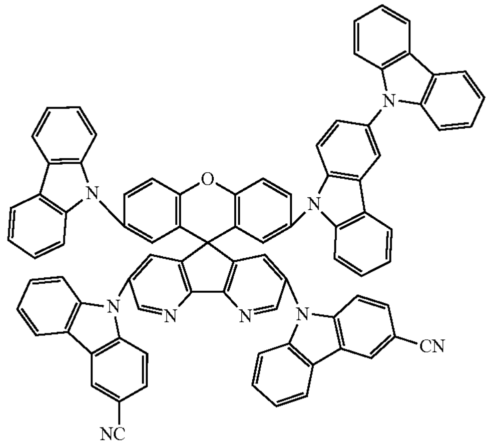
186
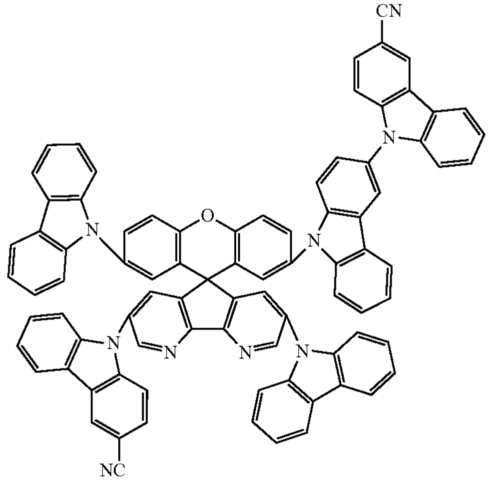
187
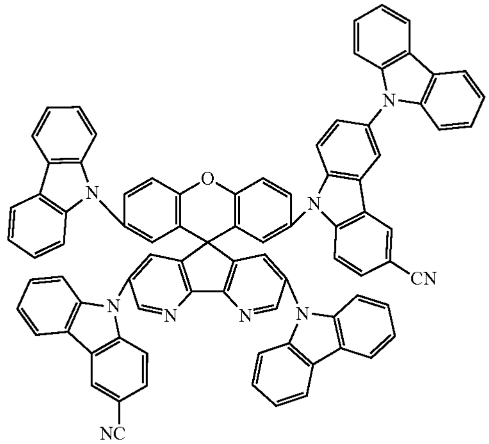
-continued
188
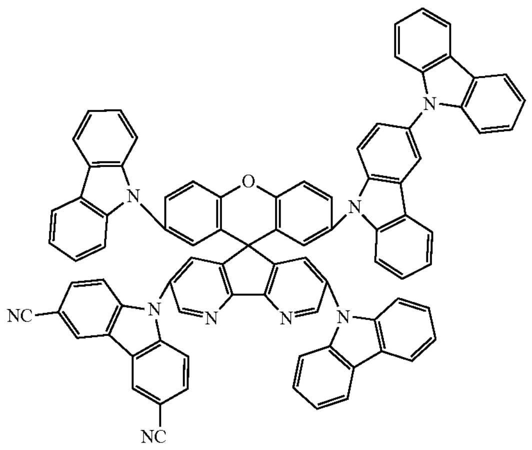
189
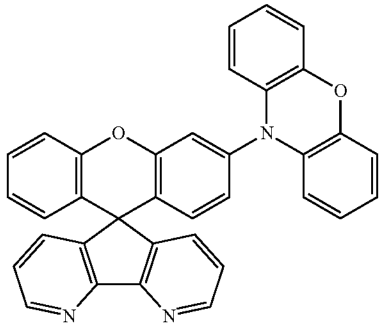
190
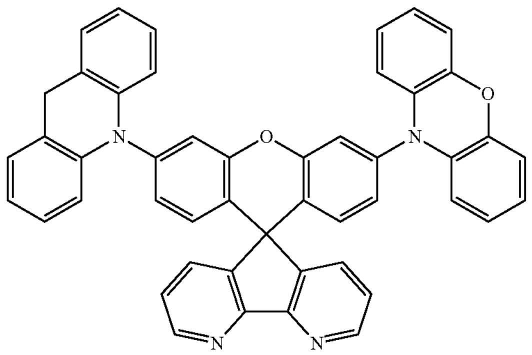
191
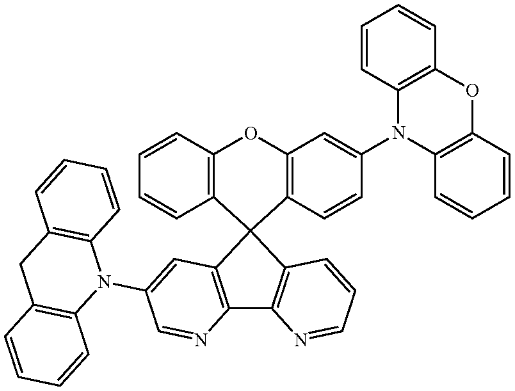

-continued
192
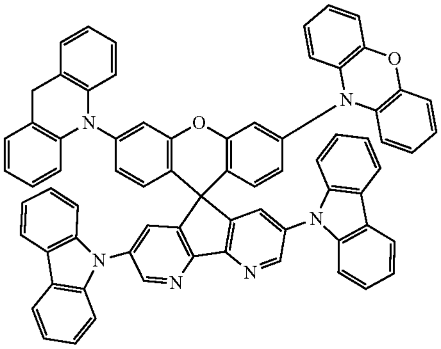
193
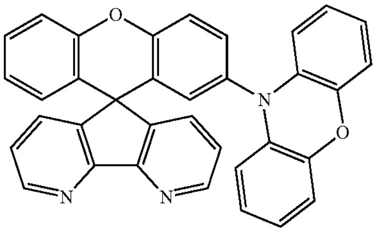
194
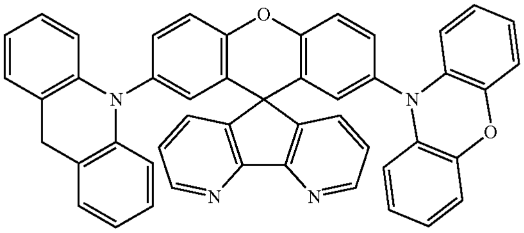
195
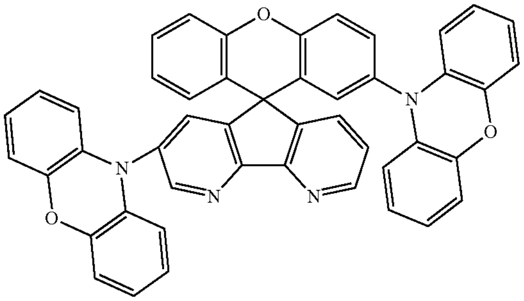
196
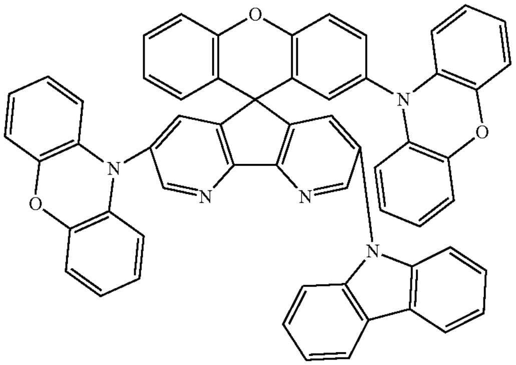
-continued
197
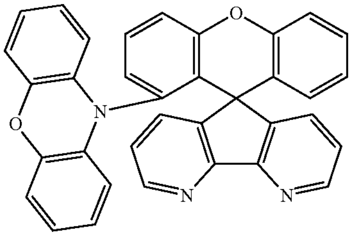
198
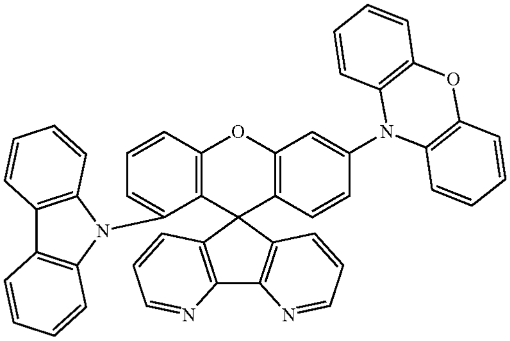
199
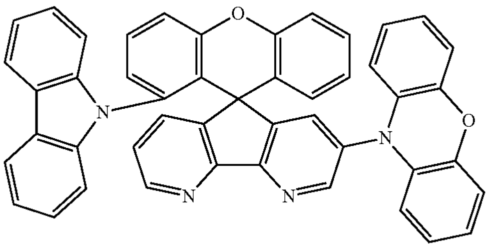
200
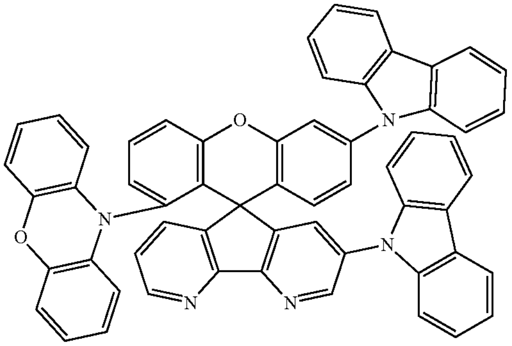
201
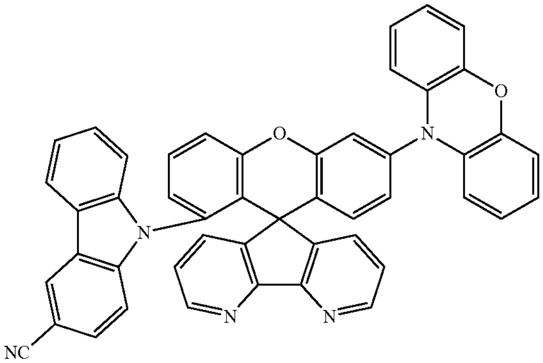

-continued
202
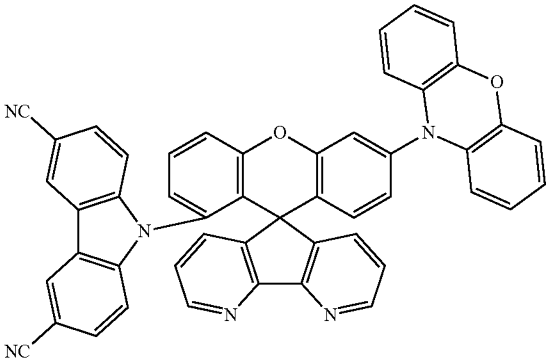
203
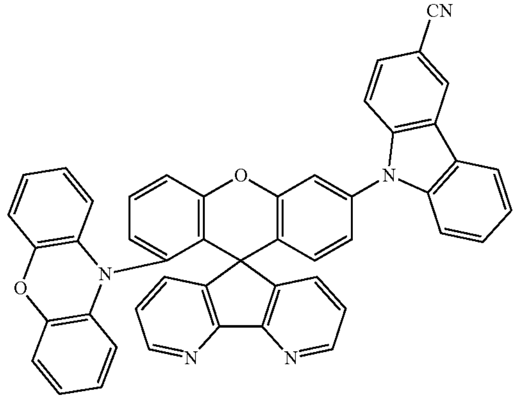
204
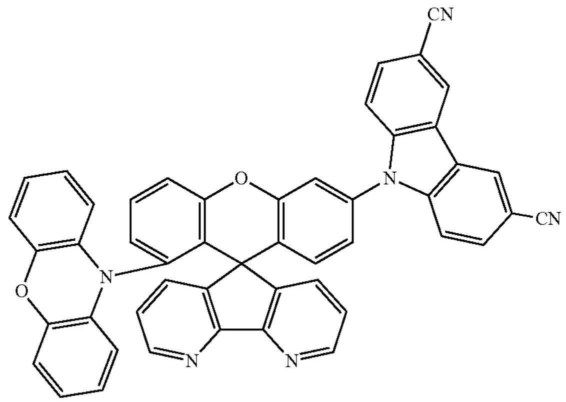
205
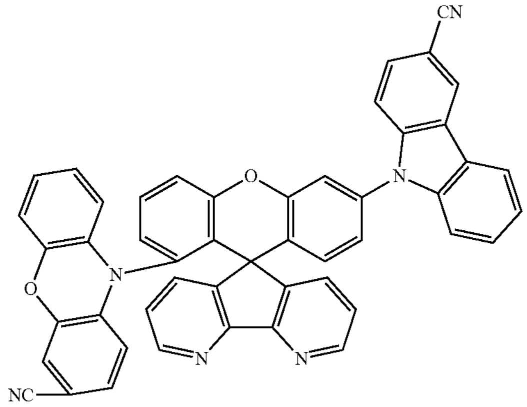
-continued
206
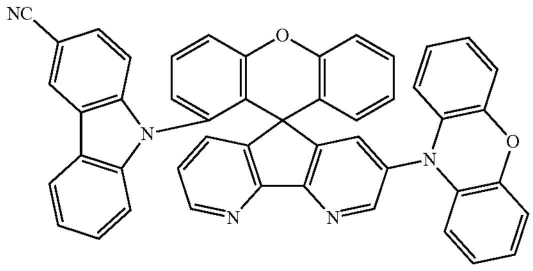
207
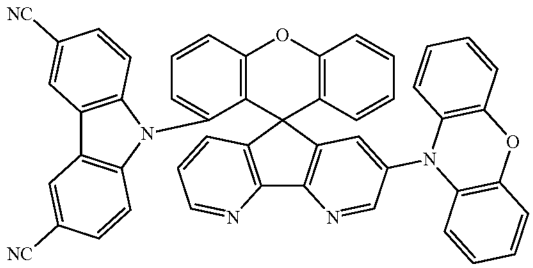
208
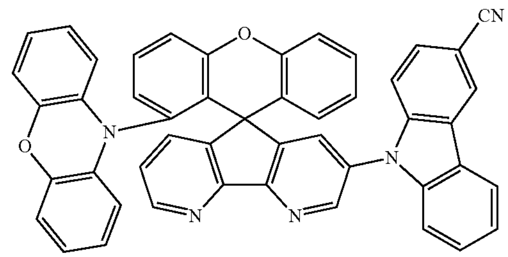
209
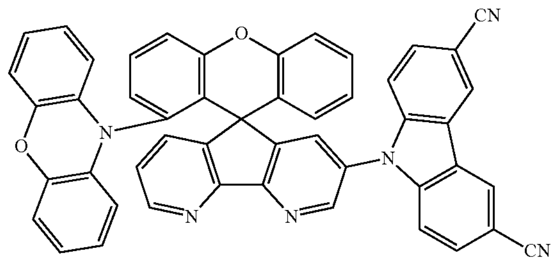
210
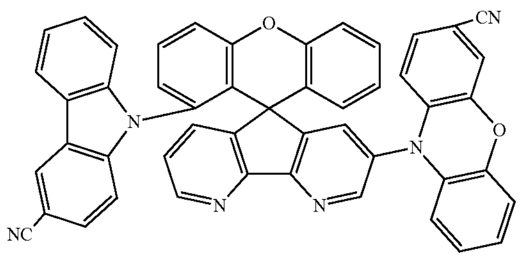

-continued
211
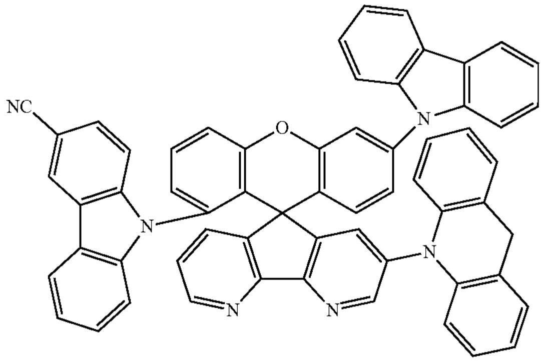
212
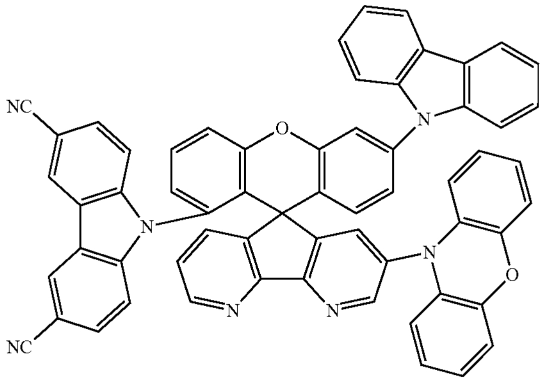
213
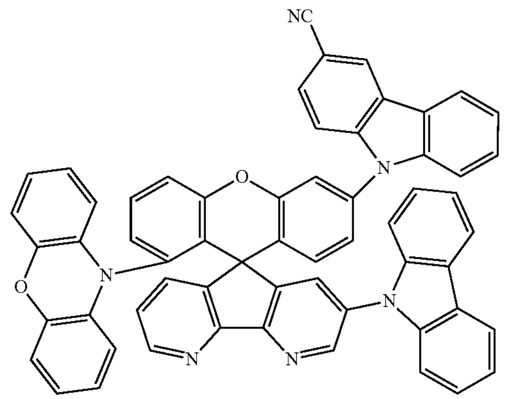
214
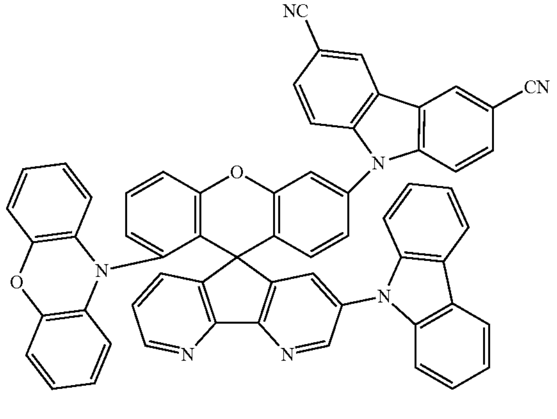
-continued
215
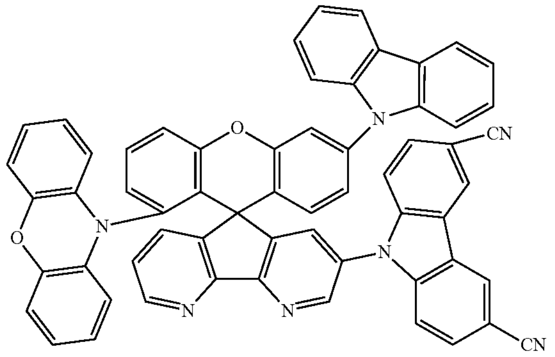
216
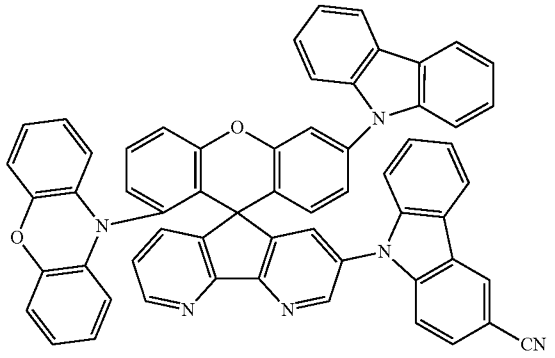
217
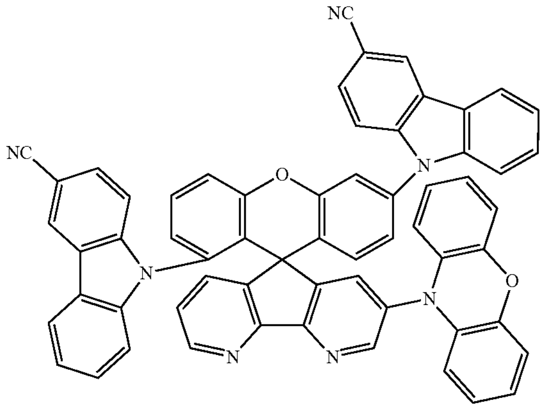
218
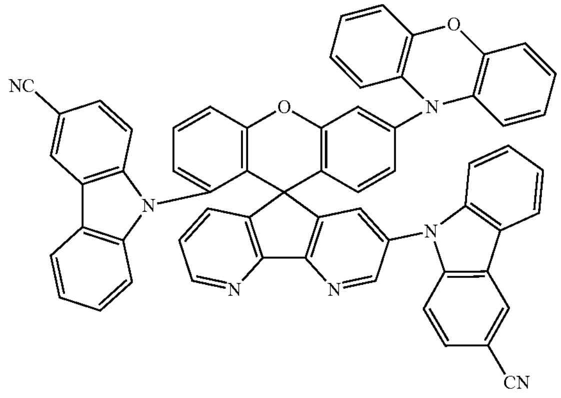

-continued
219
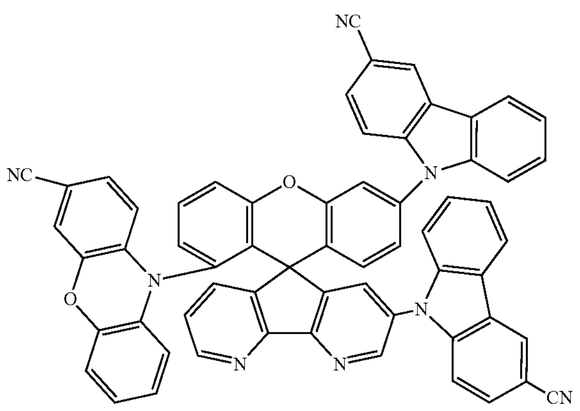
220
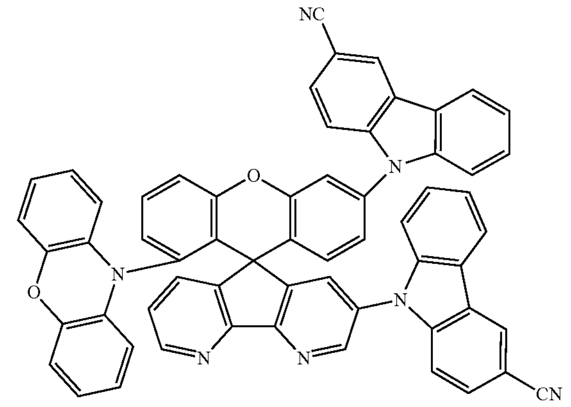
221
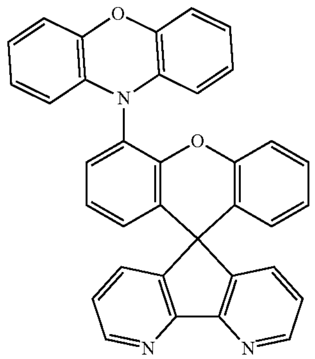
222
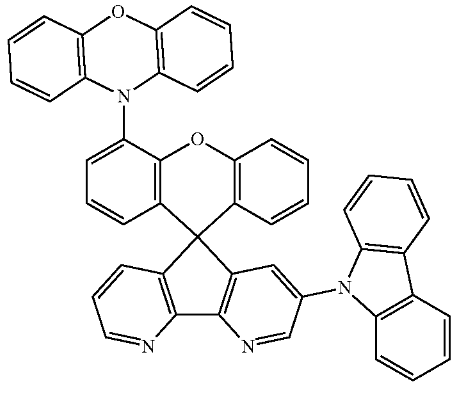
-continued
223
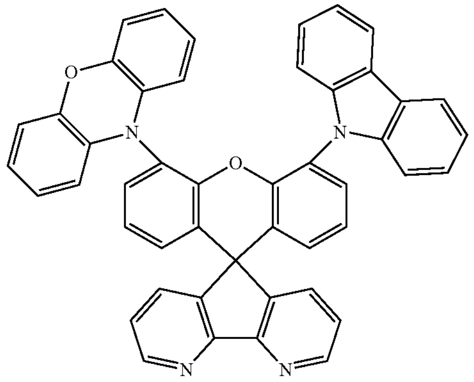
224
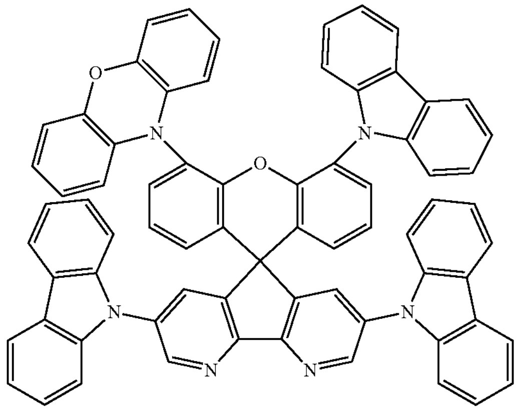
225
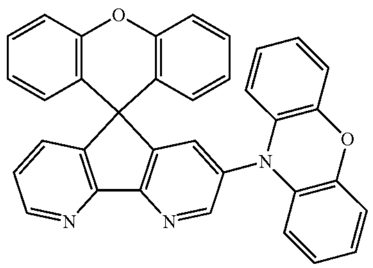
226
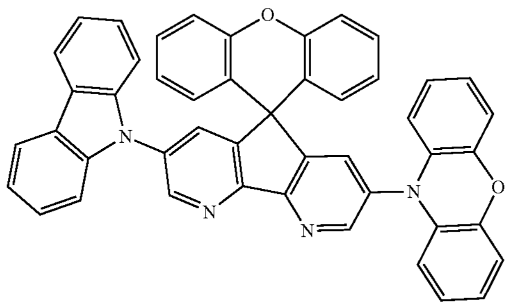

-continued
227
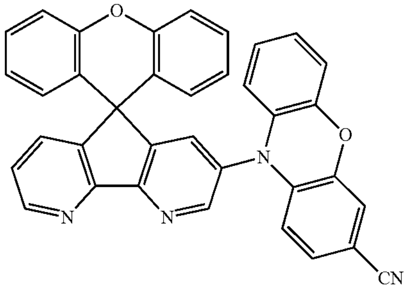
228
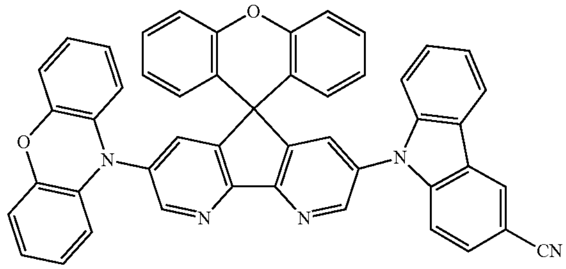
229
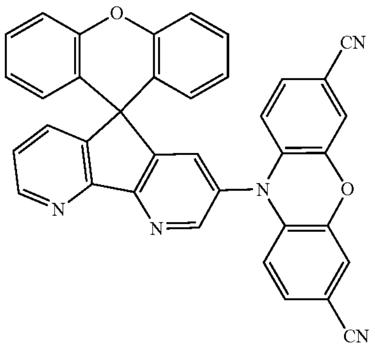
230
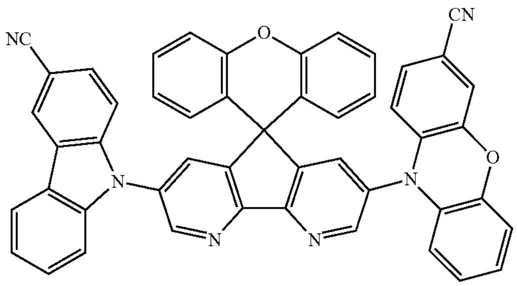
231
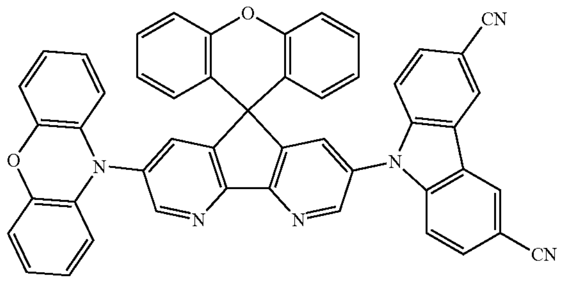
-continued
232
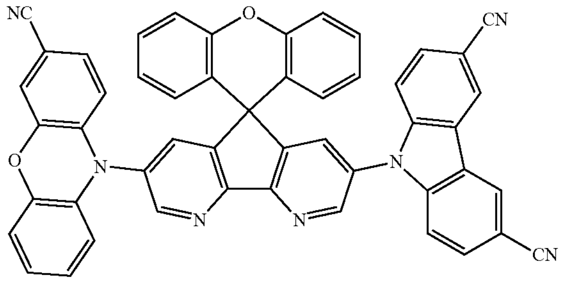
233
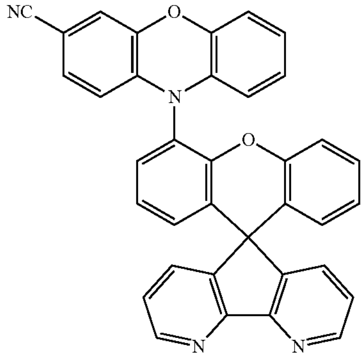
234
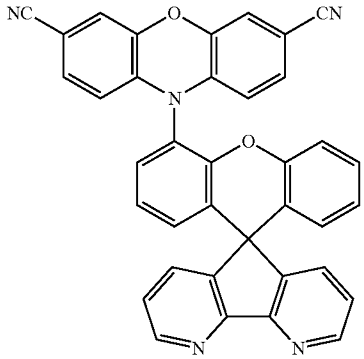
235
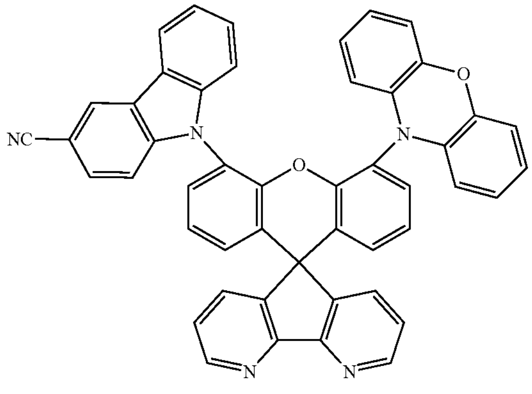

-continued
236
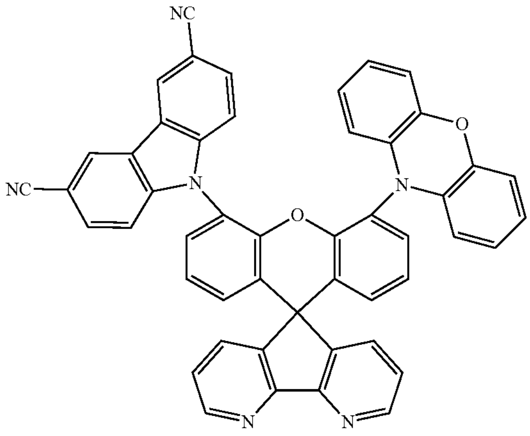
237
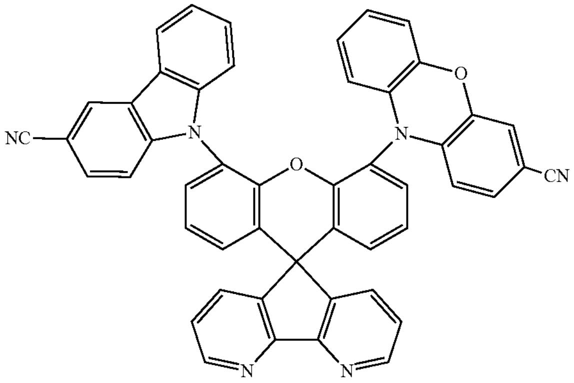
238
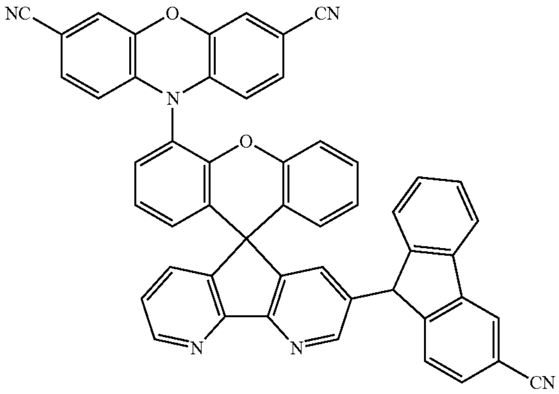
-continued
239
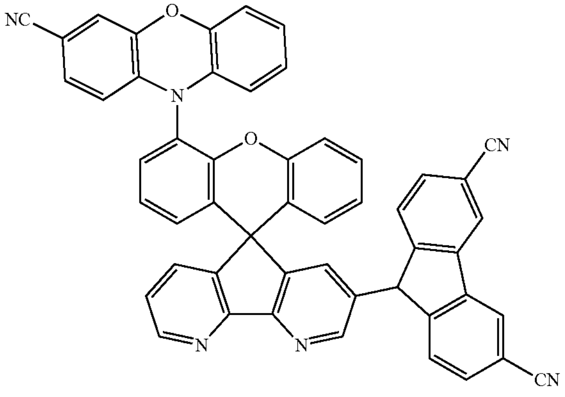
240
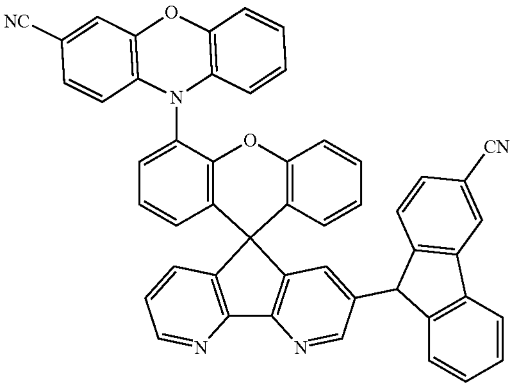
241
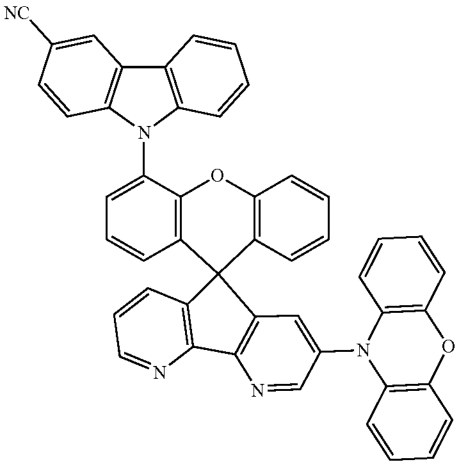

-continued
242
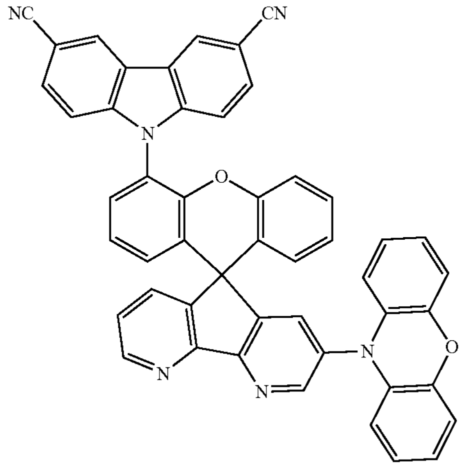
243
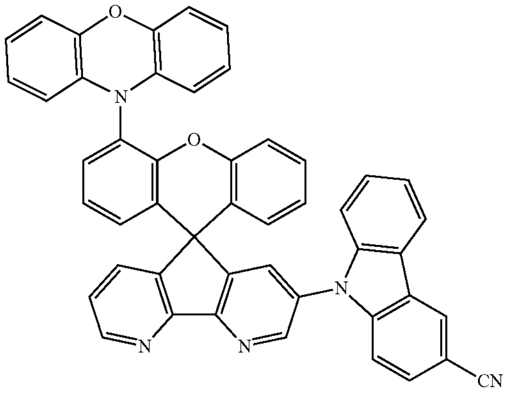
244
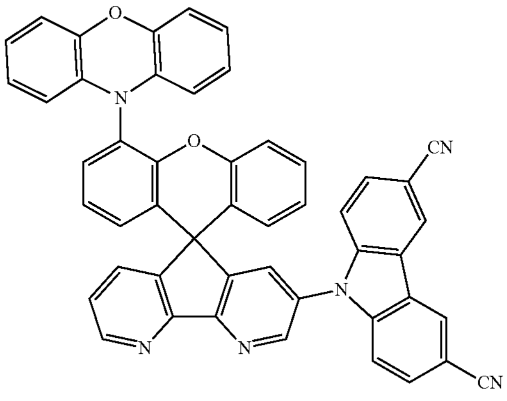
245
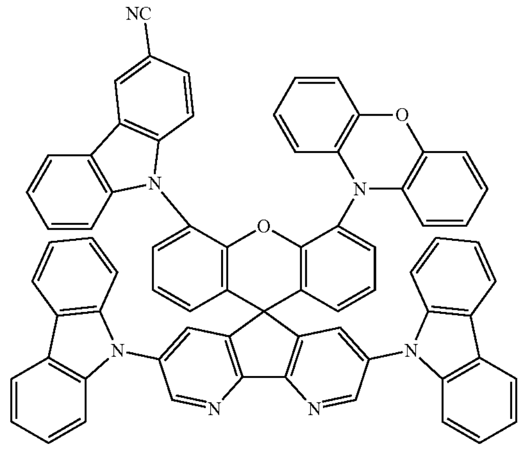
246
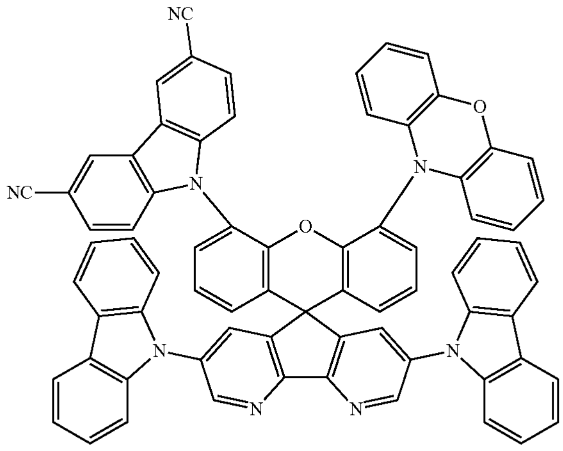
247
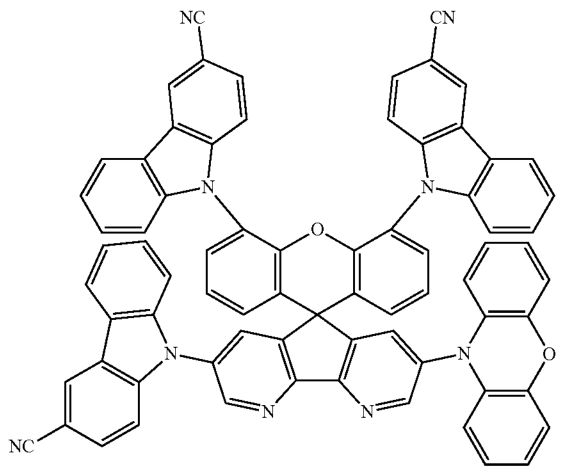

-continued
248
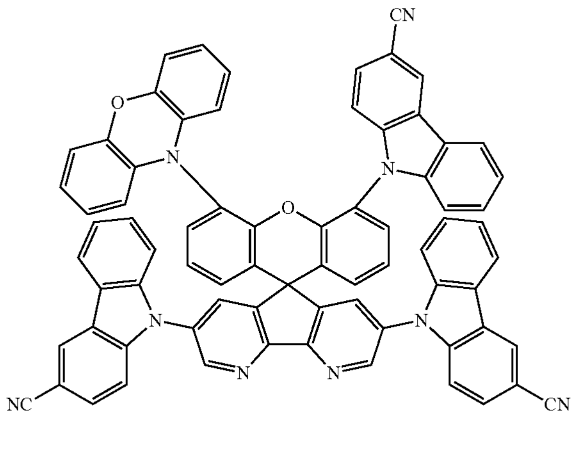
249
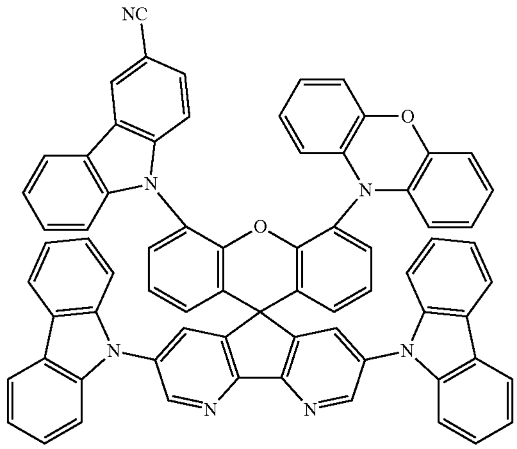
250
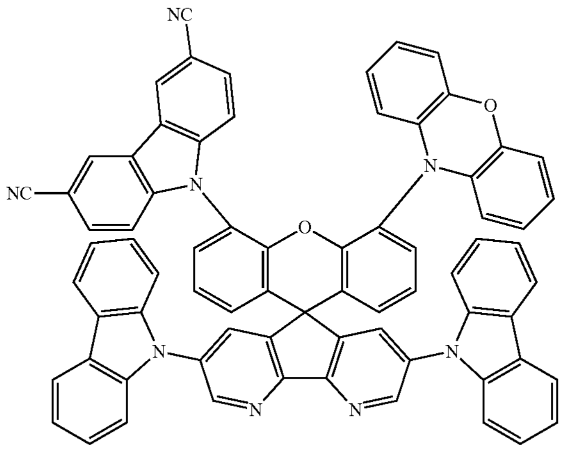
-continued
251
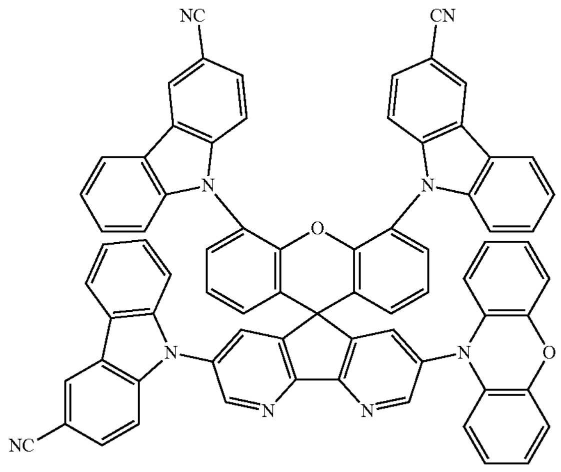
252
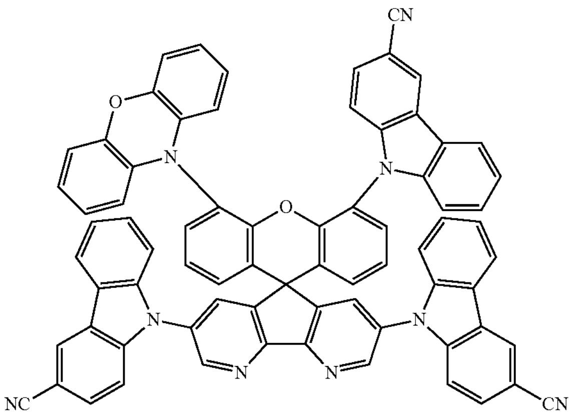
253
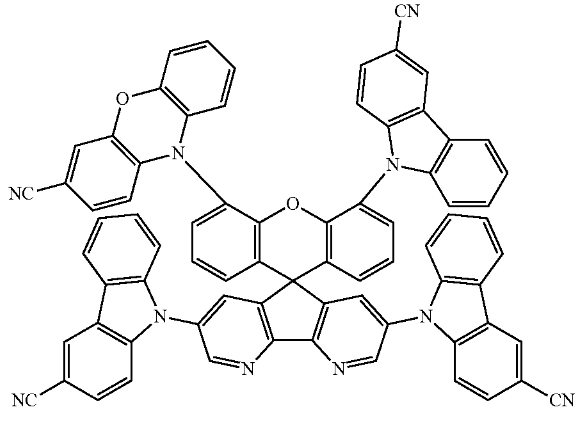

-continued
254
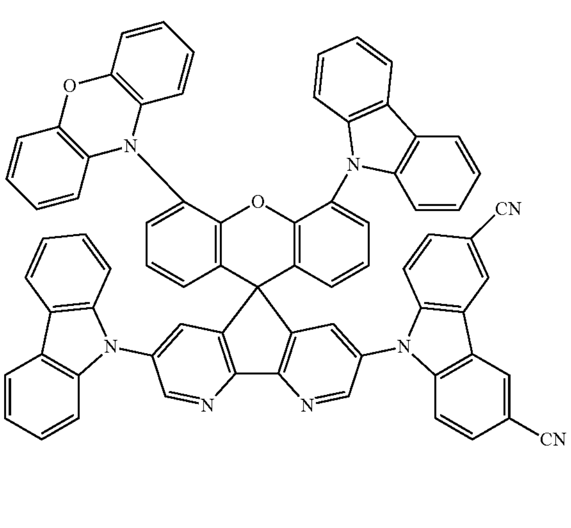
255
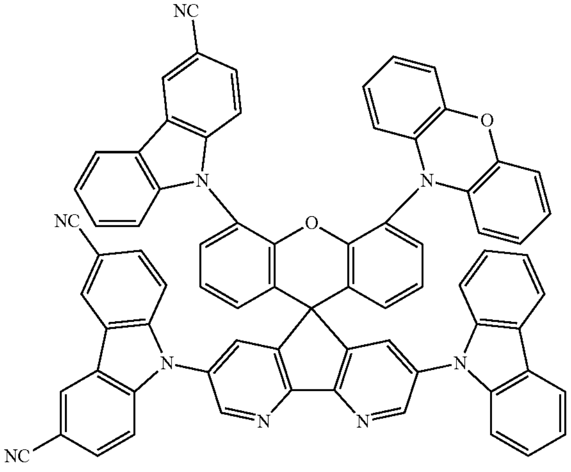
256
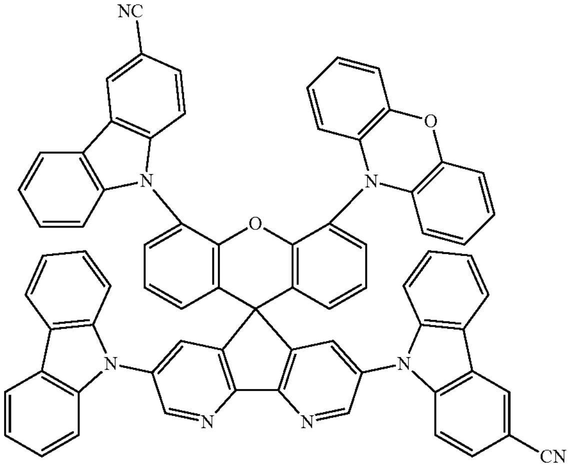
-continued
257
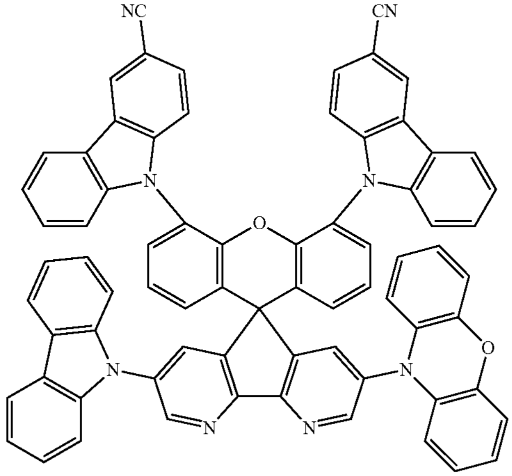
258
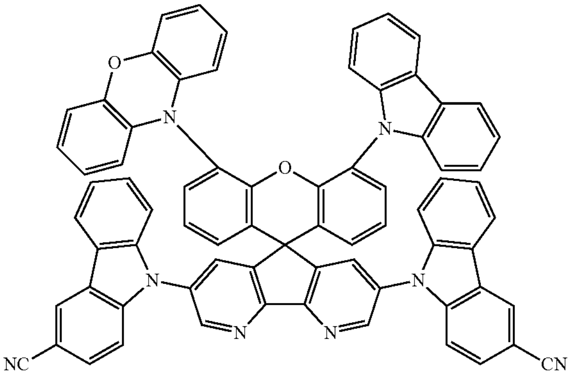
259
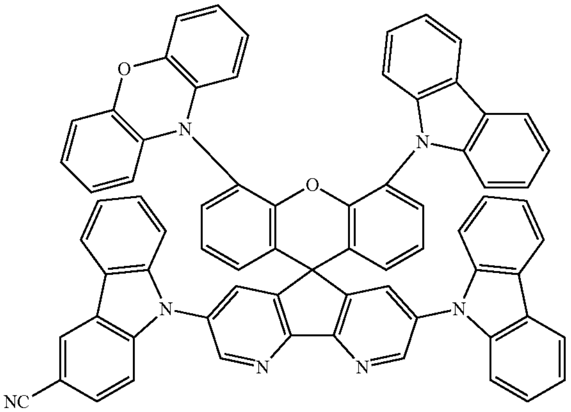

-continued
260
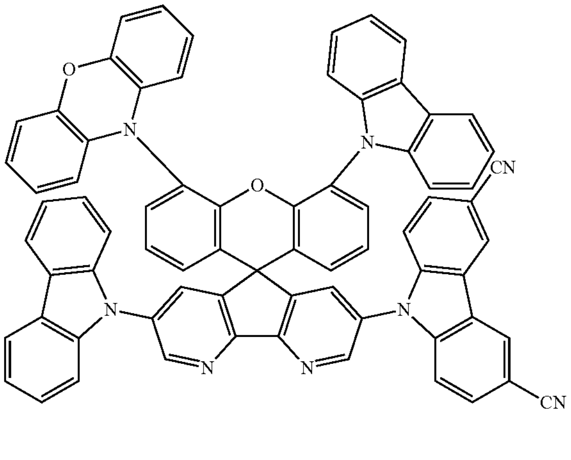
261
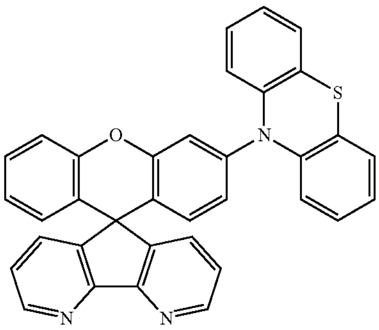
262
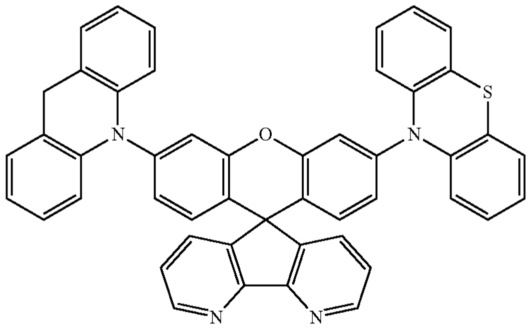
263
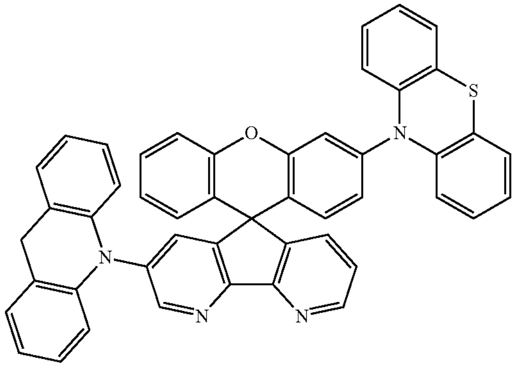
-continued
264
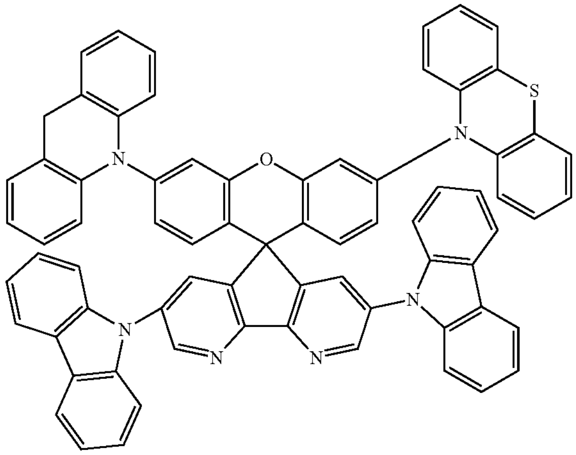
265
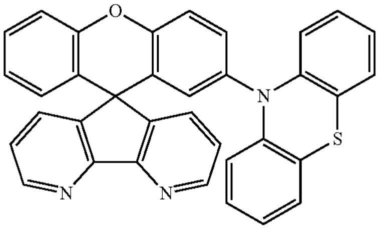
266
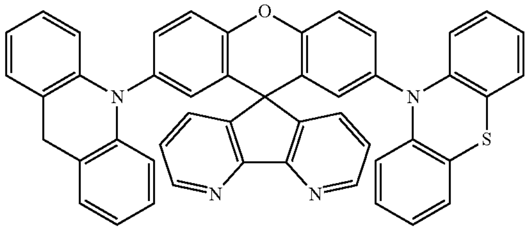
267
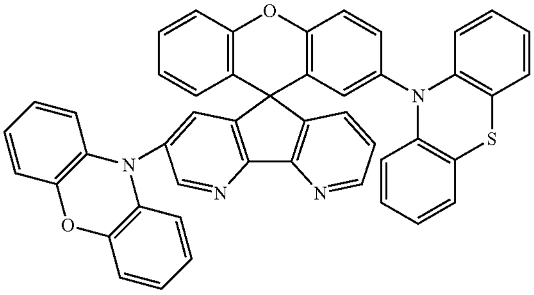

-continued
268
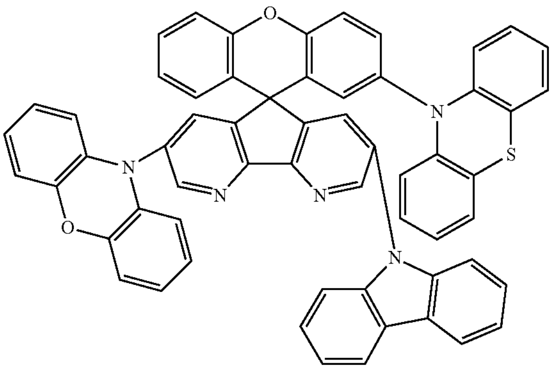
269
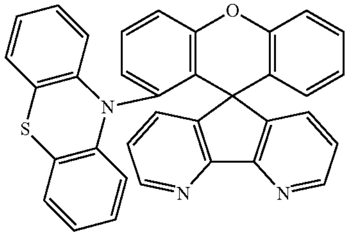
270
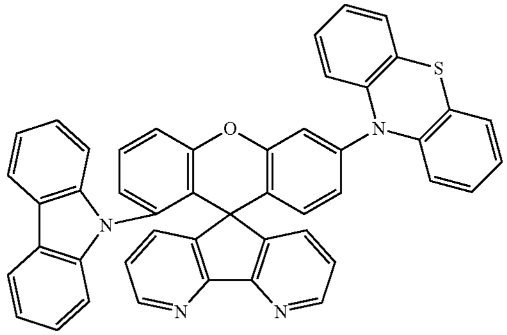
271
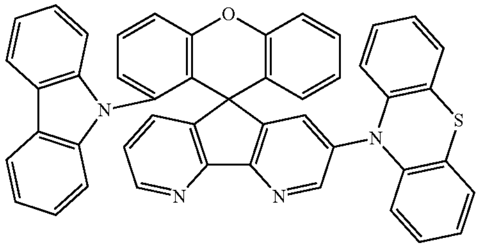
272
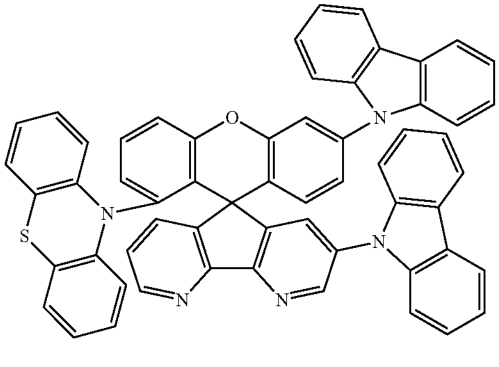
-continued
273
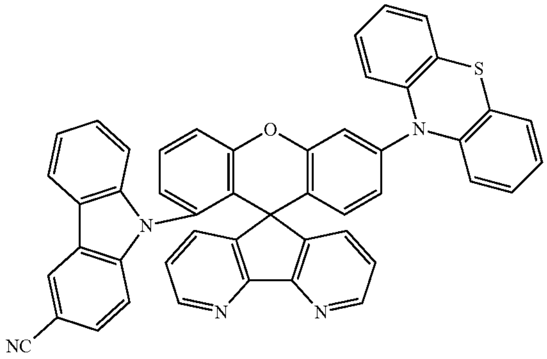
274
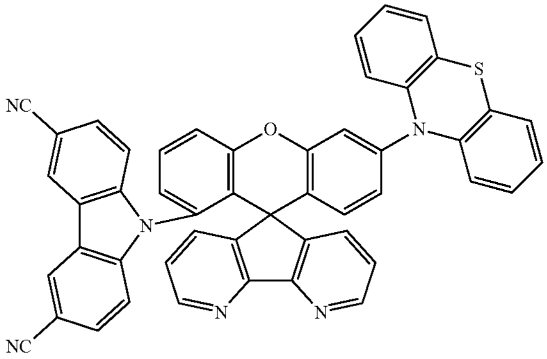
275
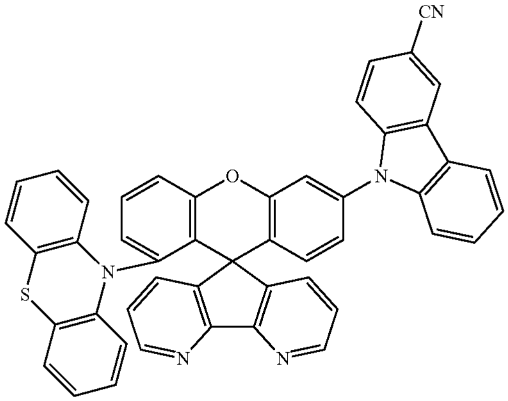
276
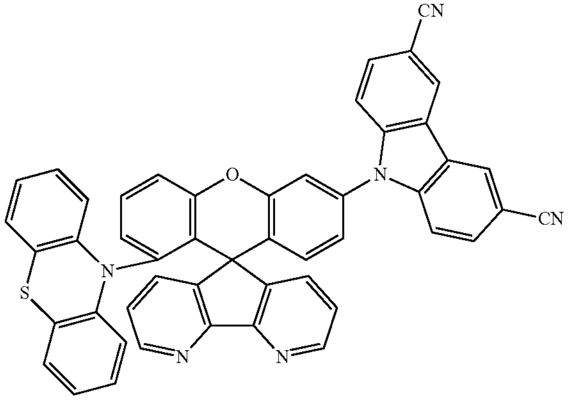

-continued
277
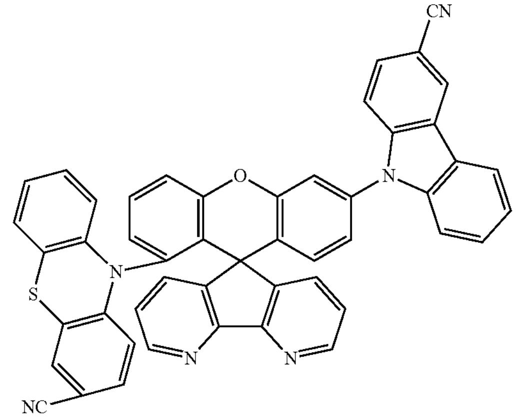
278
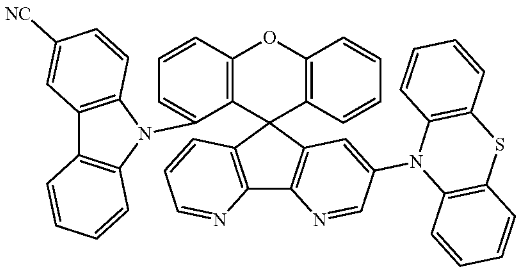
289
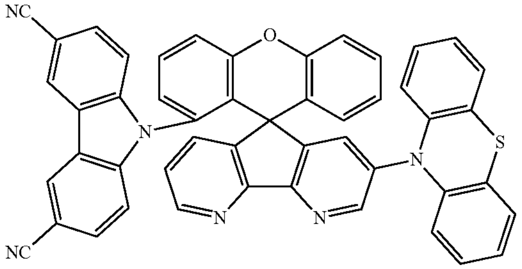
280
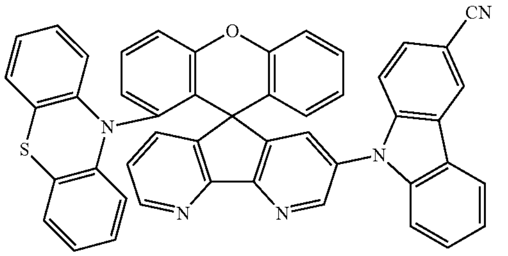
281
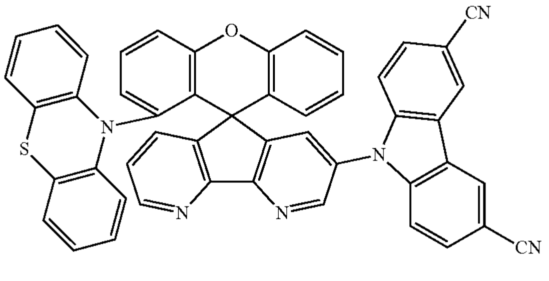
-continued
282
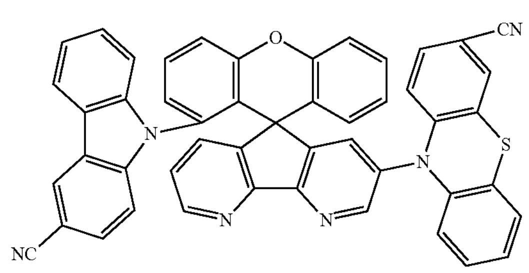
283
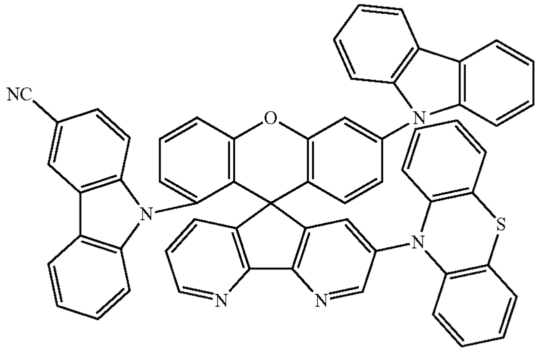
284
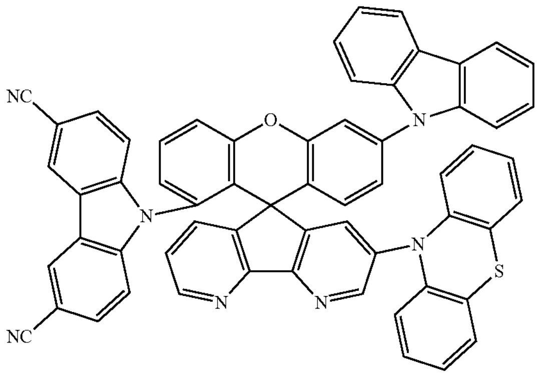
285
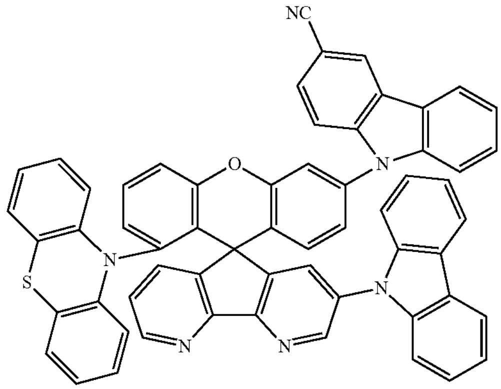

-continued
286
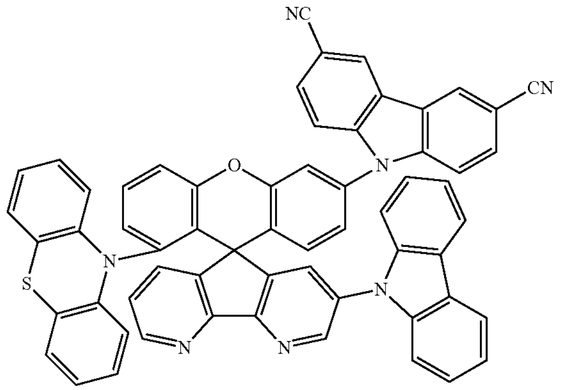
287
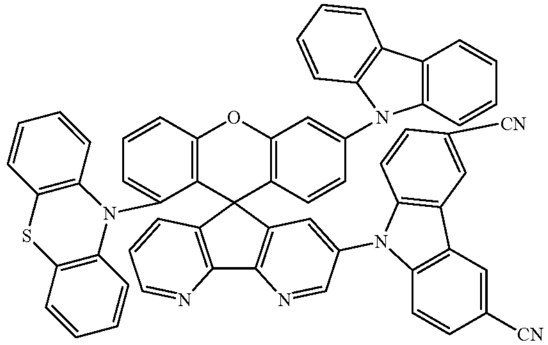
288
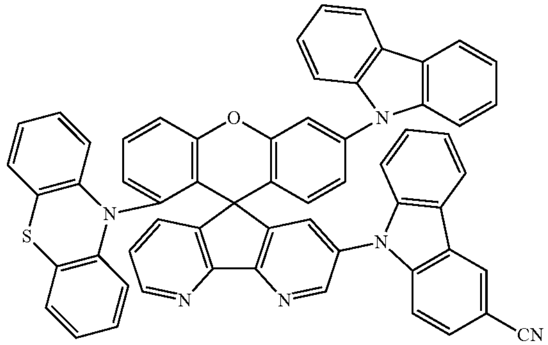
289
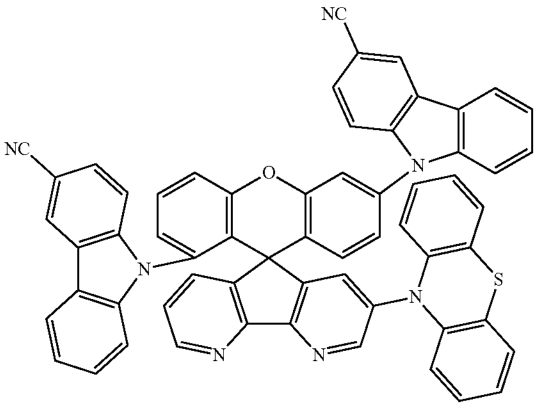
-continued
290
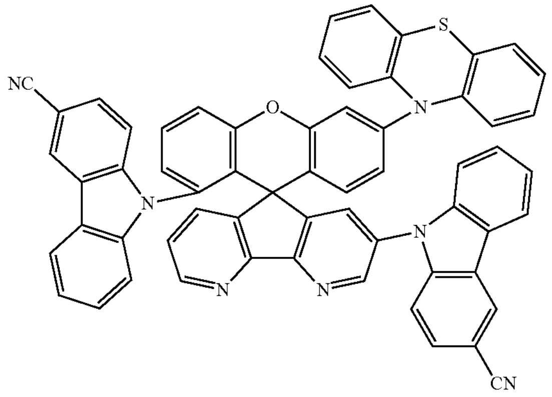
291
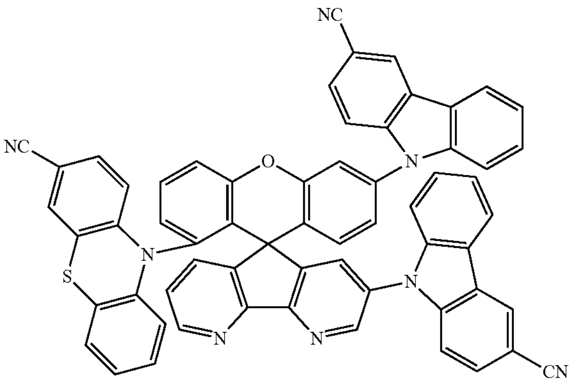
292
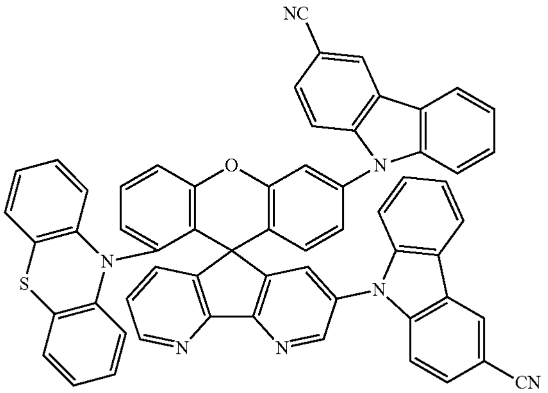
293
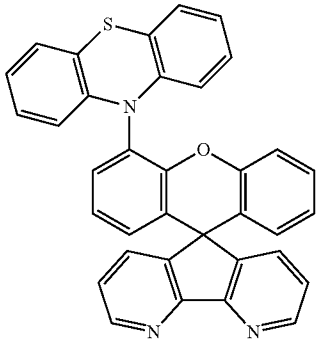

-continued
294
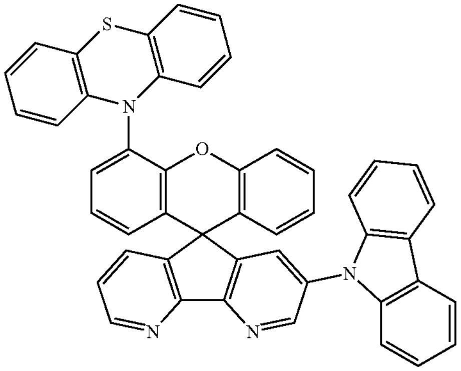
295
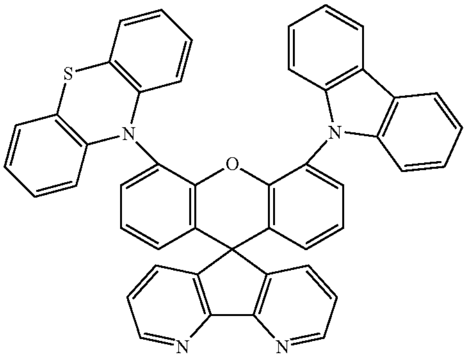
296
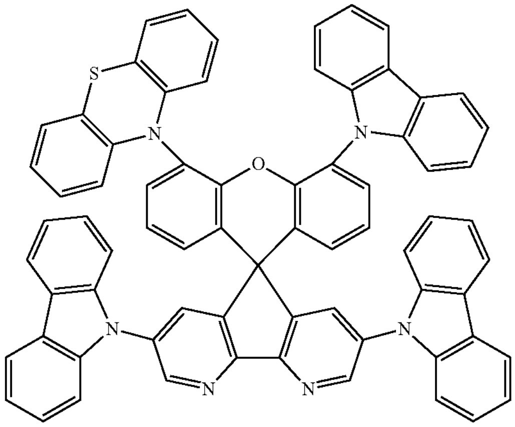
297
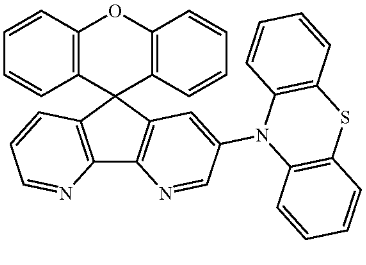
-continued
298
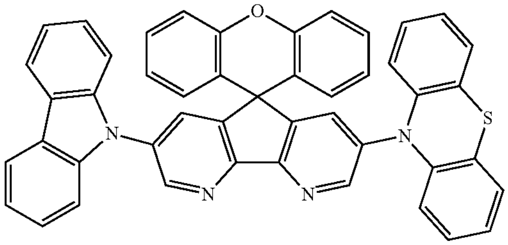
299
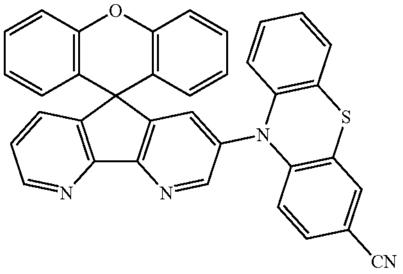
300
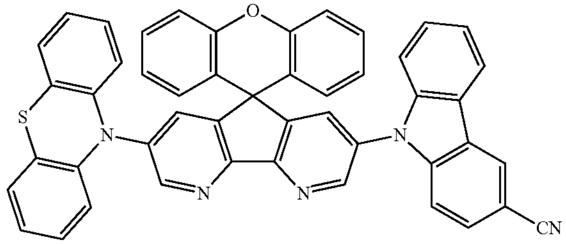
301
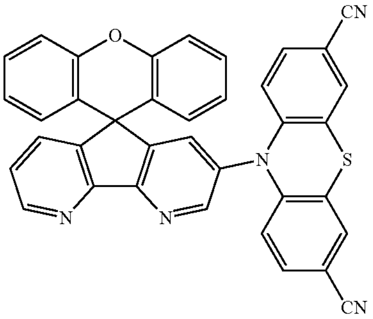
302
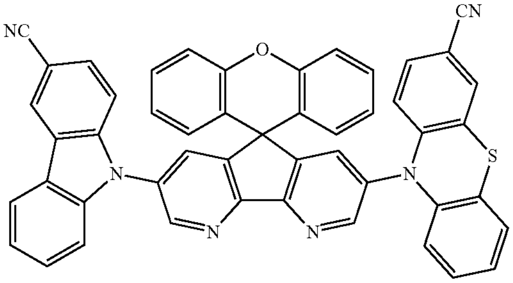

-continued
303
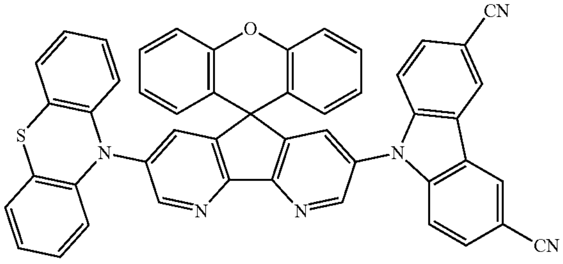
304
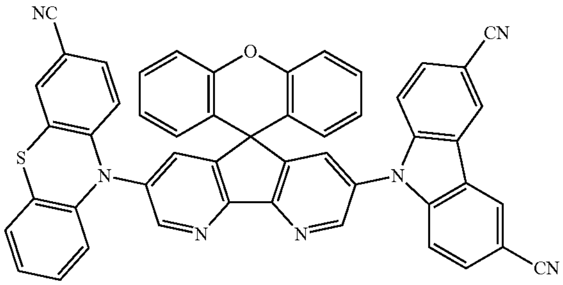
305
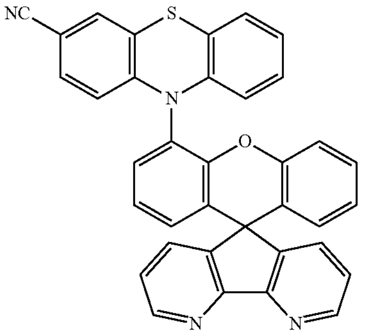
306
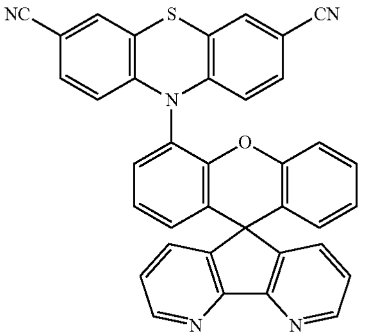
307
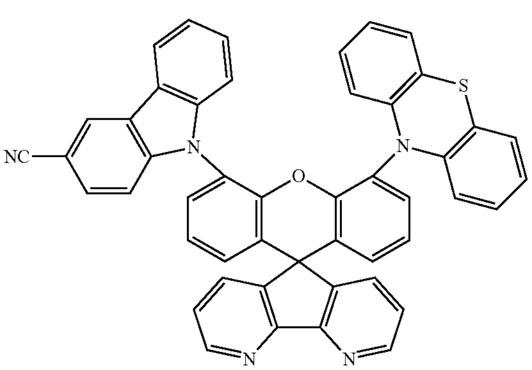
-continued
308
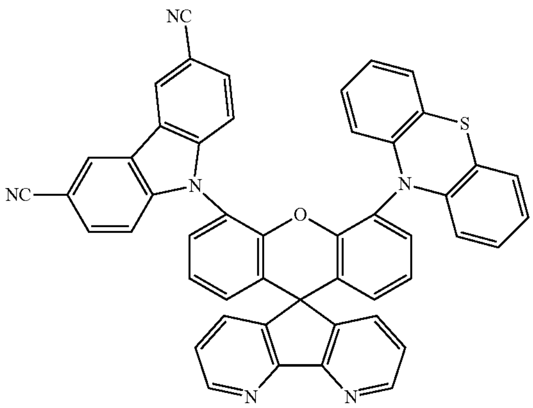
309
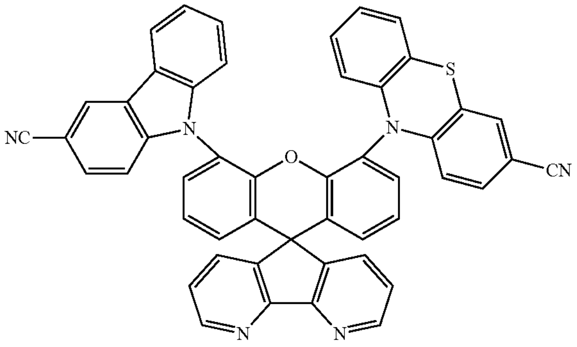
310
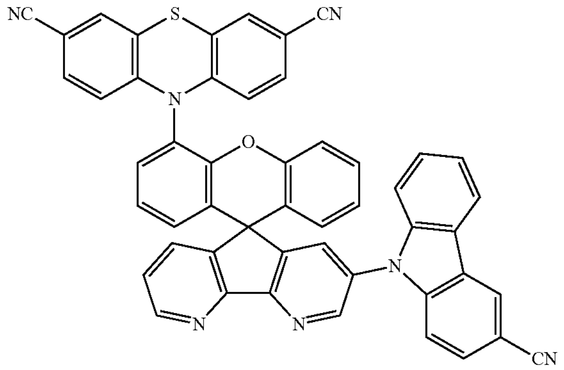
311
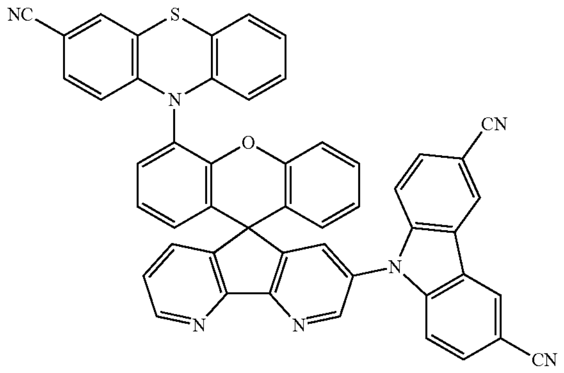

-continued
312
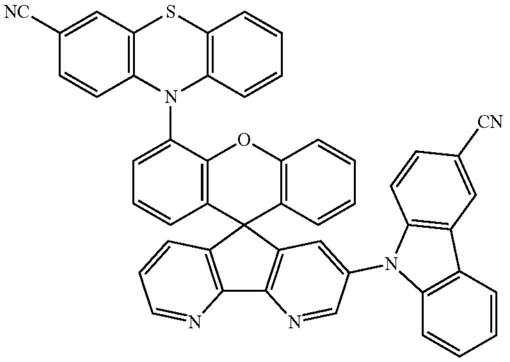
313
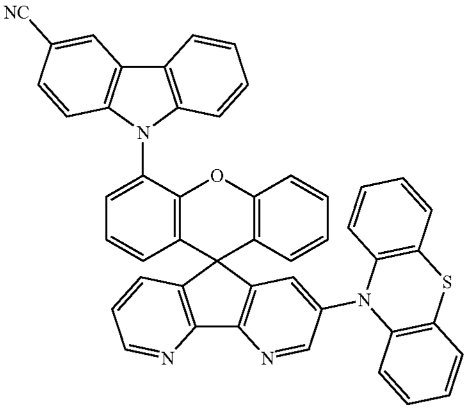
314
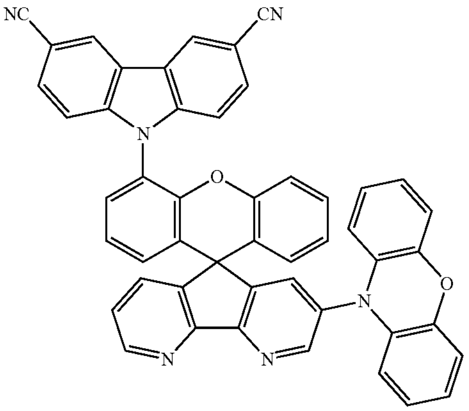
315
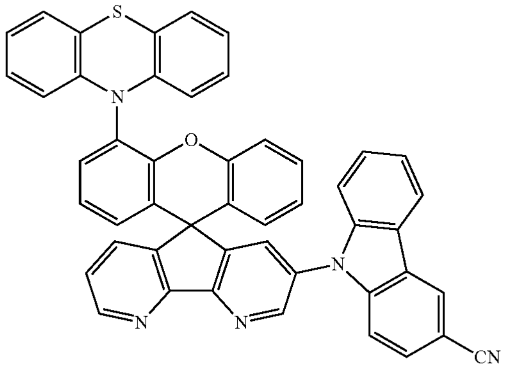
-continued
316
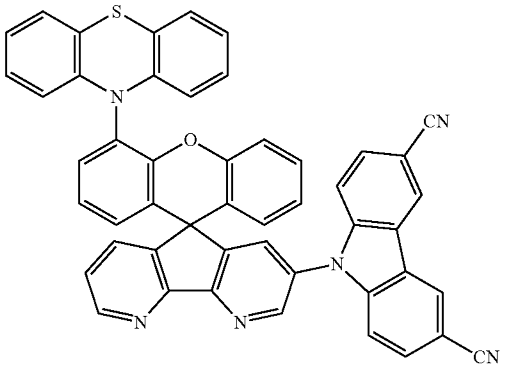
317
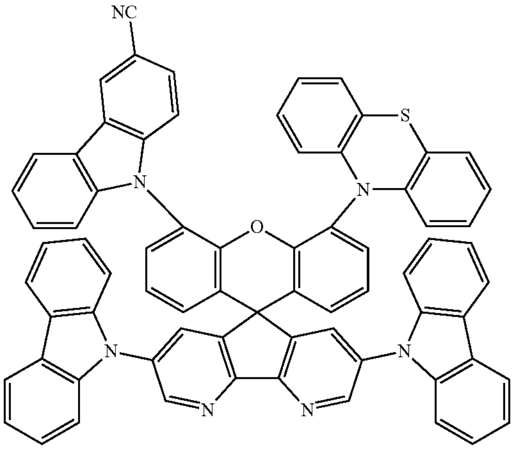
318
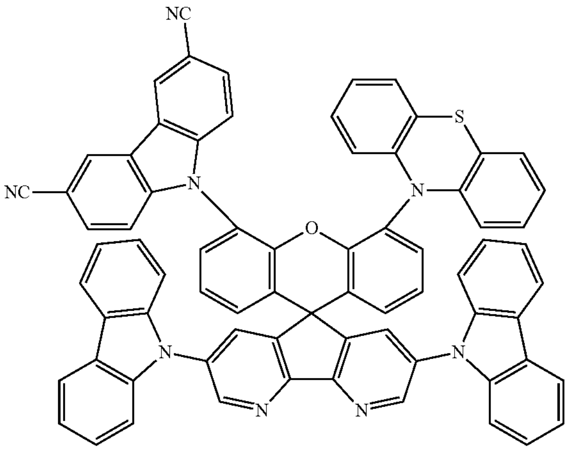

-continued
319
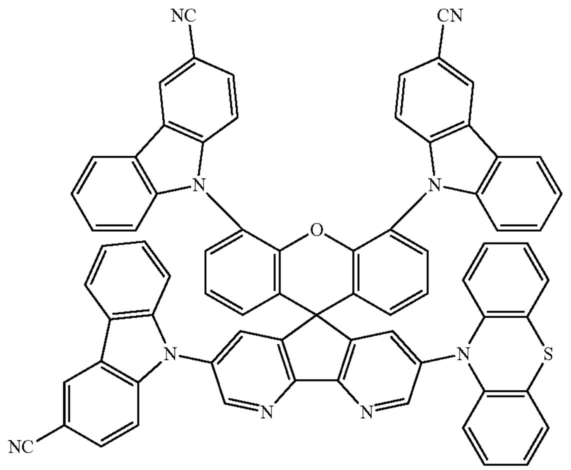
320
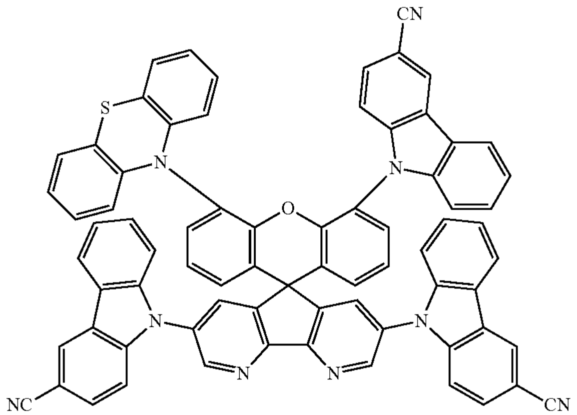
321
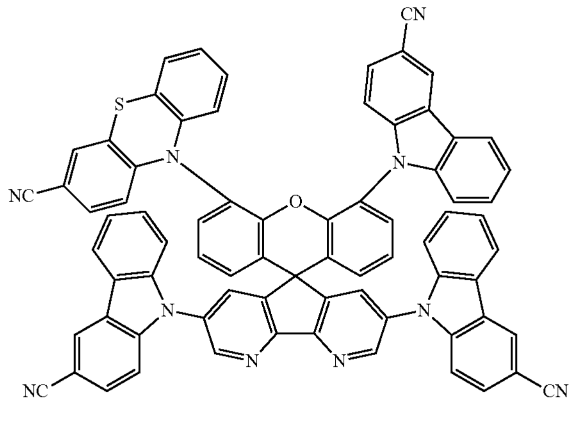
-continued
322
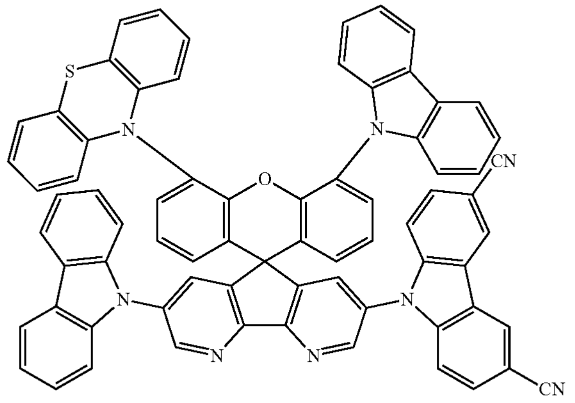
323
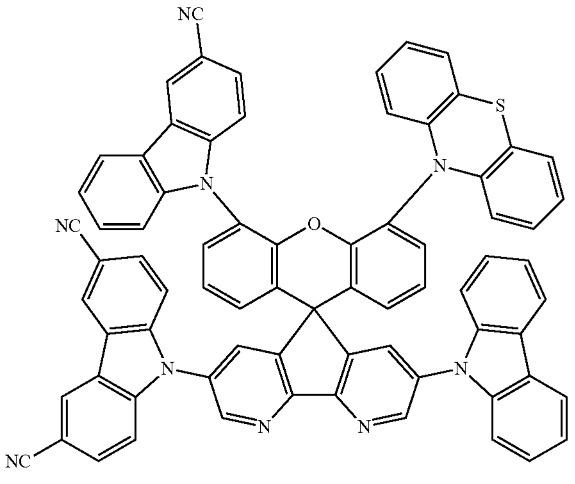
324
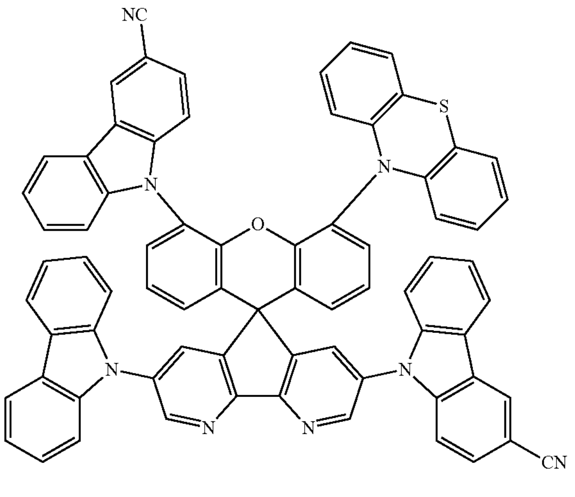

-continued
325
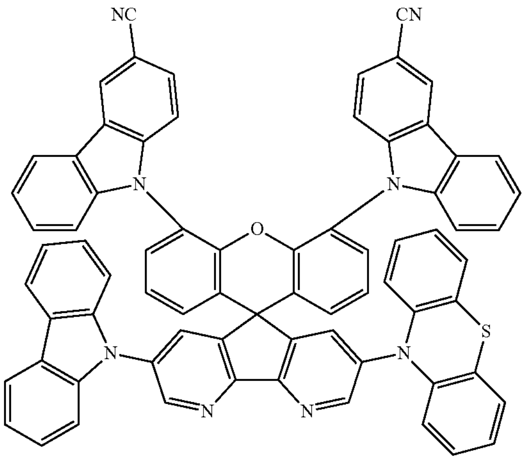
326
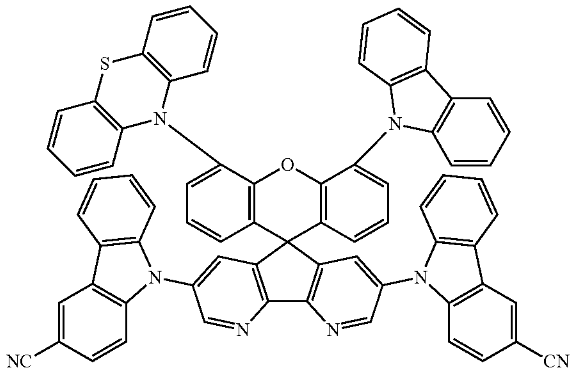
327
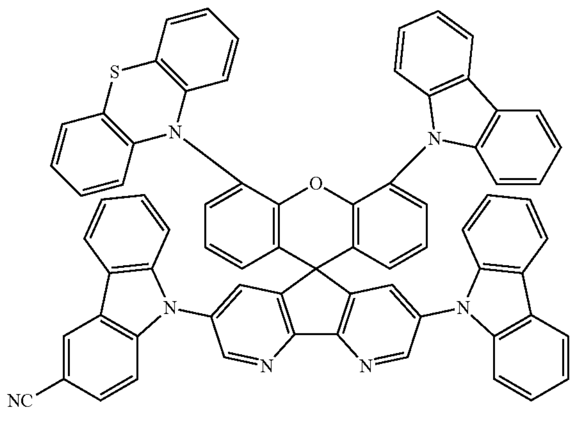
-continued
328
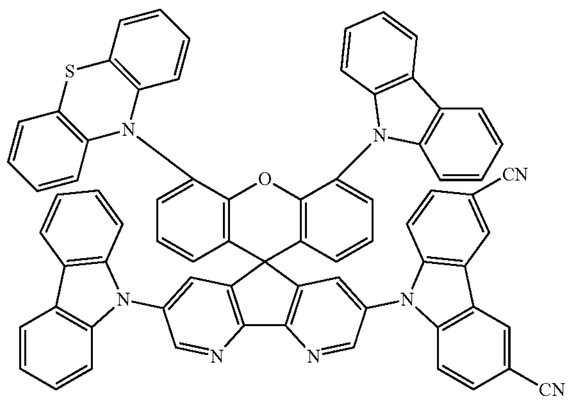
329
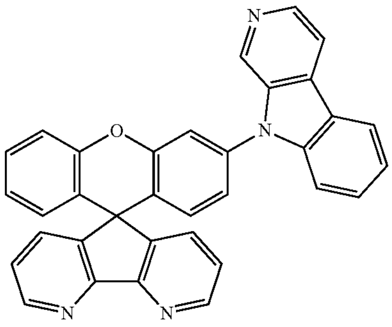
330
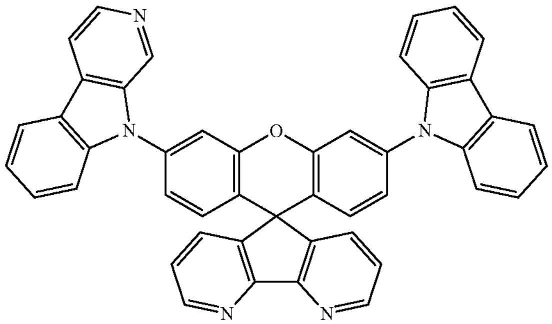
331
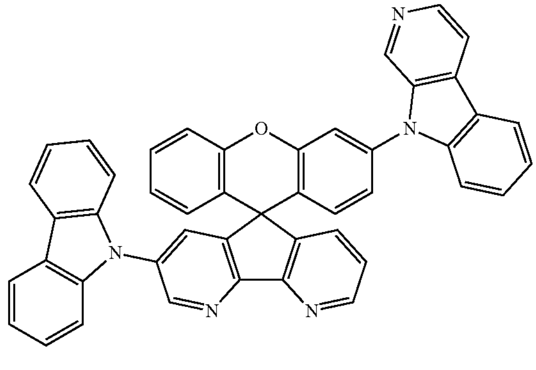

-continued
332
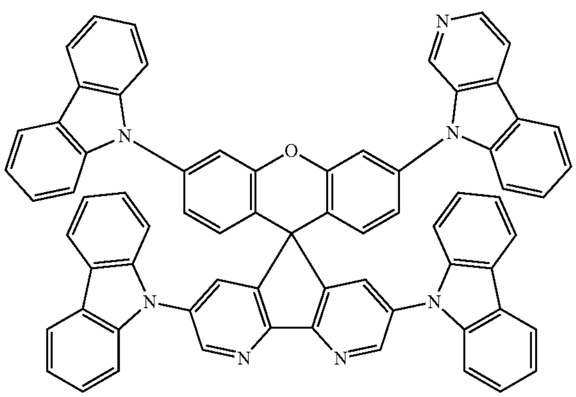
333
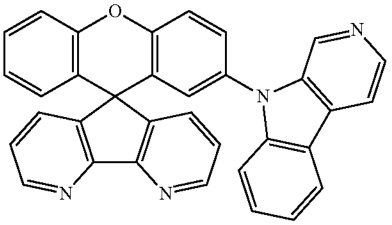
334
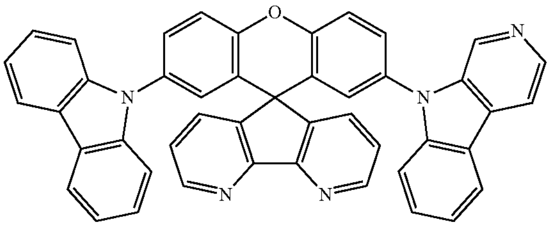
335
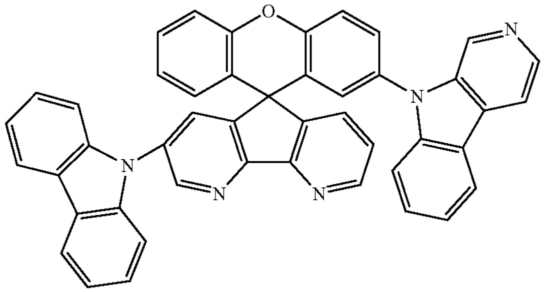
336
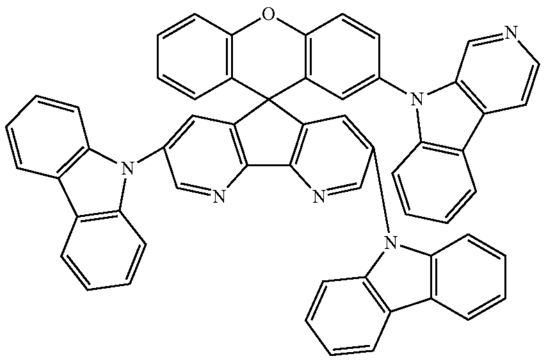
-continued
337
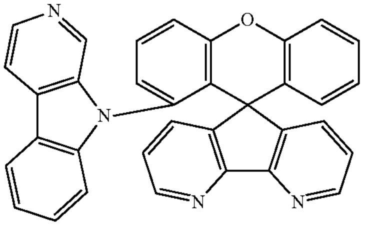
338
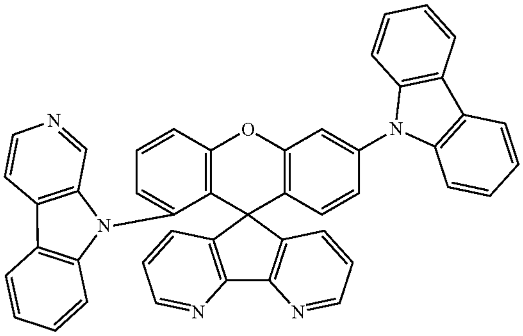
339
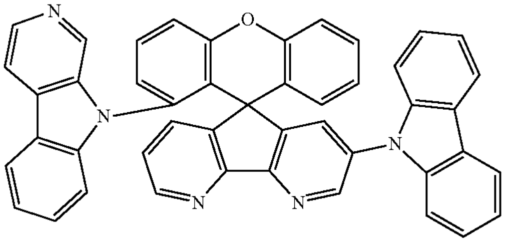
340
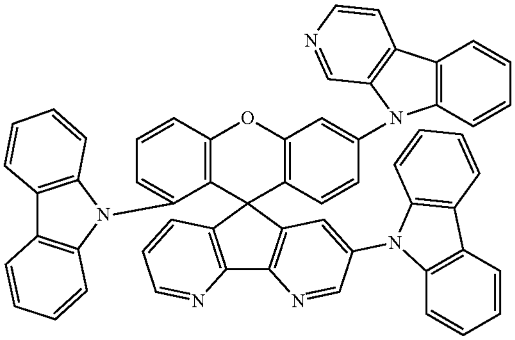
341
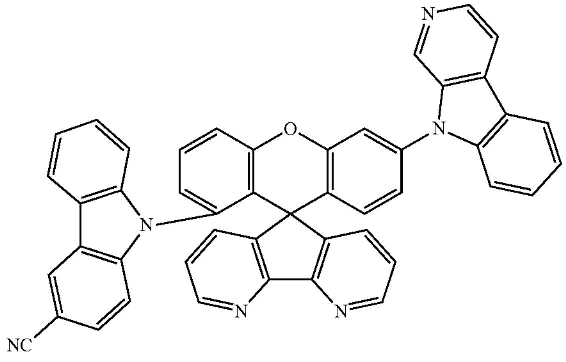

-continued
342
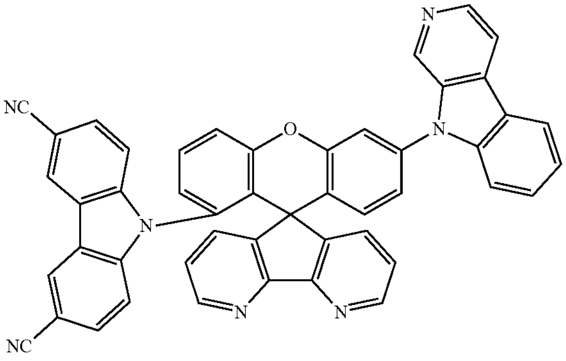
343
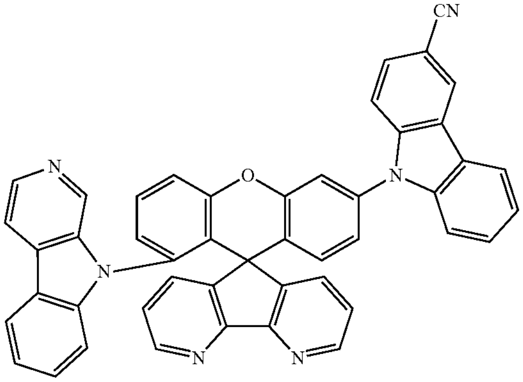
344
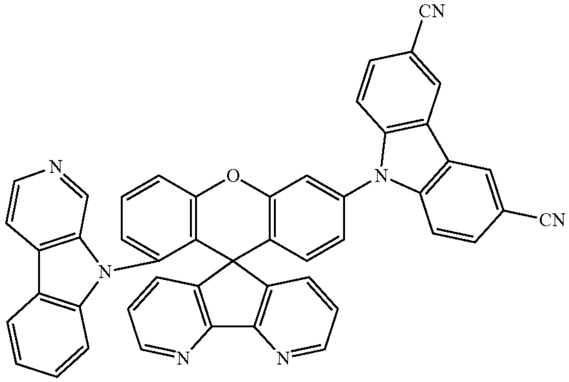
345
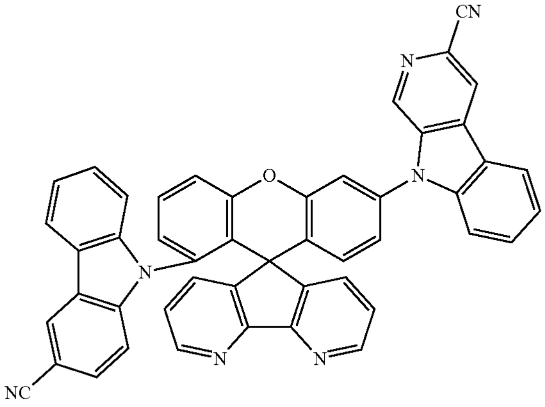
-continued
346
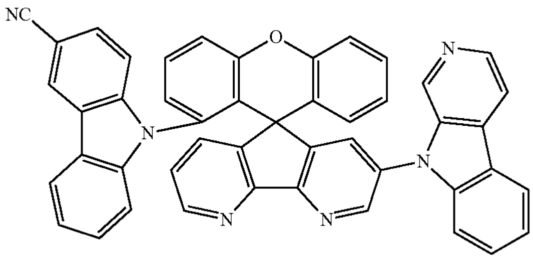
347
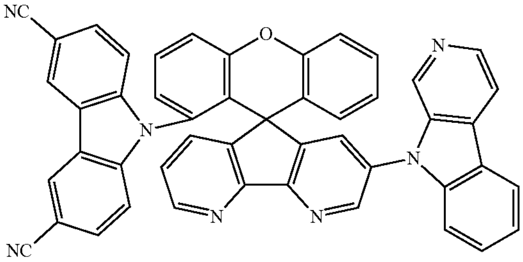
348
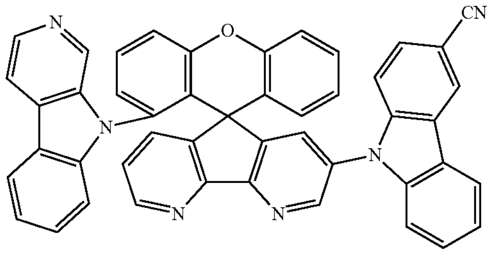
349
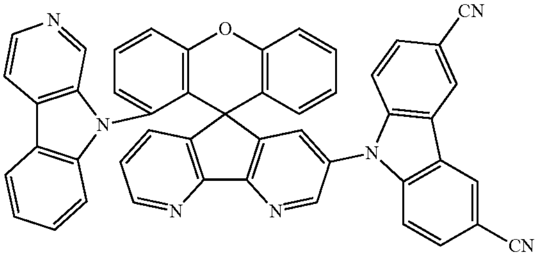
350
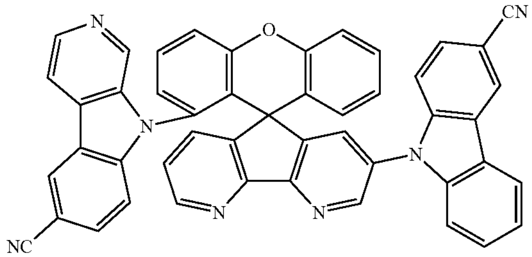

-continued
351
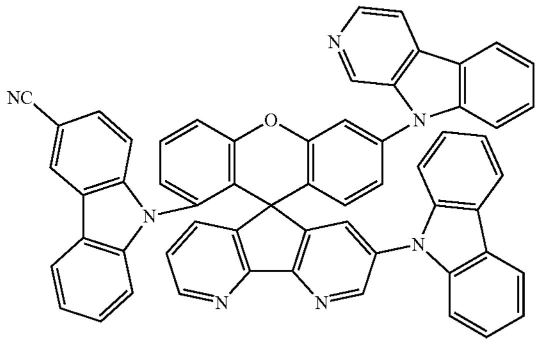
352
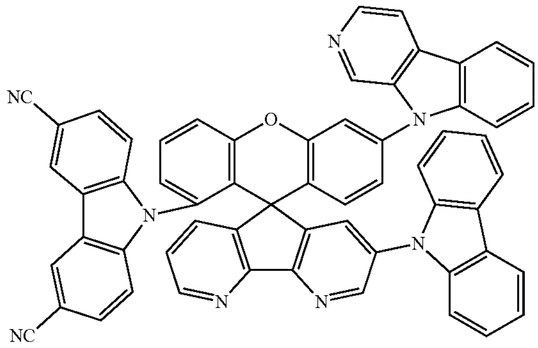
353
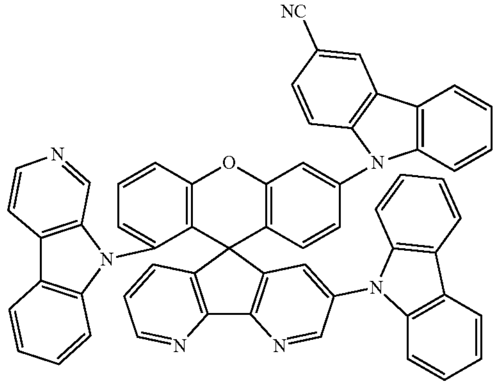
354
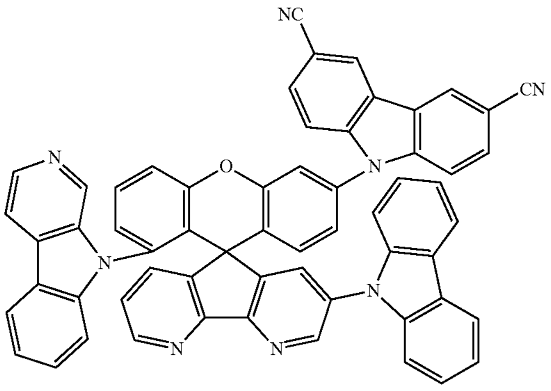
-continued
355
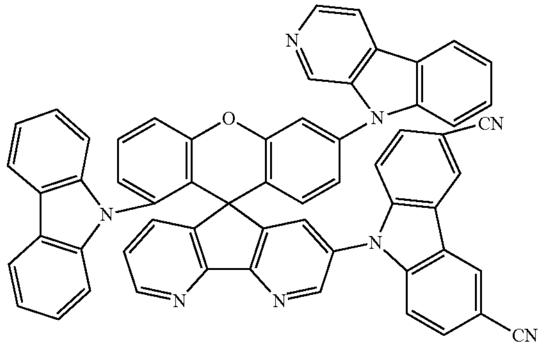
356
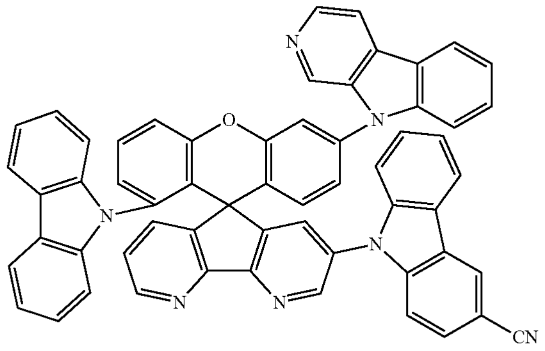
357
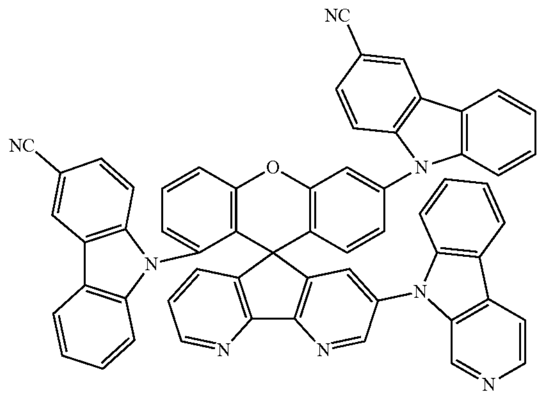
358
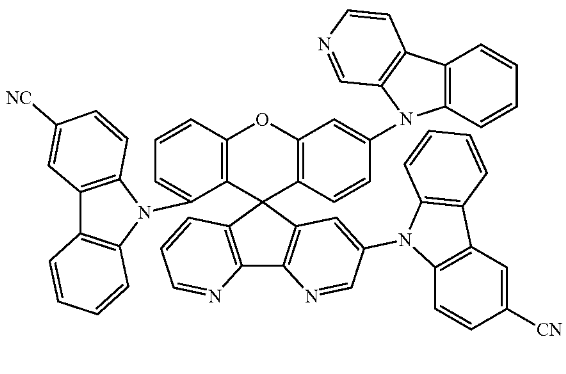

-continued
359
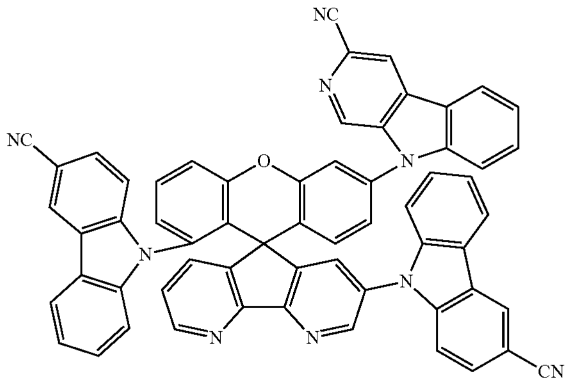
360
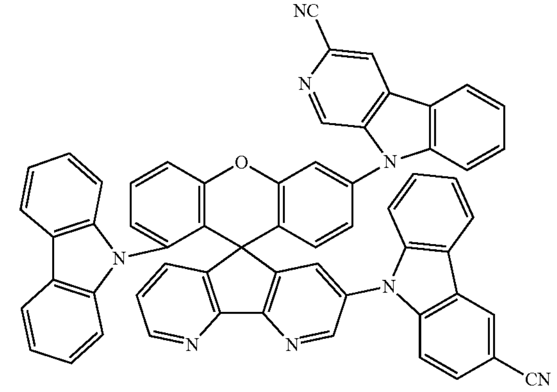
361
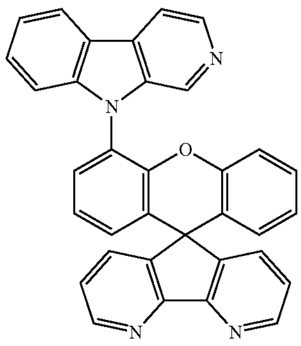
362
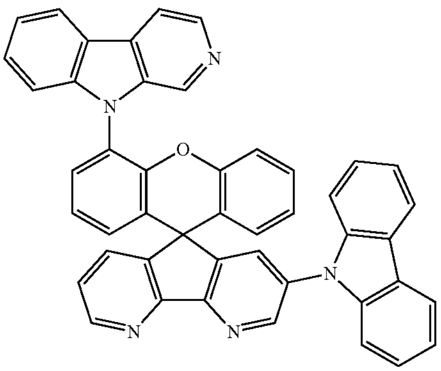
-continued
363
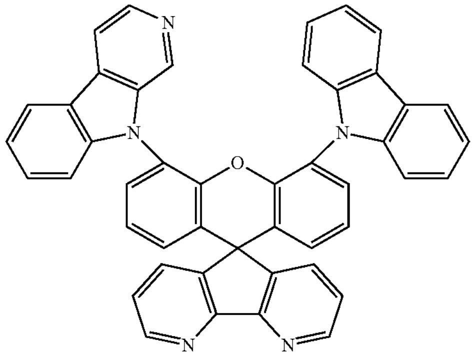
364
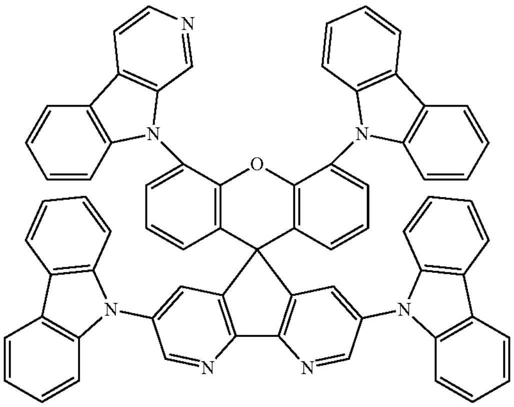
365
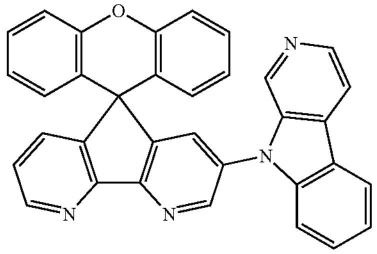
366
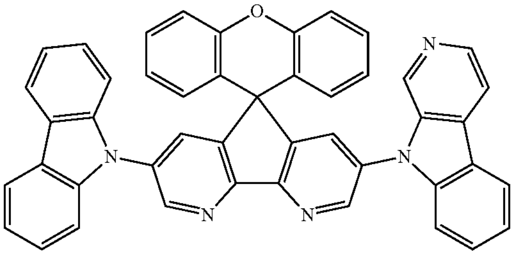
367
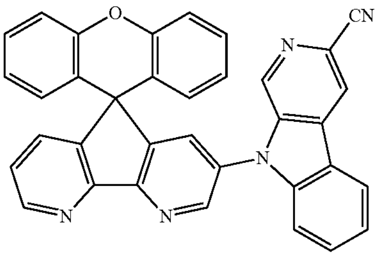

-continued
368
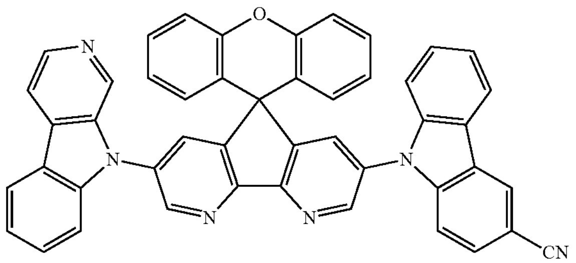
369
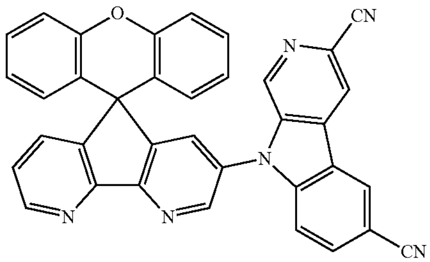
370
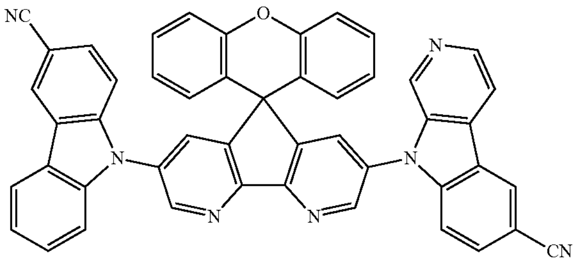
371
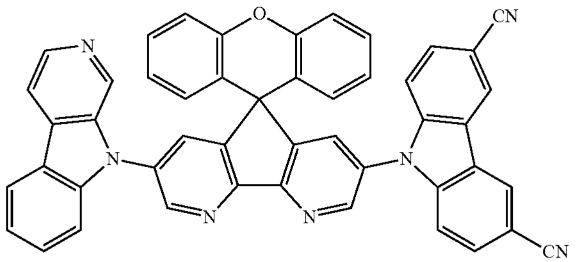
372
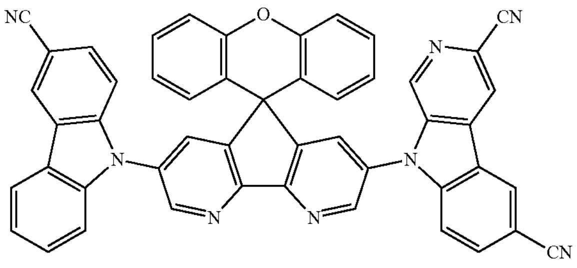
-continued
373
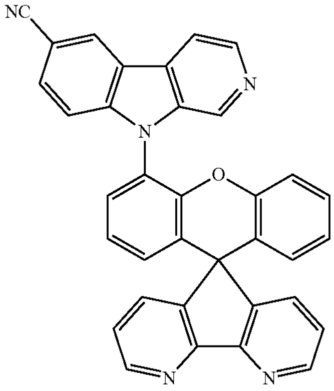
374
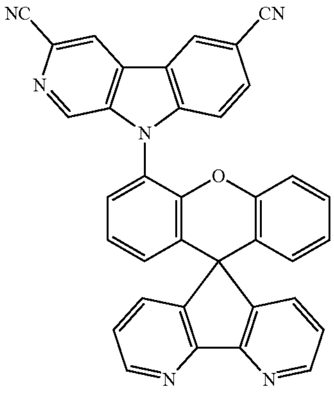
375
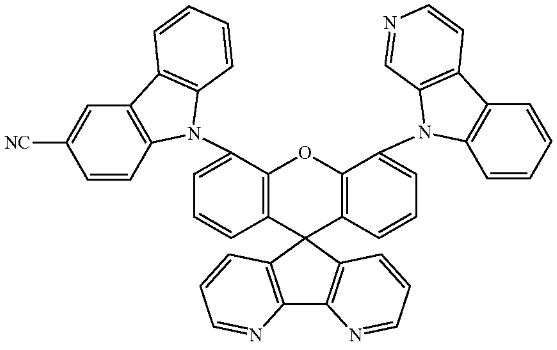
376
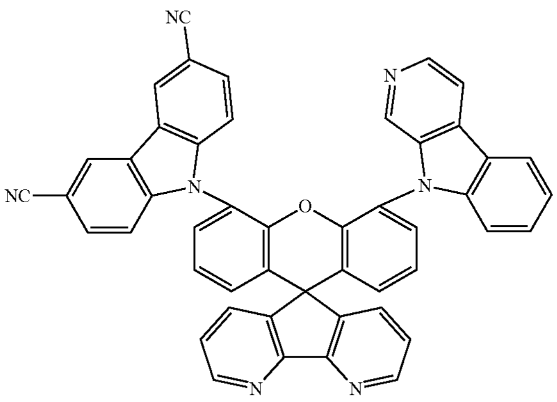

-continued
377
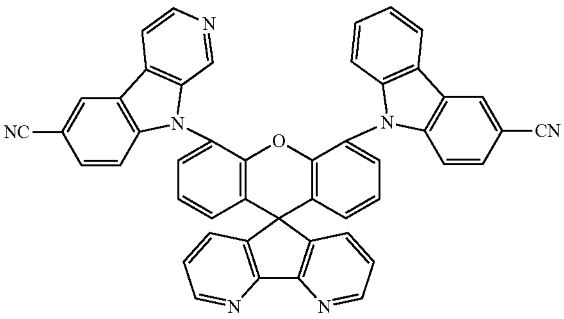
378
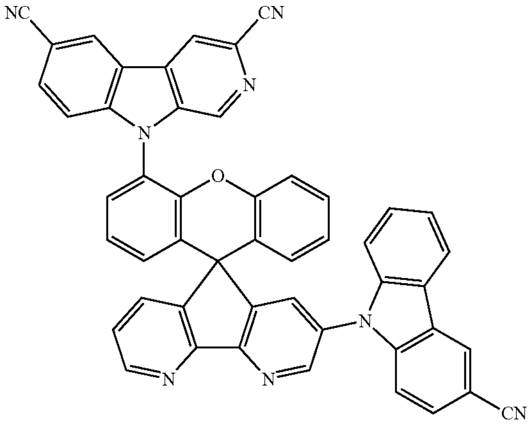
379
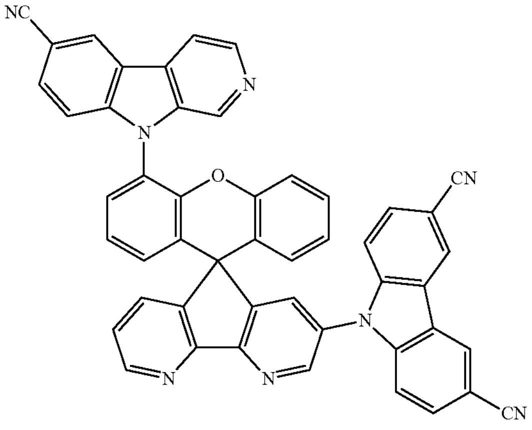
380
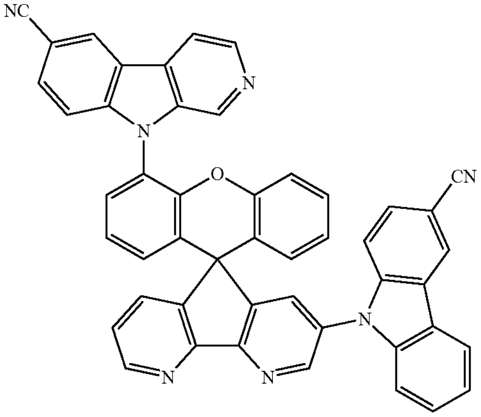
-continued
381
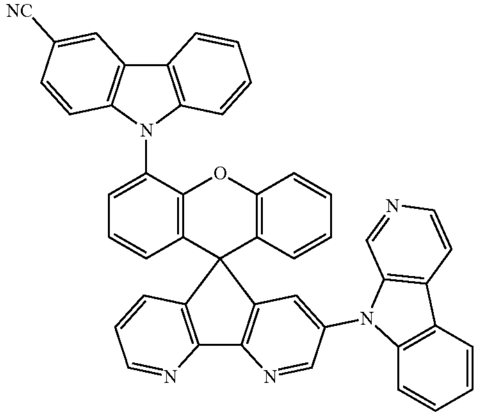
382
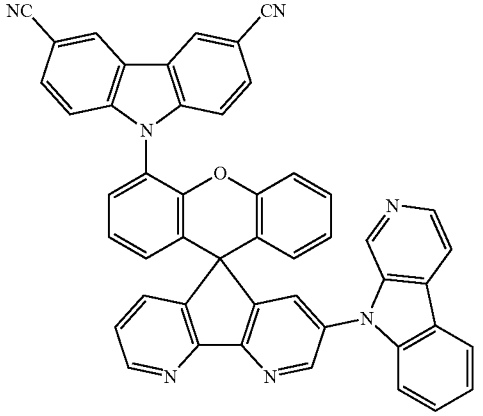
383
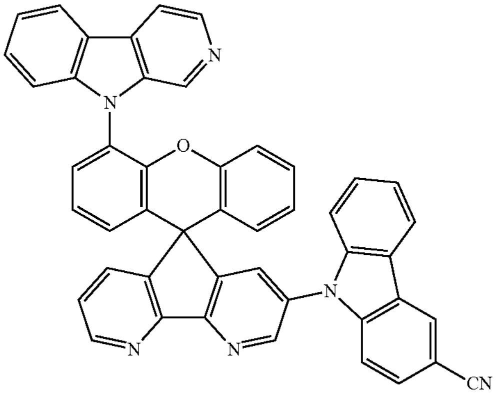
384
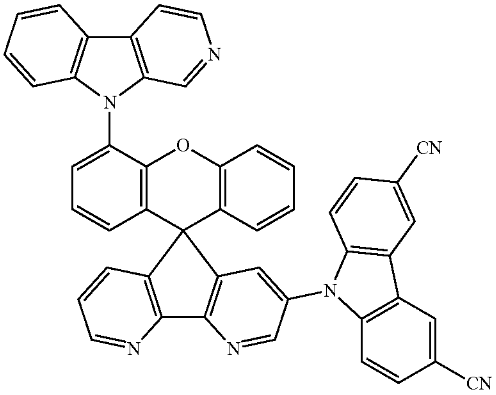

-continued
385
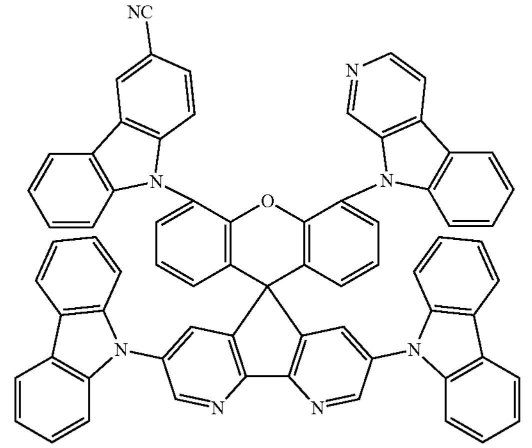
386
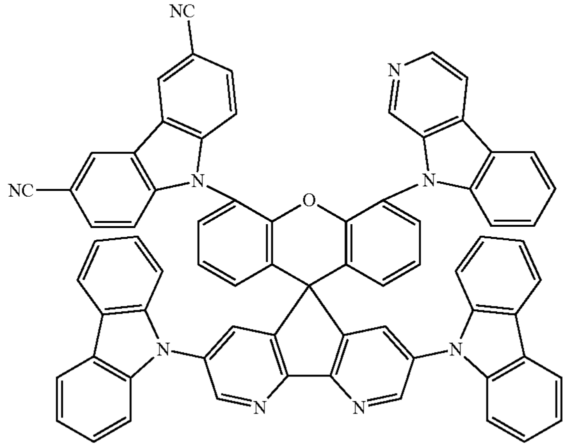
387
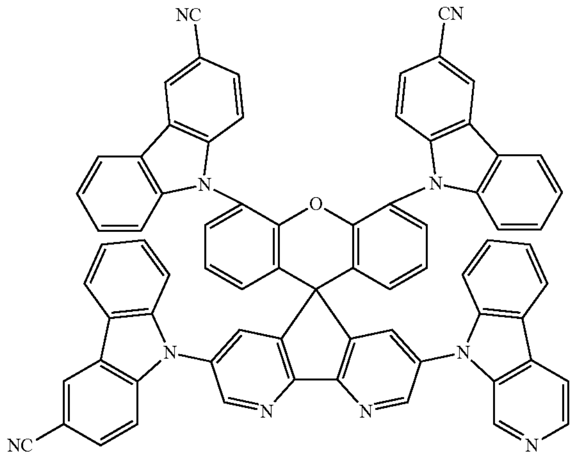
-continued
388
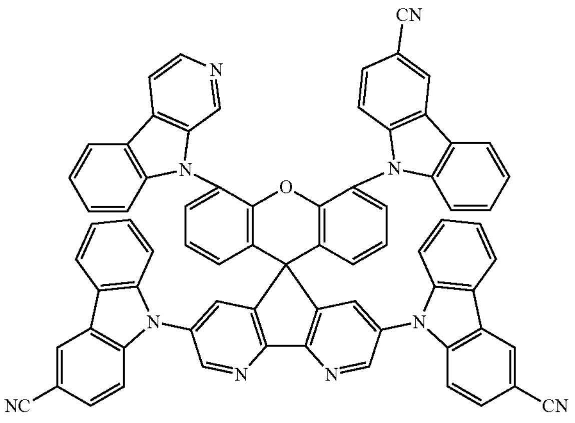
389
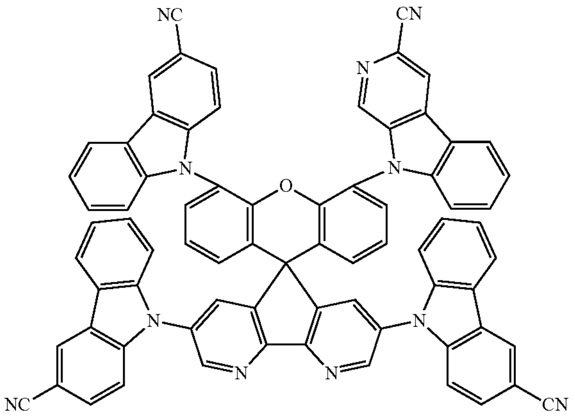
390
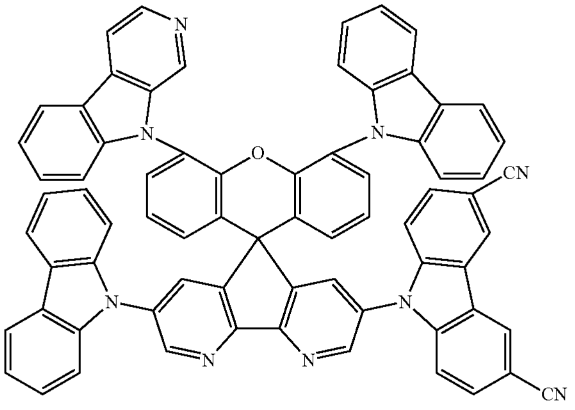

-continued
391
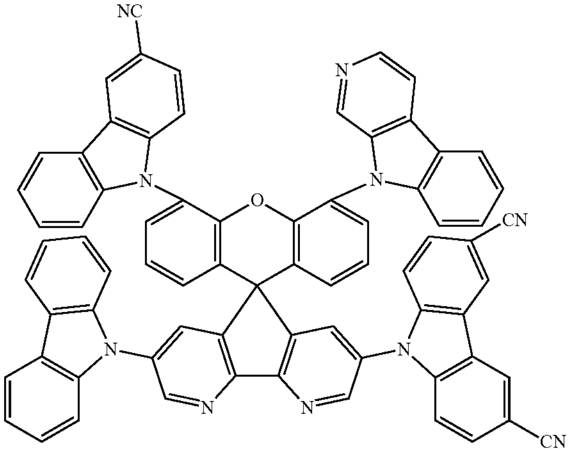
392
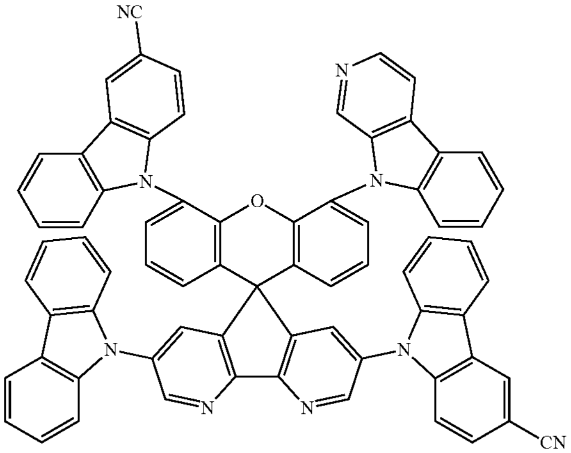
393
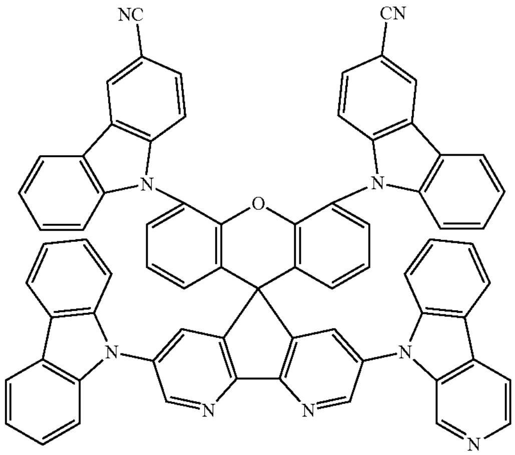
-continued
394
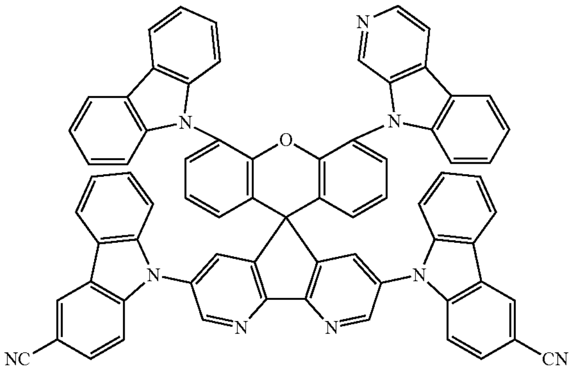
395
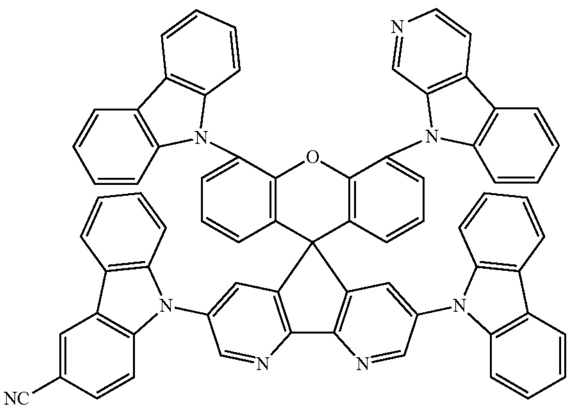
396
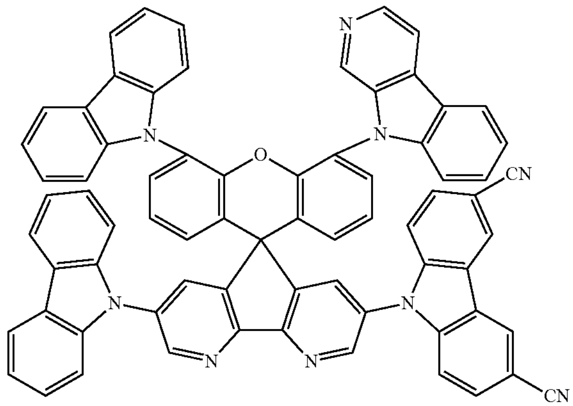
397
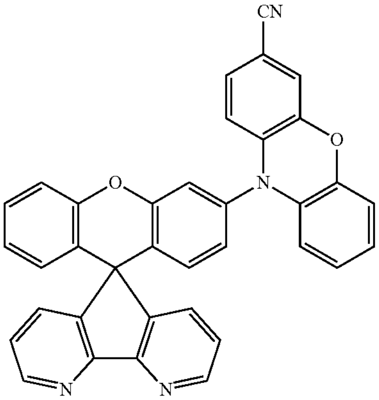

-continued
398
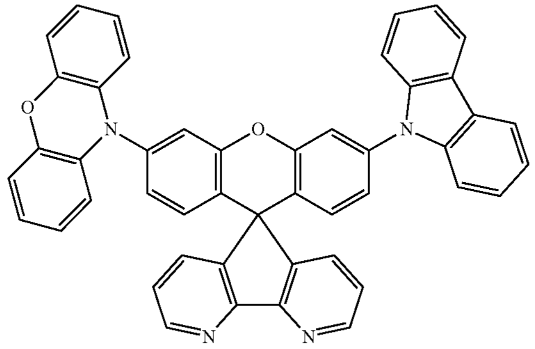
399
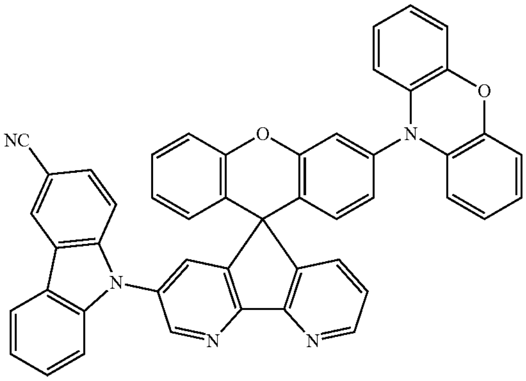
400
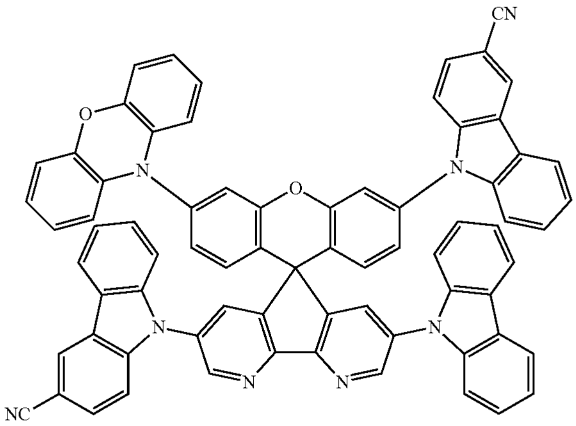
401
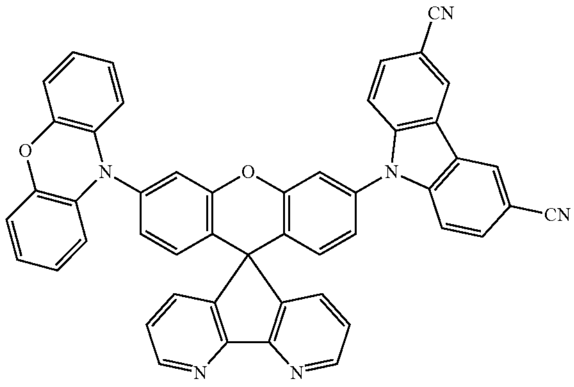
-continued
402
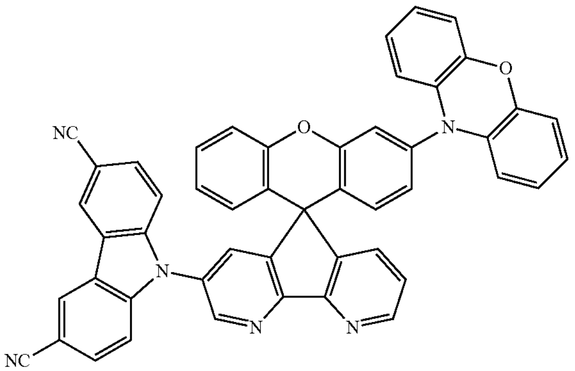
403
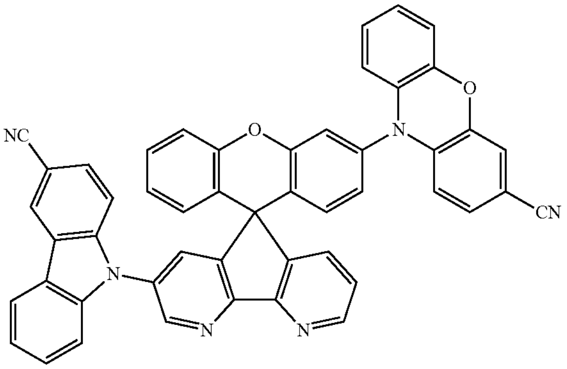
404
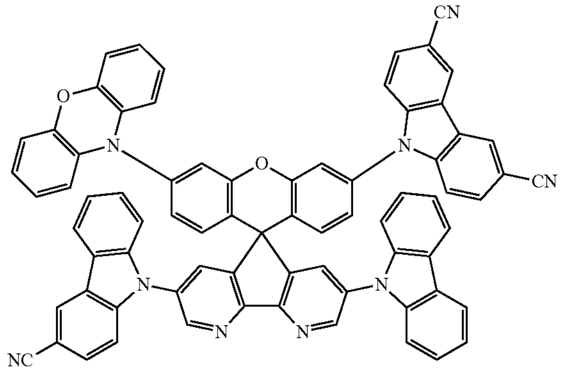
405
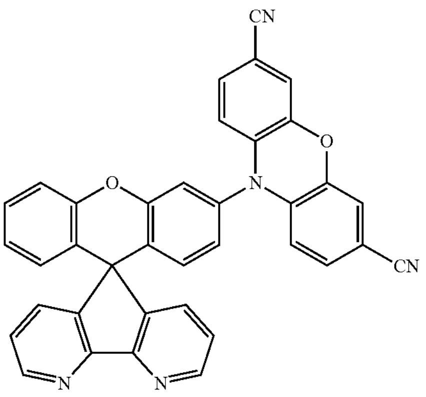

-continued
406
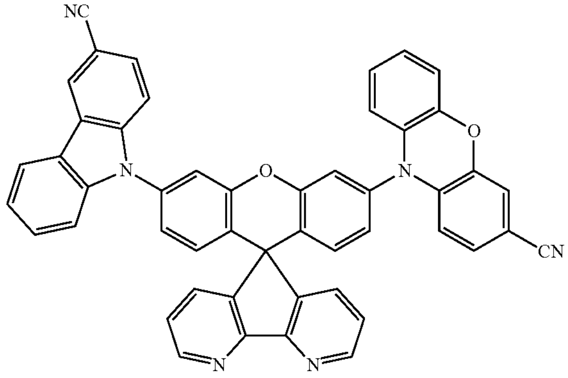
407
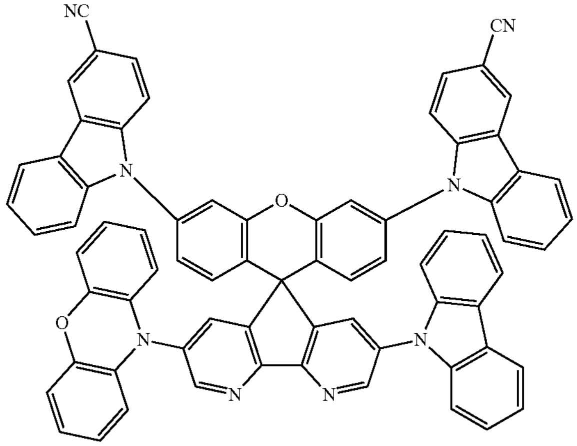
408
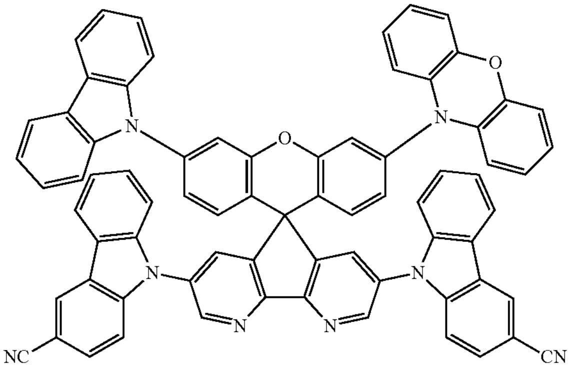
409
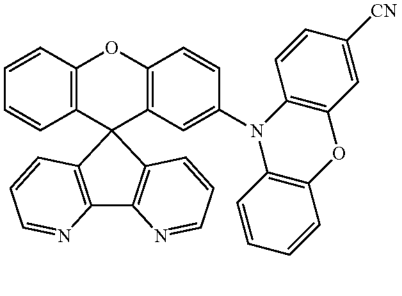
-continued
410
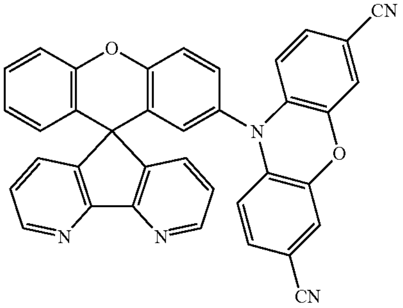
411
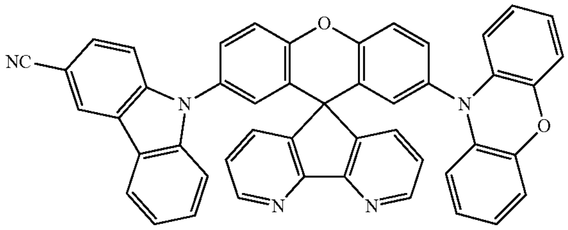
412
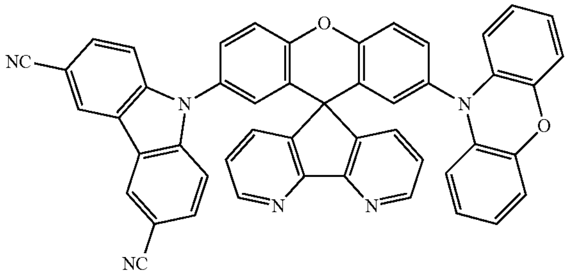
413
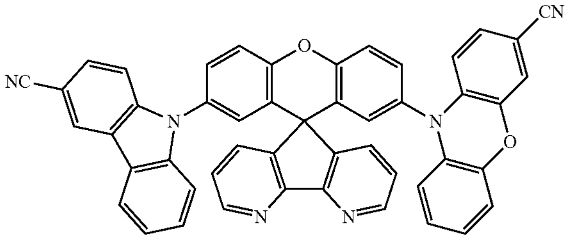
414
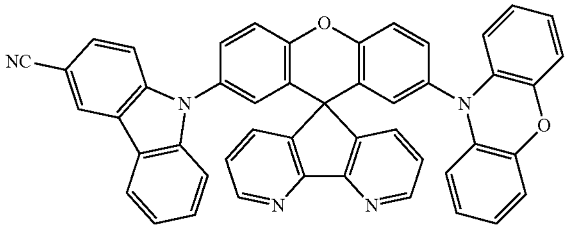

-continued
415
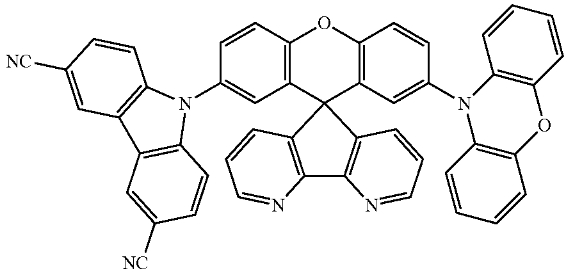
416
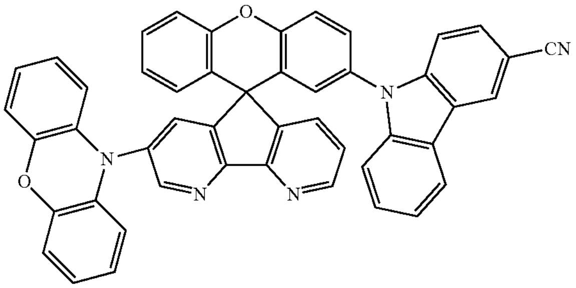
417
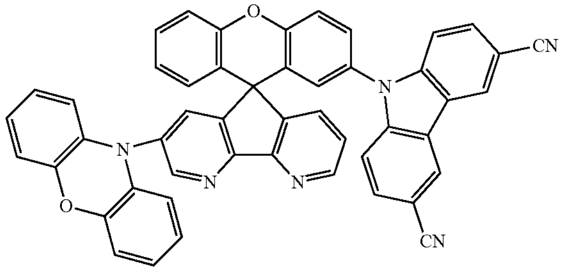
418
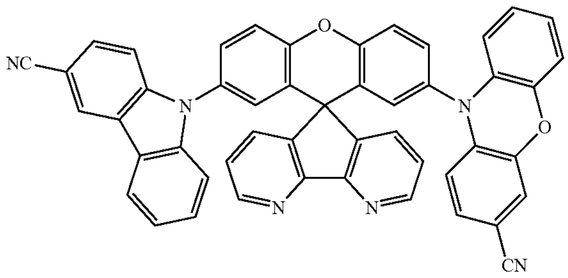
419
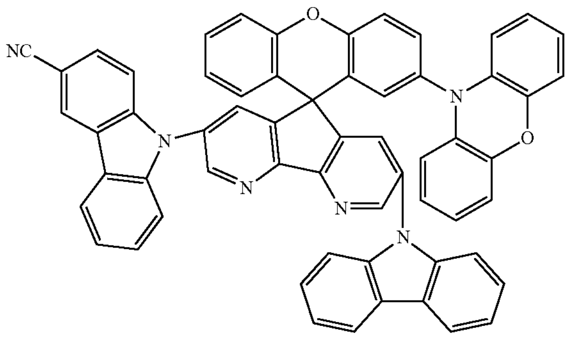
-continued
420
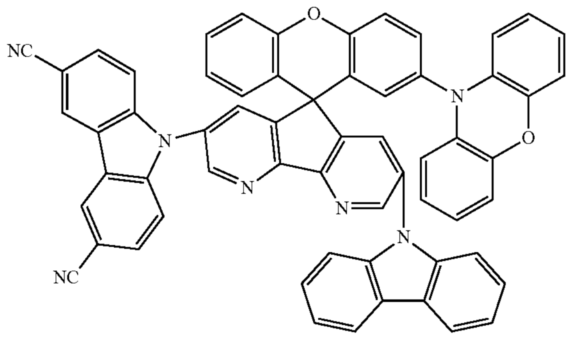
421
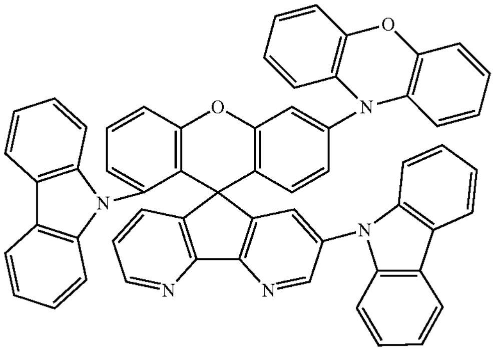
422
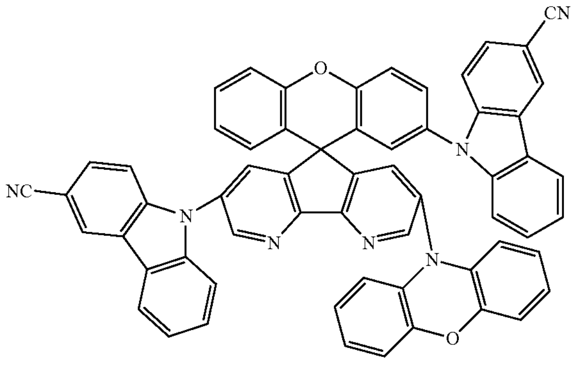
423
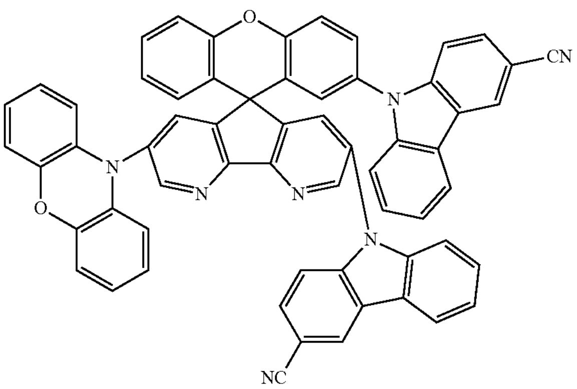

-continued
424
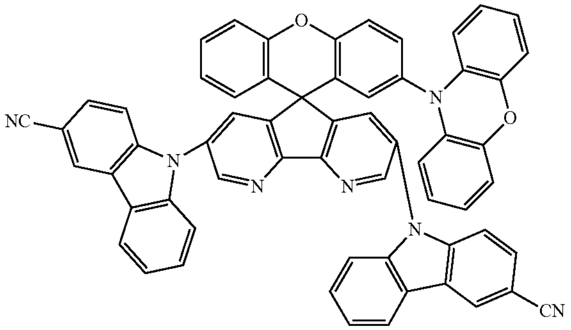
425
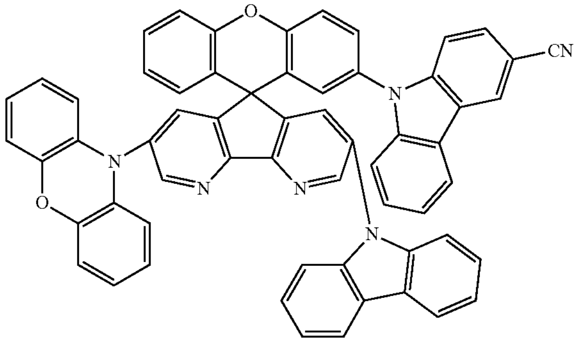
426
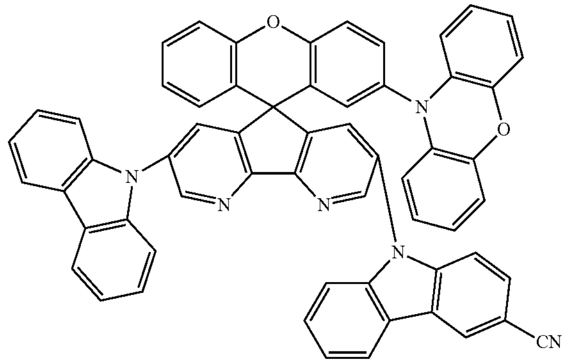
427
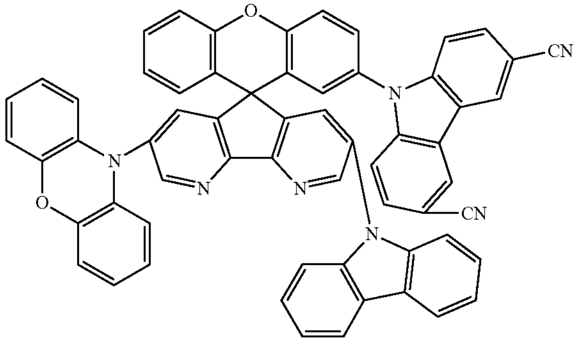
-continued
428
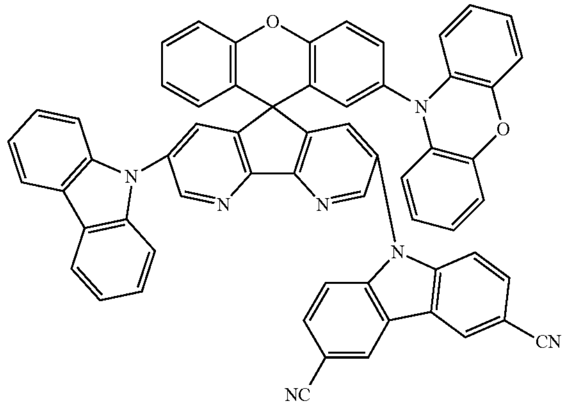
429
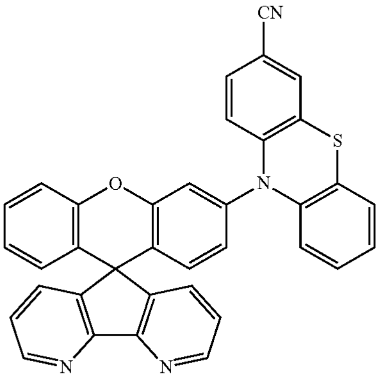
430
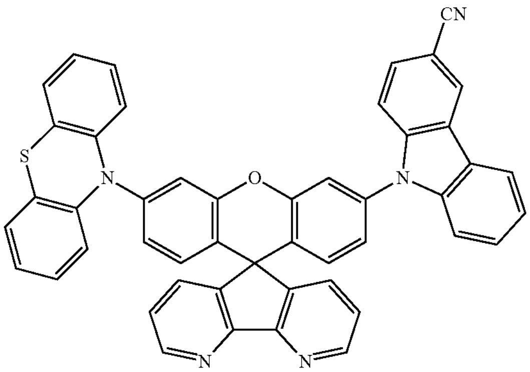
431
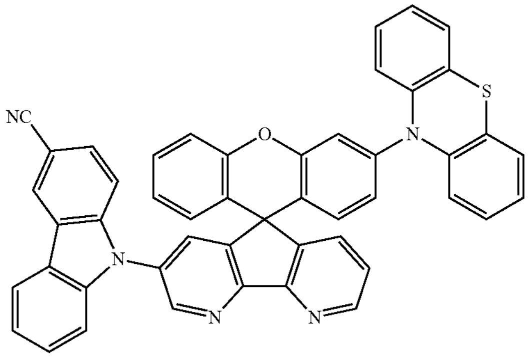

-continued
432
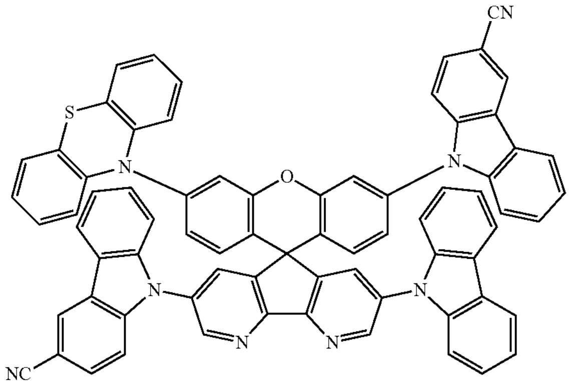
433
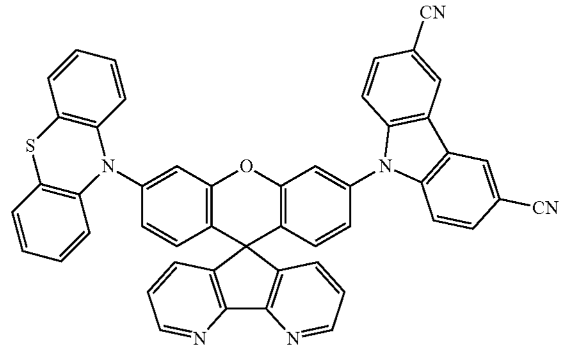
434
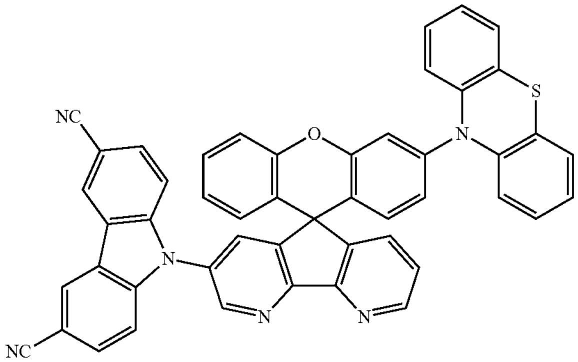
-continued
435
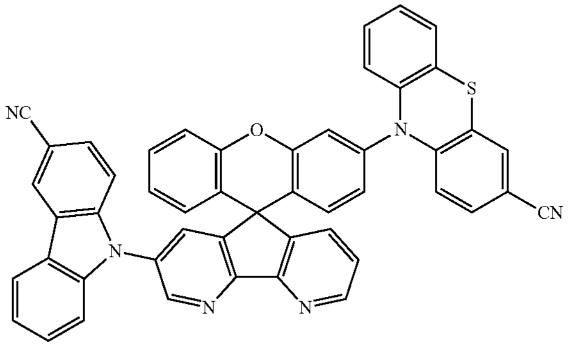
436
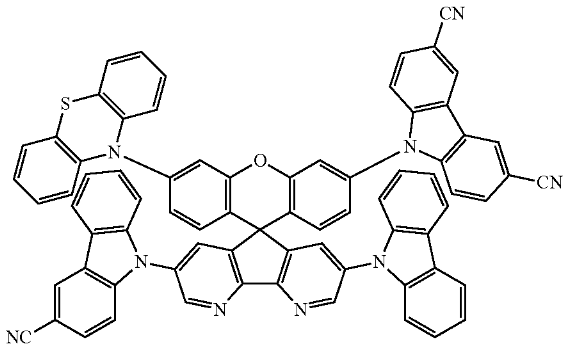
437
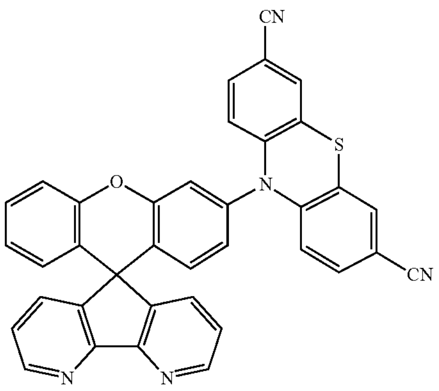
438
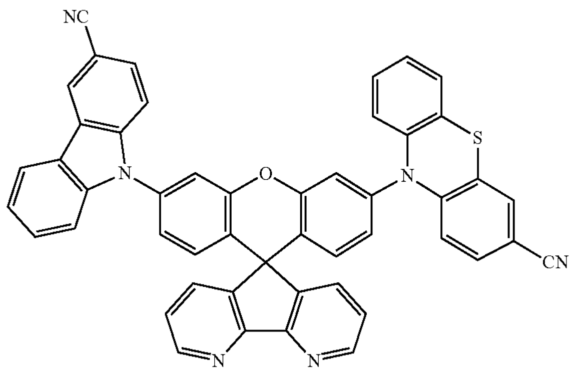

-continued
439
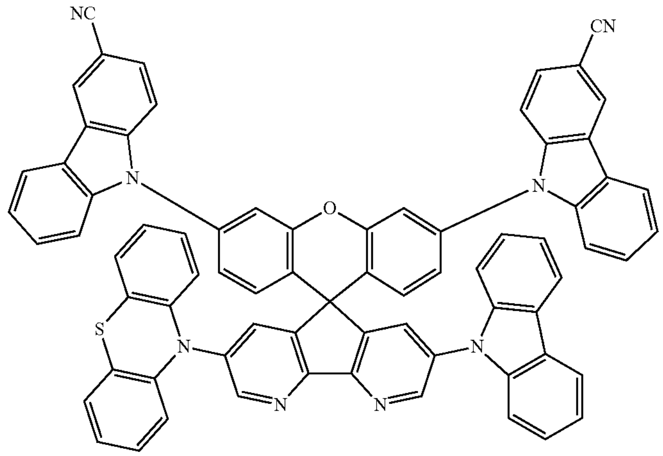
440
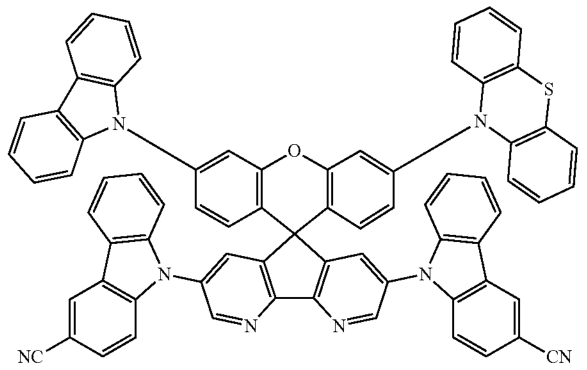
441
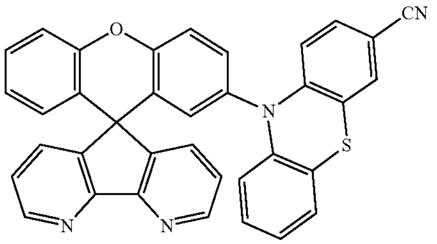
442
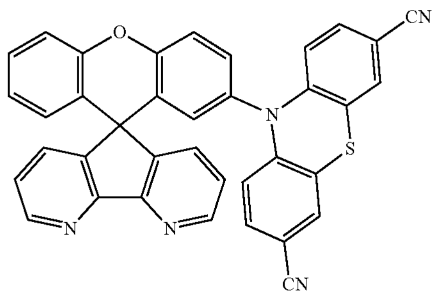
443
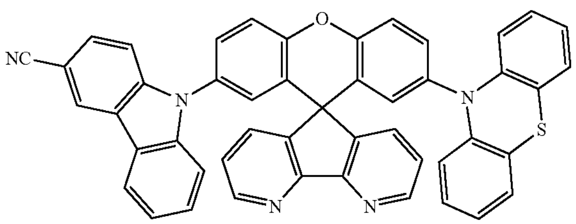
444
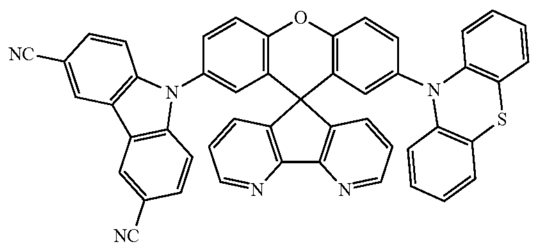
445
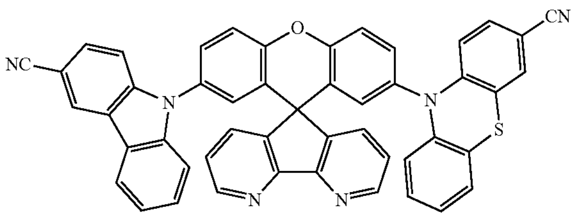

-continued
446
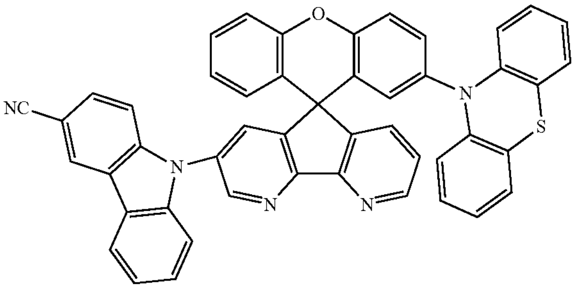
447
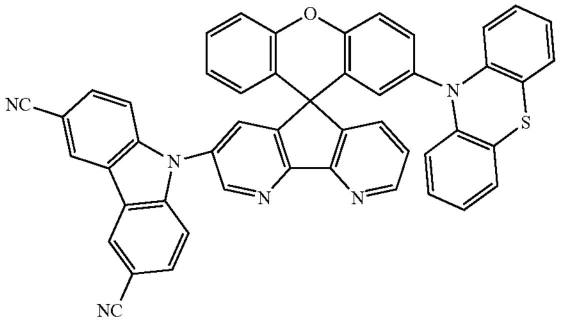
448
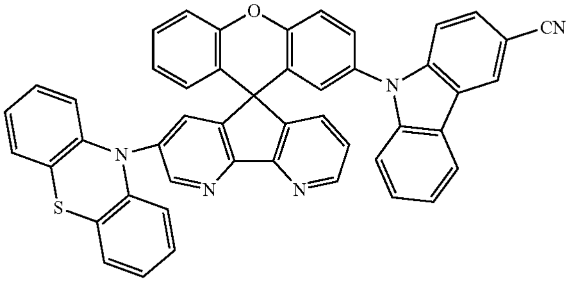
449
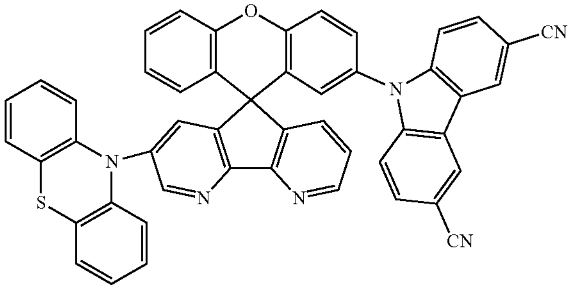
450
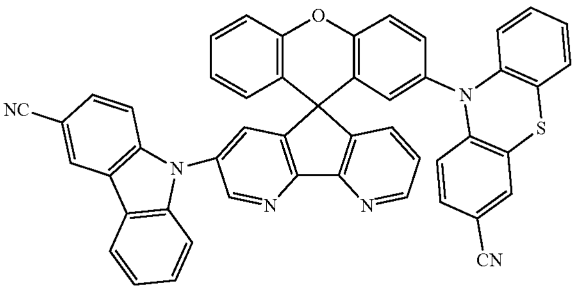
451
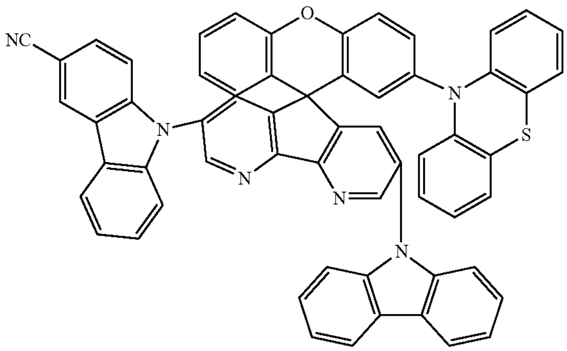
452
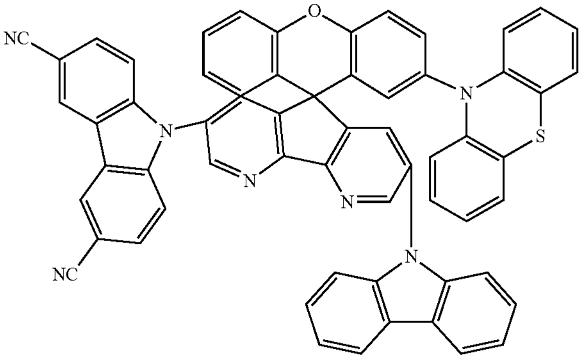

-continued
453
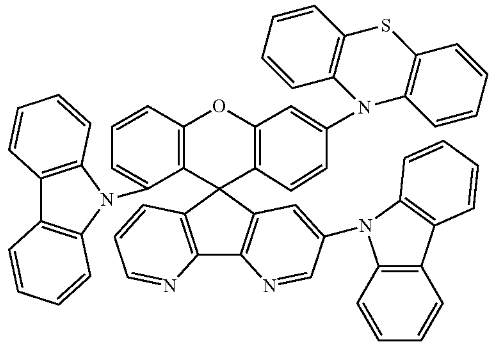
454
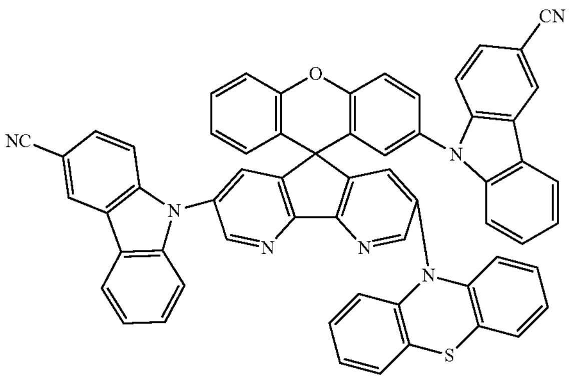
455
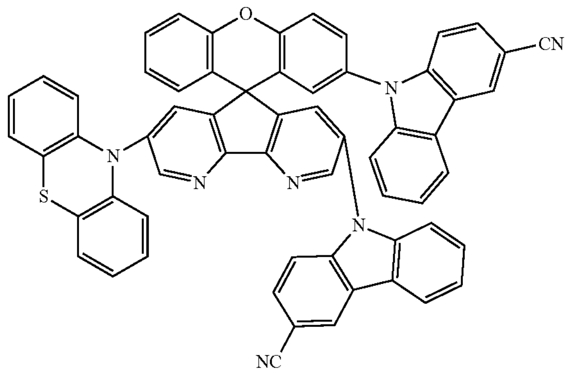
456
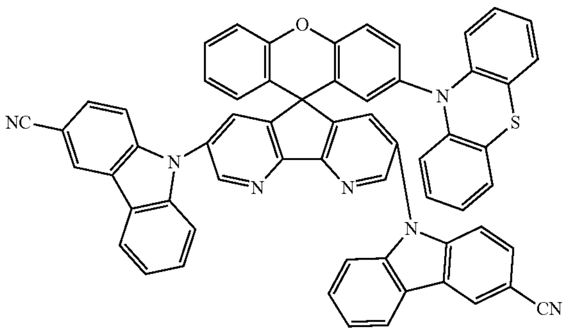
457
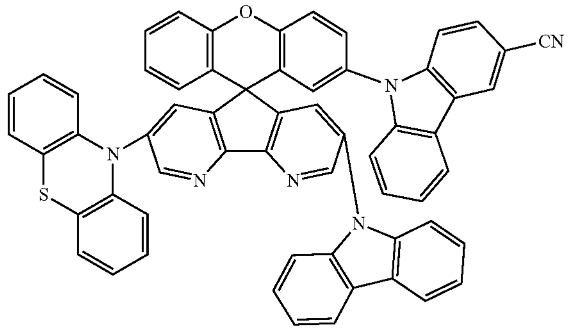
458
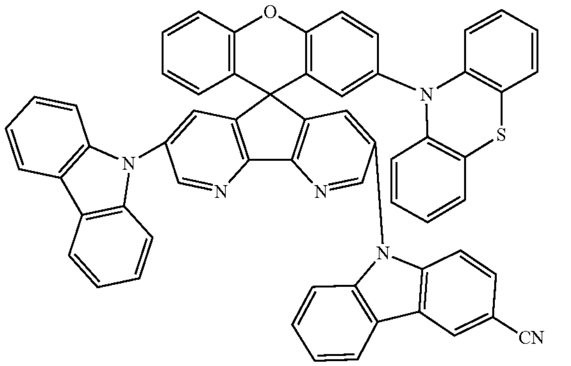
459
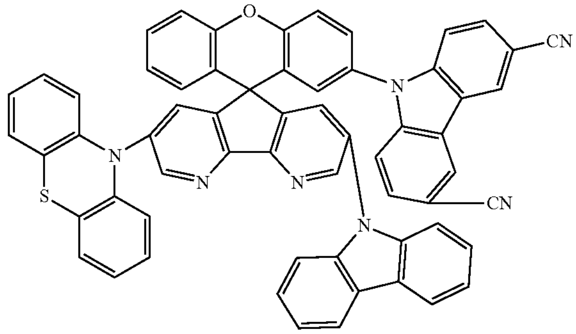
460
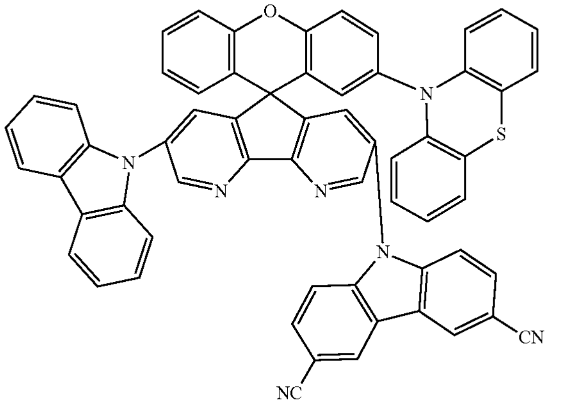

-continued
461
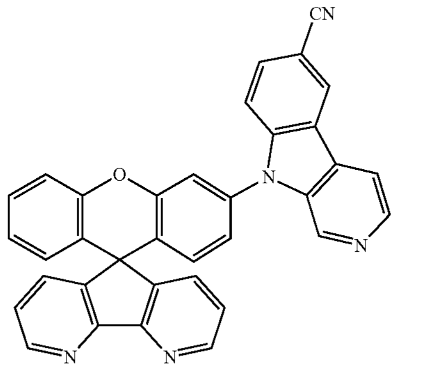
462
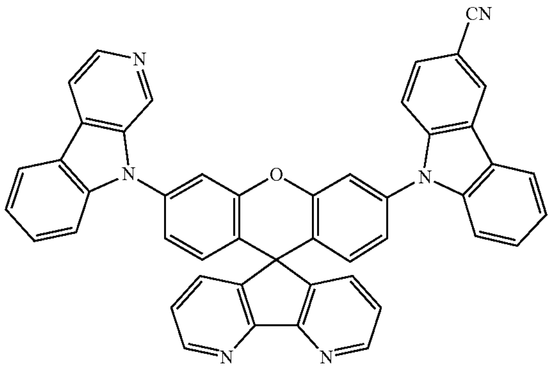
463
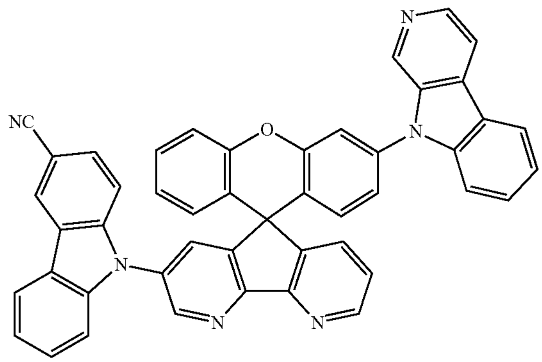
464
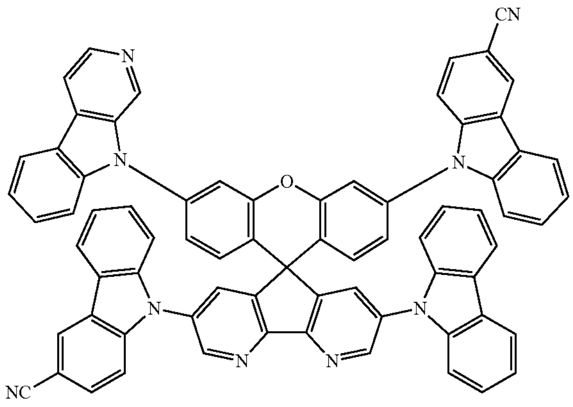
465
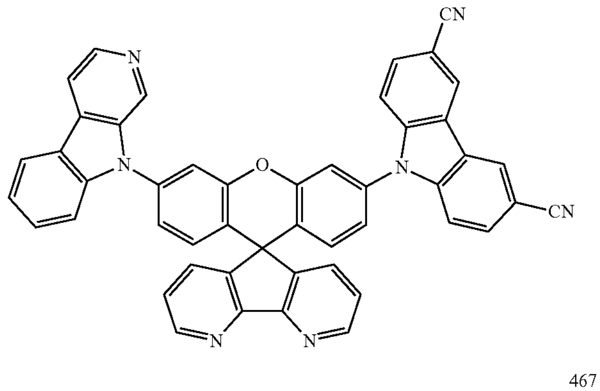
466
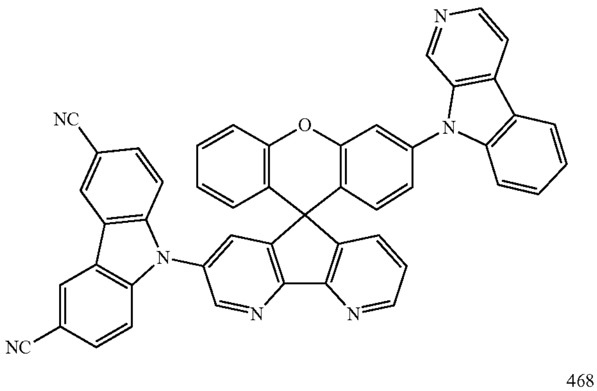
467
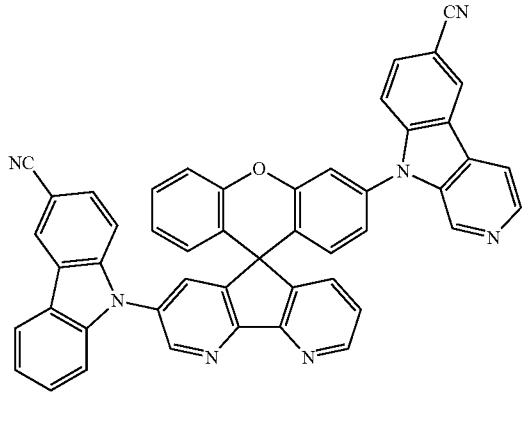
468
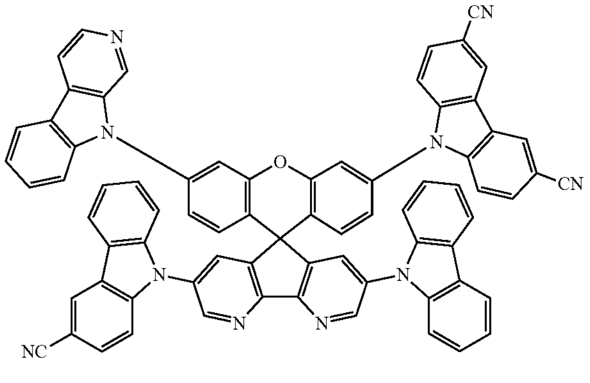

-continued
469
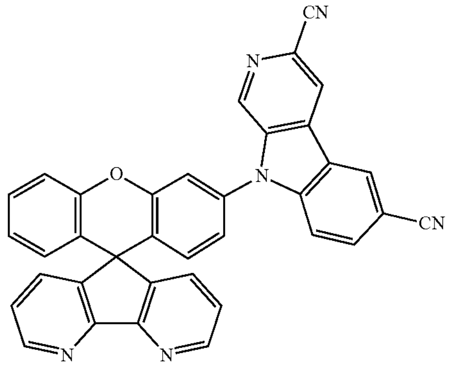
470
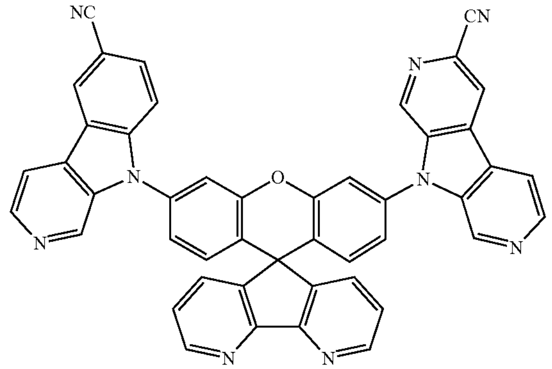
471
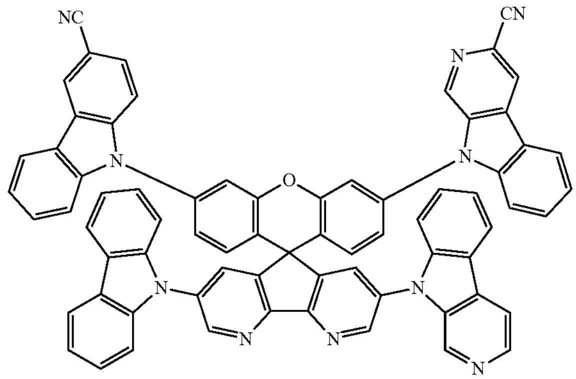
472
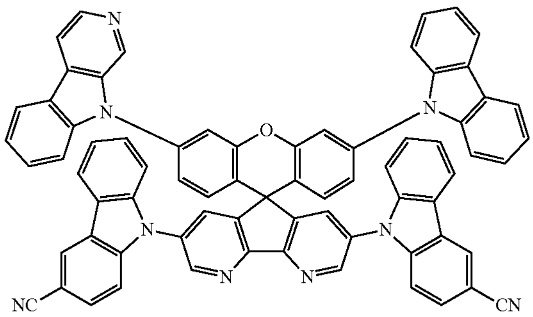
473
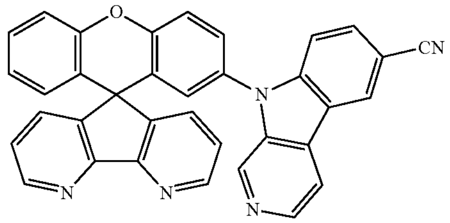
474
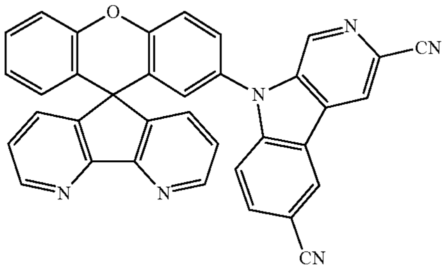
475
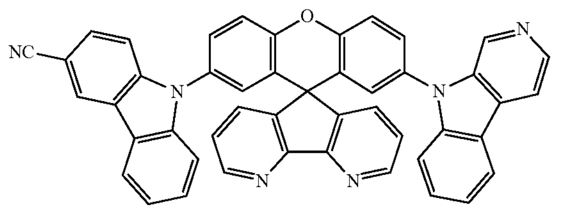
476
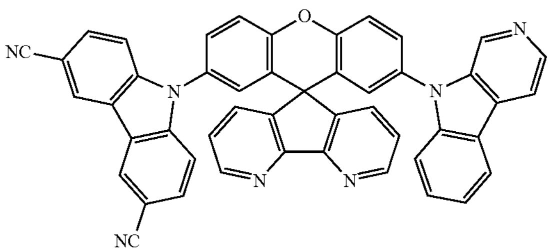
477
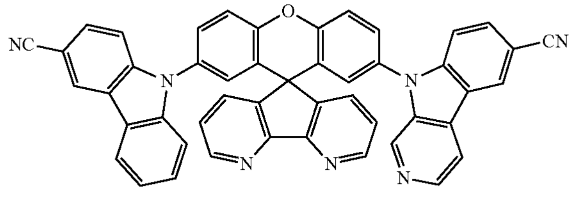
478
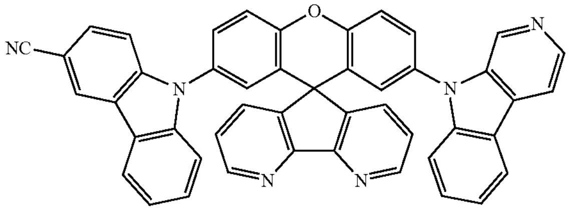

-continued
479
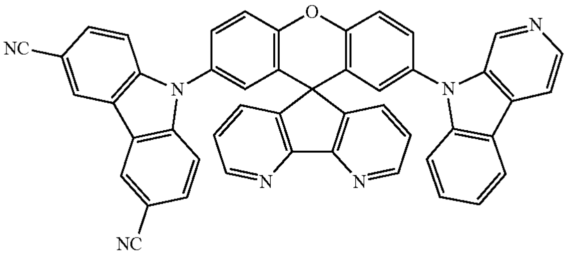
480
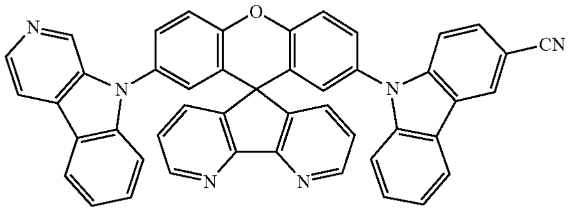
481
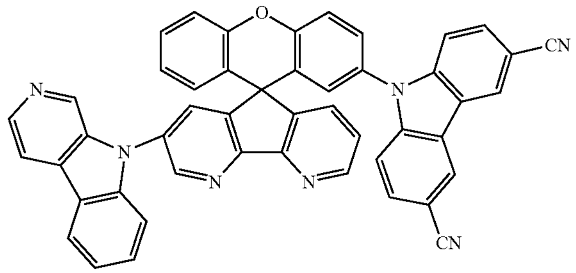
482
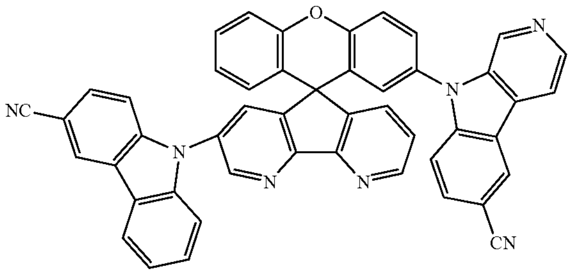
483
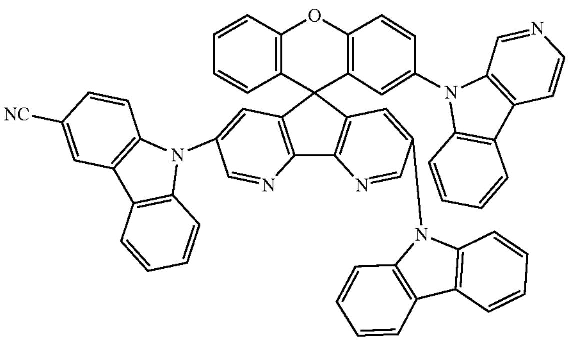
484
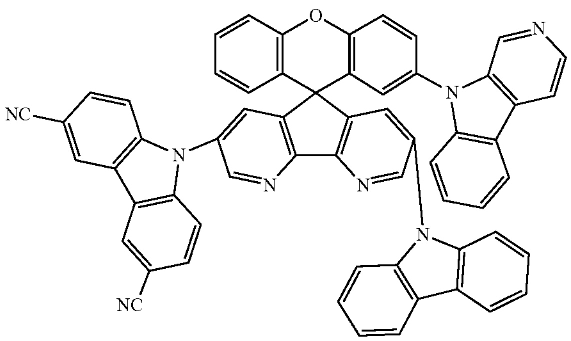
485
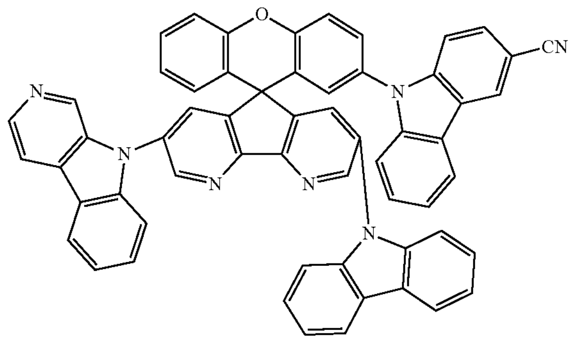
486
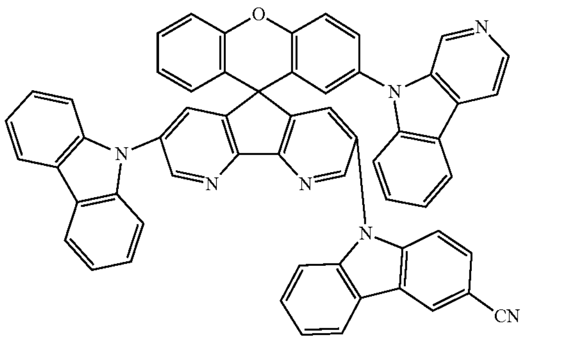

-continued
487
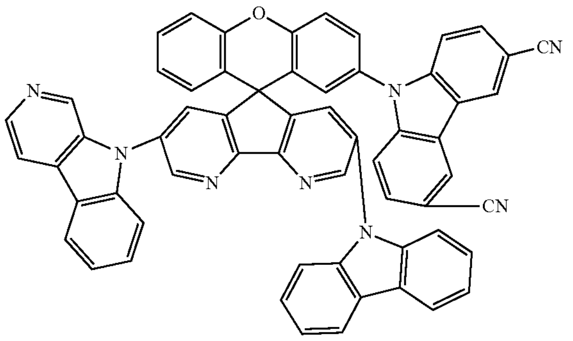
488
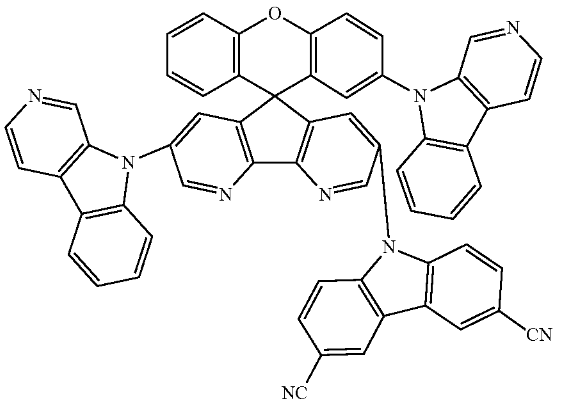
489
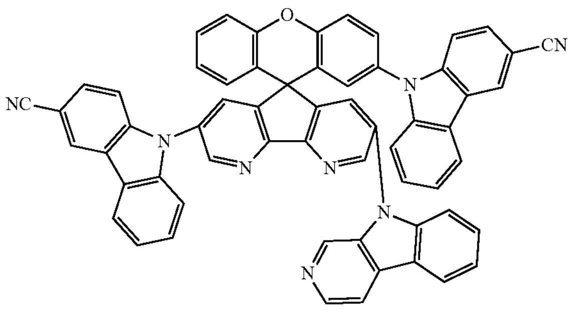
490
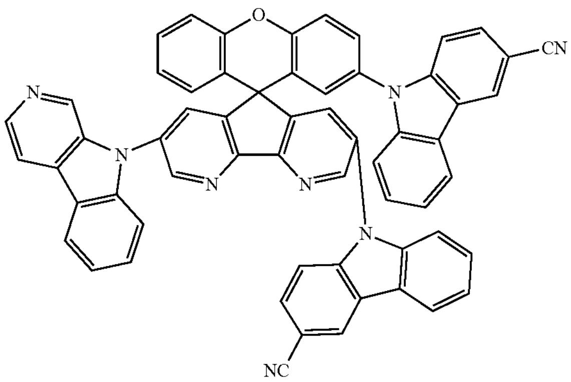
491
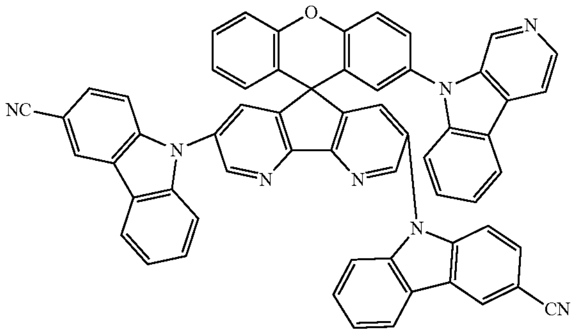
492
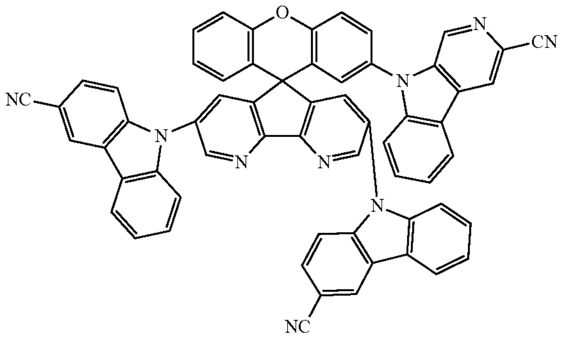
493
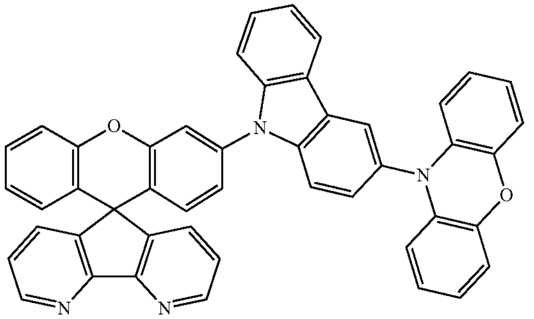
494
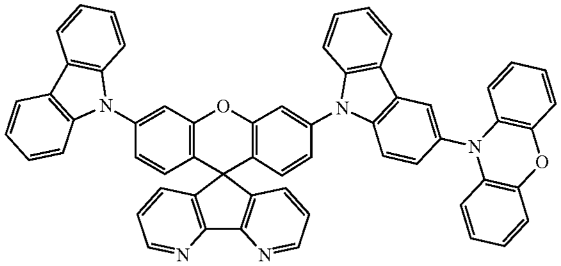

-continued
495
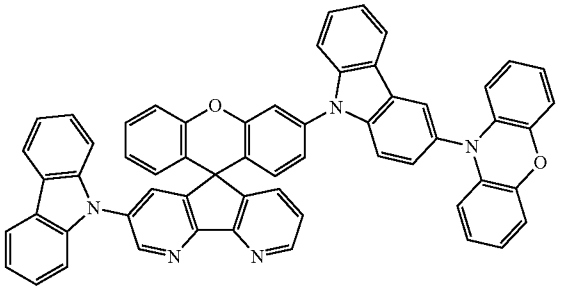
496
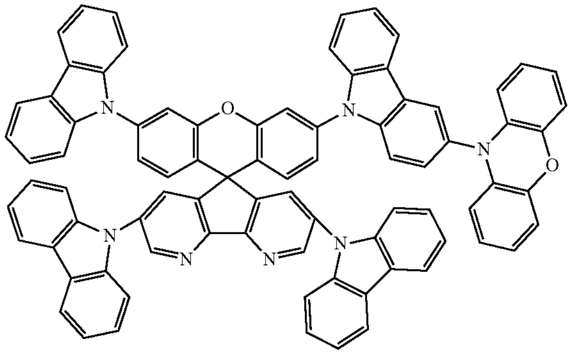
497
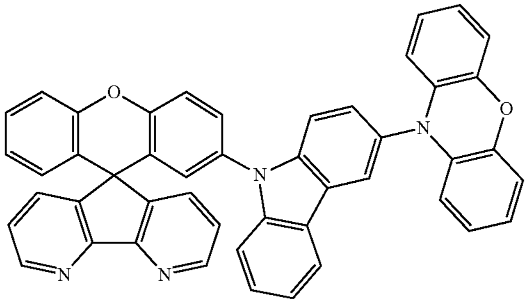
498
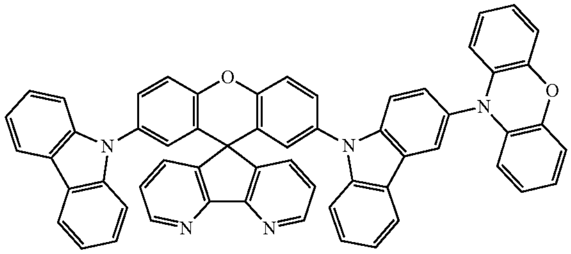
499
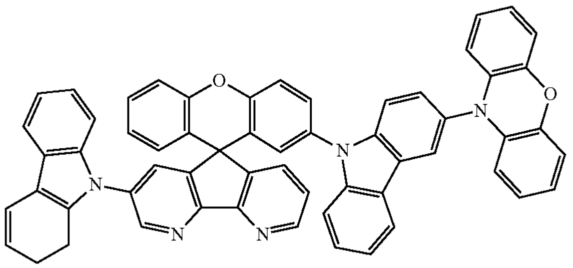
500
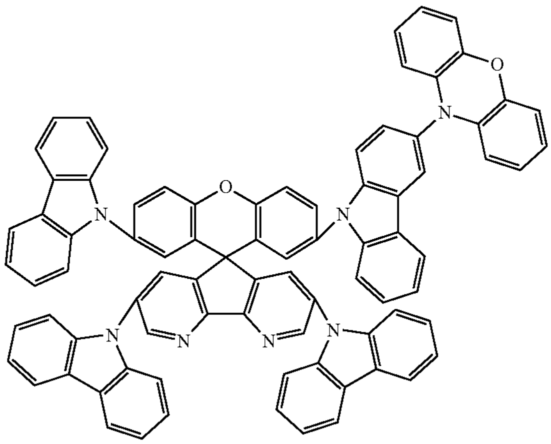
501
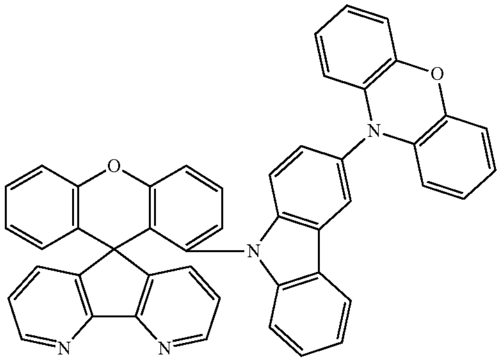
502
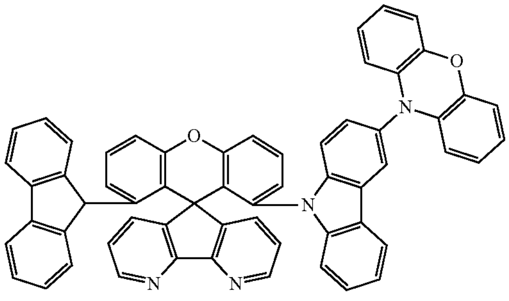

-continued
503
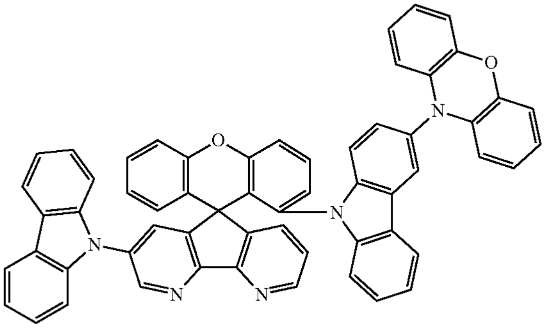
504
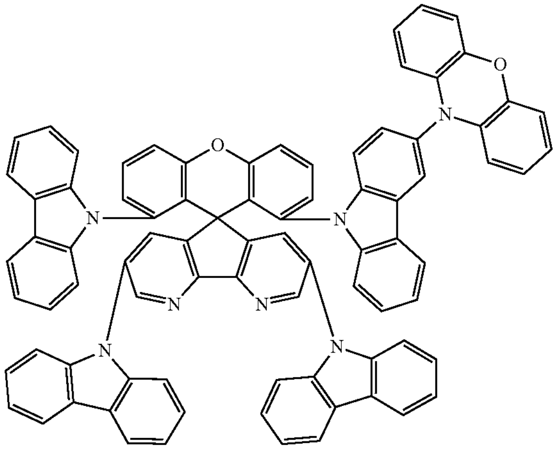
505
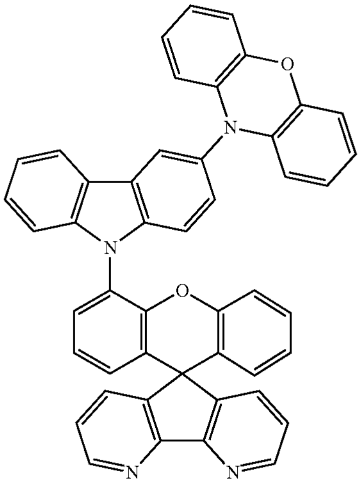
506
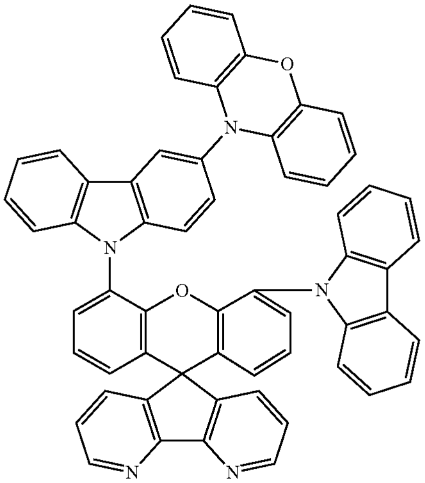
507
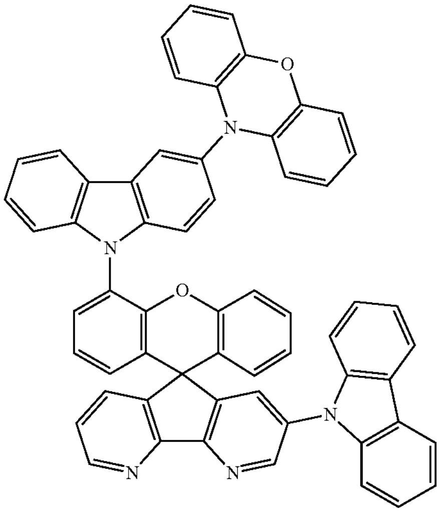
508
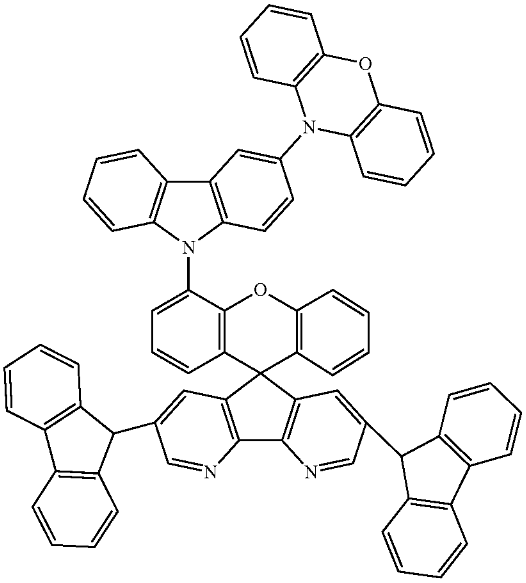

-continued
509
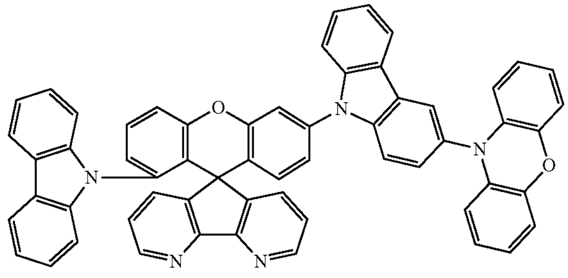
510
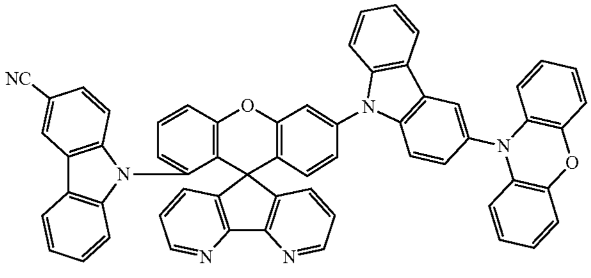
511
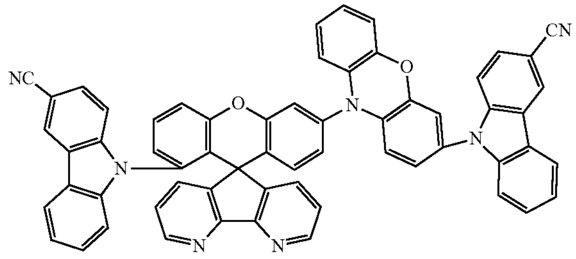
512
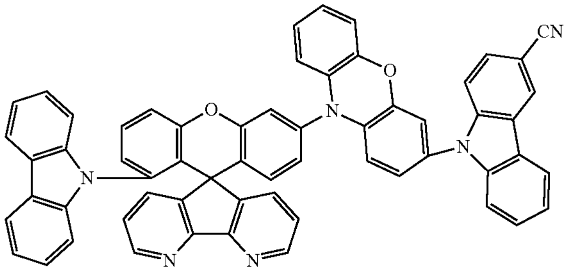
513
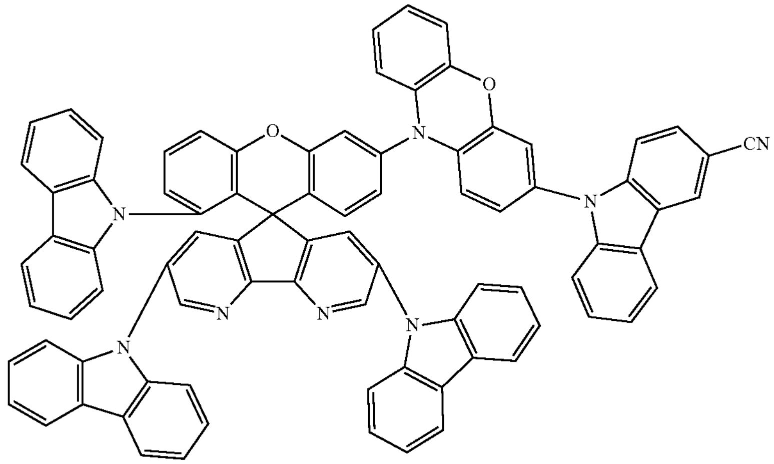
514
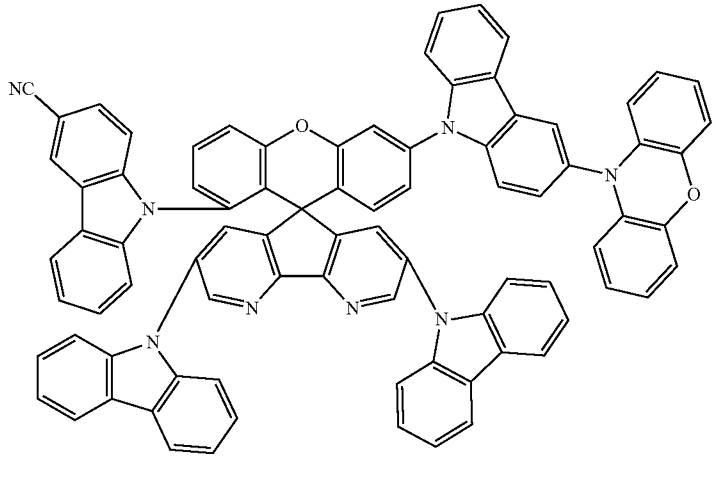

-continued
515
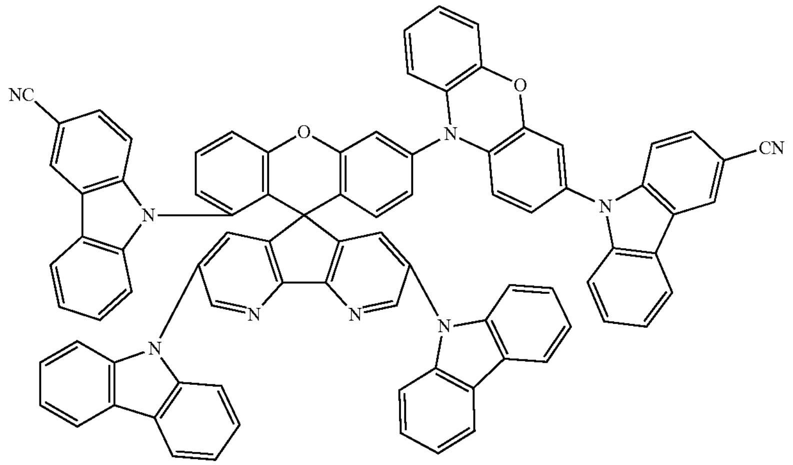
516
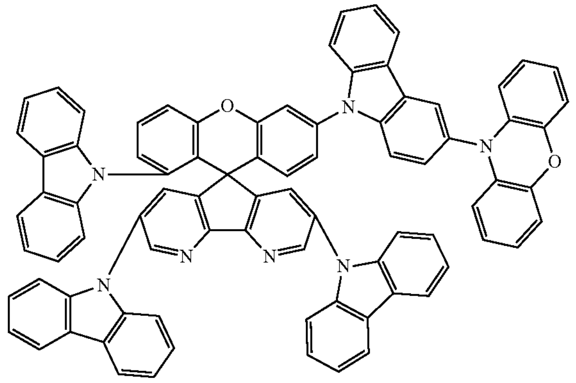
517
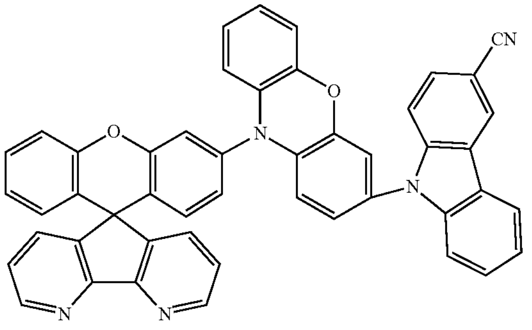
518
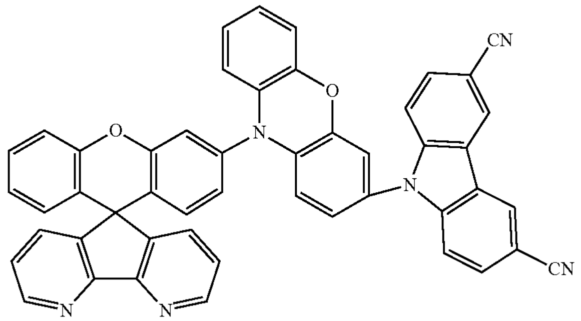
519
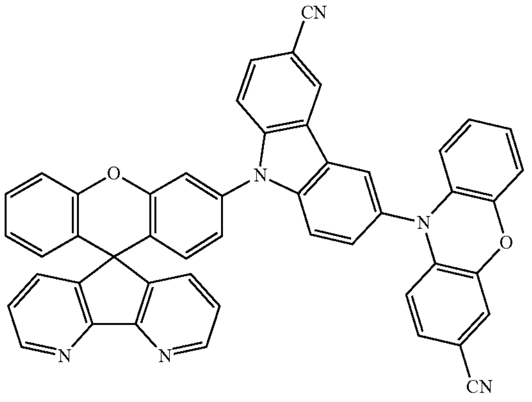
520
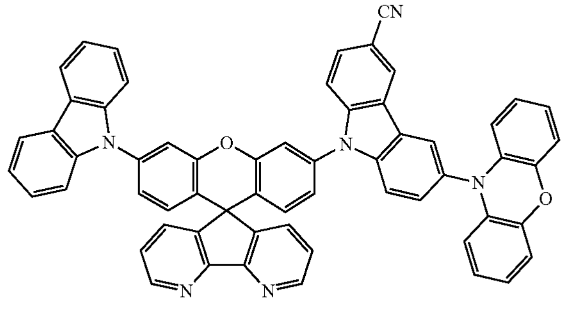
521
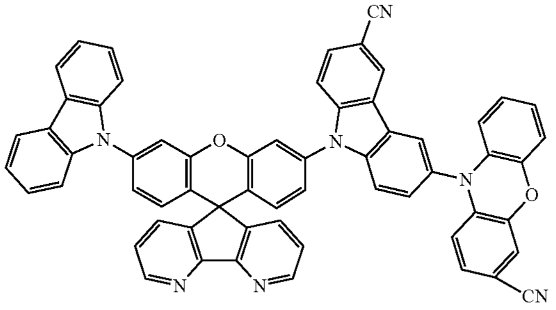

-continued
522
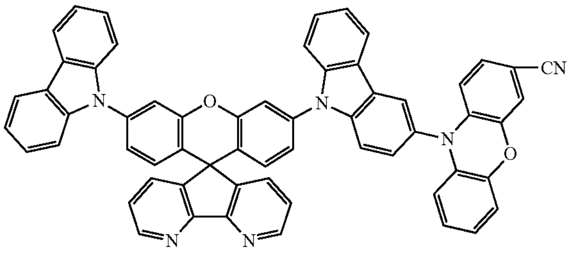
523
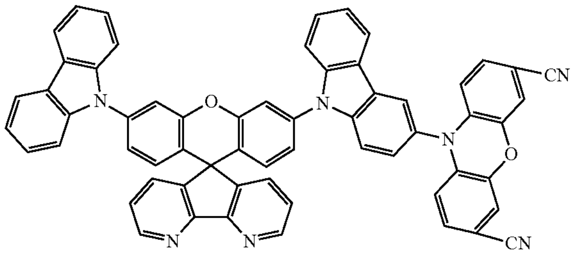
524
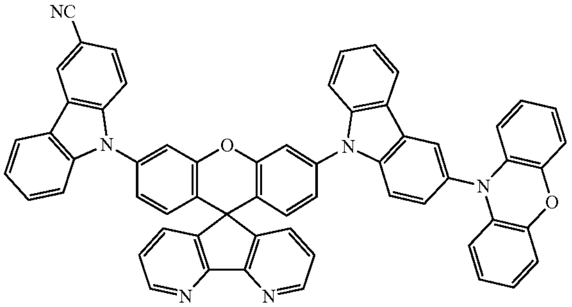
525
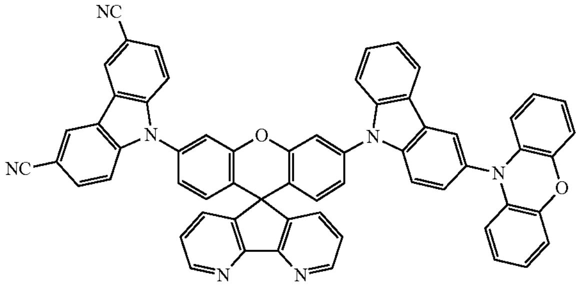
526
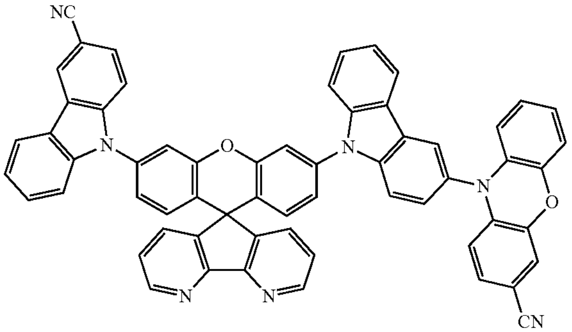
527
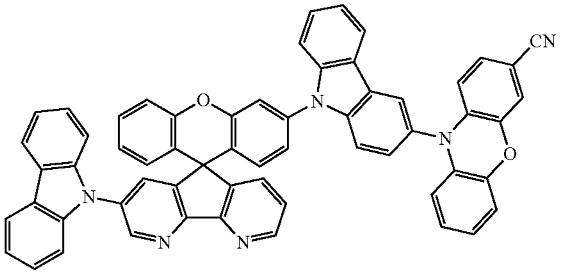
528
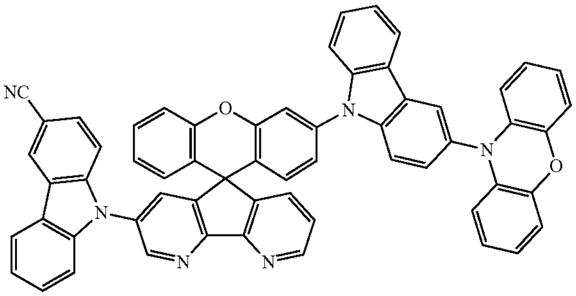
529
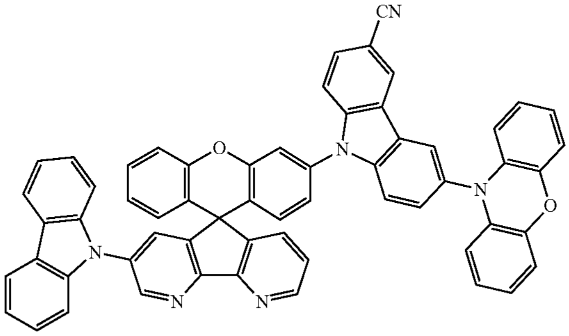
530
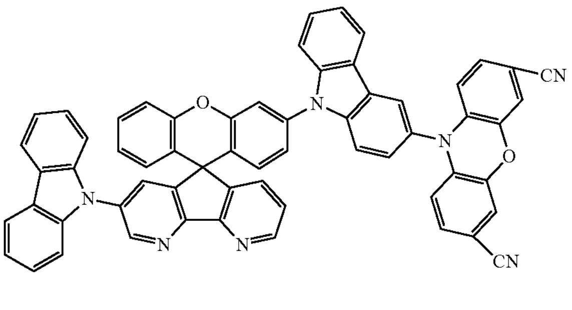
531
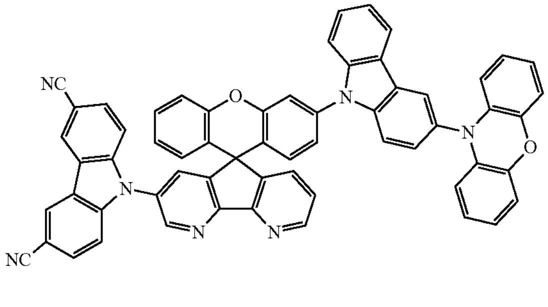

-continued
532
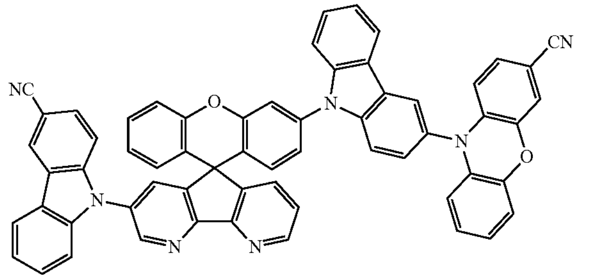
533
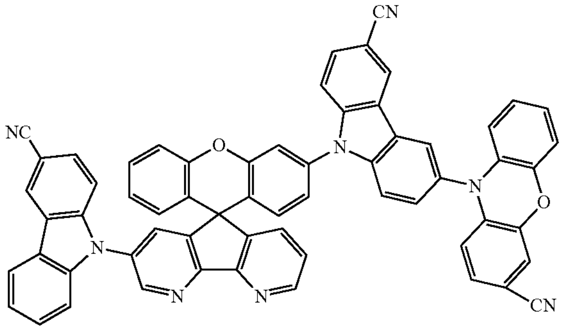
534
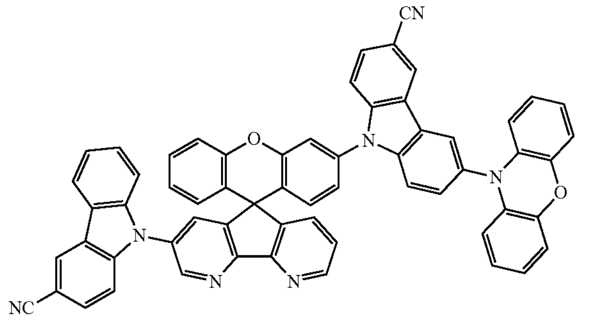
535
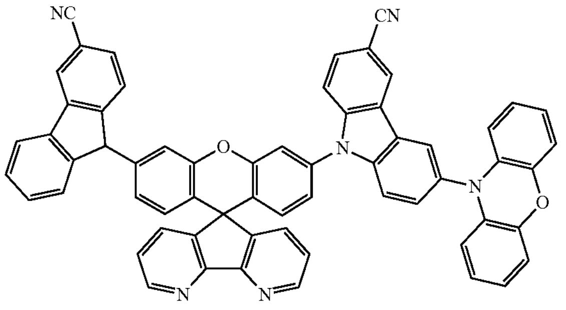
536
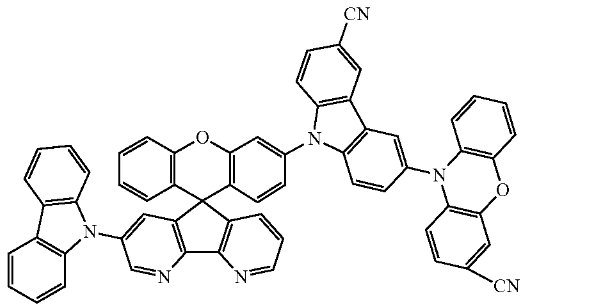
537
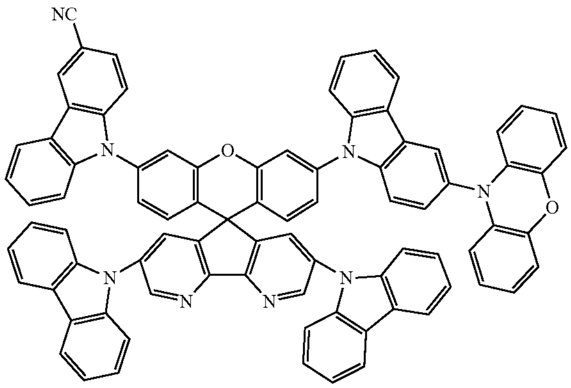
538
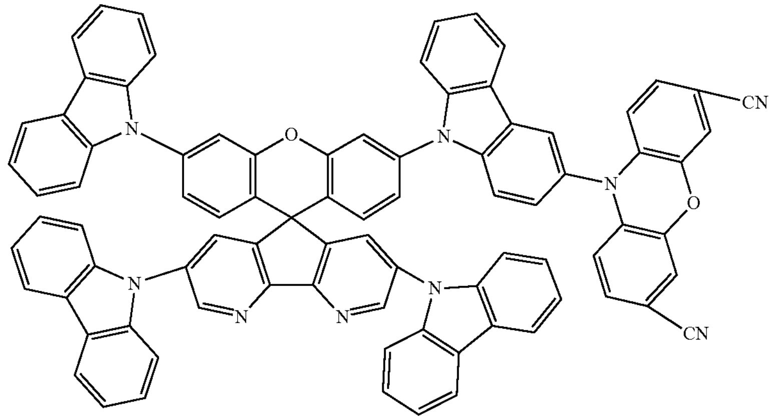

-continued
539
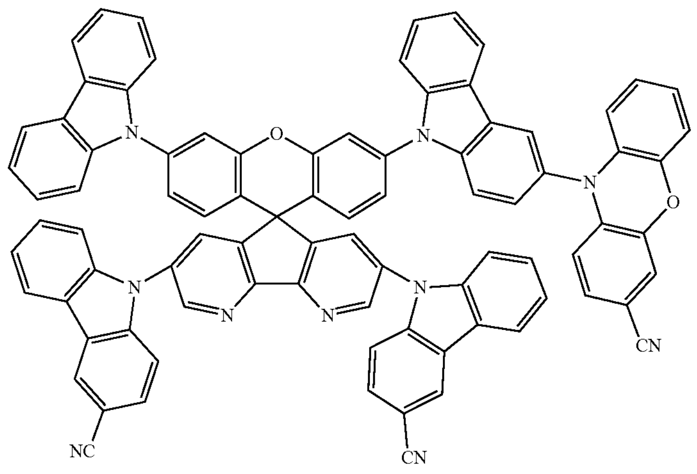
540
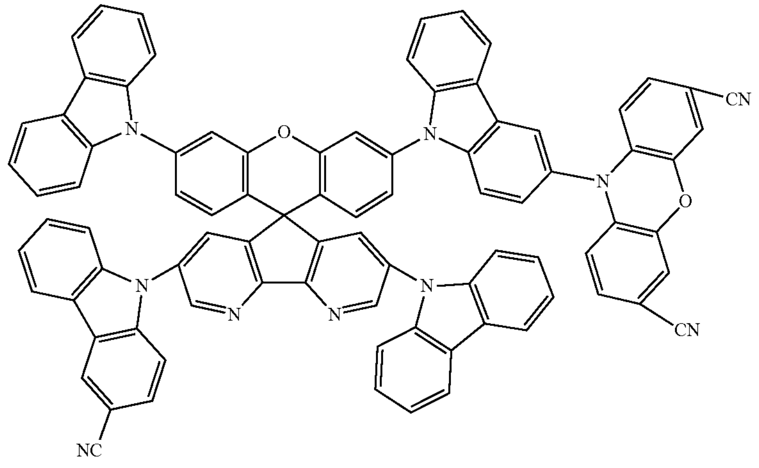
541
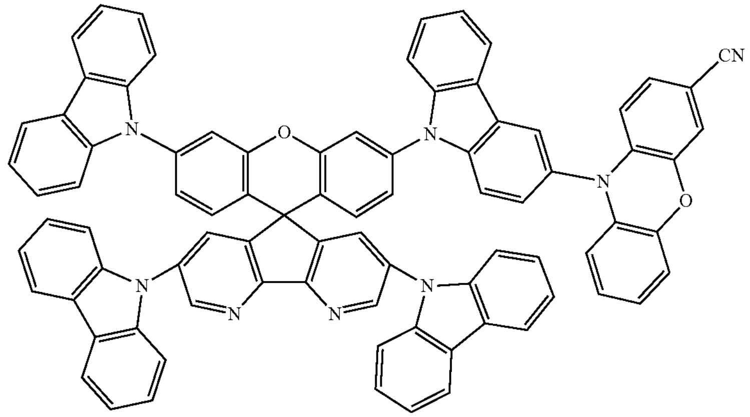

-continued
542
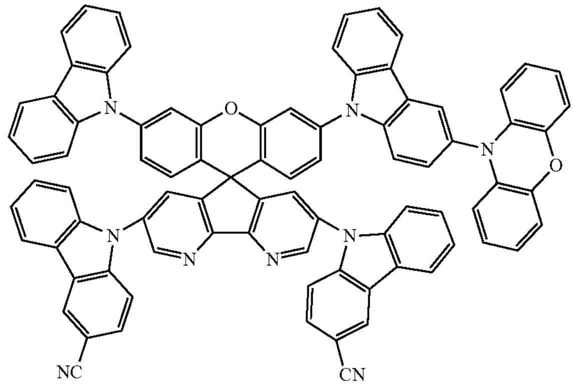
543
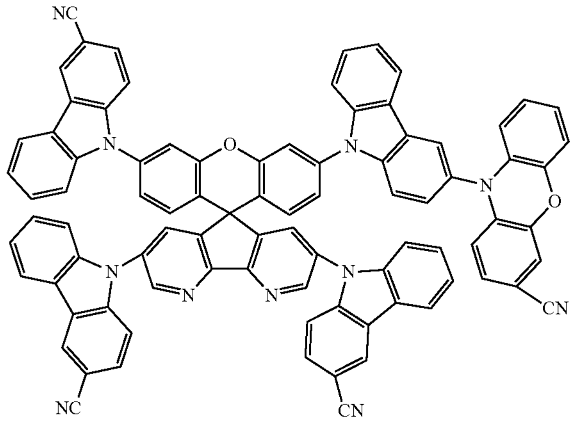
544
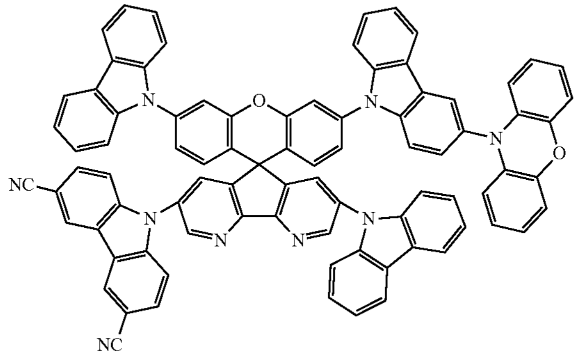
545
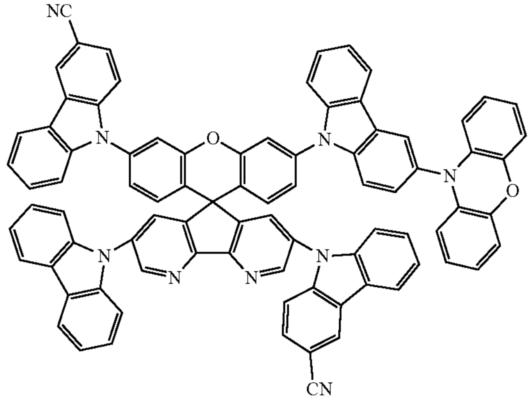
546
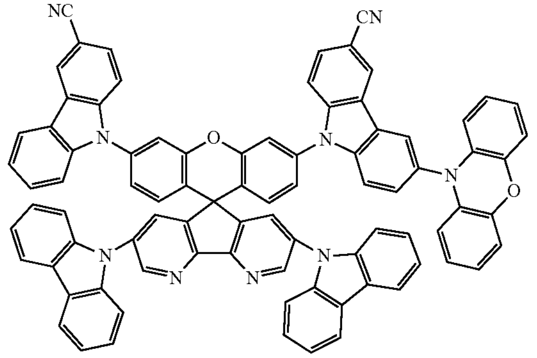
547
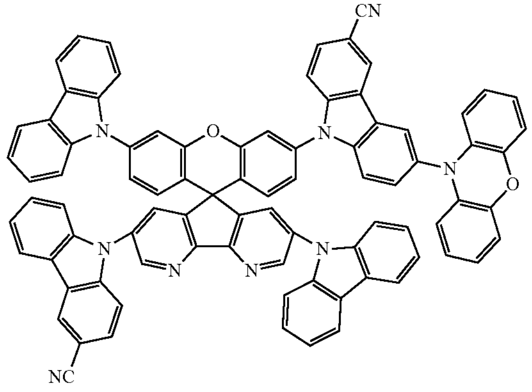
548
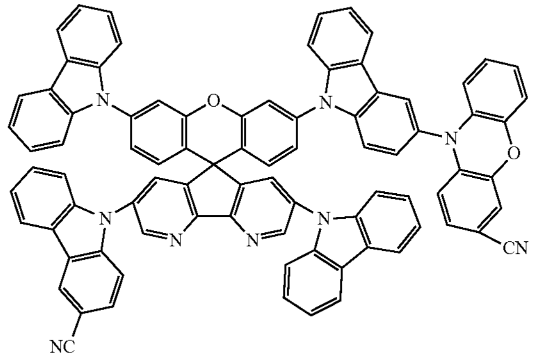
549
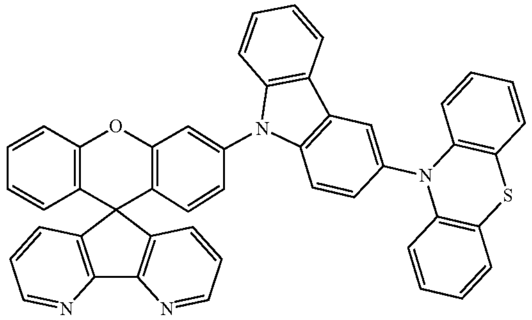

-continued
550
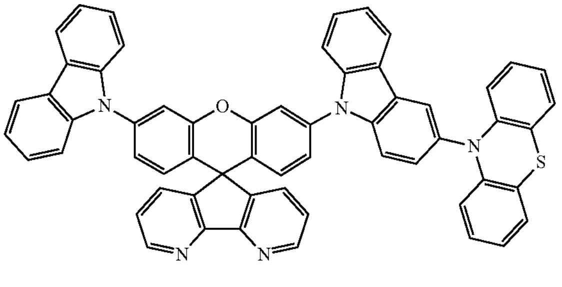
551
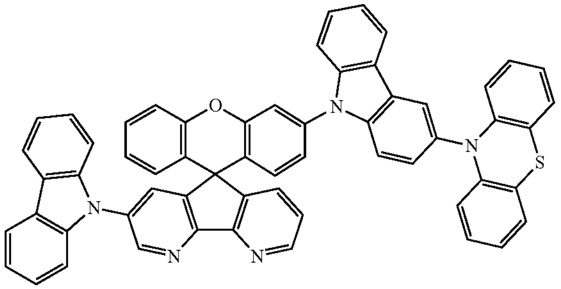
552
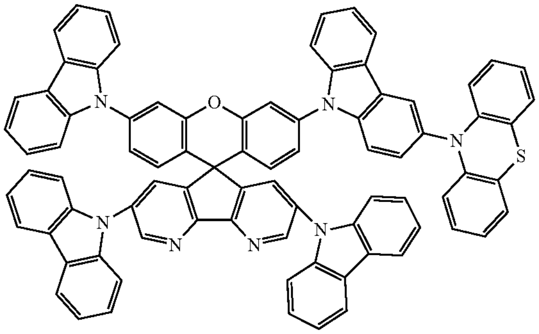
553
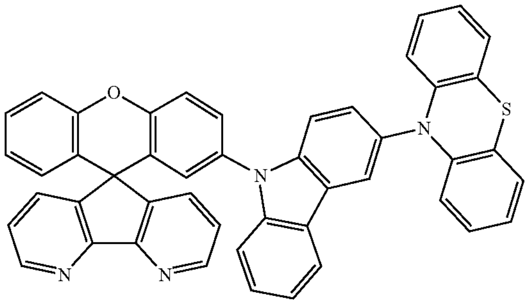
554
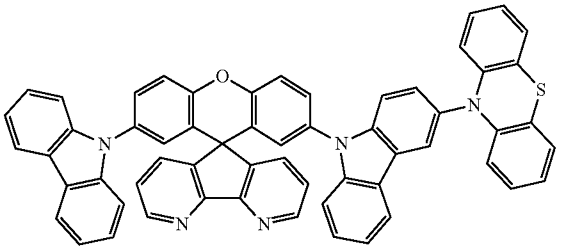
555
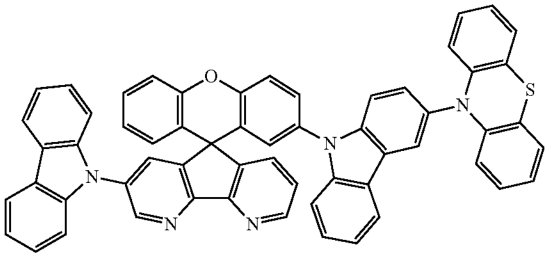
556
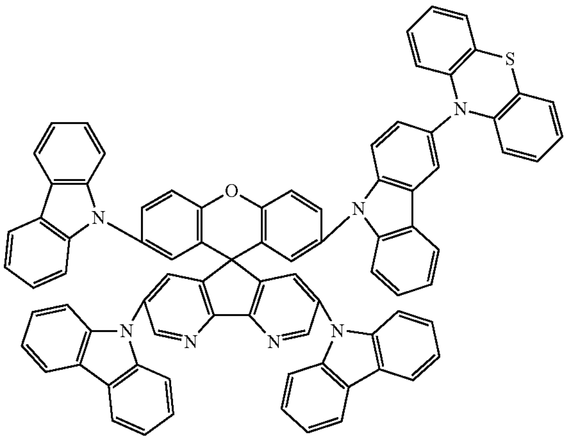
557
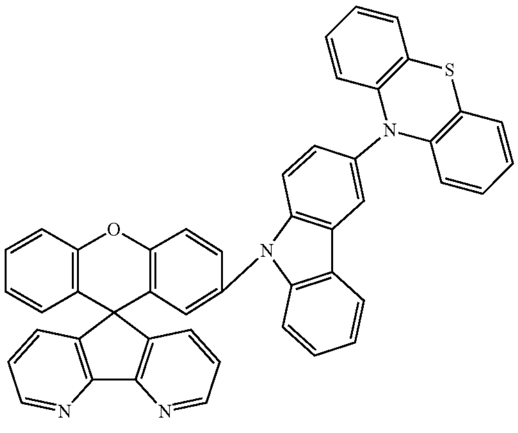

-continued
558
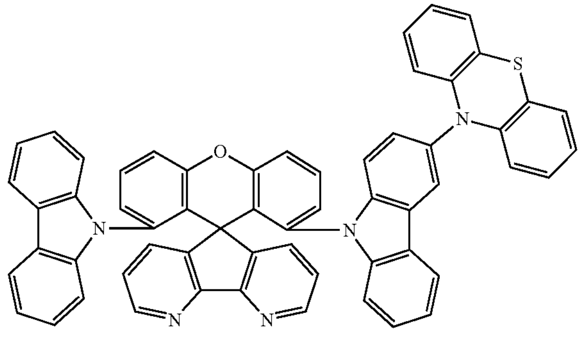
559
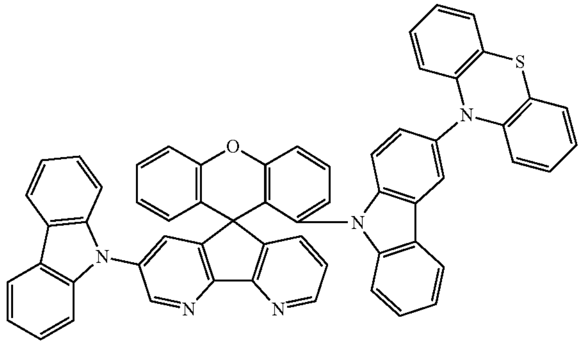
560
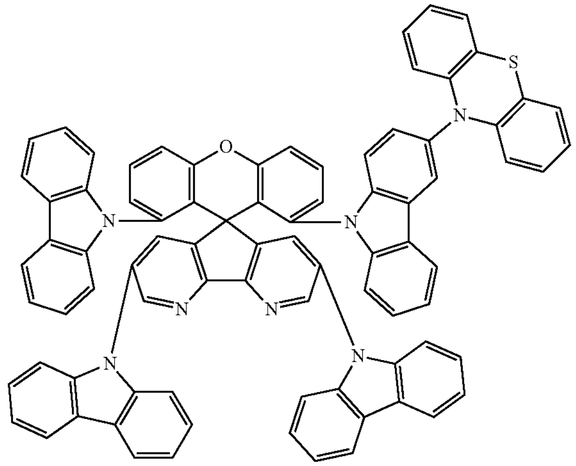
561
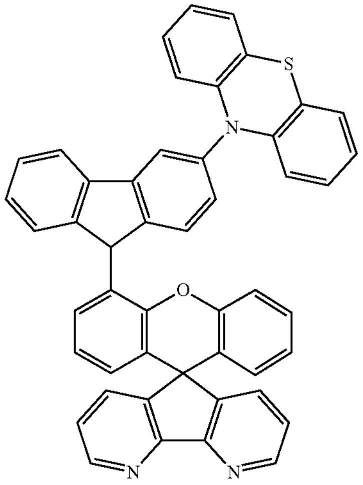
562
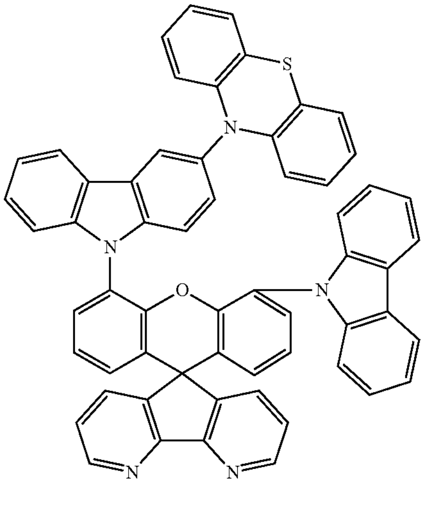
563
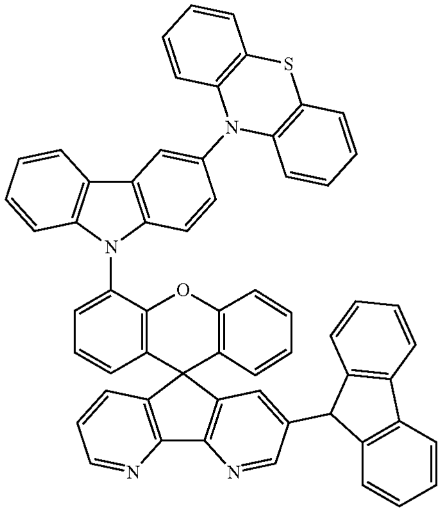

-continued
564
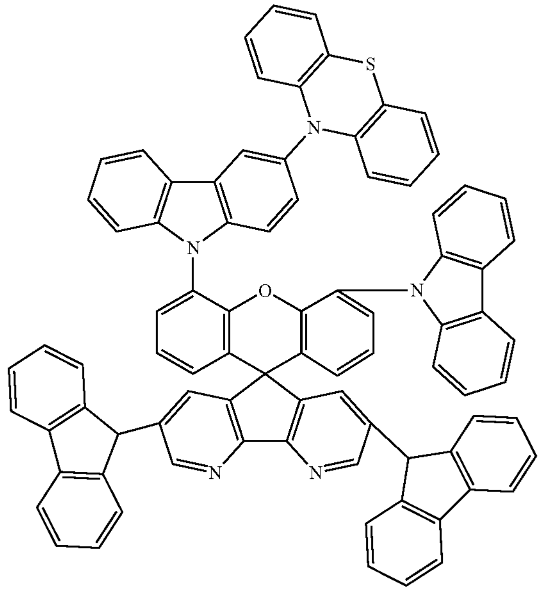
565
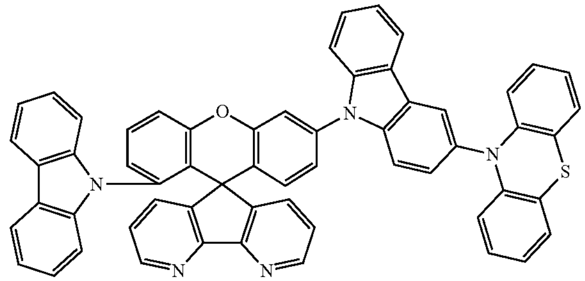
566
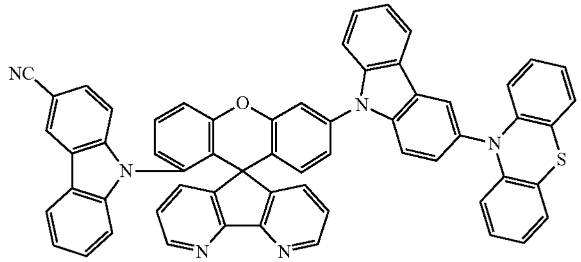
567
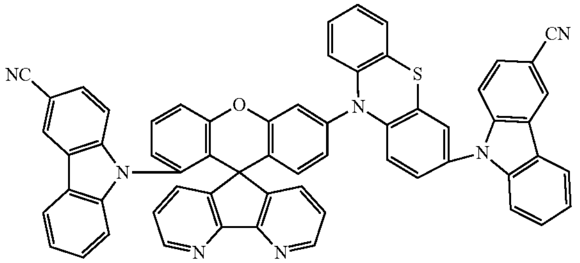
568
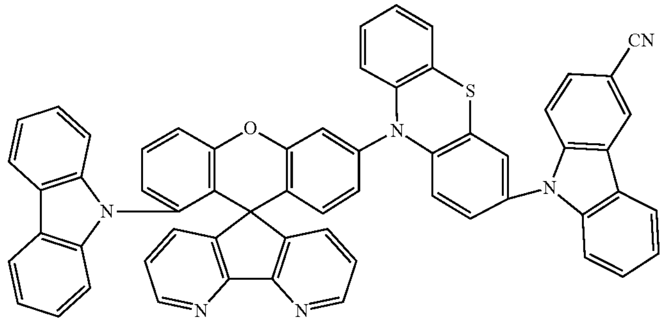

-continued
569
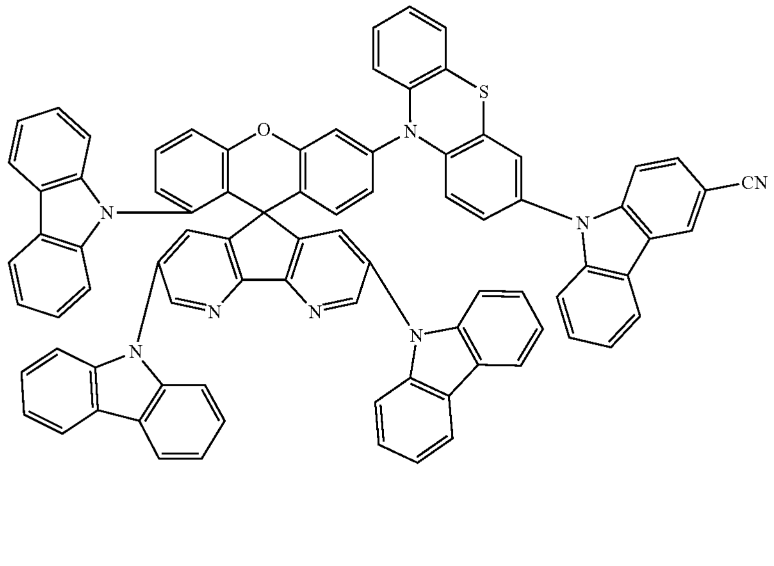
570
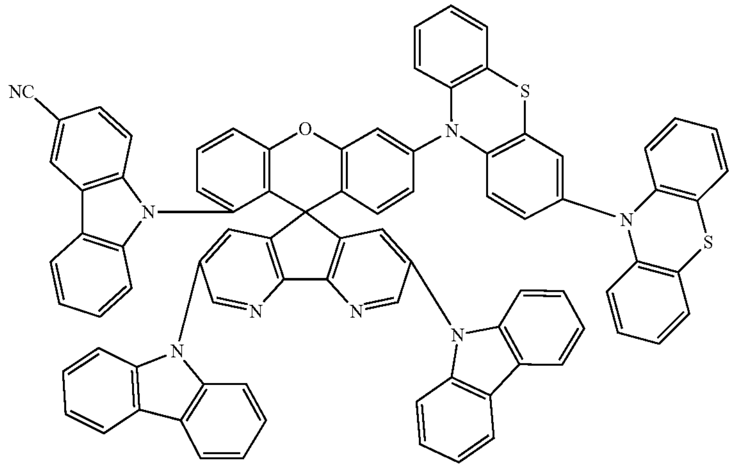
571
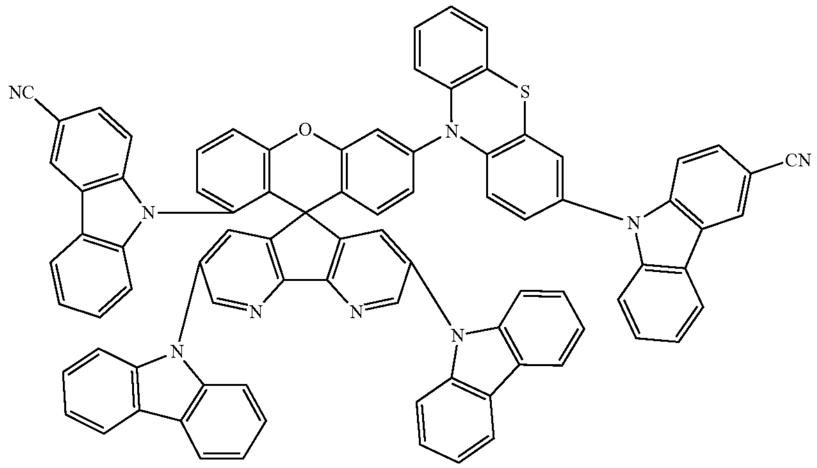

-continued
572
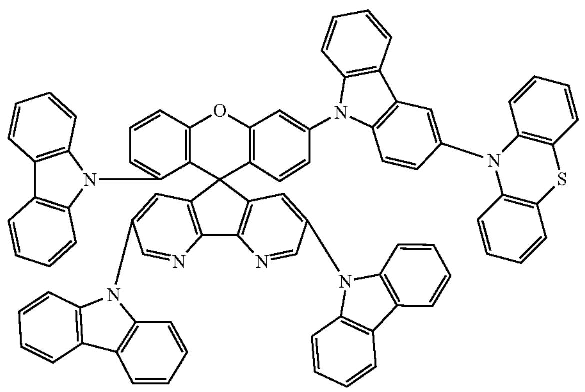
573
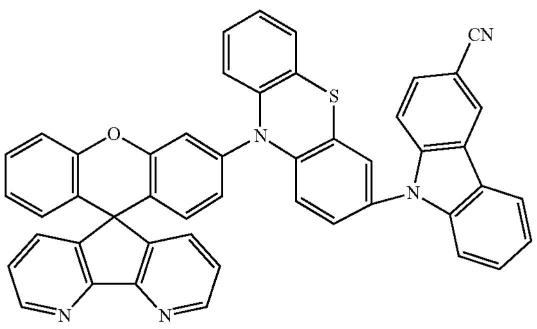
574
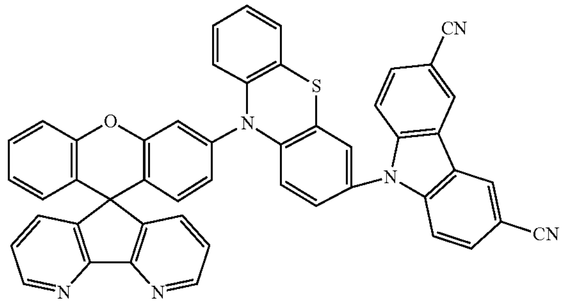
575
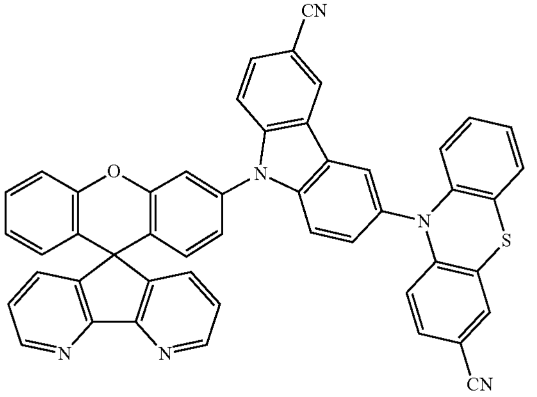
576
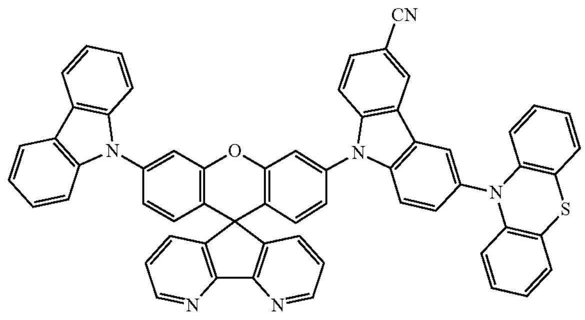
577
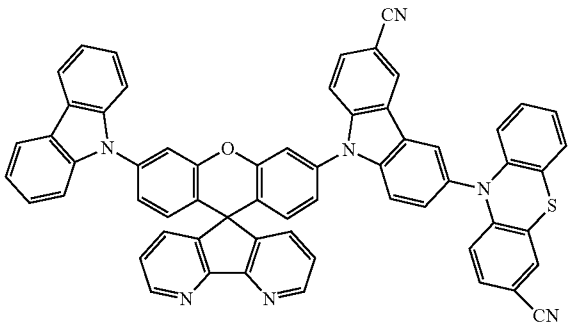
578
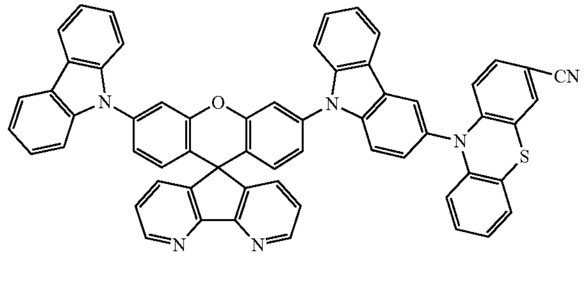
579
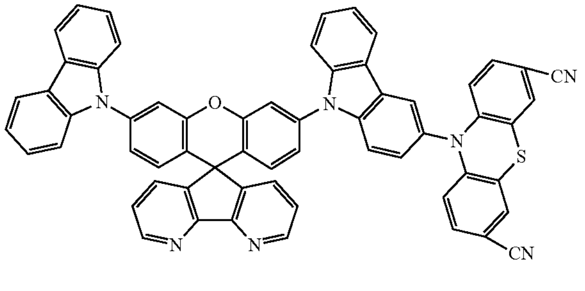

-continued
580
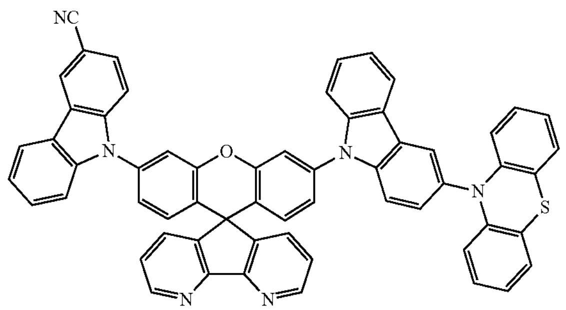
581
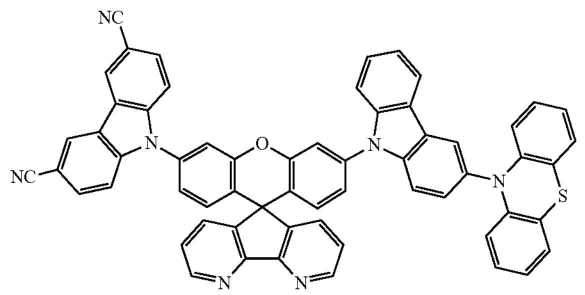
582
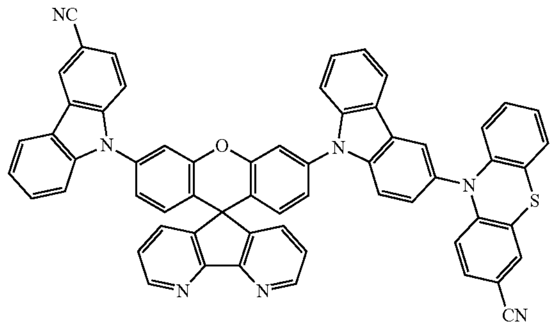
583
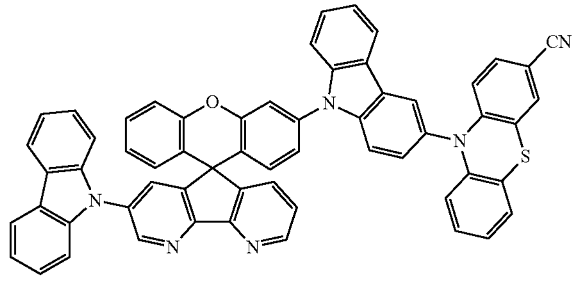
584
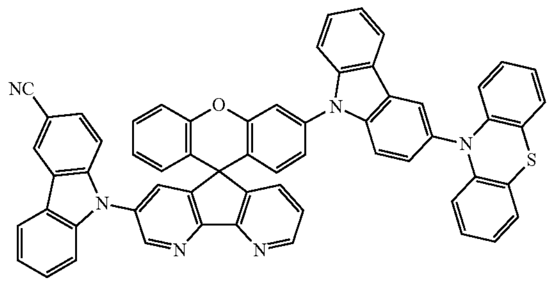
585
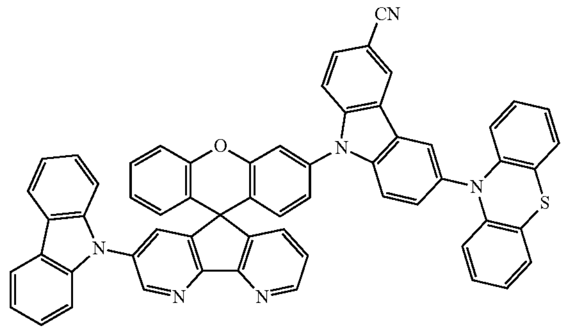
586
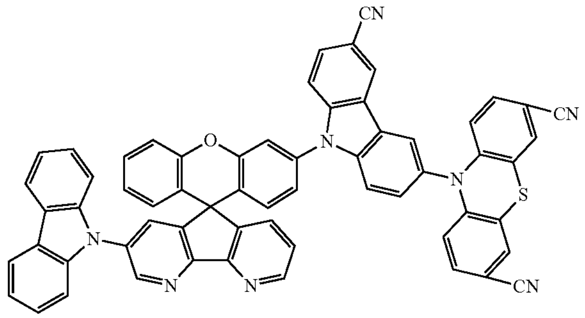
587
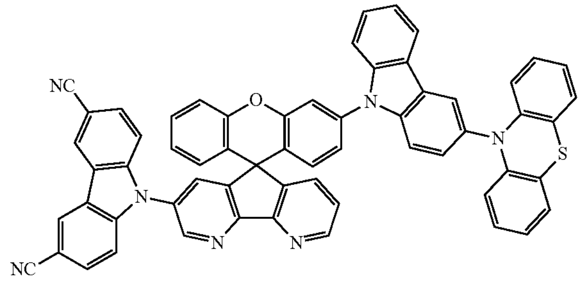

-continued
588
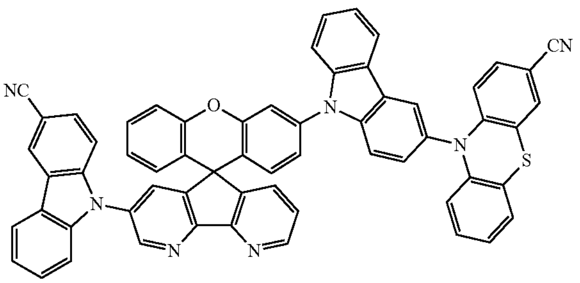
589
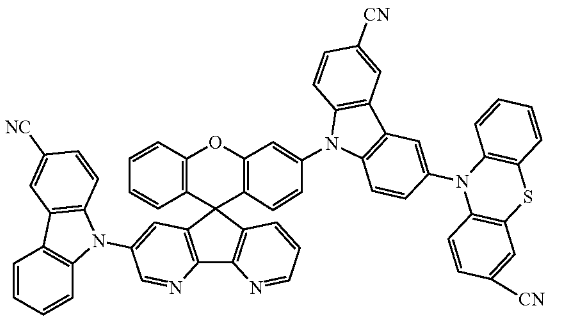
590
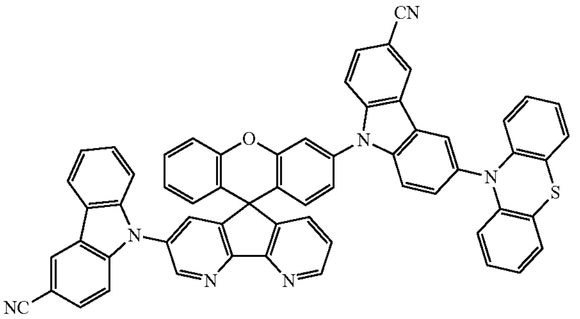
591
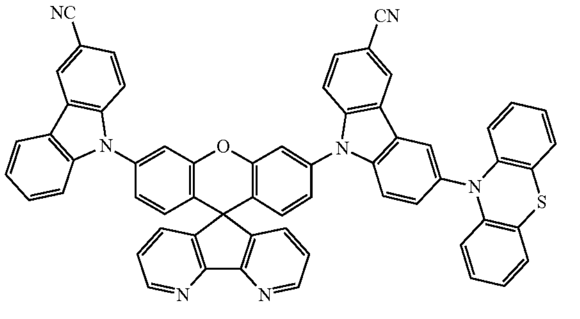
592
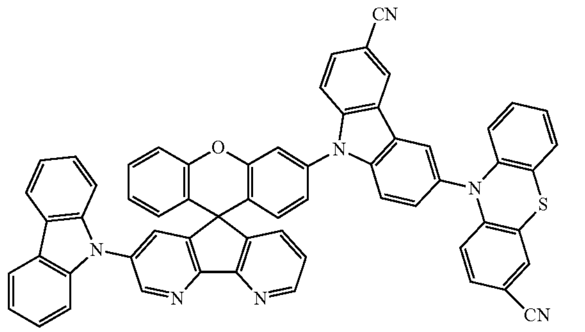
593
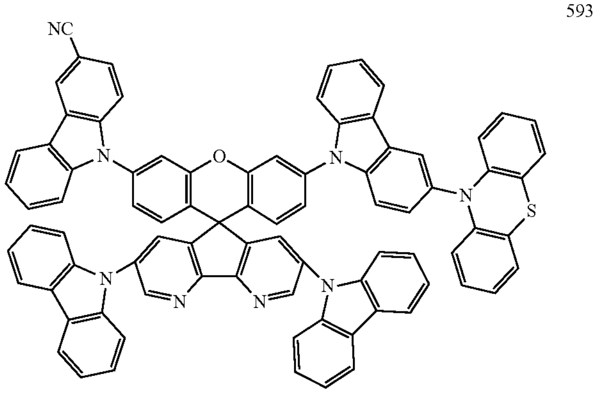
594
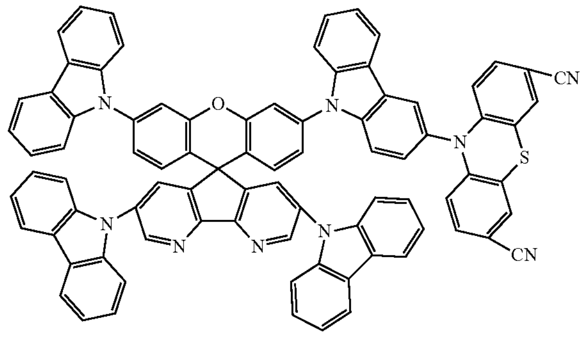
595
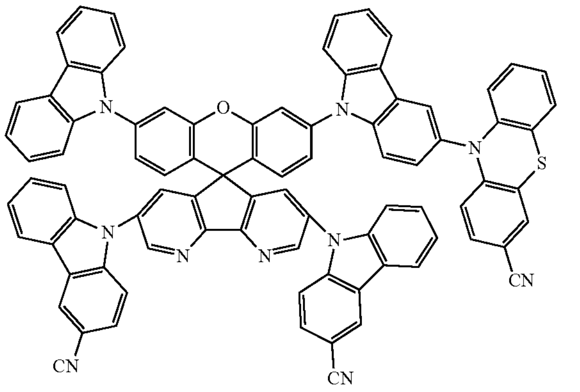

-continued
596
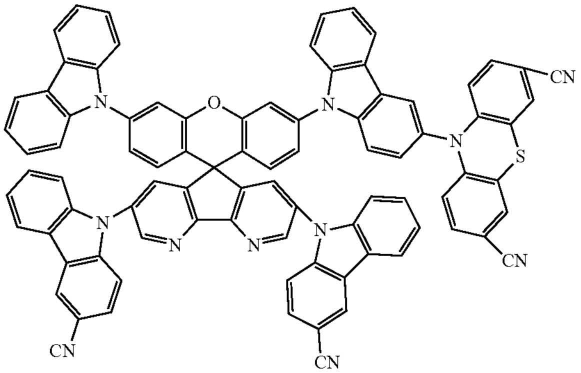
597
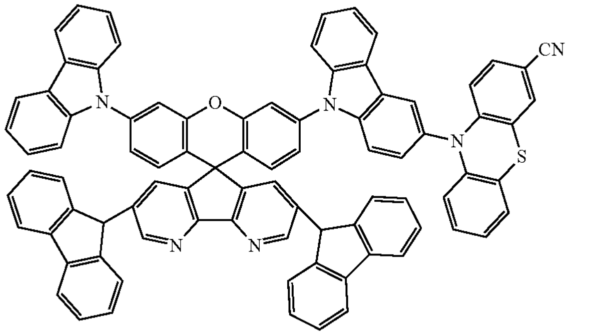
598
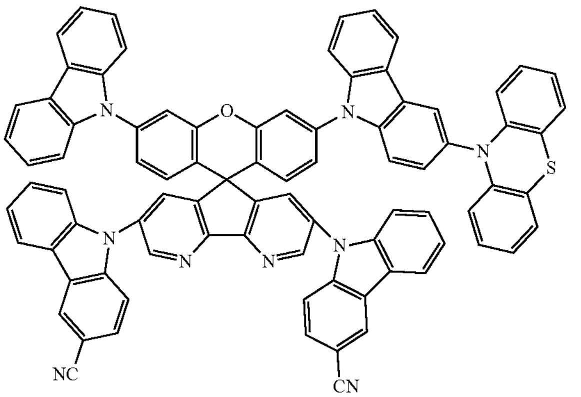
599
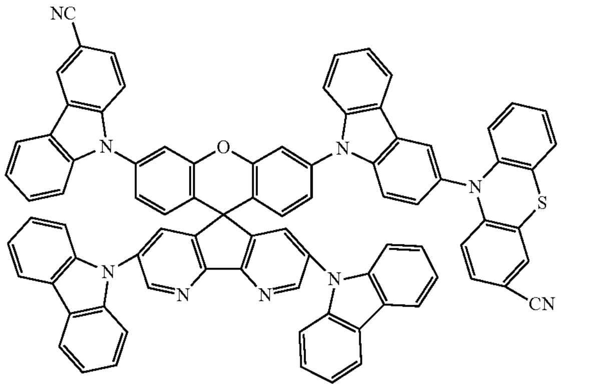
600
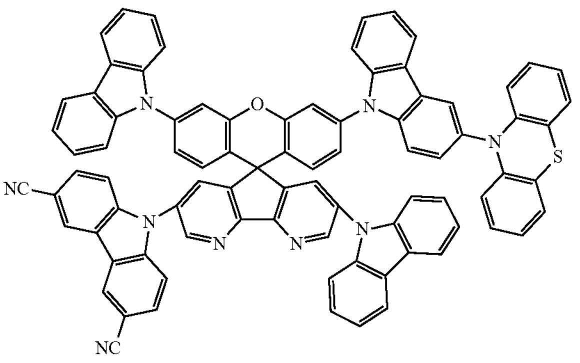
601
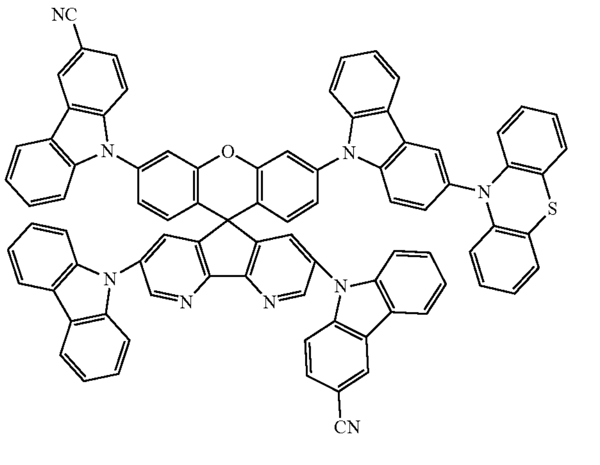

-continued
602
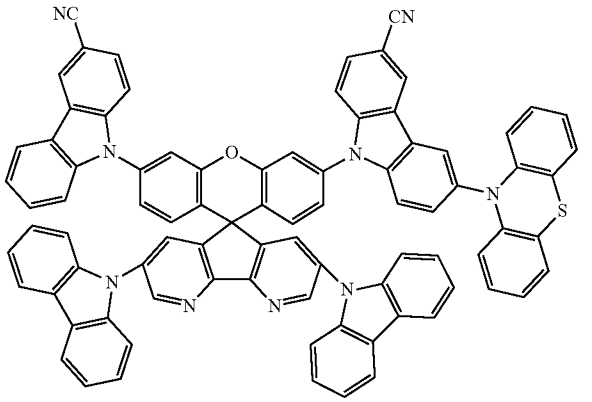
603
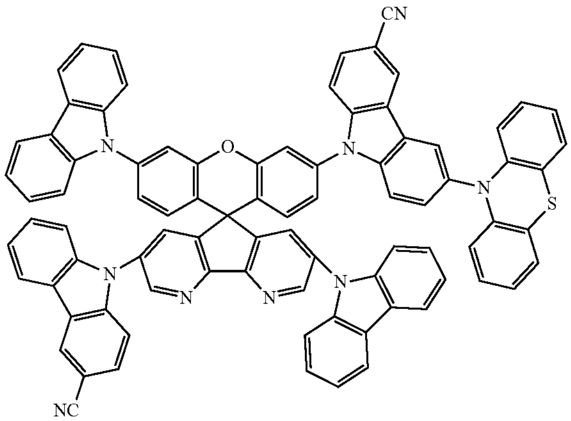
604
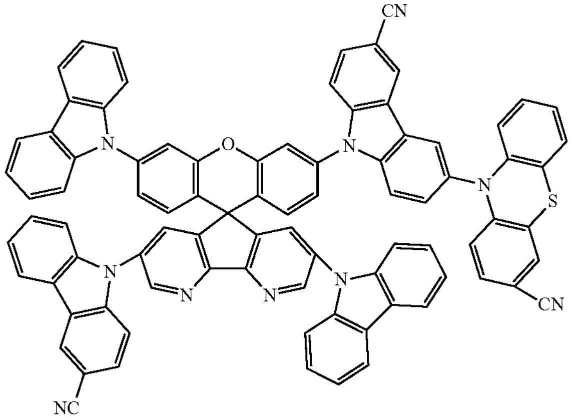
605
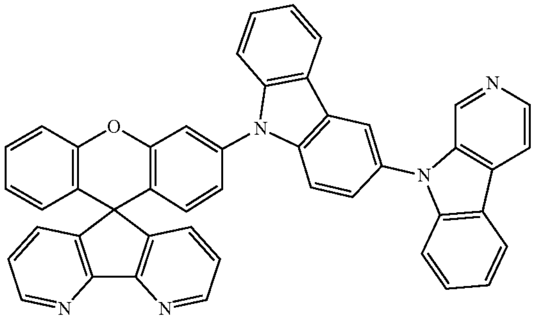
606
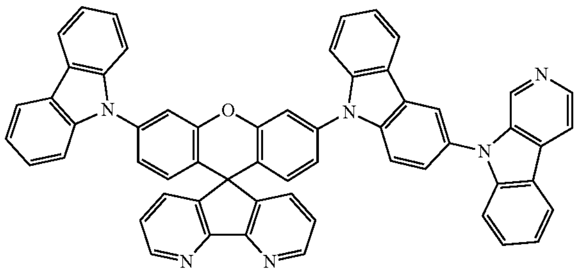
607
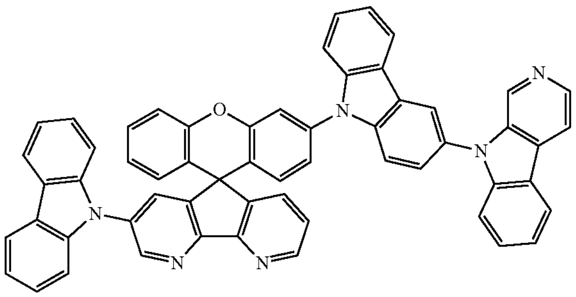
608
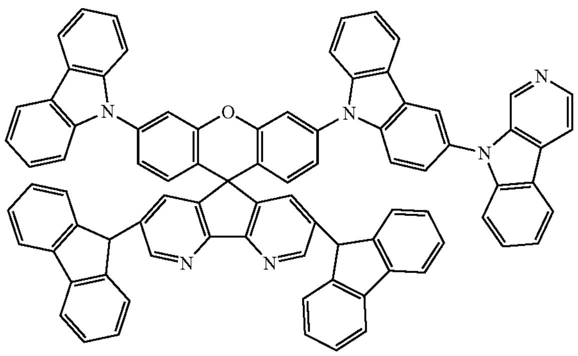
609
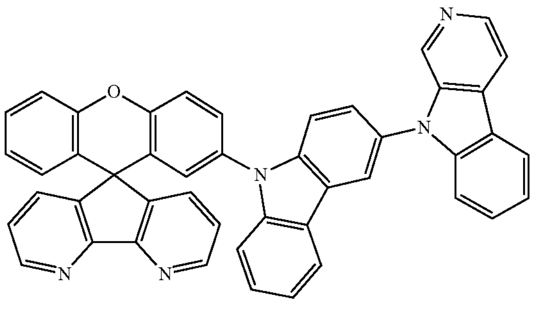

-continued
610
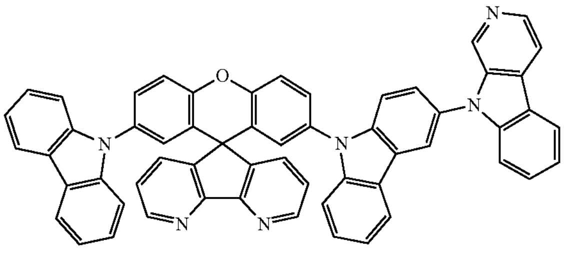
611
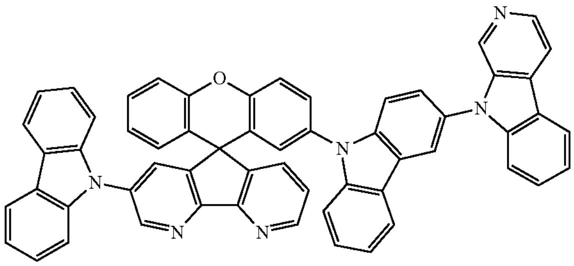
612
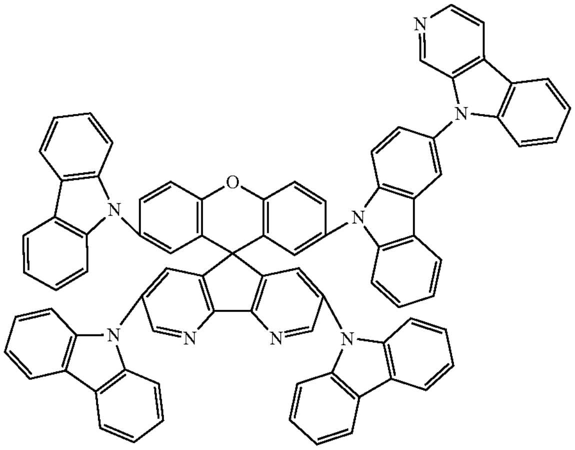
613
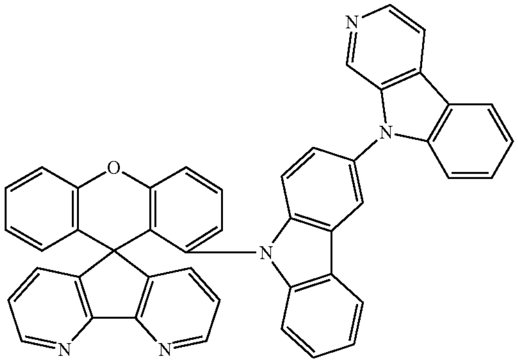
614
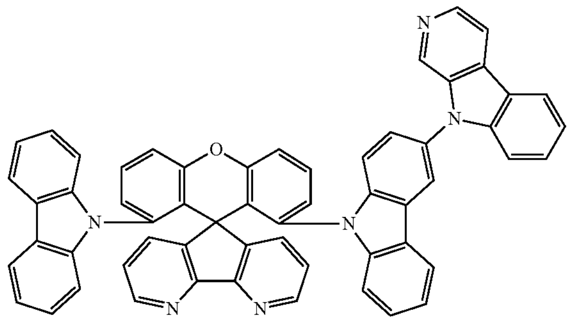
615
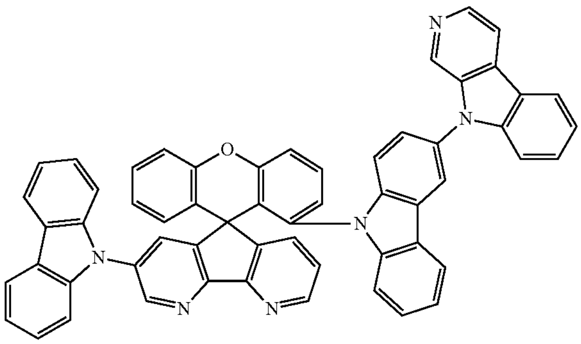
616
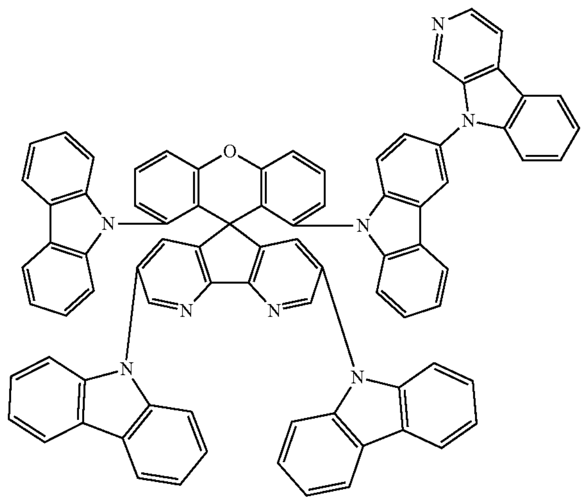
617
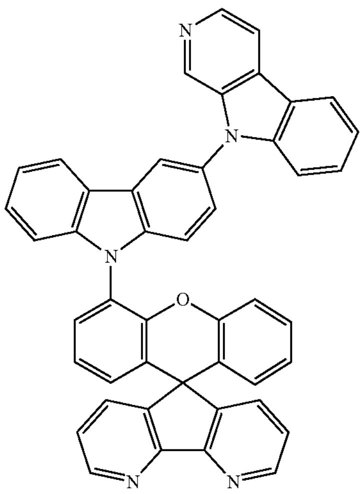

-continued
618
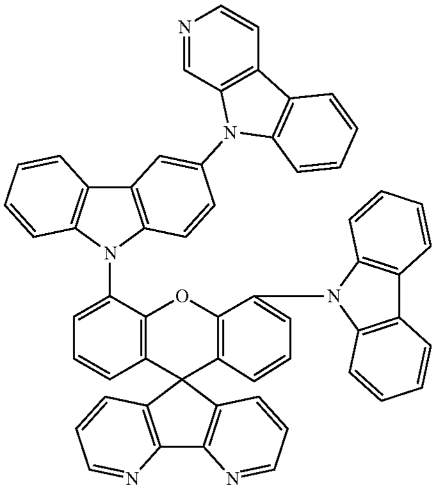
619
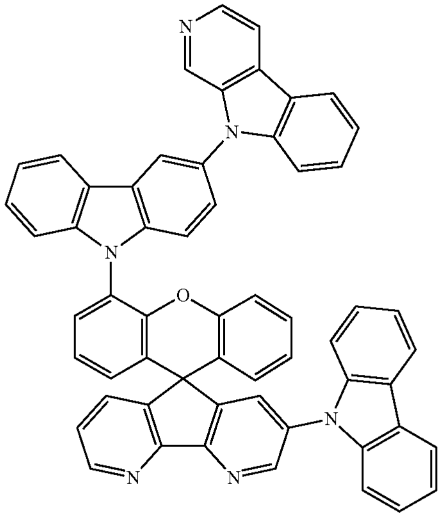
620
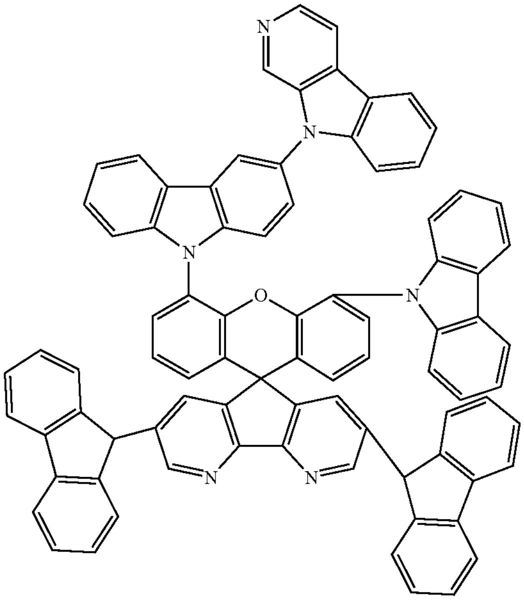
621
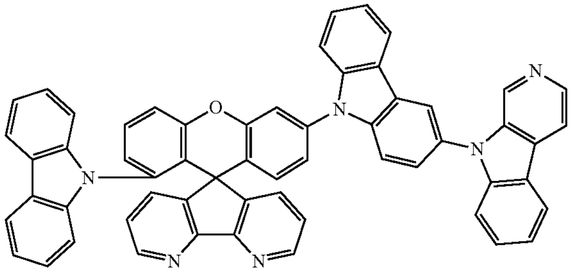
622
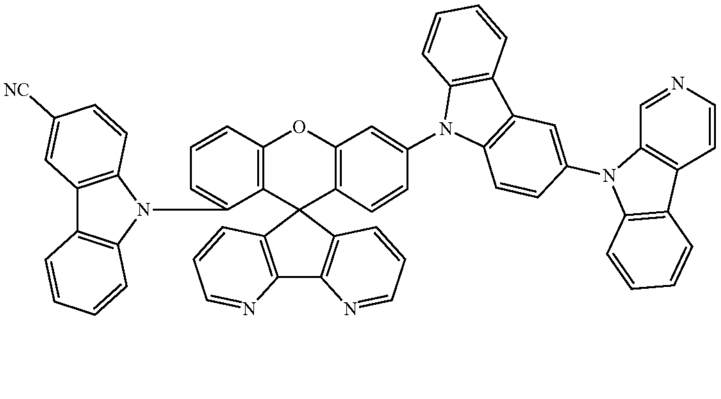

-continued
623
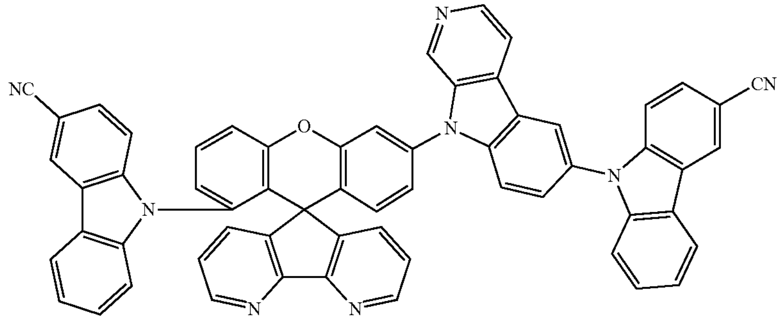
624
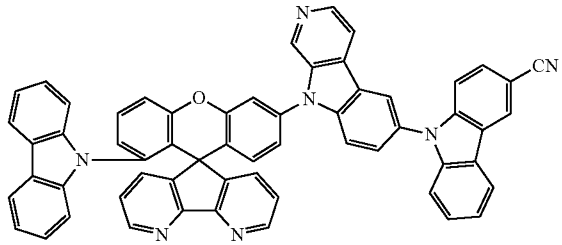
625
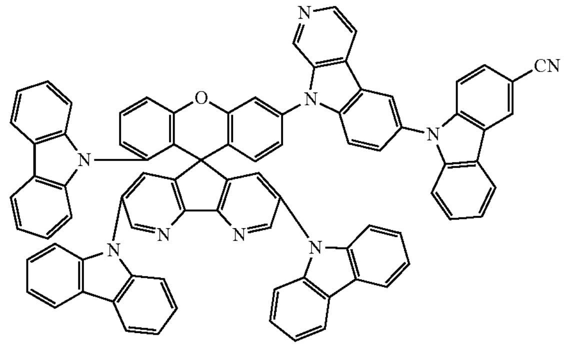
626
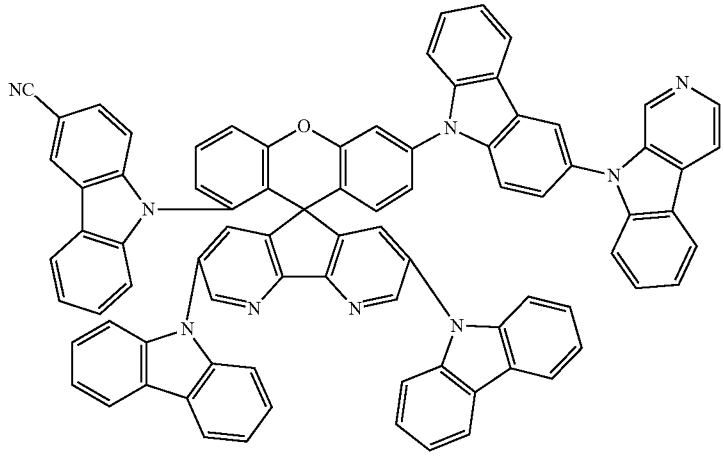
627
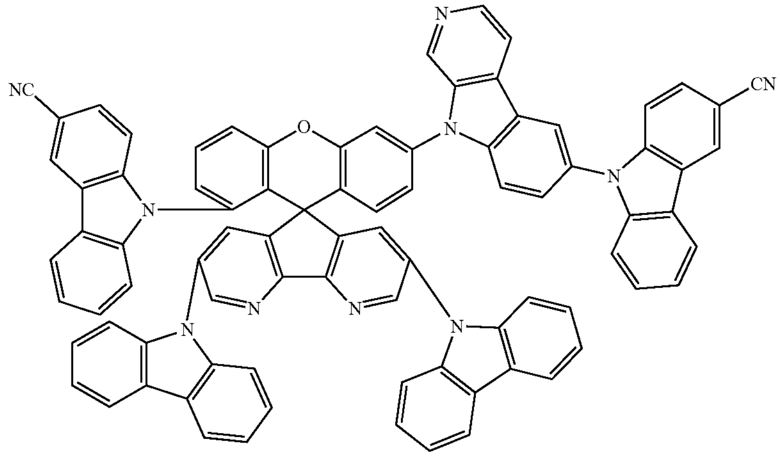

-continued
628
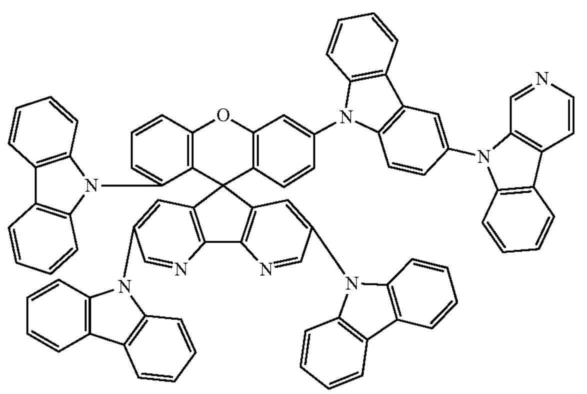
629
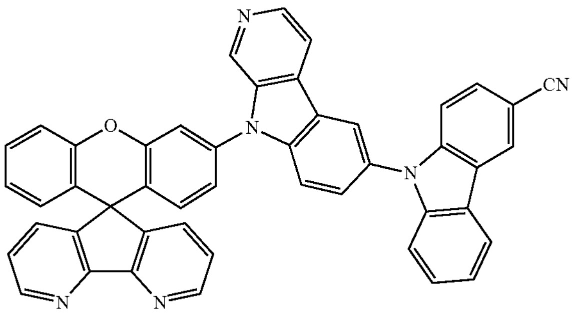
630
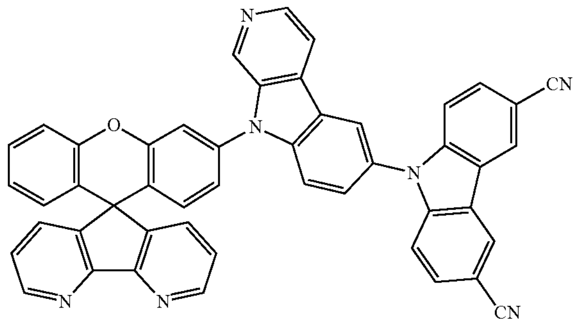
631
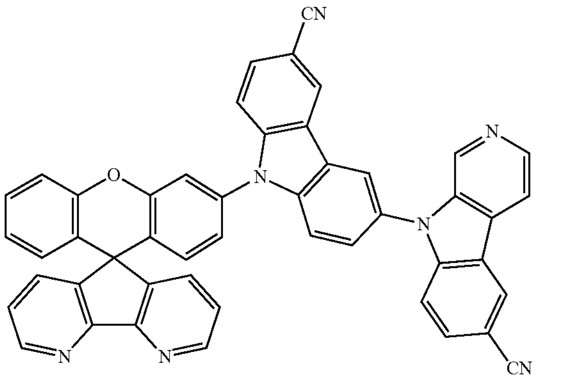
632
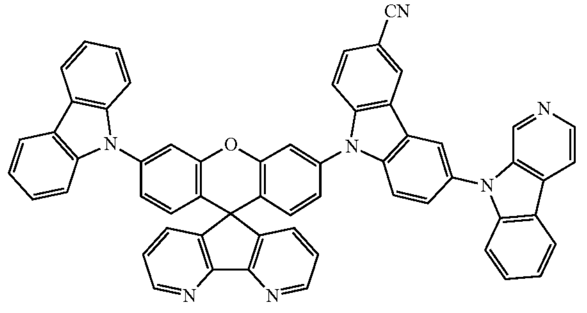
633
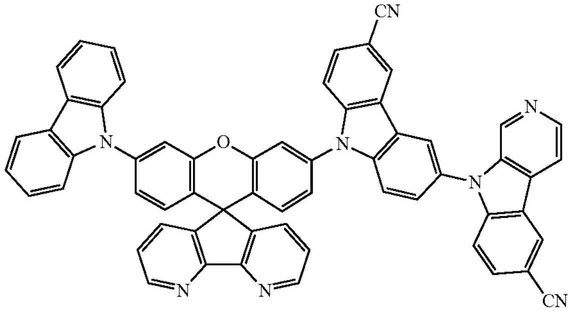
634
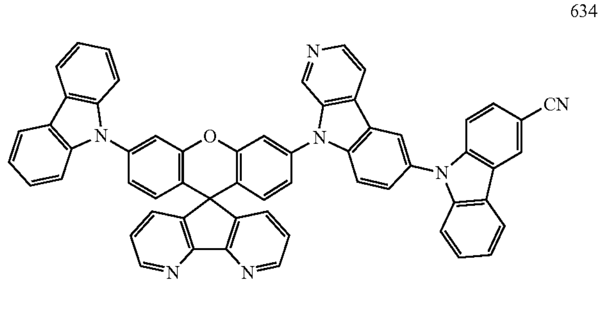
635
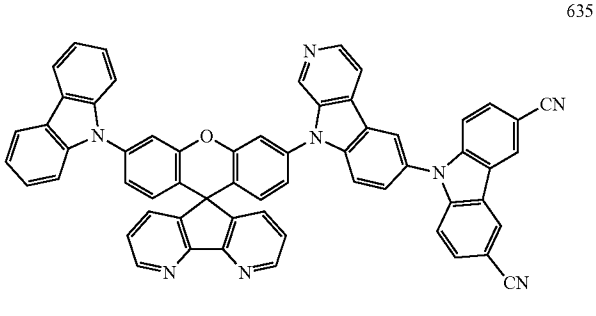

-continued
636
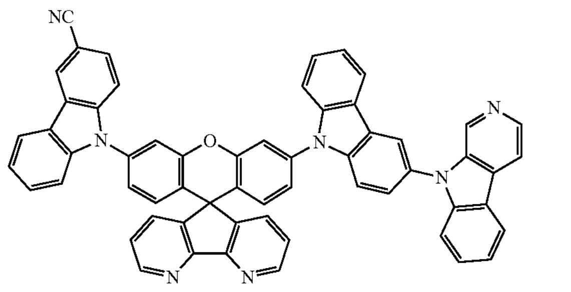
637
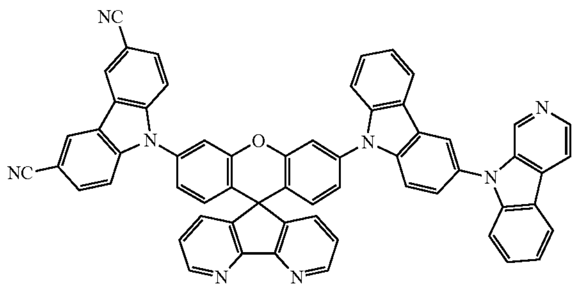
638
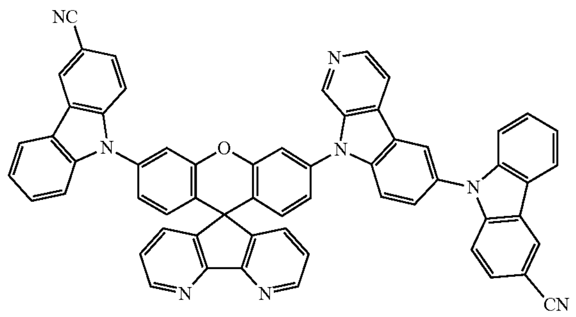
639
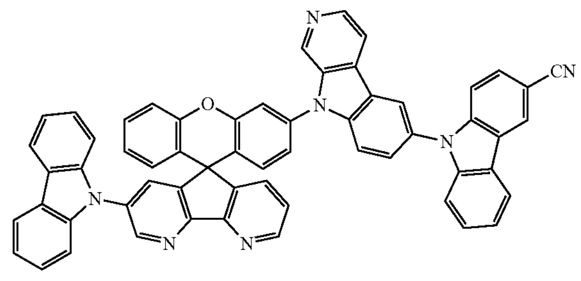
640
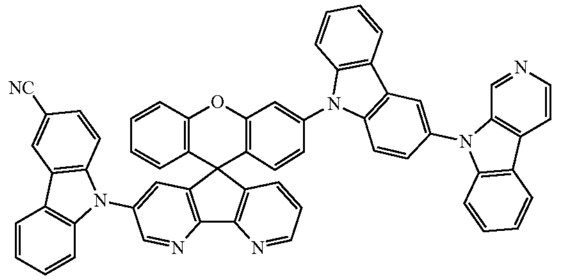
41
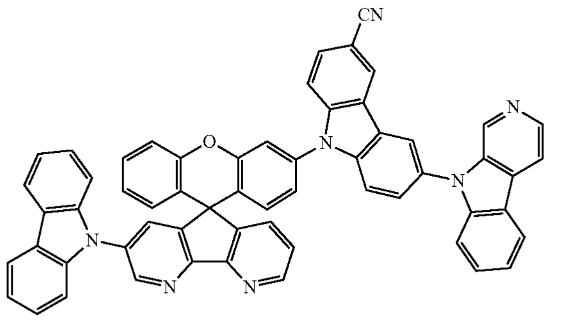
642
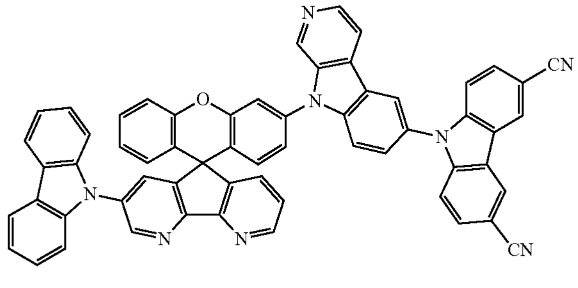
643
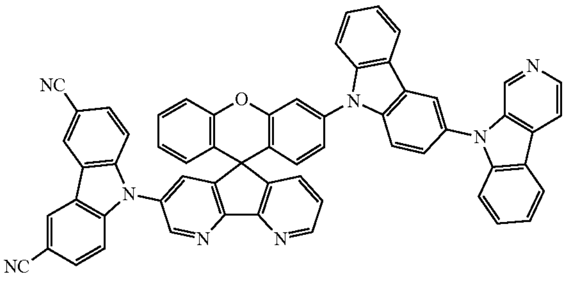
644
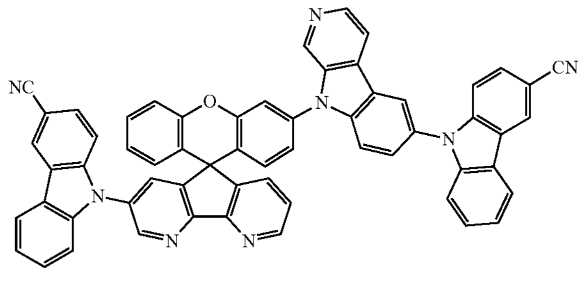
645
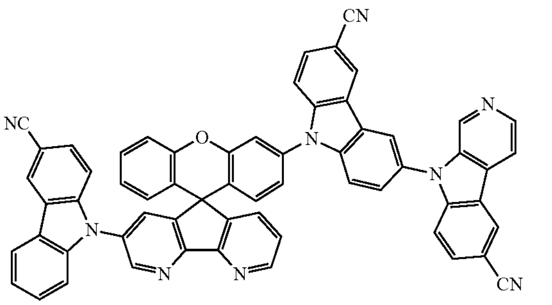

-continued
646
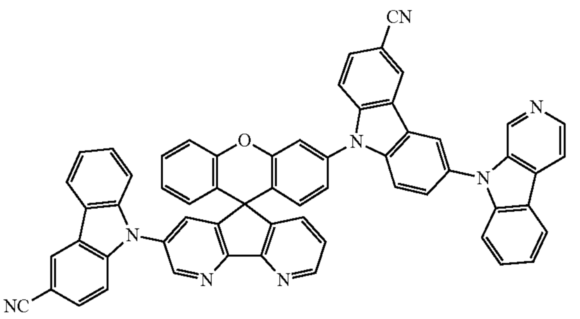
647
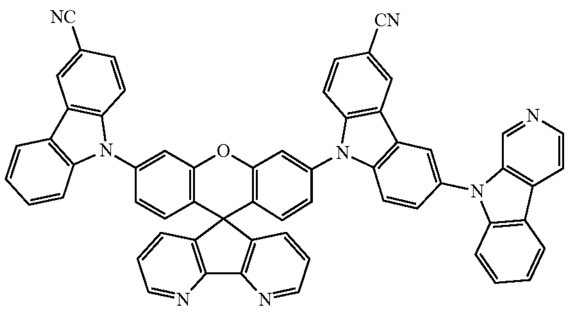
648
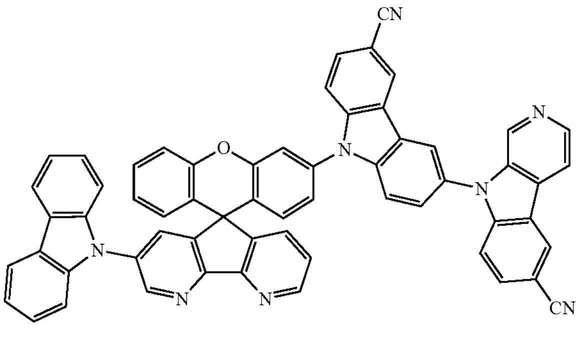
649
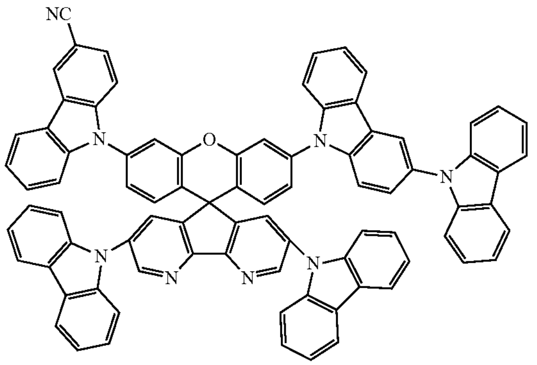
650
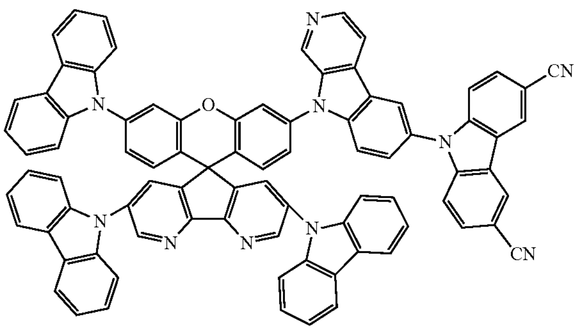
651
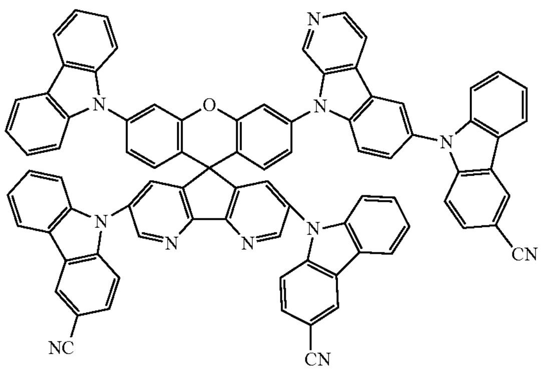
652
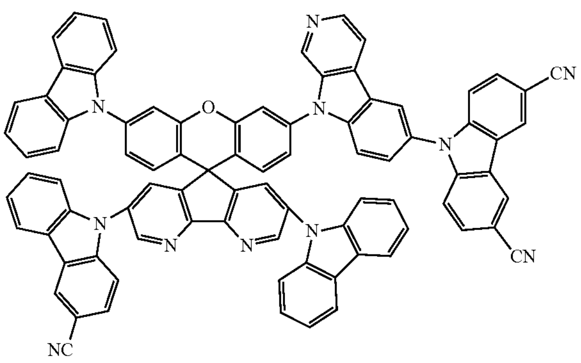
653
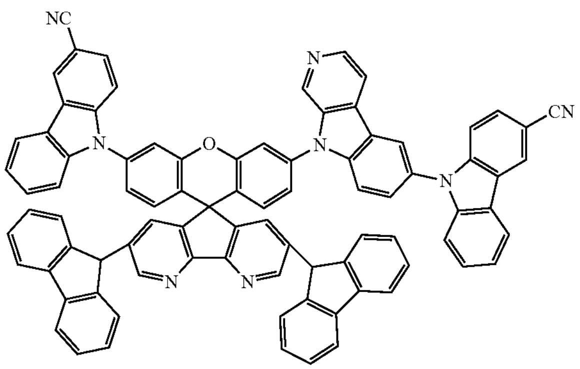

-continued
654
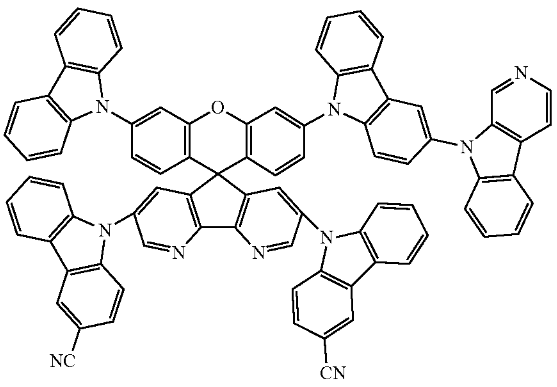
655
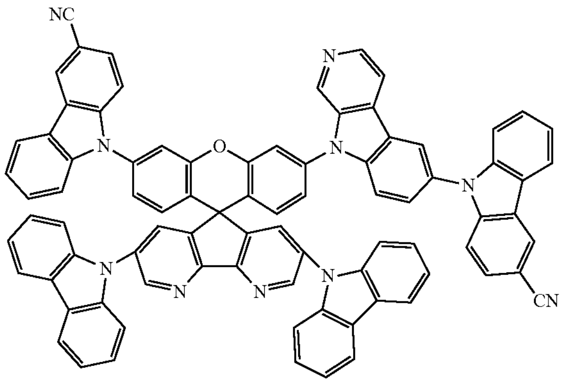
656
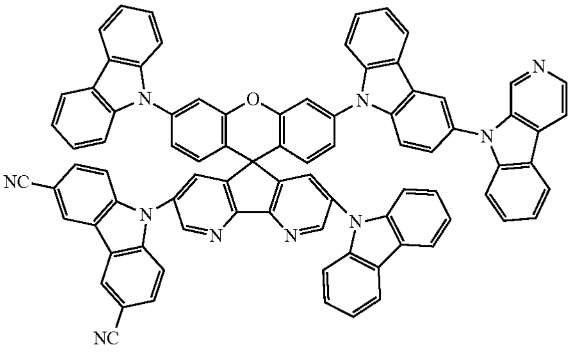
657
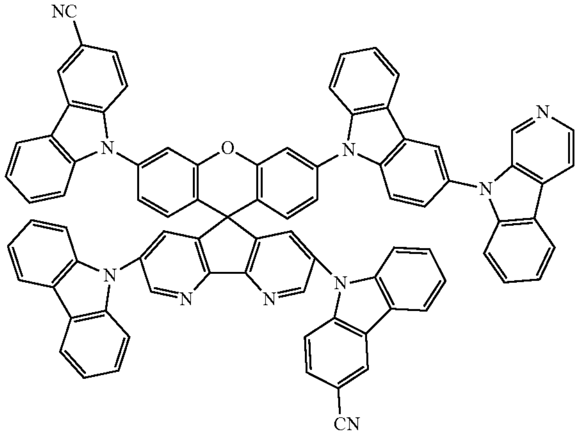
658
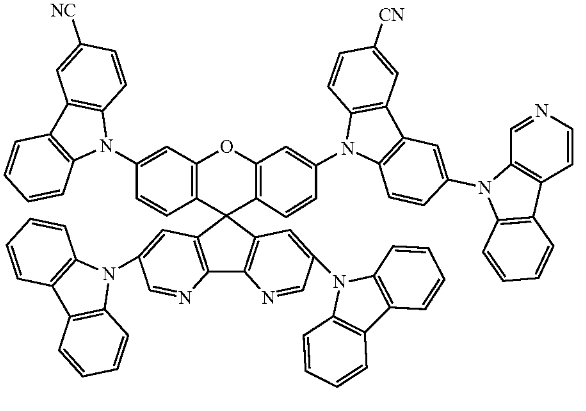
659
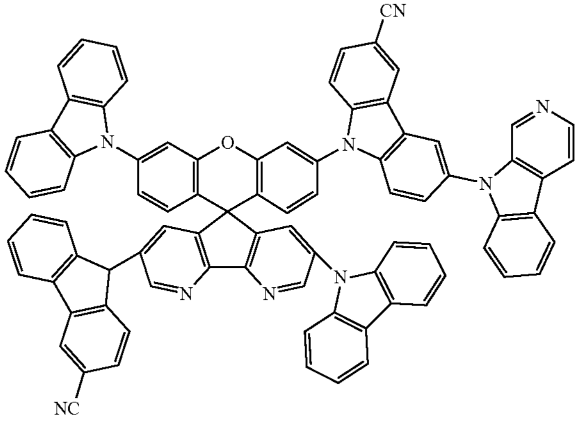

-continued
660
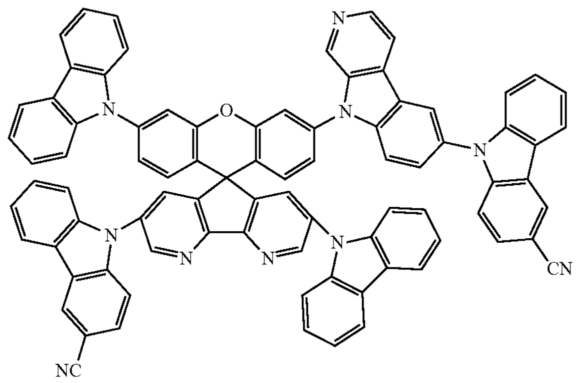
661
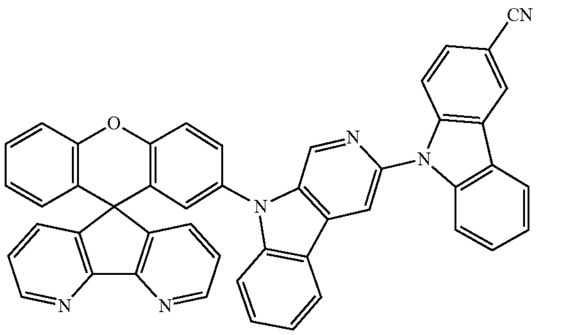
662
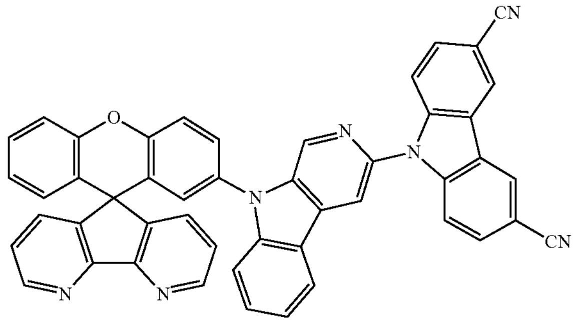
663
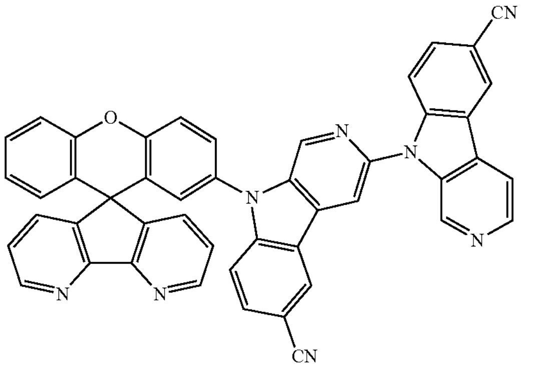
664
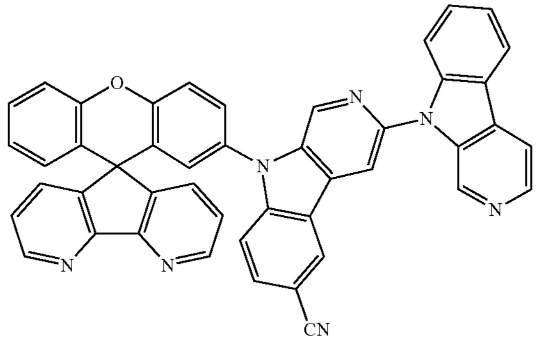
665
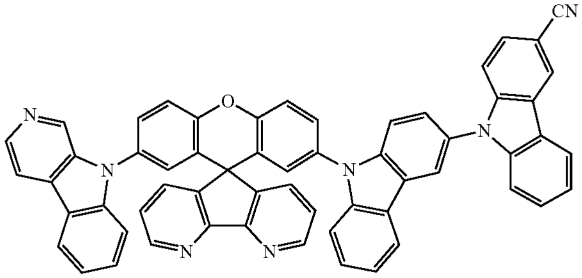
666
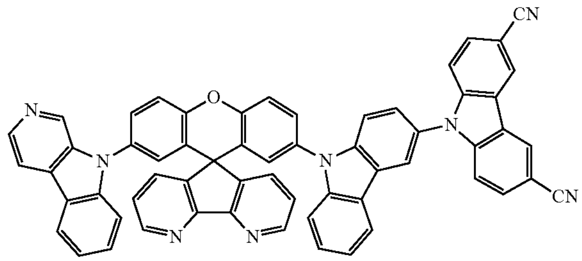
667
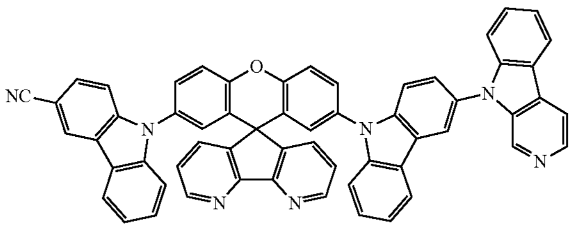

-continued
668
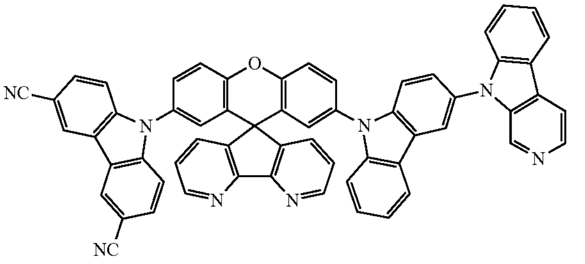
669
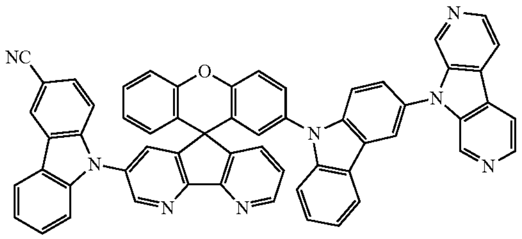
670
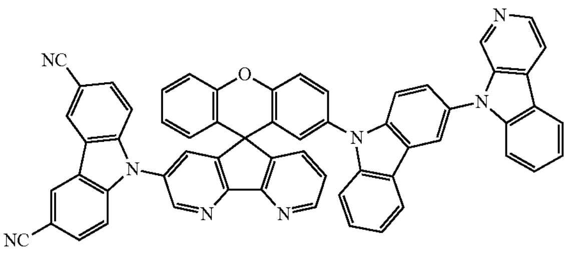
671
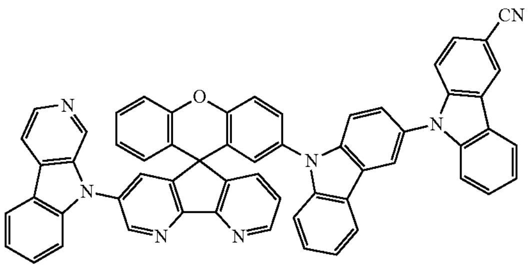
672
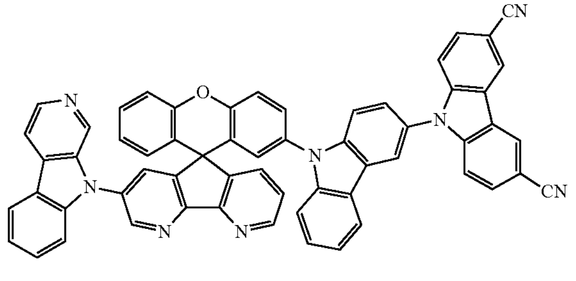
673
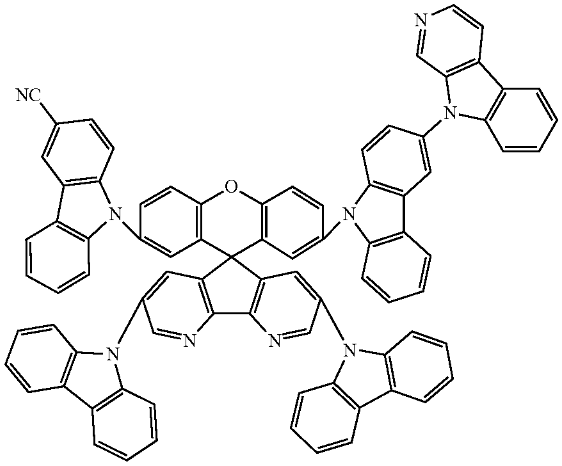
674
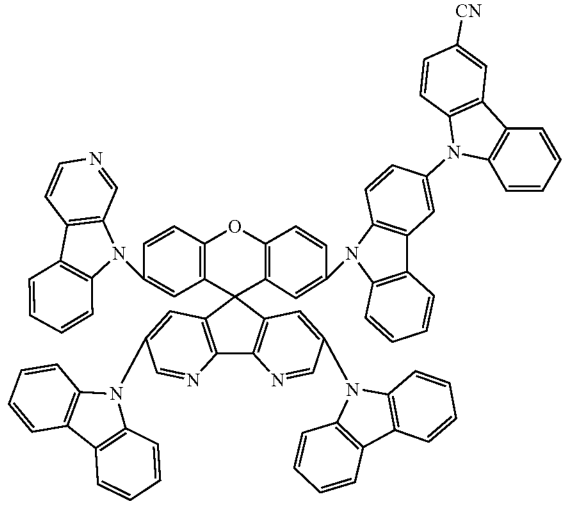
675
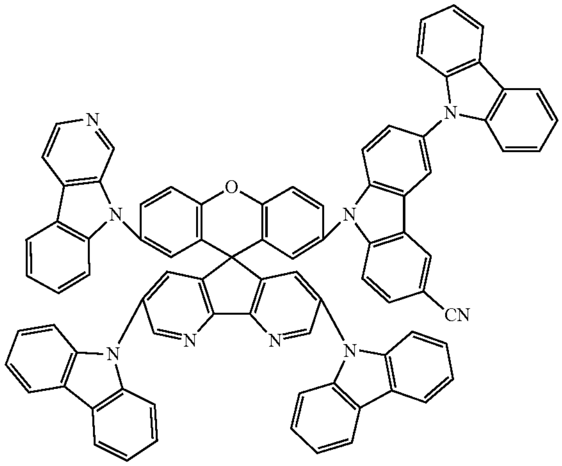

-continued
676
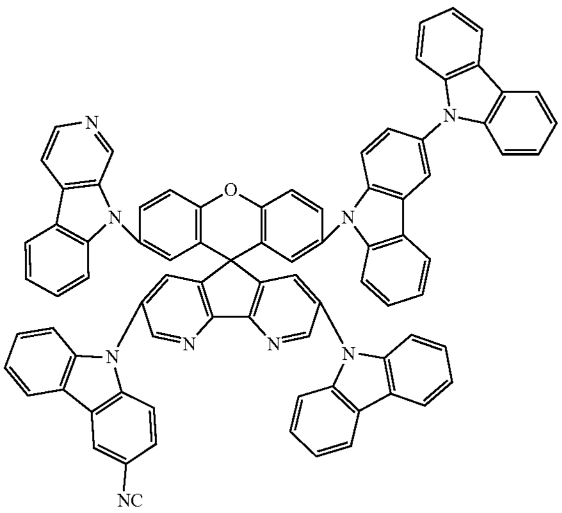
677
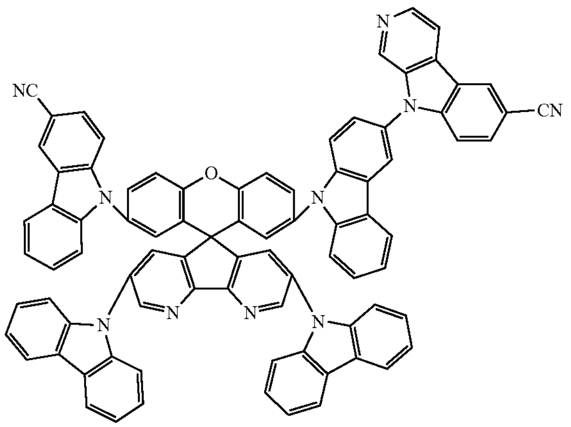
678
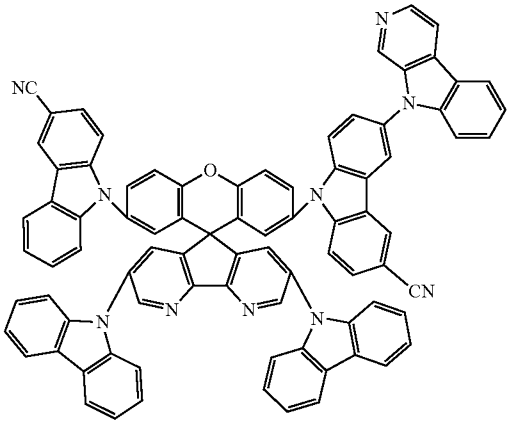
679
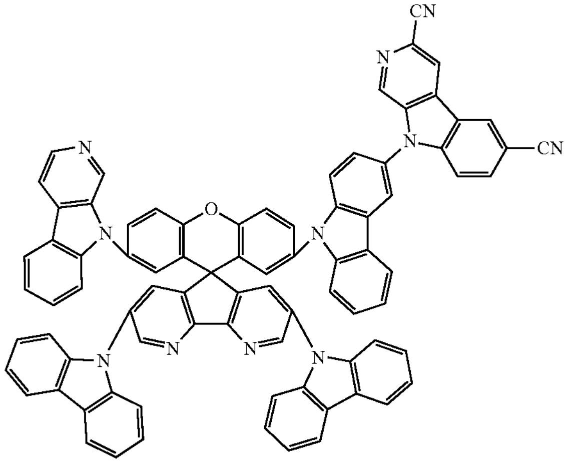
680
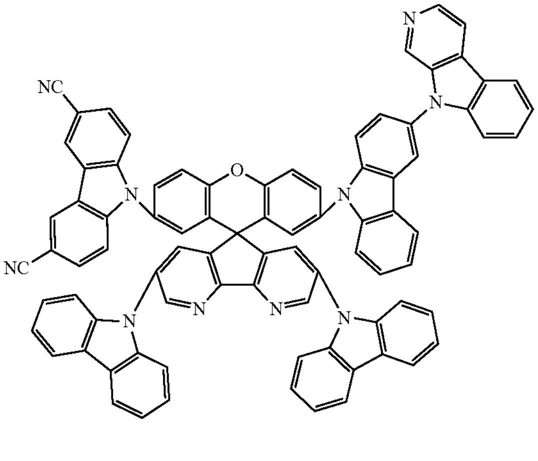
681
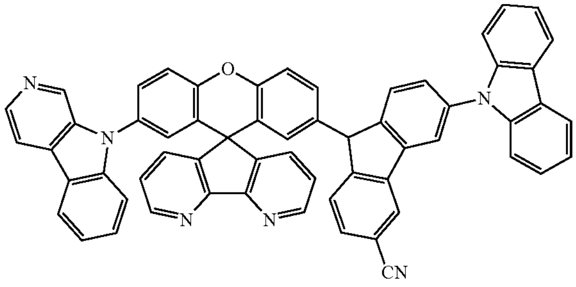

-continued
682
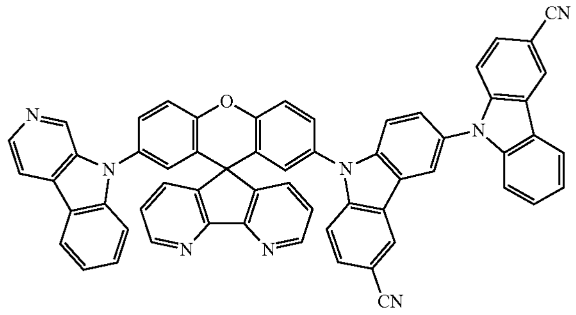
683
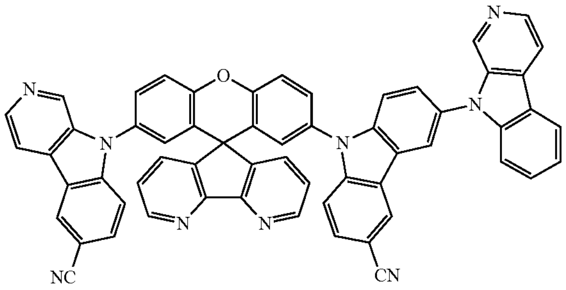
684
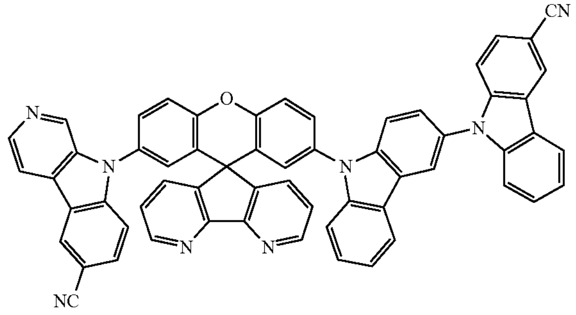
685
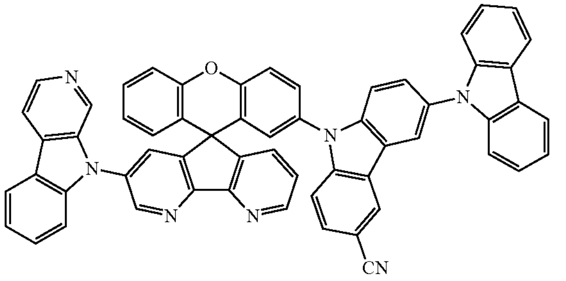
686
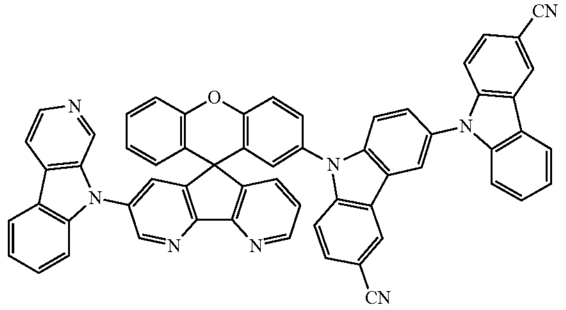
687
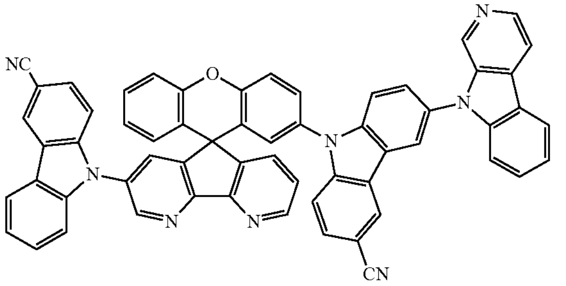
688
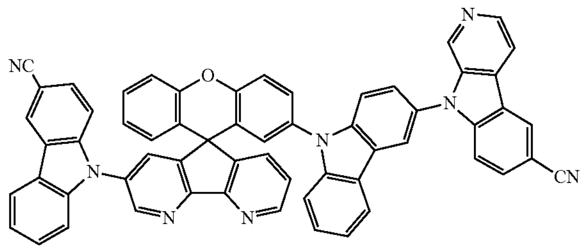
689
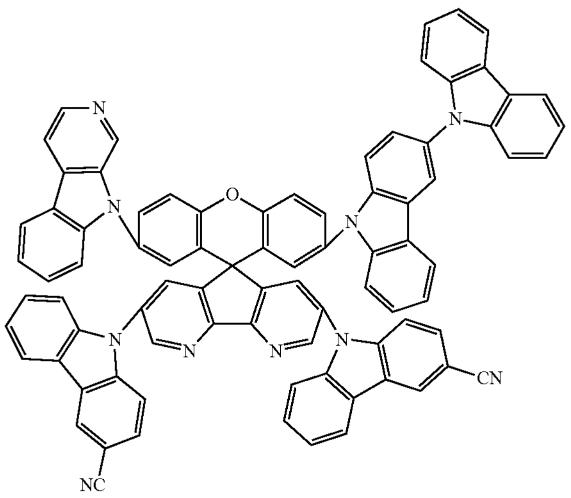

-continued
690
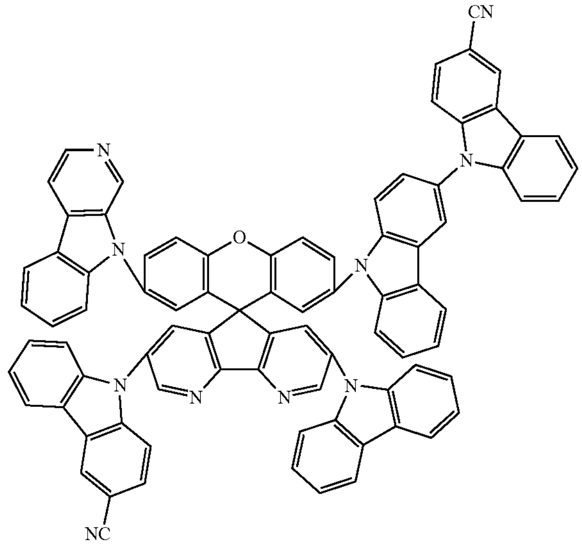
691
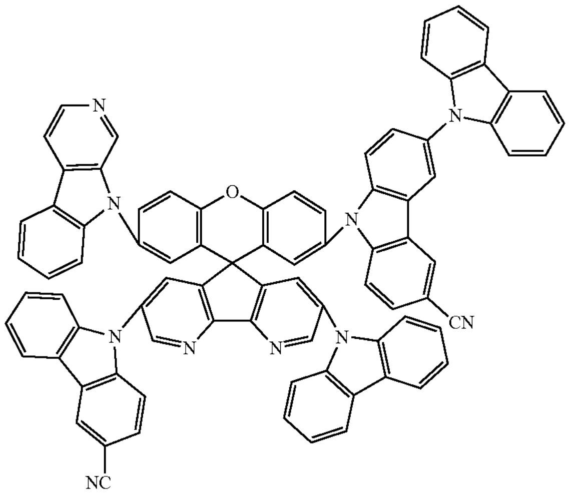
692
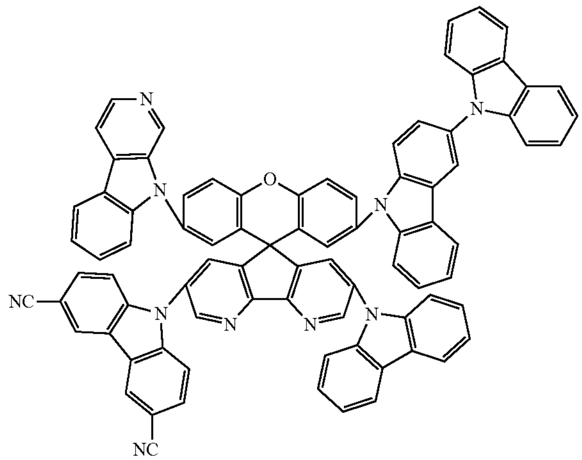
693
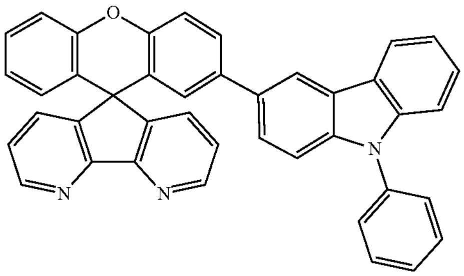
694
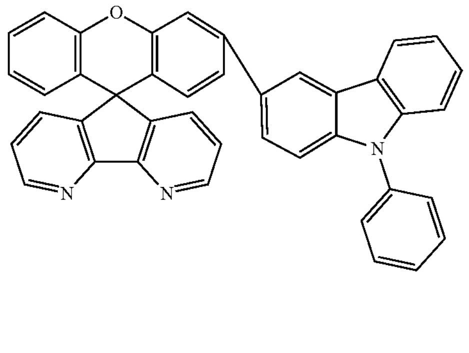
695
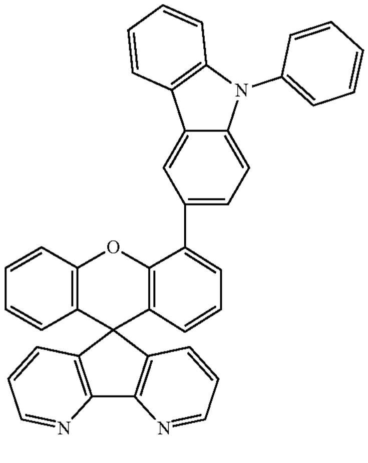

-continued
696
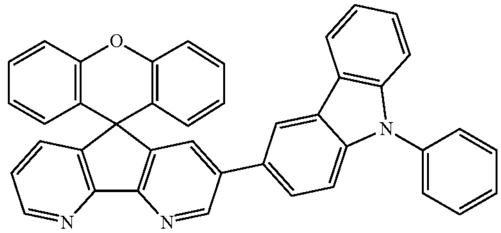
697
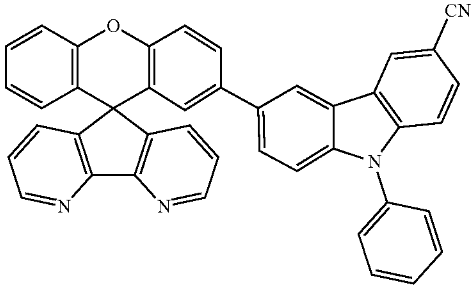
698
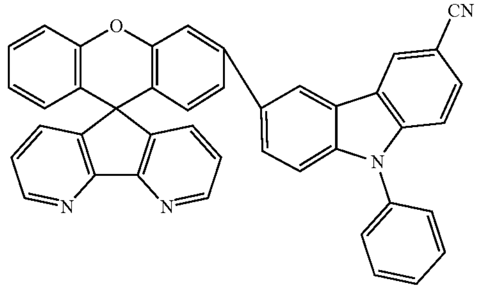
699
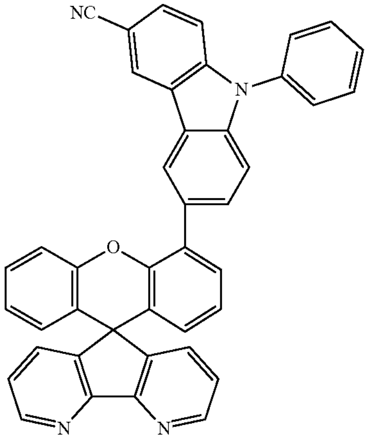
700
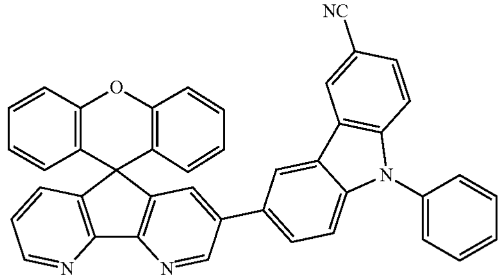
701
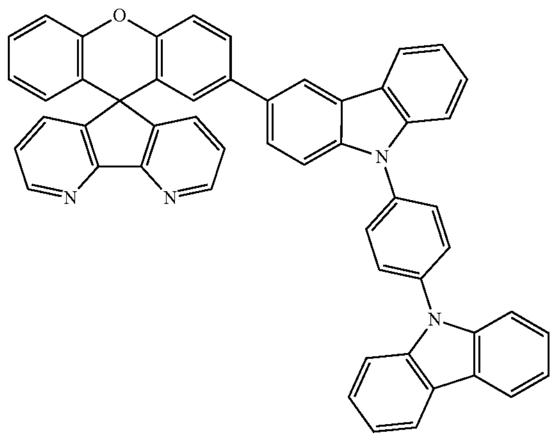
702
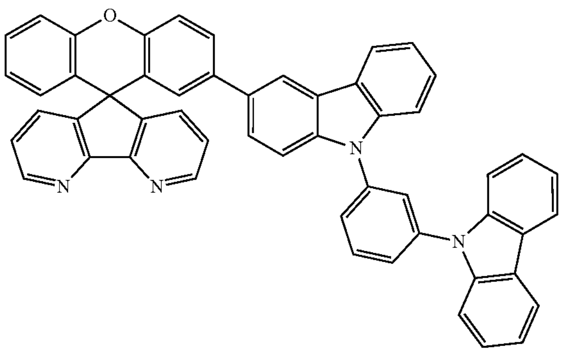

-continued
703
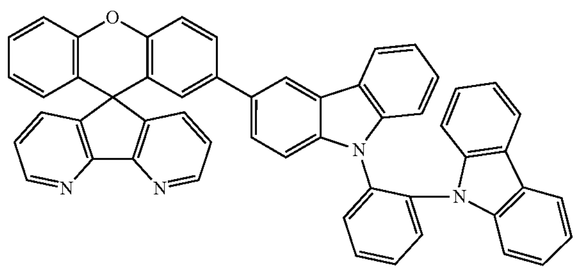
704
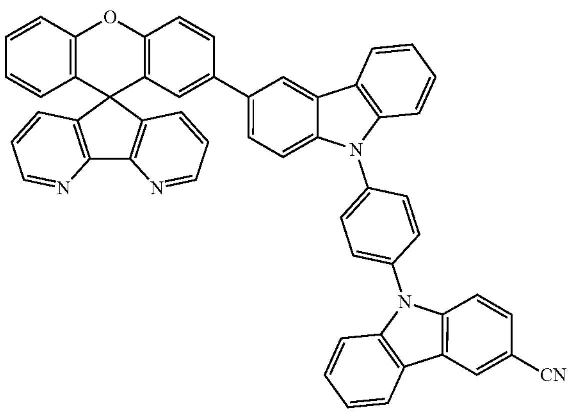
705
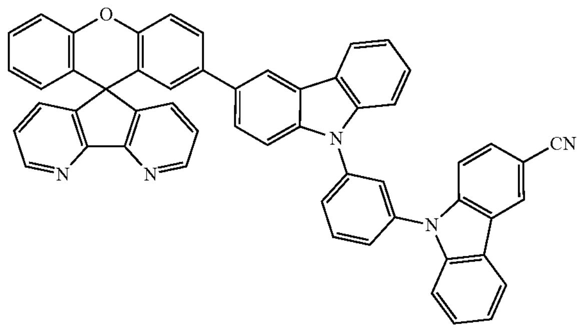
706
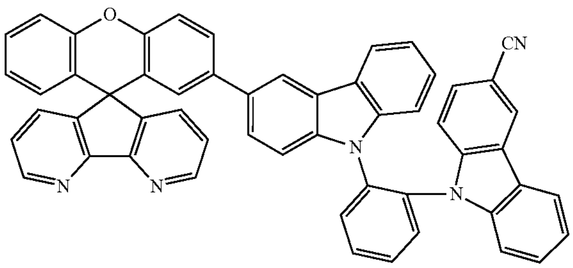
707
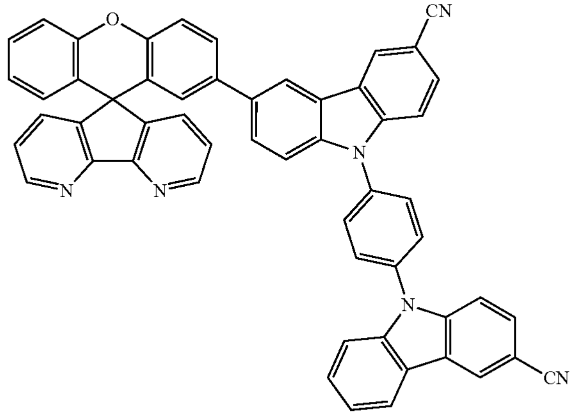
708
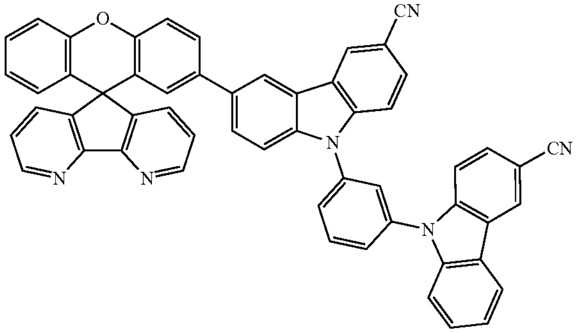

-continued
709
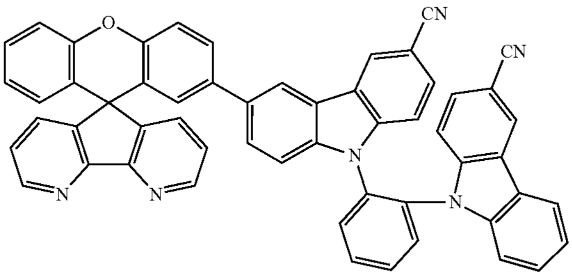
710
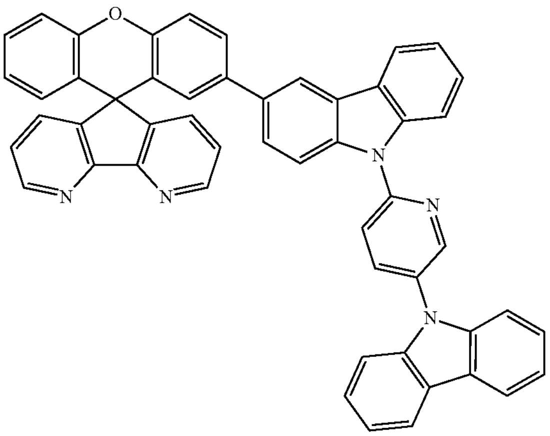
711
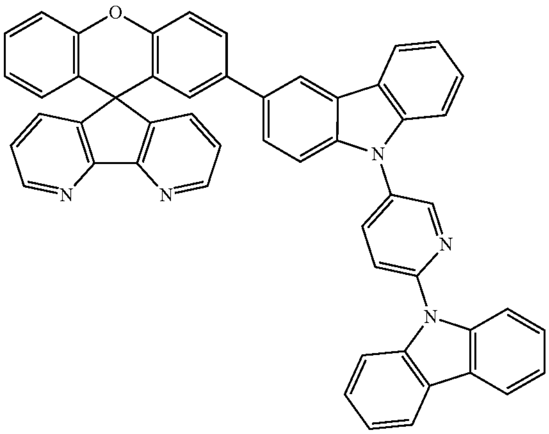
712
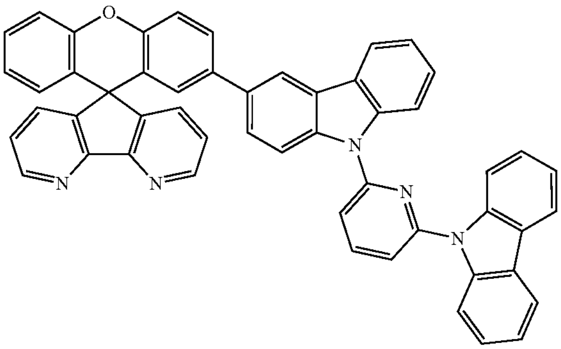
713
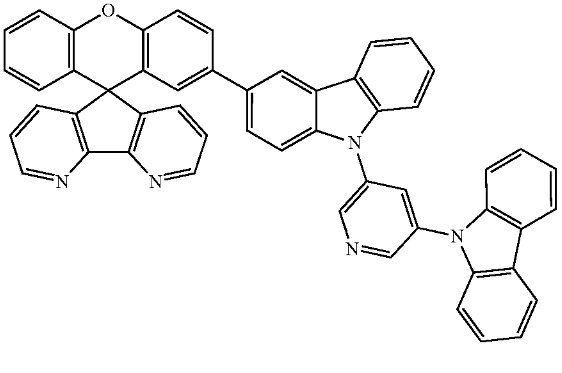
714
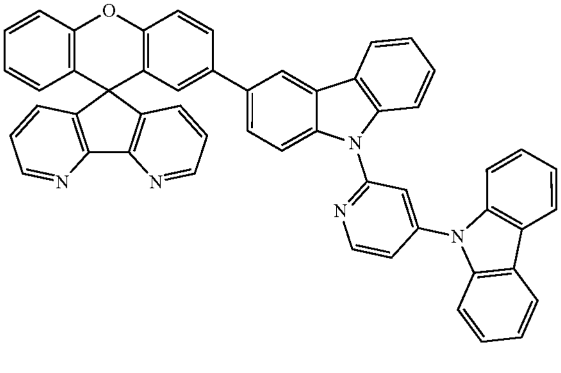
715
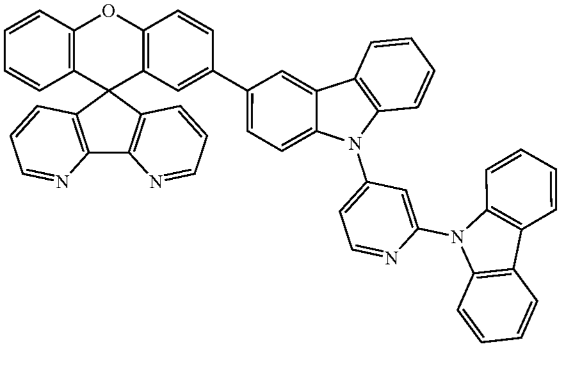
716
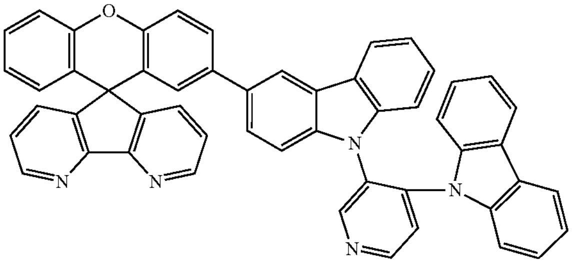

-continued
717
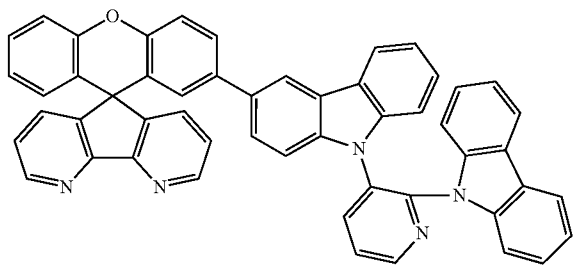
718
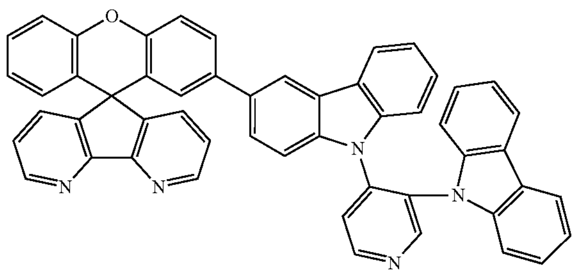
719
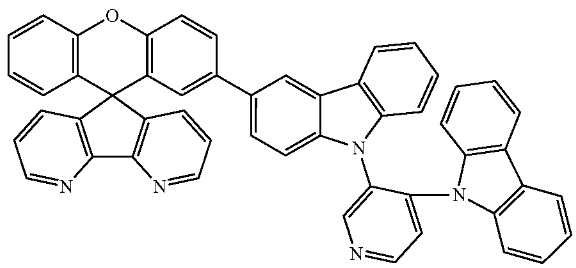
720
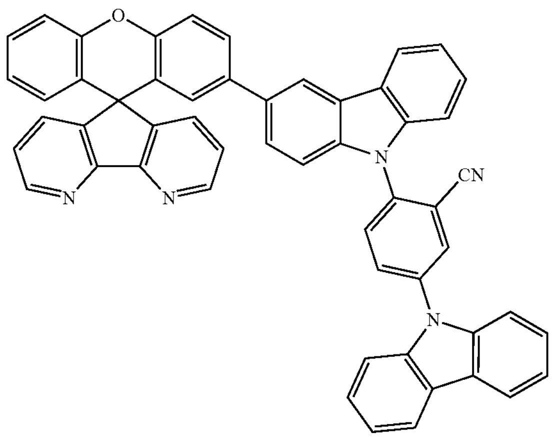
721
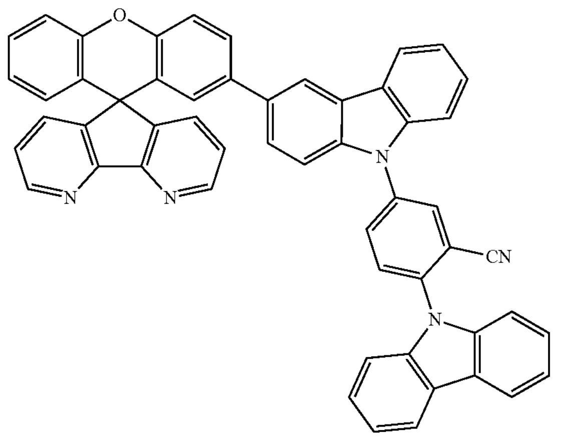
722
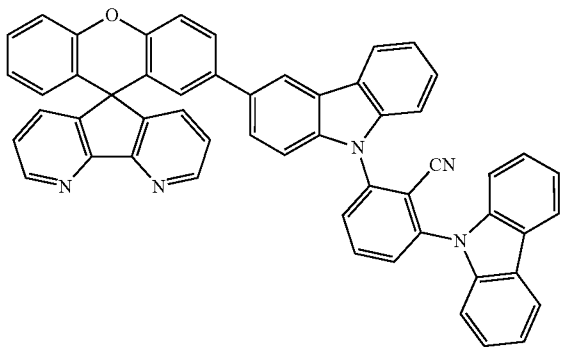
723
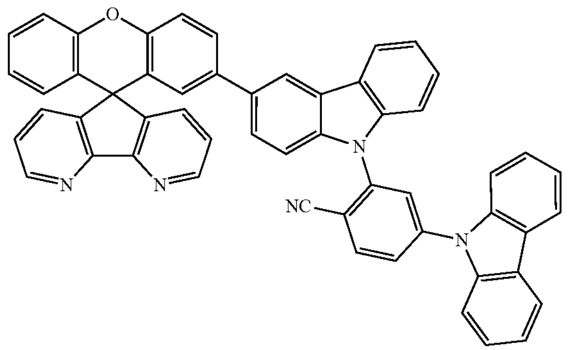
724
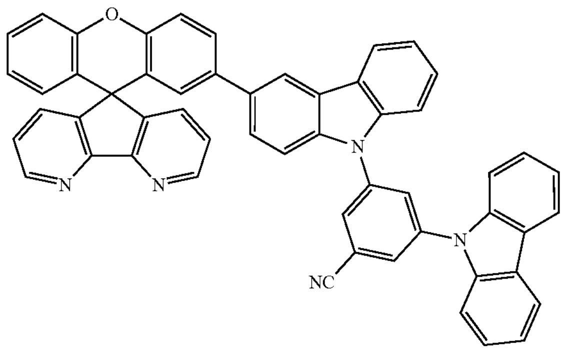

-continued
725
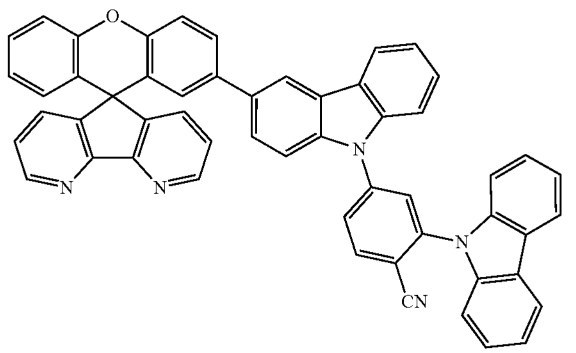
726
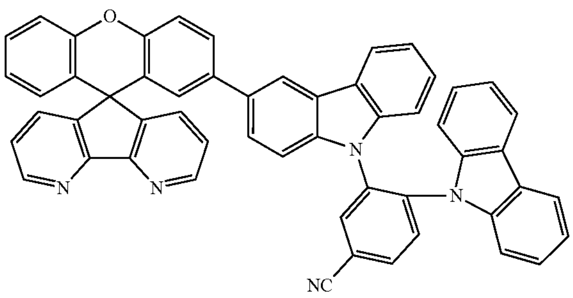
727
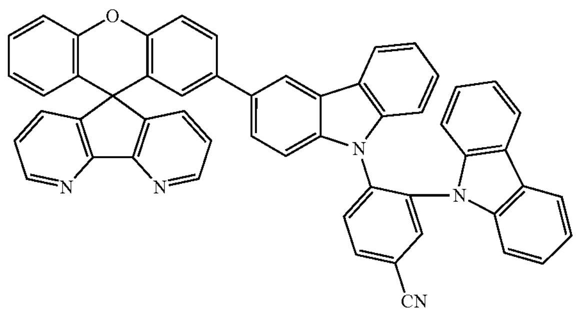
728
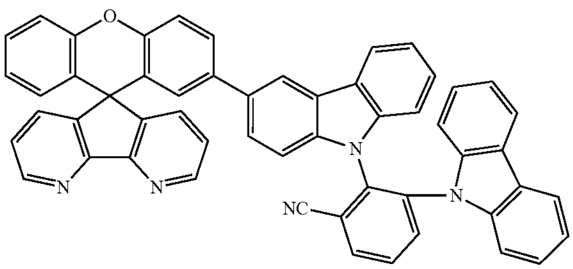
729
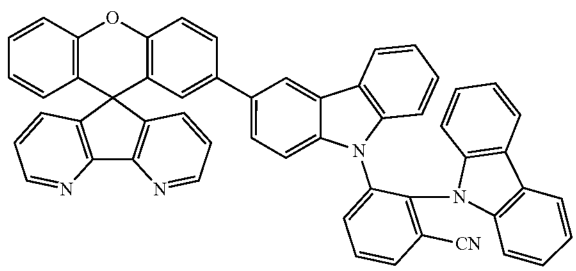
730
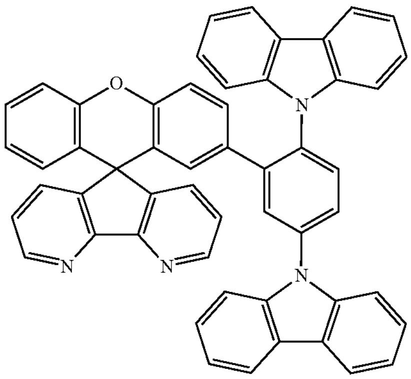
731
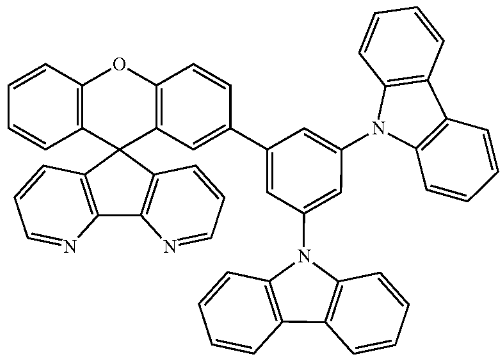
732
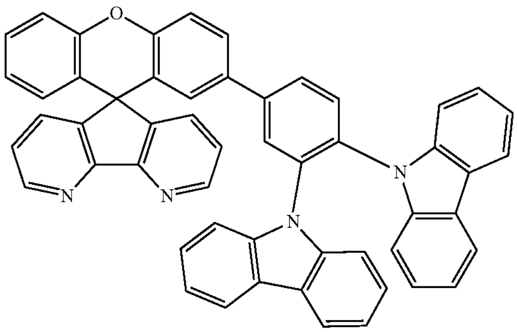

-continued
733
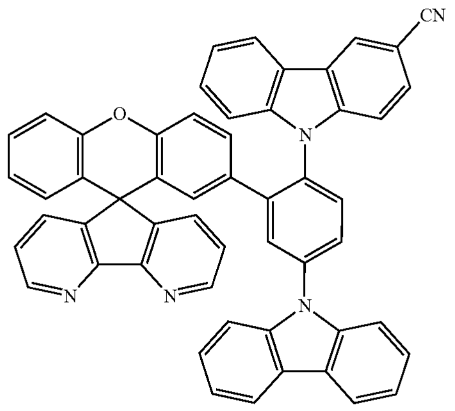
734
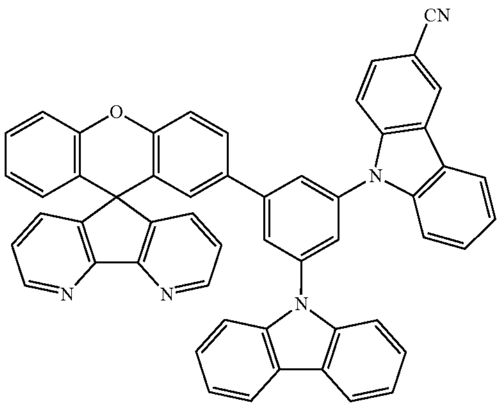
735
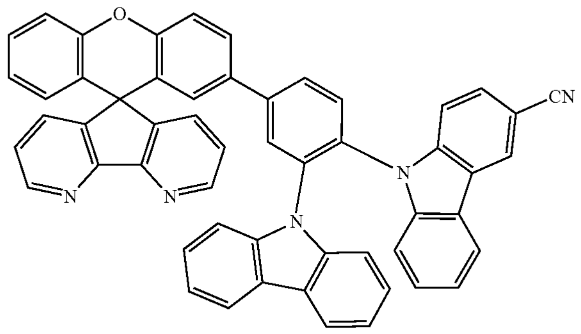
736
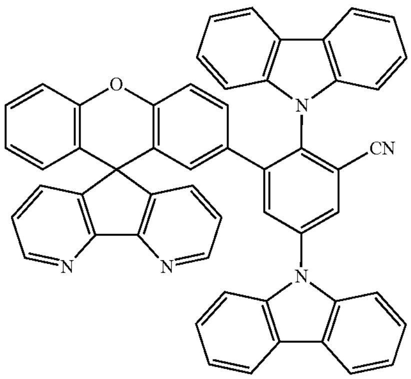
737
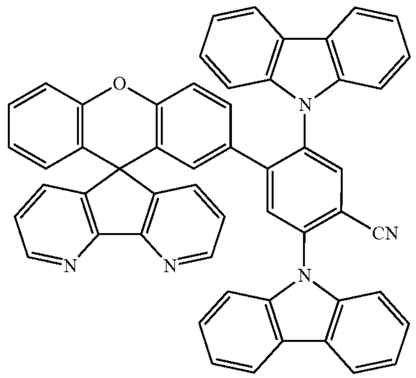
738
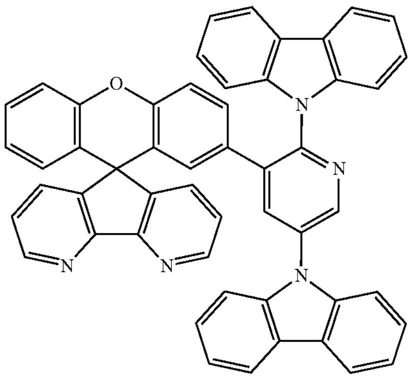
739
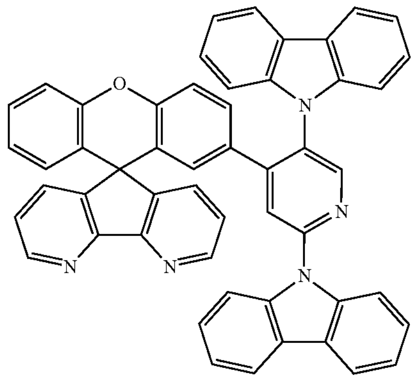
740
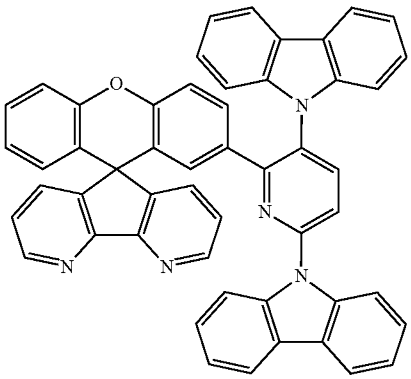

-continued
741
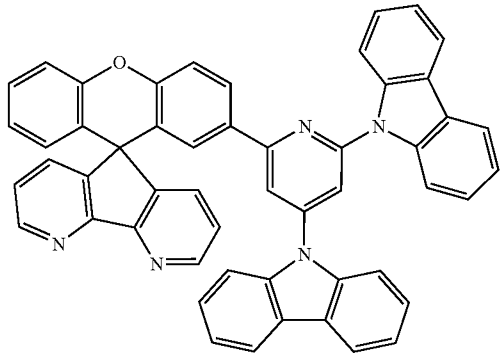
742
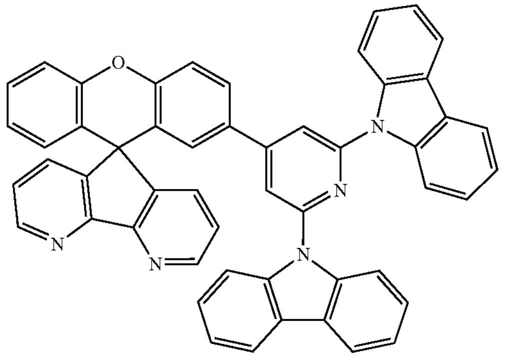
743
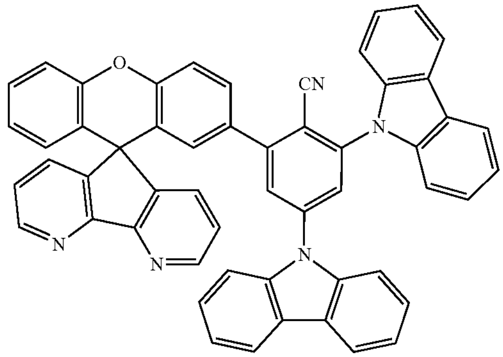
744
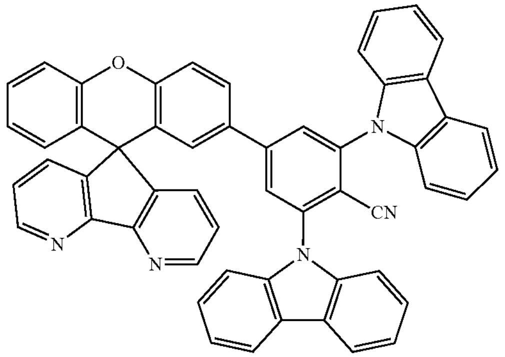
745
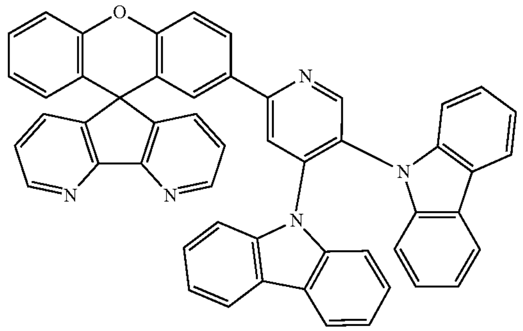
746
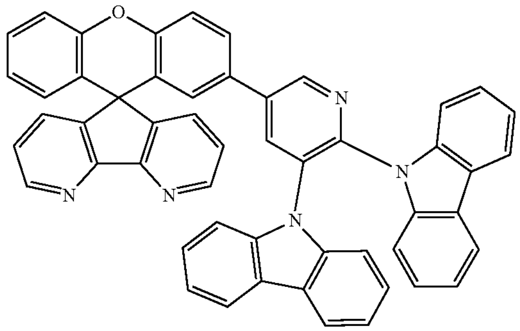
747
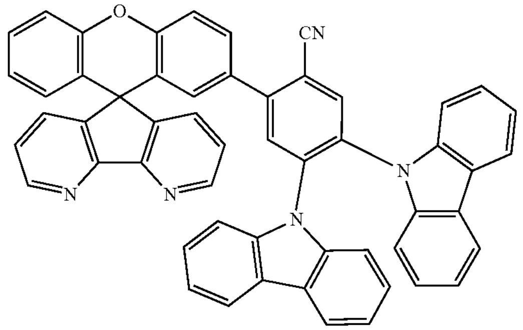
748
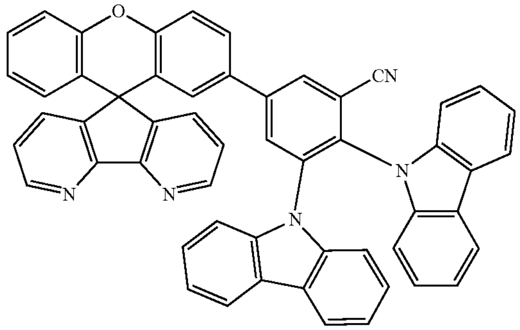

-continued
749
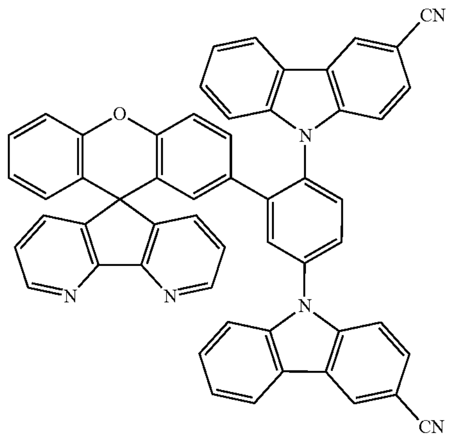
750
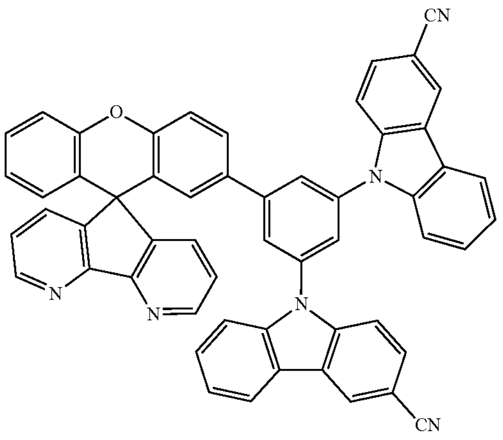
751
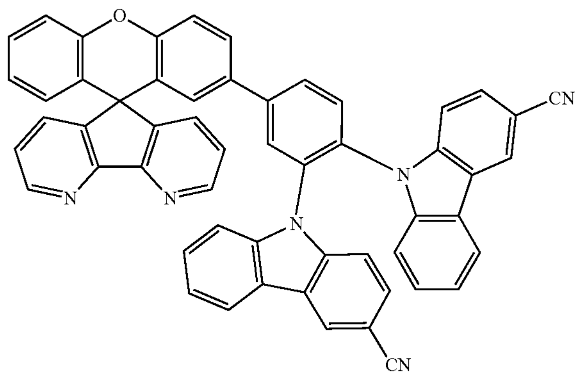
752
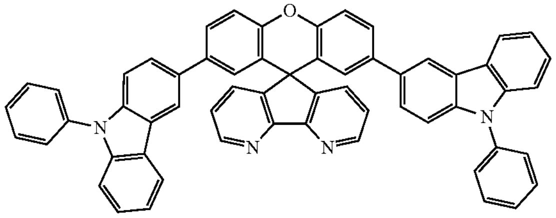
753
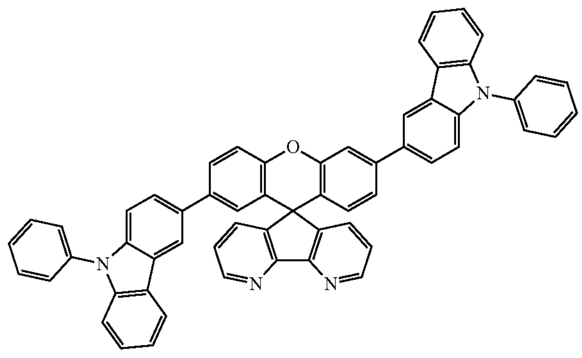
754
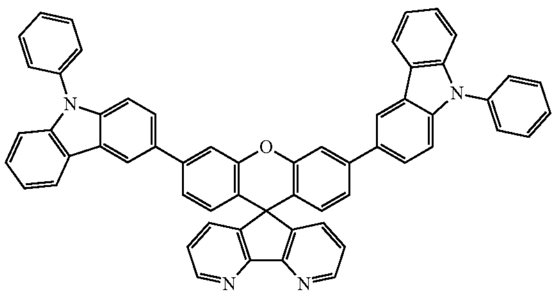

-continued
755
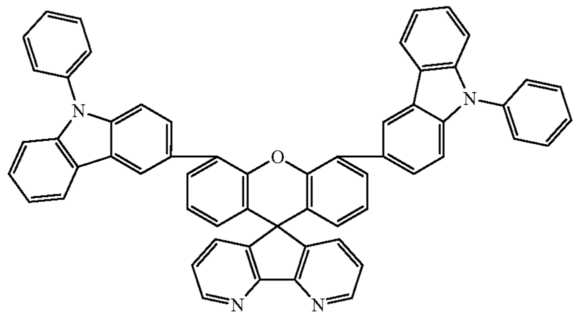
756
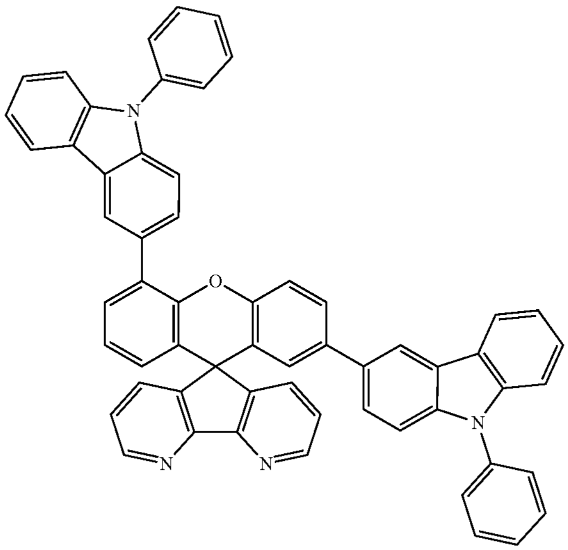
757
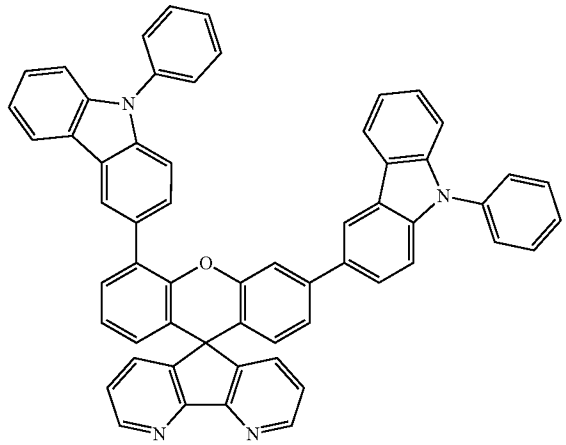
758
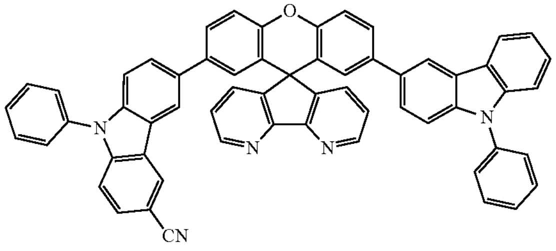
759
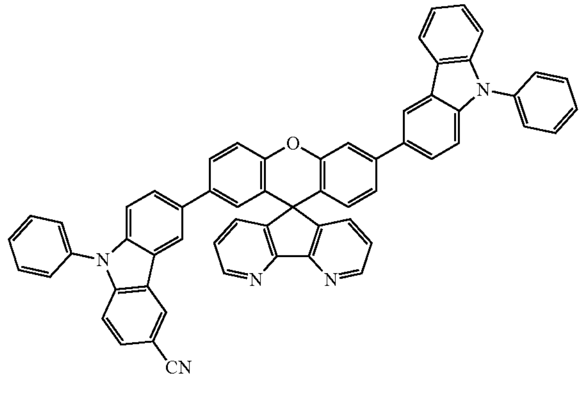
760
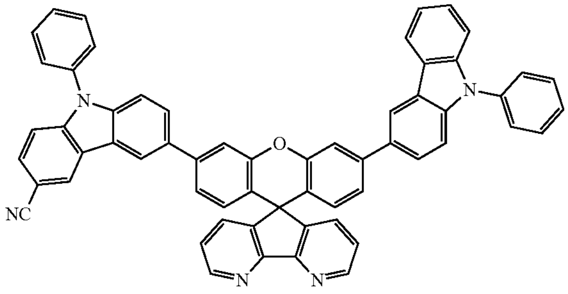

-continued
761
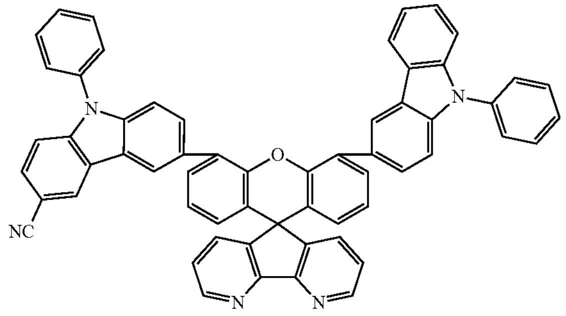
762
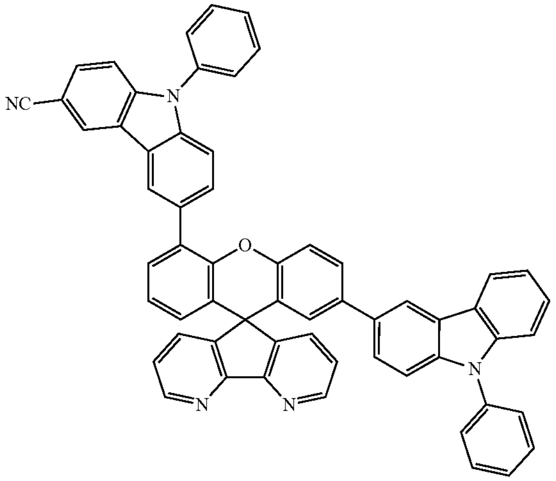
763
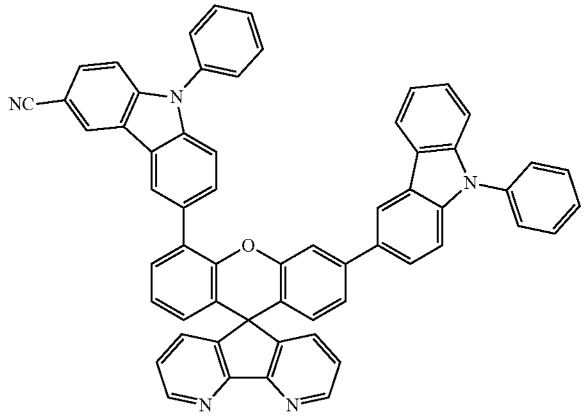
764
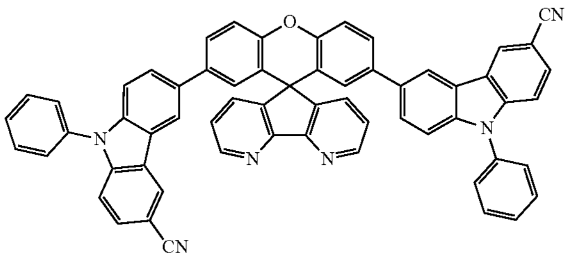
765
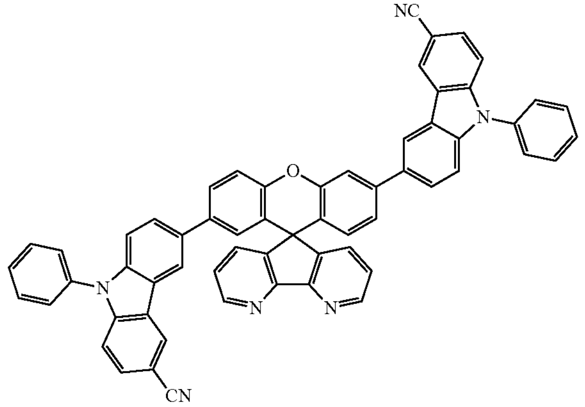
766
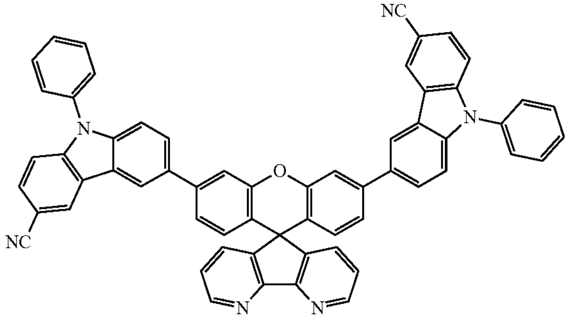

-continued
767
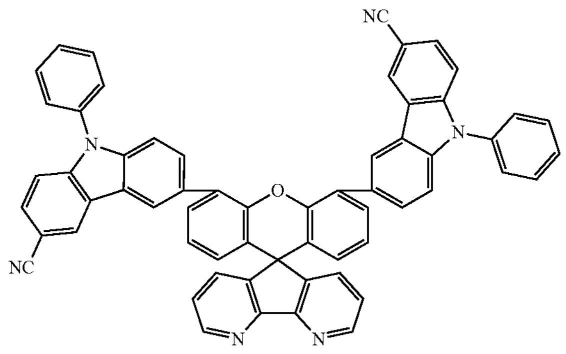
768
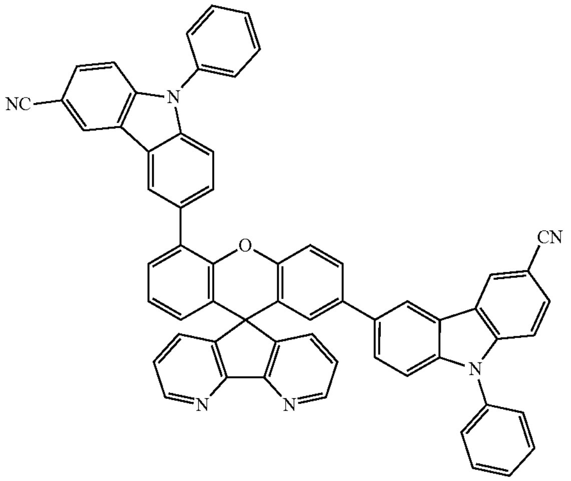
769
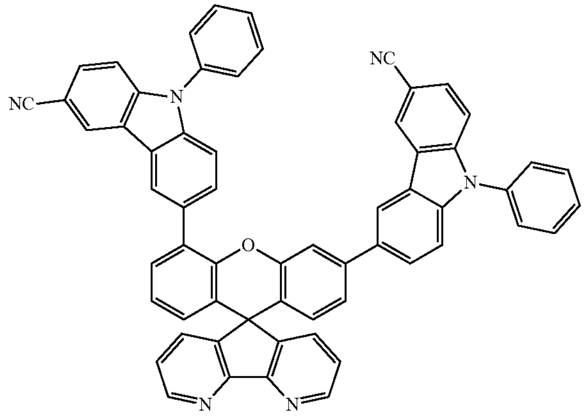
770
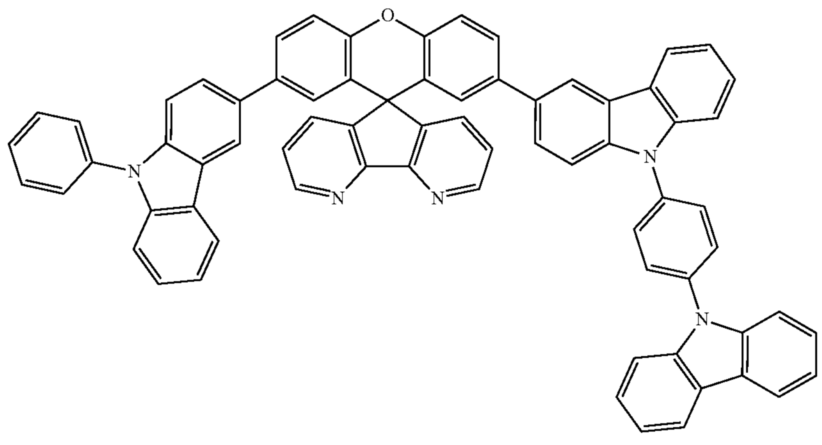

-continued
771
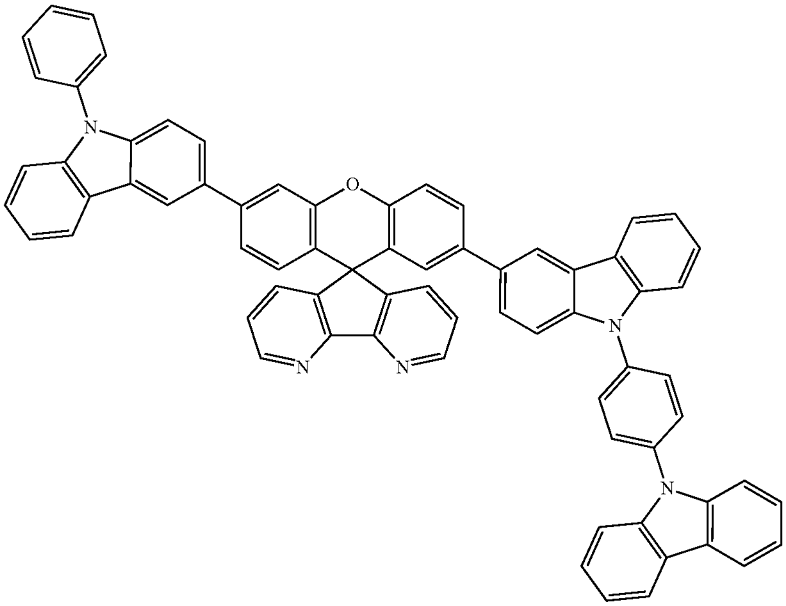
772
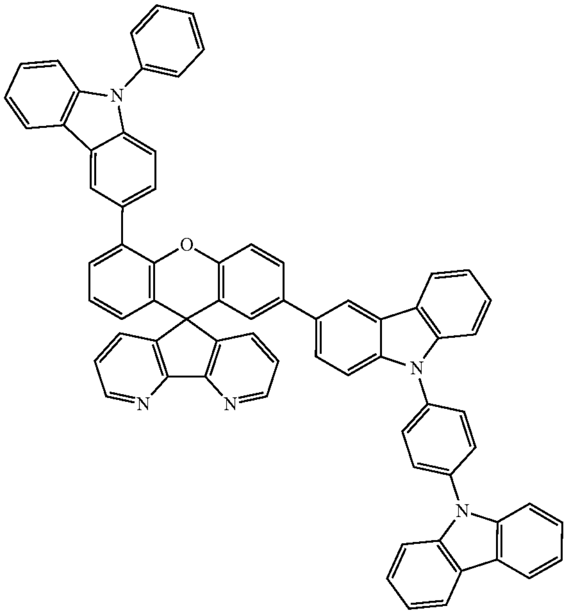

-continued
773
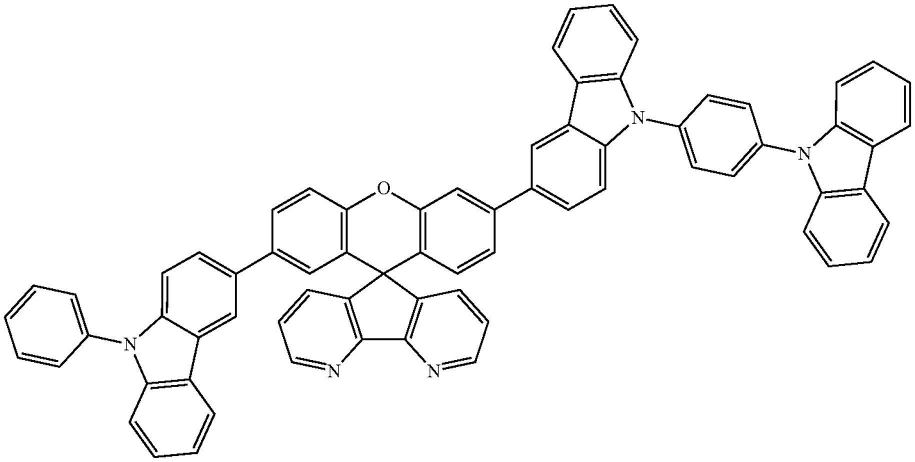
774
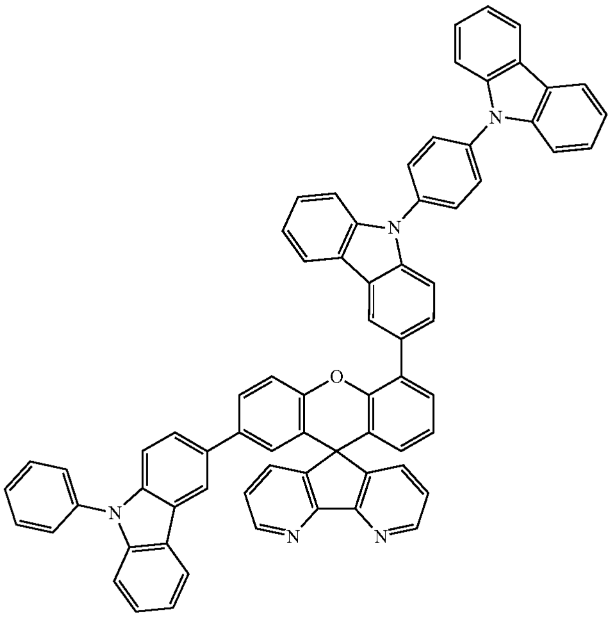
775
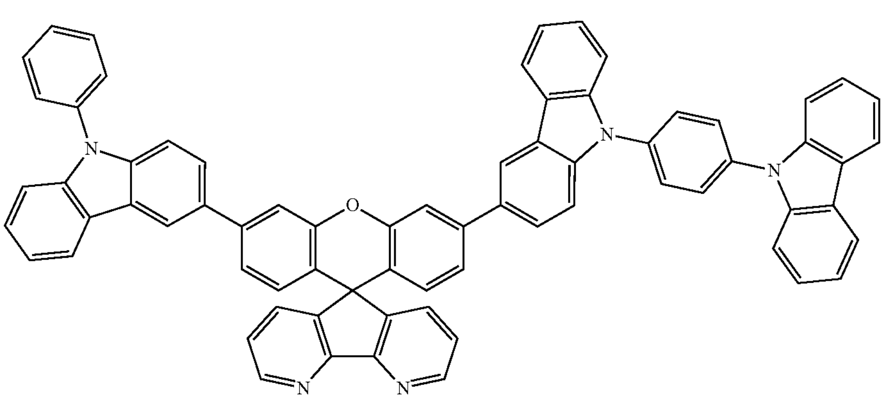

-continued
776
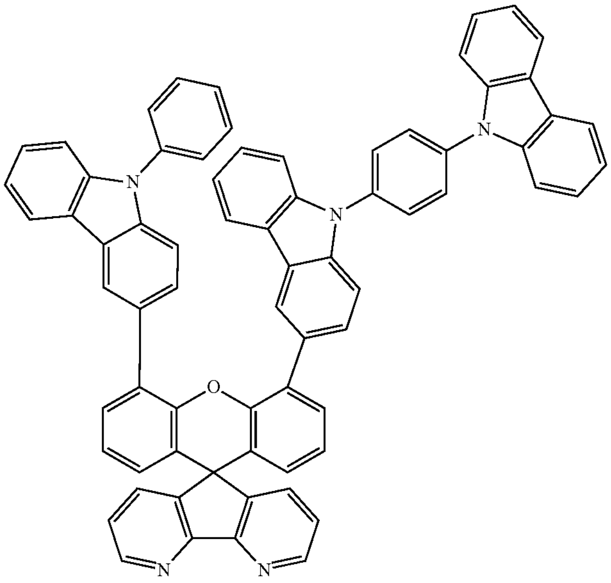
777
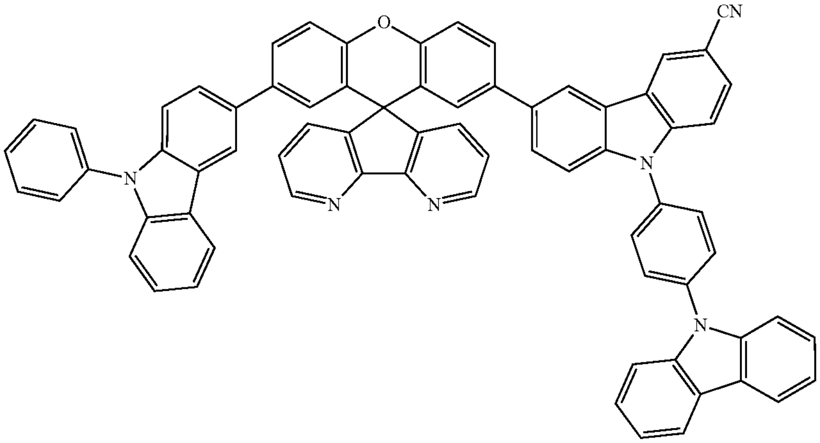
778
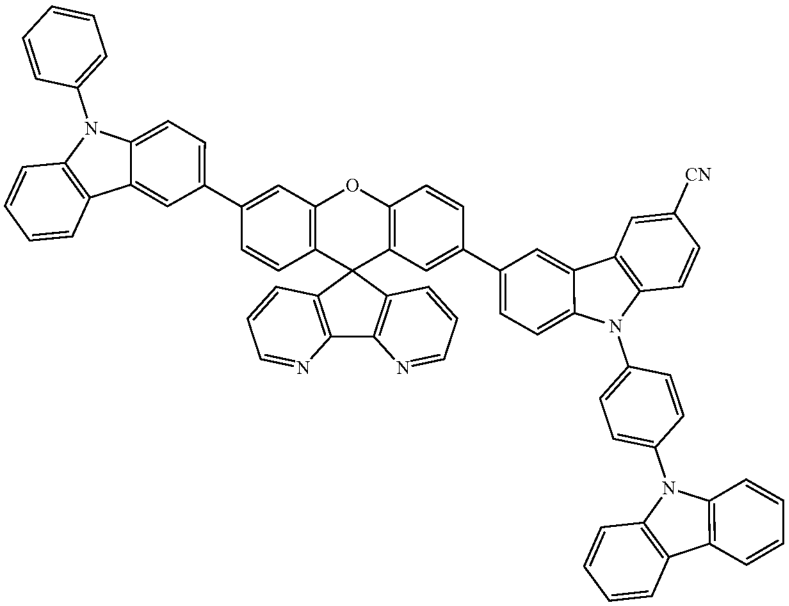

-continued
779
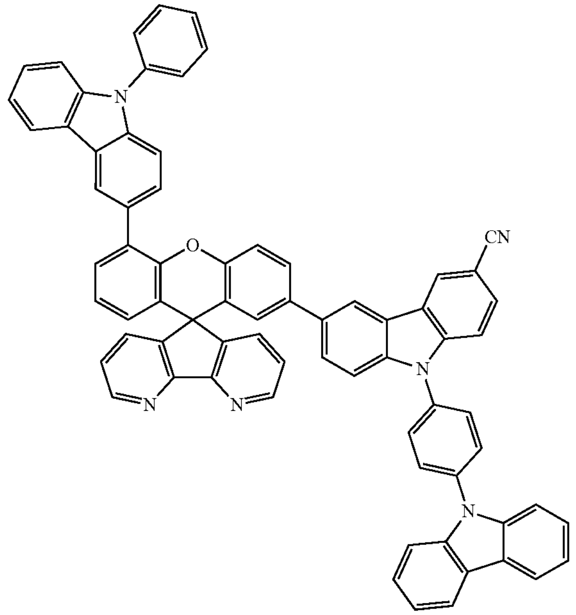
780
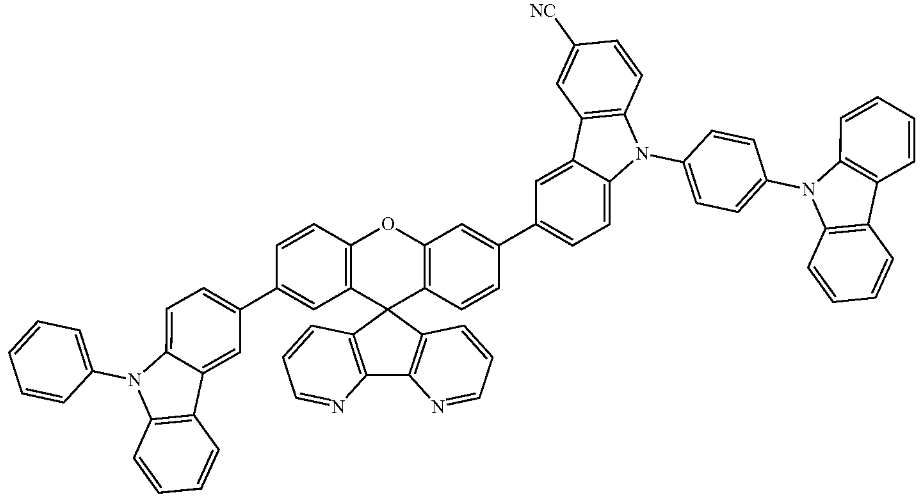

-continued
781
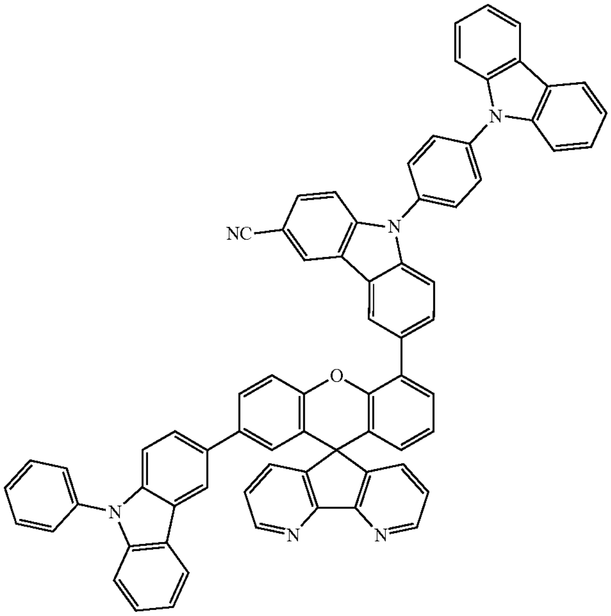
782
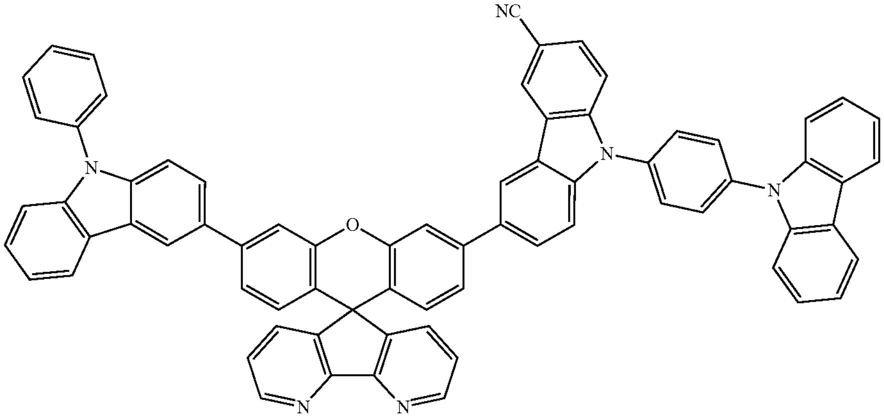
783
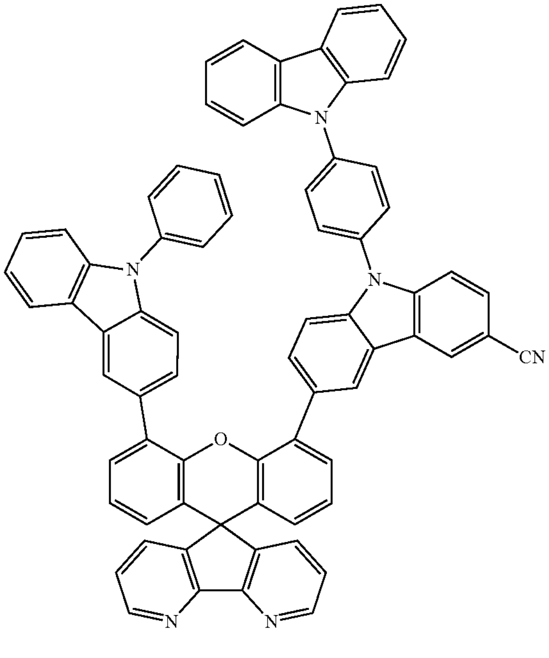

-continued
784
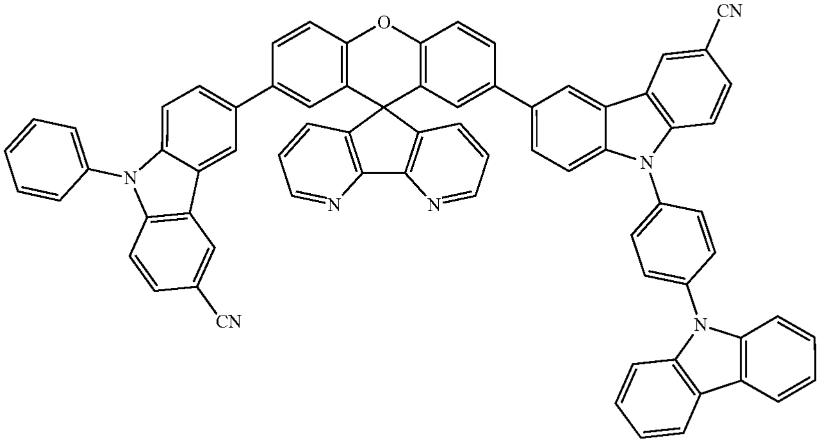
785
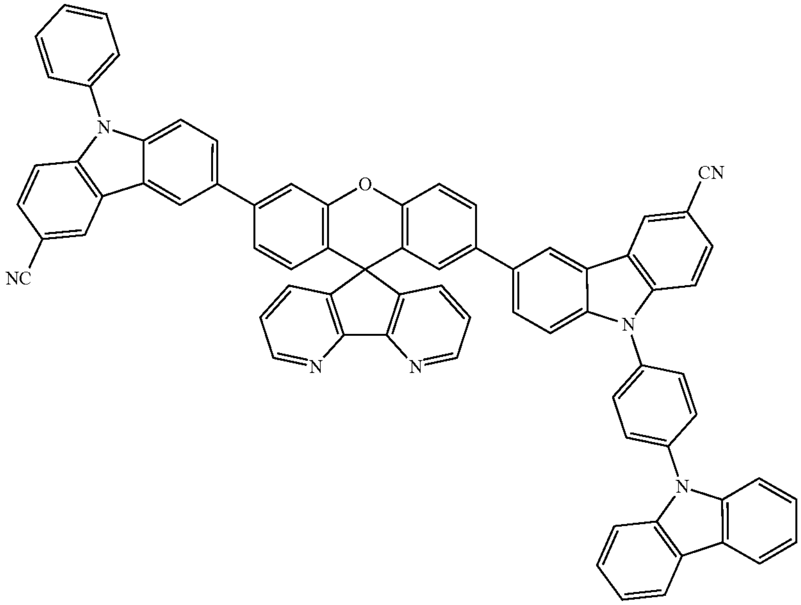
786
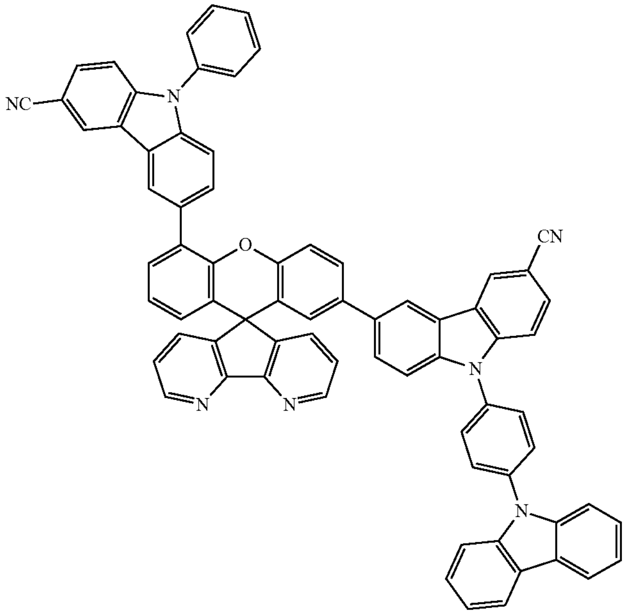

-continued
787
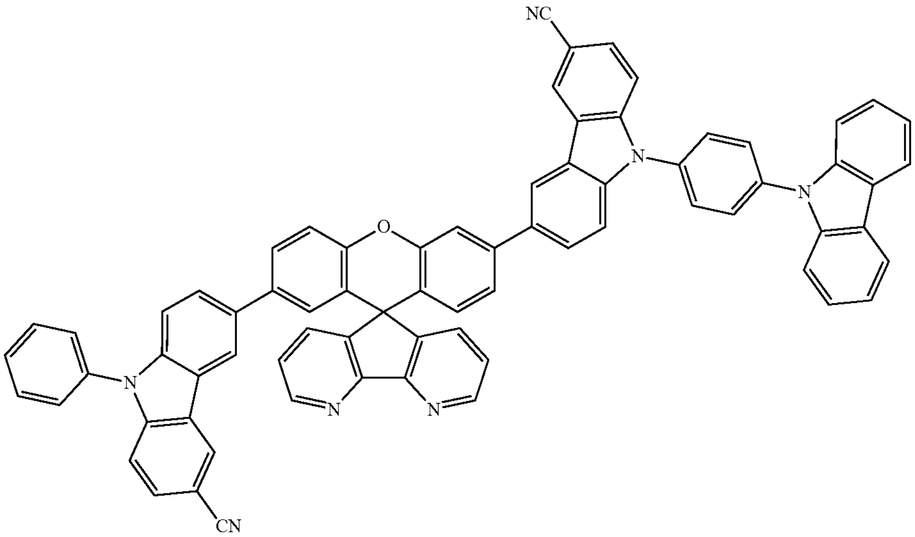
788
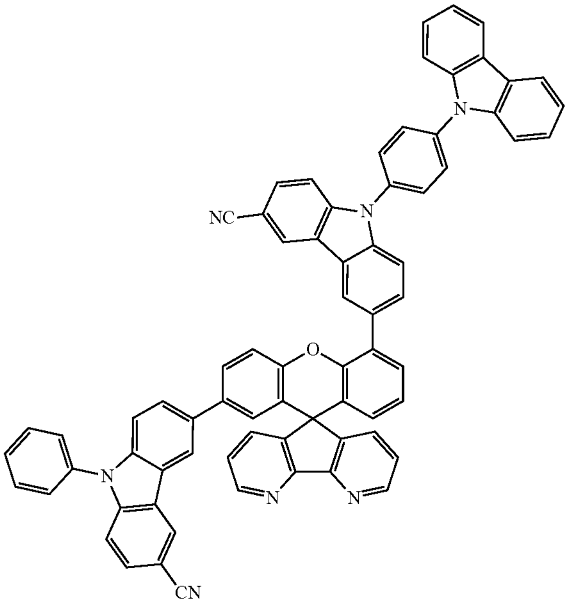
789
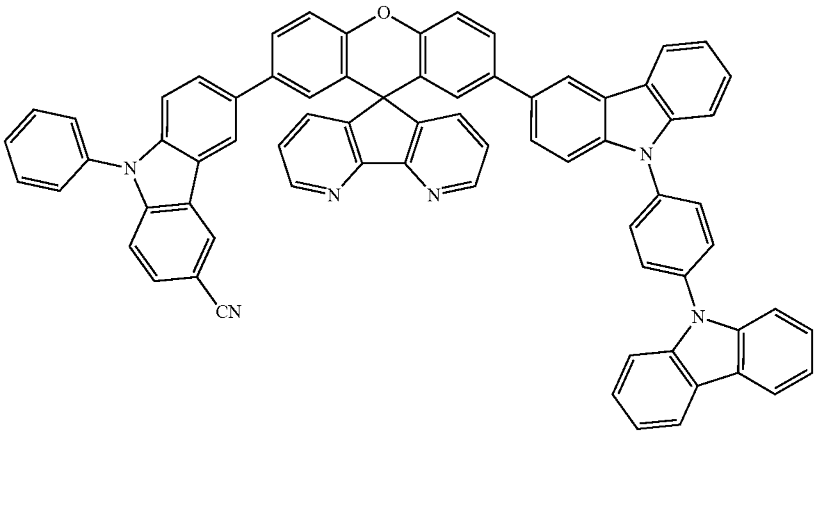

-continued
790
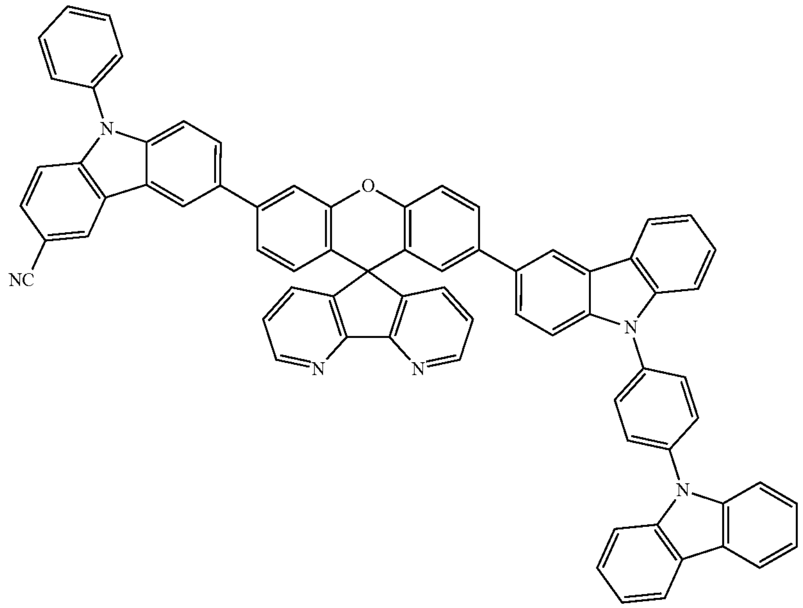
791
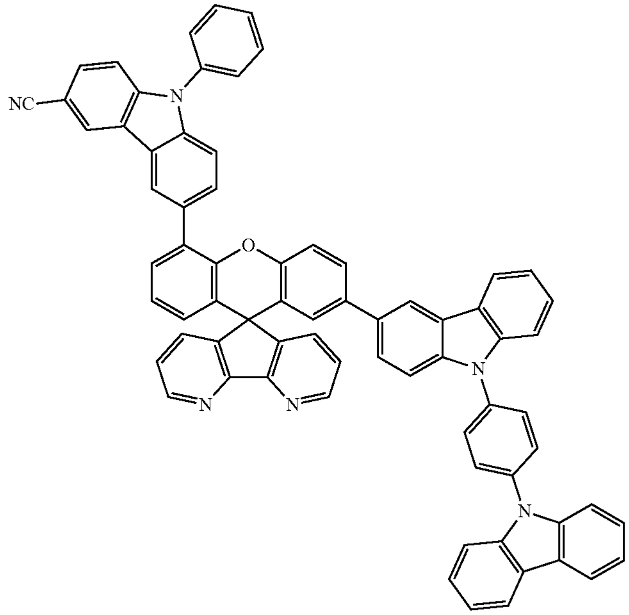

-continued
792
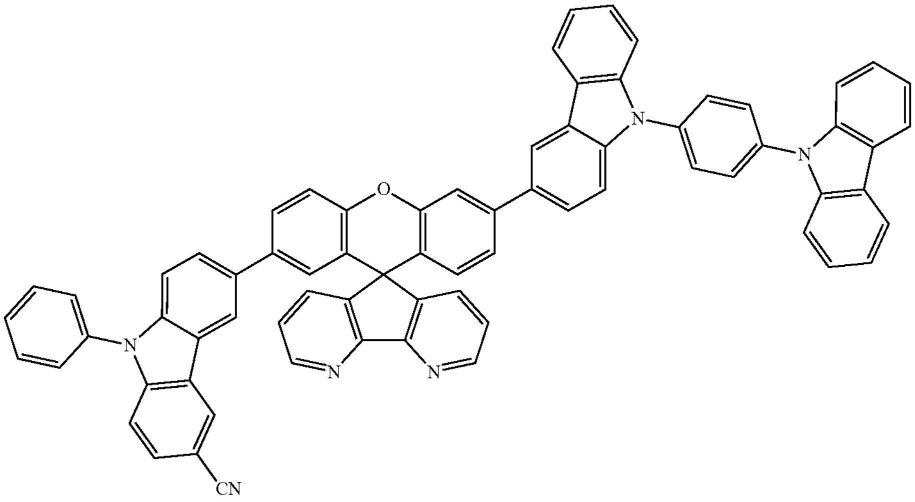
793
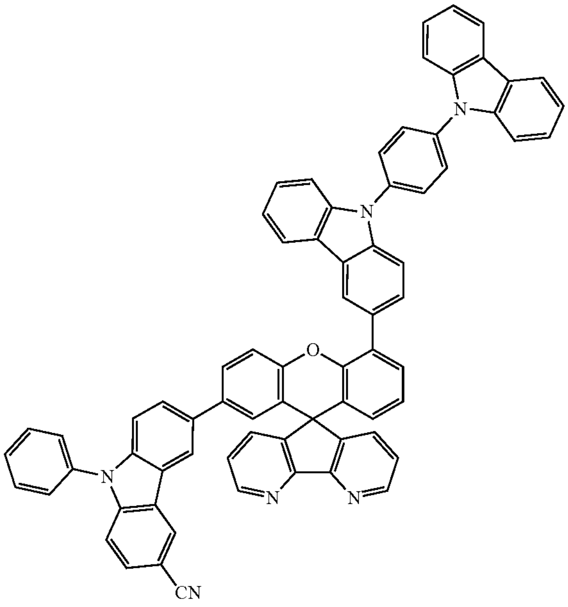
794
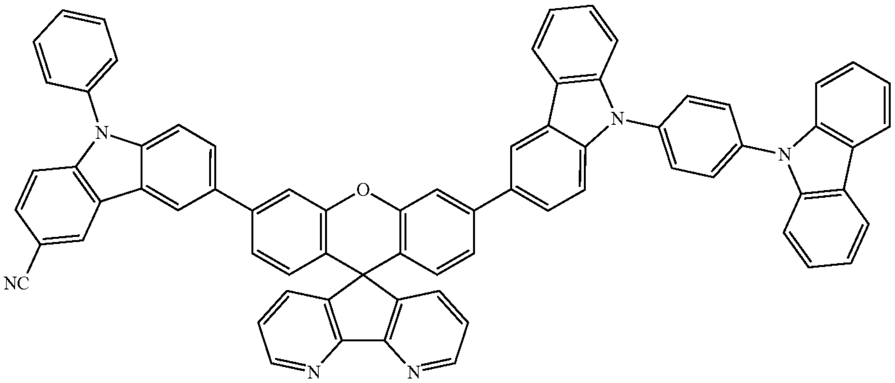

-continued
795
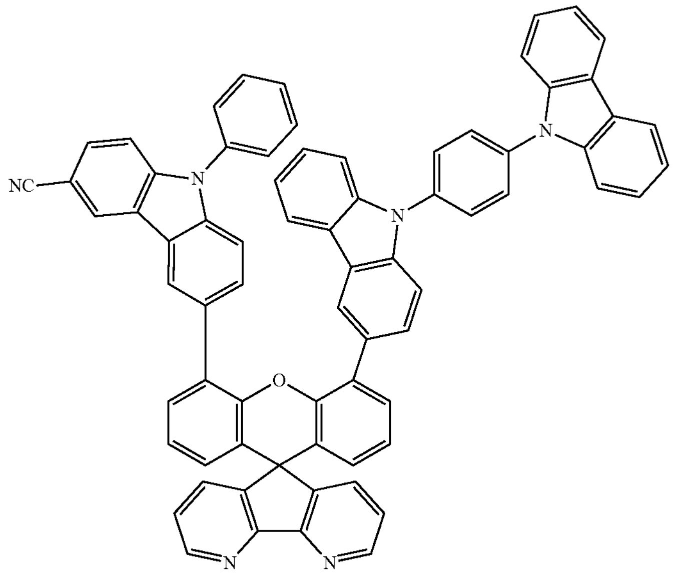
796
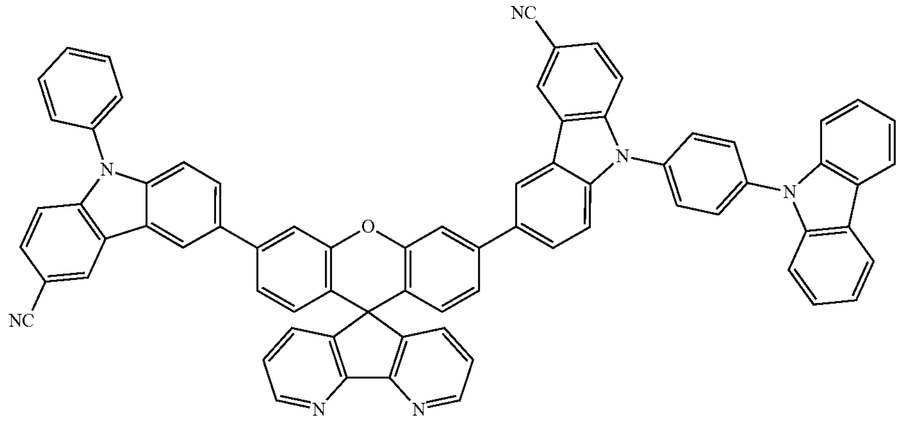
797
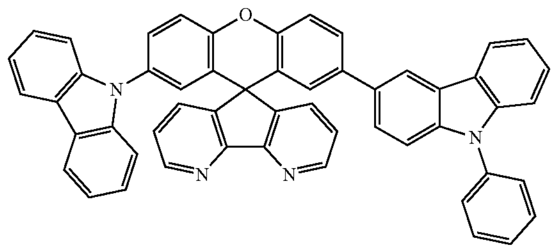
798
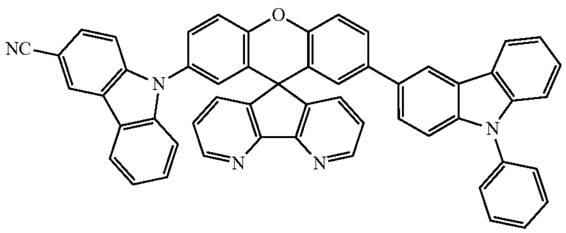
799
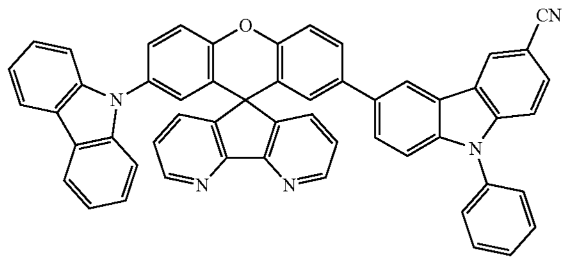
800
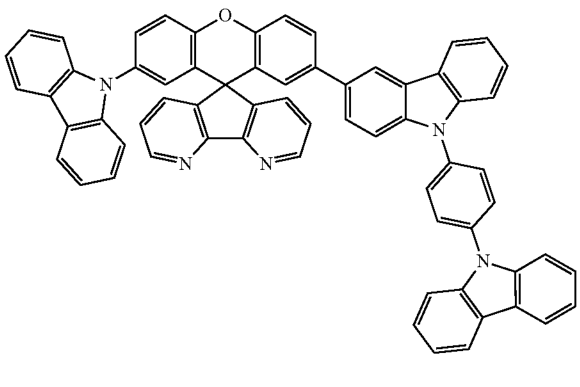

-continued
801
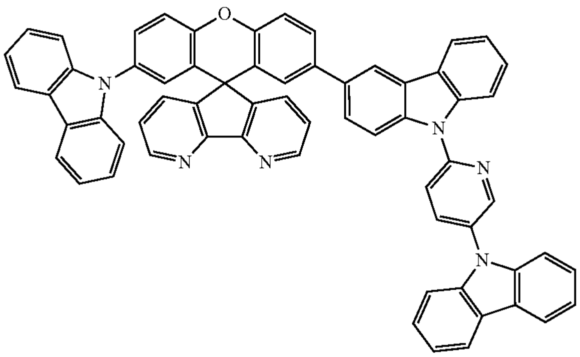
802
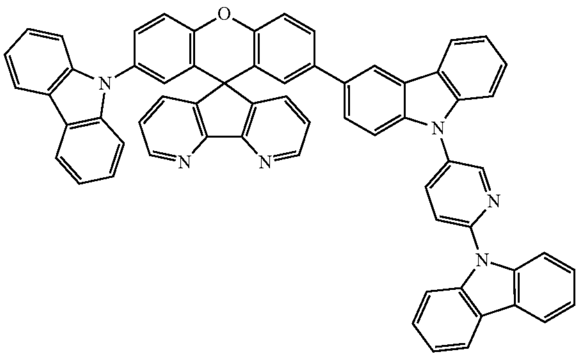
803
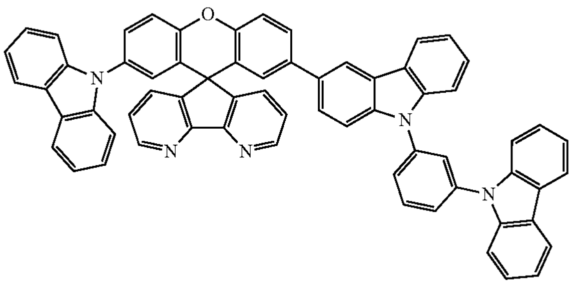
804
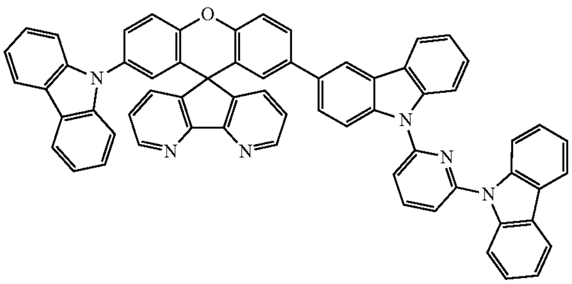
805
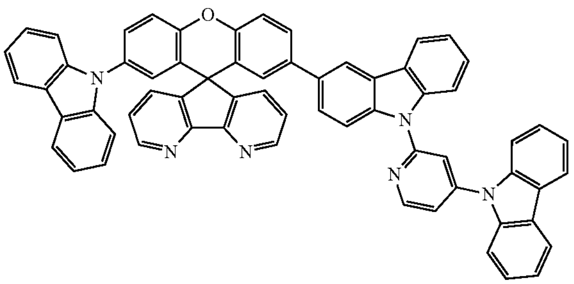
806
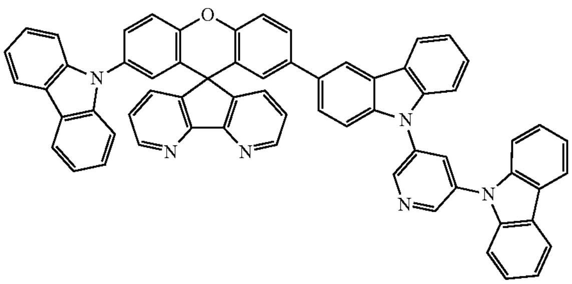
807
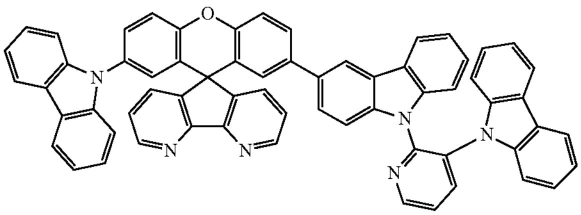
808
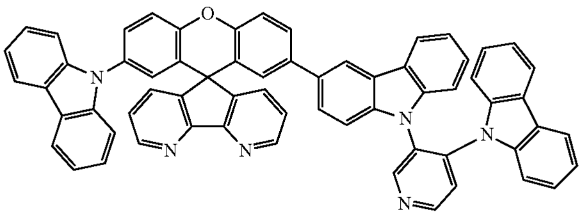
809
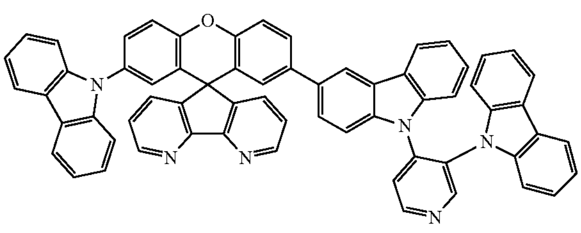
810
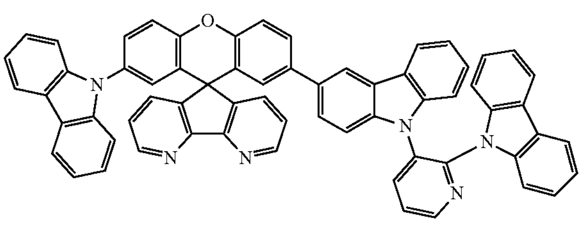

-continued
811
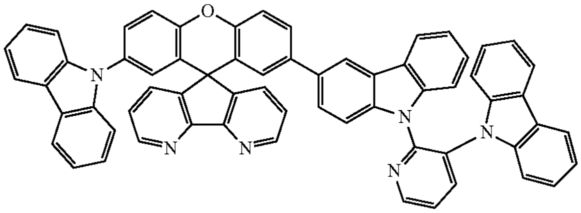
812
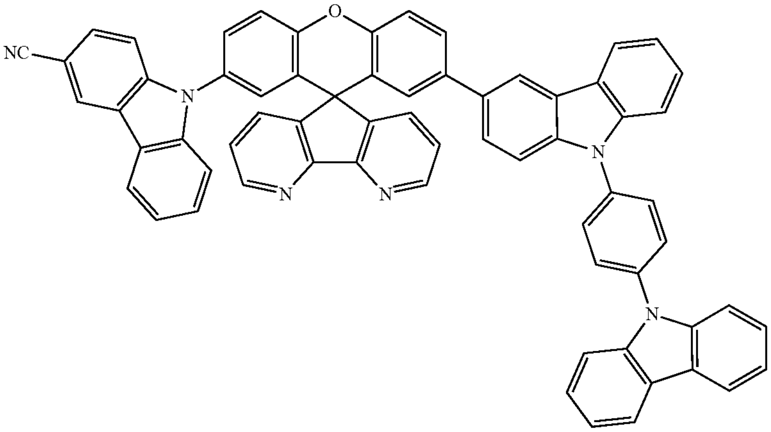
813
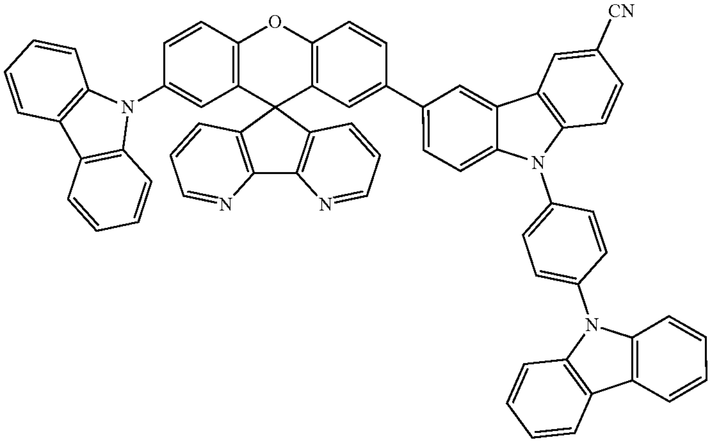
814
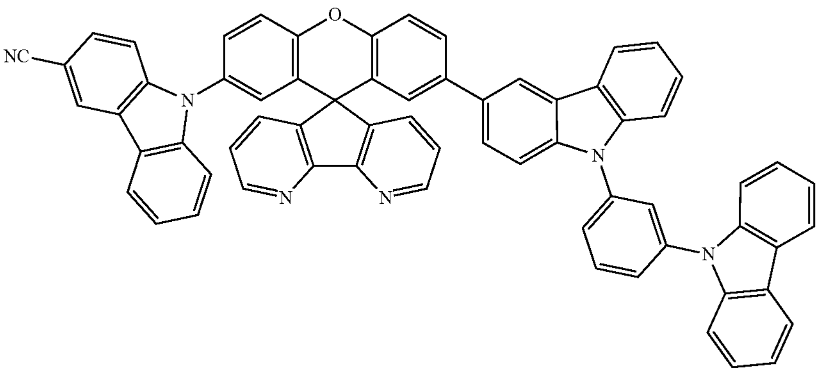

-continued
815
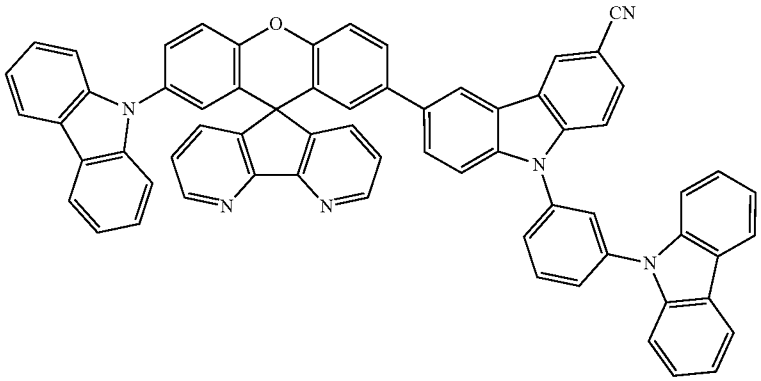
816
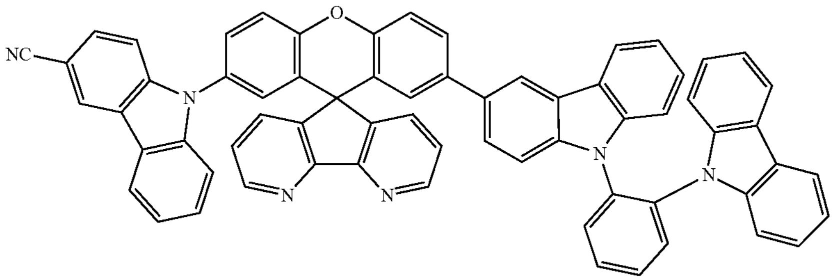
817
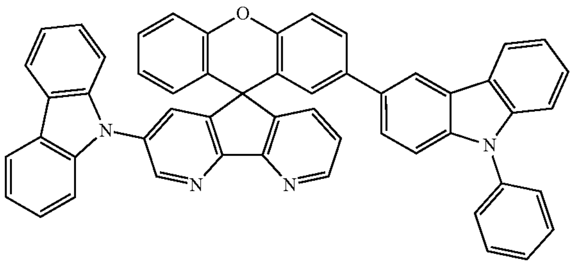
818
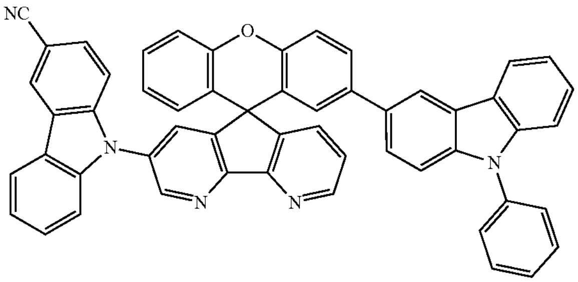
819
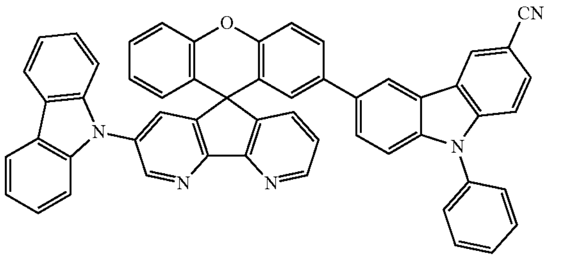
820
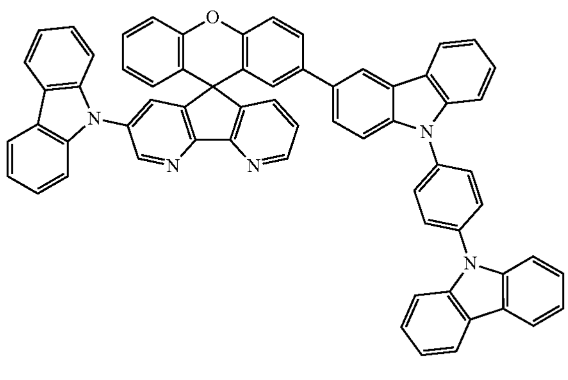

-continued
821
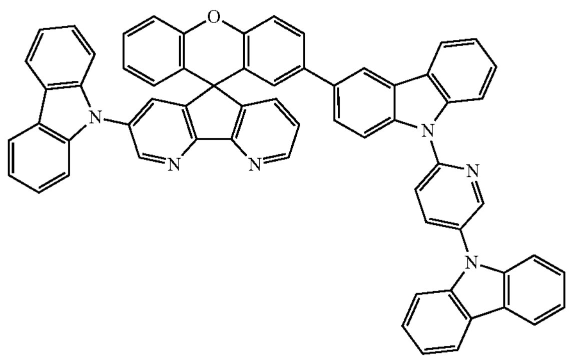
822
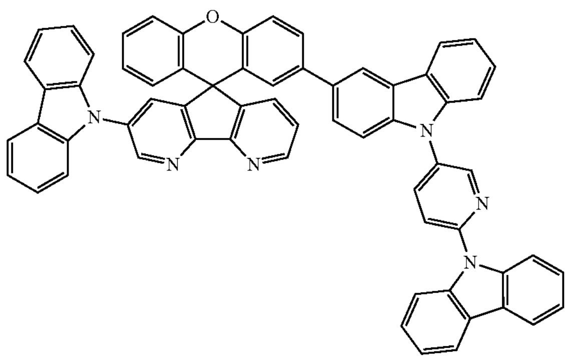
823
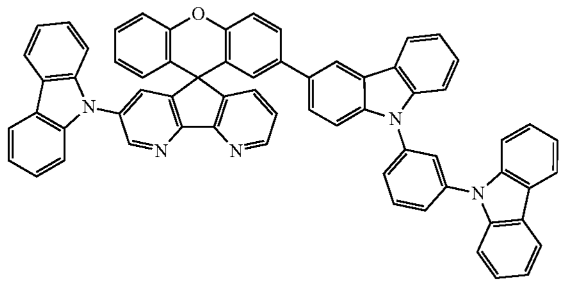
824
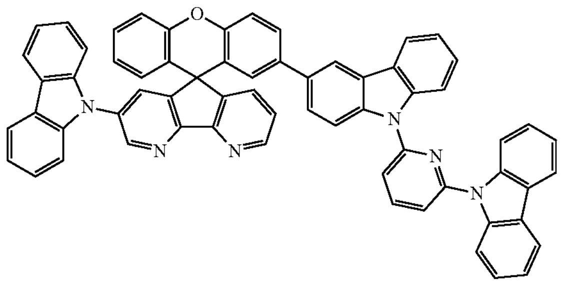
825
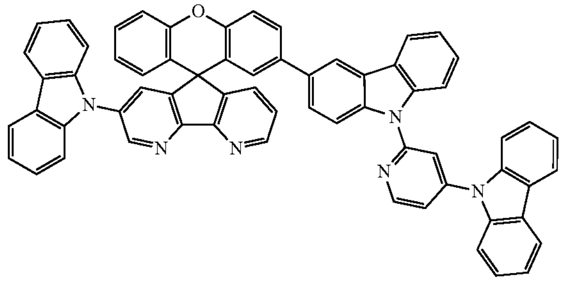
826
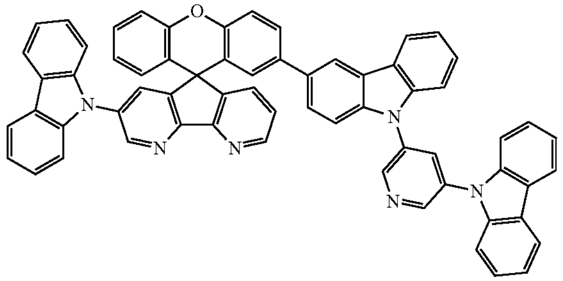
827
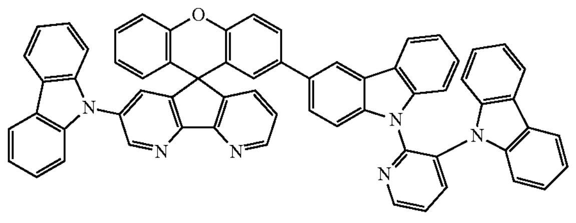
828
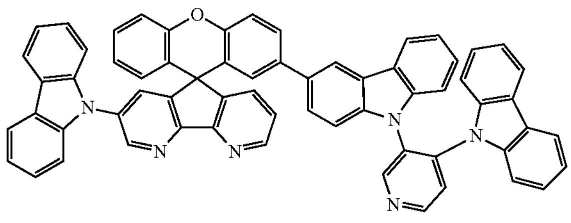
829
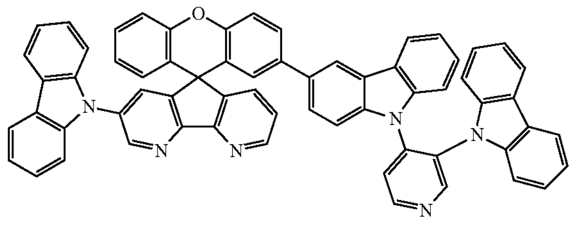
830
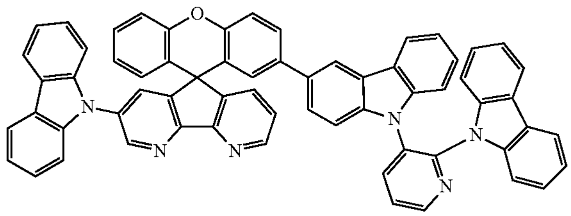

-continued
831
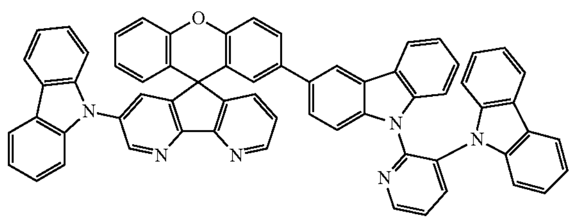
832
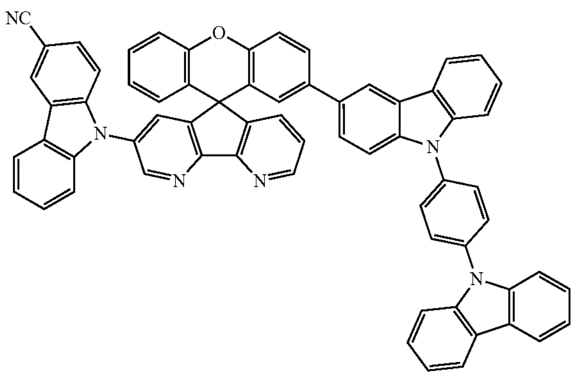
833
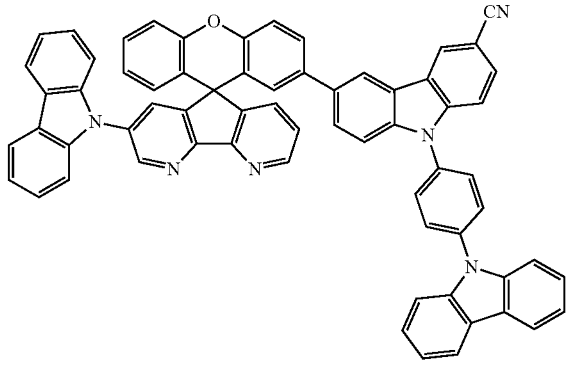
834
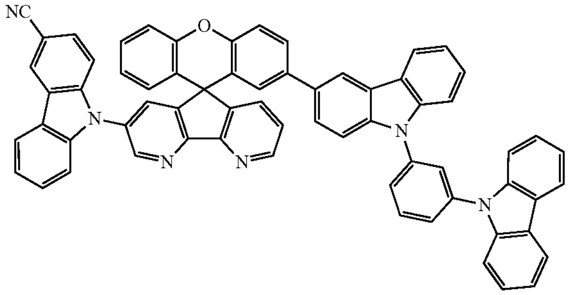
835
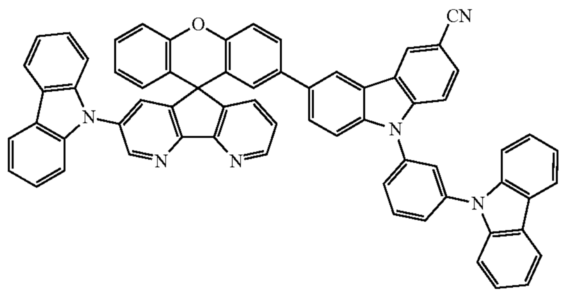
836
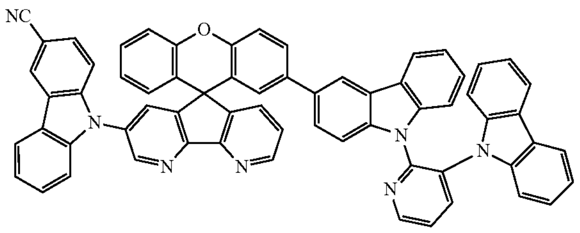
837
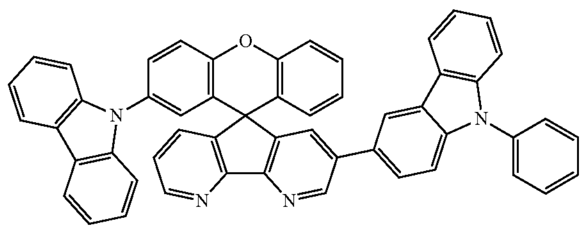
838
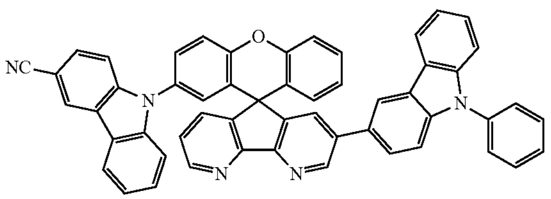
839
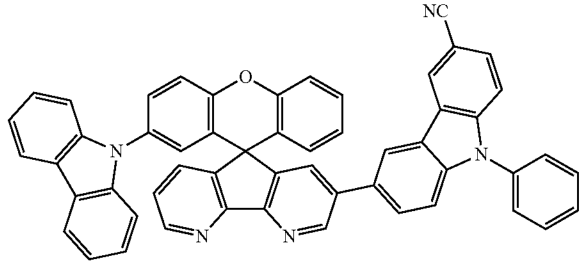

-continued
840
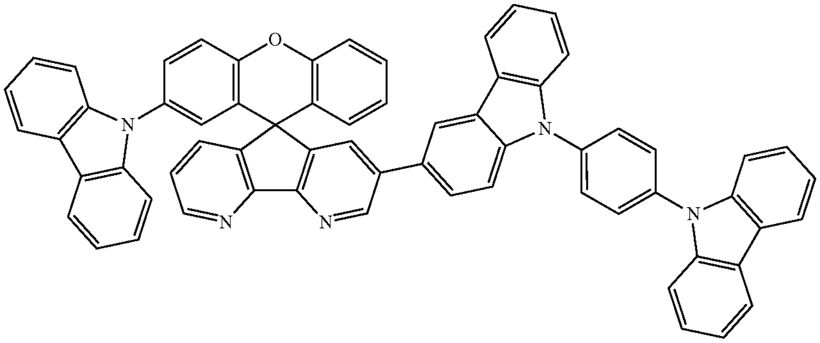
841
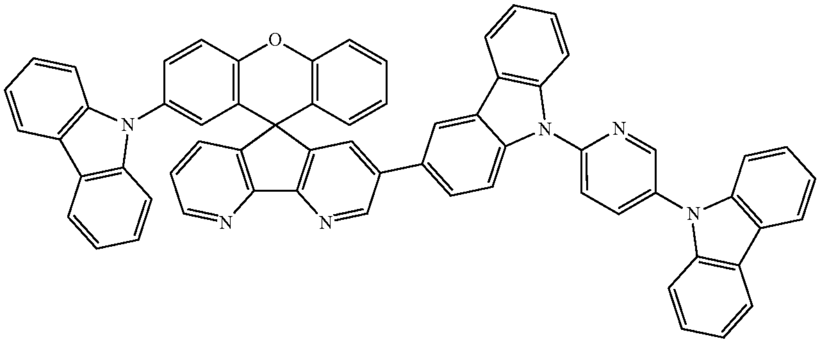
842
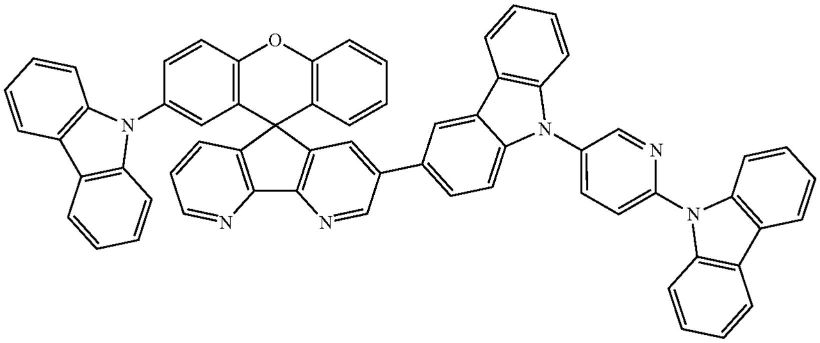
843
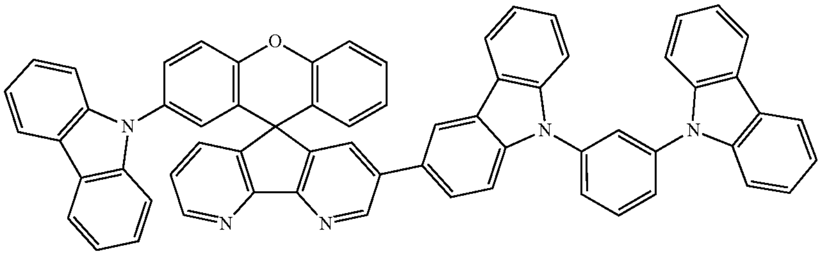
844
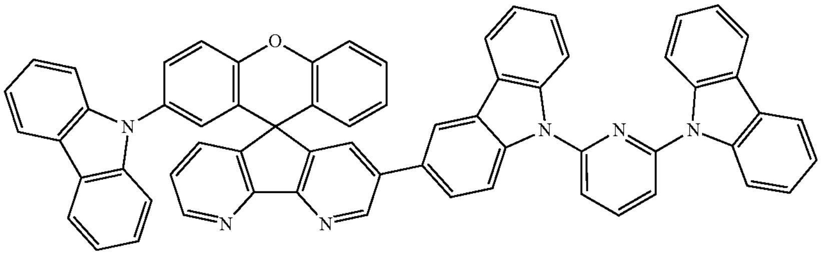

-continued
845
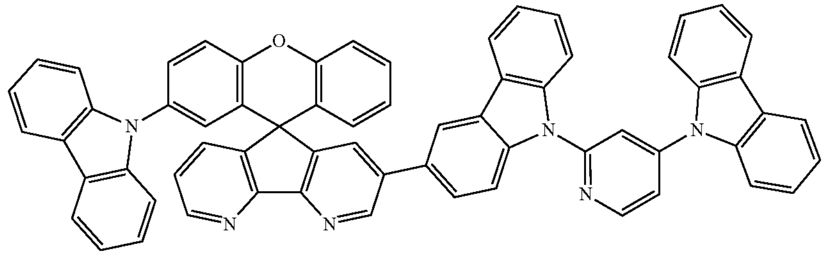
846
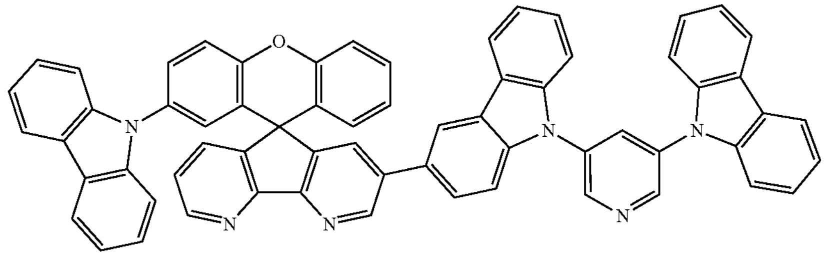
847
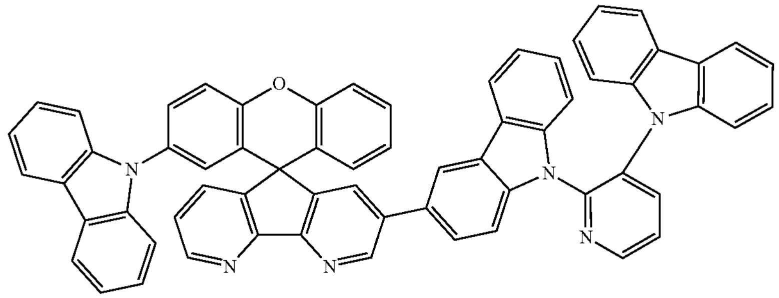
848
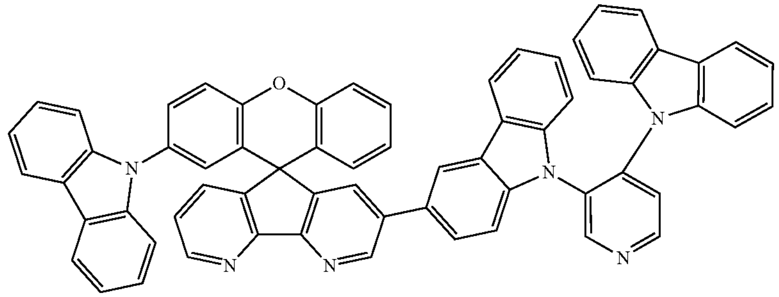
849
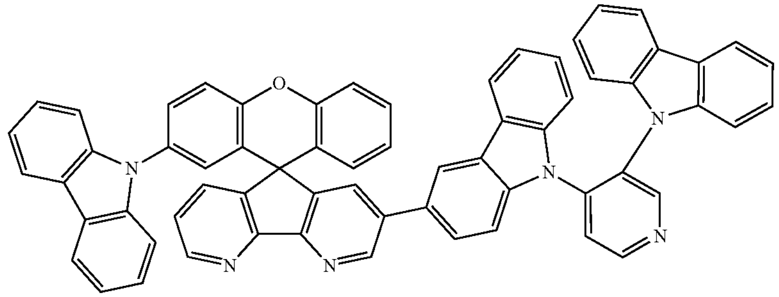

-continued
850
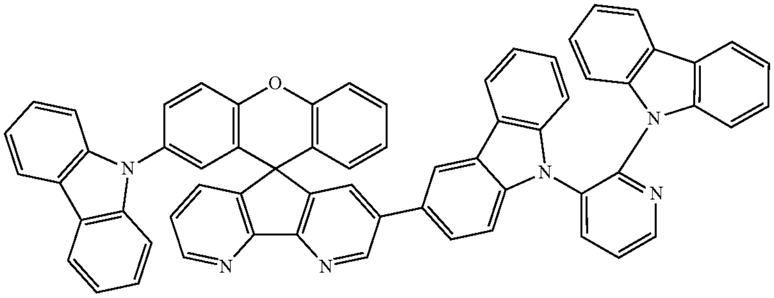
851
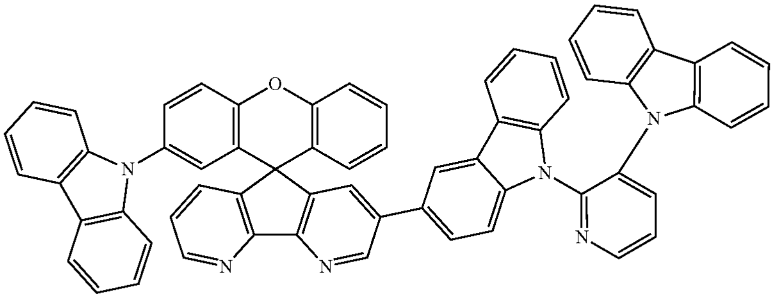
852
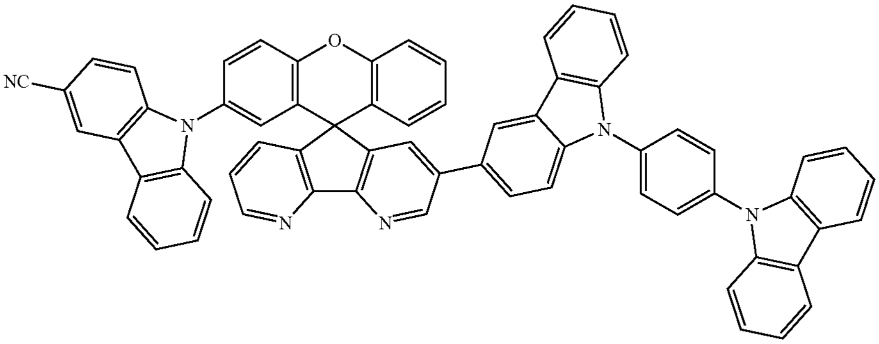
853
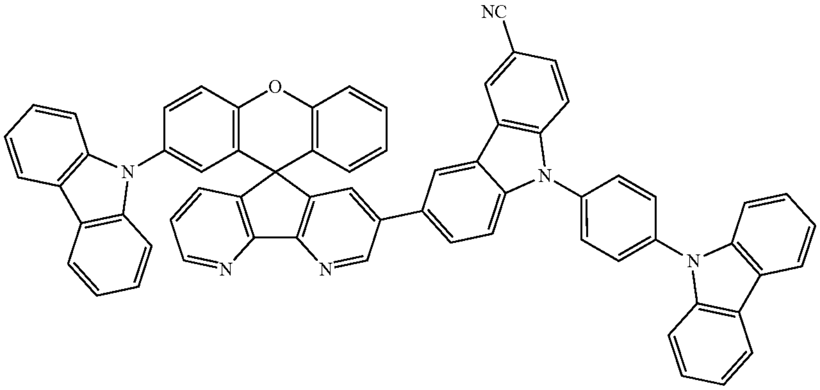
854
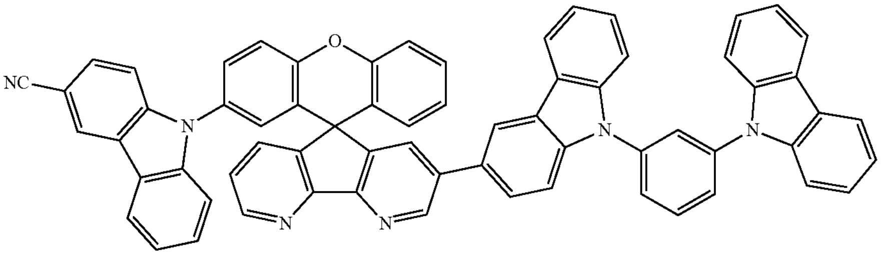

-continued
855
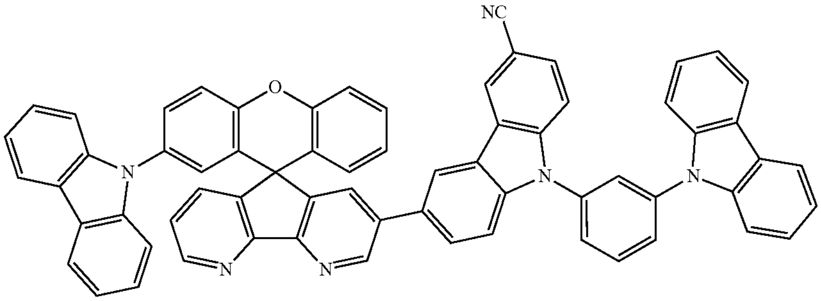
856
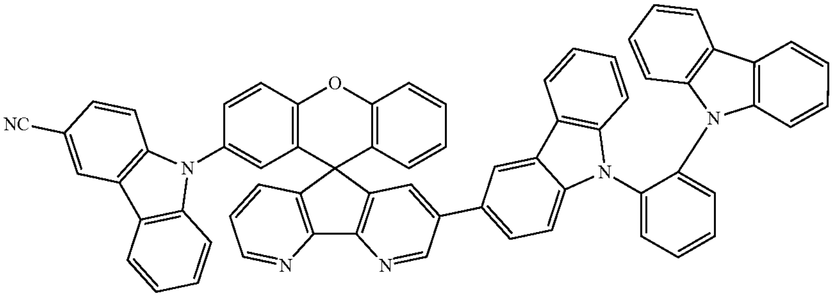
857
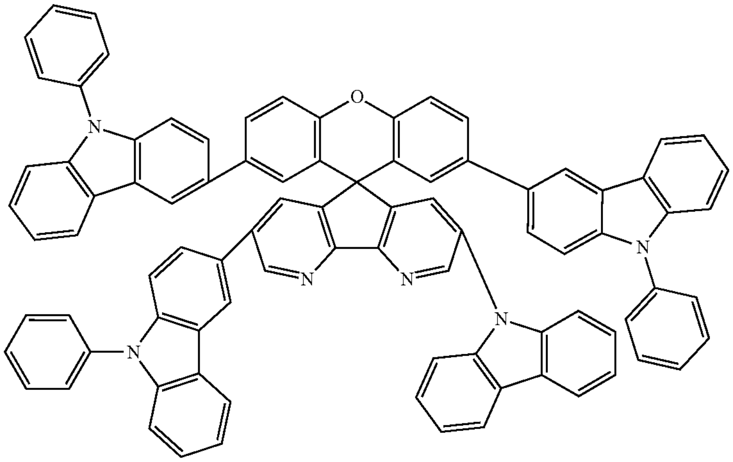
858
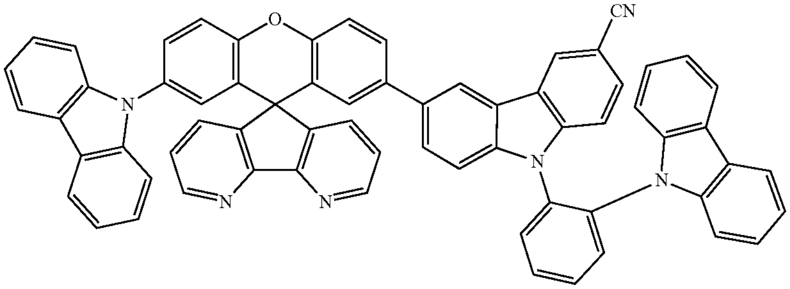
859
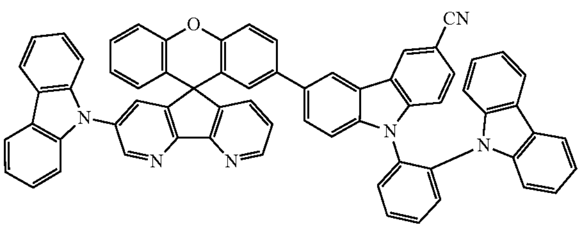
860
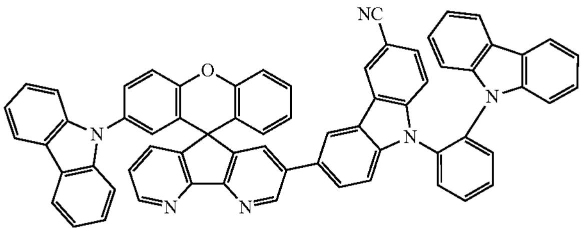

-continued
861
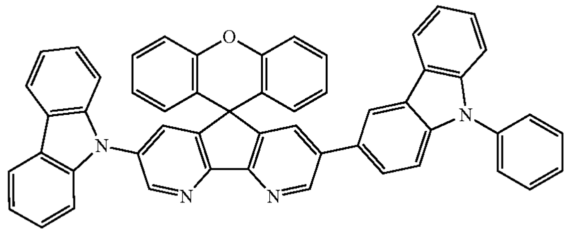
862
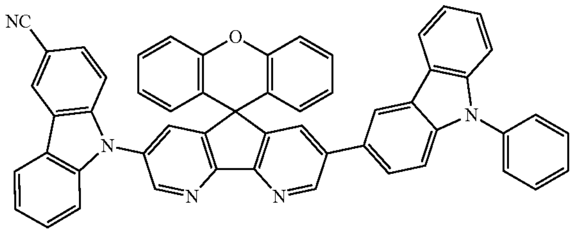
863
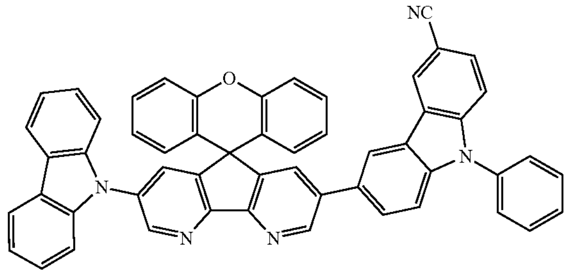
864
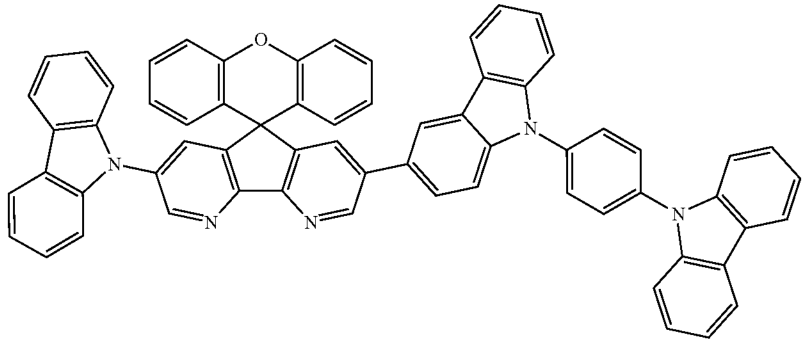
865
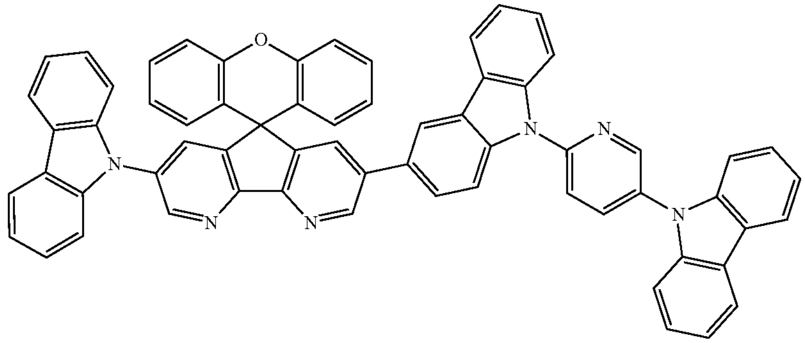
866
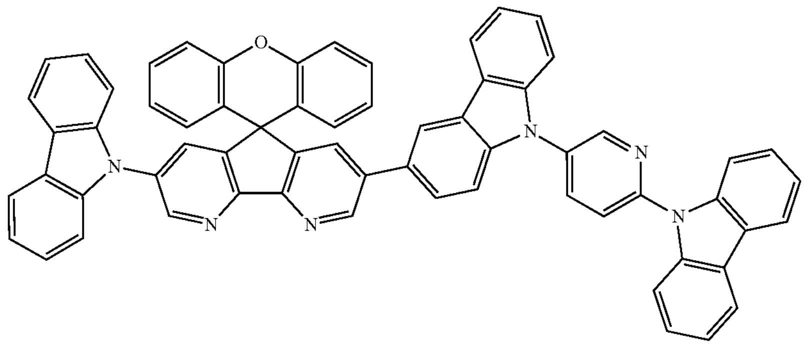

-continued
867
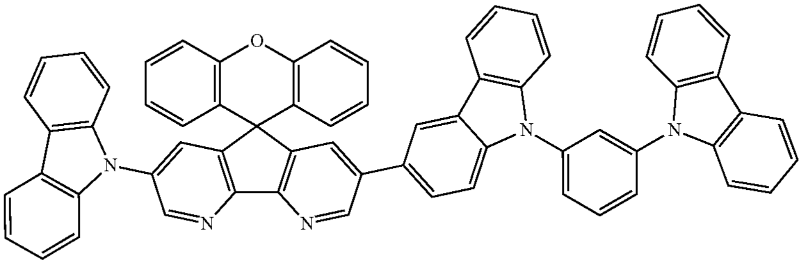
868
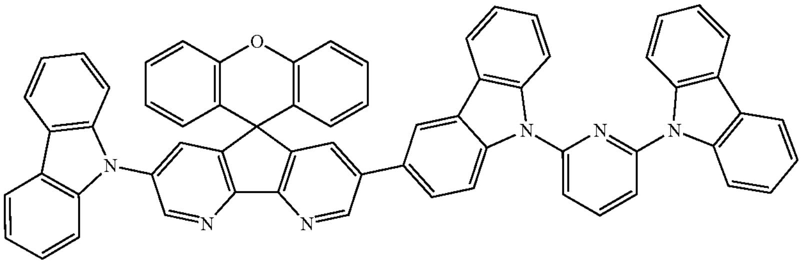
869
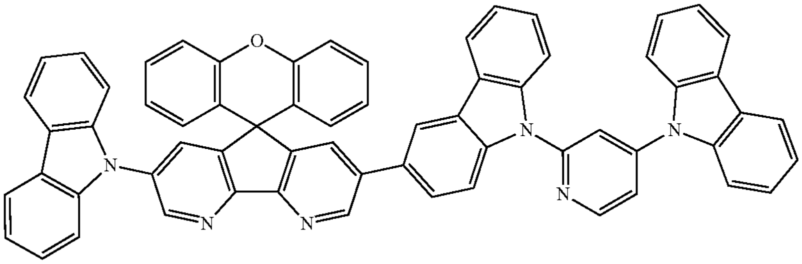
870
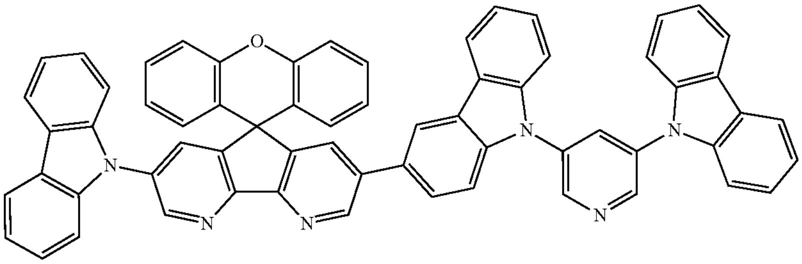
871
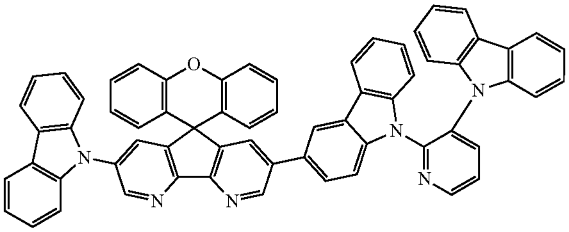
872
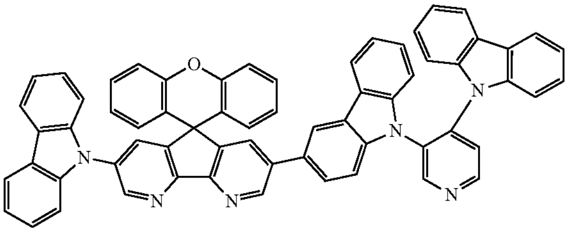
873
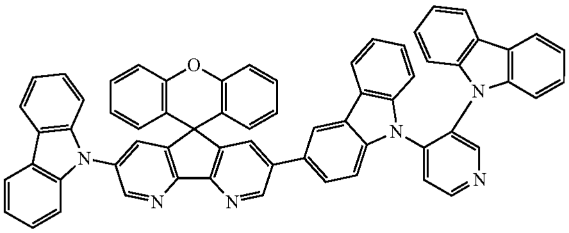
874
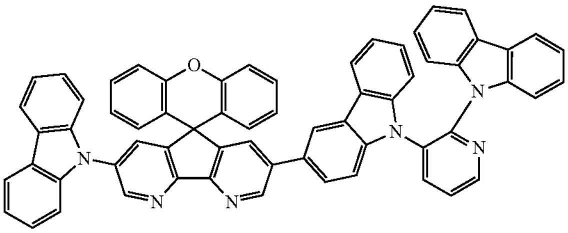

-continued
875
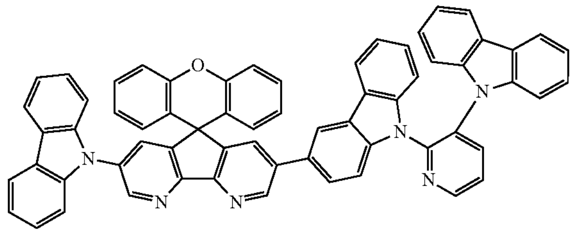
876
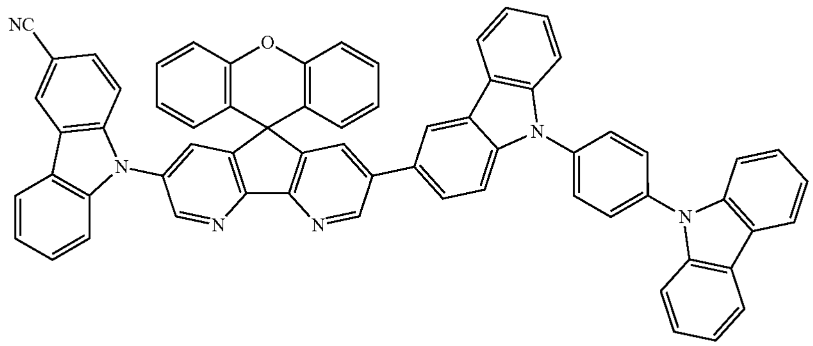
877
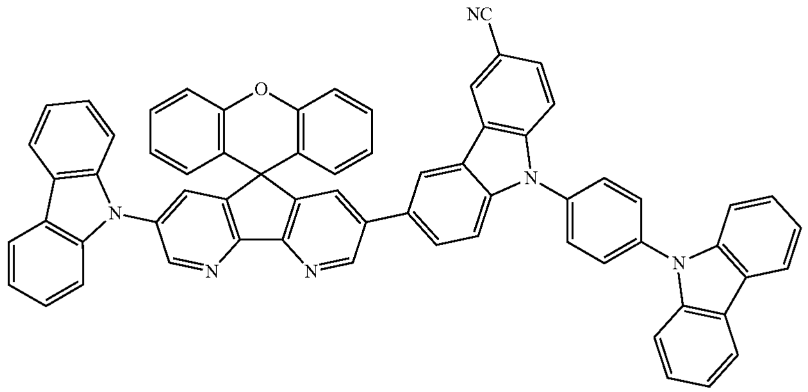
878
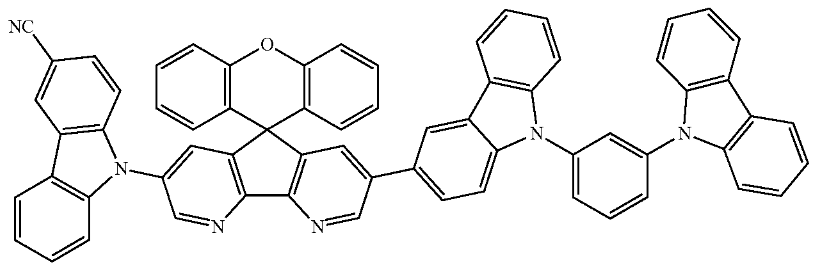
879
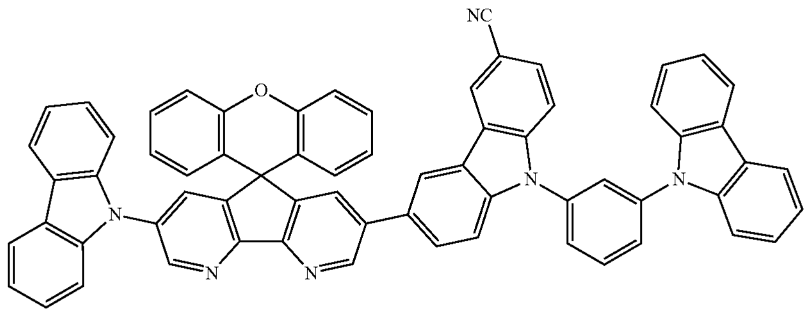

-continued
880
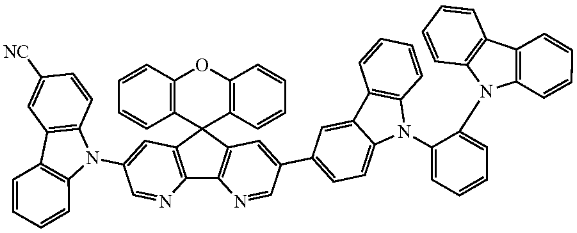
881
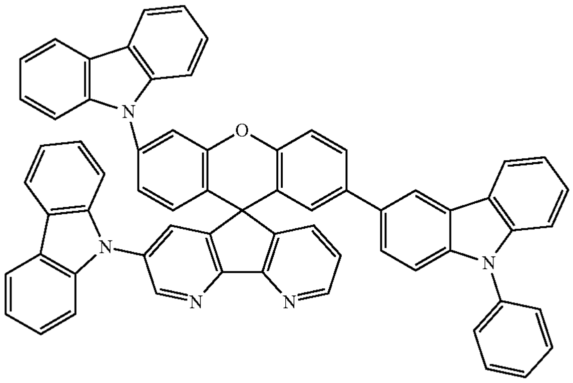
882
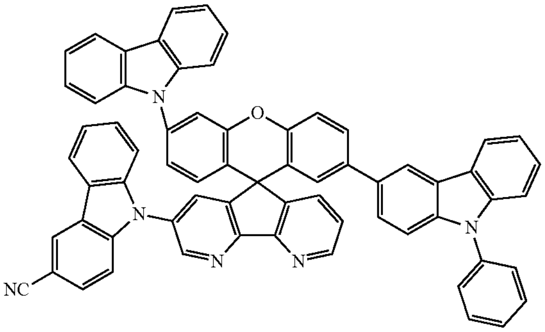
883
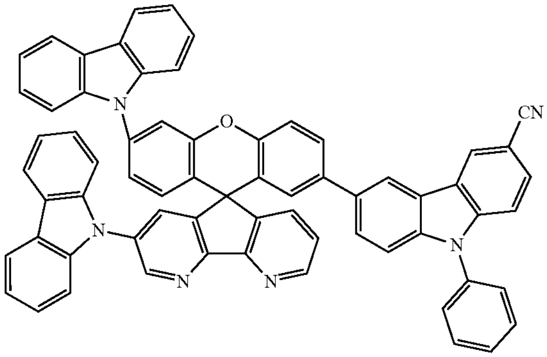
884
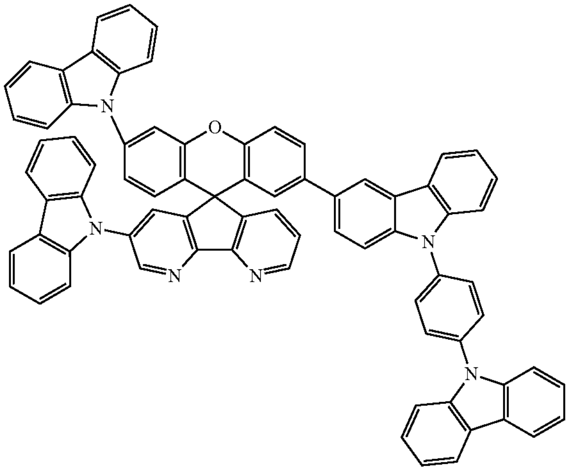
885
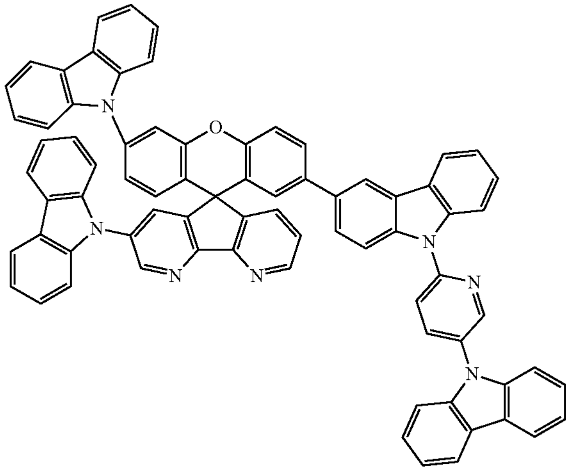

-continued
886
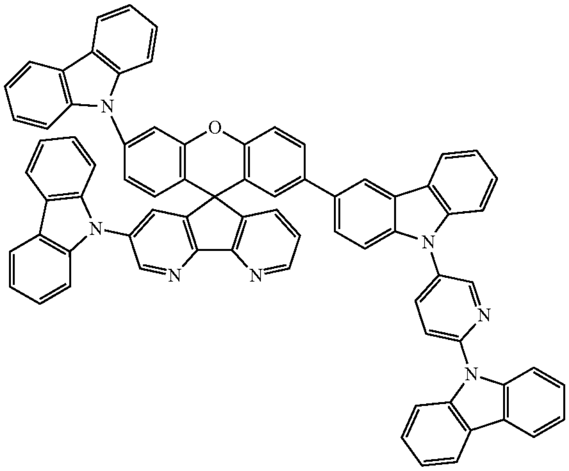
887
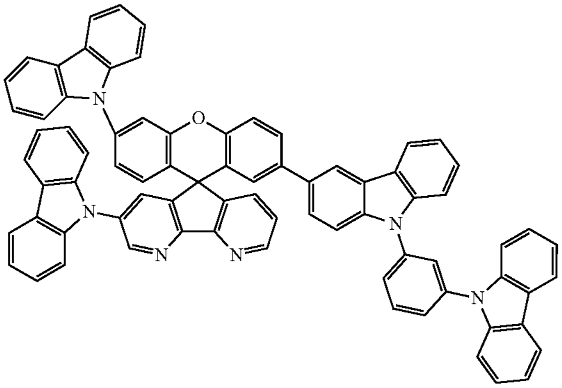
888
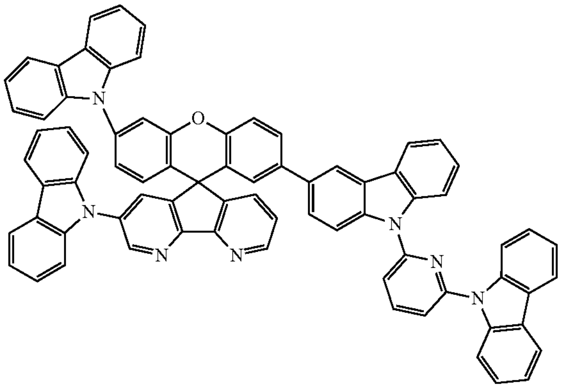
889
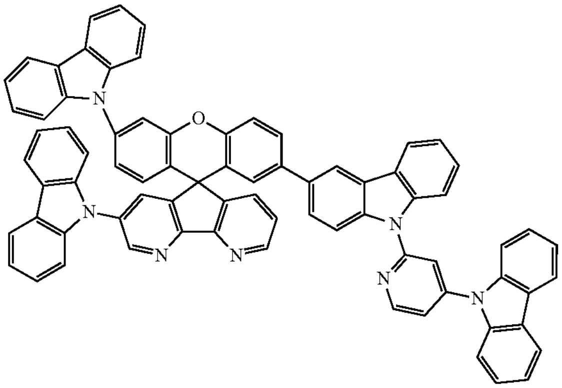
890
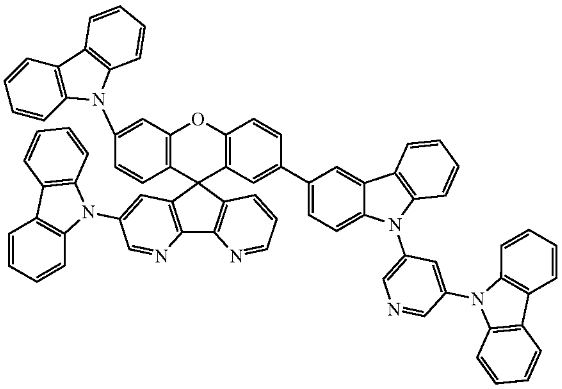
891
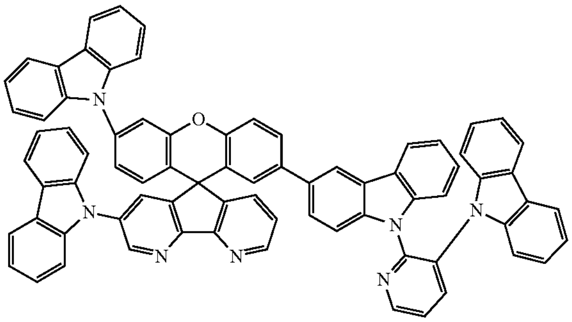

-continued
892
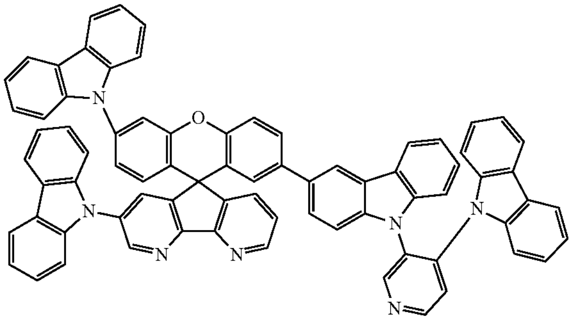
893
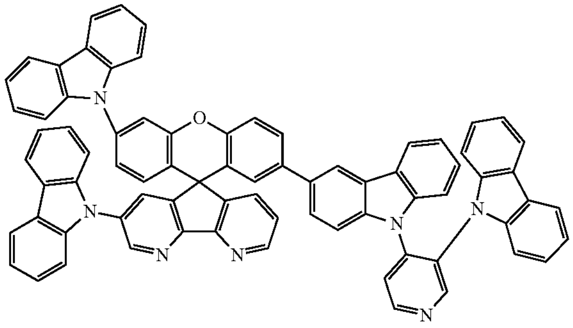
894
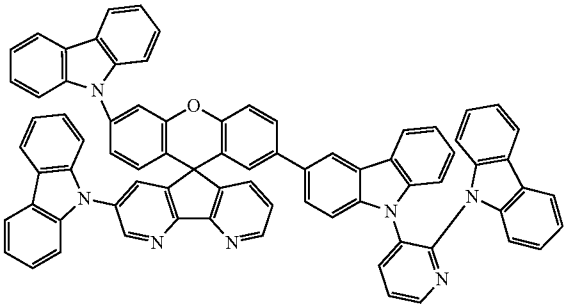
895
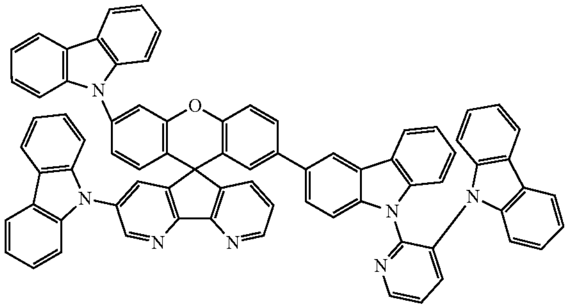
896
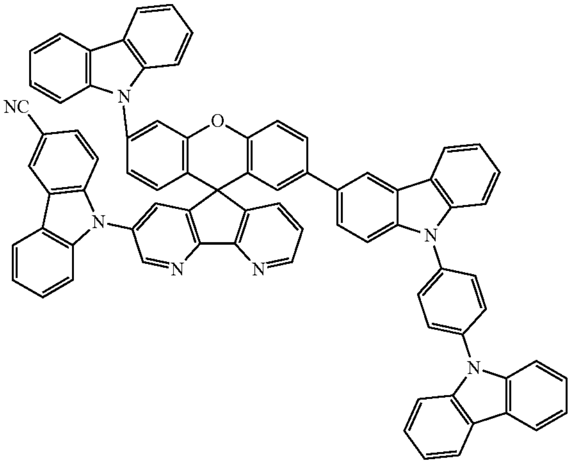
897
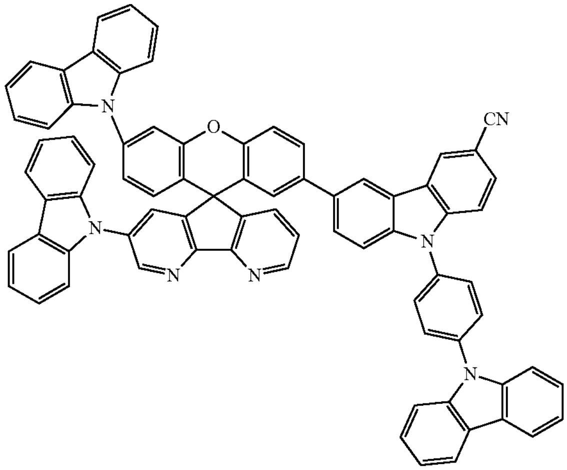
898
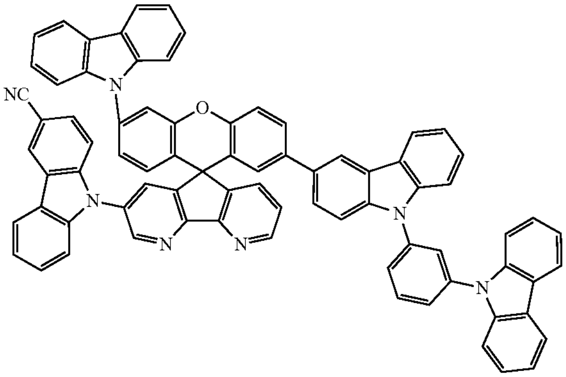
899
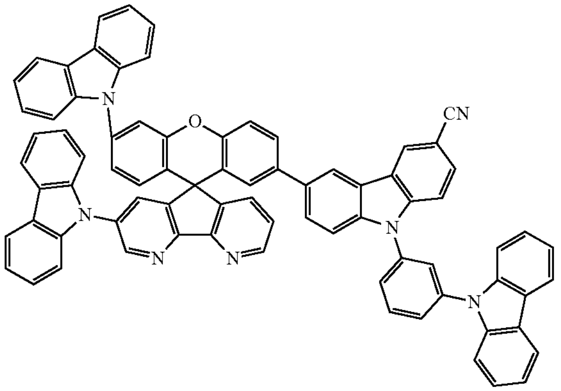

-continued
900
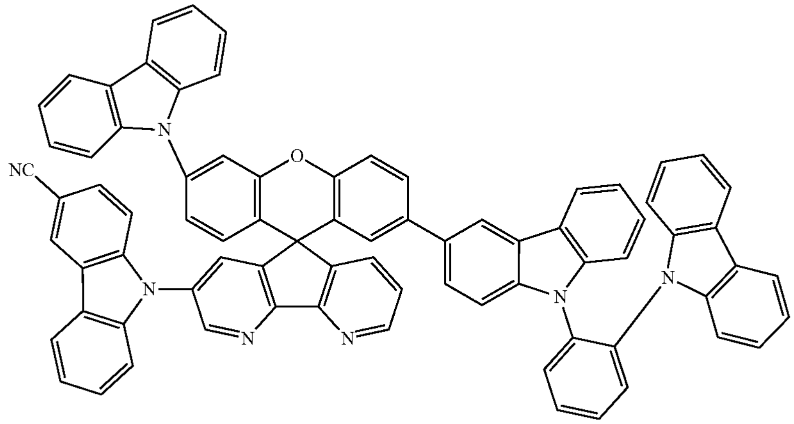
901
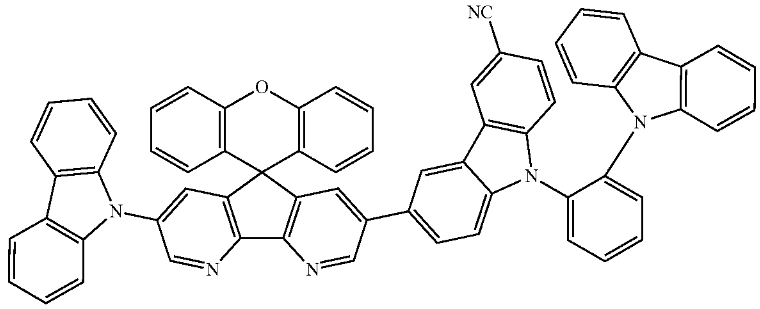
902
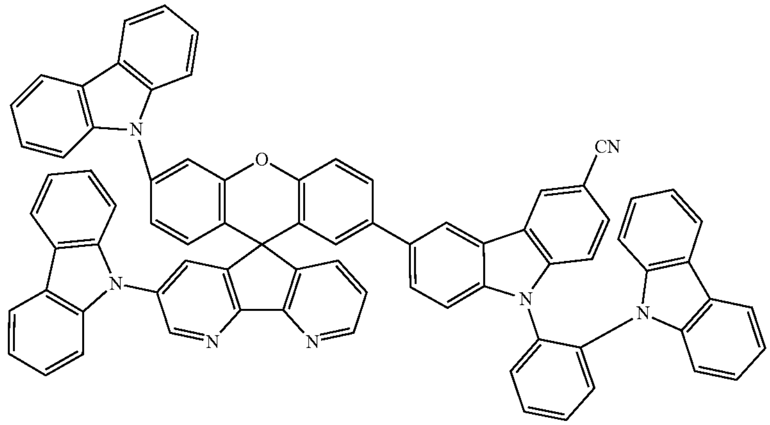
903
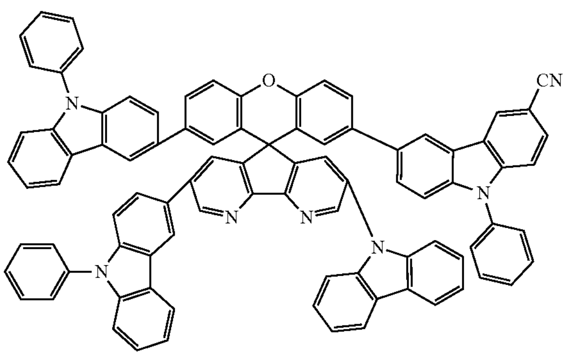
904
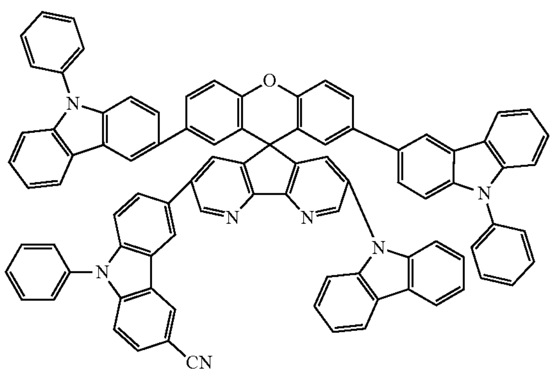

-continued
905
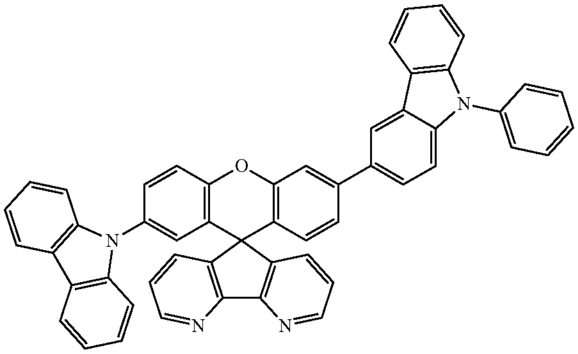
906
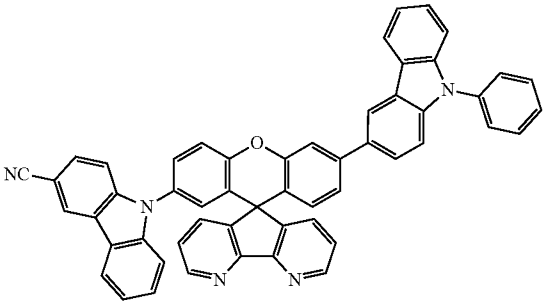
907
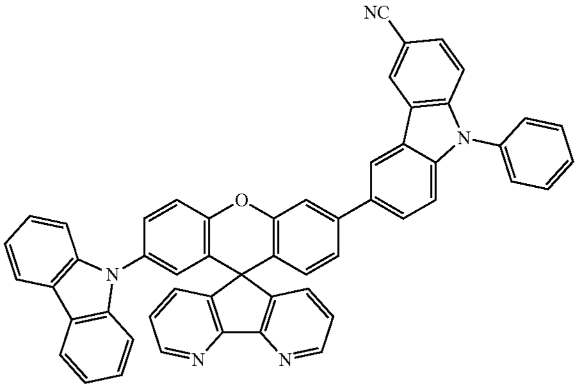
908
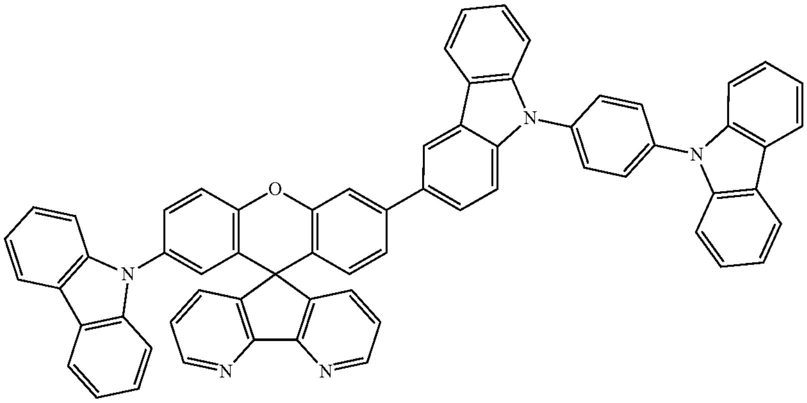
909
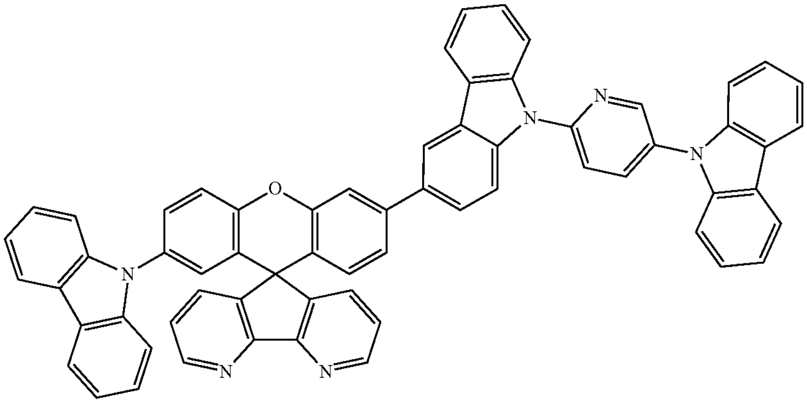

-continued
910
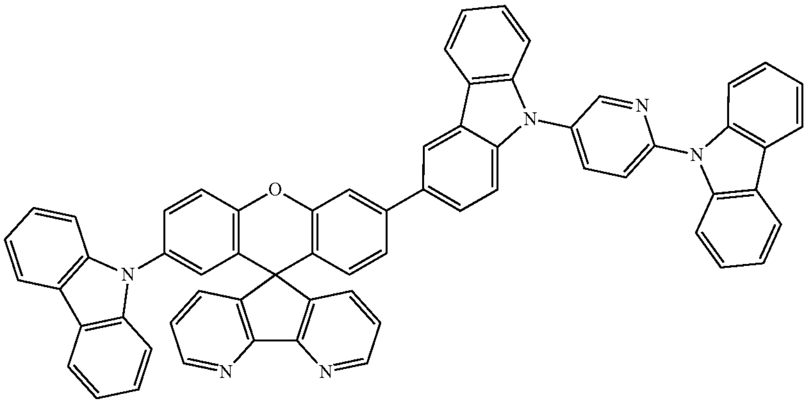
911
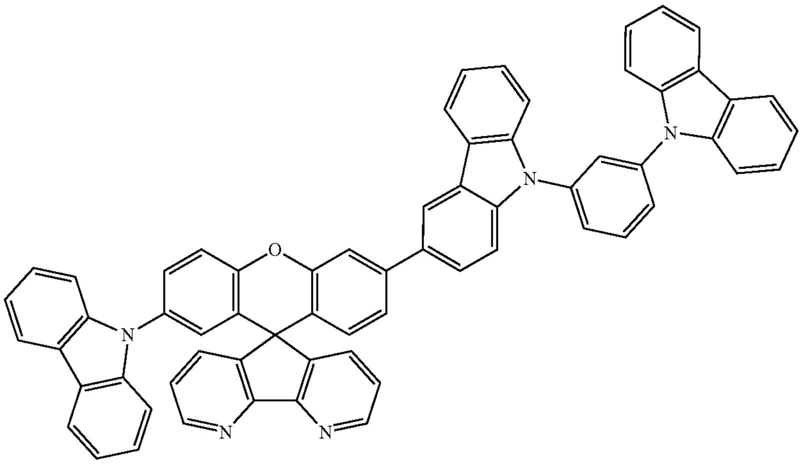
912
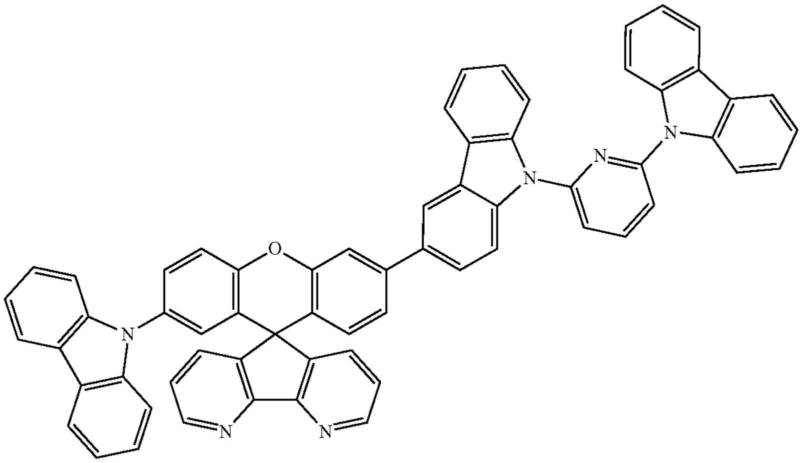

-continued
913
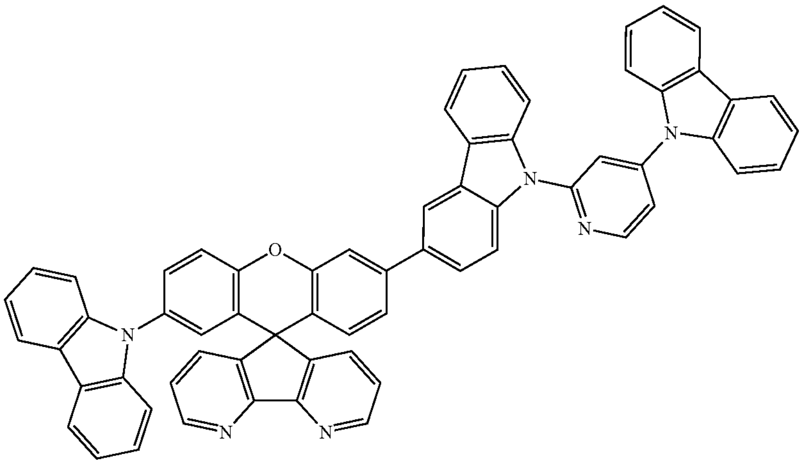
914
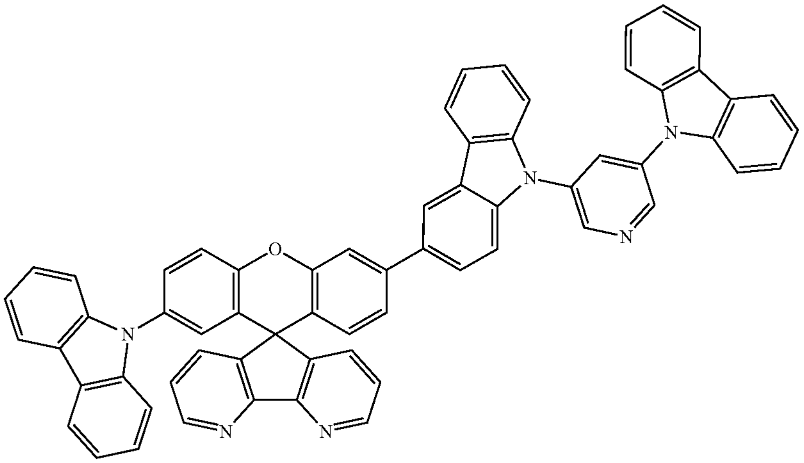
915
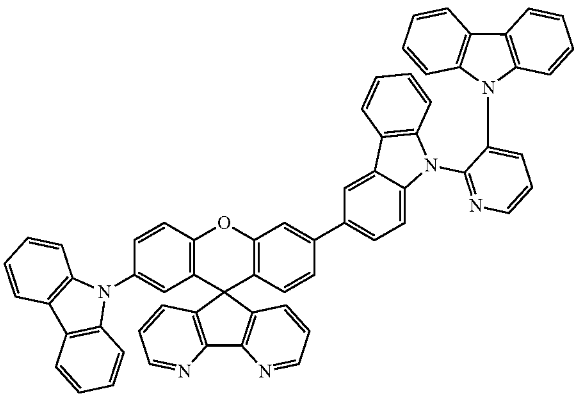
916
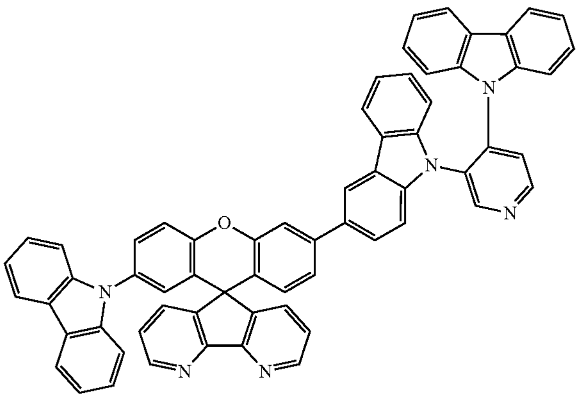

-continued
917
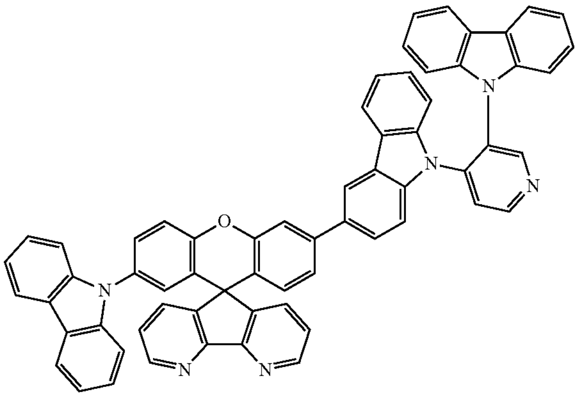
918
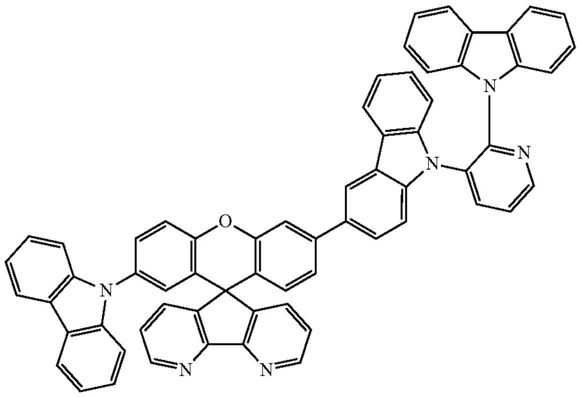
919
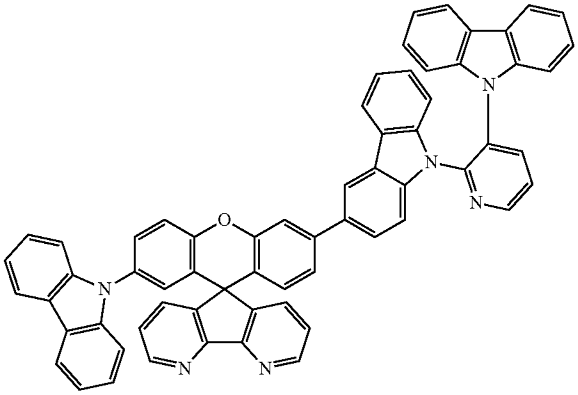
920
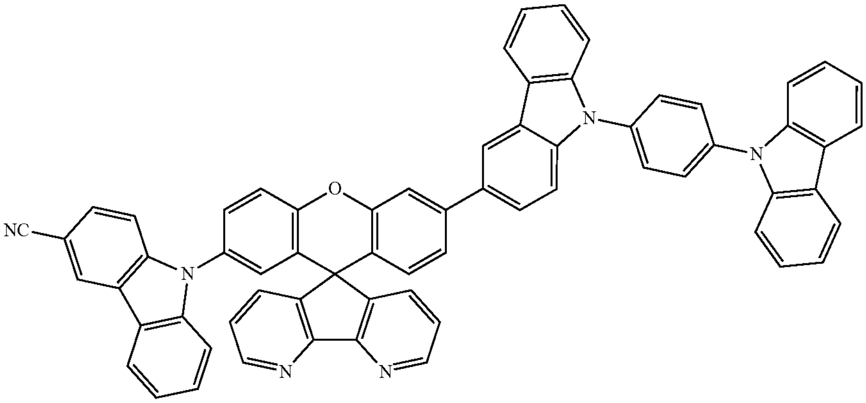
921
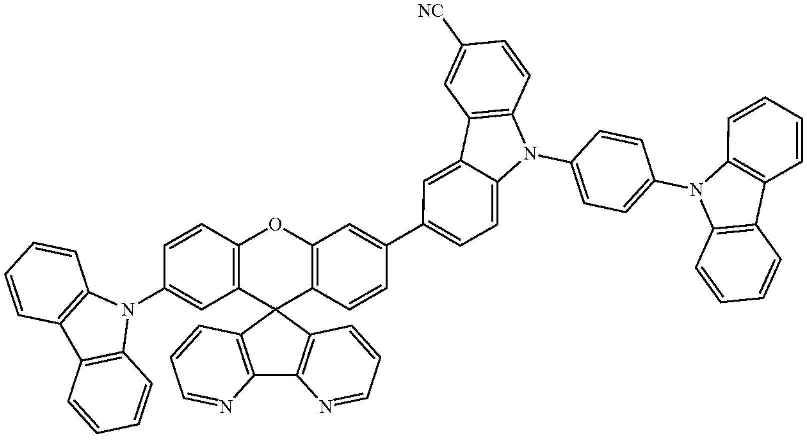

-continued
922
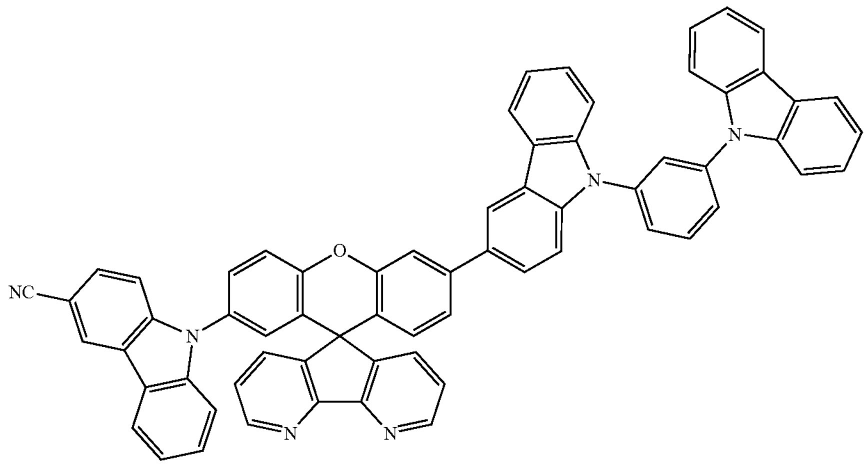
923
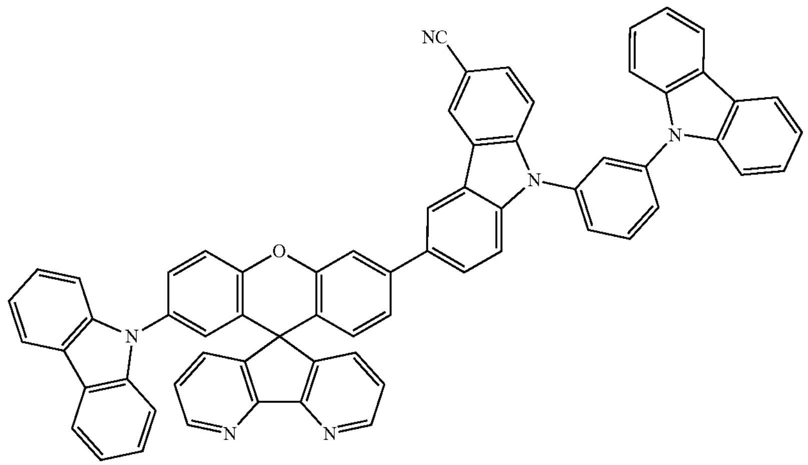
924
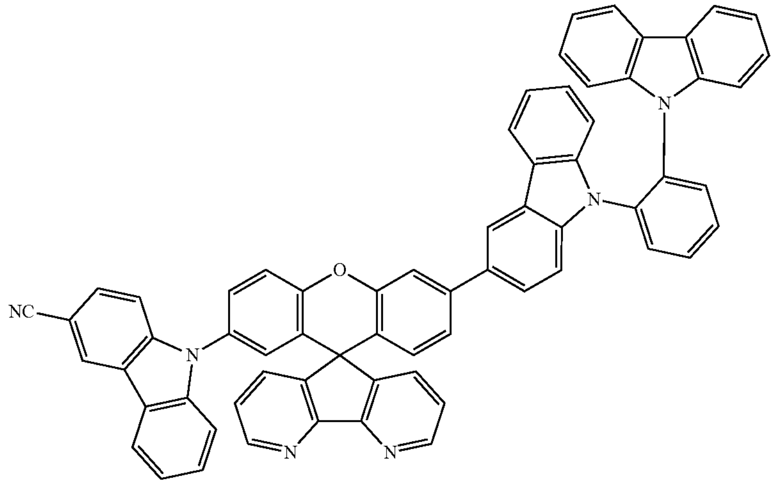

-continued
925
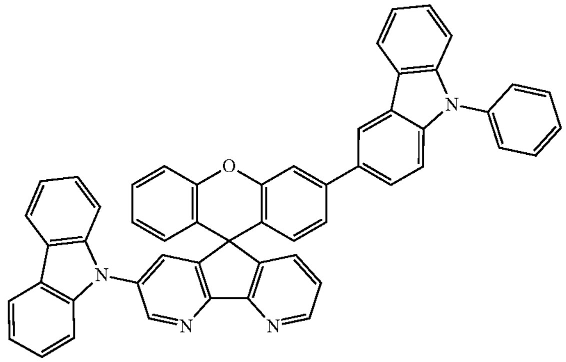
926
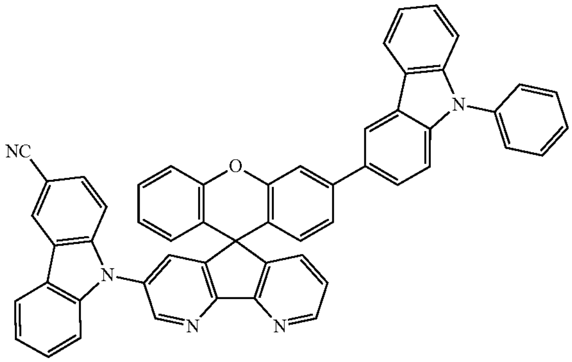
927
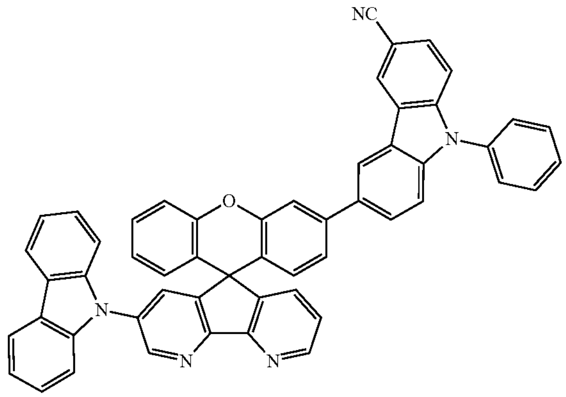
928
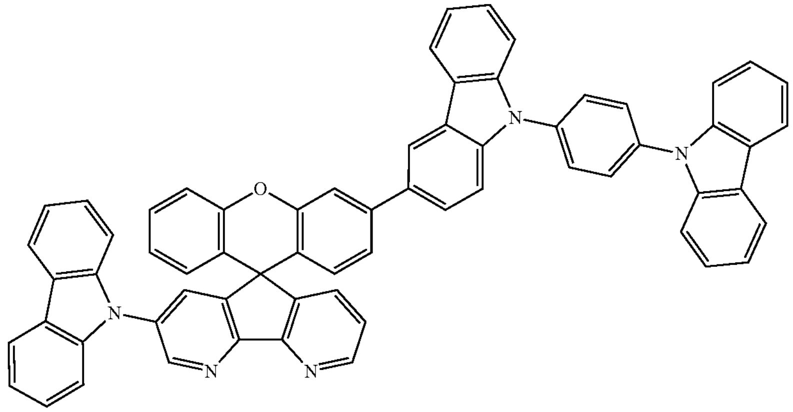
929
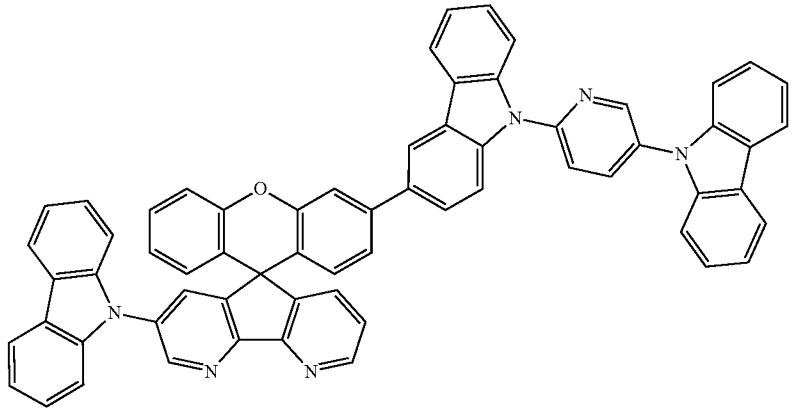

-continued
930
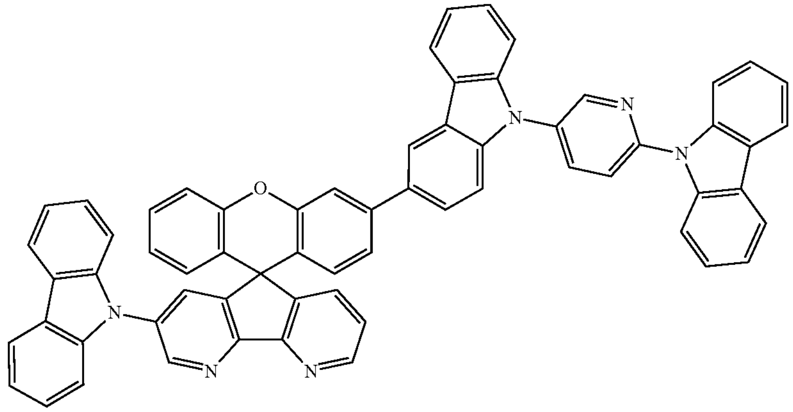
931
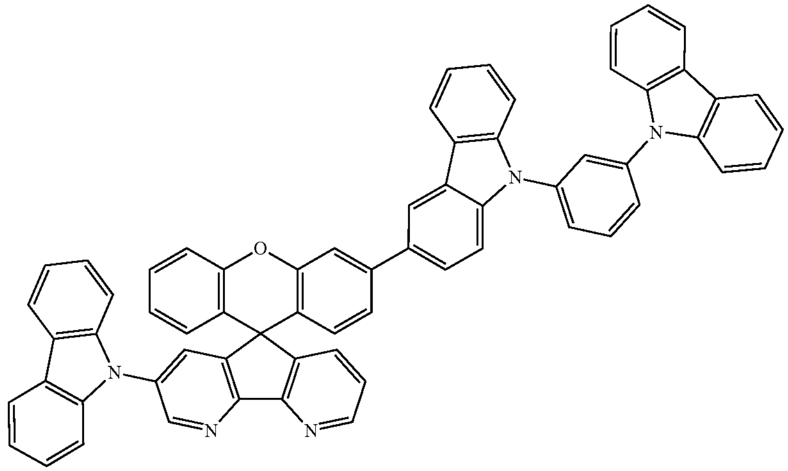
932
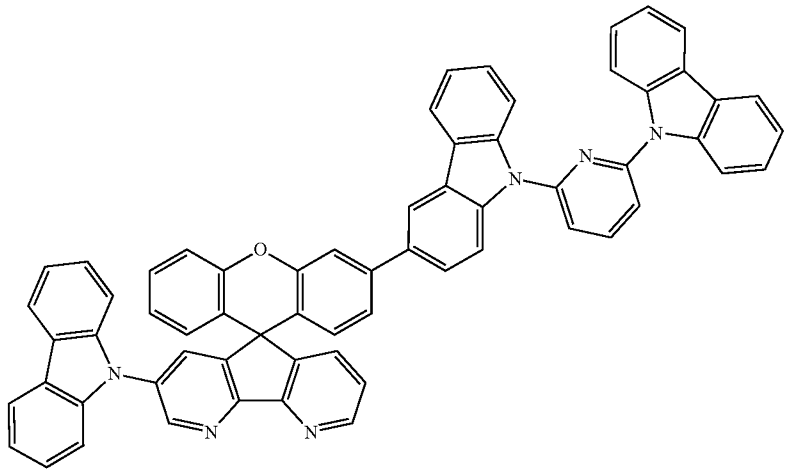

-continued
933
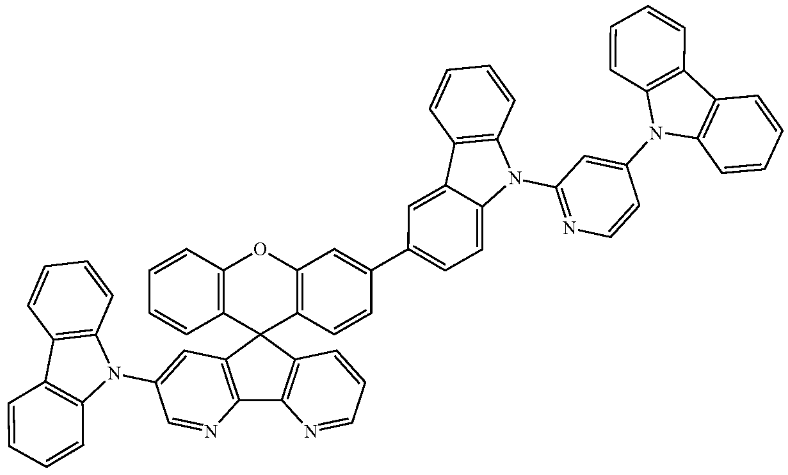
934
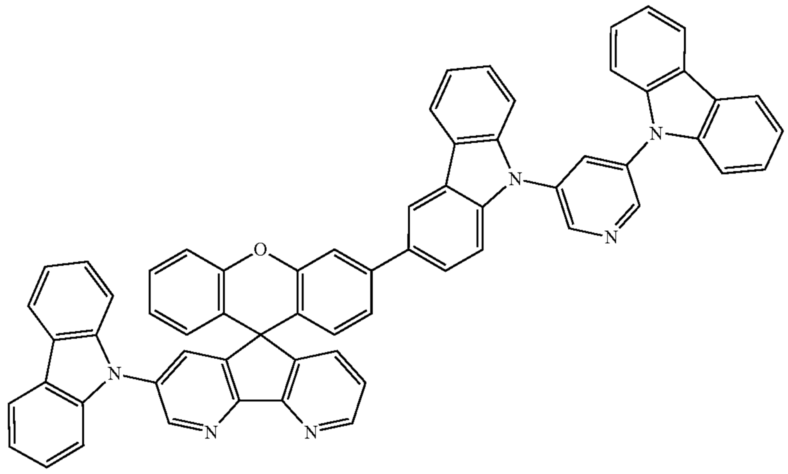
935
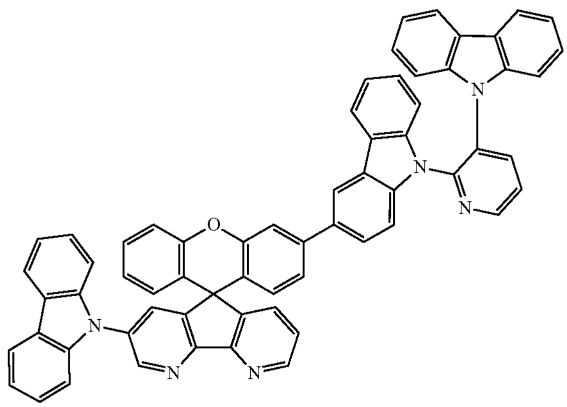
936
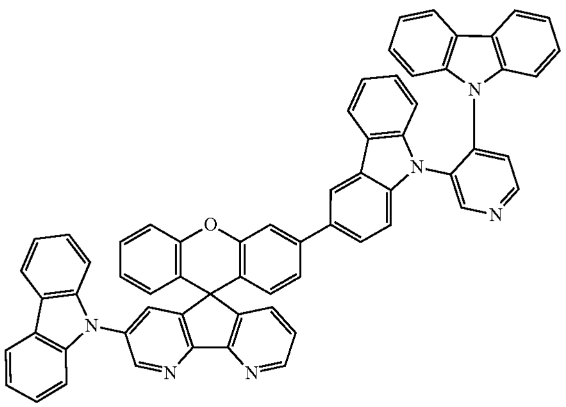

-continued
937
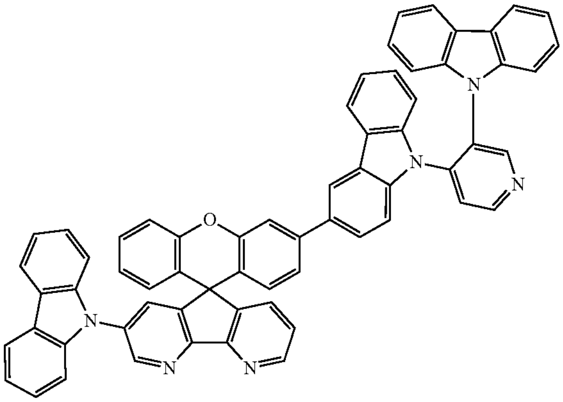
938
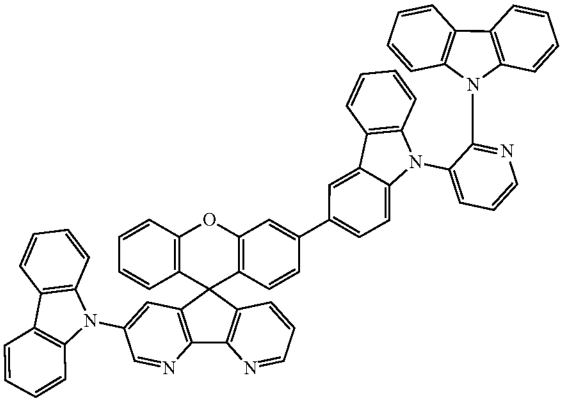
939
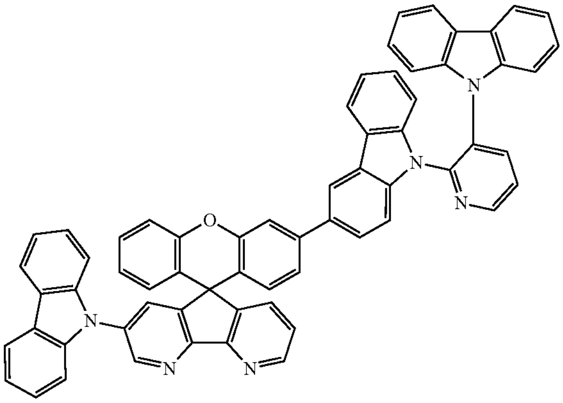
940
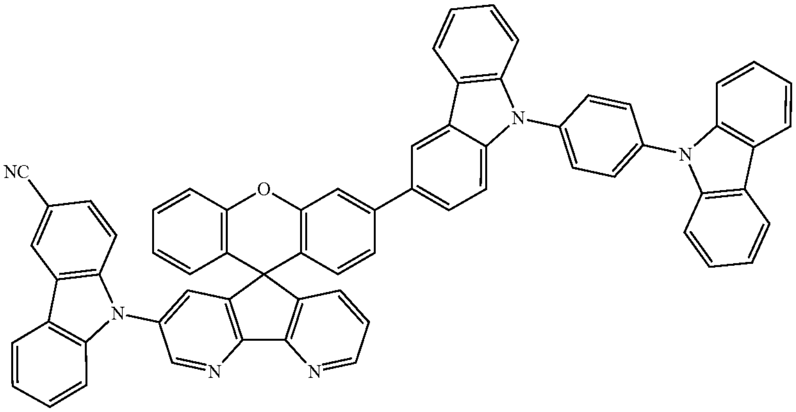

-continued
941
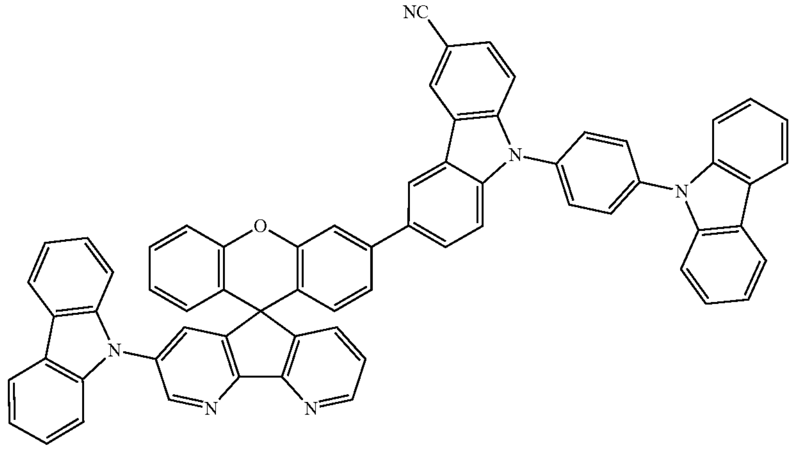
942
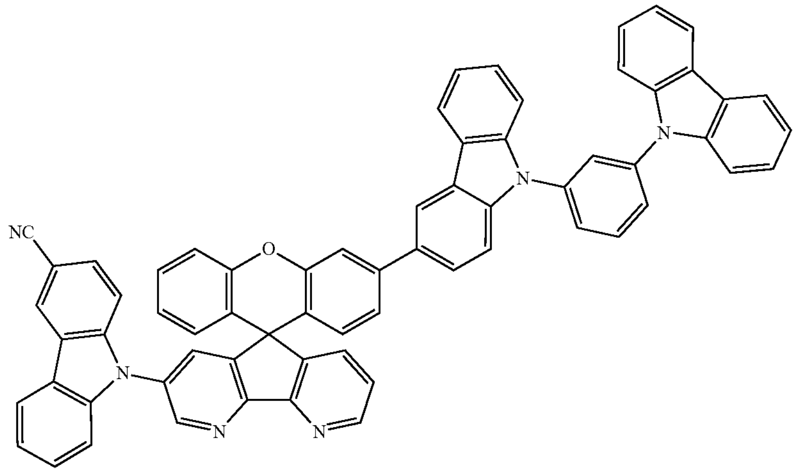
943
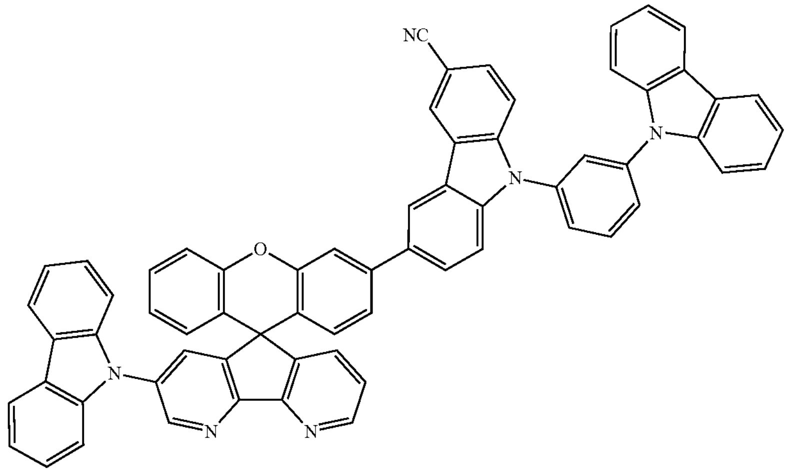

-continued
944
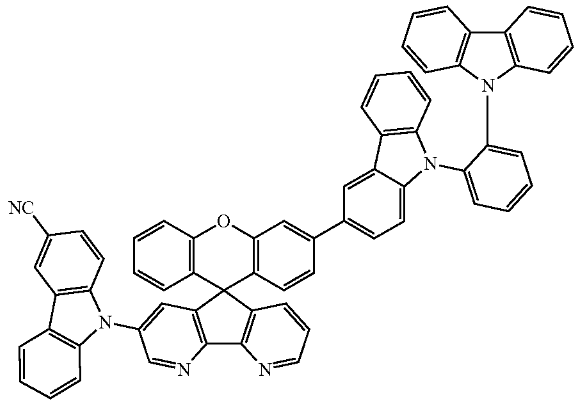
945
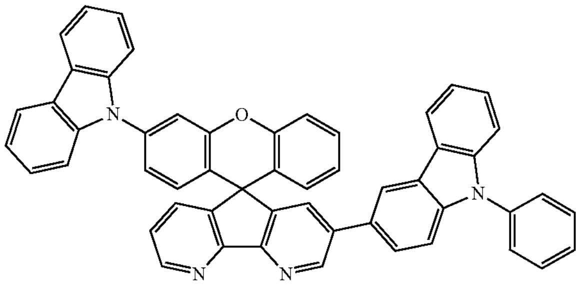
946
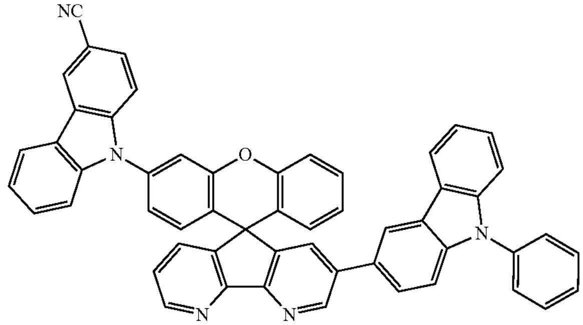
947
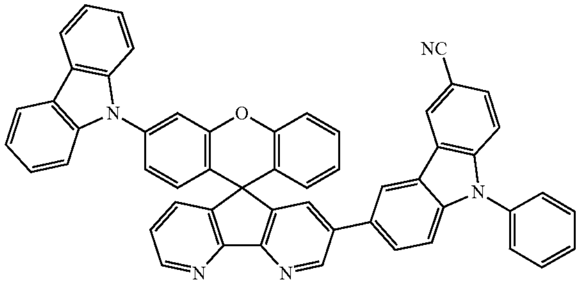
948
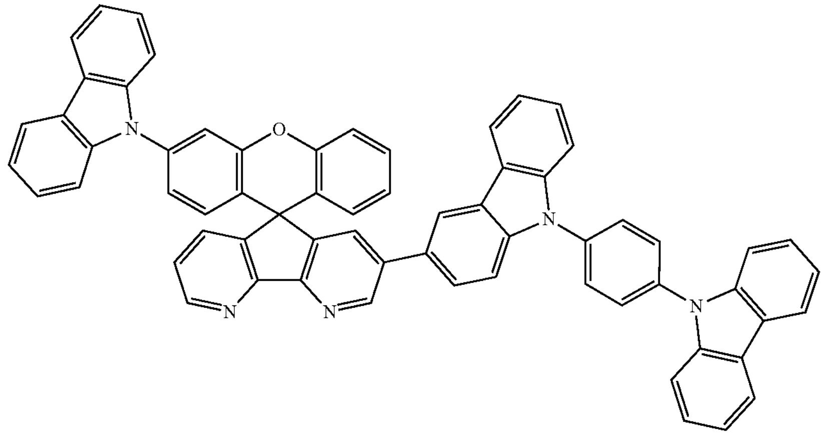
949
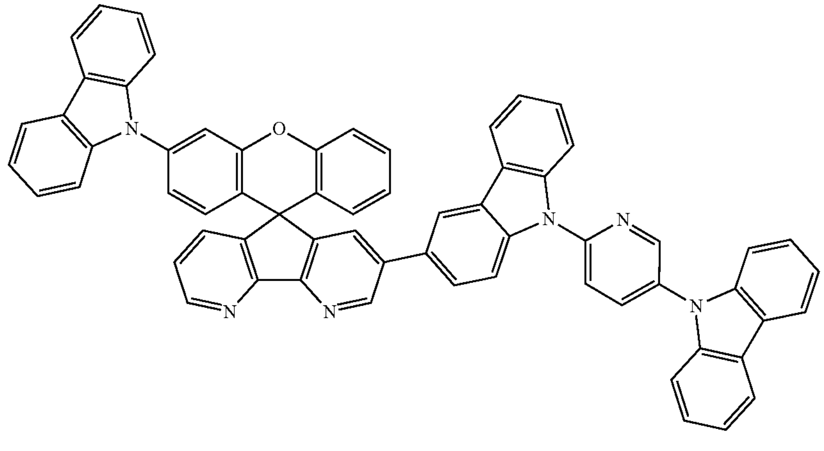

-continued
950
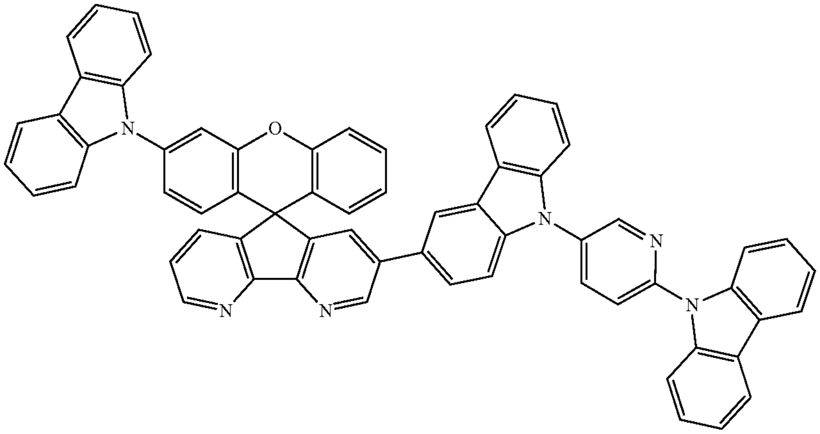
lp;2p
951
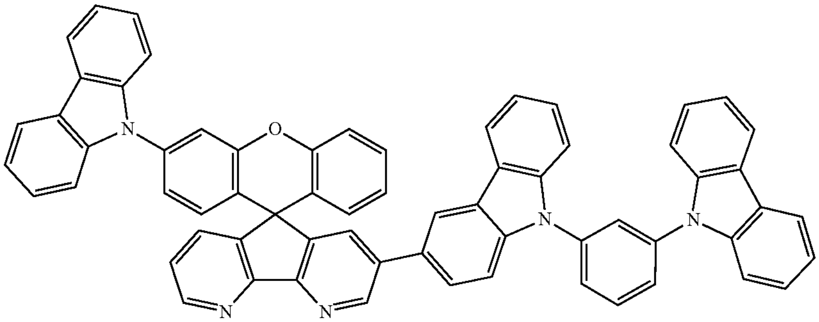
952
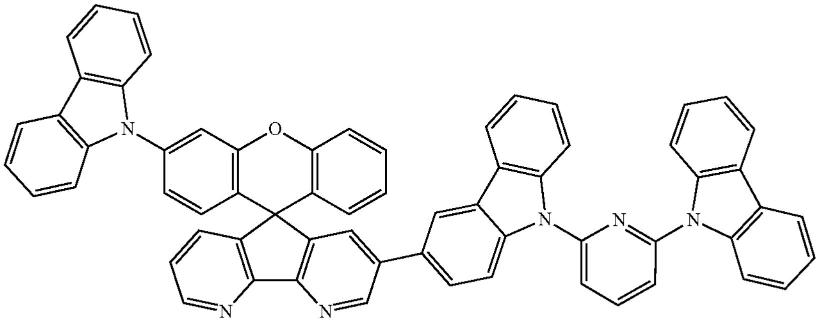
953
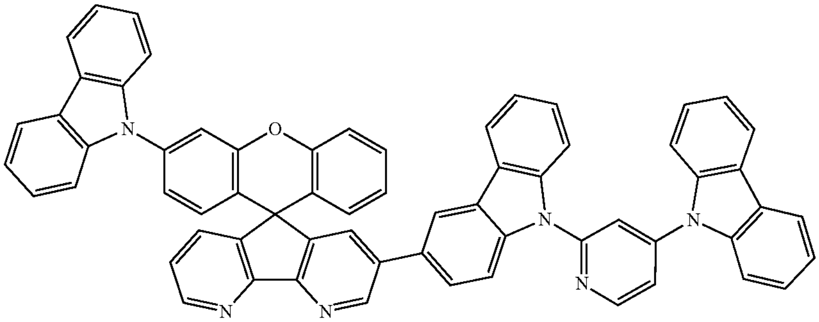

-continued
954
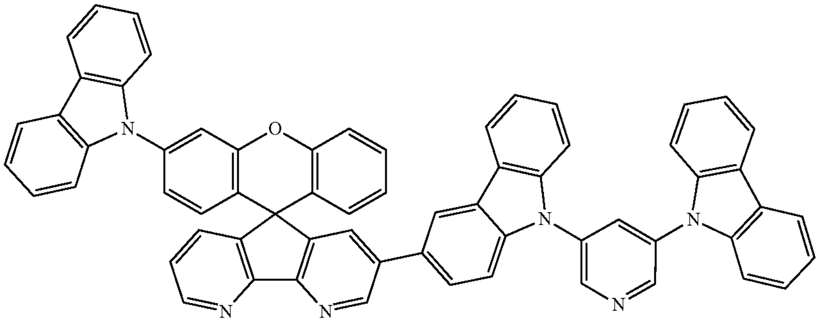
955
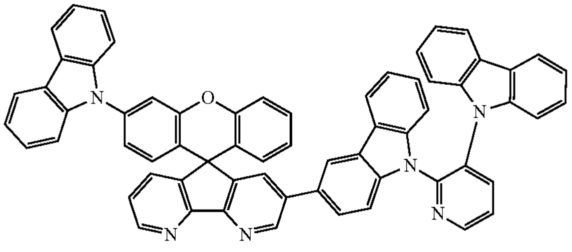
956
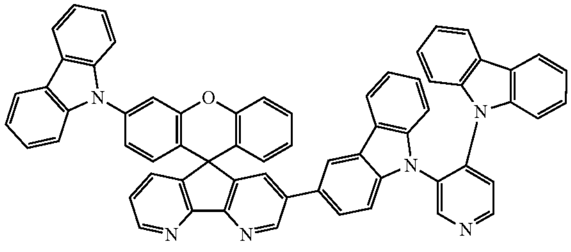
957
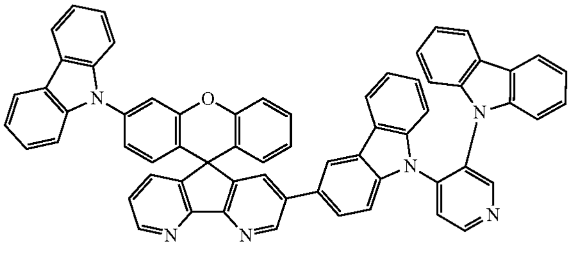
958
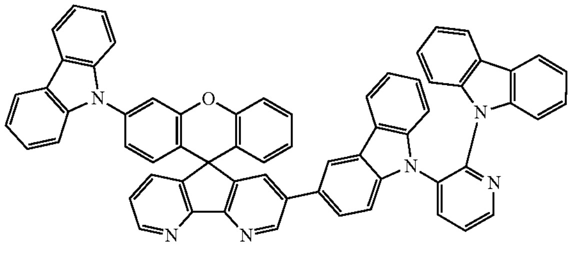
959
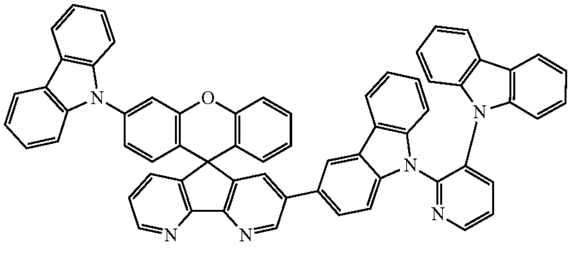
960
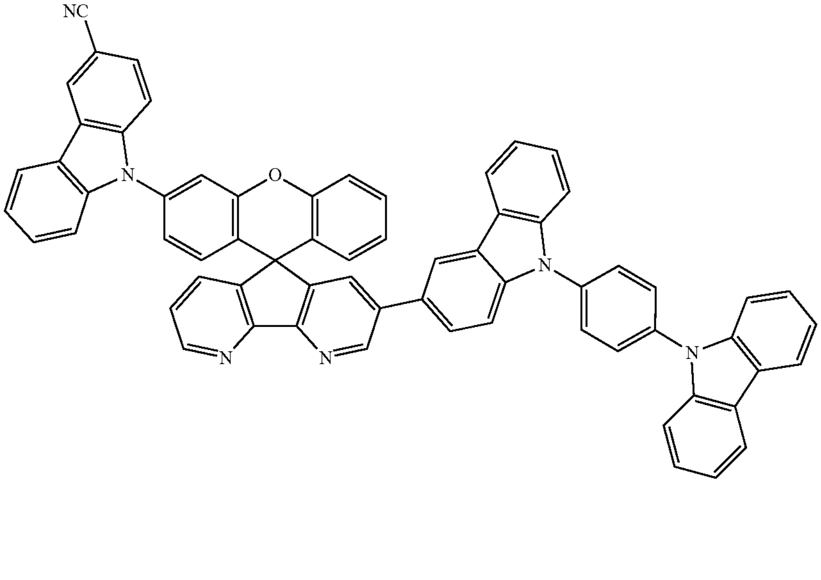

-continued
961
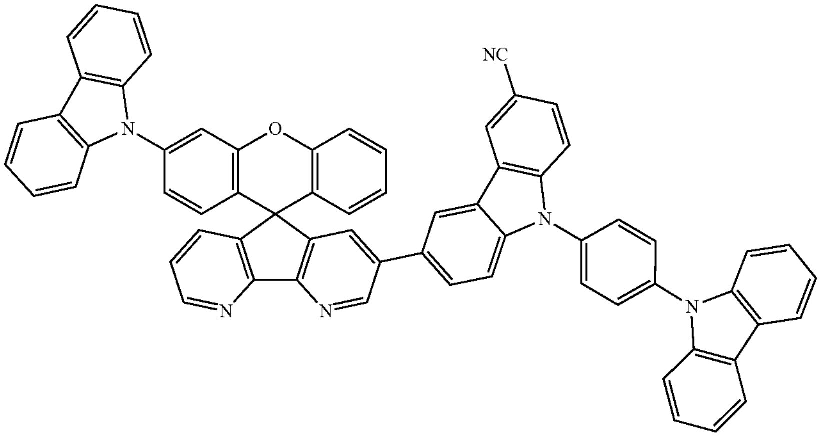
962
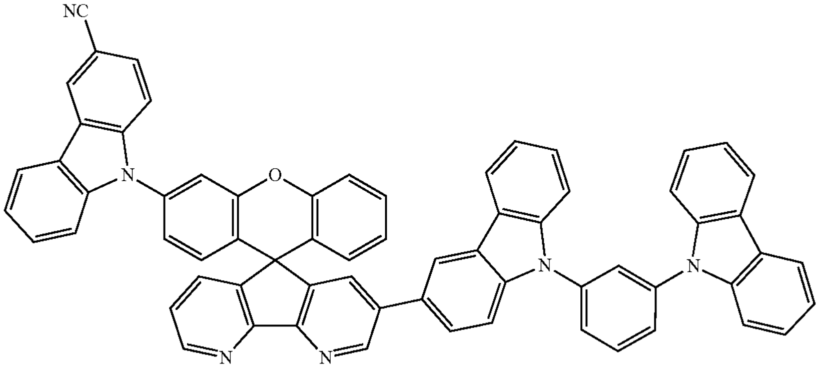
963
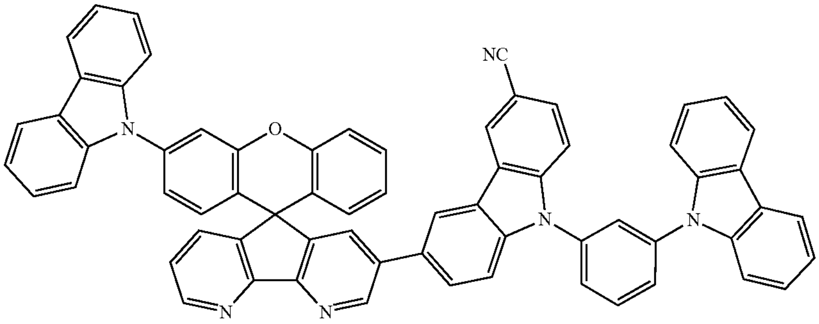
964
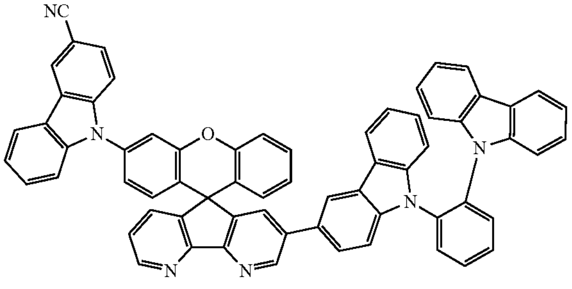
965
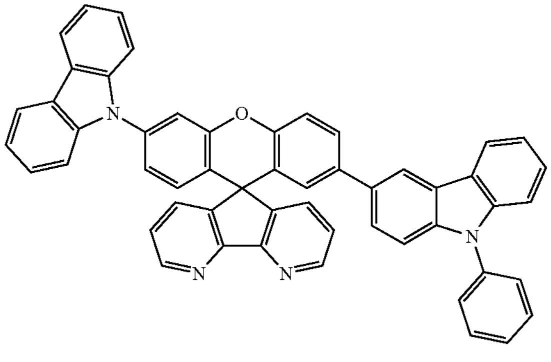

-continued
966
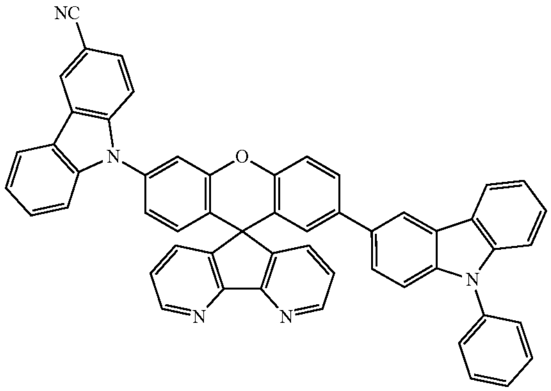
967
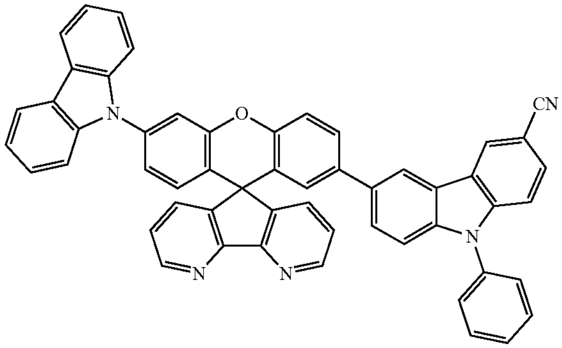
968
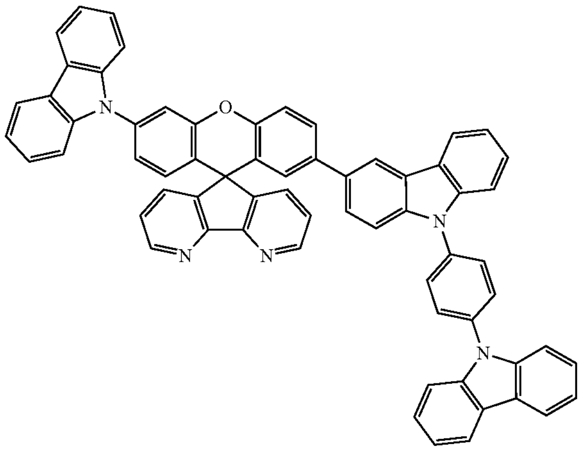
969
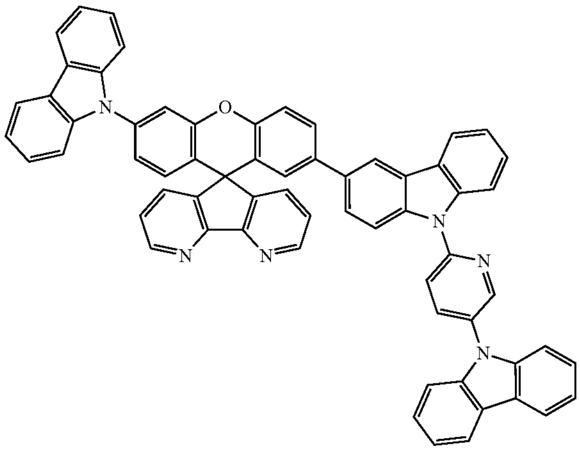
970
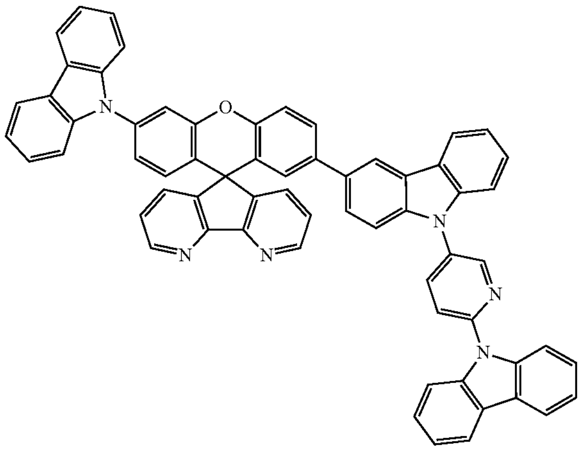
971
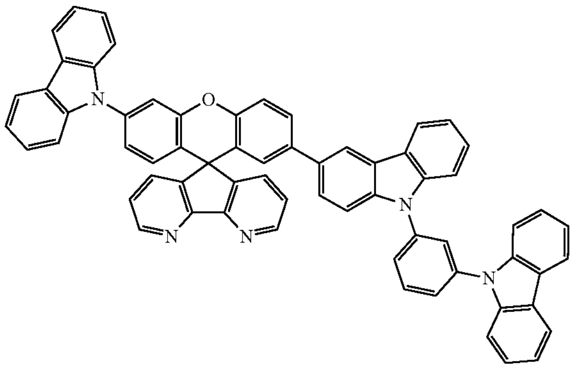

-continued
972
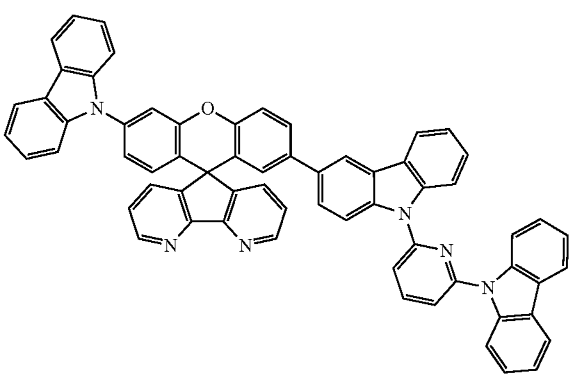
973
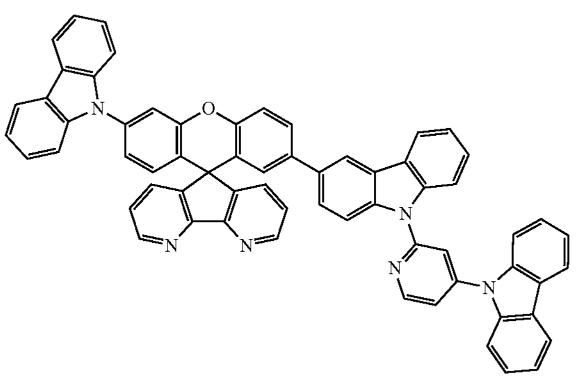
974
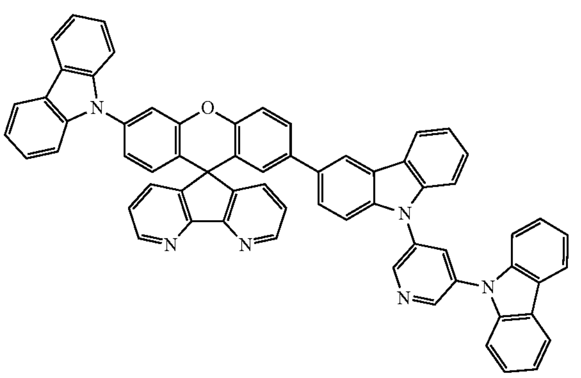
975
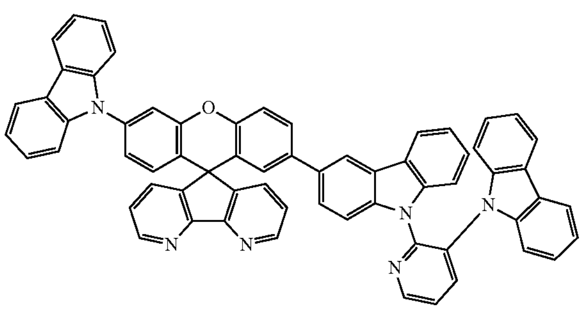
976
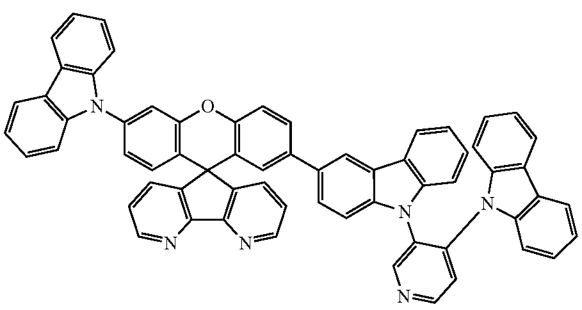
977
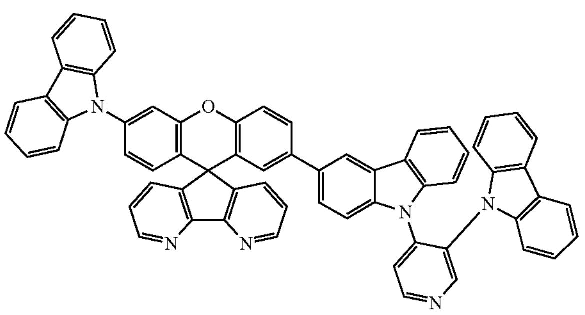
978
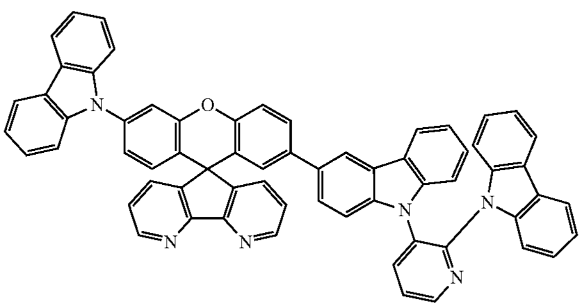
979
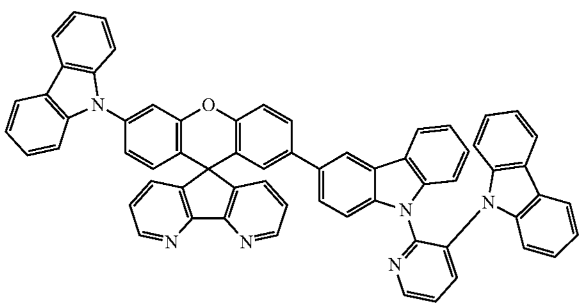

-continued
980
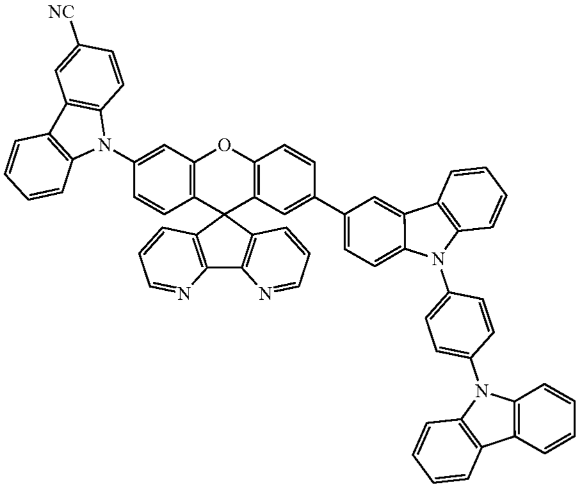
981
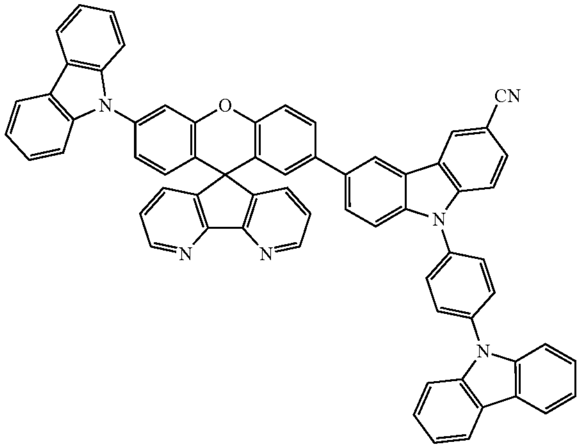
982
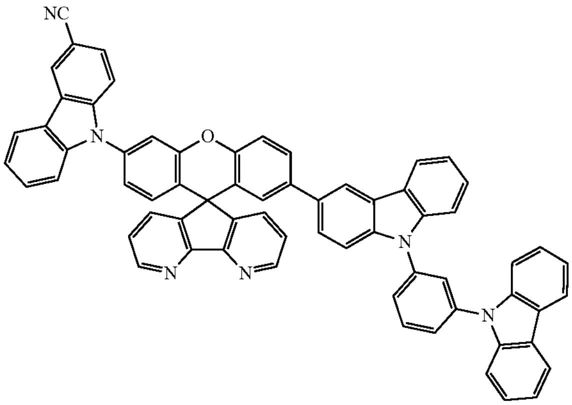
983
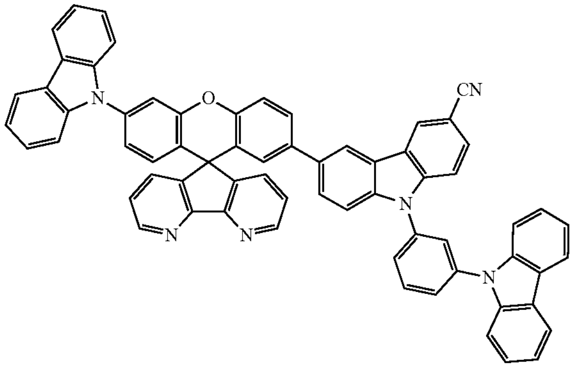
984
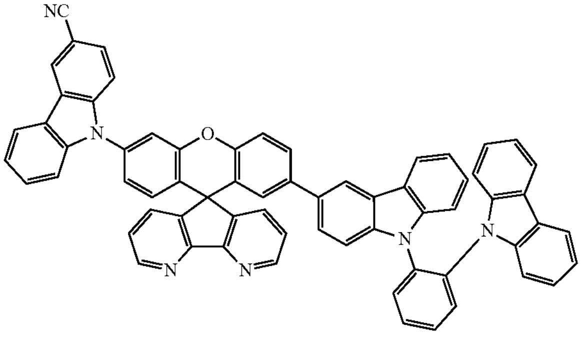
985
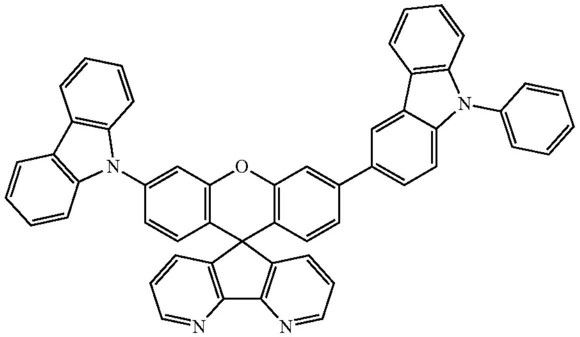

-continued
986
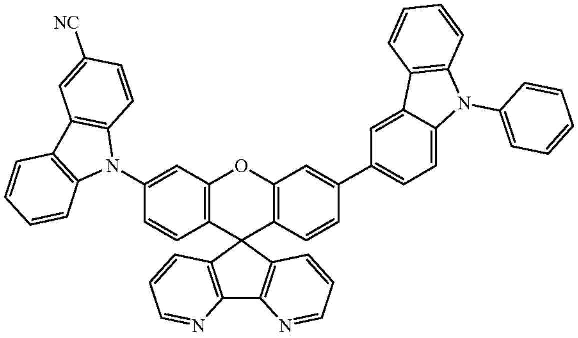
987
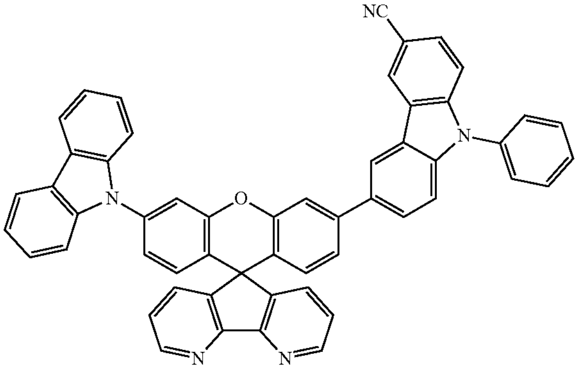
988
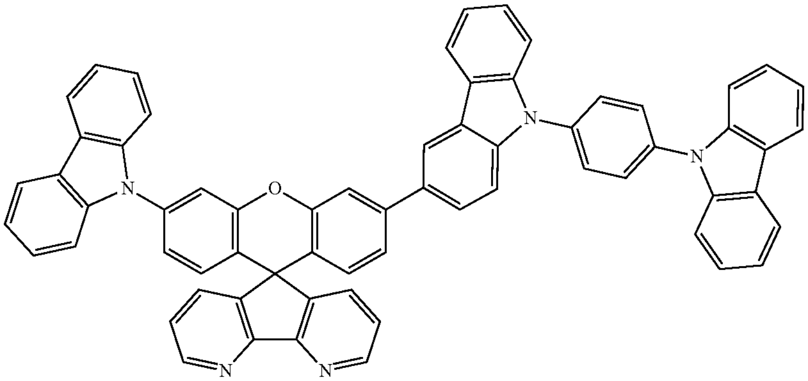
989
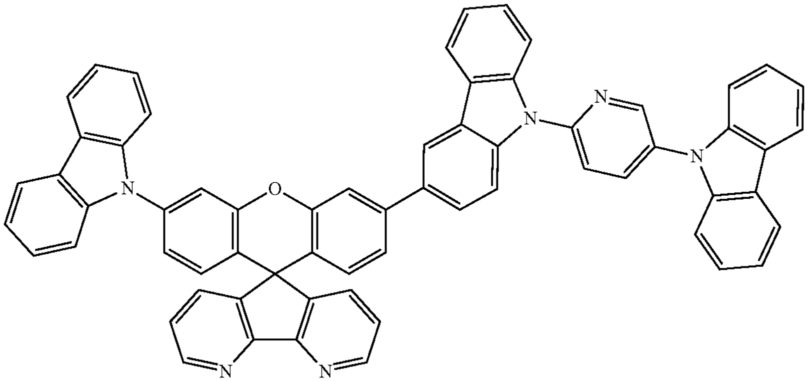
990
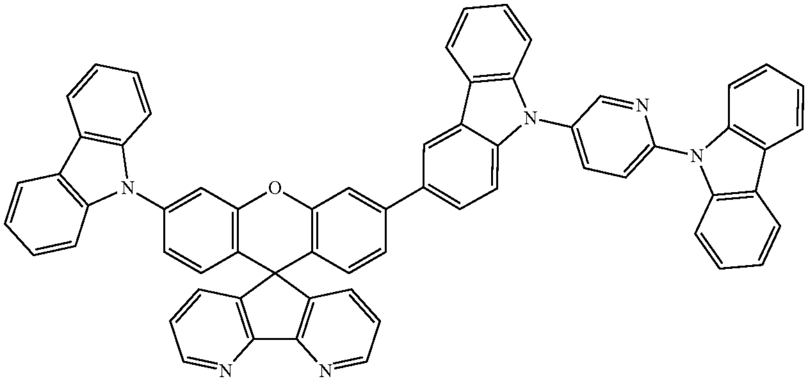

-continued
991
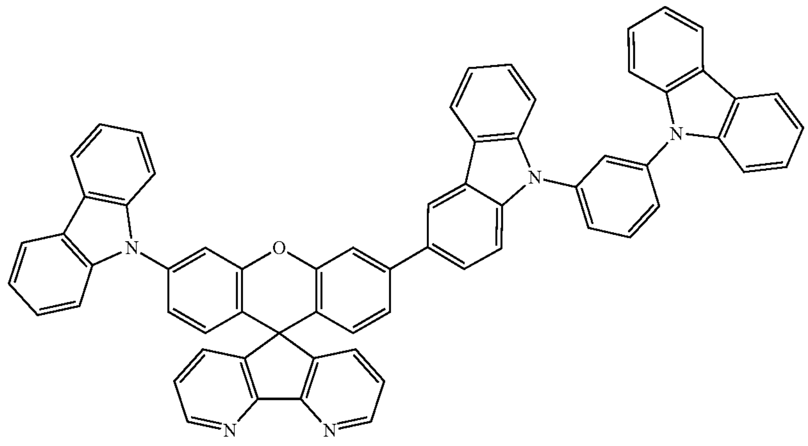
992
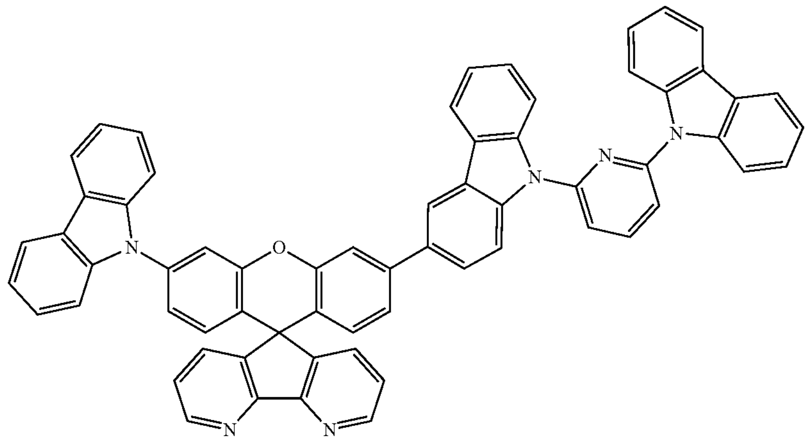
993
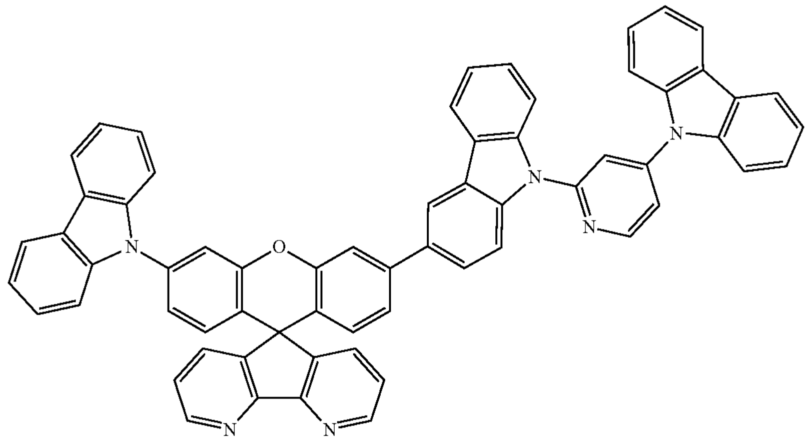

-continued
994
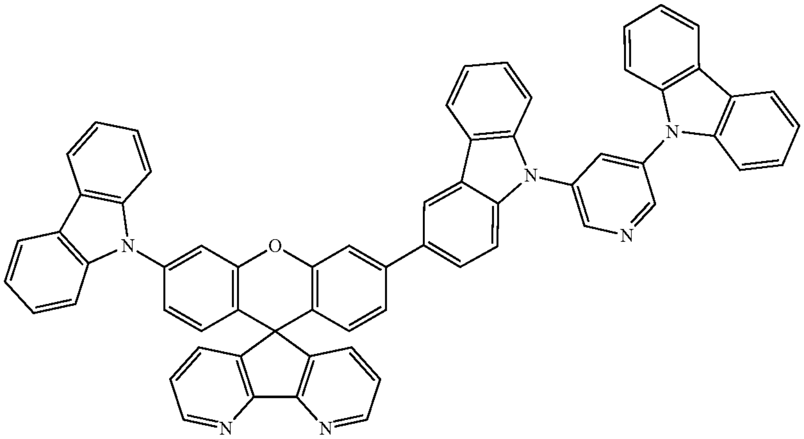
995
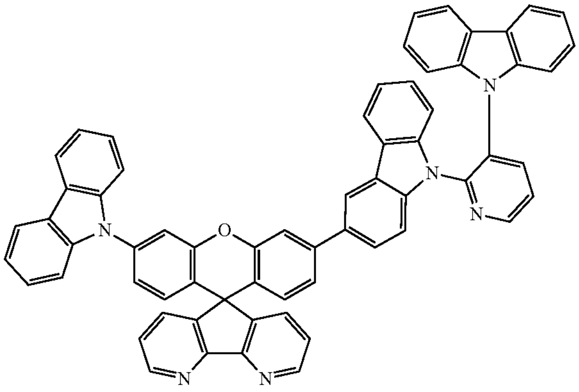
996
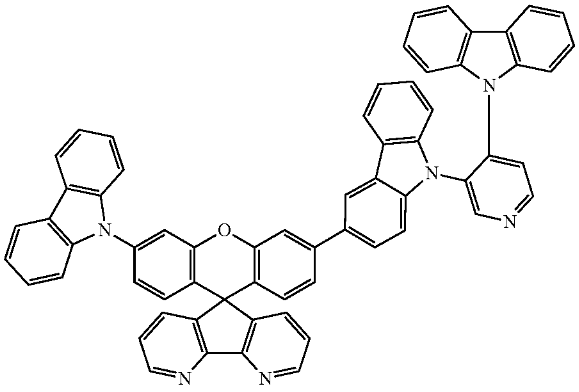
997
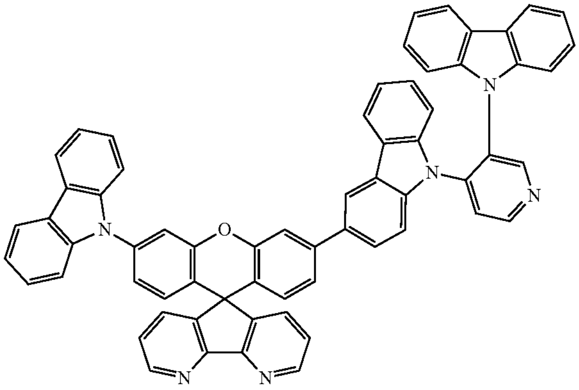
998
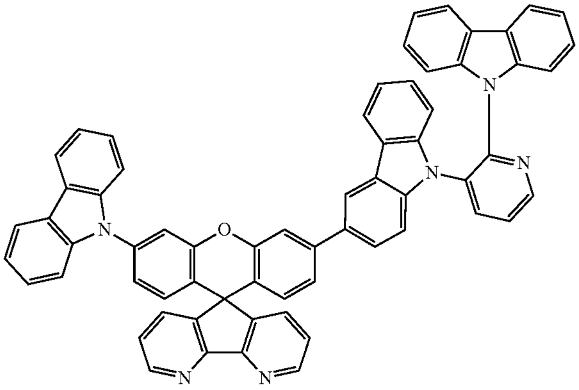

-continued
999
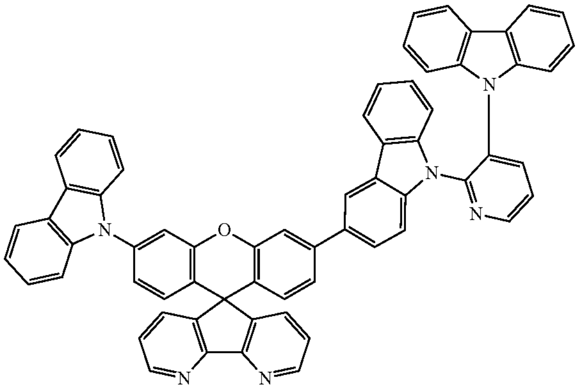
1000
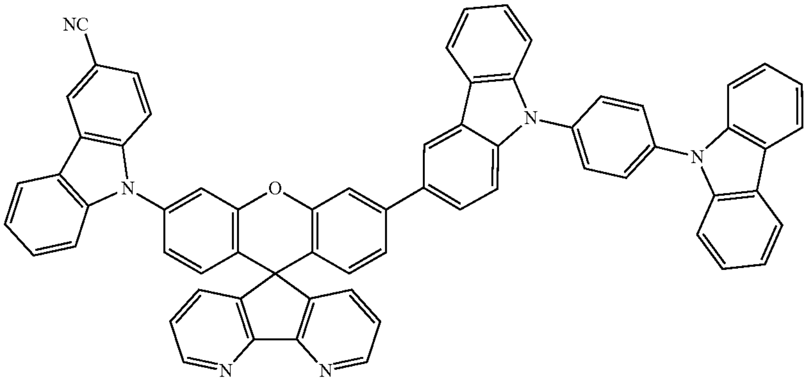
1001
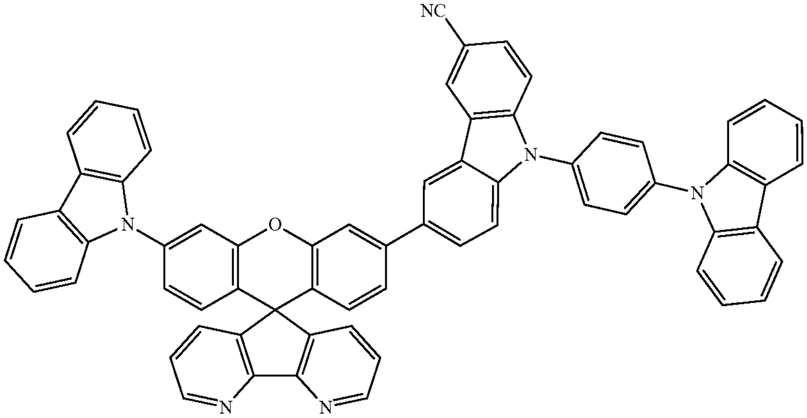
1002
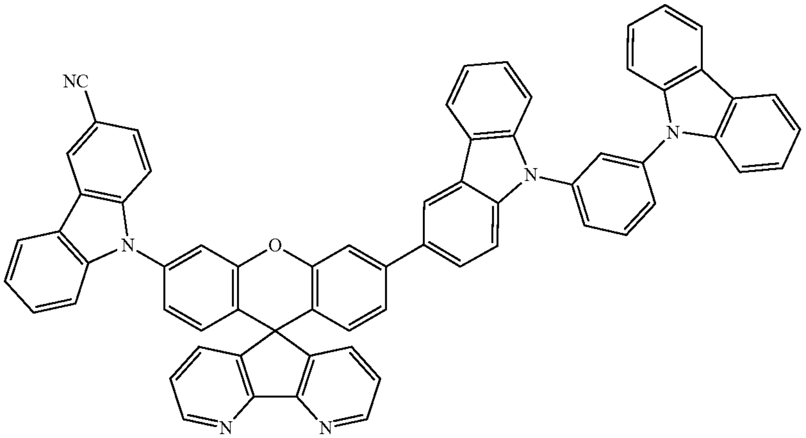

-continued
1003
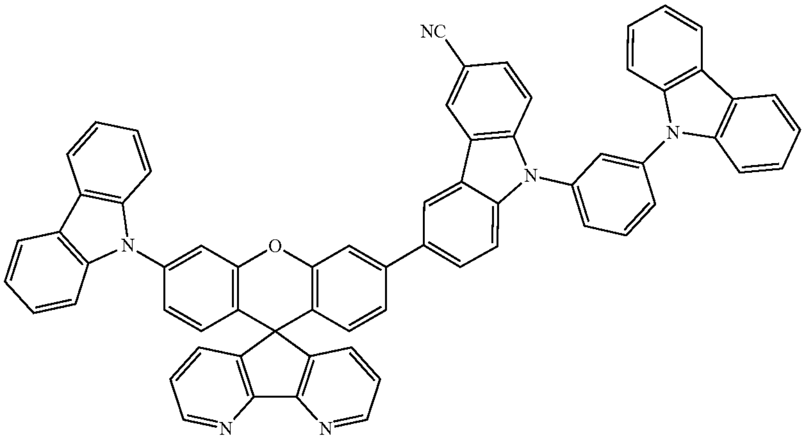
1004
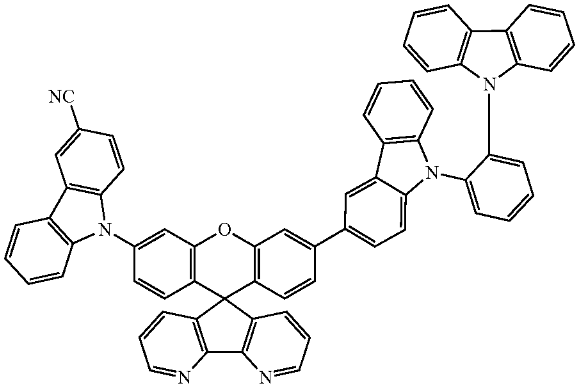
1005
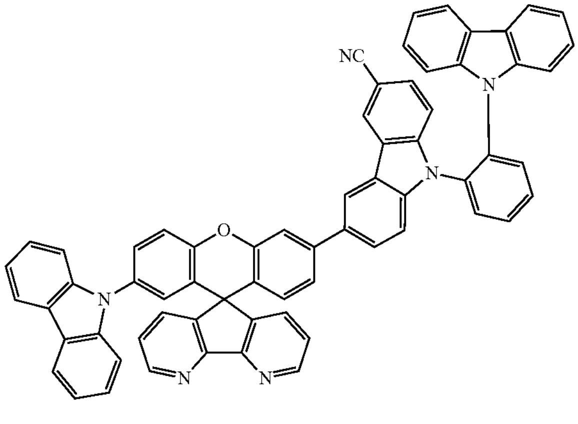
1006
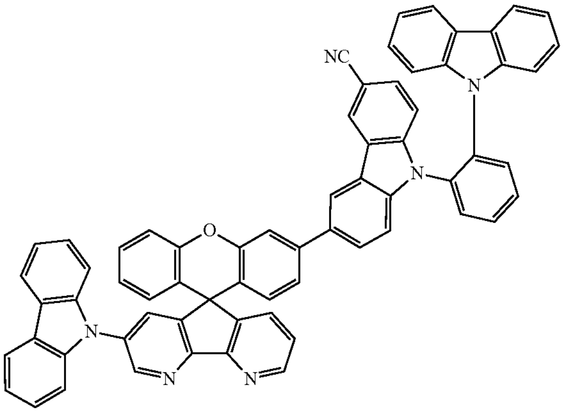
1007
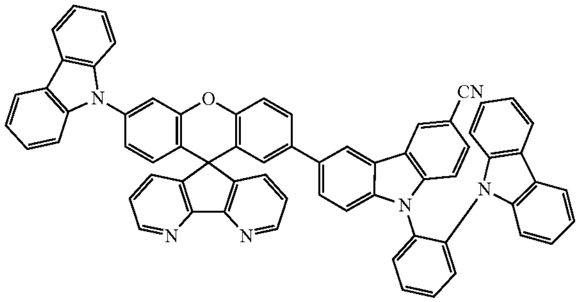

-continued
1008
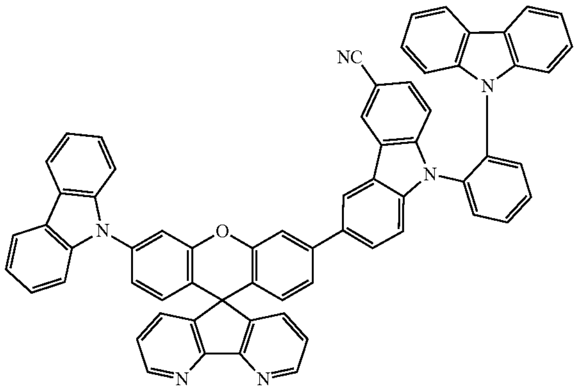
1009
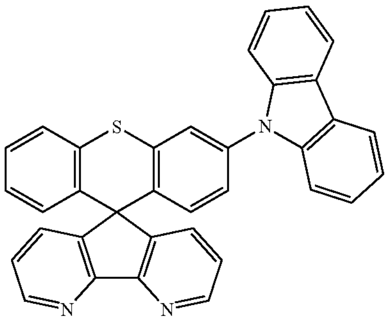
1010
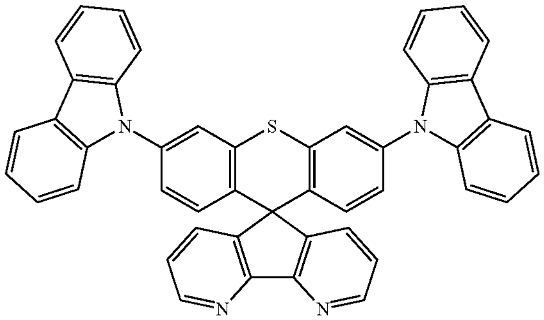
1011
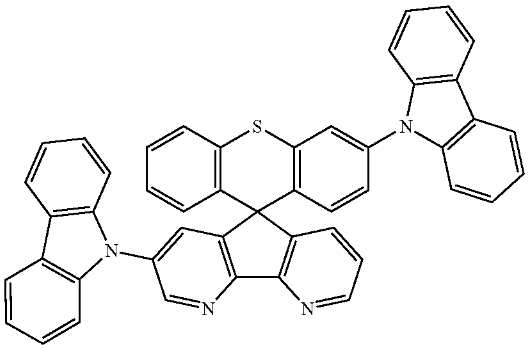
1012
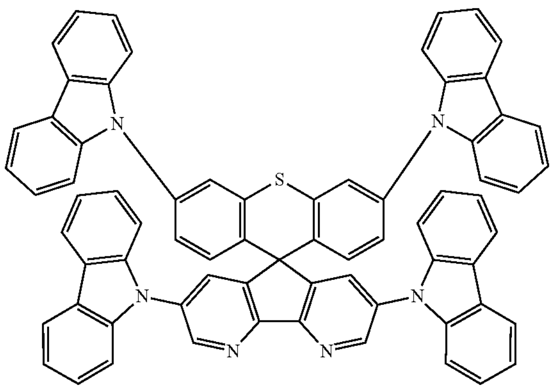
1013
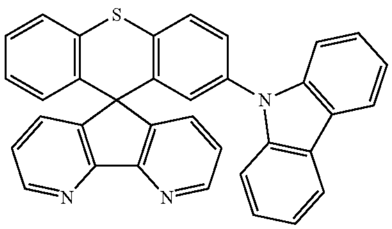
1014
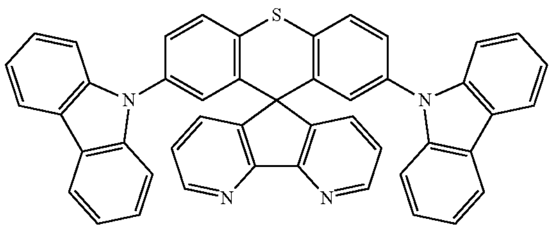
1015
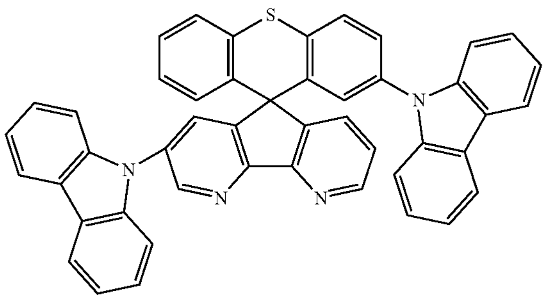

-continued
1016
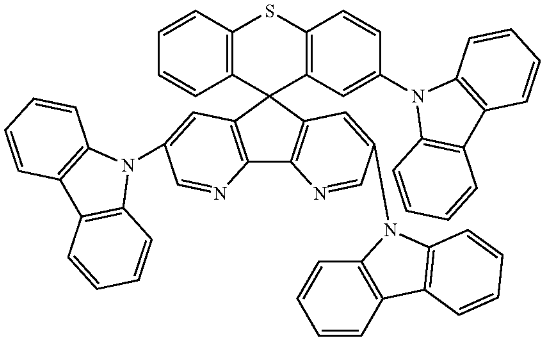
1017
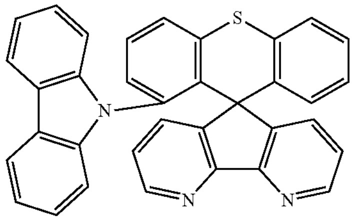
1018
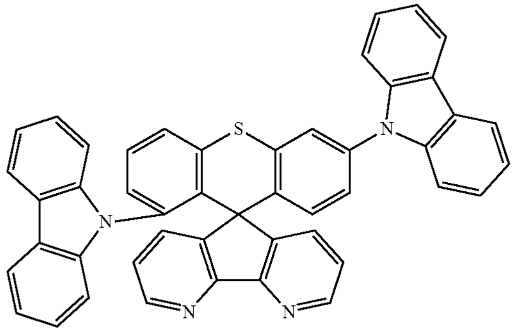
1019
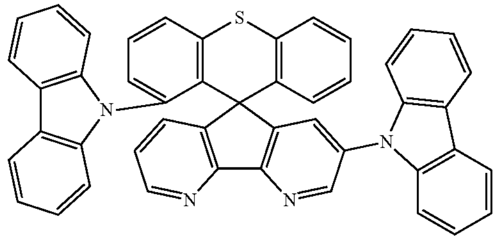
1020
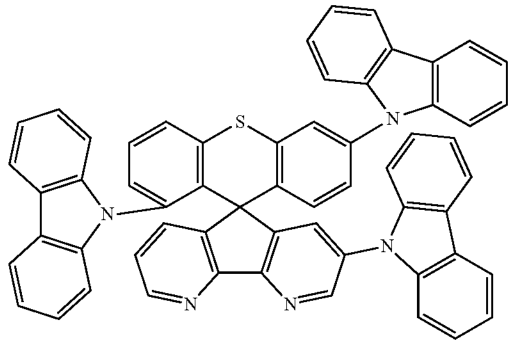
-continued
1021
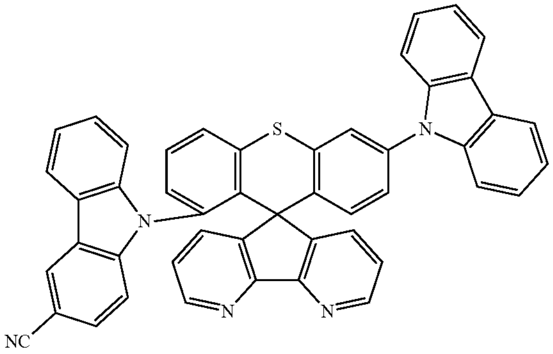
1022
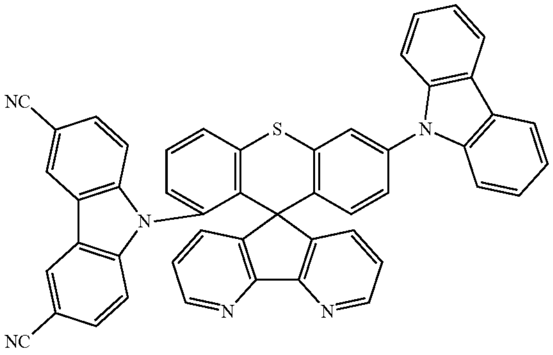
1023
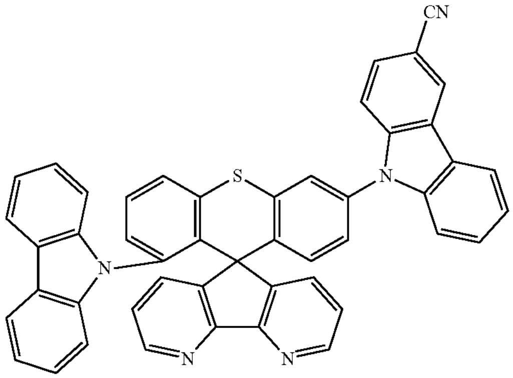

-continued
1024
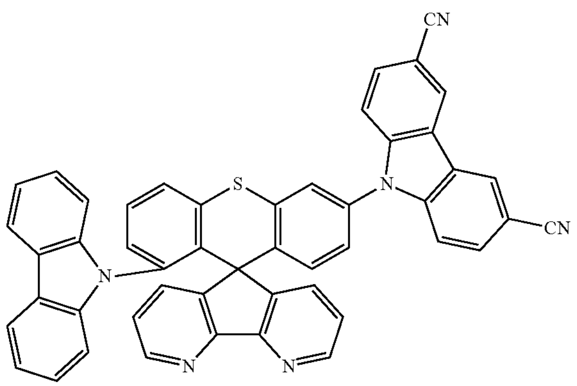
1025
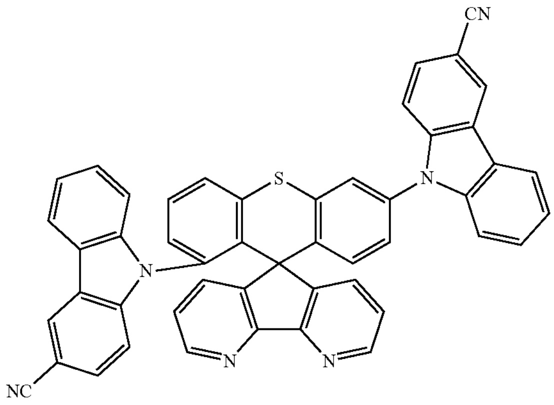
1026
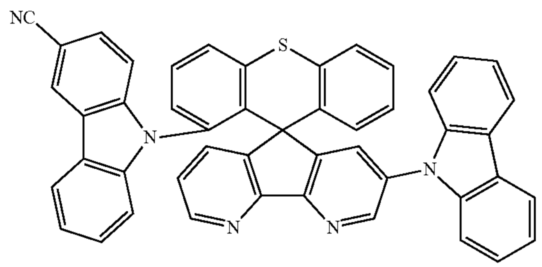
1027
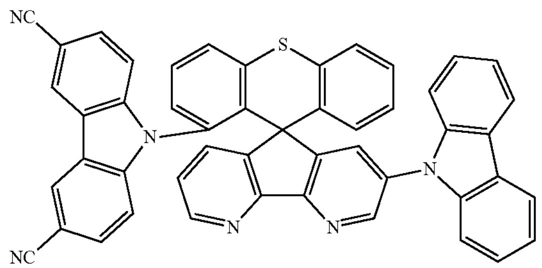
-continued
1028
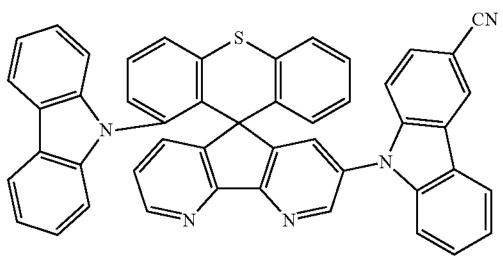
1029
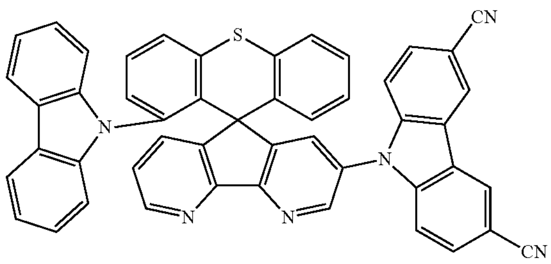
1030
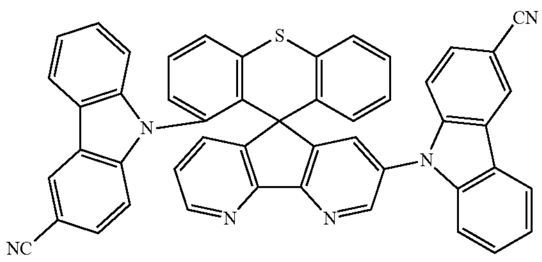
1031
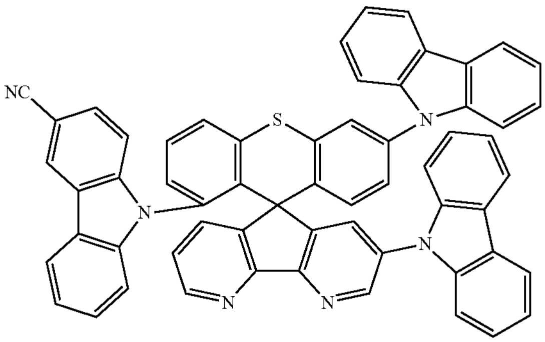
1032
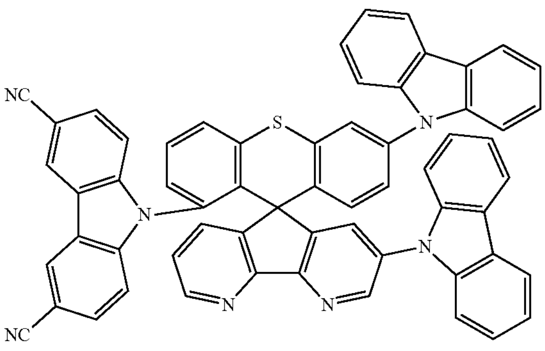

1033
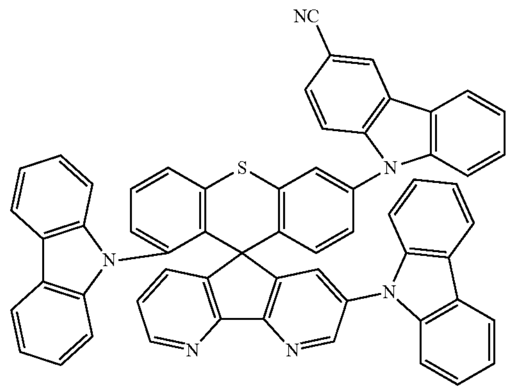
1034
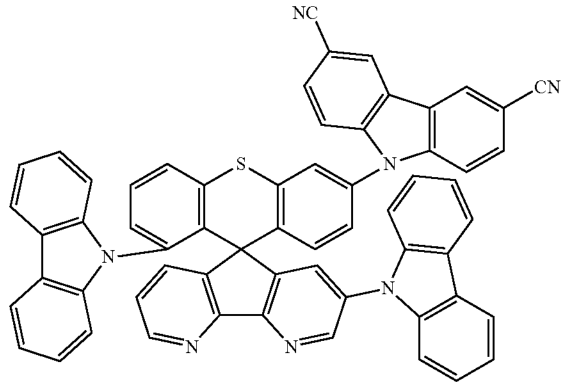
1035
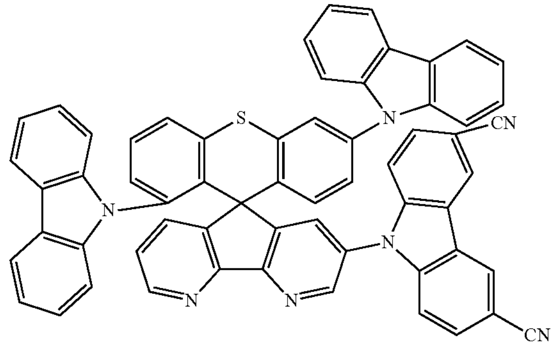
1036
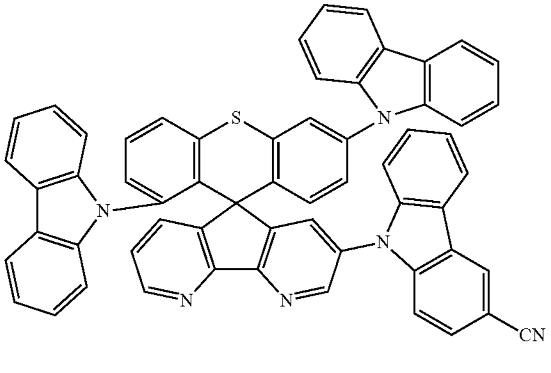
1037
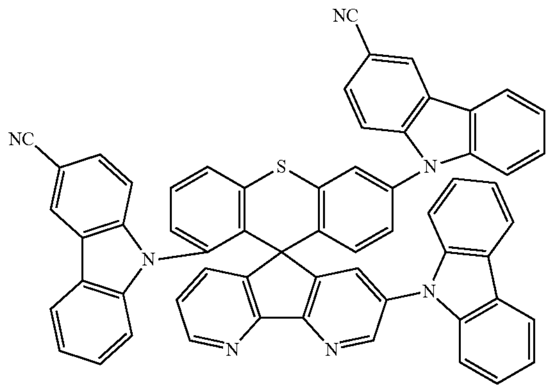
1038
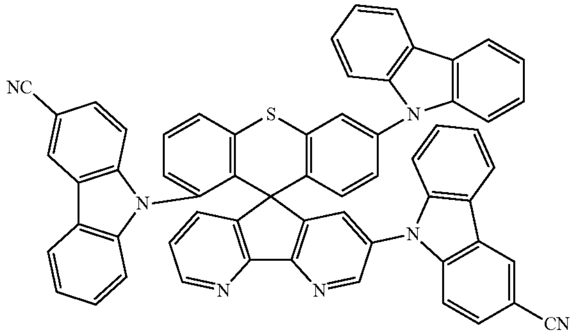
1039
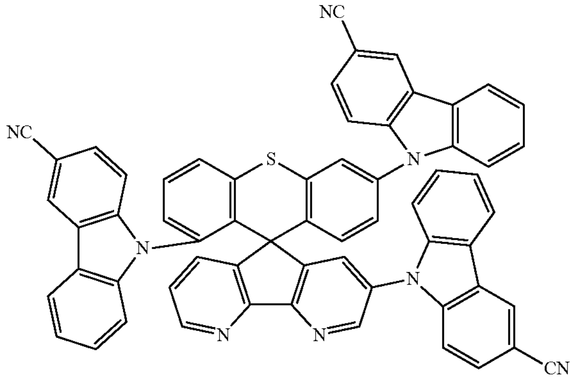
1040
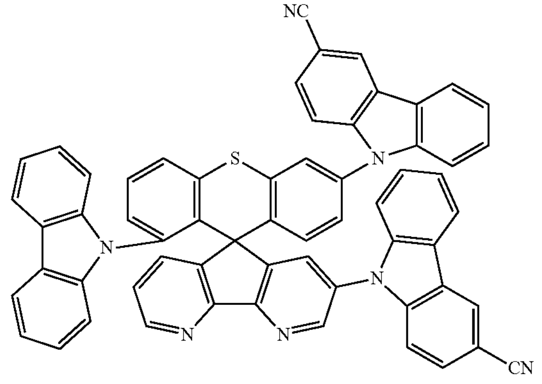

-continued
1041
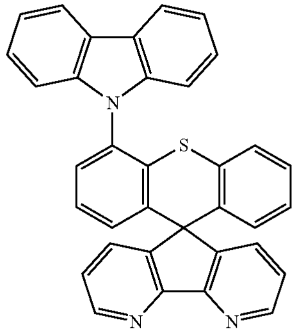
1042
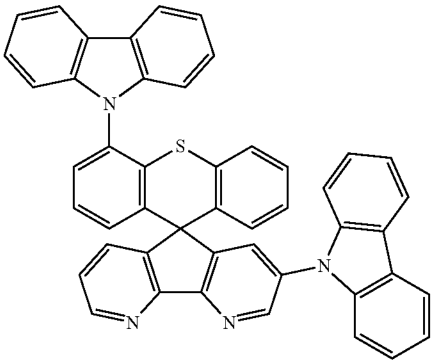
1043
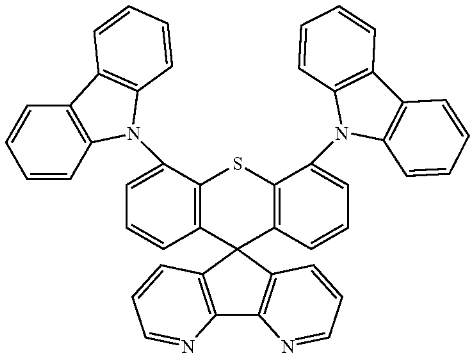
1044
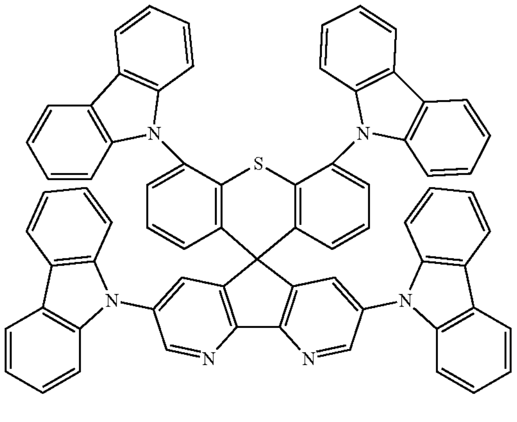
-continued
1045
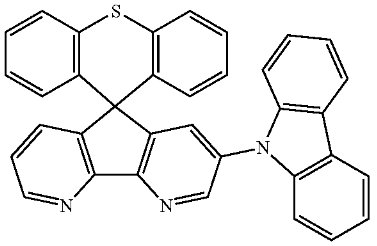
1046
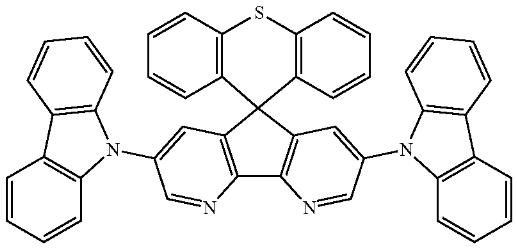
1047
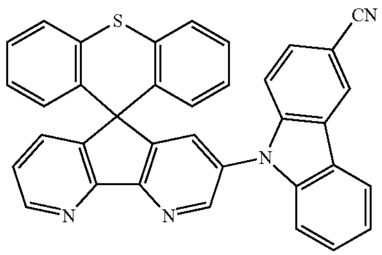
1048
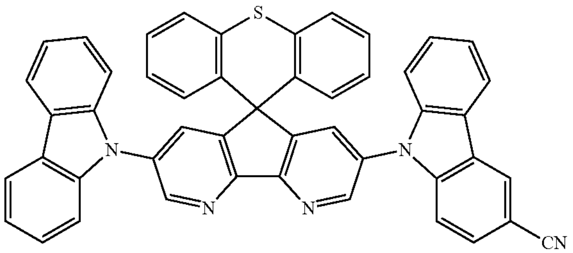
1049
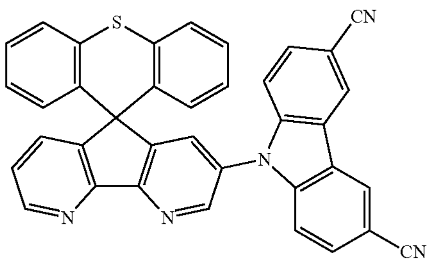
1050
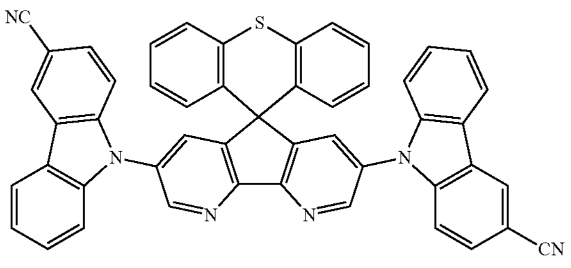

-continued
1051
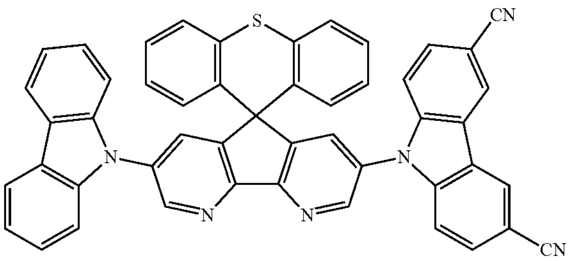
1052
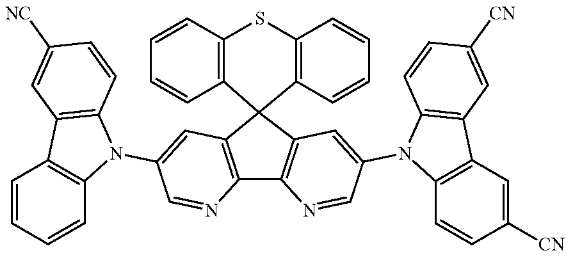
1053
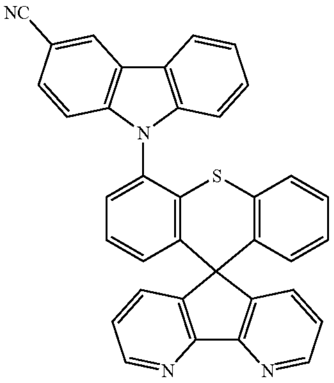
1054
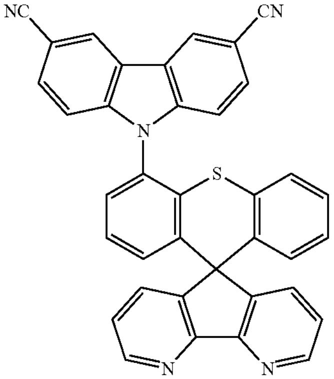
-continued
1055
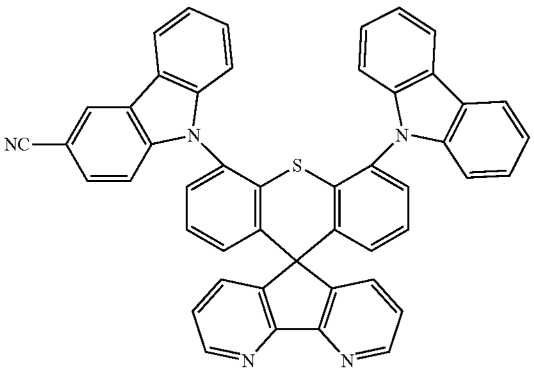
1056
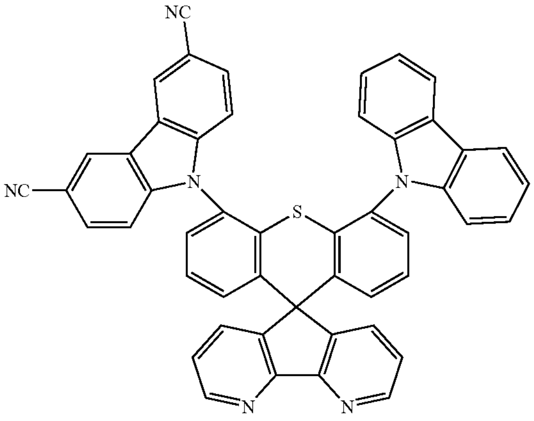
1057
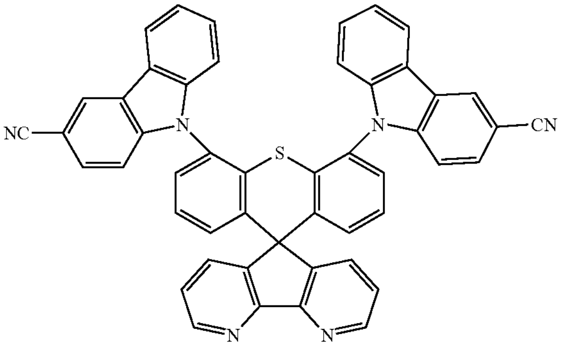
1058
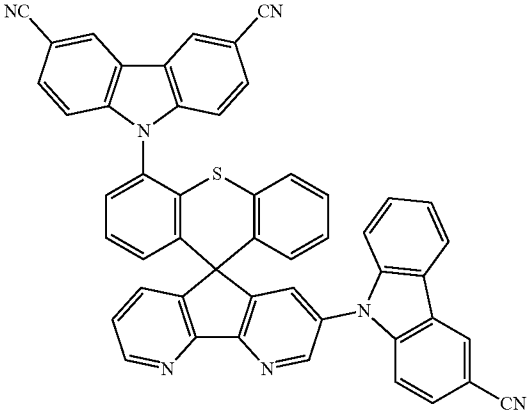

-continued
1059
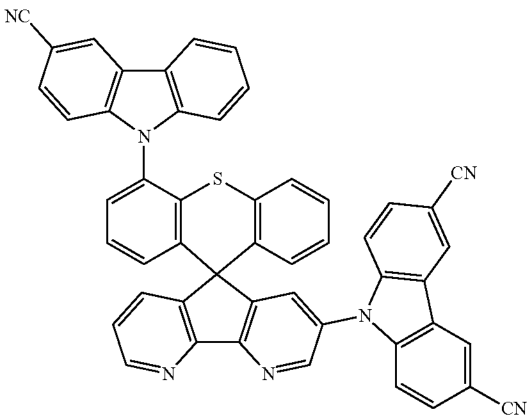
1060
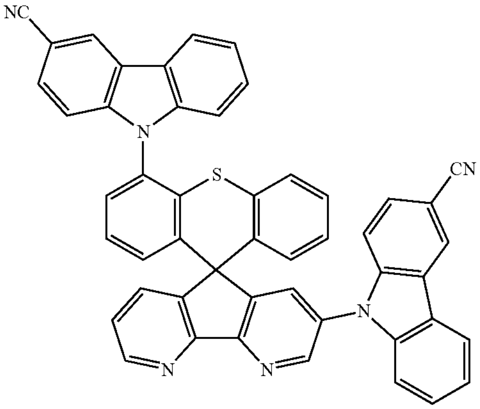
1061
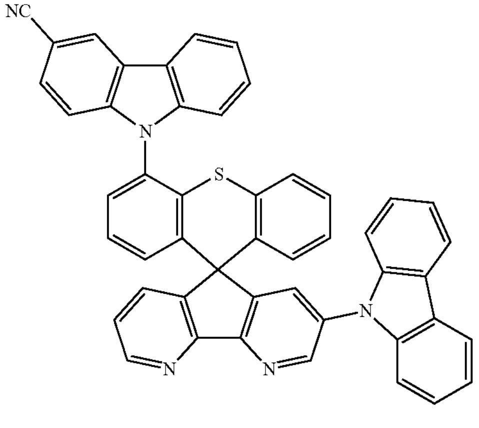
-continued
1062
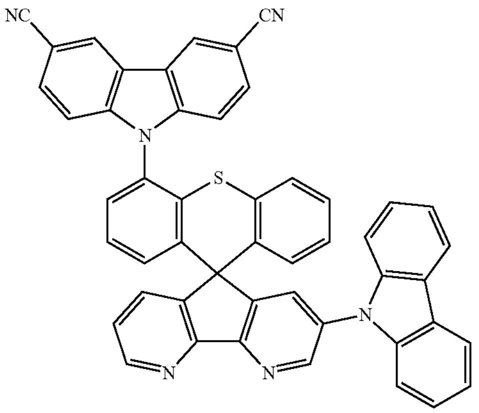
1063
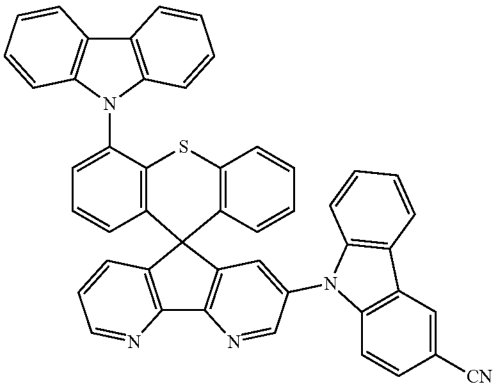
1064
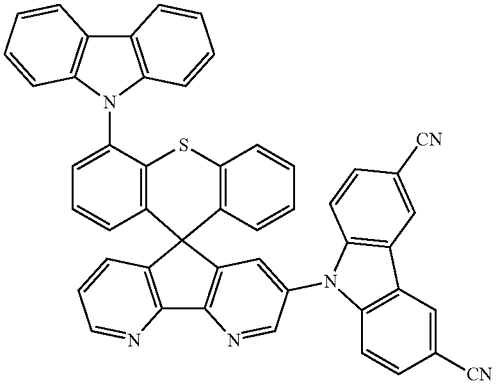

-continued
1065
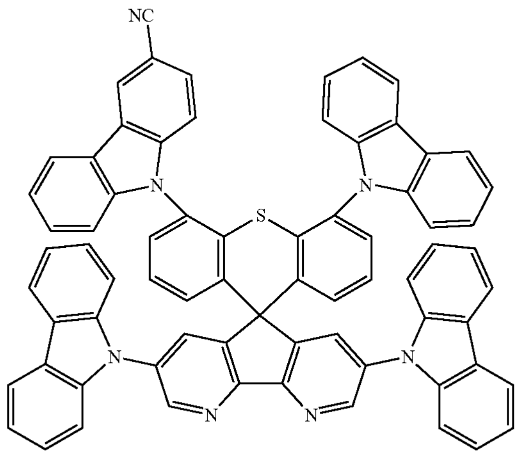
1066
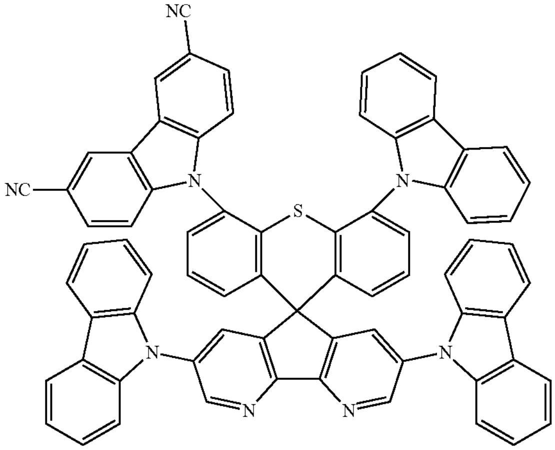
1067
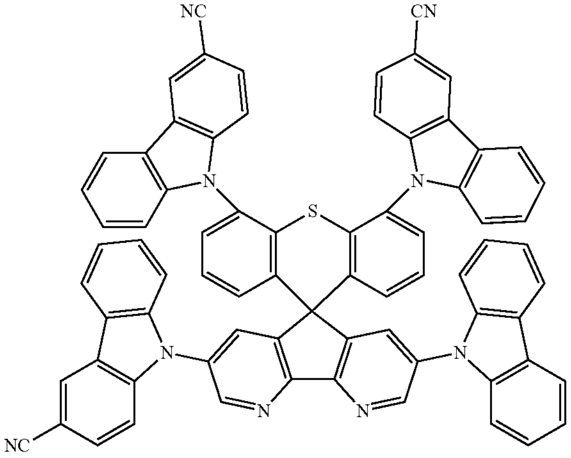
-continued
1068
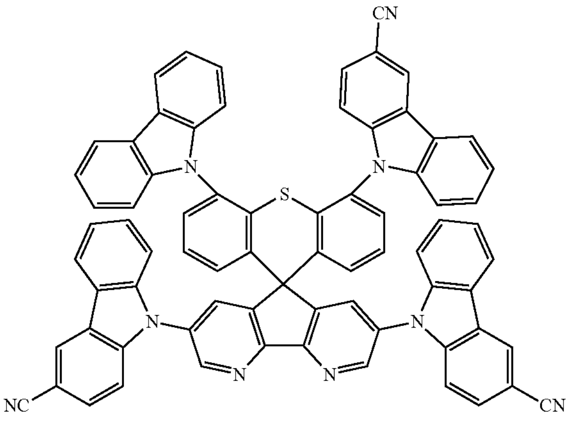
1069
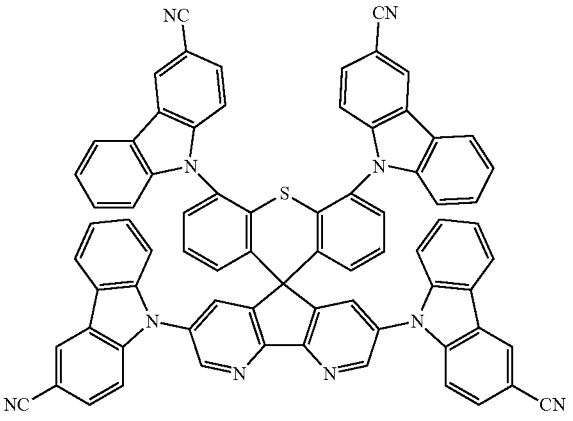
1070
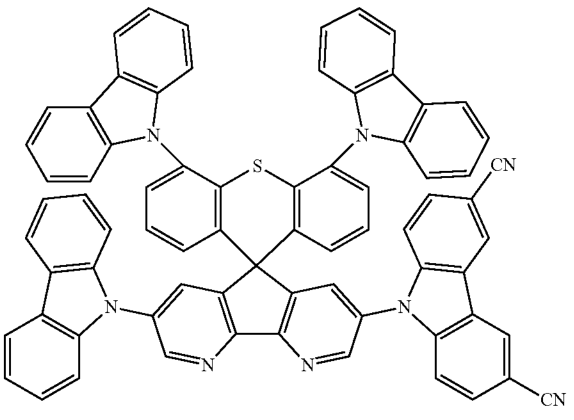

-continued
1071
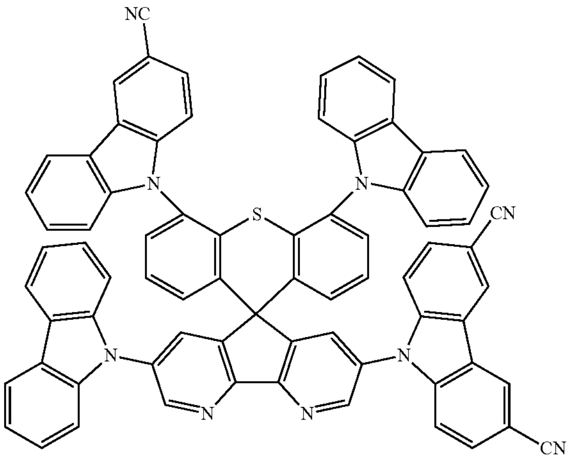
1072
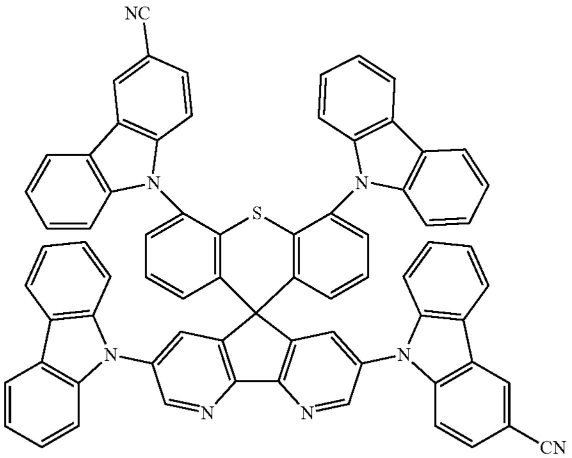
1073
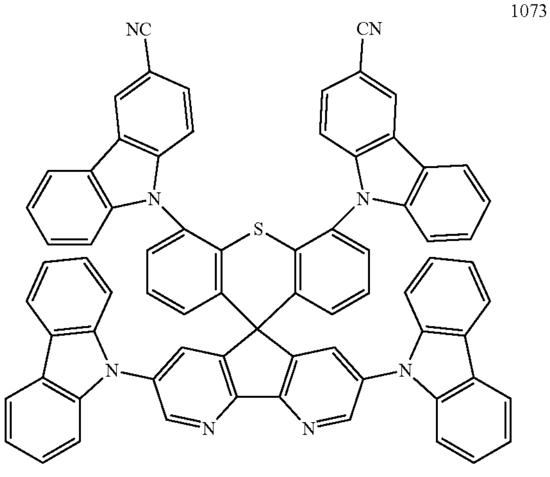
-continued
1074
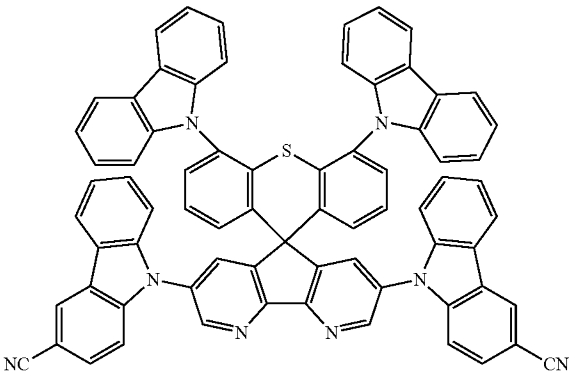
1075
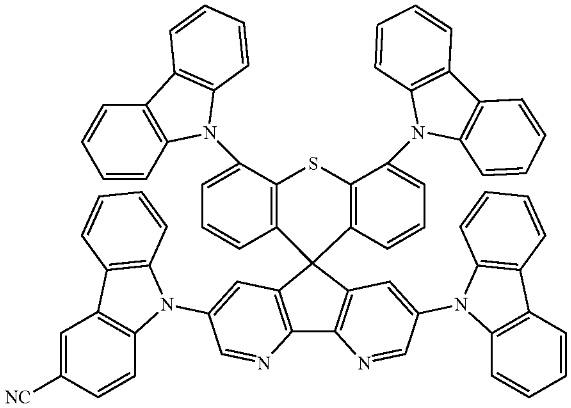
1076
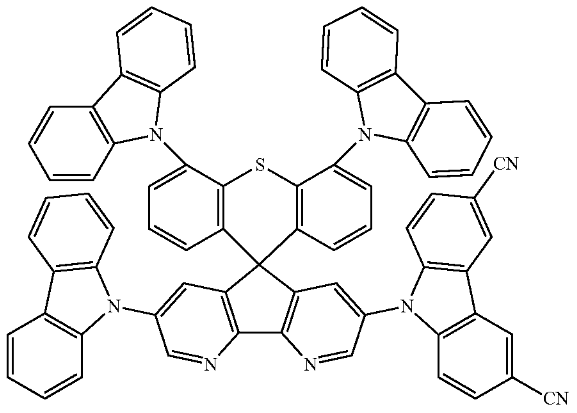
1077
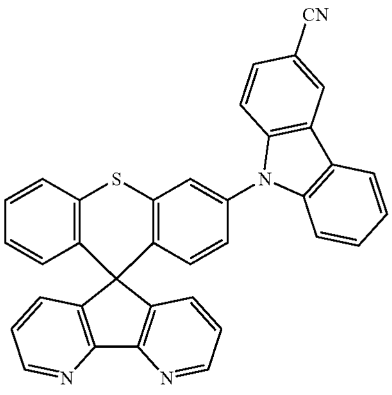

-continued
1078
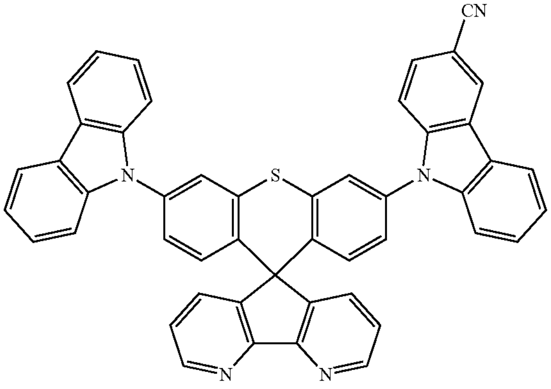
1079
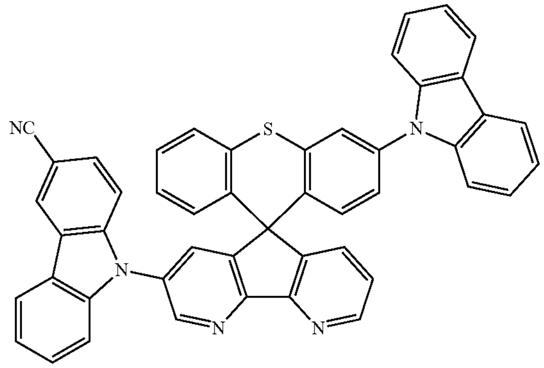
1080
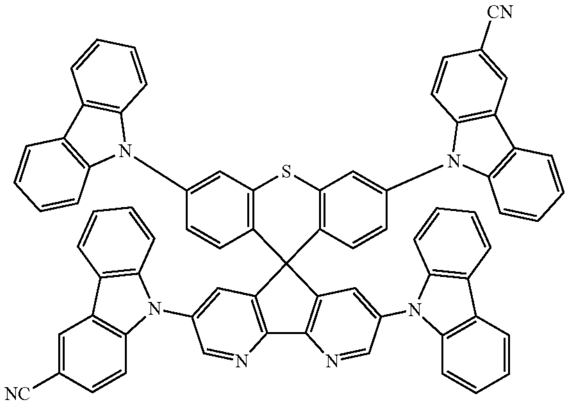
1081
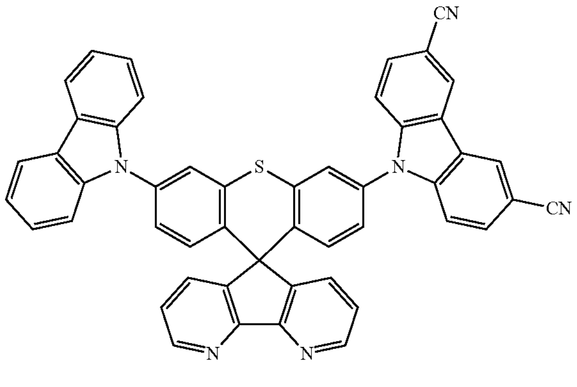
-continued
1082
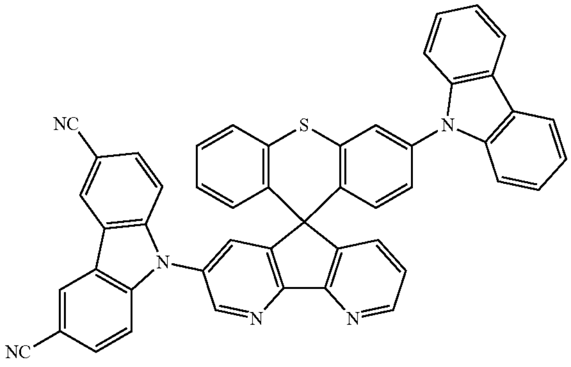
1083
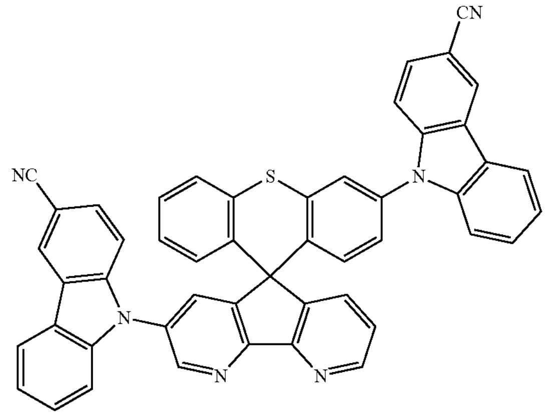
1084
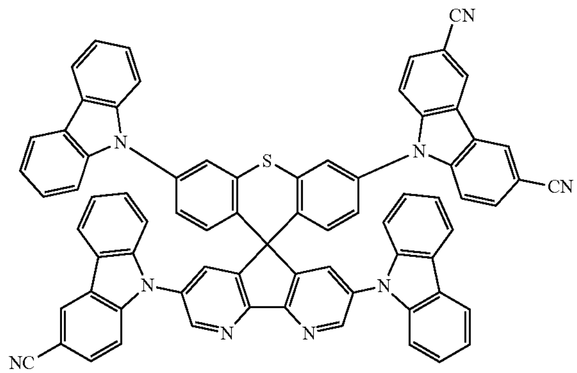
1085
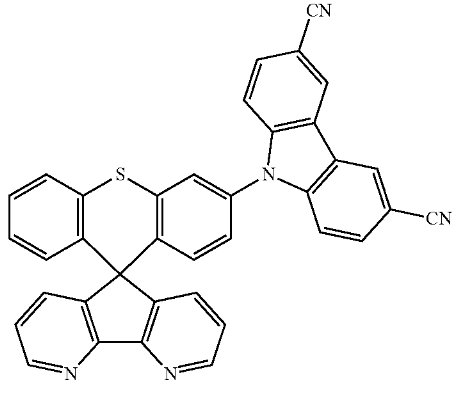

-continued
1086
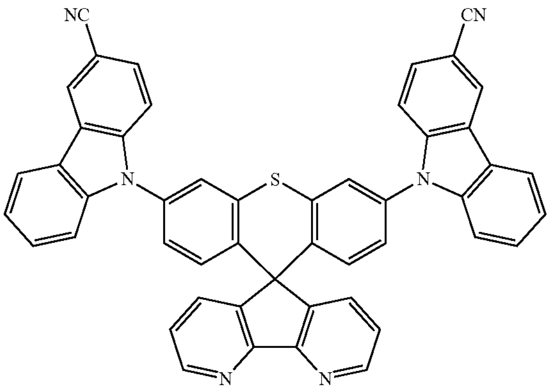
1087
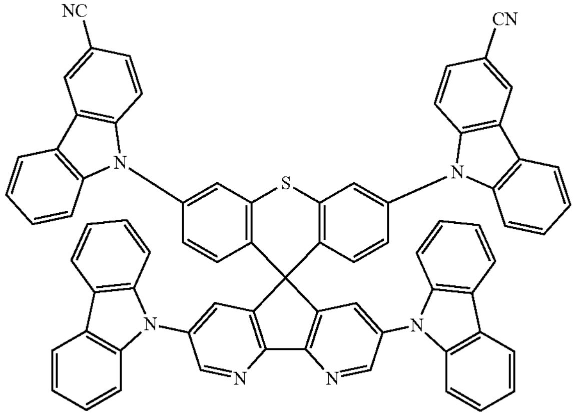
1088
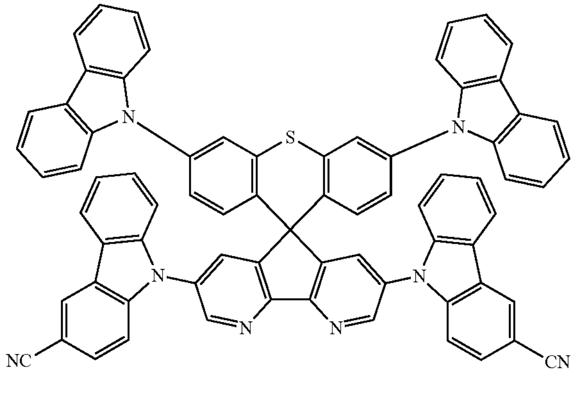
1089
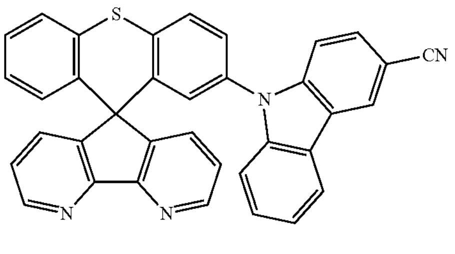
-continued
1090
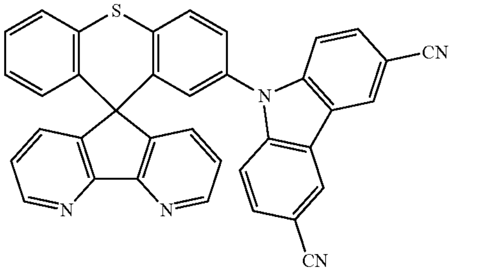
1091
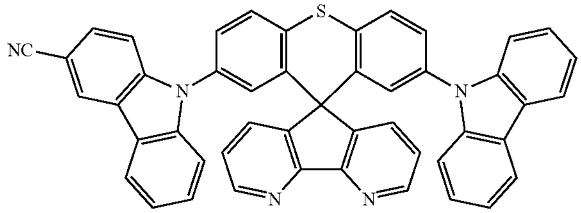
1092
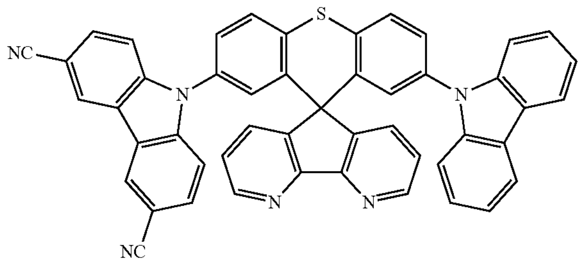
1093
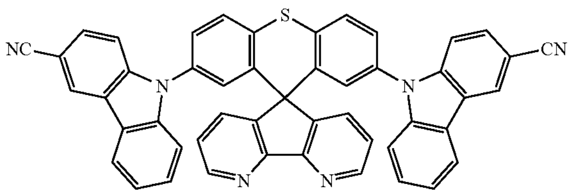
1094
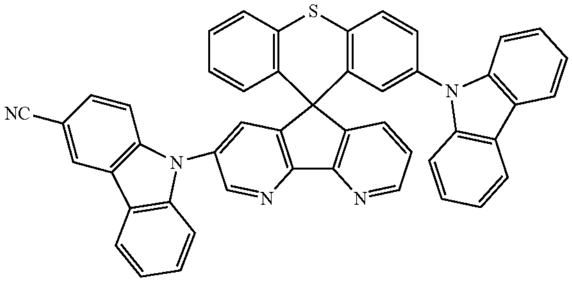

-continued
1095
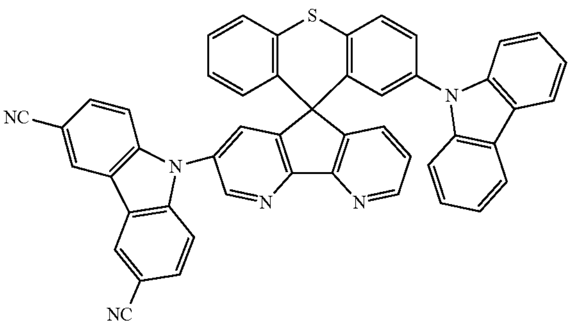
1096
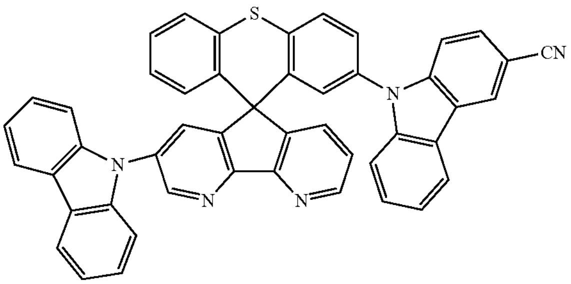
1097
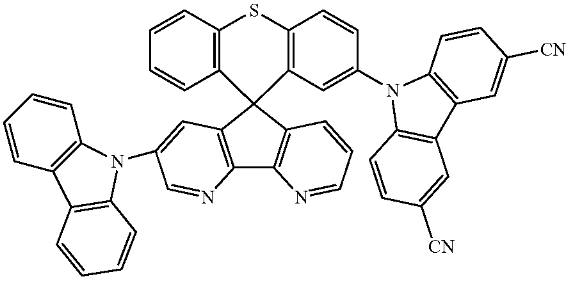
1098
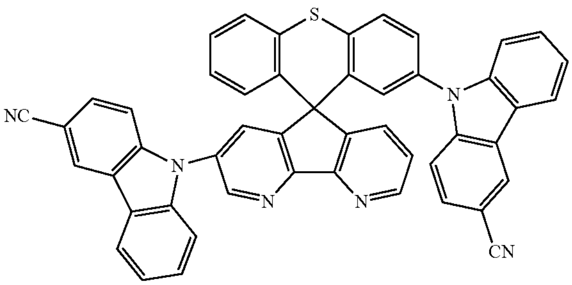
1099
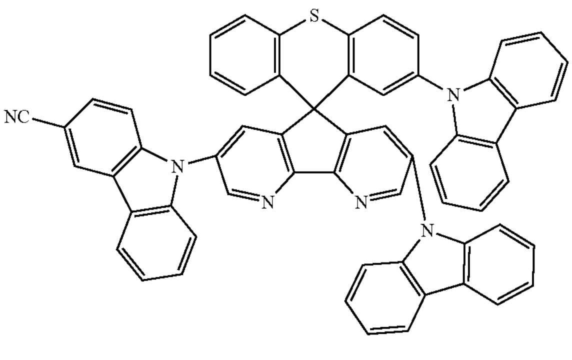
-continued
1100
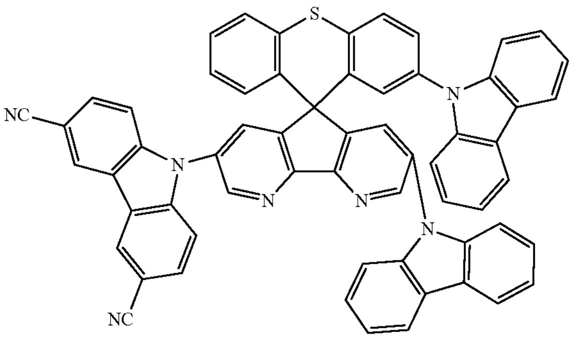
1101
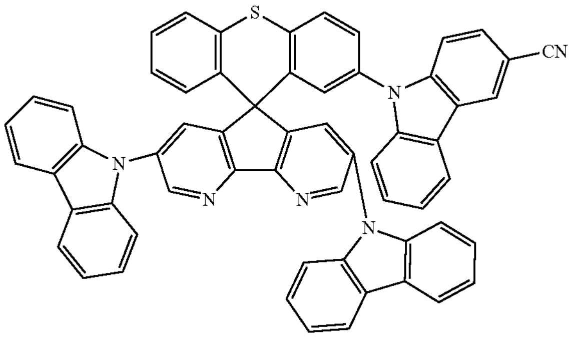
1102
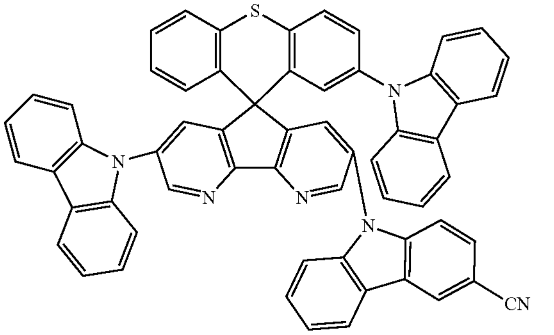
1103
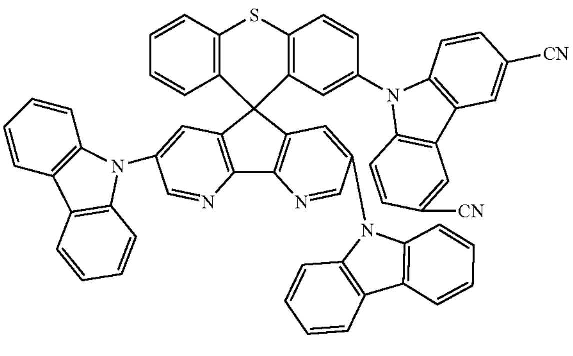

-continued
1104
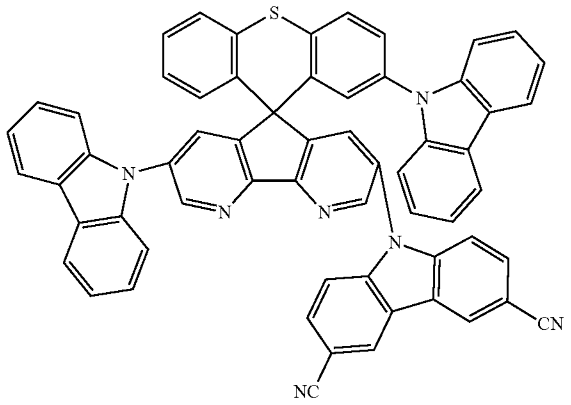
1105
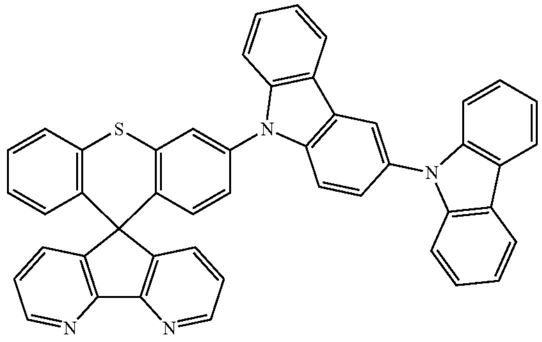
1106
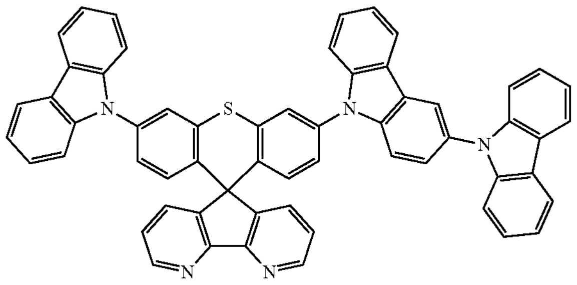
1107
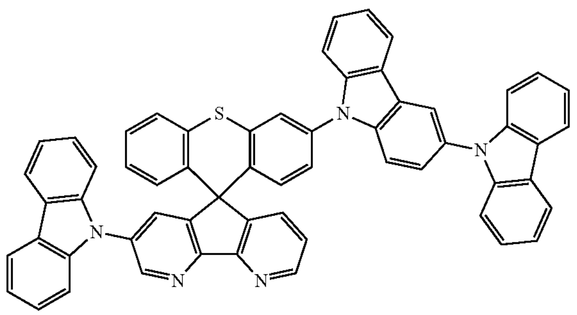
-continued
1108
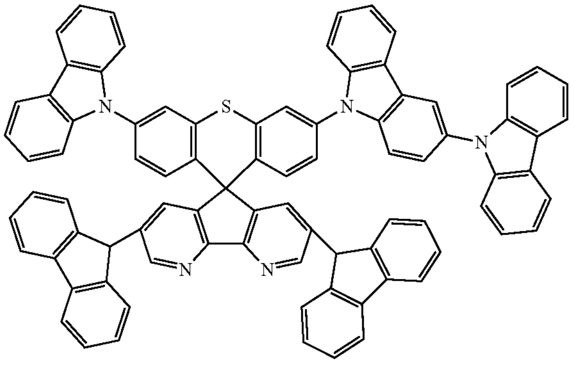
1109
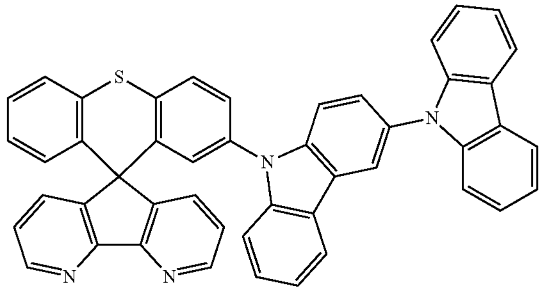
1110
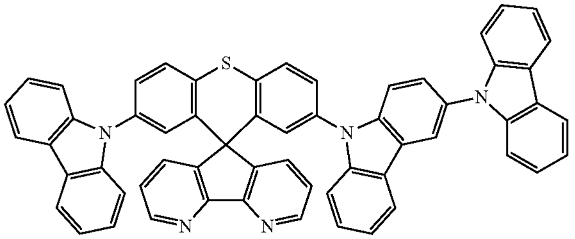
1111
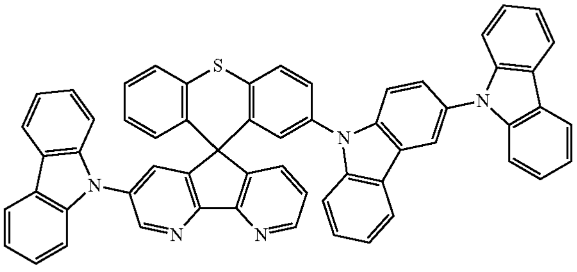

-continued
1112
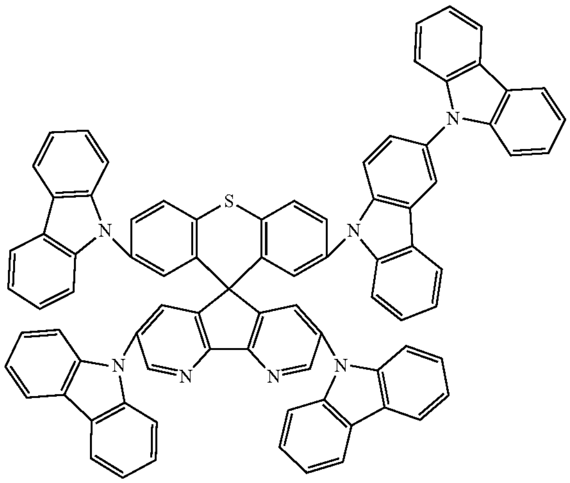
1113
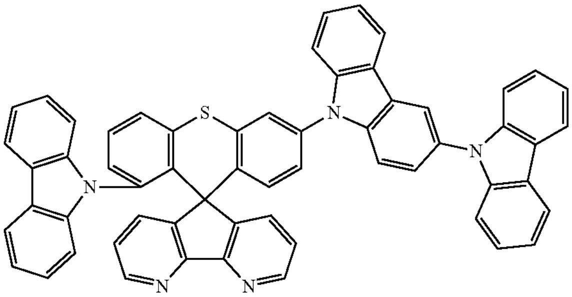
1114
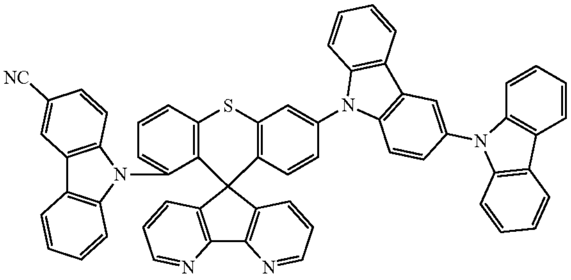
1115
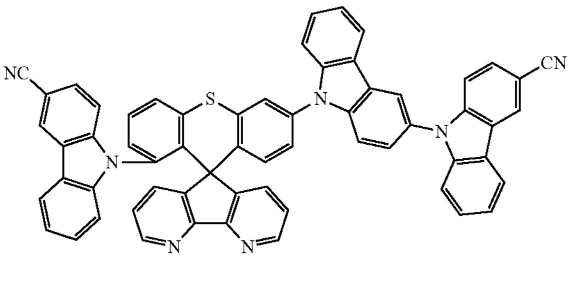
-continued
1116
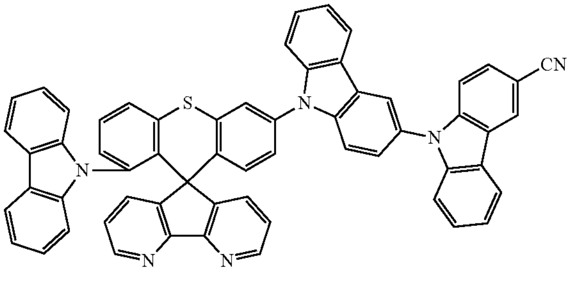
1117
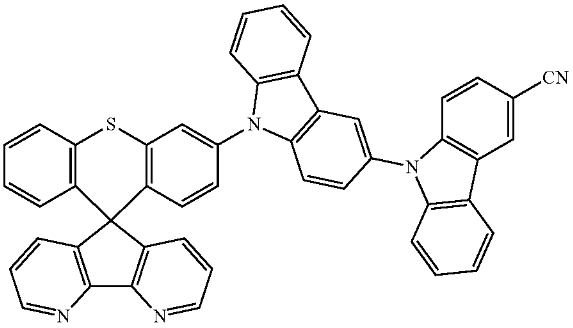
1118
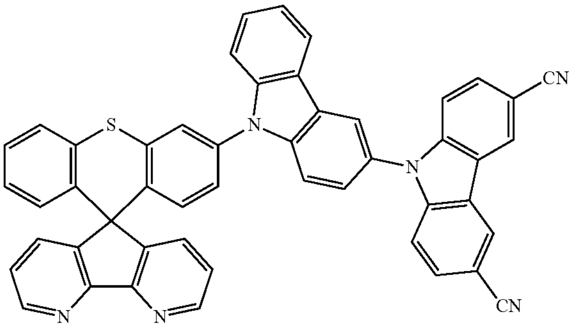
1119
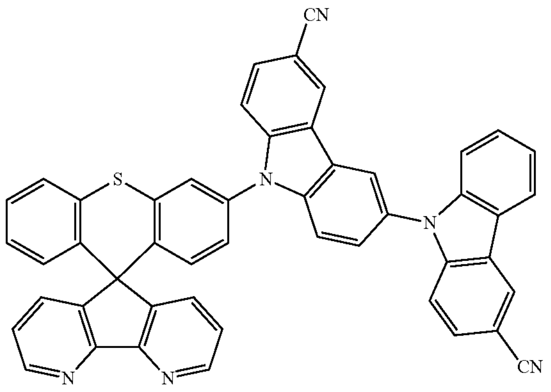

1120
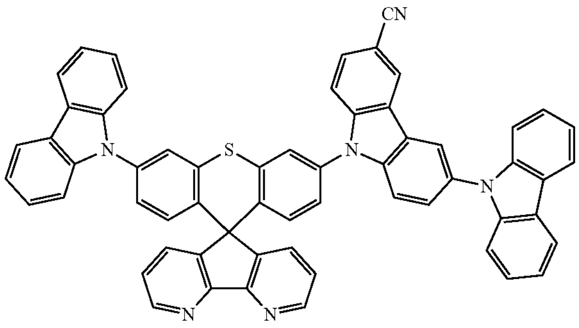
1121
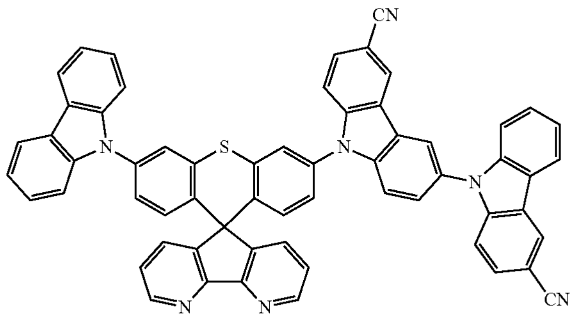
1122
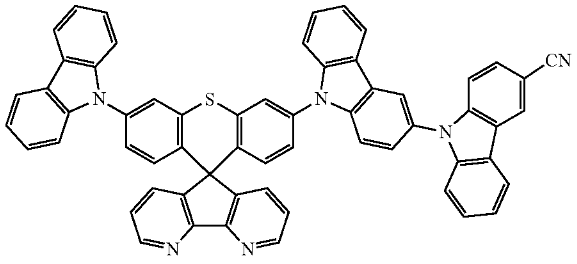
1123
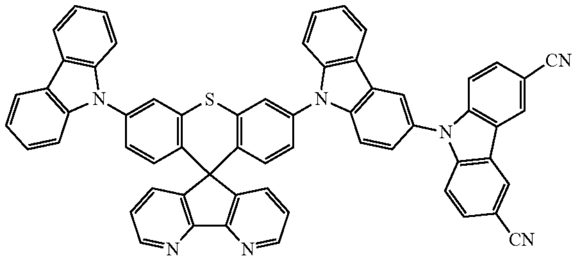
1124
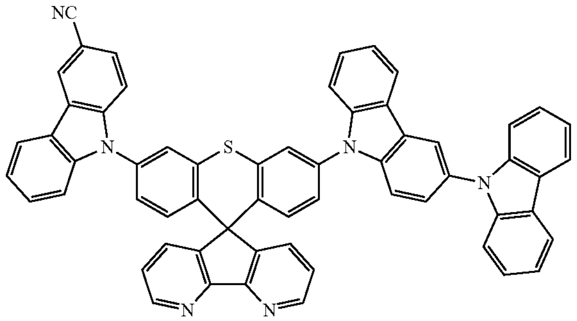
1125
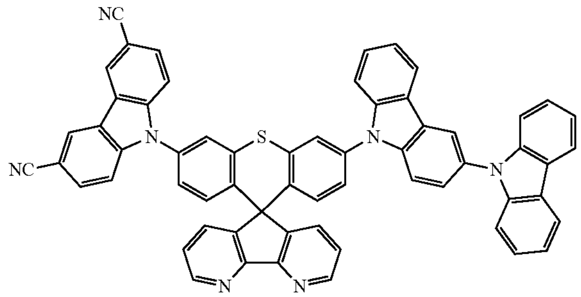
1126
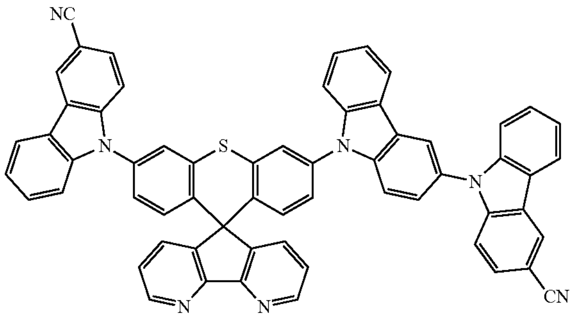
1127
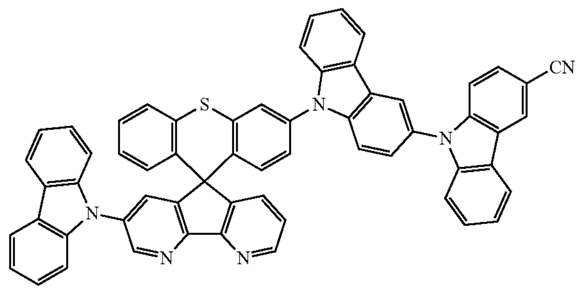
1128
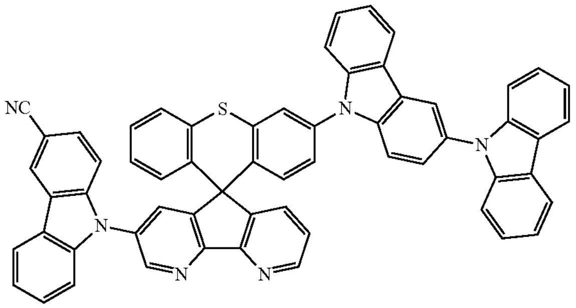

-continued
1129
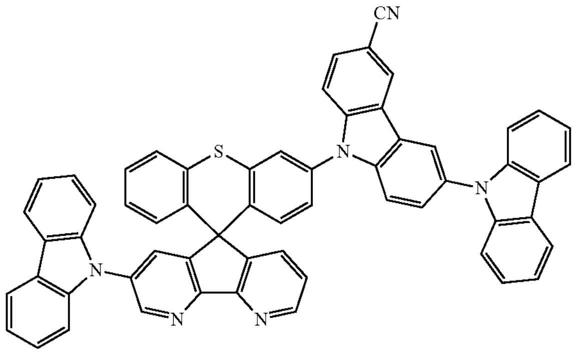
1130
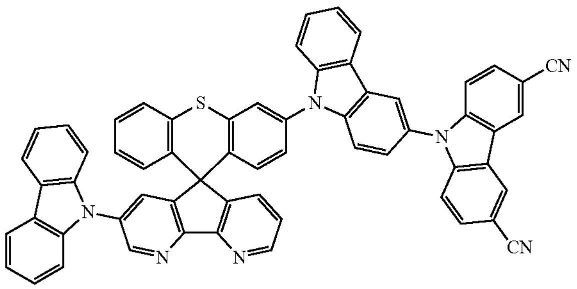
1131
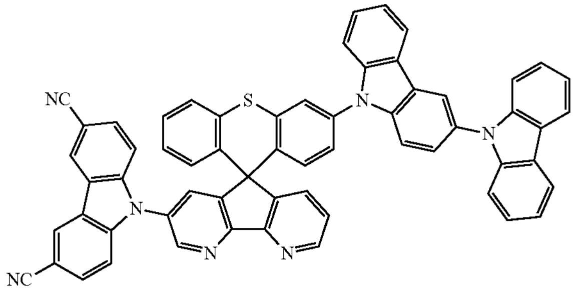
1132
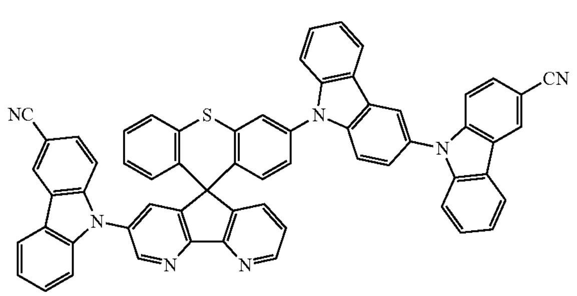
-continued
1133
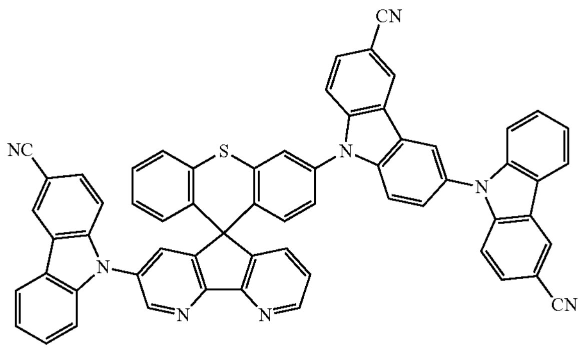
lp;1p
1134
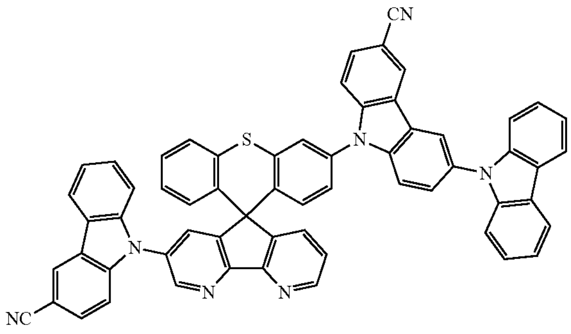
1135
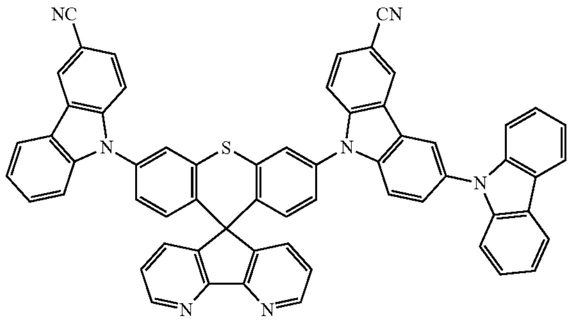
1136
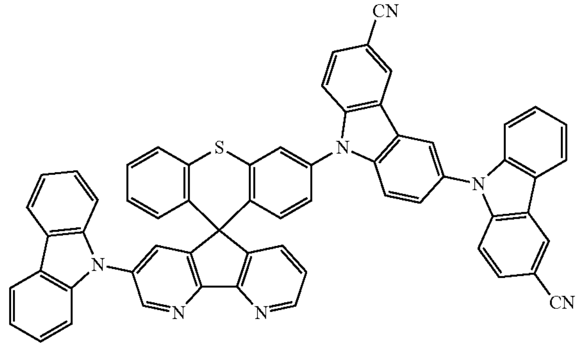

-continued
1137
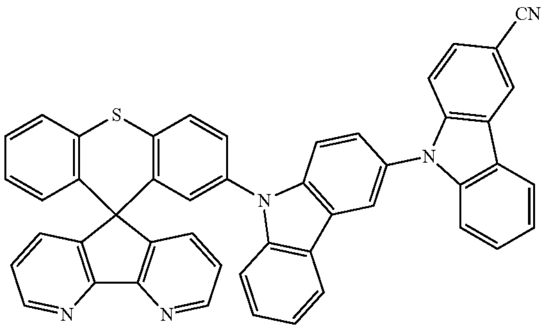
1138
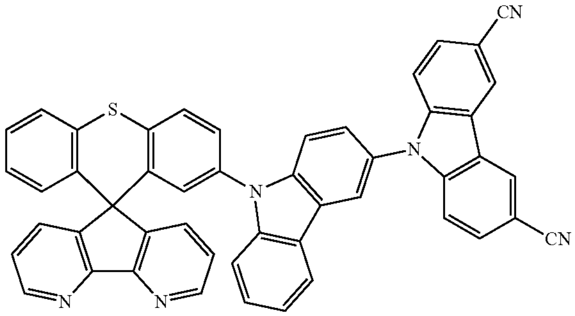
1139
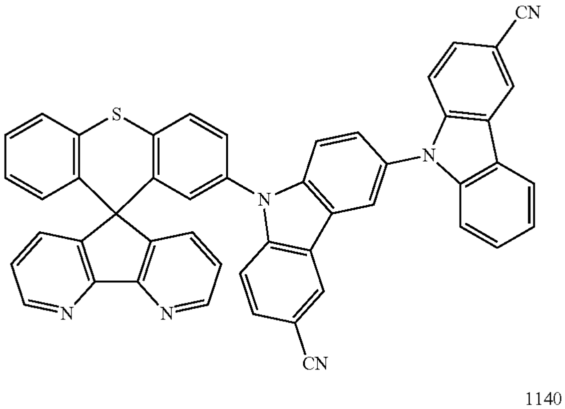
1140
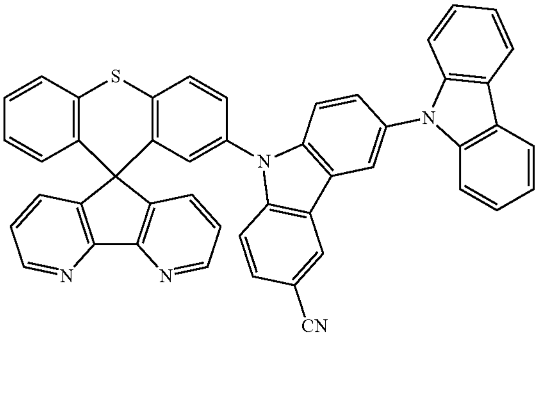
-continued
1141
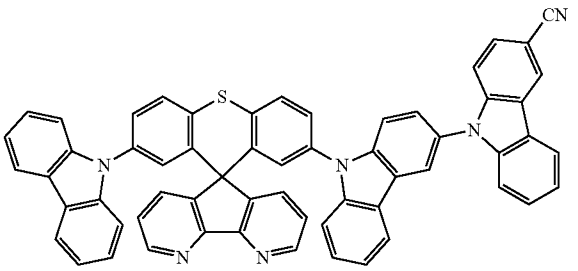
1142
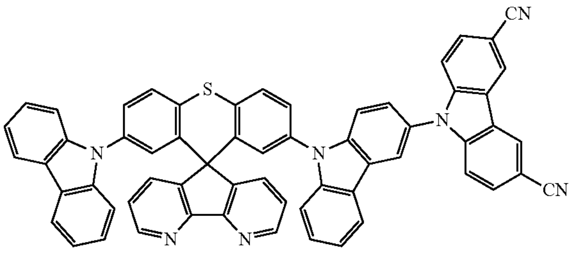
1143
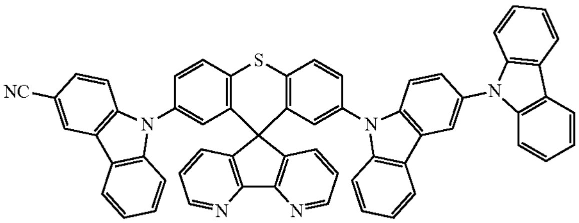
1144
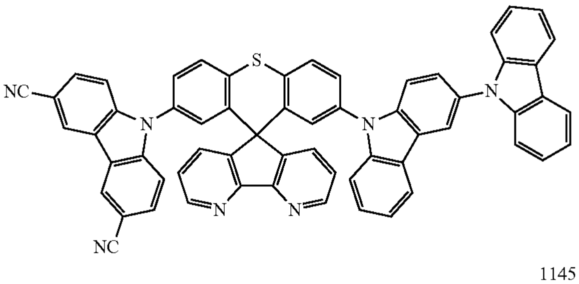
1145
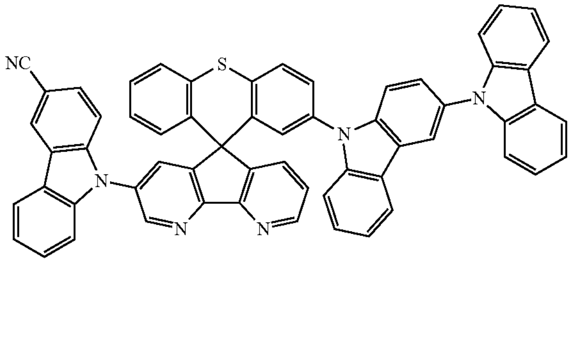

1146
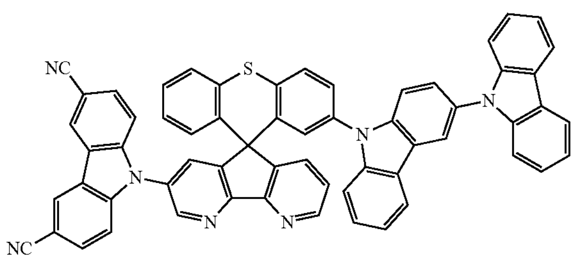
1147
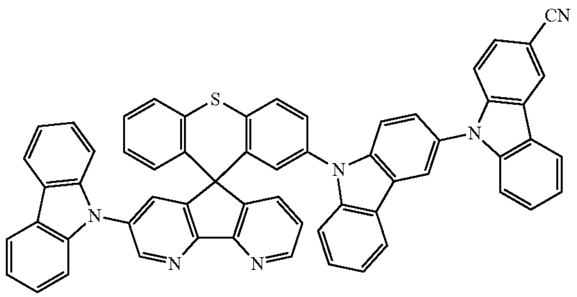
1148
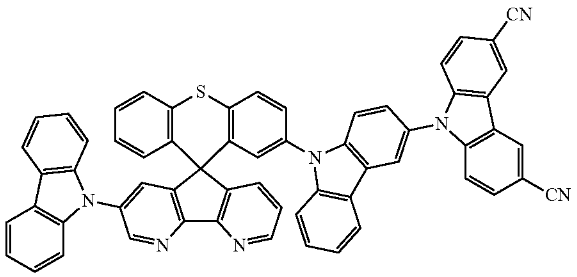
1149
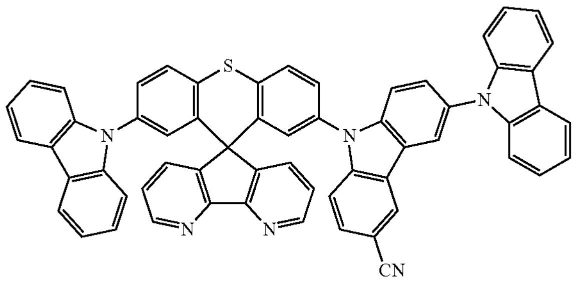
1150
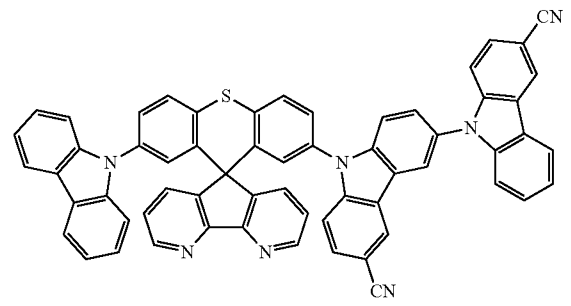
1151
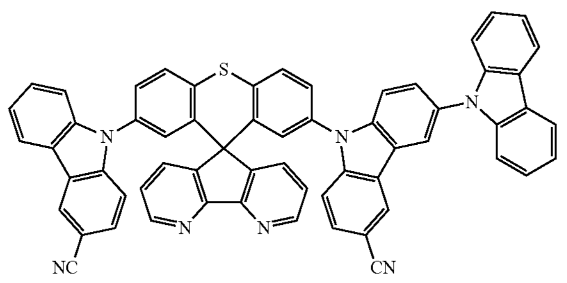
1152
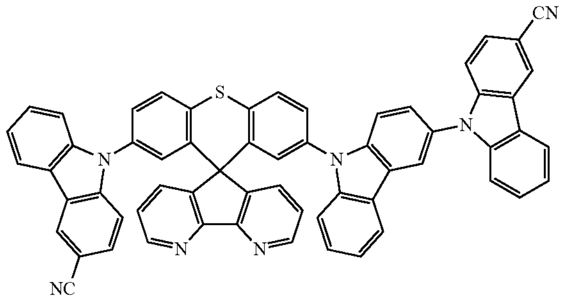
1153
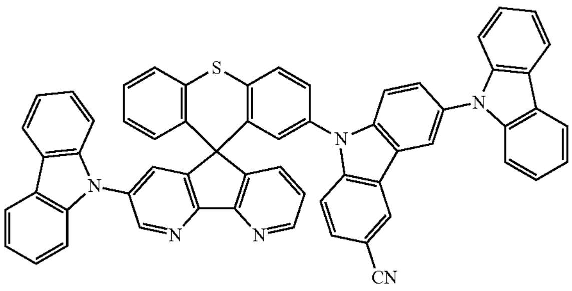
1154
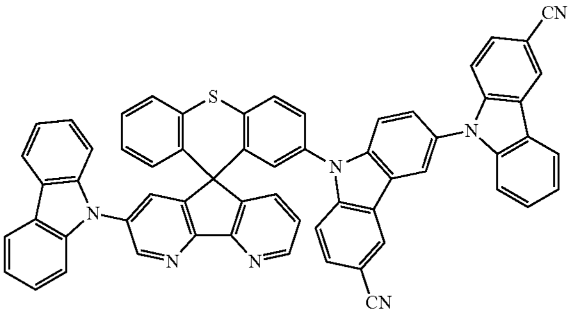
1155
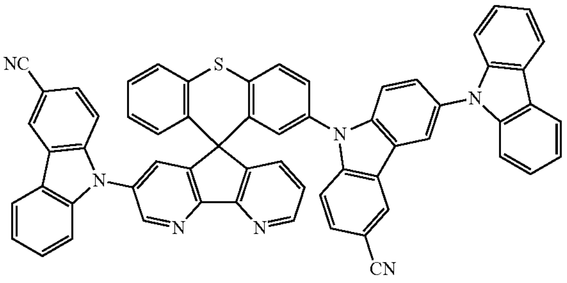

-continued
1156
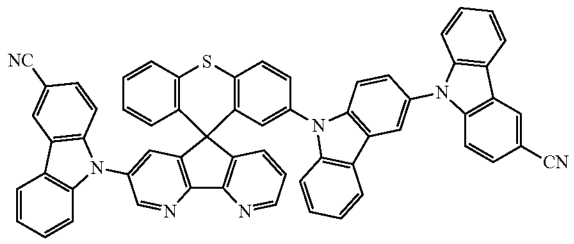
1157
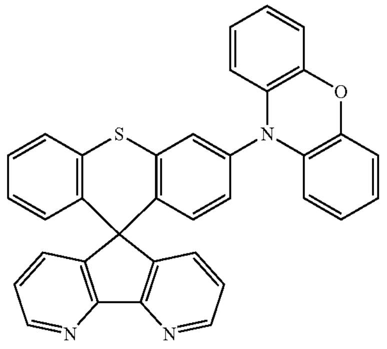
1158
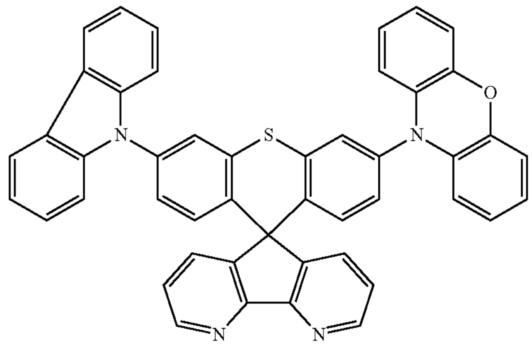
1159
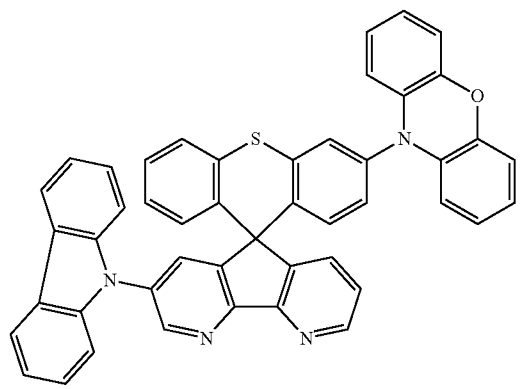
-continued
1160
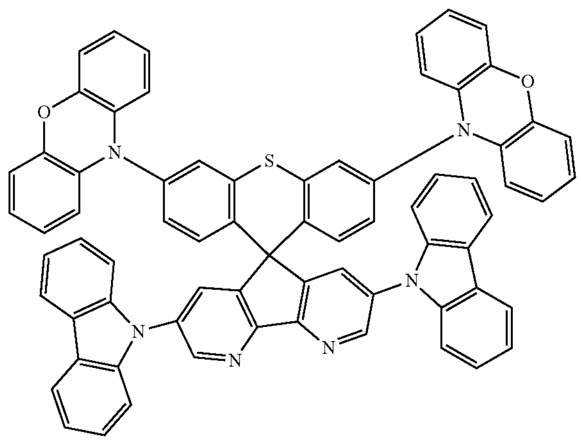
1161
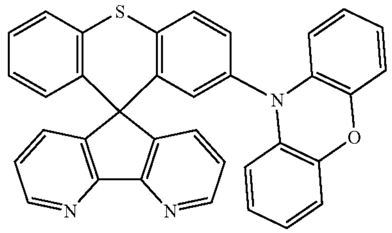
1162
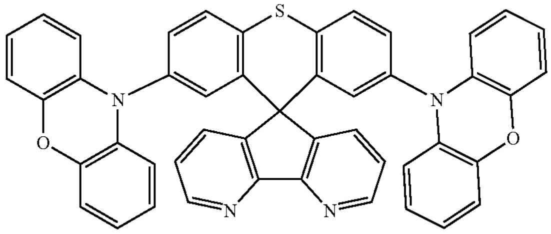
1163
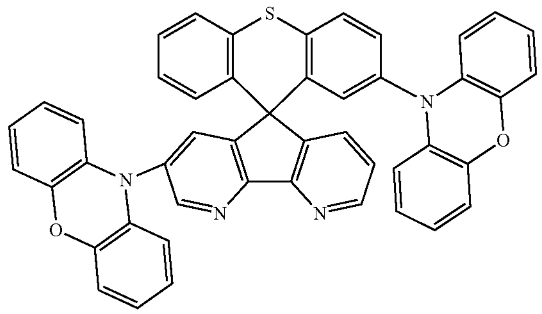

1164
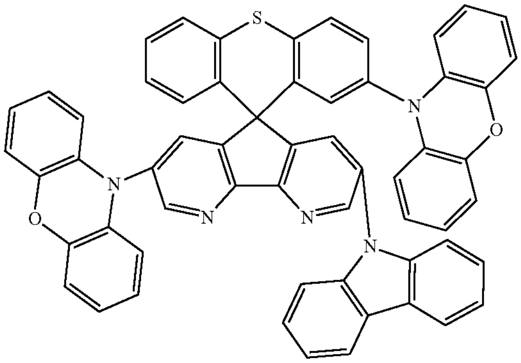
1165
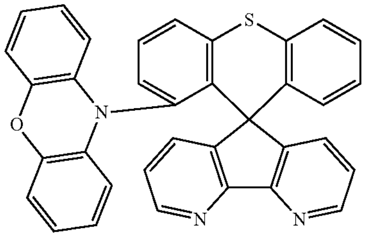
1166
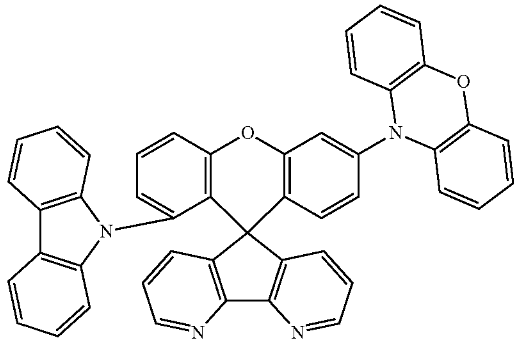
1167
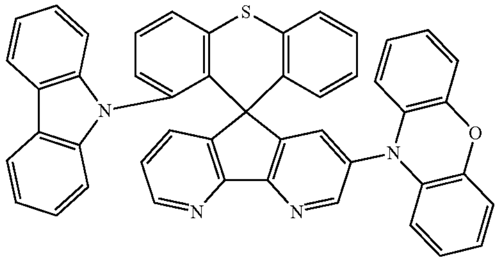
1168
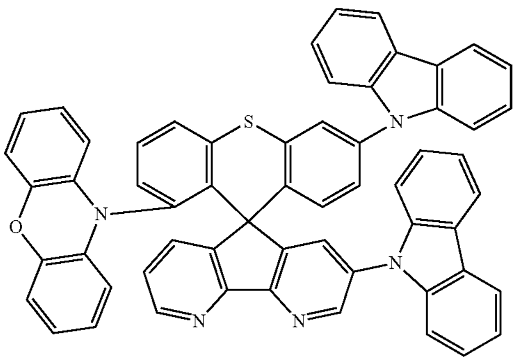
1169
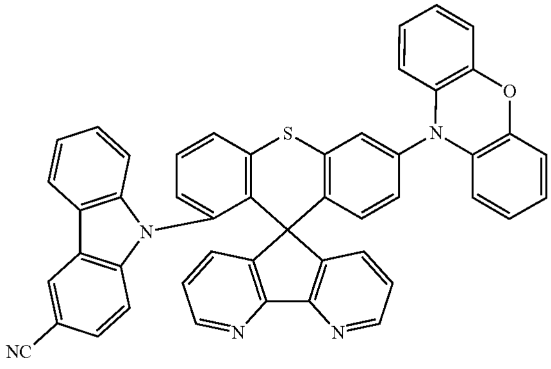
1170
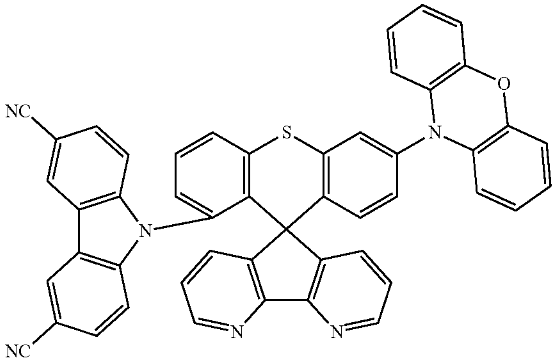
1171
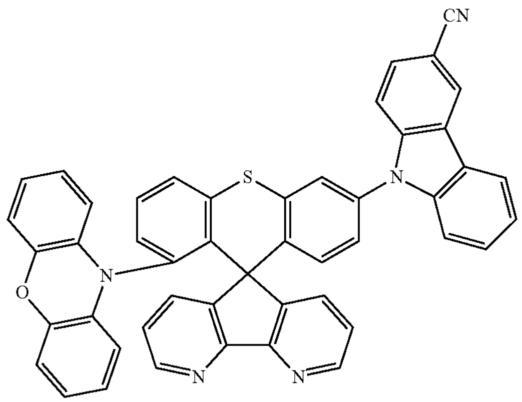
1172
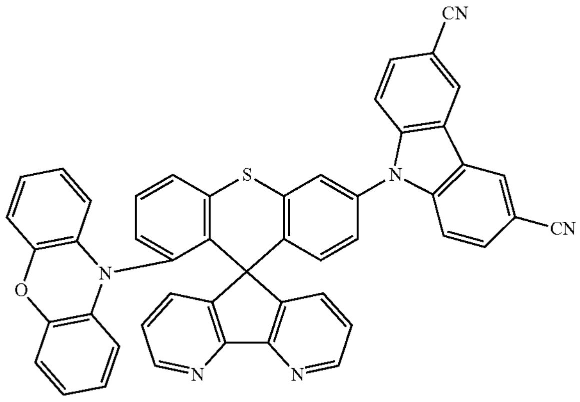

1173
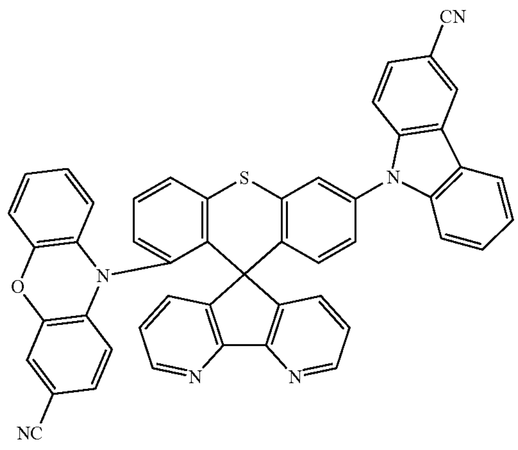
1174
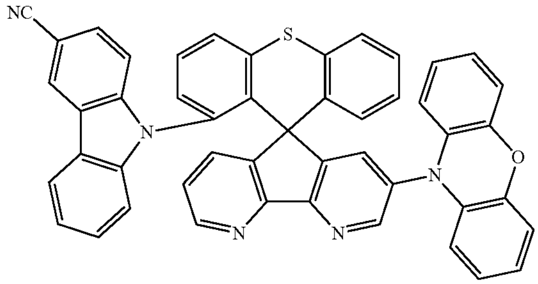
1175
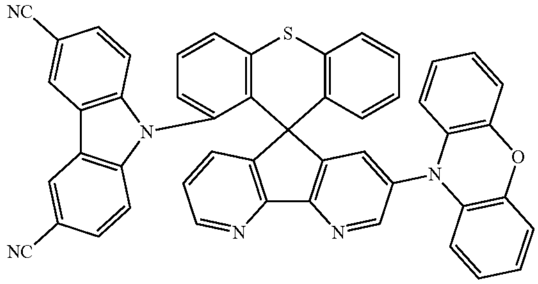
1176
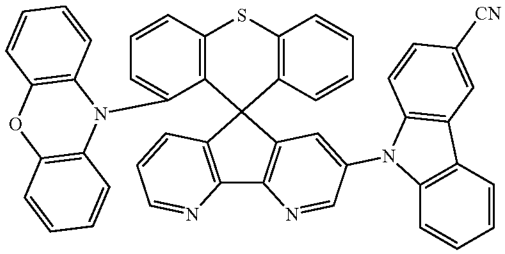
1177
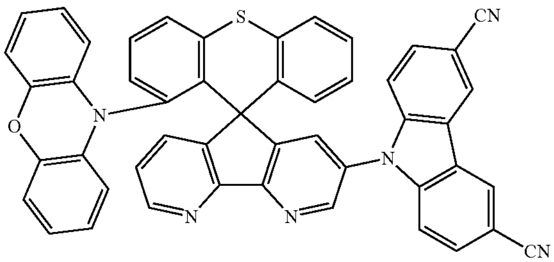
1178
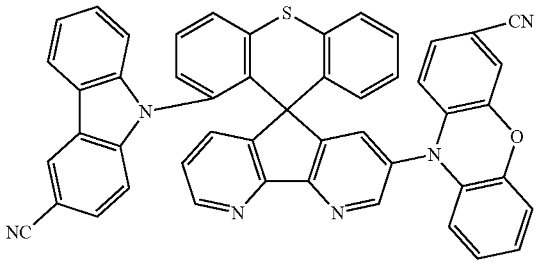
1179
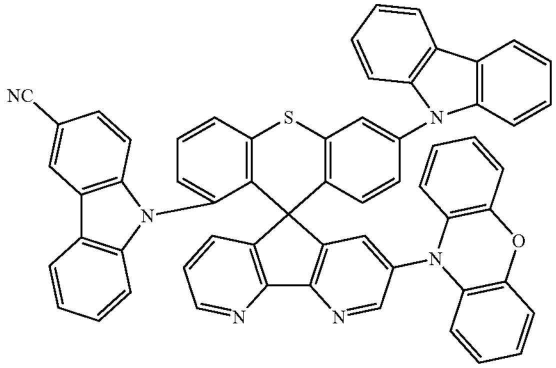
1180
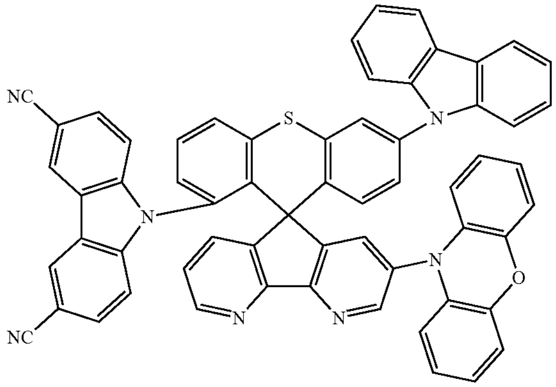
1181
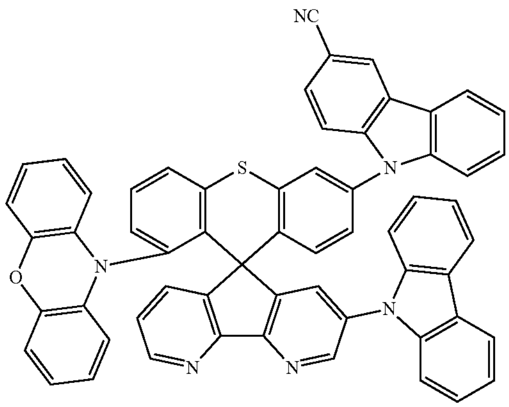

-continued
1182
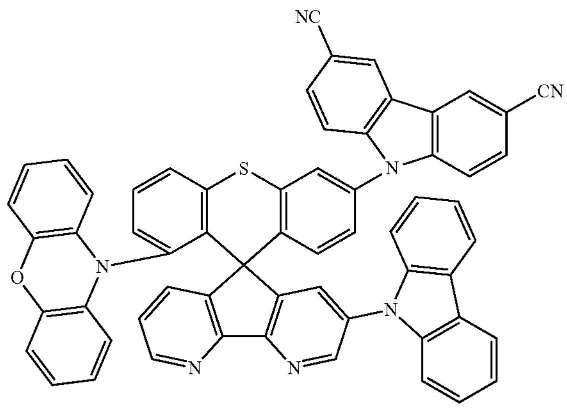
1183
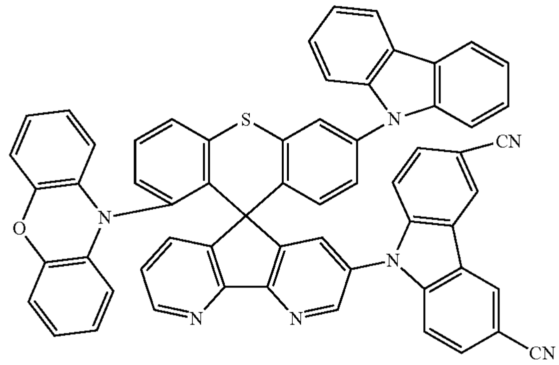
1184
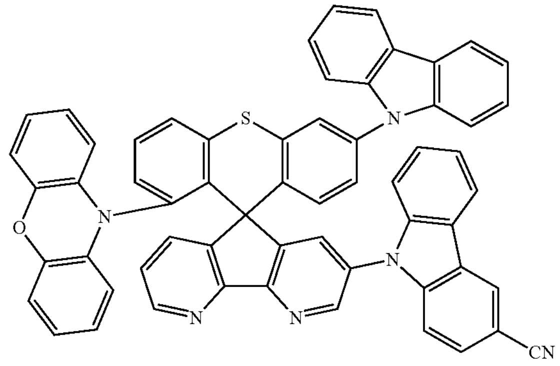
1185
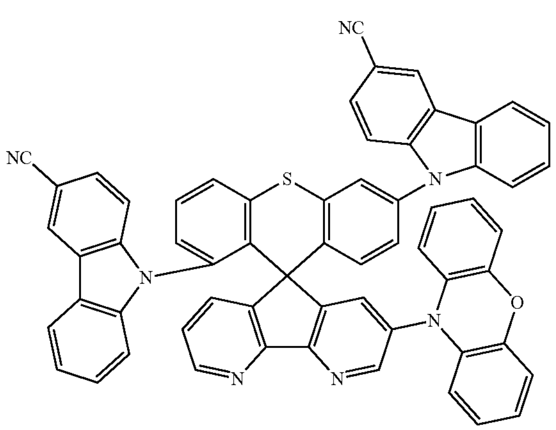
-continued
1186
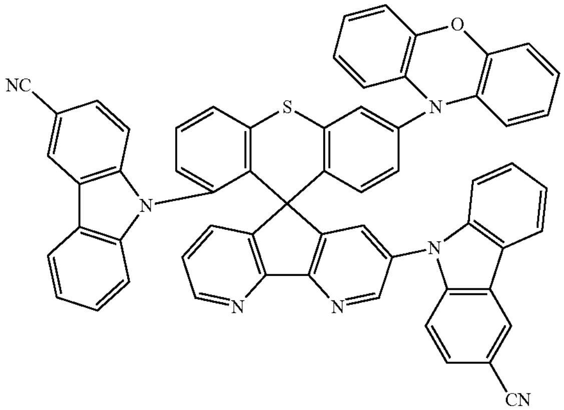
1187
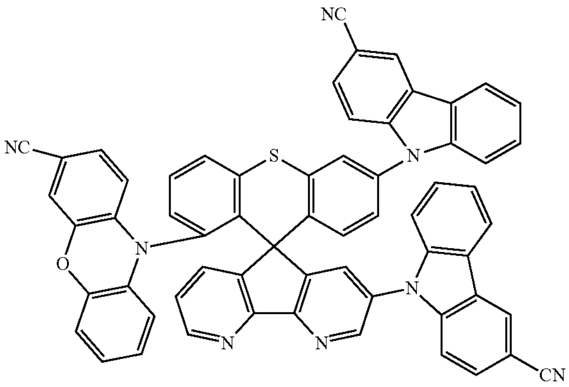
1188
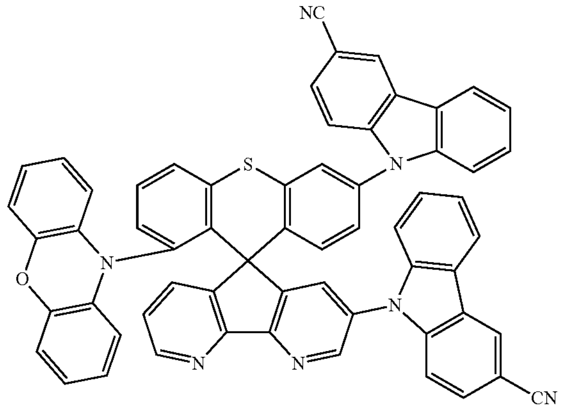
1189
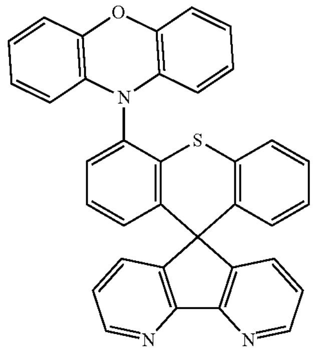

-continued
1190
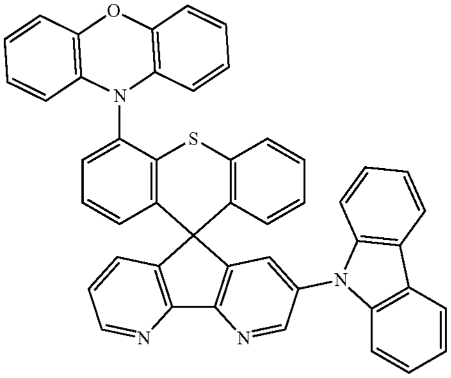
1191
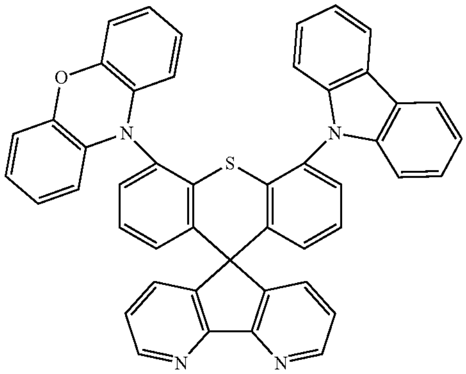
1192
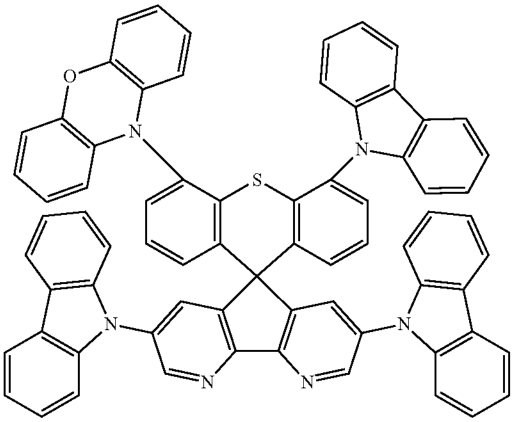
1193
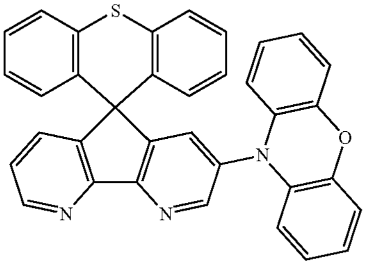
-continued
1194
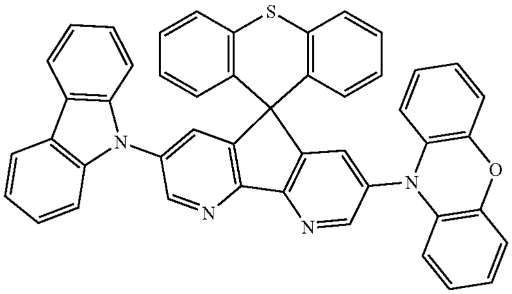
1195
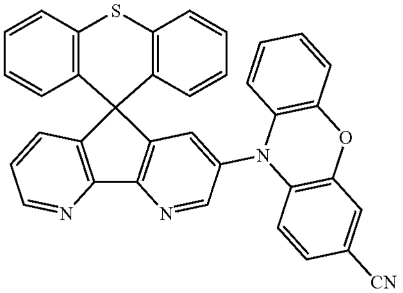
1196
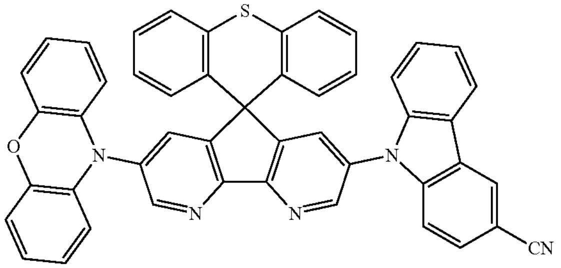
1197
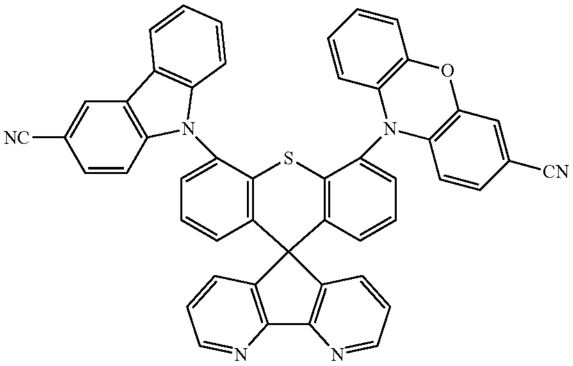

-continued
1198
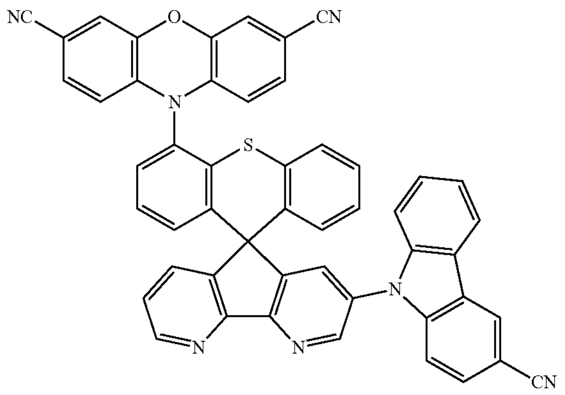
1199
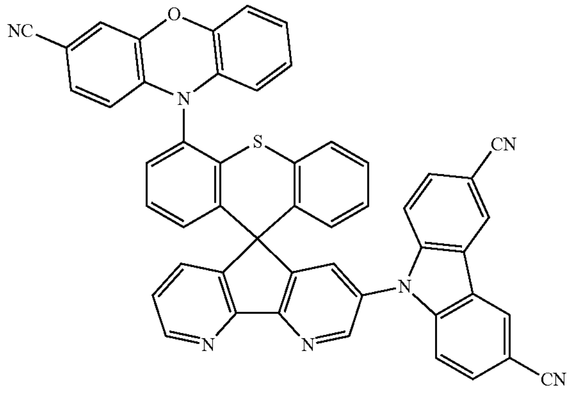
1200
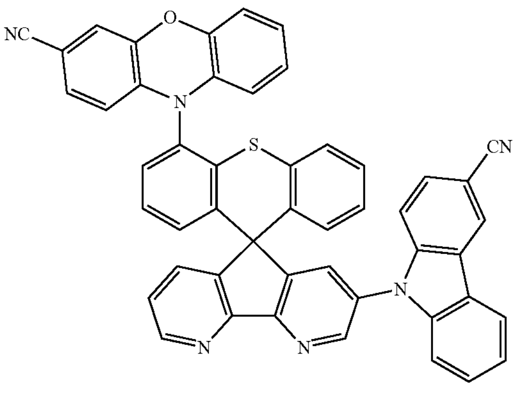
1201
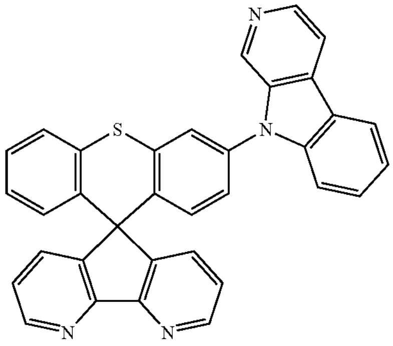
-continued
1202
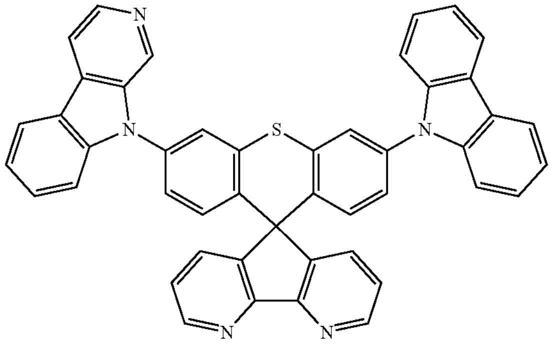
1203
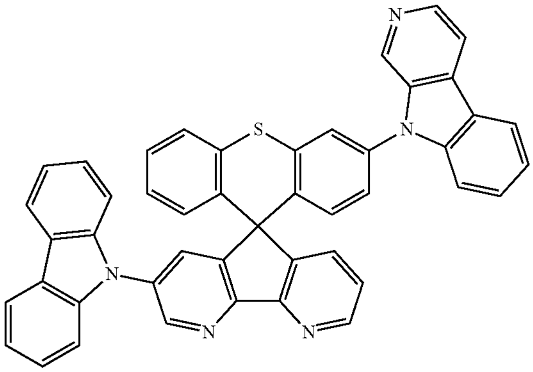
1204
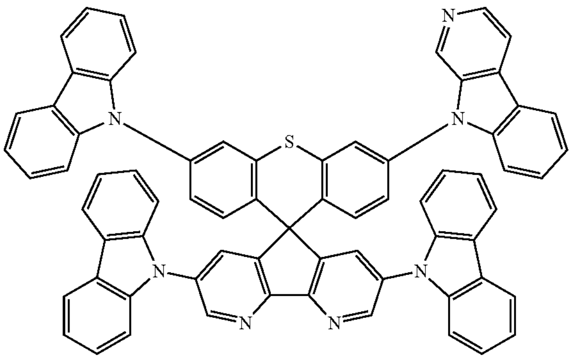
1205
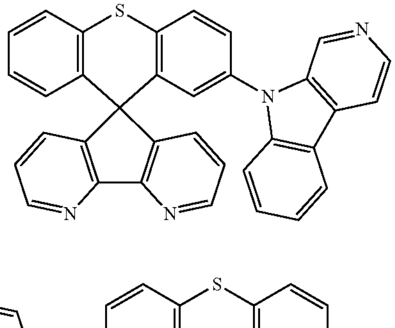
1206
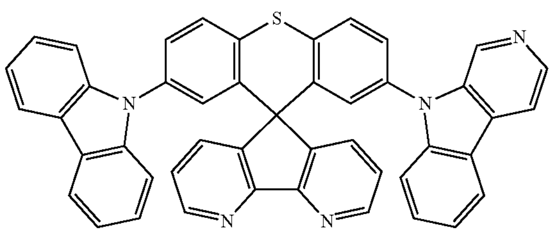

-continued
1207
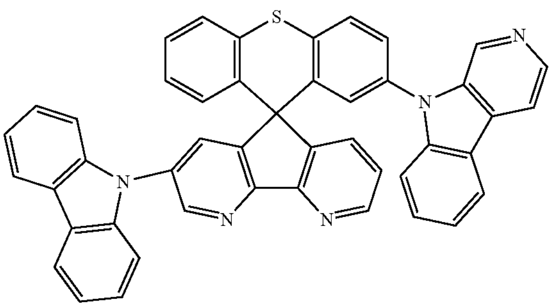
1208
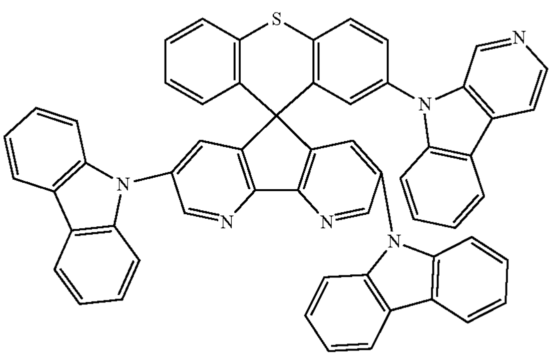
1209
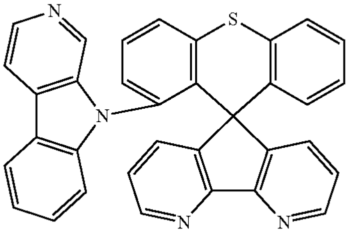
1210
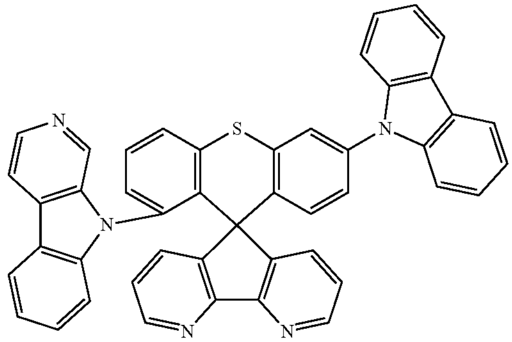
1211
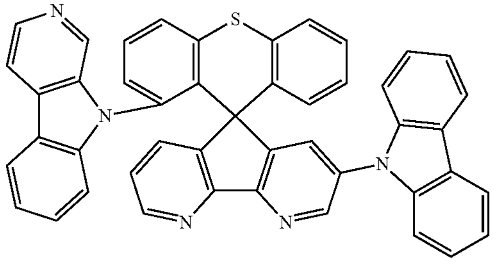
-continued
1212
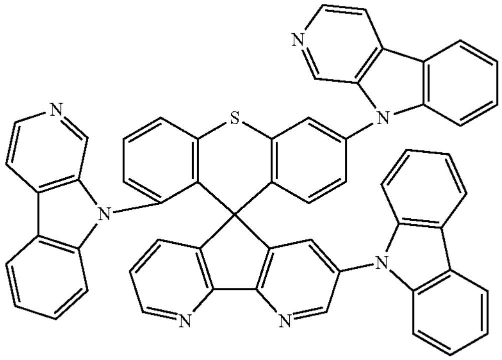
1213
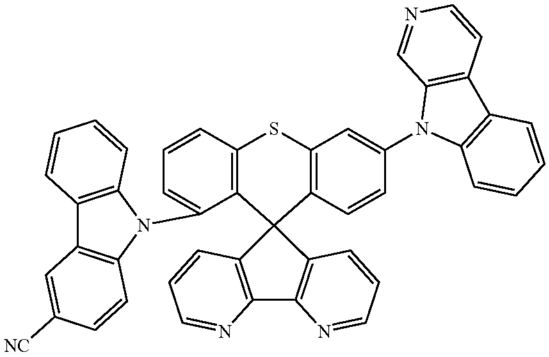
1214
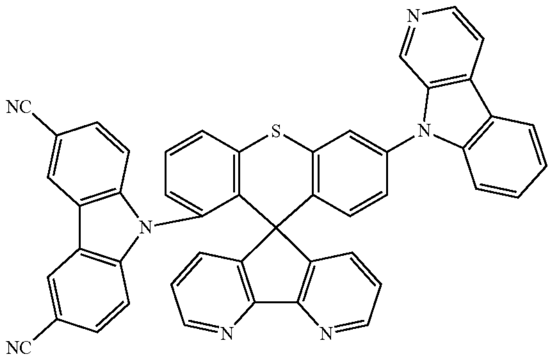
1215
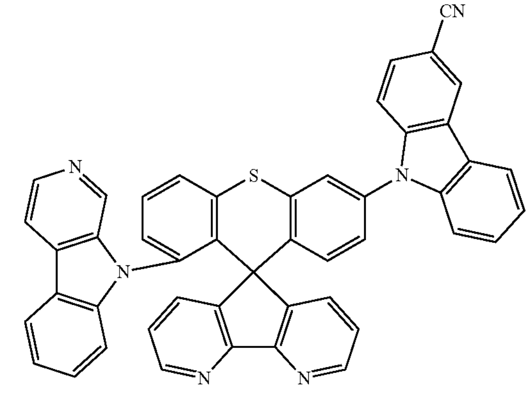

-continued
1216
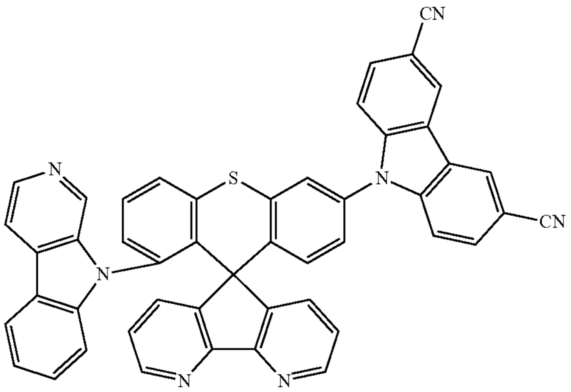
1217
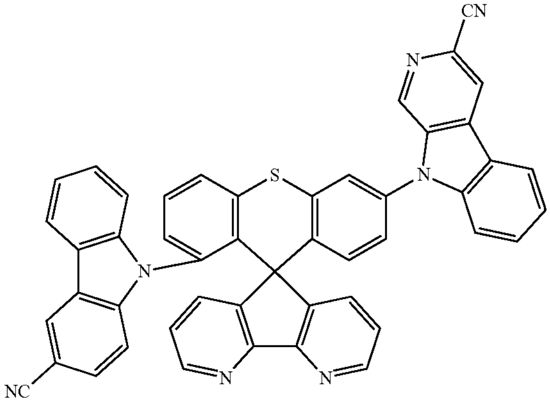
1218
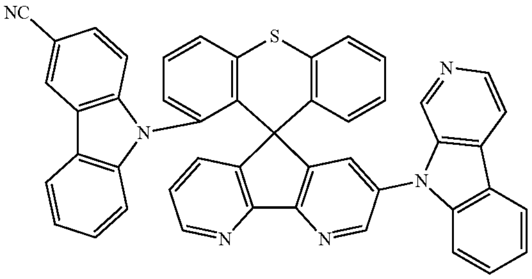
1219
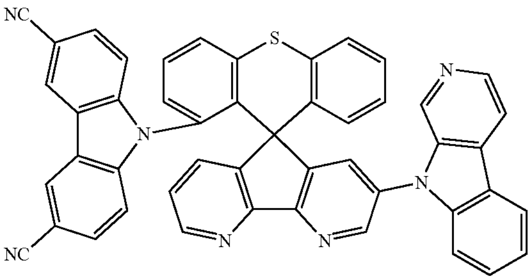
-continued
1220
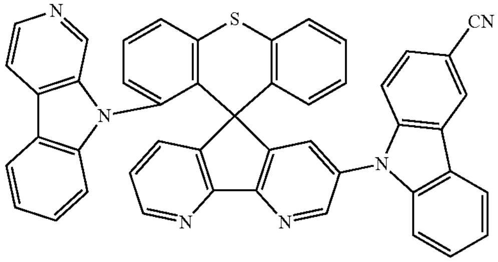
1221
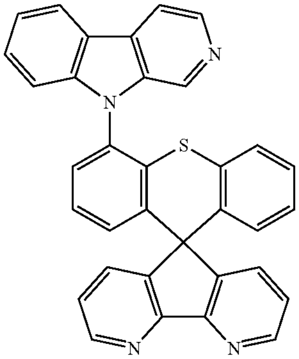
1222
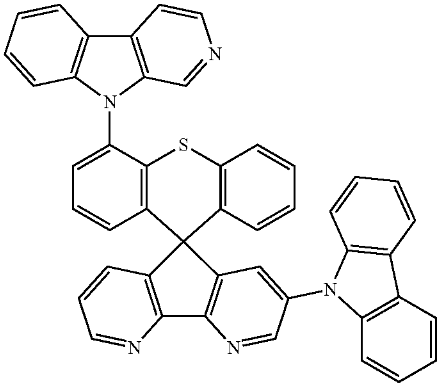
1223
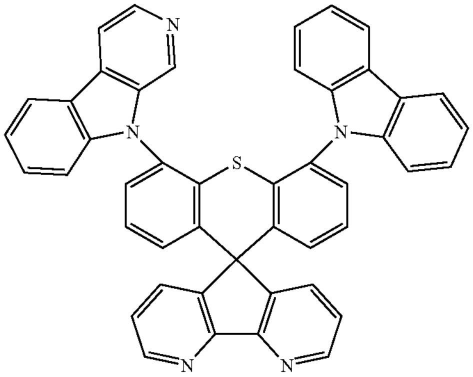

-continued
1224
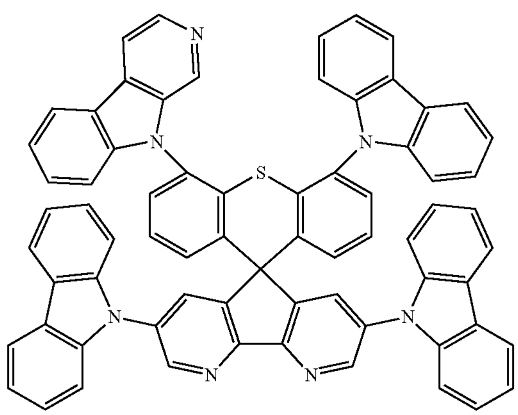
1225
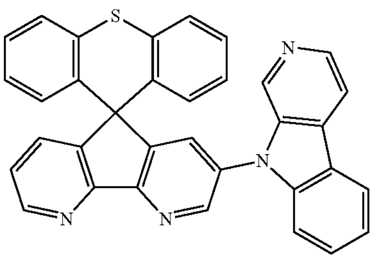
1226
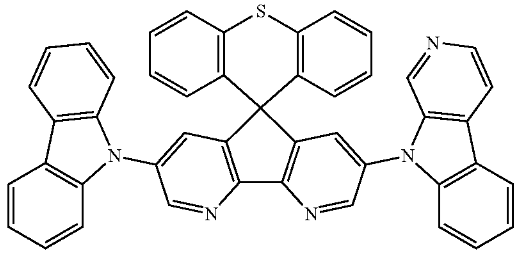
1227
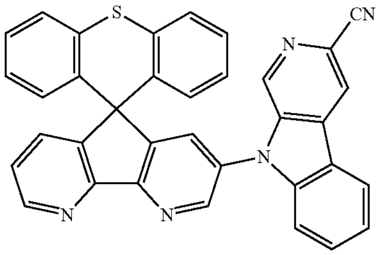
1228
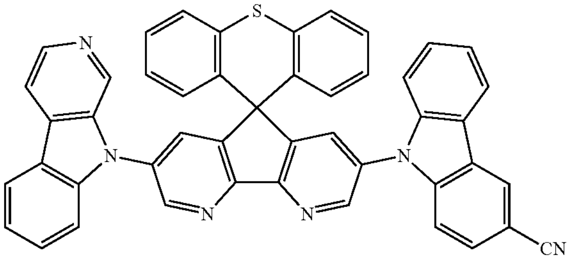
-continued
1229
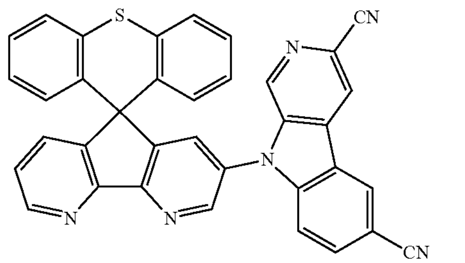
1230
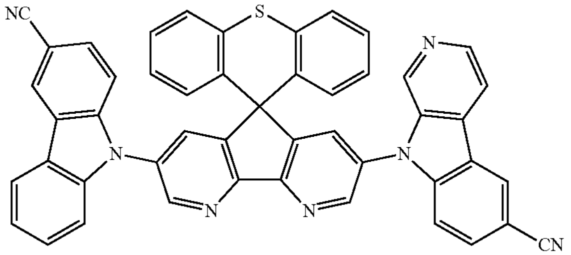
1231
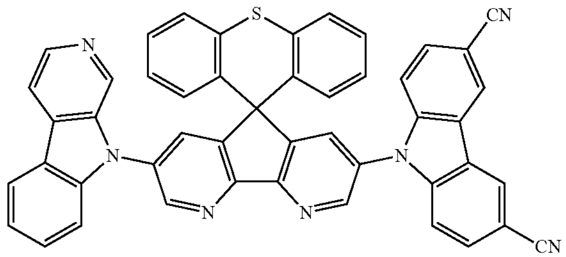
1232
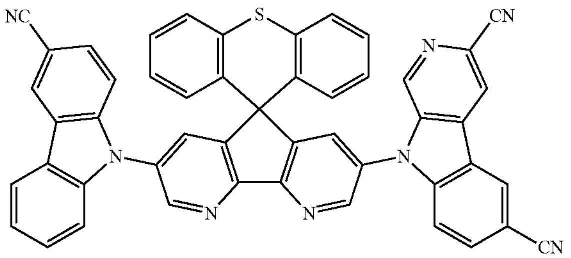

1233
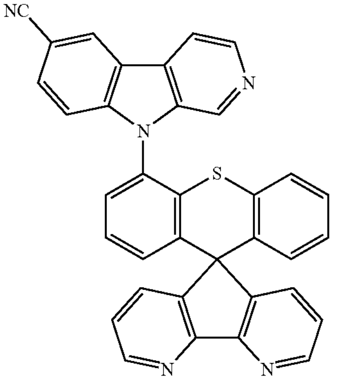
1234
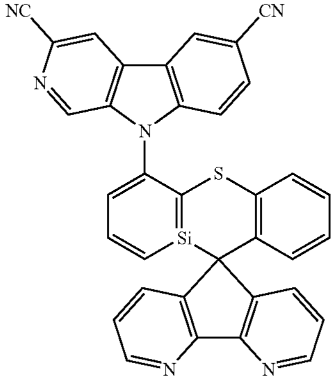
1235
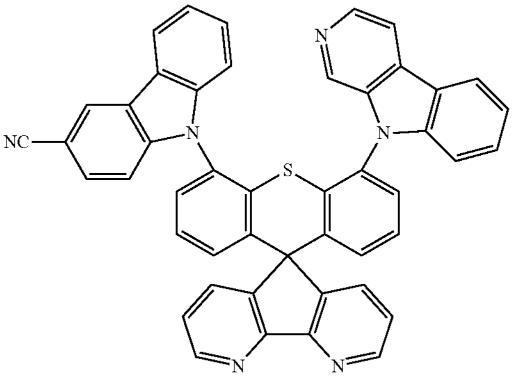
1236
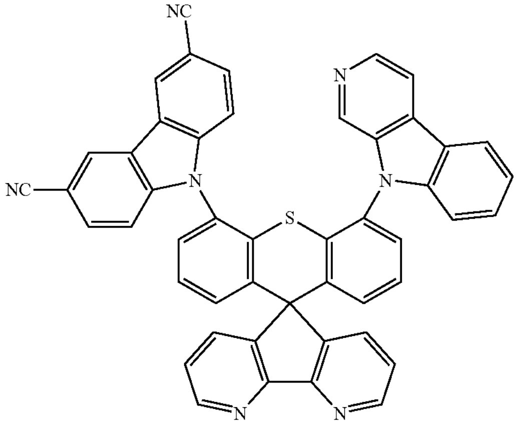
1237
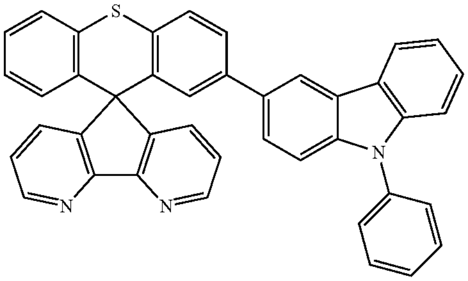
1238
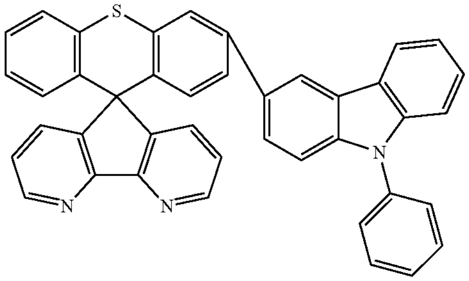
1239
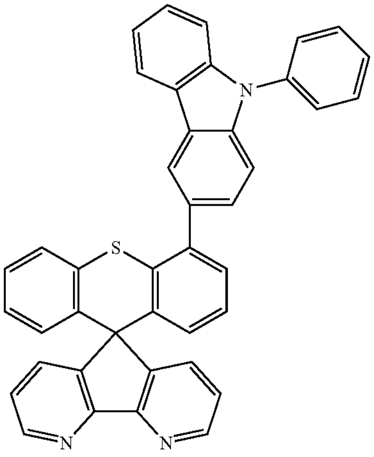
1240
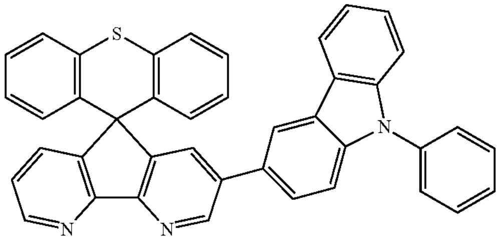

-continued
1241
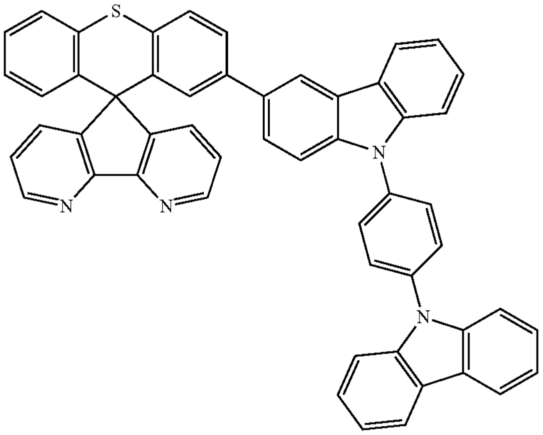
1242
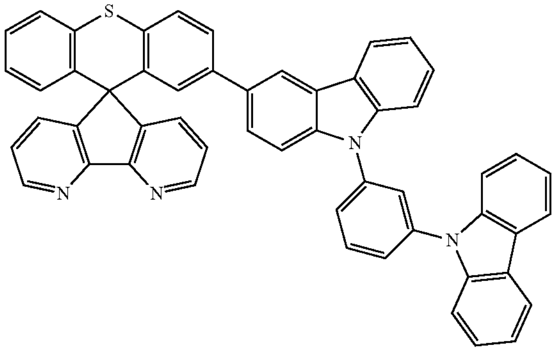
1243
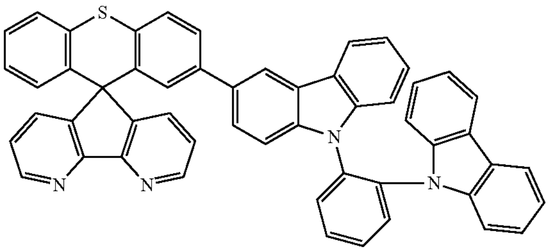
1244
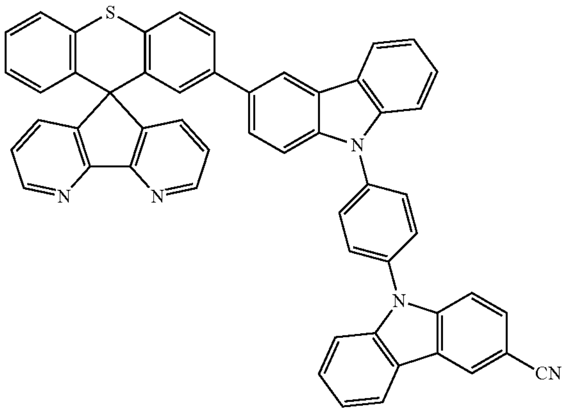
1245
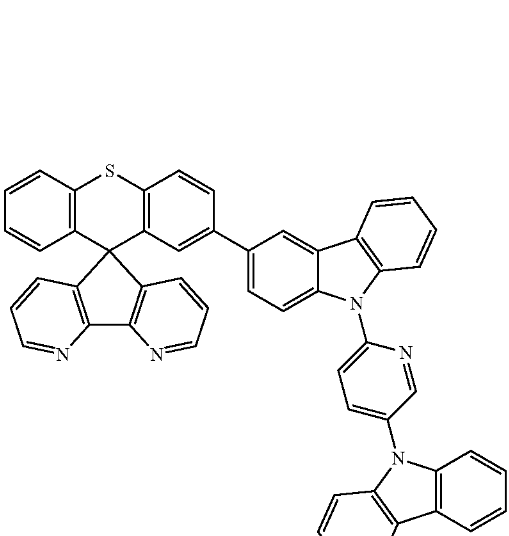
1246
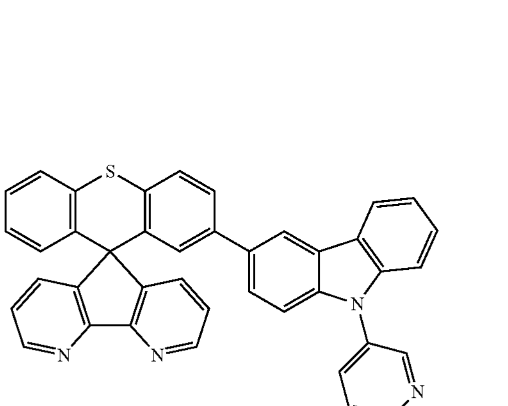

-continued
1247
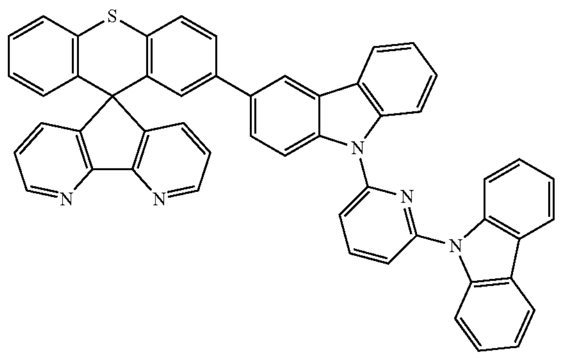
1248
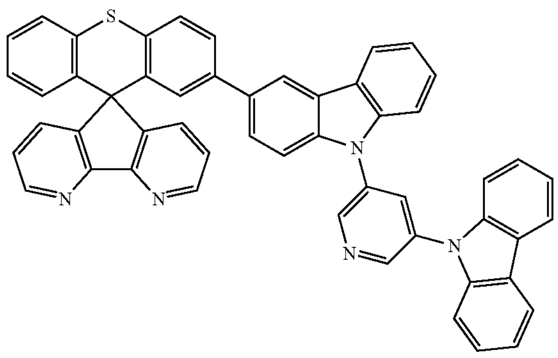
1249
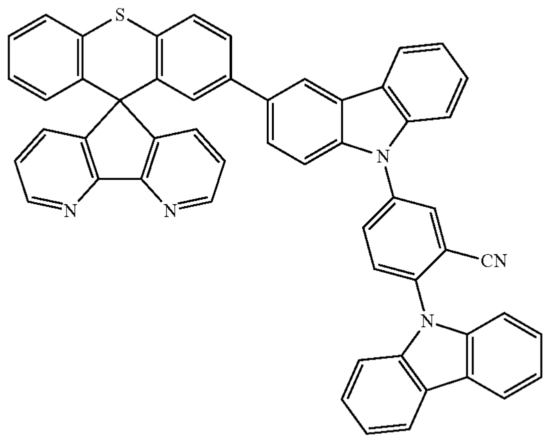
1250
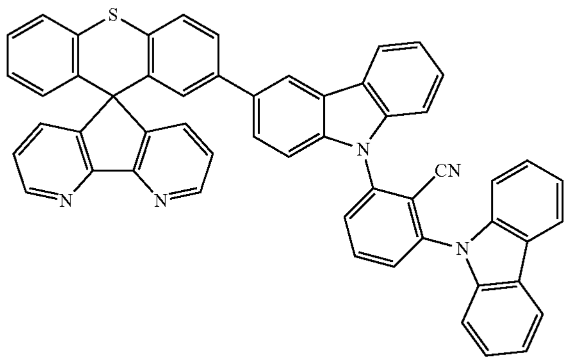
1251
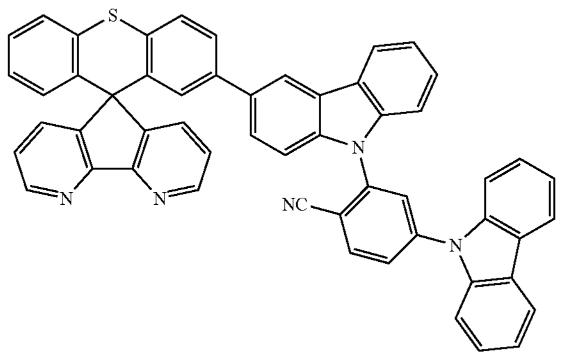
1252
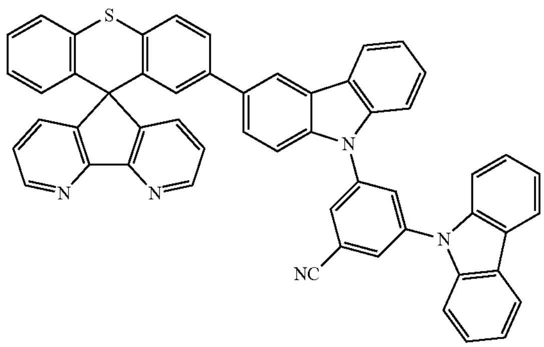
1253
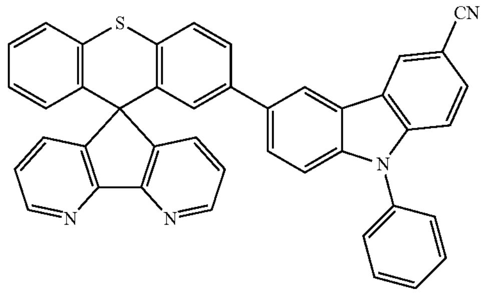
1254
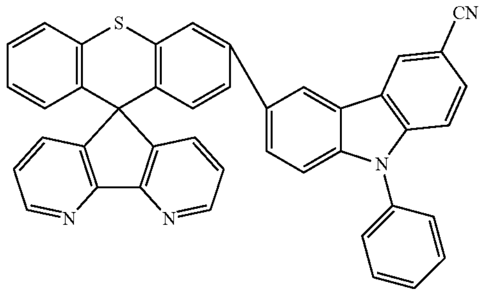

-continued
1255
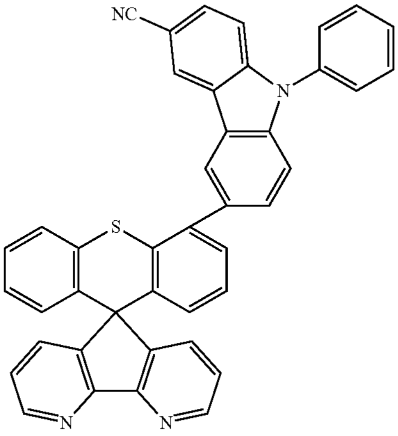
1256
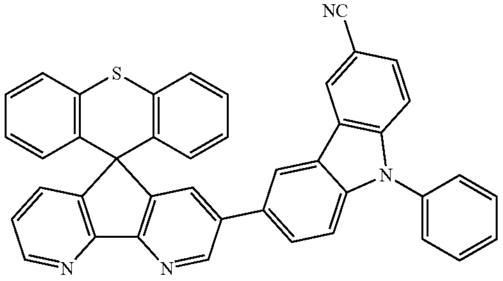
1257
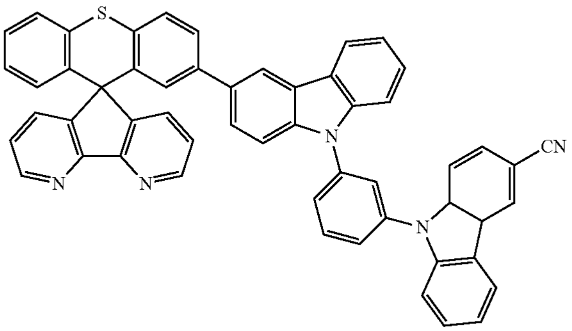
1258
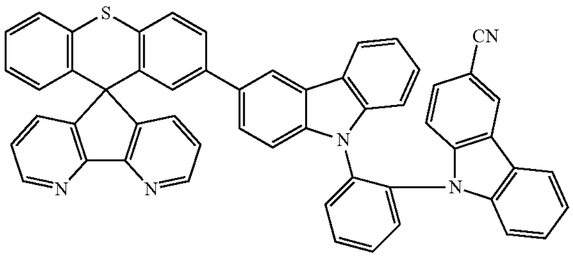
1259
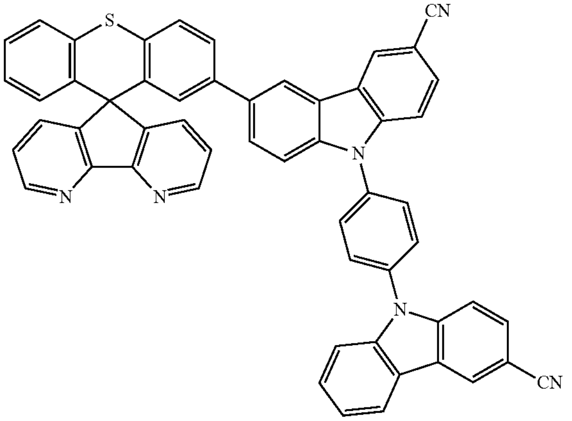
1260
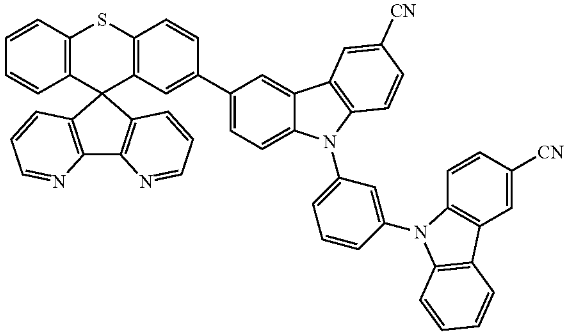
1261
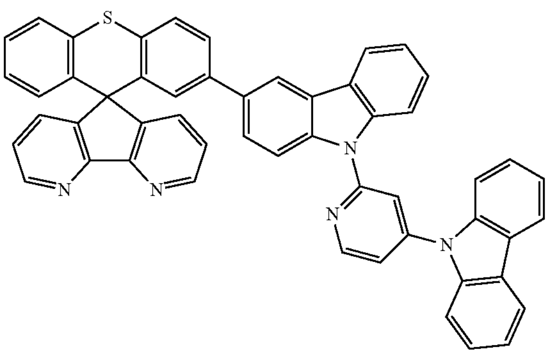
1262
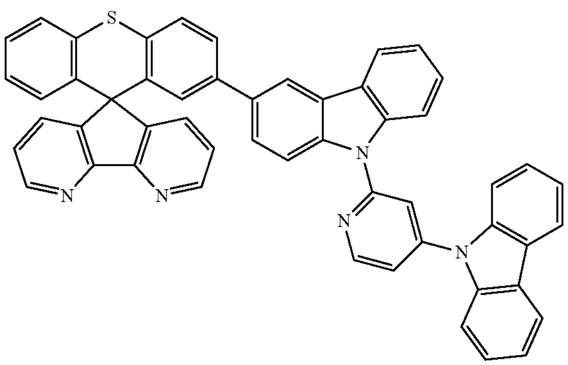

-continued
1263
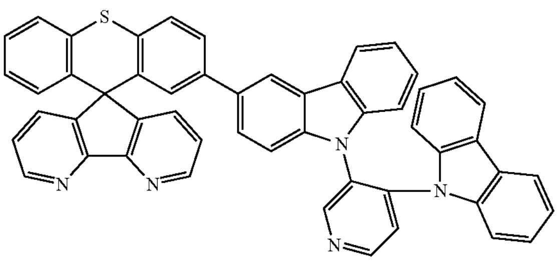
1264
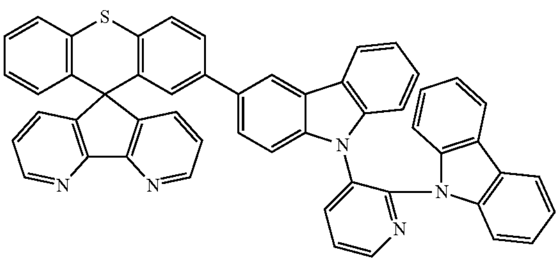
1265
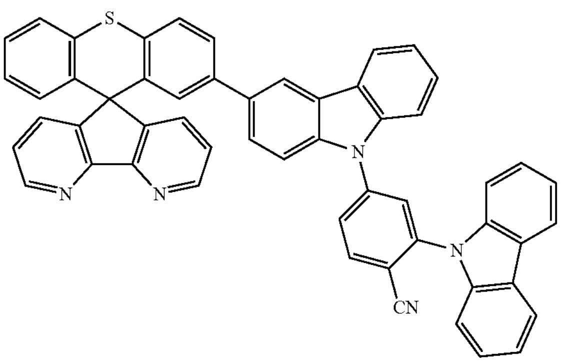
1266
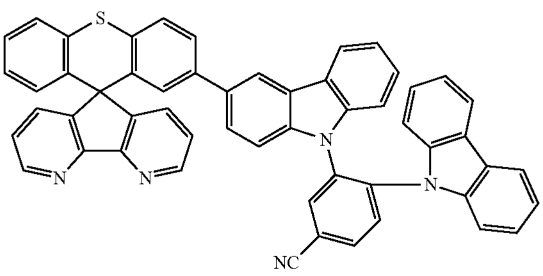
1267
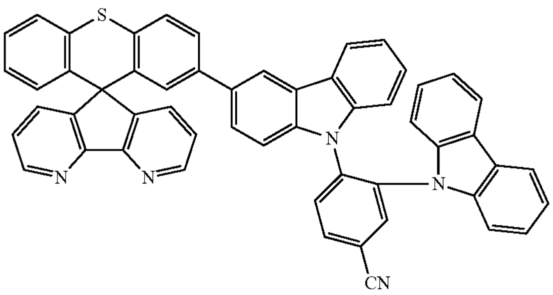
1268
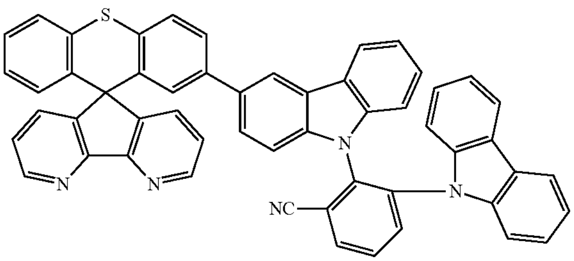
1269
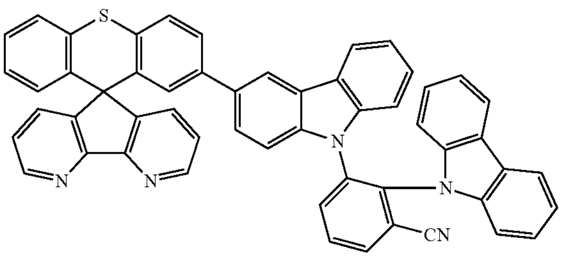
1270
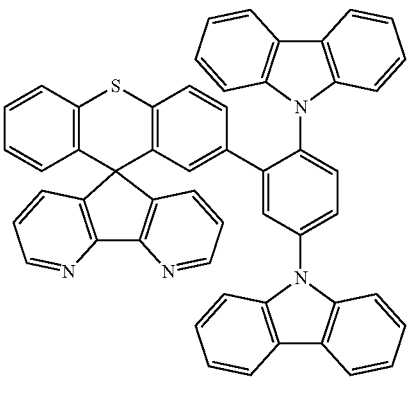

-continued
1271
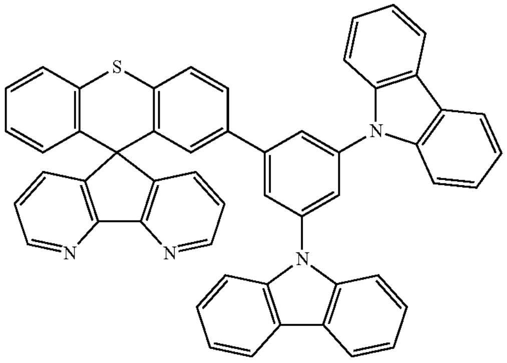
1272
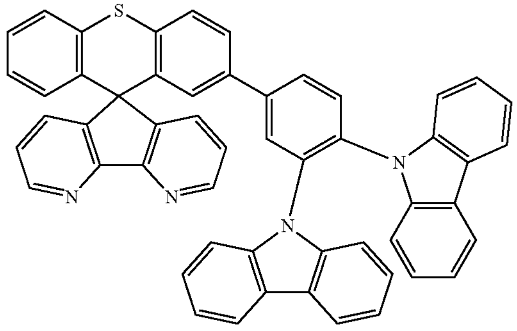
1273
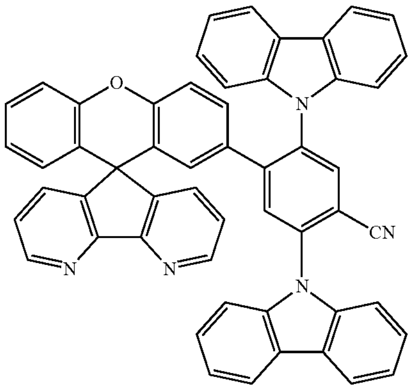
1274
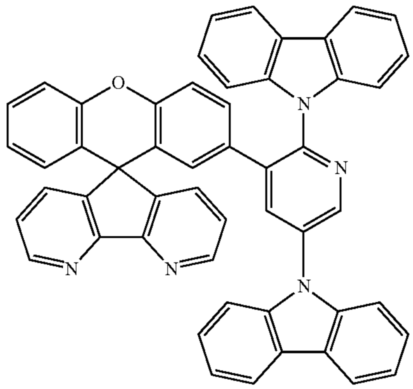
1275
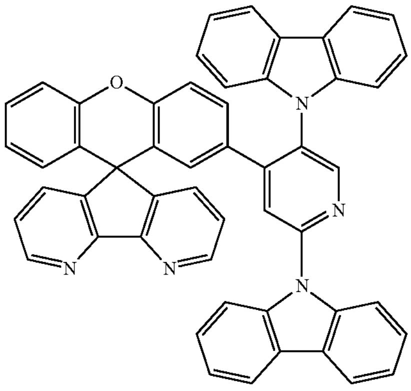
1276
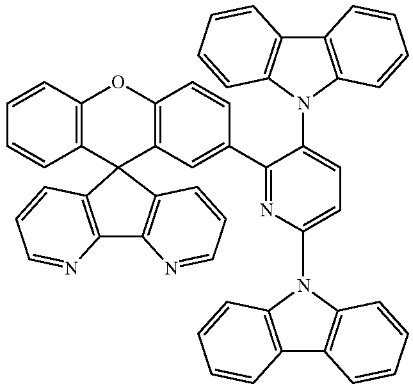
1278
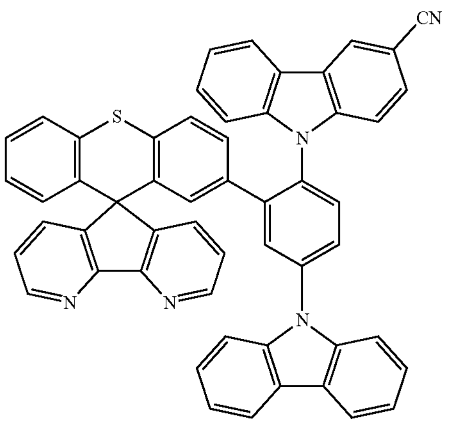
1279
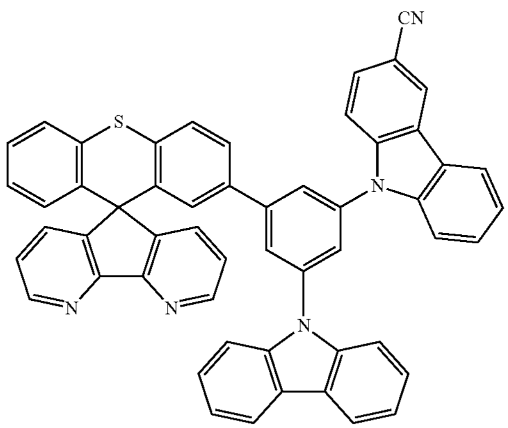

-continued
1280
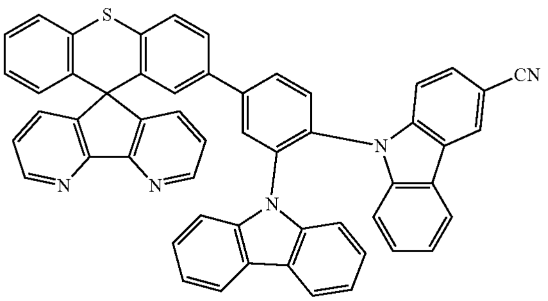
1281
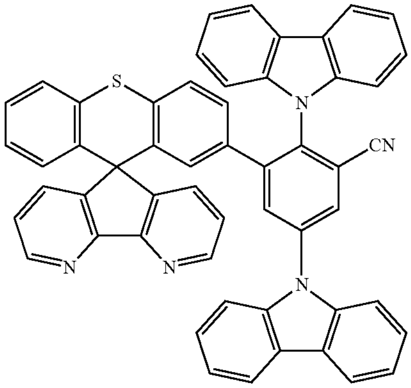
1282
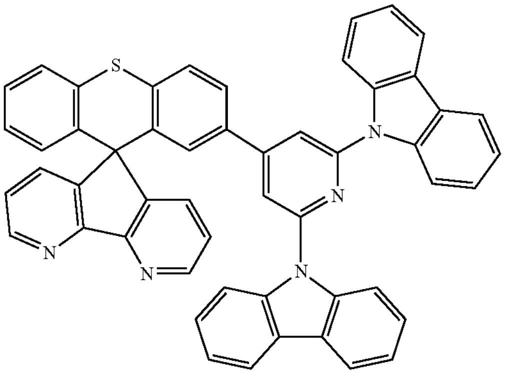
1283
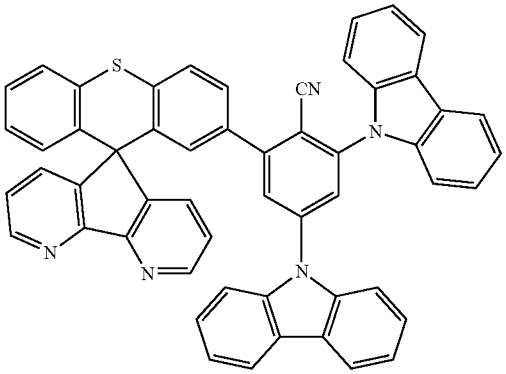
1284
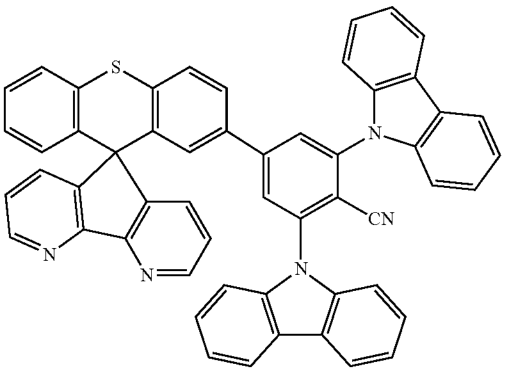
1285
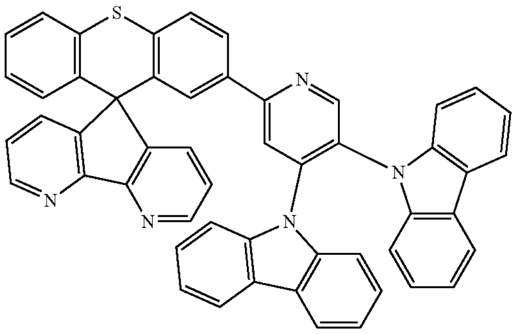
1286
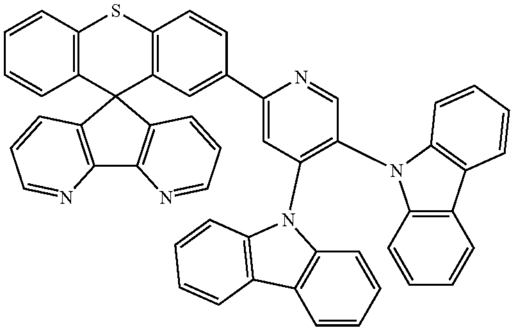
1287
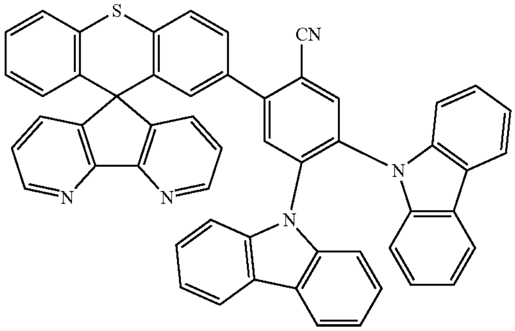

-continued
1288
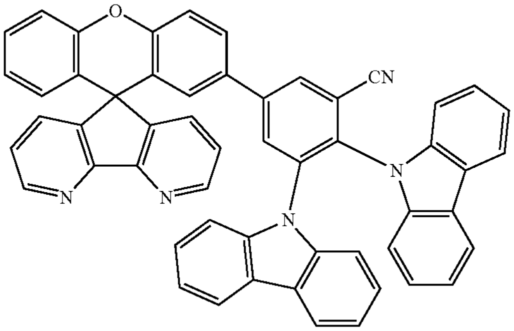
1289
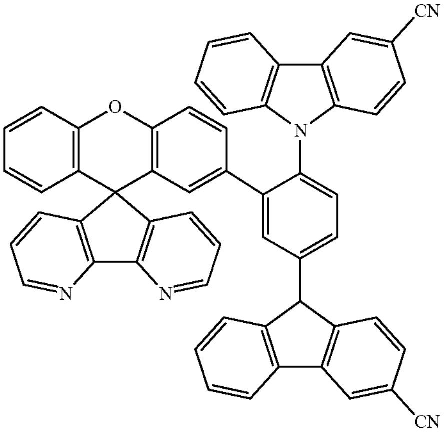
1290
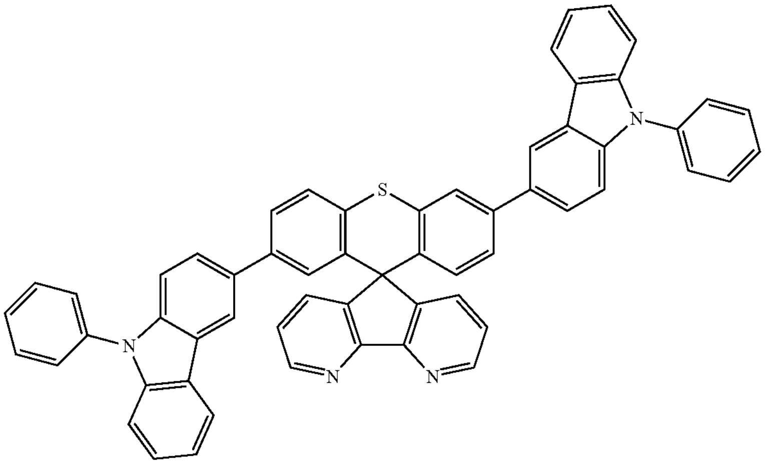
1291
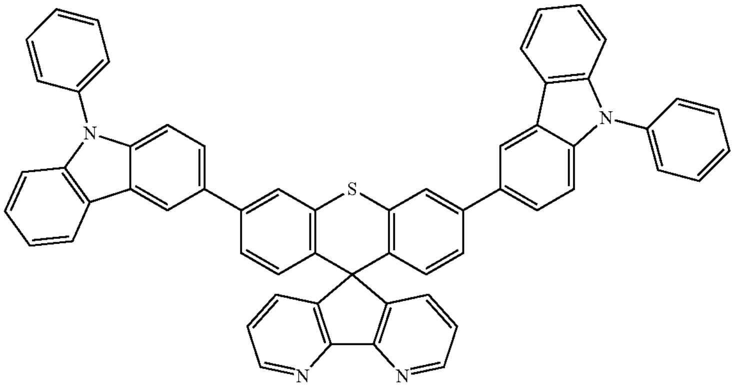

-continued
1292
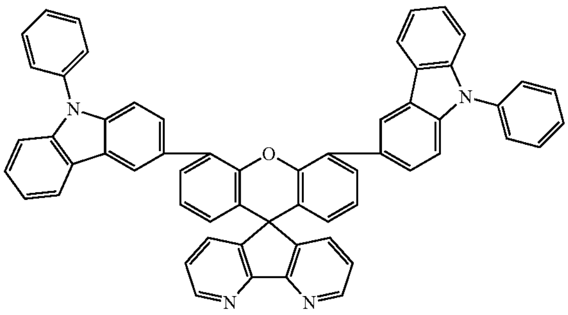
1293
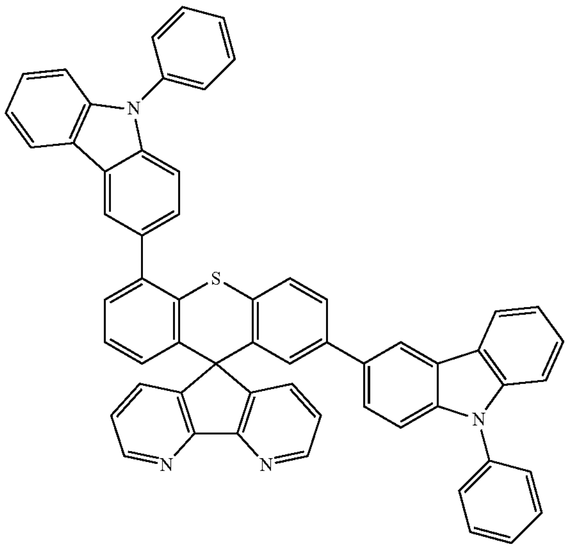
1294
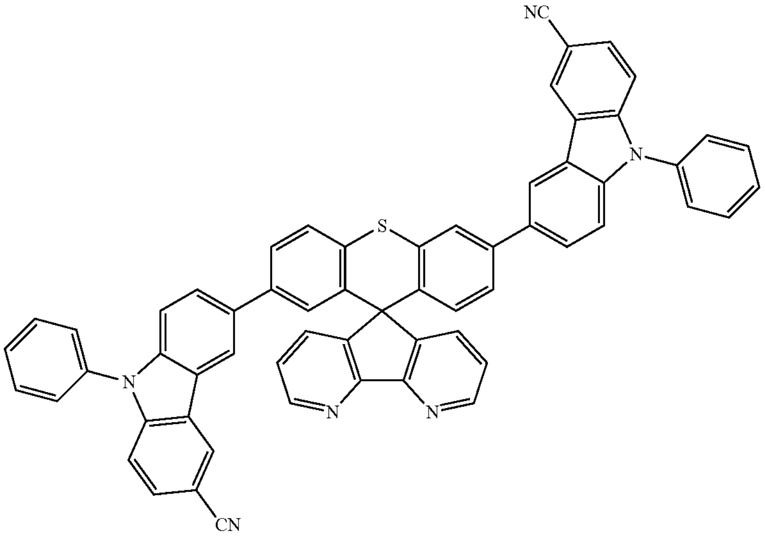
1295
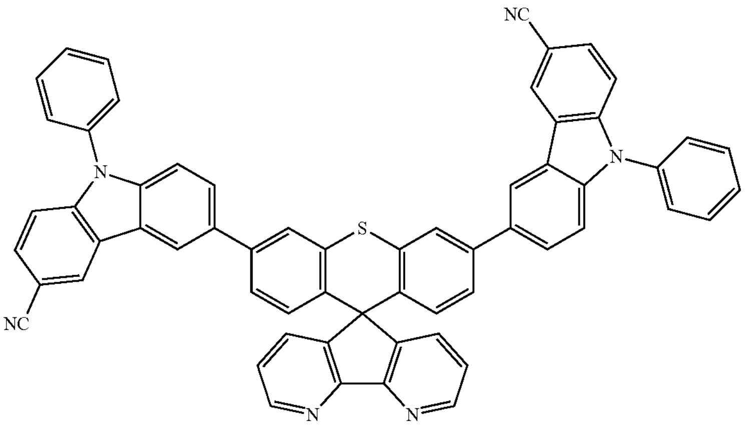

-continued
1296
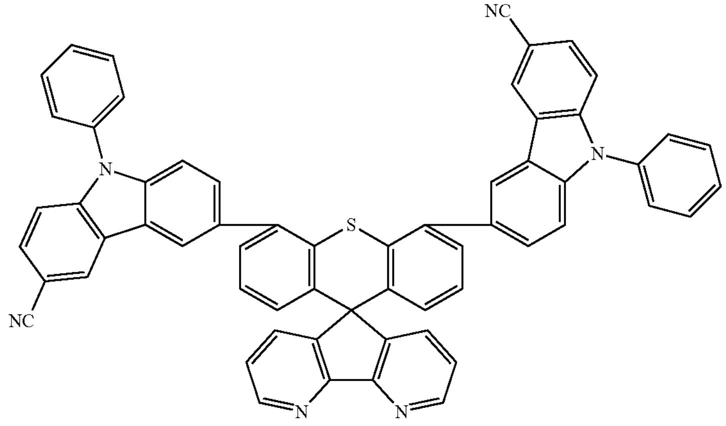
1297
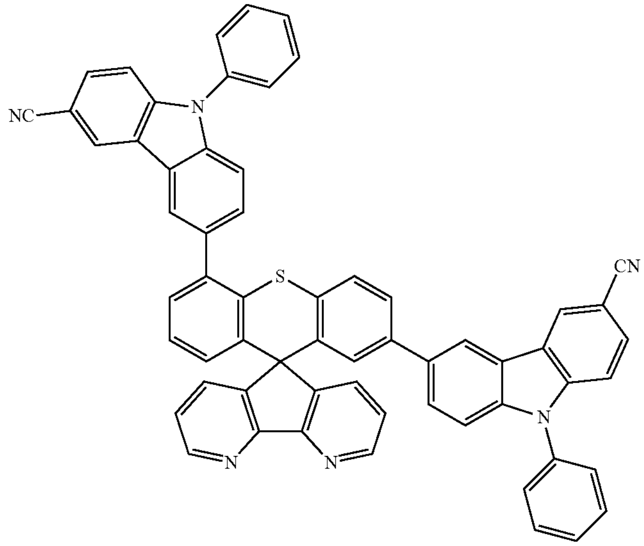
1298
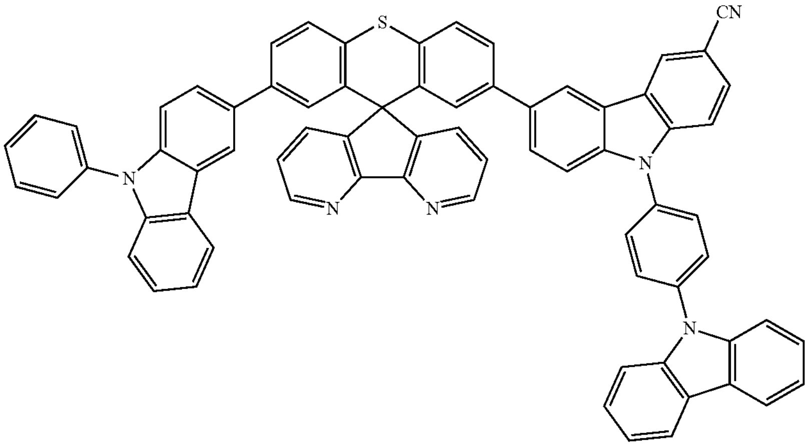

-continued
1299
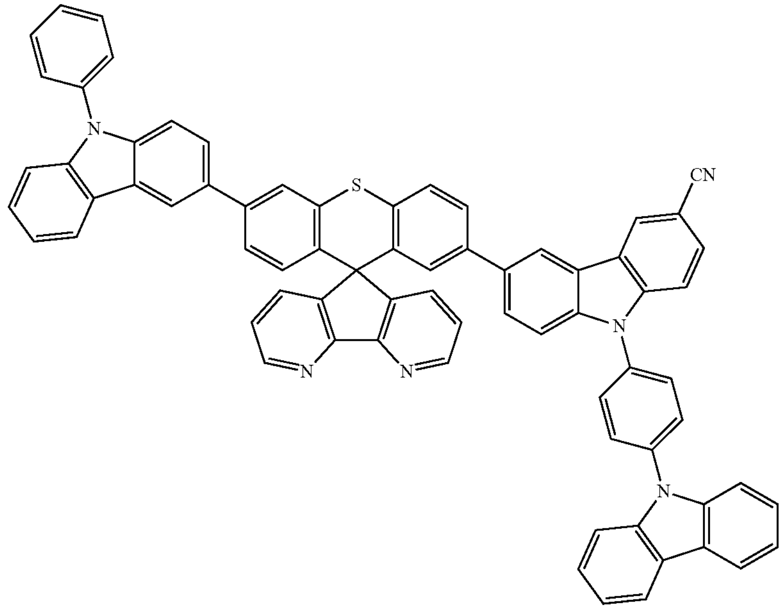
1300
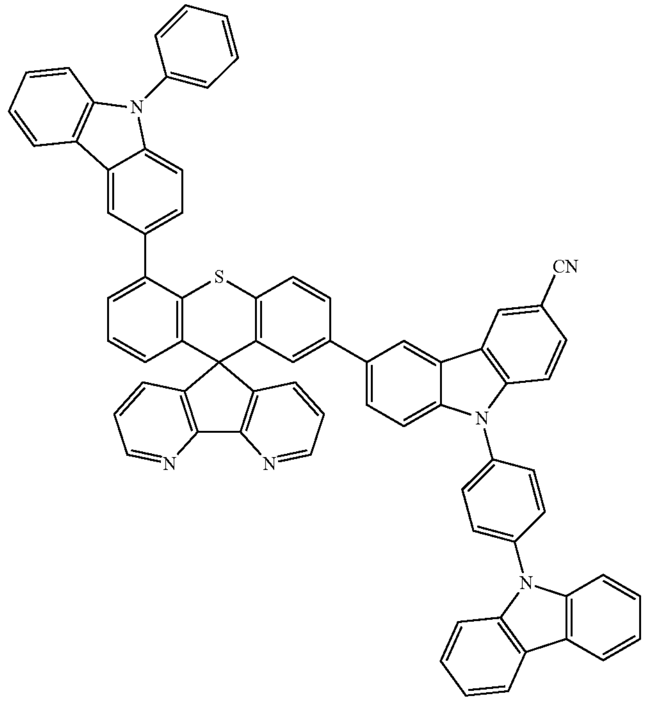

-continued
1301
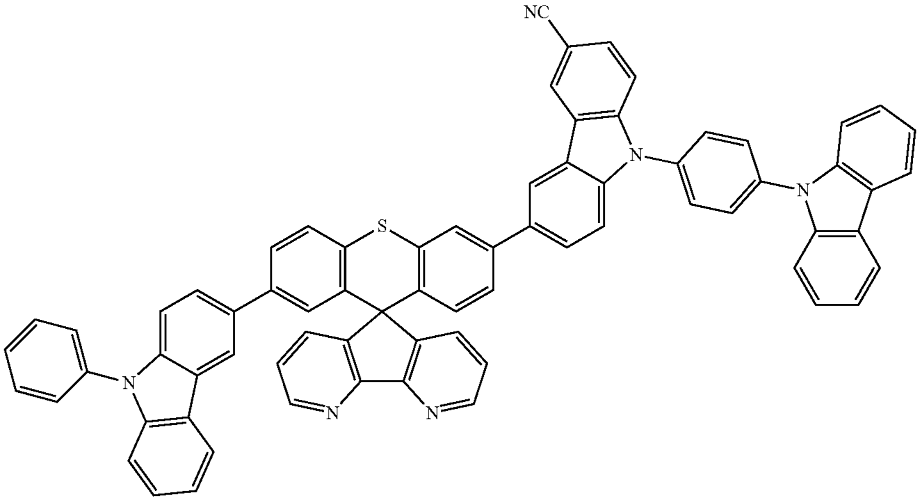
1302
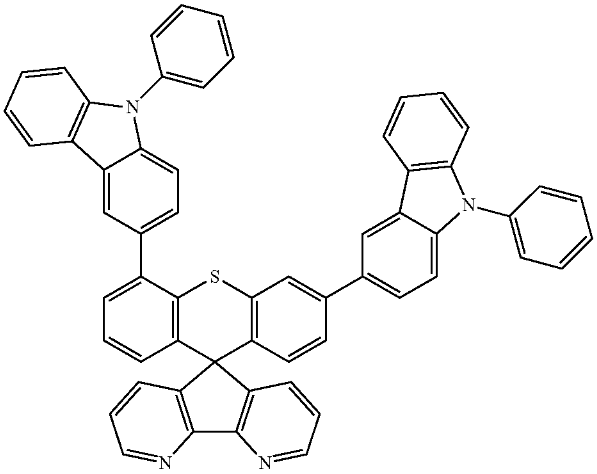
1303
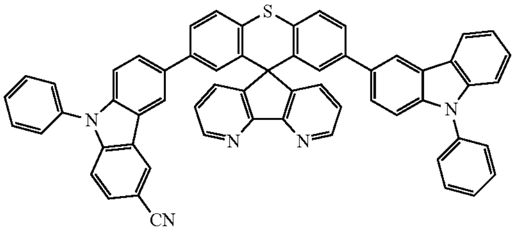
1304
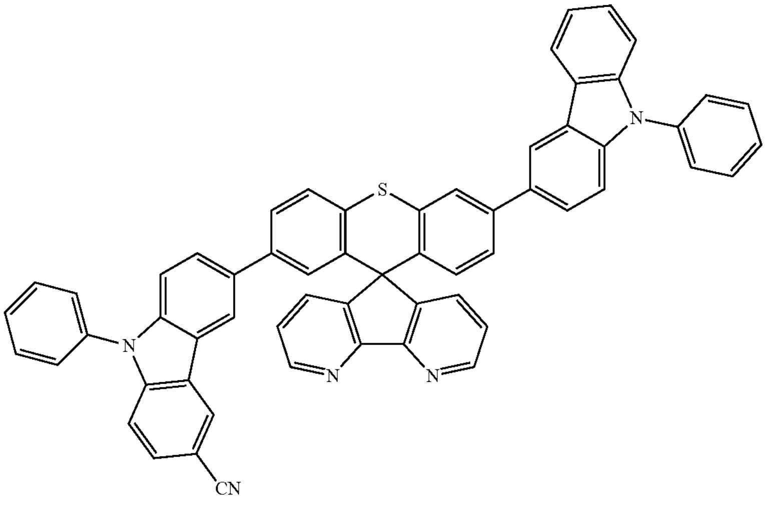

-continued
1305
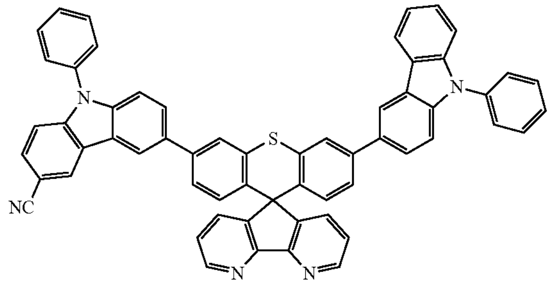
1306
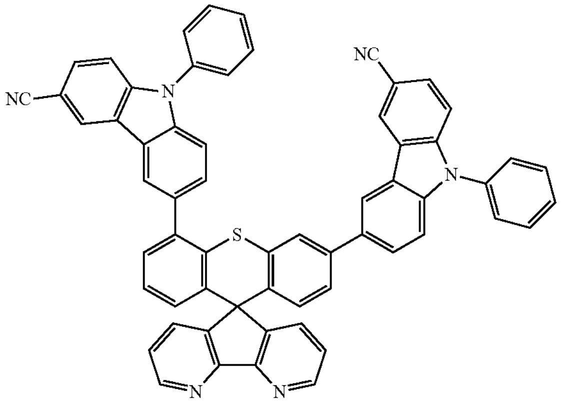
1307
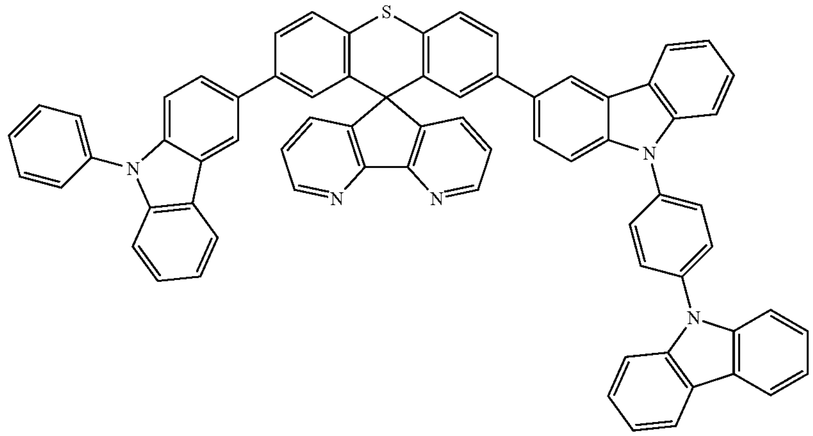
1308
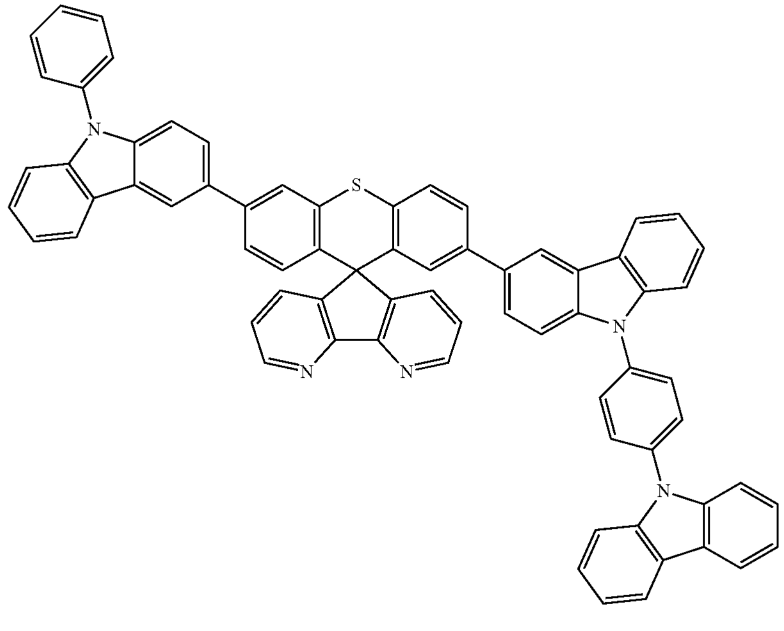

-continued
1309
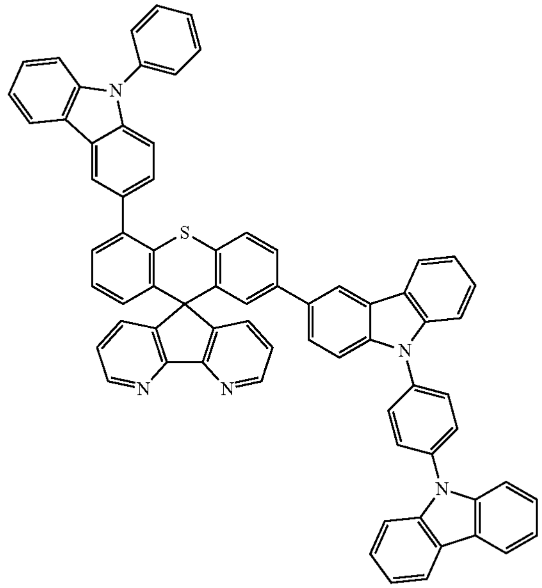
1310
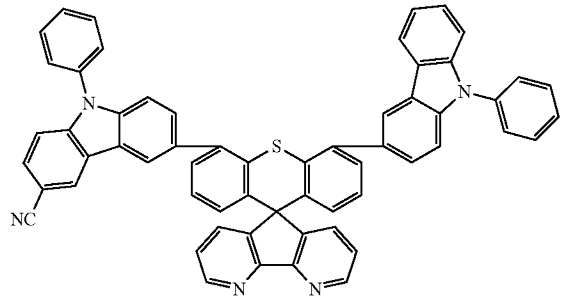
1311
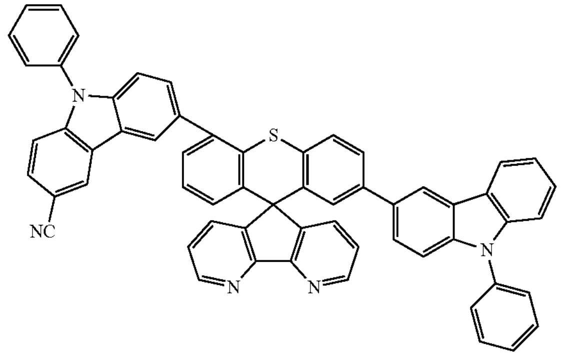
1312
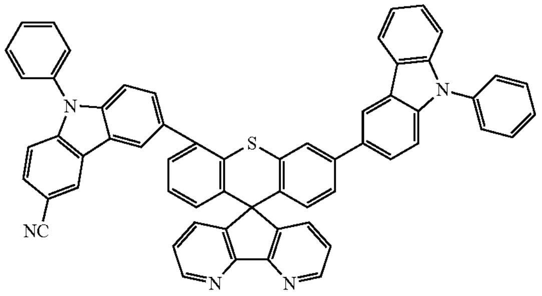
1313
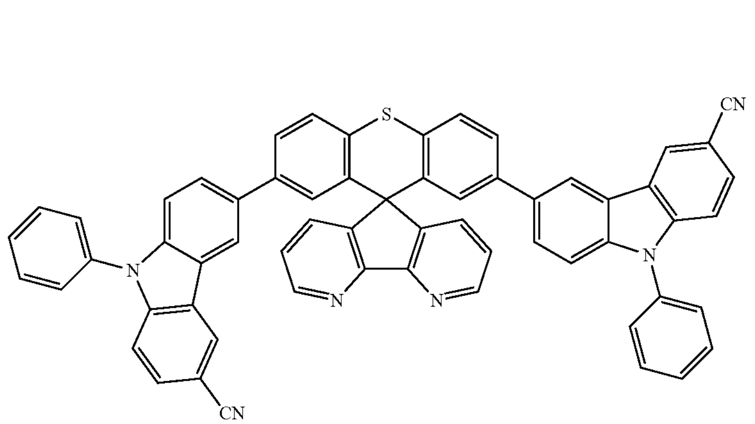

-continued
1314
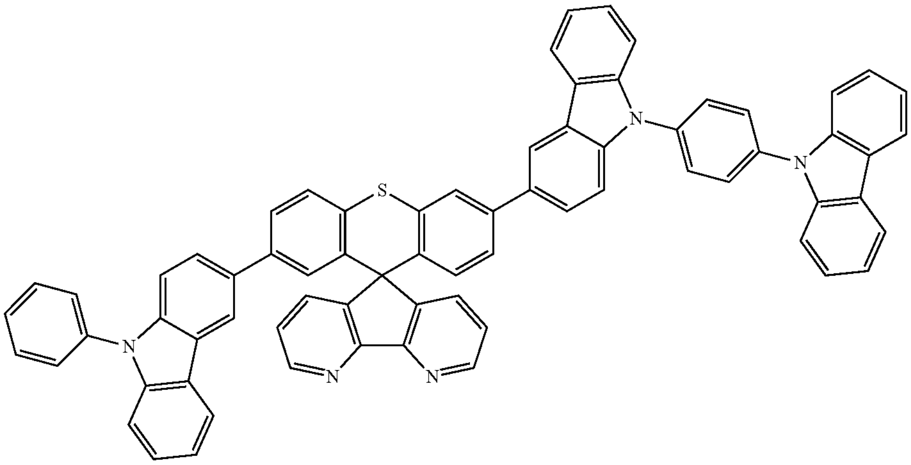
1315
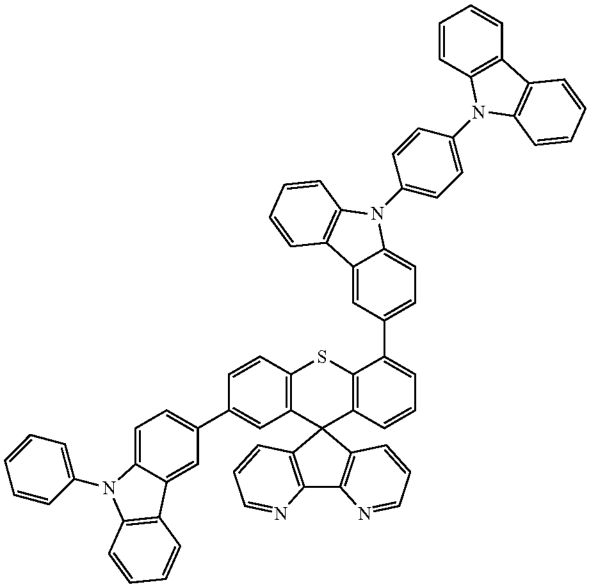
1316
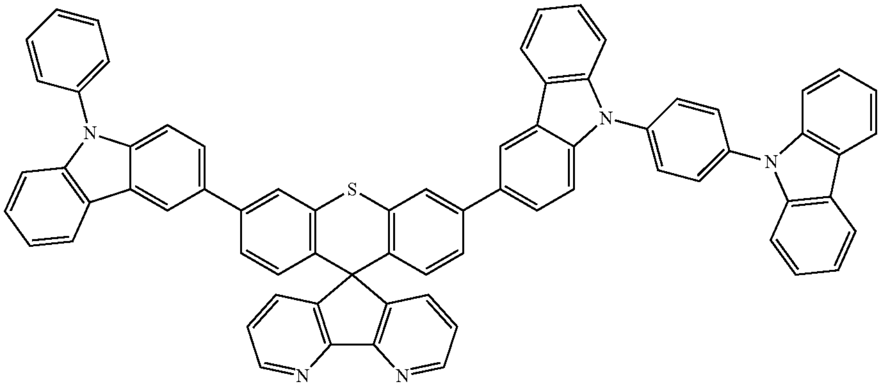

-continued
1317
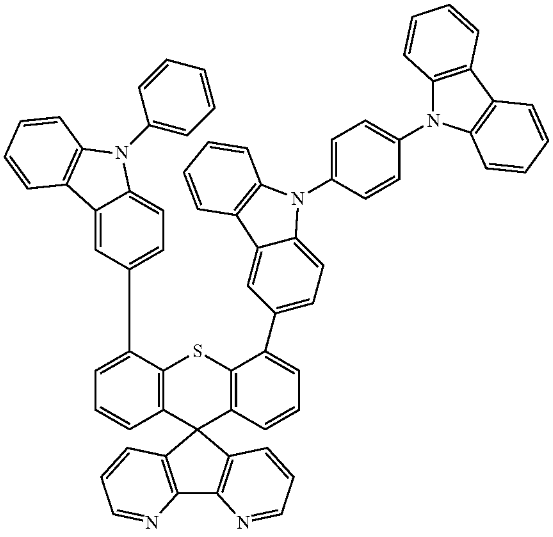
1318
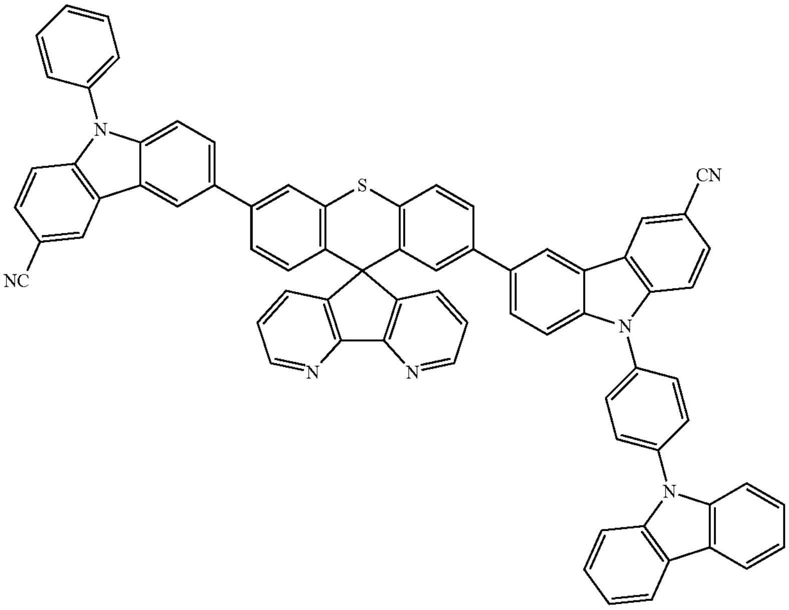

-continued
1319
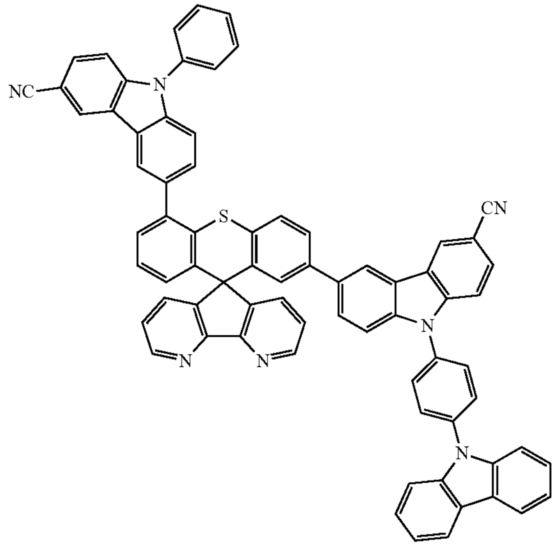
1320
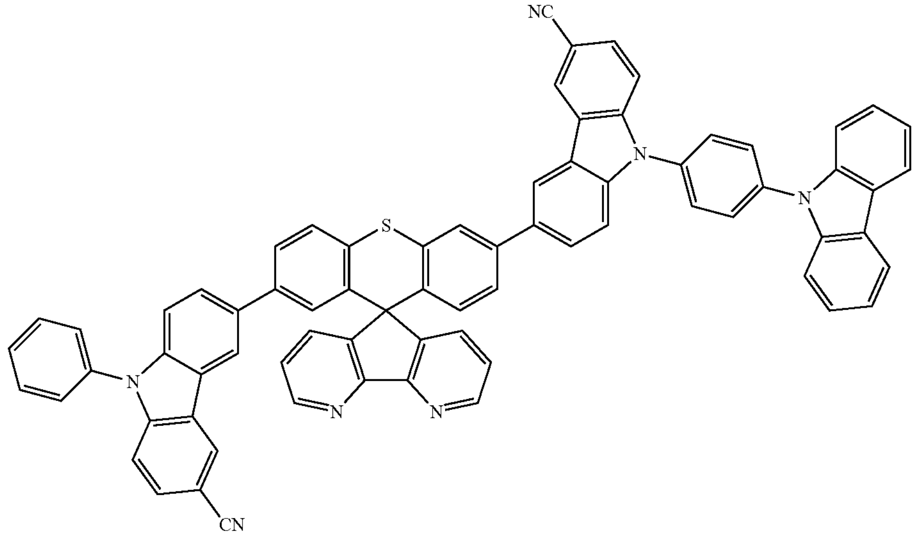
1321
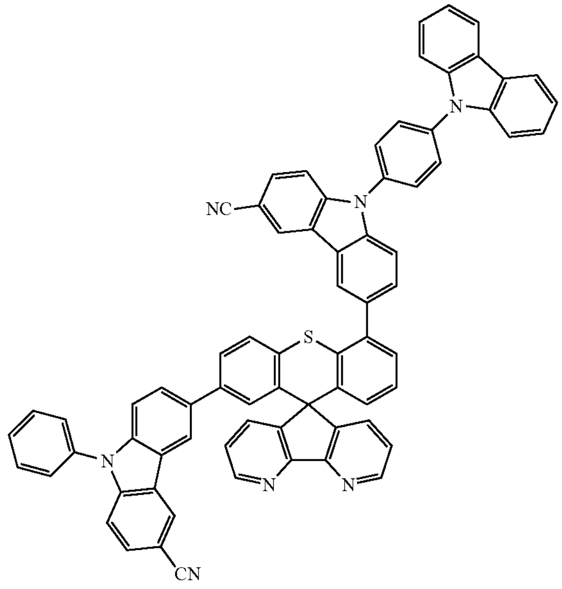

-continued
1322
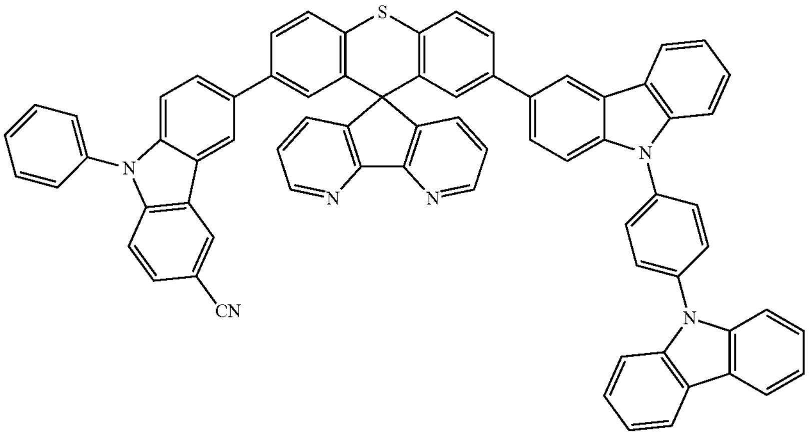
1323
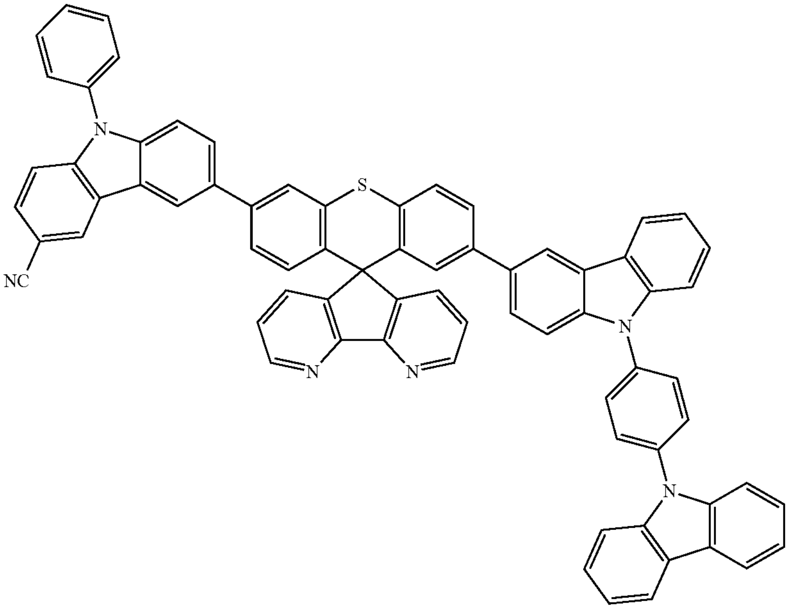
1324
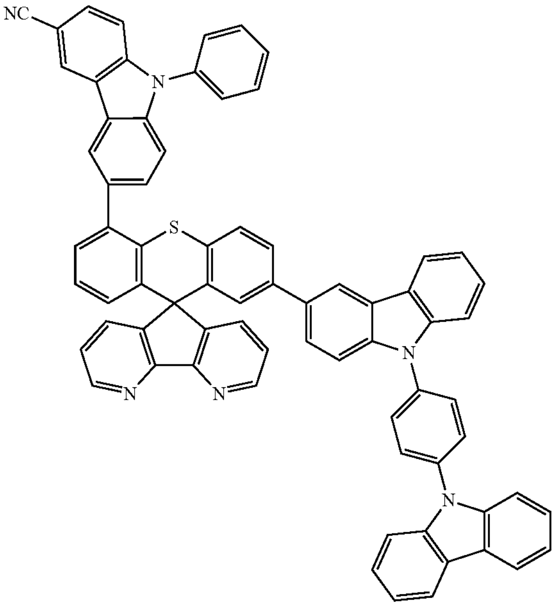

-continued
1325
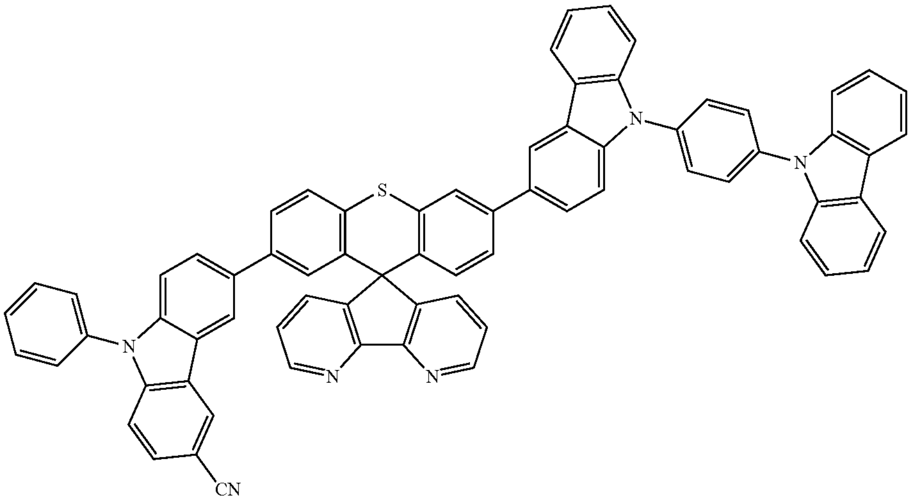
1326
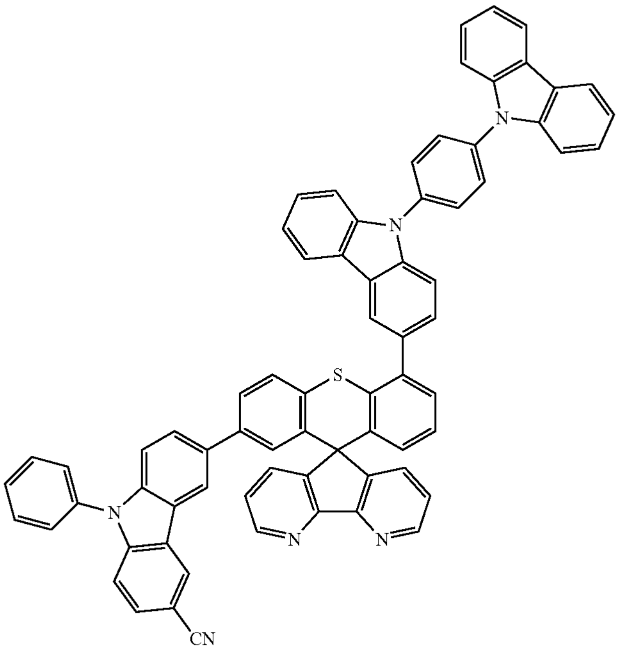
1327
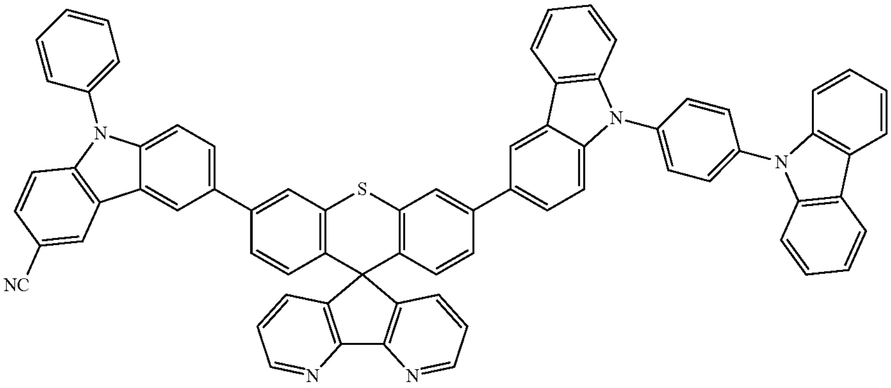

-continued
1328
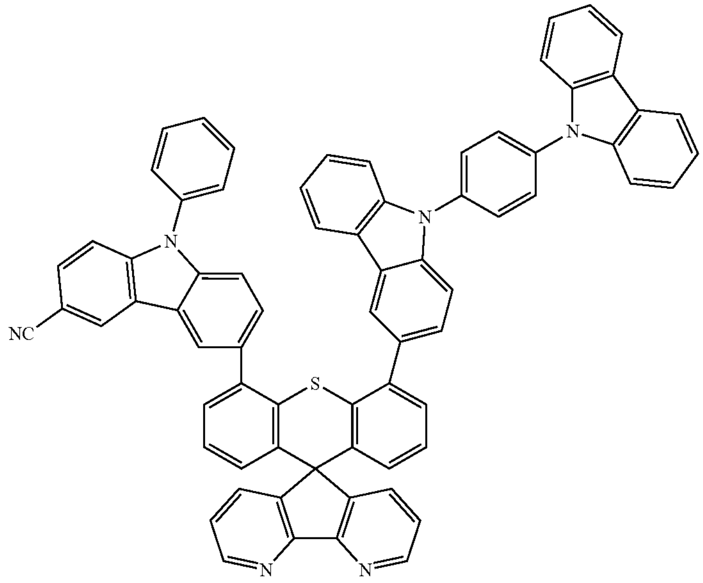
1329
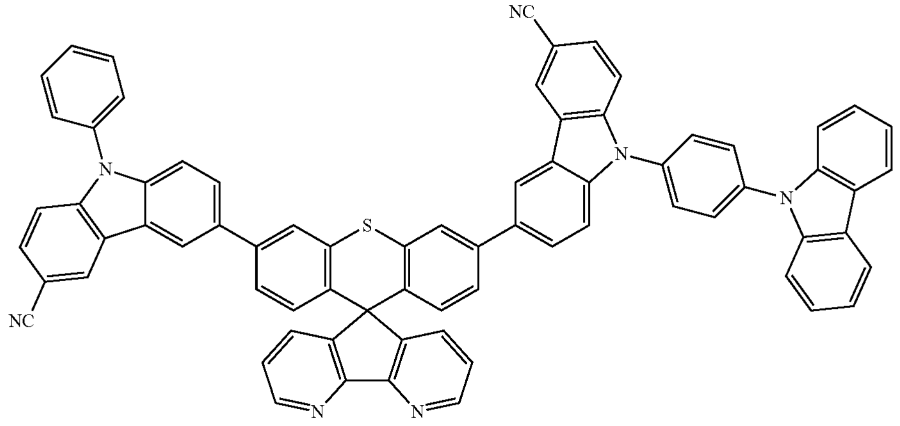
1330
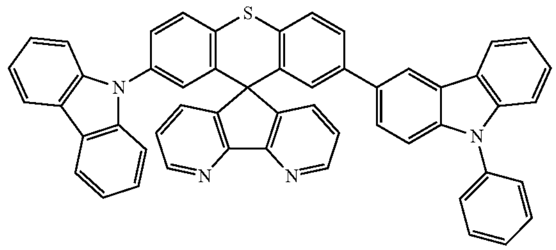
1331
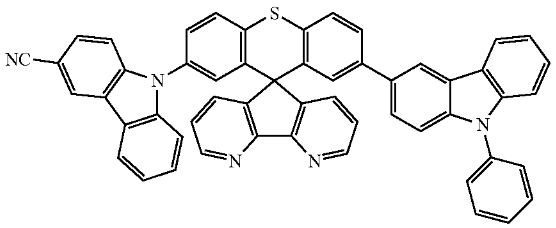
1332
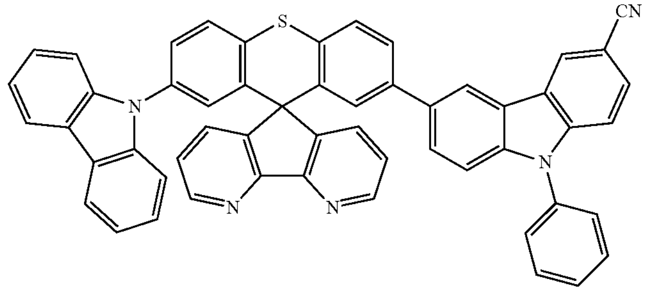

-continued
1333
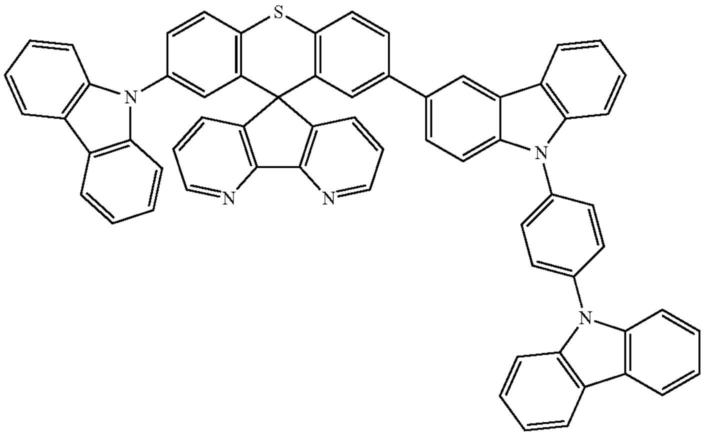
1334
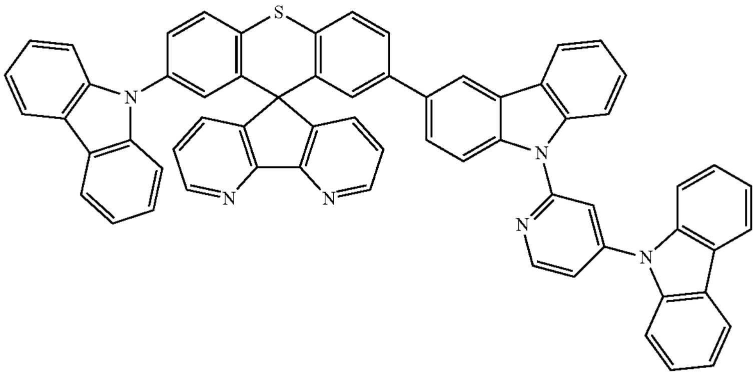
1335
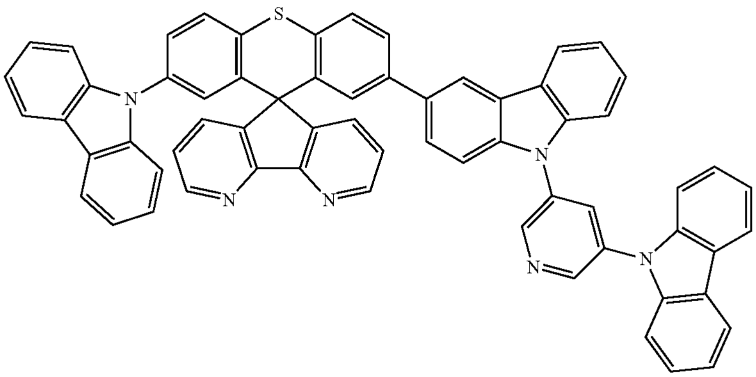
1336
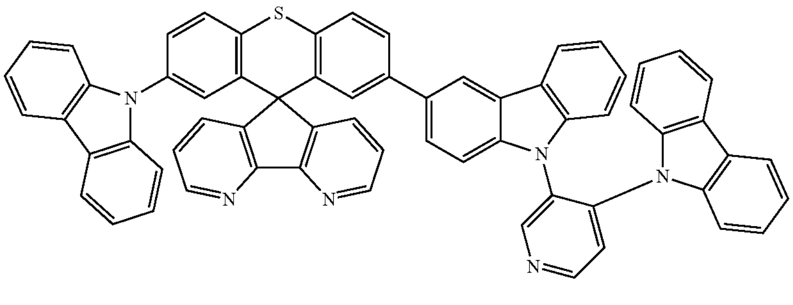

-continued
1337
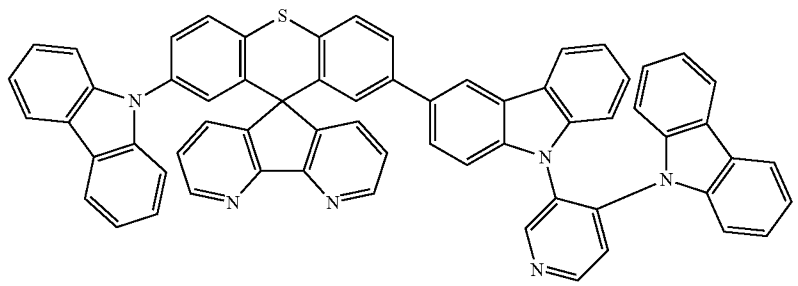
1338
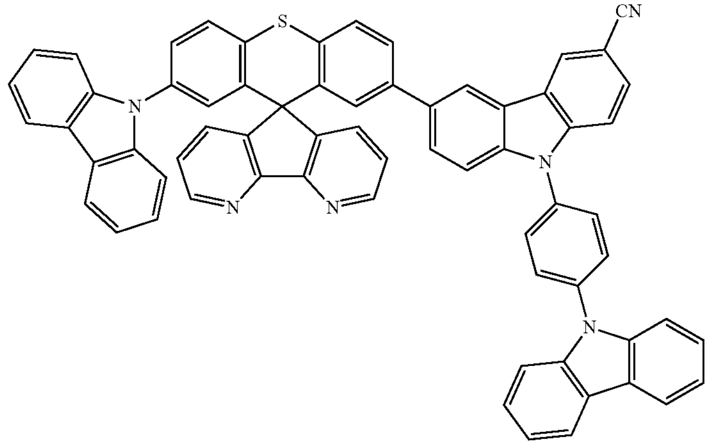
1339
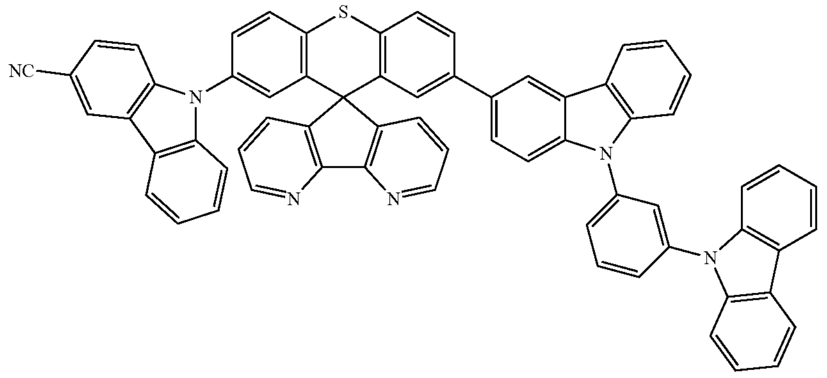
1340
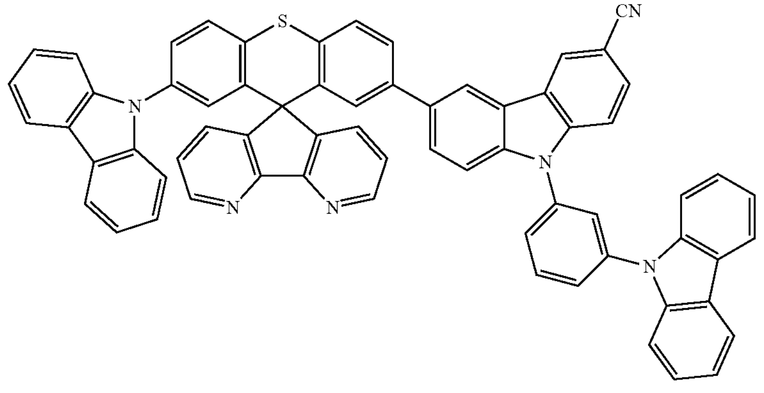

-continued
1341
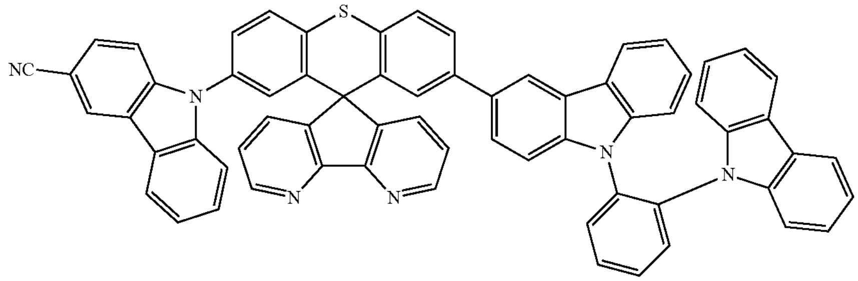
1342
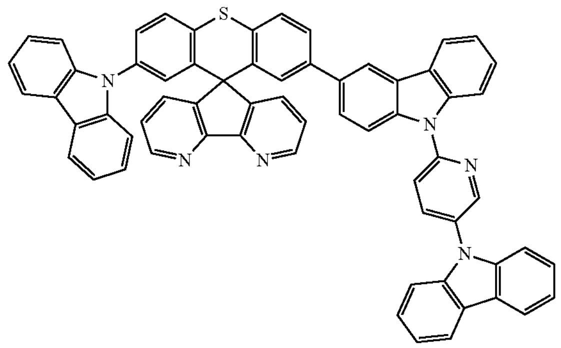
1343
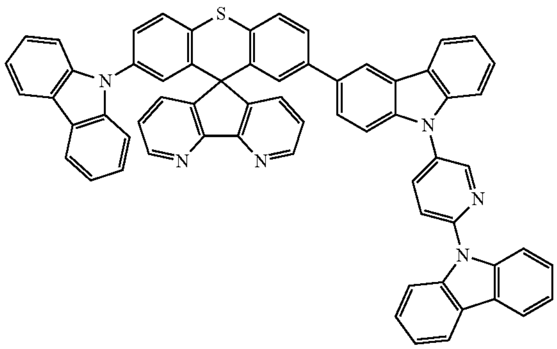
1344
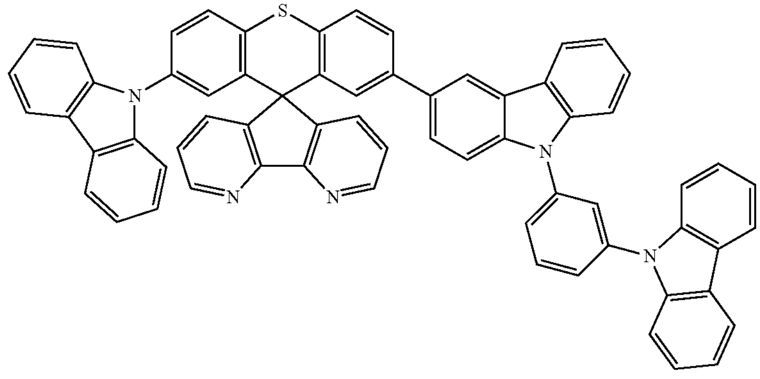
1345
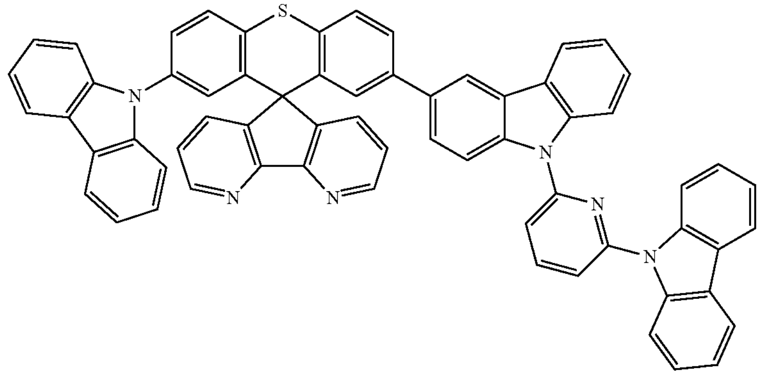

-continued
1346
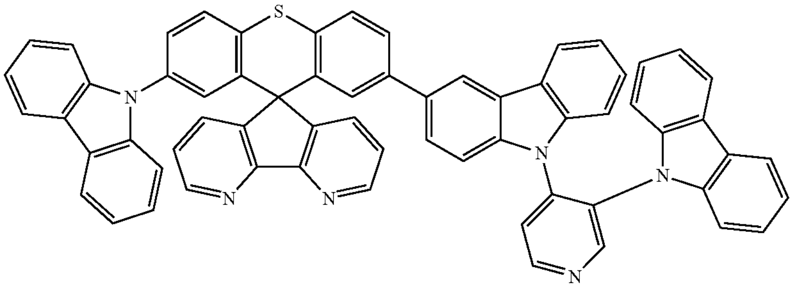
1347
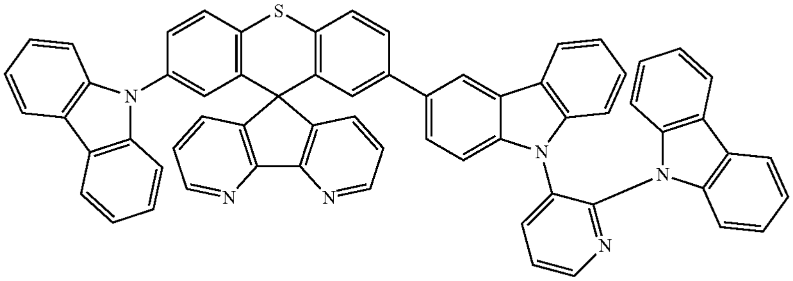
1348
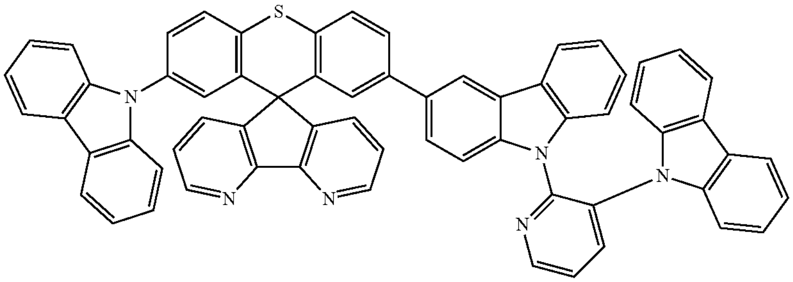
1349
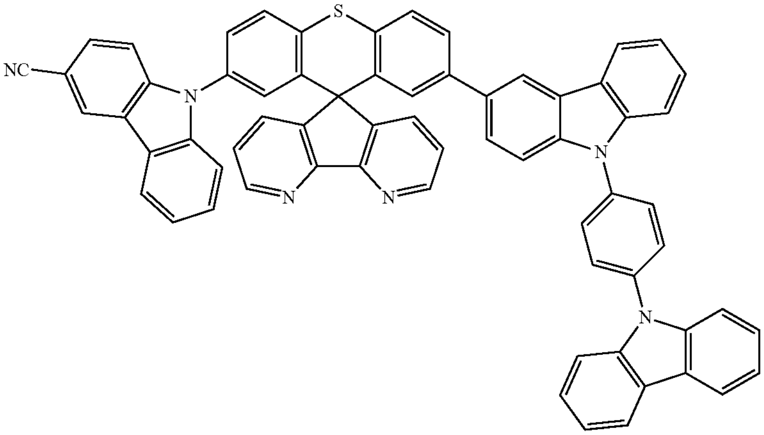
1350
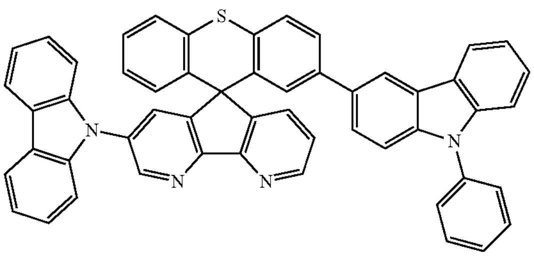
1351
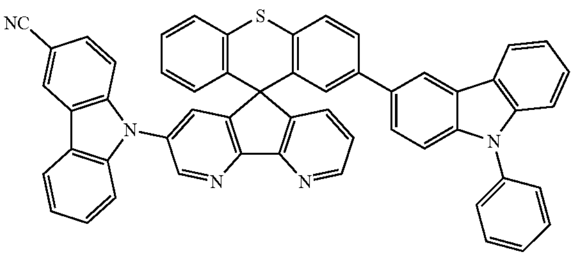

-continued
1352
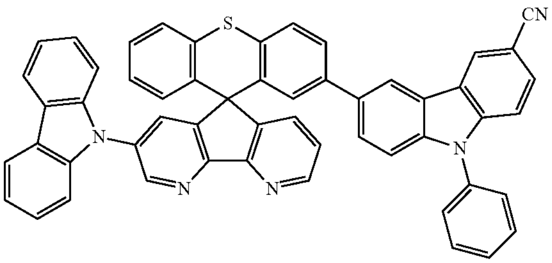
1353
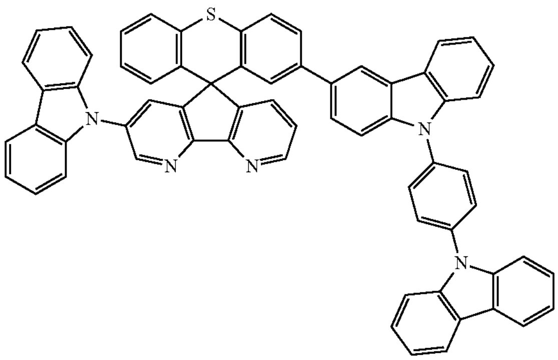
1354
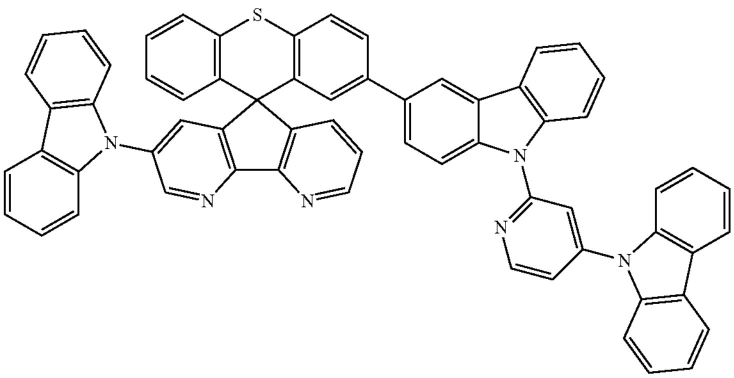
1355
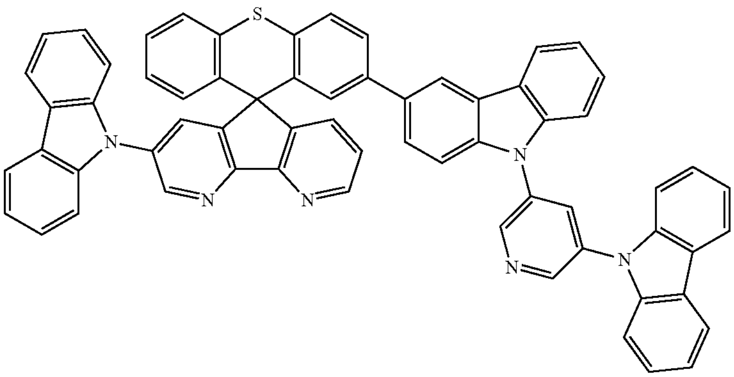
1356
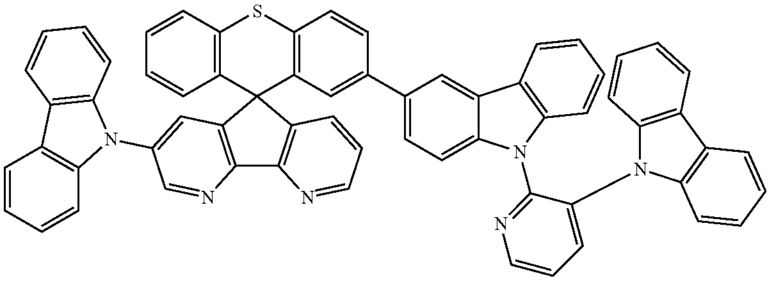

-continued
1357
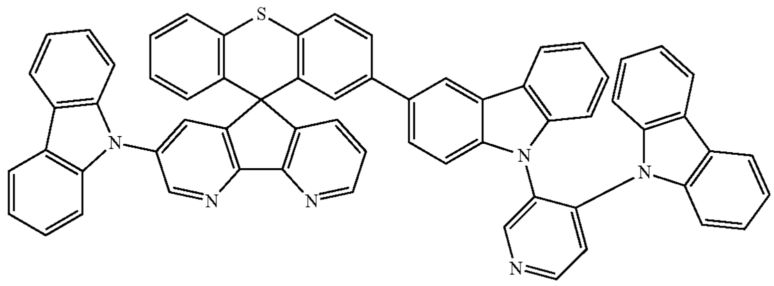
1358
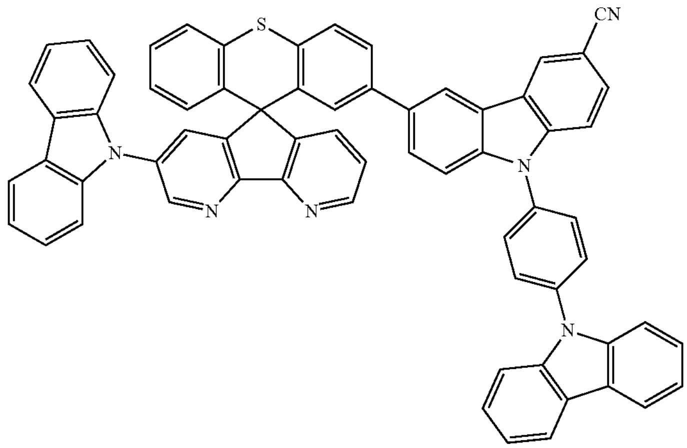
1359
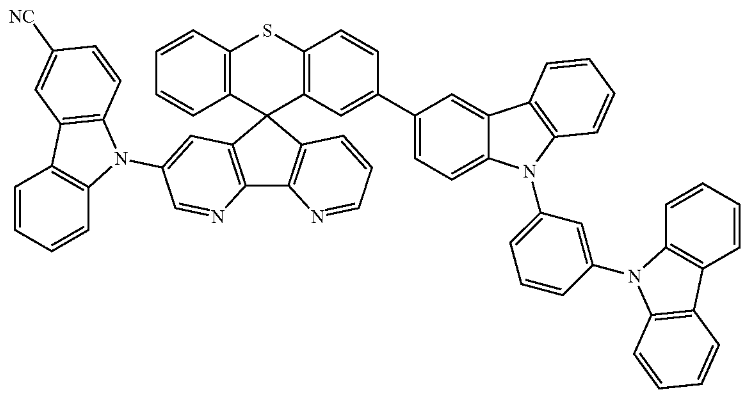
1360
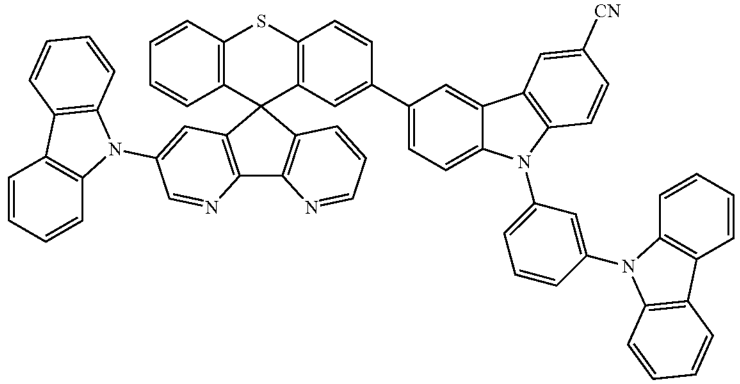

-continued
1361
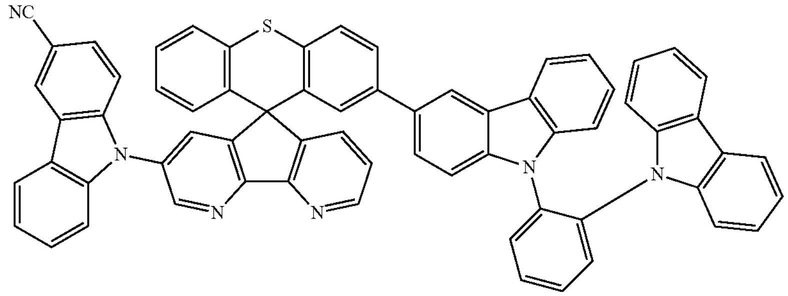
1362
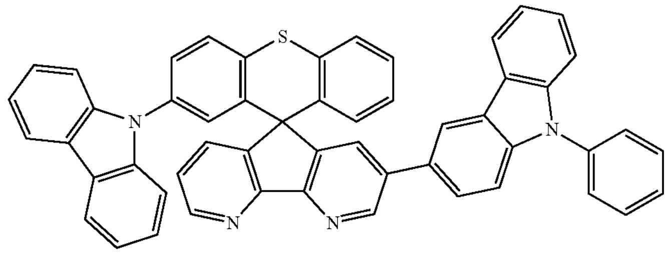
1363
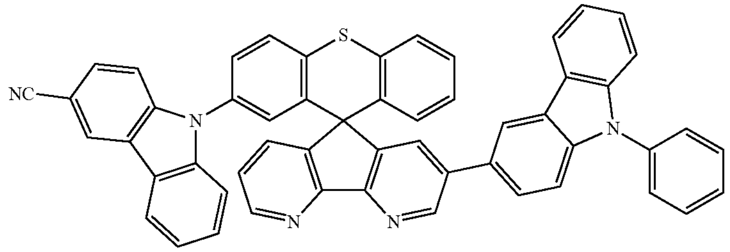
1364
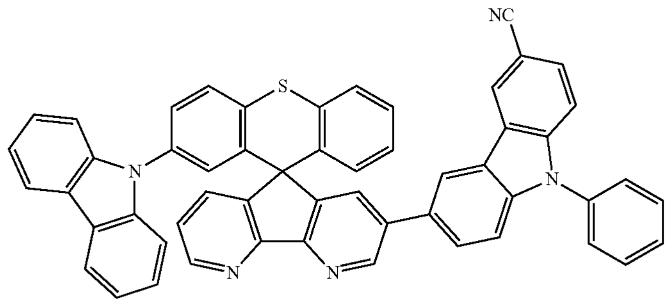
1365
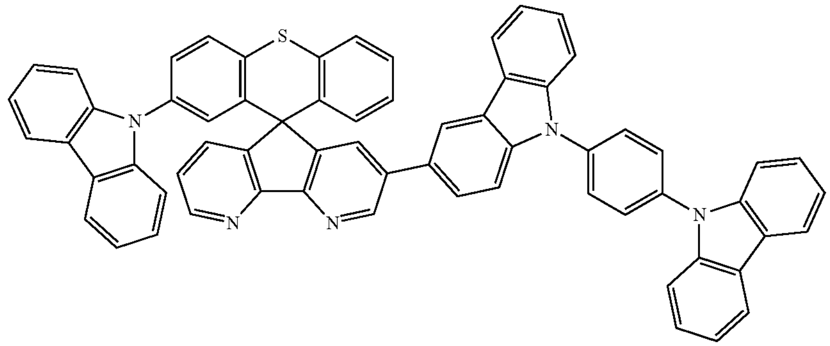

-continued
1366
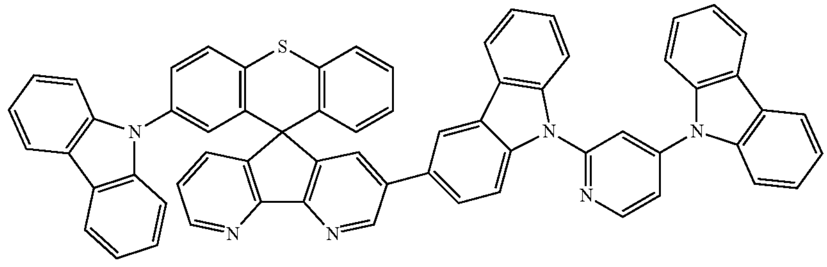
1367
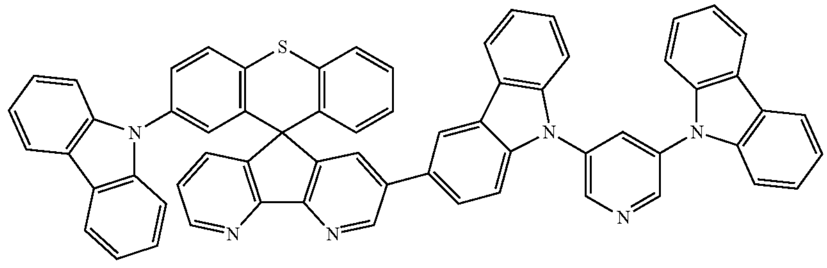
1368
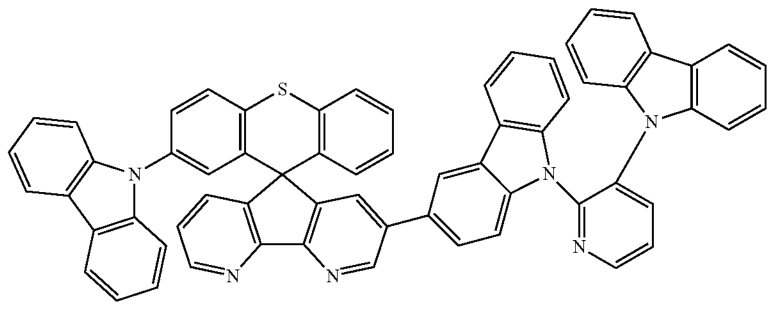
1369
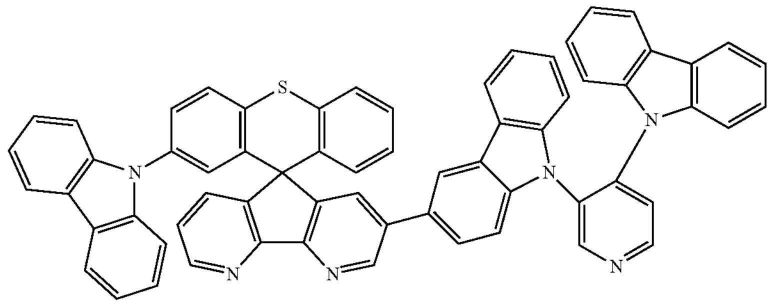
1370
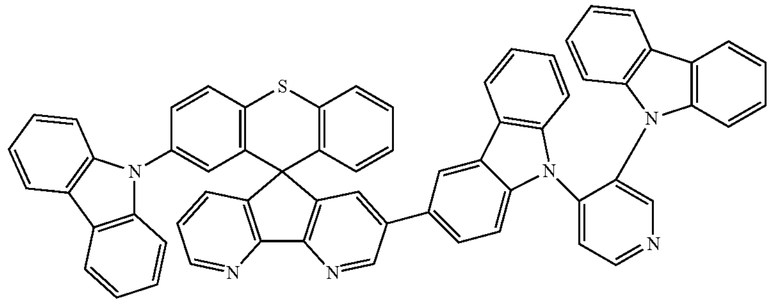

-continued
1371
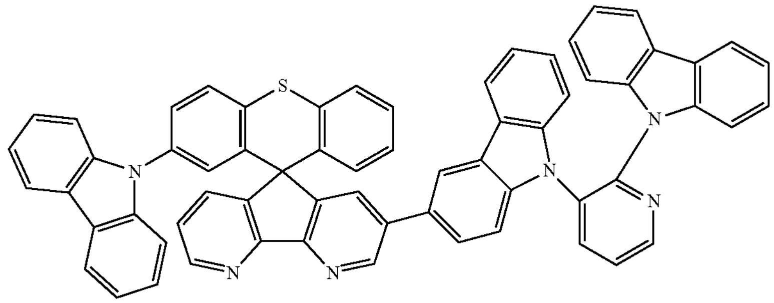
1372
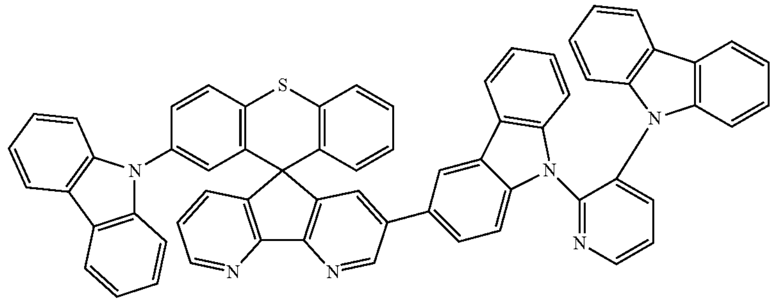
1373
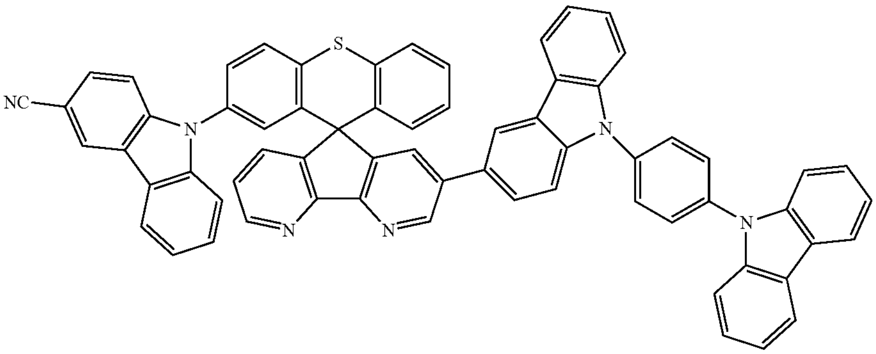
1374
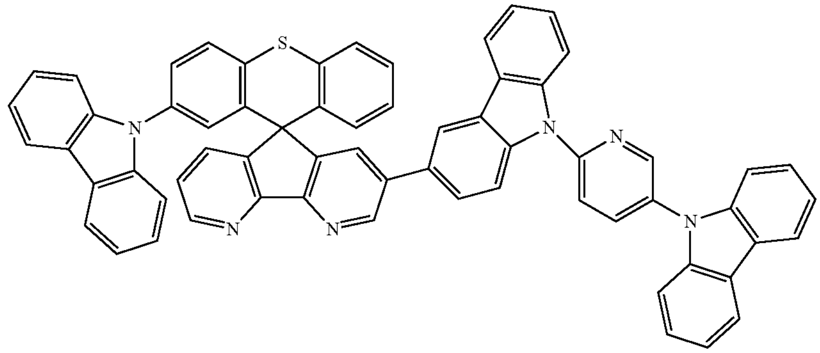

-continued
1375
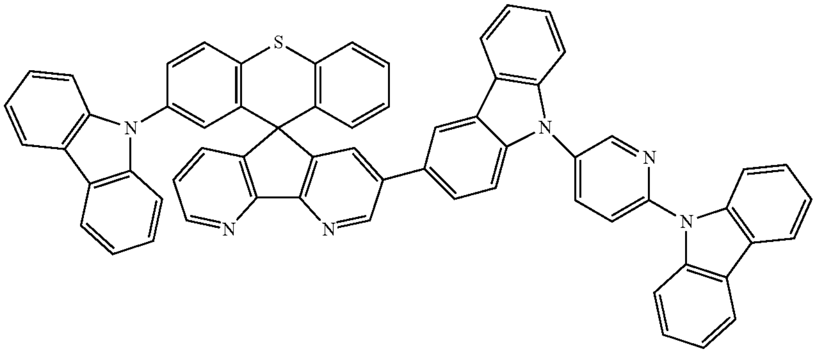
1376
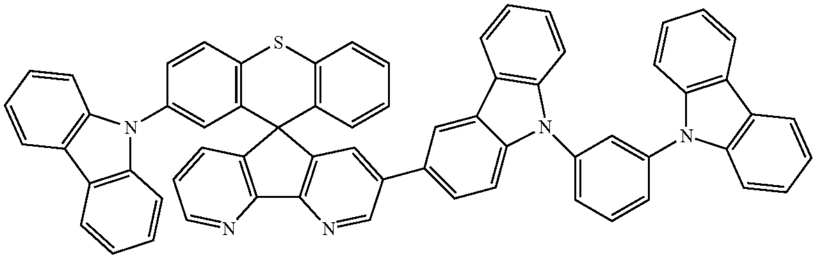
1377
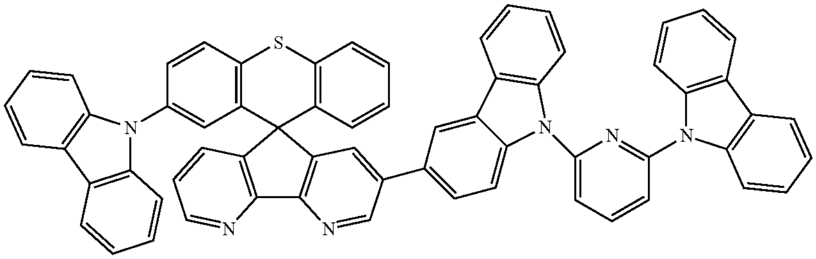
1378
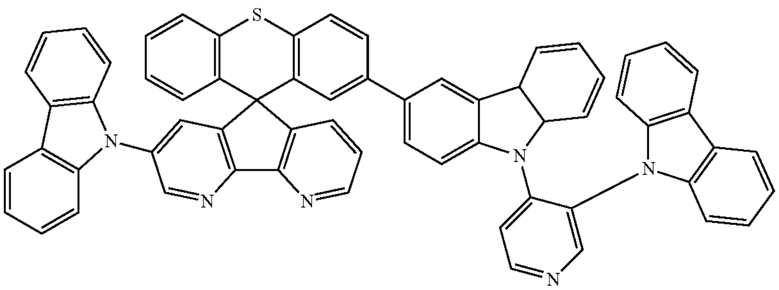
1379
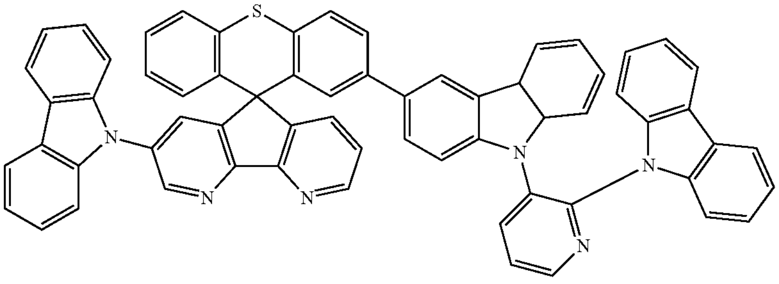

-continued
1380
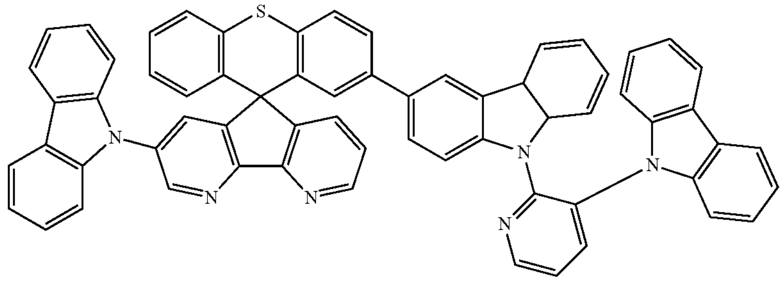
1381
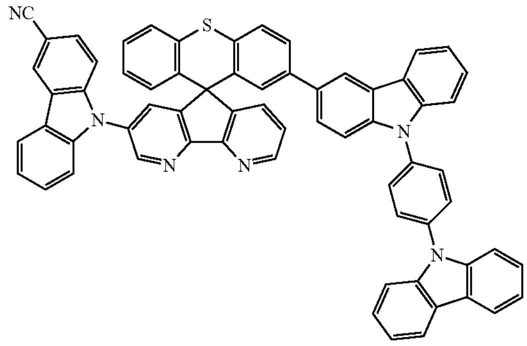
1382
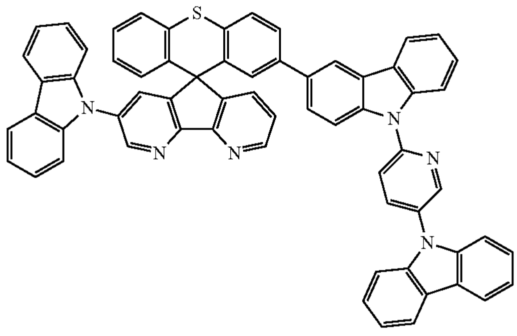
1383
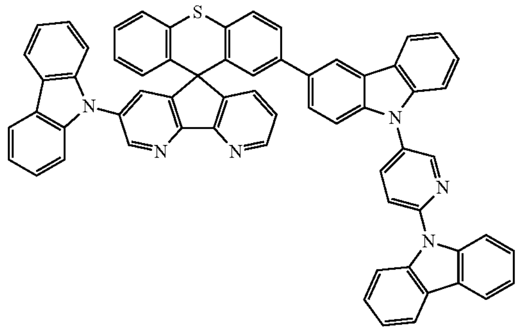
1384
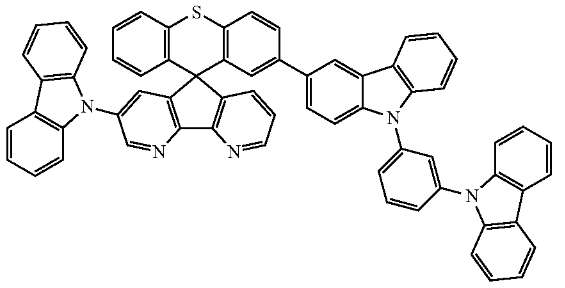
1385
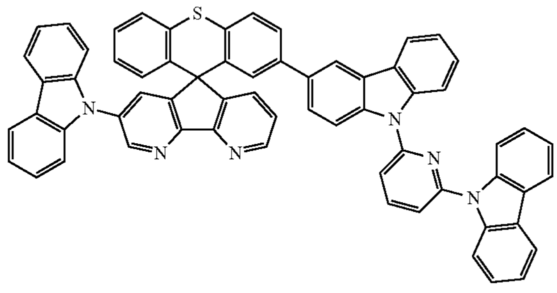
1386
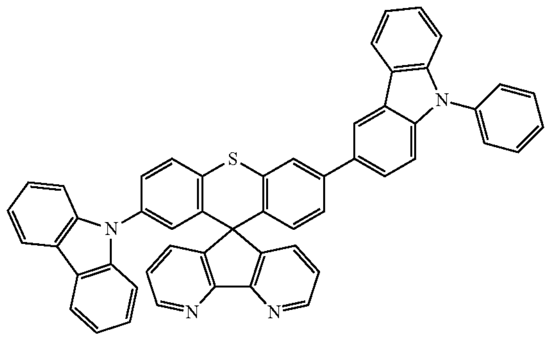

-continued
1387
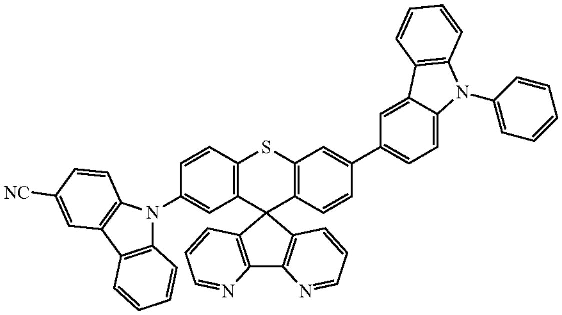
1388
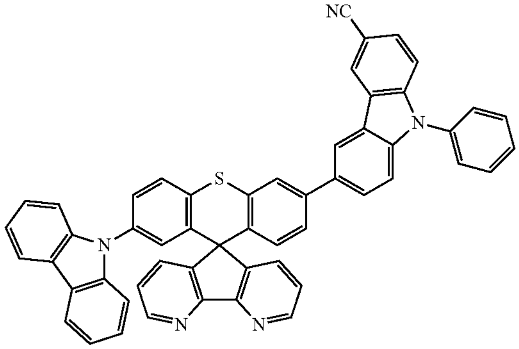
1389
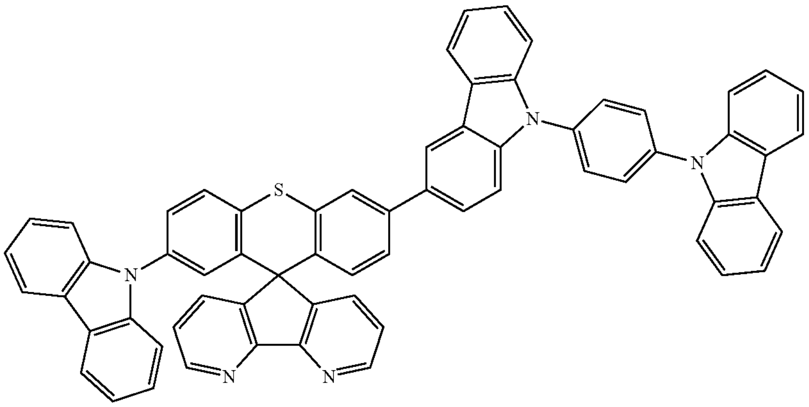
1390
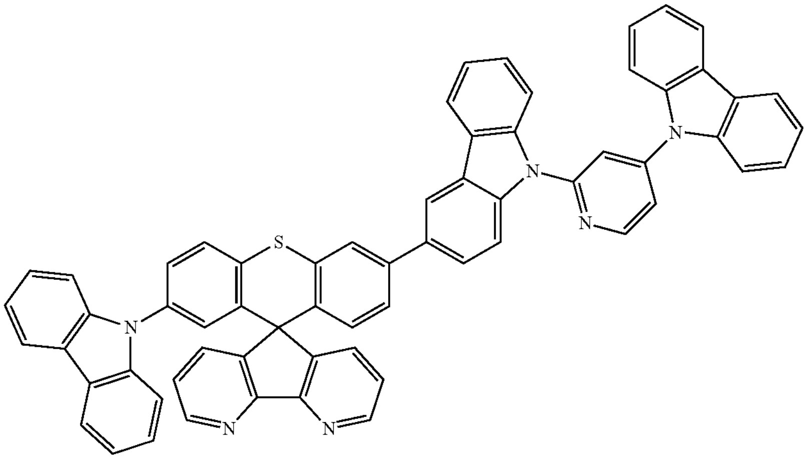

-continued
1391
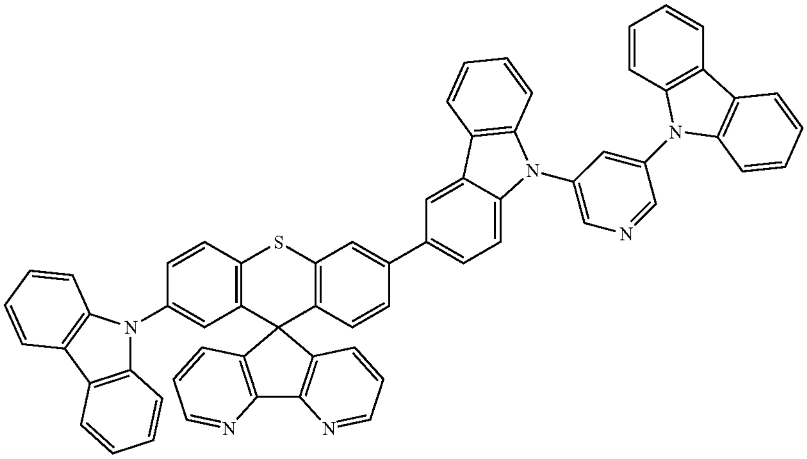
1392
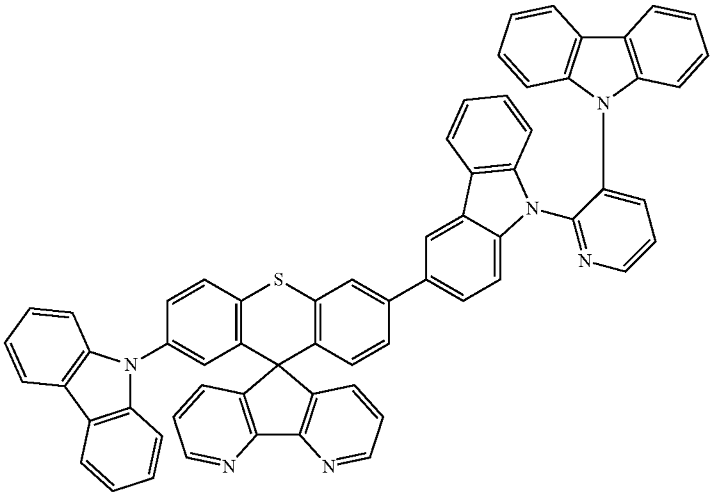
1393
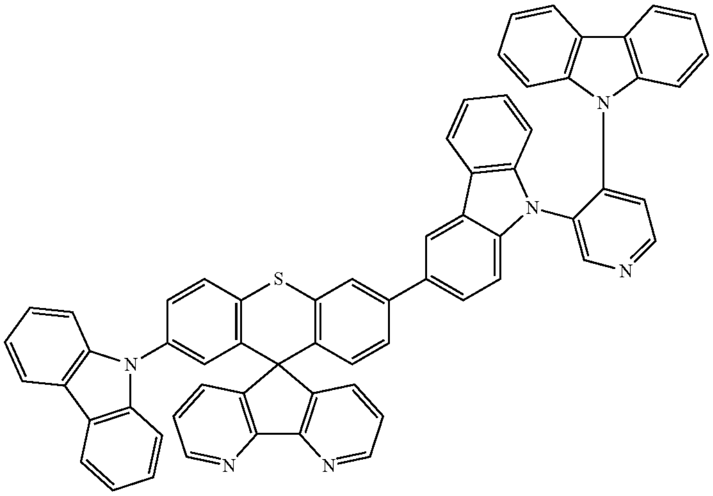

-continued
1394
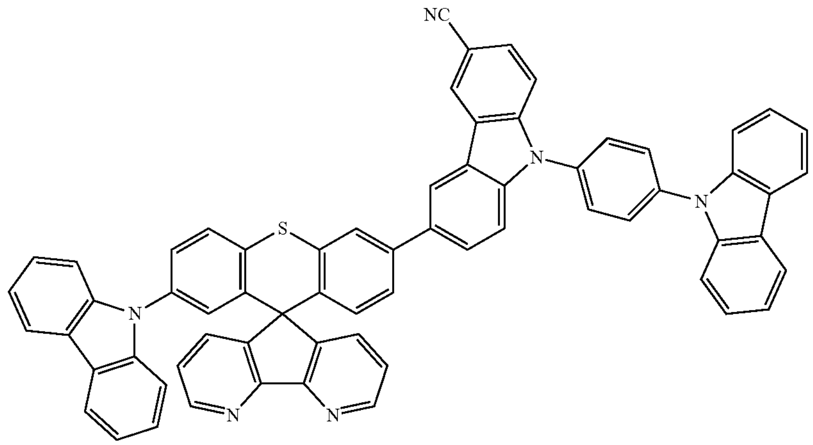
1395
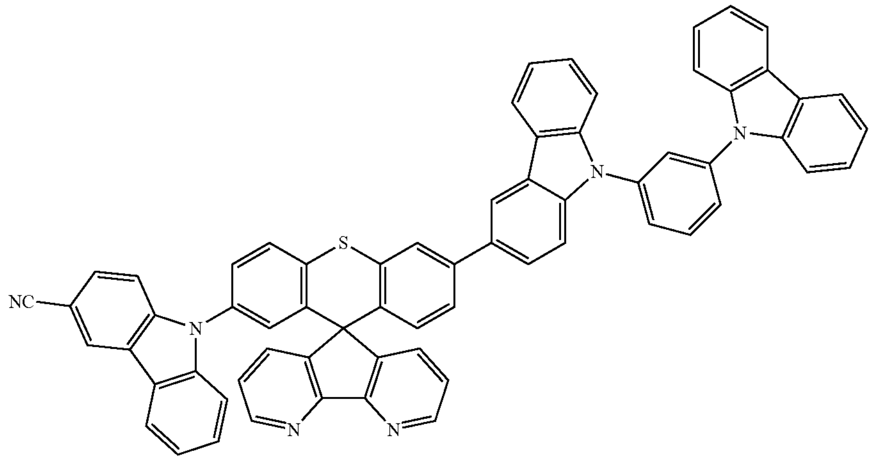
1396
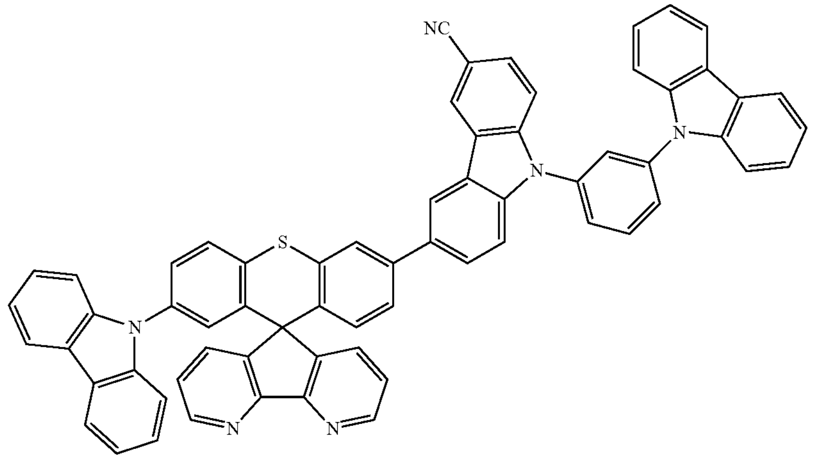

-continued
1397
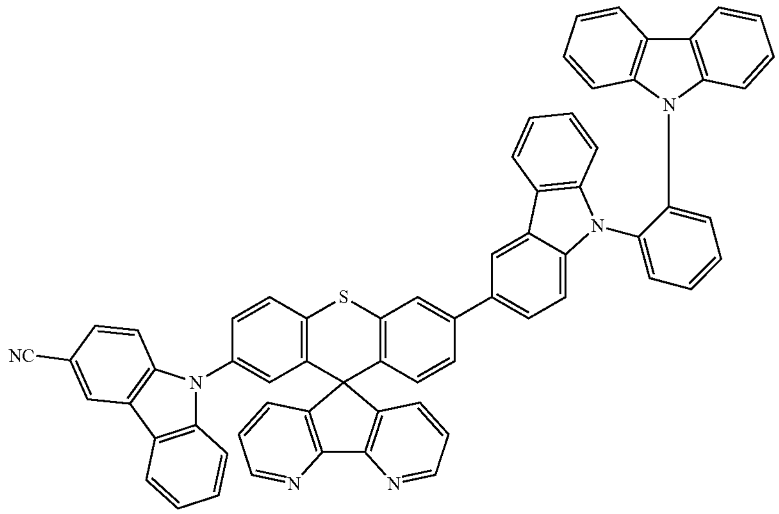
1398
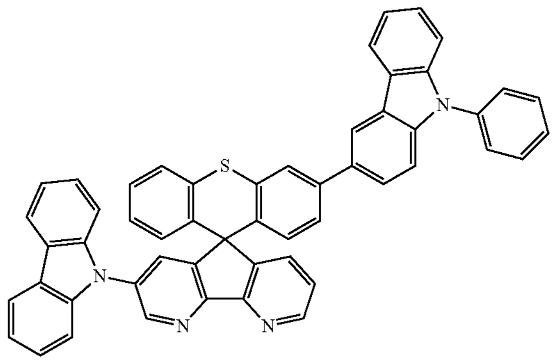
1400
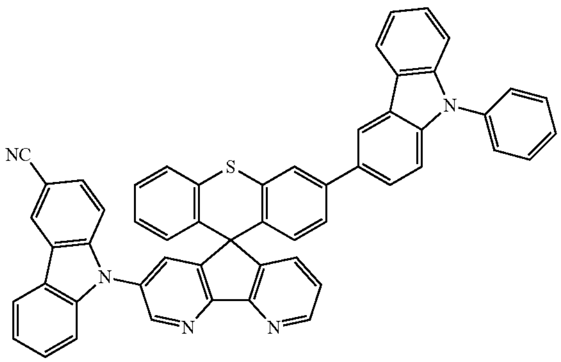
1401
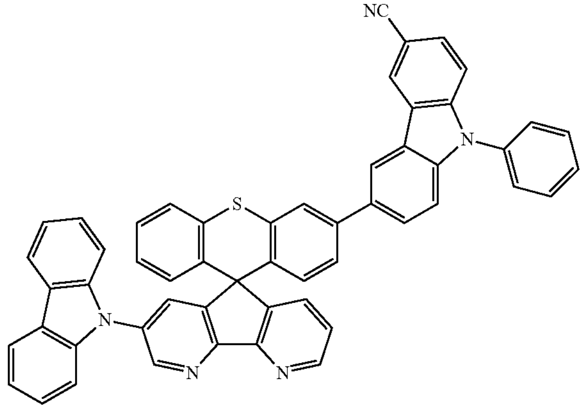

-continued
1402
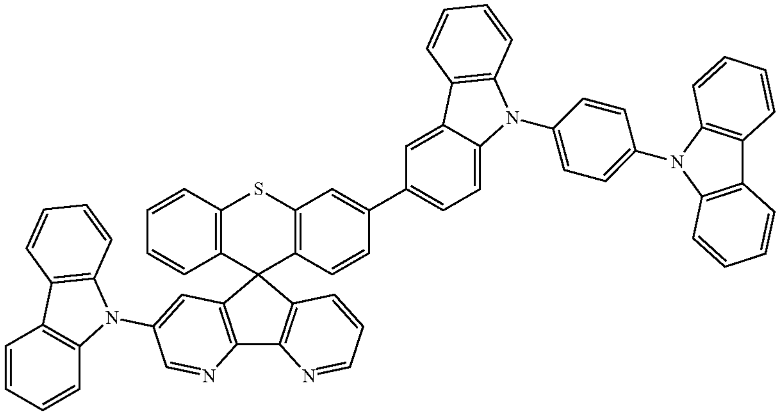
1403
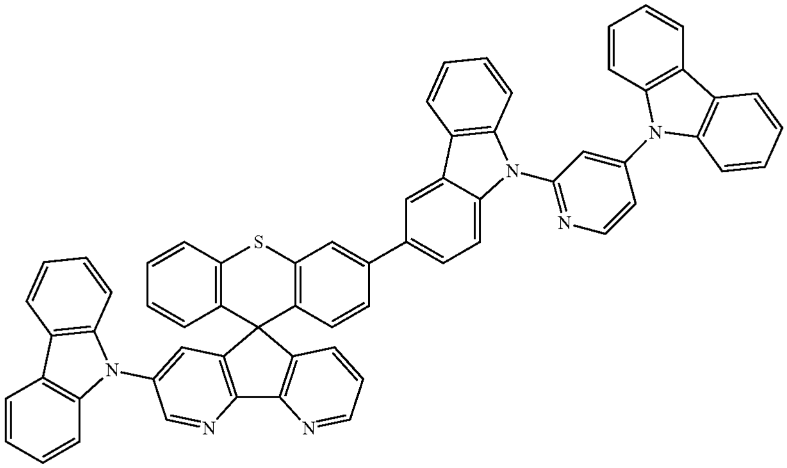
1404
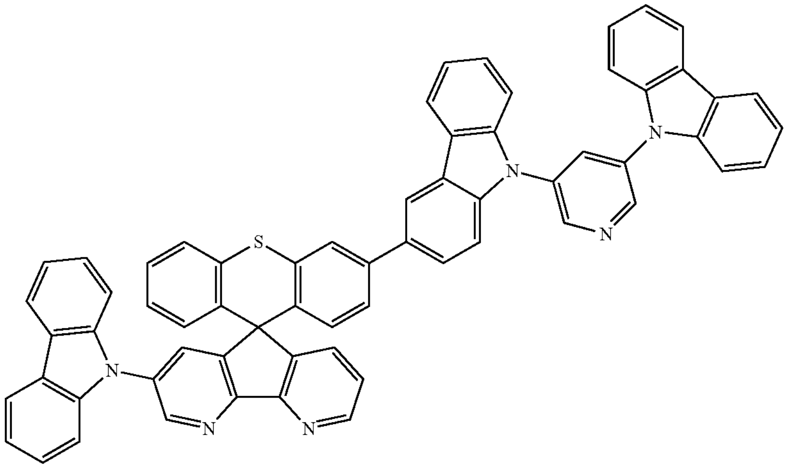

-continued
1405
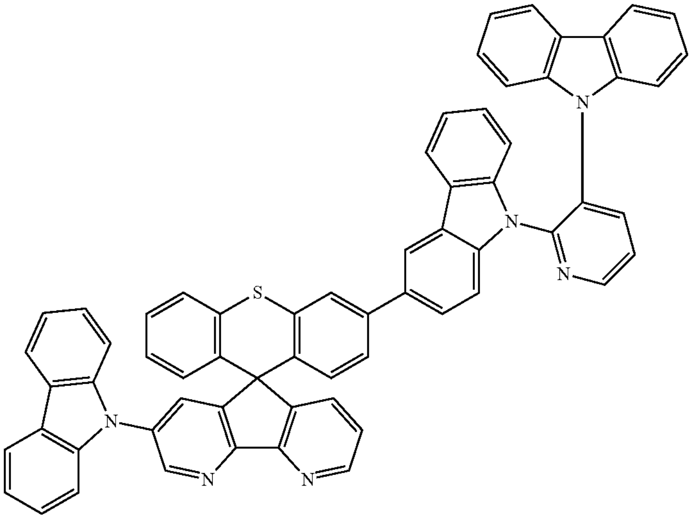
1406
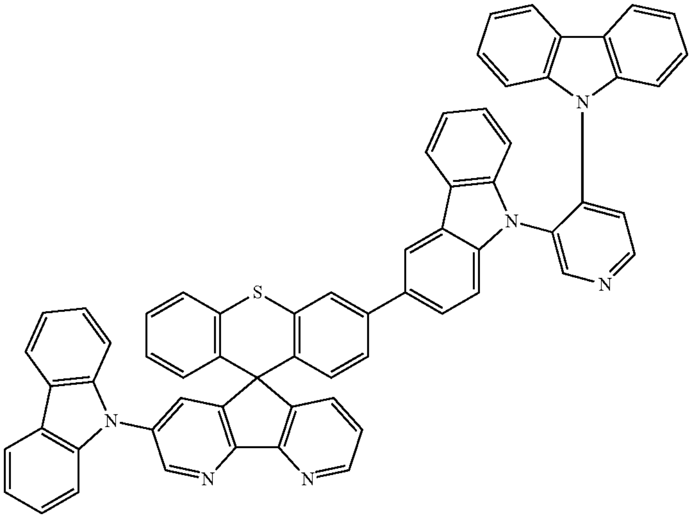
1407
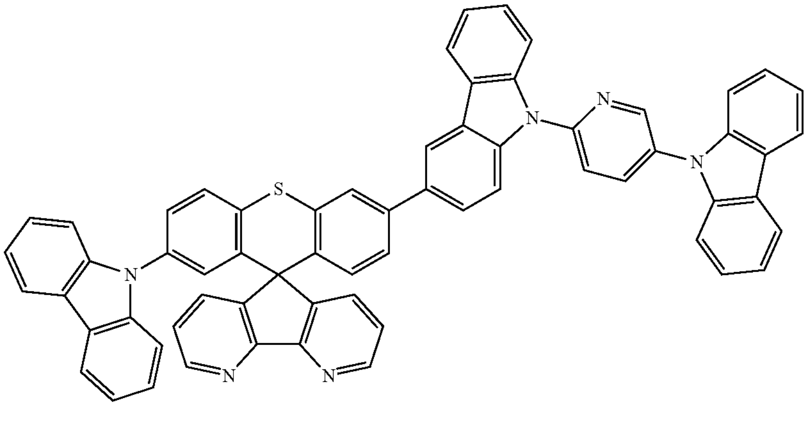

-continued
1408
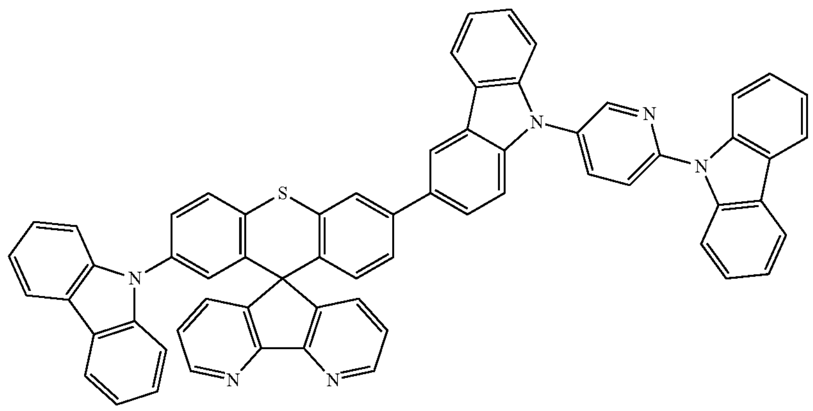
1409
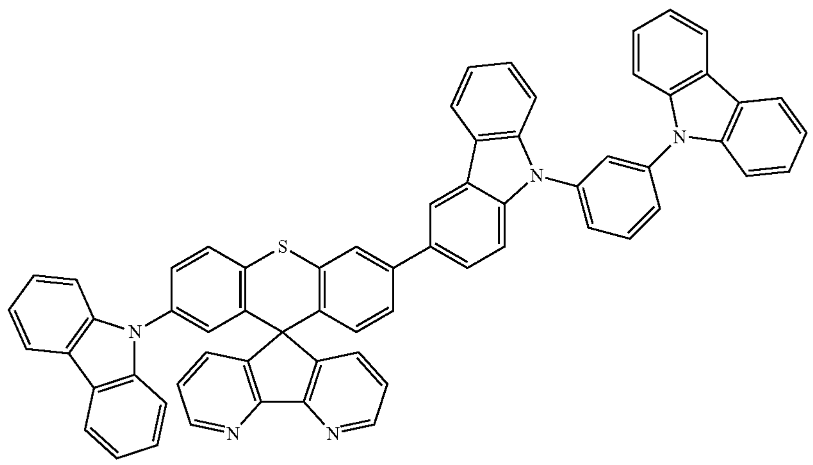
1410
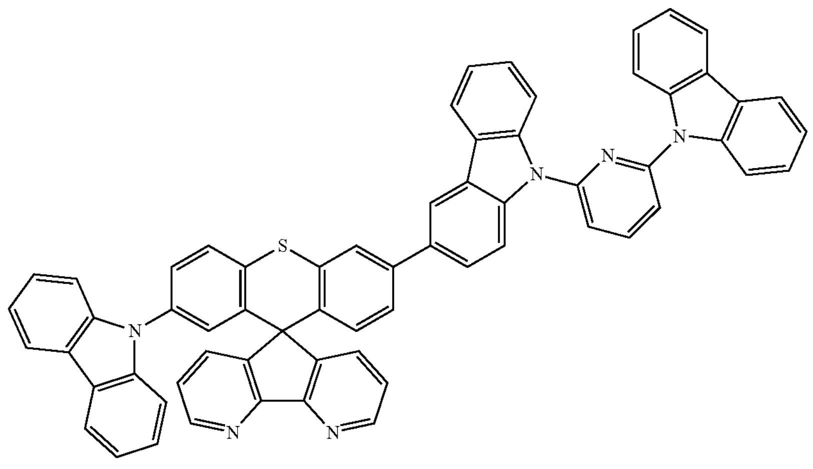

-continued
1411
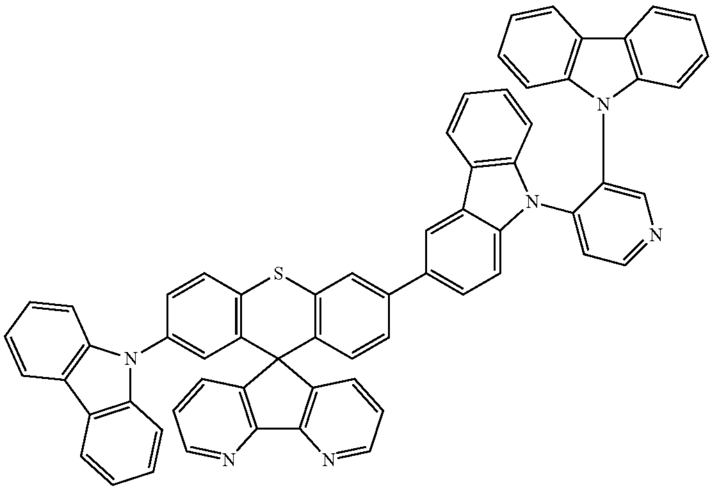
1412
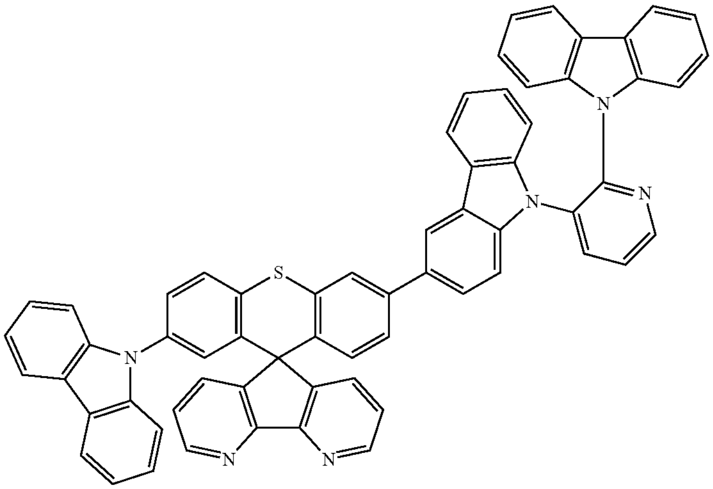
1413
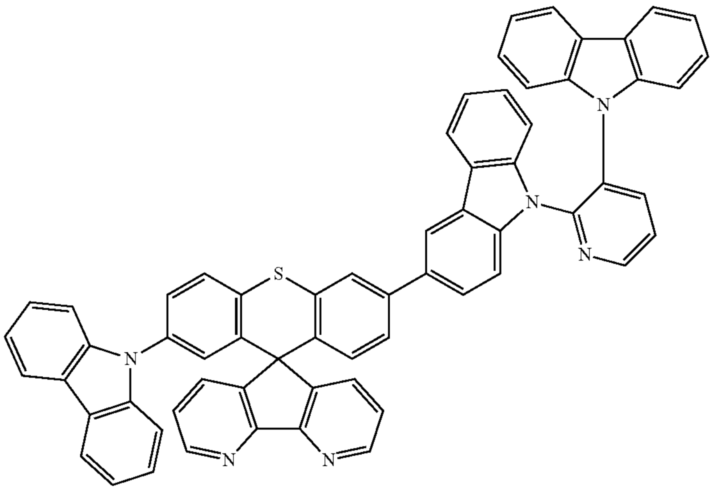

-continued
1414
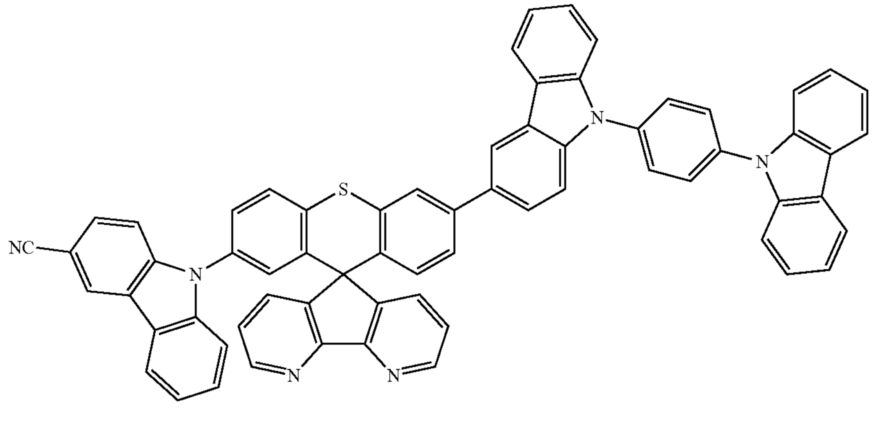
1415
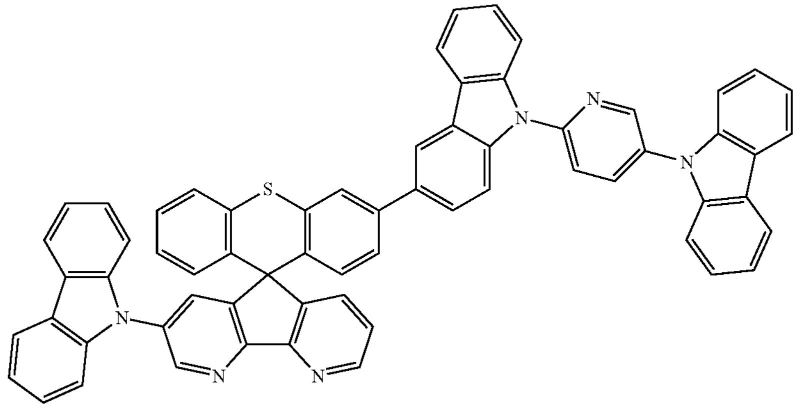
1416
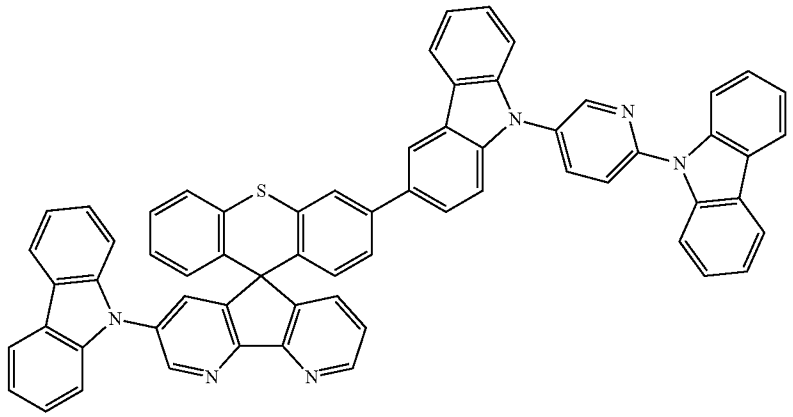

-continued
1417
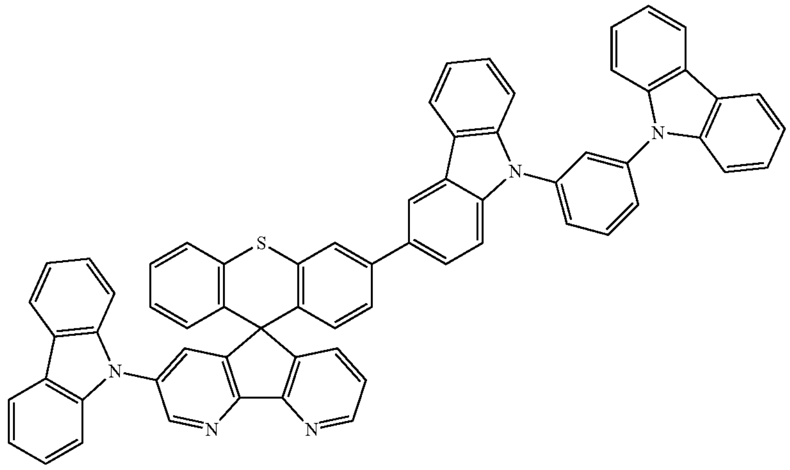
1418
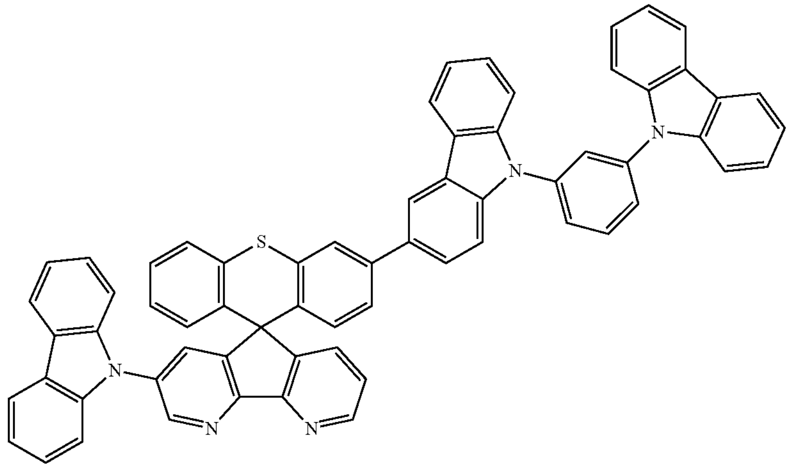
1419
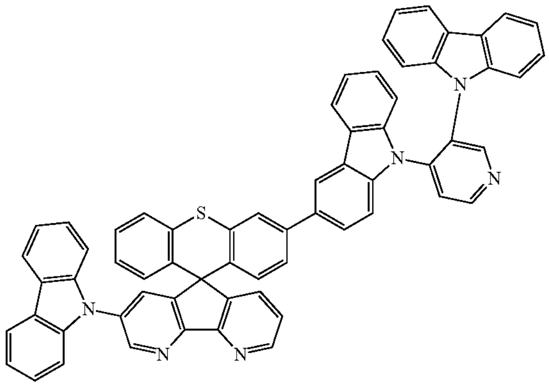
-continued
1420
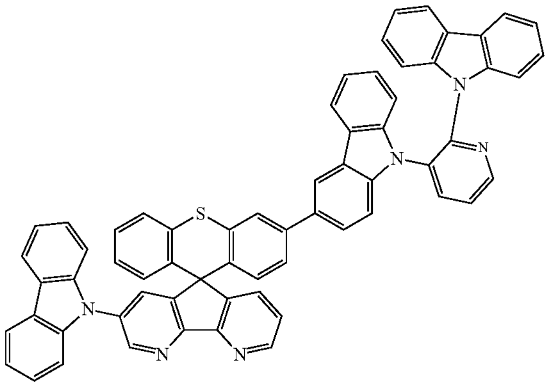

-continued
1421
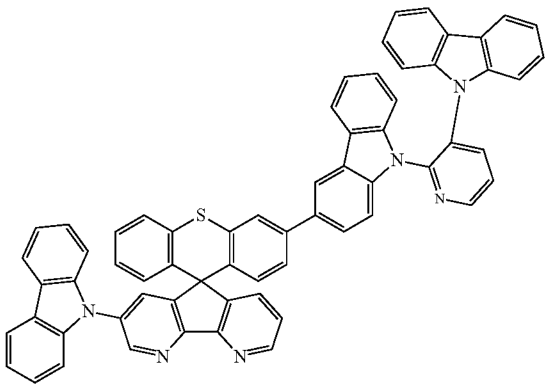
1422
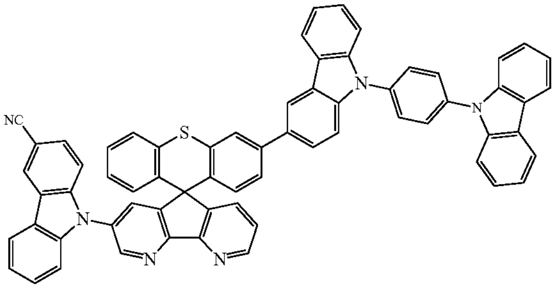
1423
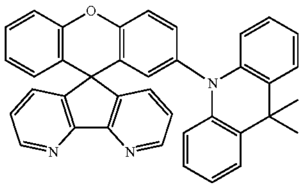
1424
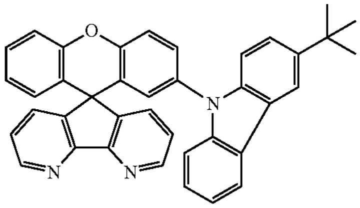
1425
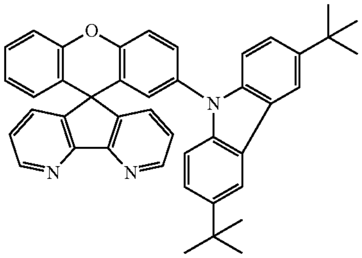
1426
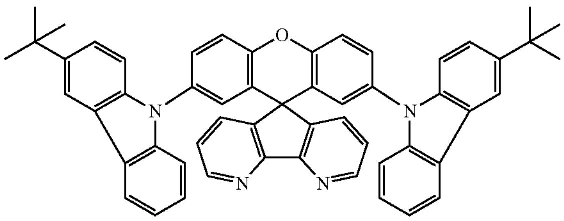
-continued
1427
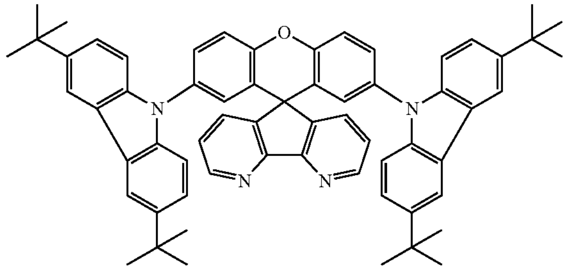
In an embodiment of the present disclosure, the compound of Formula 1 may be one of Formula 23. The compound of the present disclosure may include a diazafluorene core such that a high T1 value is provided. As a result, properties of high emitting efficiency, long lifespan and low driving voltage are provided.
Formula 23
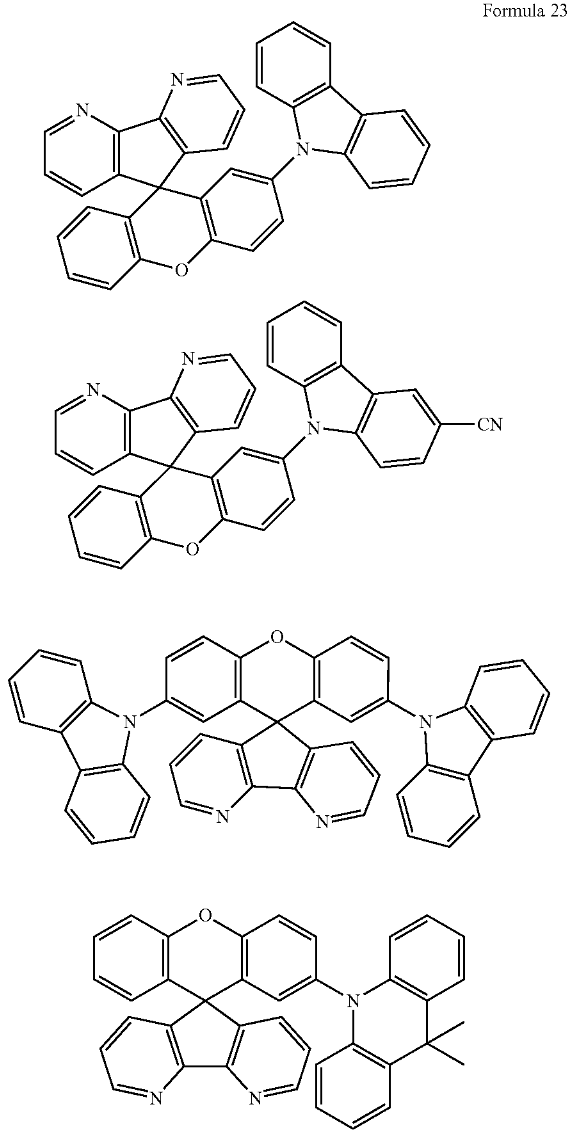

-continued
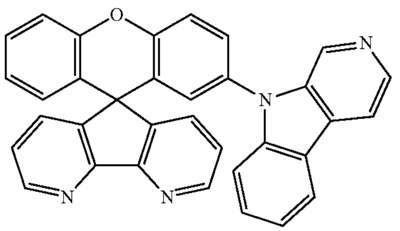
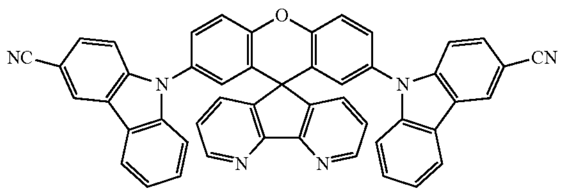
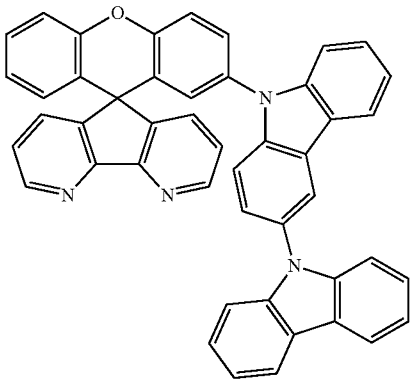
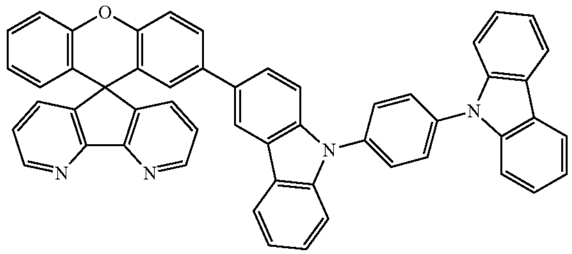
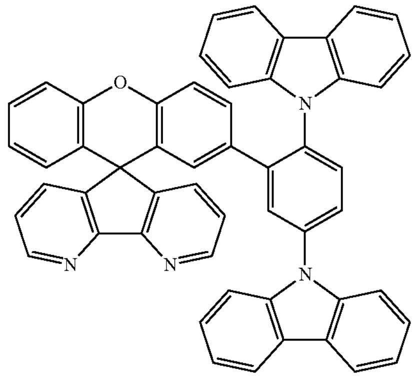
-continued
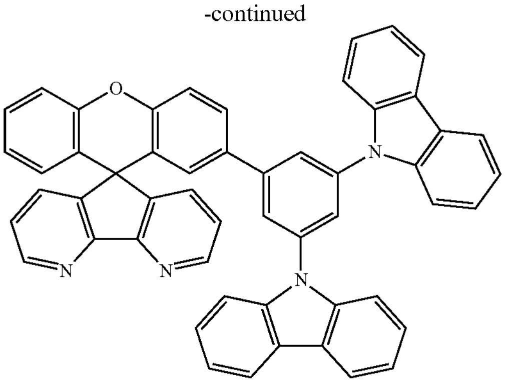
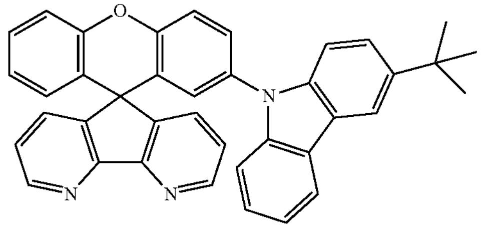
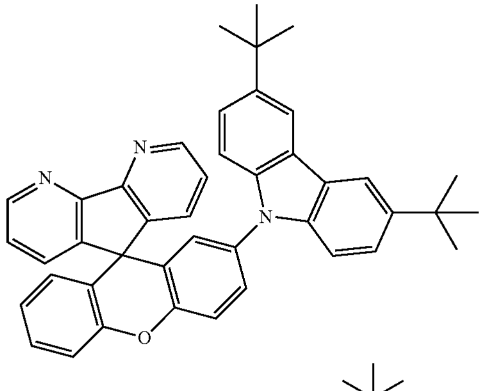
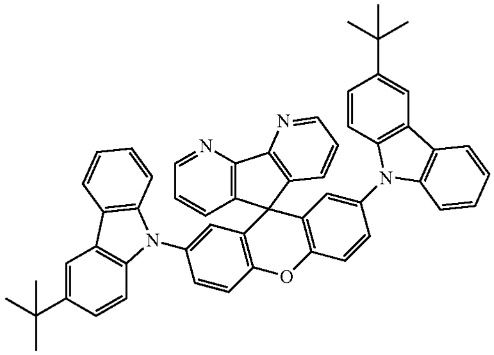
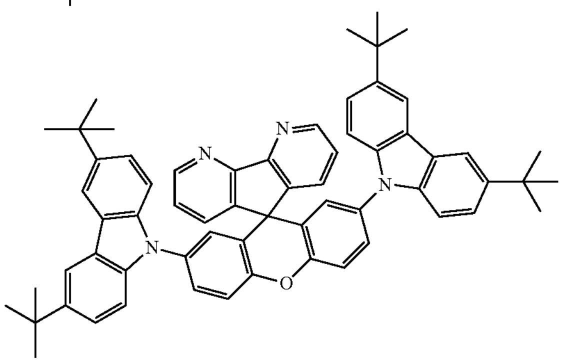
The compound of the present disclosure may be an organic emitting material providing fluorescent emission or delayed fluorescent emission. Accordingly, the compound of the present disclosure may be used for the OLED.

FIG. 1 is a schematic cross-sectional view of an organic light emitting display device according to the present disclosure.

As shown in FIG. 1, the organic light emitting display device 100 includes a substrate 110, a TFT Tr and an OLED (organic light emitting diode) D connected to the TFT Tr.

The substrate 110 may be a glass substrate or a plastic substrate. For example, the substrate 110 may be a polyimide substrate.

A buffer layer 120 is formed on the substrate, and the TFT Tr is formed on the buffer layer 120. The buffer layer 120 may be omitted.

A semiconductor layer 122 is formed on the buffer layer 120. The semiconductor layer 122 may include an oxide semiconductor material or polycrystalline silicon.

When the semiconductor layer 122 includes the oxide semiconductor material, a light-shielding pattern (not shown) may be formed under the semiconductor layer 122. The light to the semiconductor layer 122 is shielded or blocked by the light-shielding pattern such that thermal degradation of the semiconductor layer 122 can be prevented. On the other hand, when the semiconductor layer 122 includes polycrystalline silicon, impurities may be doped into both sides of the semiconductor layer 122.

A gate insulating layer 124 is formed on the semiconductor layer 122. The gate insulating layer 124 may be formed of an inorganic insulating material such as silicon oxide or silicon nitride.

A gate electrode 130, which is formed of a conductive material, e.g., metal, is formed on the gate insulating layer 124 to correspond to a center of the semiconductor layer 122.

In FIG. 1, the gate insulating layer 124 is formed on an entire surface of the substrate 110. Alternatively, the gate insulating layer 124 may be patterned to have the same shape as the gate electrode 130.

An interlayer insulating layer 132, which is formed of an insulating material, is formed on the gate electrode 130. The interlayer insulating layer 132 may be formed of an inorganic insulating material, e.g., silicon oxide or silicon nitride, or an organic insulating material, e.g., benzocyclobutene or photo-acryl.

The interlayer insulating layer 132 includes first and second contact holes 134 and 136 exposing both sides of the semiconductor layer 122. The first and second contact holes 134 and 136 are positioned at both sides of the gate electrode 130 to be spaced apart from the gate electrode 130.

The first and second contact holes 134 and 136 are formed through the gate insulating layer 124. Alternatively, when the gate insulating layer 124 is patterned to have the same shape as the gate electrode 130, the first and second contact holes 134 and 136 is formed only through the interlayer insulating layer 132.

A source electrode 140 and a drain electrode 142, which are formed of a conductive material, e.g., metal, are formed on the interlayer insulating layer 132.

The source electrode 140 and the drain electrode 142 are spaced apart from each other with respect to the gate electrode 130 and respectively contact both sides of the semiconductor layer 122 through the first and second contact holes 134 and 136.

The semiconductor layer 122, the gate electrode 130, the source electrode 140 and the drain electrode 142 constitute the TFT Tr. The TFT Tr serves as a driving element.

In the TFT Tr, the gate electrode 130, the source electrode 140, and the drain electrode 142 are positioned over the semiconductor layer 122. Namely, the TFT Tr has a coplanar structure.

Alternatively, in the TFT Tr, the gate electrode may be positioned under the semiconductor layer, and the source and drain electrodes may be positioned over the semiconductor layer such that the TFT Tr may have an inverted staggered structure. In this instance, the semiconductor layer may include amorphous silicon.

Although not shown, a gate line and a data line cross each other to define a pixel region, and a switching TFT is formed to be connected to the gate and data lines. The switching TFT is connected to the TFT Tr as the driving element.

In addition, a power line, which may be formed to be parallel to and spaced apart from one of the gate and data lines, and a storage capacitor for maintaining the voltage of a gate electrode of the TFT Tr in one frame may be further formed.

A passivation layer 150, which includes a drain contact hole 152 exposing the drain electrode 142 of the TFT Tr, is formed to cover the TFT Tr.

A first electrode 160, which is connected to the drain electrode 142 of the TFT Tr through the drain contact hole 152, is separately formed in each pixel region. The first electrode 160 may be an anode, i.e., a hole injection electrode, and may be formed of a conductive material having a relatively high work function. For example, the first electrode 160 may be formed of a transparent conductive material such as indium-tin-oxide (ITO), indium-zinc-oxide (IZO) or graphene.

When the organic light emitting display device 100 is operated in a top-emission type, a reflection electrode or a reflection layer may be formed under the first electrode 160. For example, the reflection electrode or the reflection layer may be formed of aluminum-palladium-copper (APC) alloy.

A bank layer 166 is formed on the passivation layer 150 to cover an edge of the first electrode 160. Namely, the bank layer 166 is positioned at a boundary of the pixel region and exposes a center of the first electrode 160 in the pixel region.

An organic material layer (emitting layer) 162 is formed on the first electrode 160. The organic material layer 162 may have a single-layered structure of an emitting material layer (EML) including the organic emitting compound. To increase an emitting efficiency of the OLED device, the organic material layer 162 may have a multi-layered structure.

A second electrode 164 is formed over the substrate 110 where the organic emitting layer 162 is formed. The second electrode 164 covers an entire surface of the display area and may be formed of a conductive material having a relatively low work function to serve as a cathode, i.e., an electron injection electrode. For example, the second electrode 164 may be formed of aluminum (Al), magnesium (Mg), Al—Mg alloy (AlMg), gold (Au) or silver (Ag).

The first electrode 160, the organic emitting layer 162 and the second electrode 164 constitute the OLED D.

An encapsulation film 170 is formed on the second electrode 164 to prevent penetration of moisture into the OLED D. The encapsulation film 170 includes a first inorganic insulating layer 172, an organic insulating layer 174 and a second inorganic insulating layer 176 sequentially stacked, but it is not limited thereto. The encapsulation film 170 may be omitted.

A polarization plate (not shown) for reducing an ambient light reflection may be disposed on the encapsulation film 170 of the top-emission type OLED D. For example, the polarization plate may be a circular polarization plate.

In addition, a cover window (not shown) may be attached to the encapsulation film 170 or the polarization plate. In this instance, the substrate 110 and the cover window have a flexible property such that a flexible display device may be provided.

The organic material layer 162 includes the compound of the present disclosure.

The compound of the present disclosure may be included in the emitting material layer, but it is not limited thereto. In addition, the compound of the present disclosure may be used alone or in combination with known compounds when forming the organic material layer 162.

Figure 2:
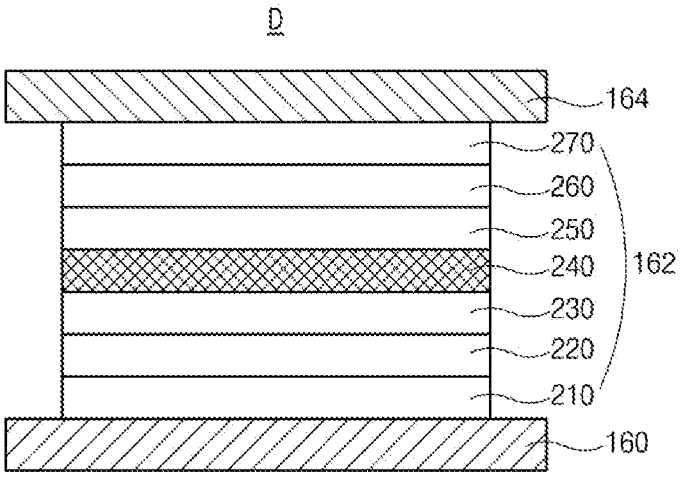
FIG. 2 is a schematic cross-sectional view of an OLED according to a first embodiment of the present disclosure.

FIG. 2 is a schematic cross-sectional view of an OLED according to a first embodiment of the present disclosure.

As shown in FIG. 2, the OLED D includes the first and second electrodes 160 and 164, which face each other, and the organic emitting layer 162 therebetween. The organic emitting layer 162 includes an emitting material layer (EML) 240 between the first and second electrodes 160 and 164, a hole transporting layer (HTL) 220 between the first electrode 160 and the EML 240 and an electron transporting layer (ETL) 260 between the second electrode 164 and the EML 240.

In addition, the organic emitting layer 162 may further include a hole injection layer (HIL) 210 between the first electrode 160 and the HTL 220 and an electron injection layer (EIL) 270 between the second electrode 164 and the ETL 260.

Moreover, the organic emitting layer 162 may further include an electron blocking layer (EBL) 230 between the HTL 220 and the EML 240 and a hole blocking layer (HBL) 250 between the EML 240 and the ETL 260.

For example, each of the hole injection layer 210, the hole transporting layer 220, the electron blocking layer 230, the emitting material layer 240, the hole blocking layer 250, the electron transporting layer 260, the electron injection layer 270 may be formed by a vacuum deposition method, a spin coating method, a casting method, or a Langmuir-Blodgett (LB) method. Each of the above layers may be deposited under the deposition temperature of about 50-500° C., the degree of vacuum of about $10^{-8}$ to $10^{-3}$ torr and the deposition rate of about 0.01 to 100 Å/sec to have a thickness of about 10 Å to 5 μm.

The hole injection layer 210, the hole transporting layer 220, the emitting material layer 240, the electron transporting layer 260 of the organic light emitting device may use the compound of the present disclosure or may use the following materials. In addition, the compounds according to the present disclosure can be used together with known materials.

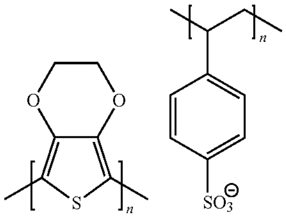

PEDOT:PSS

-continued

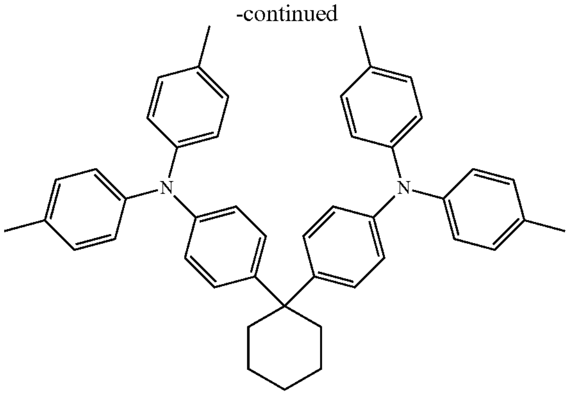

TAPC

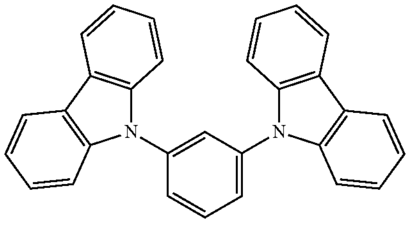

mCP

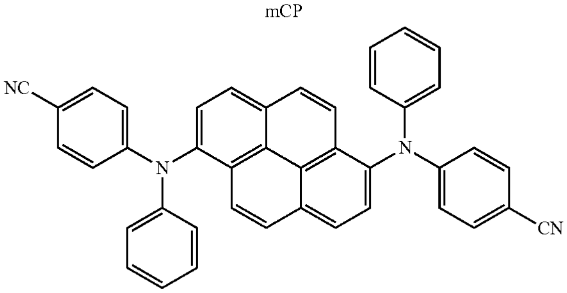

BD01

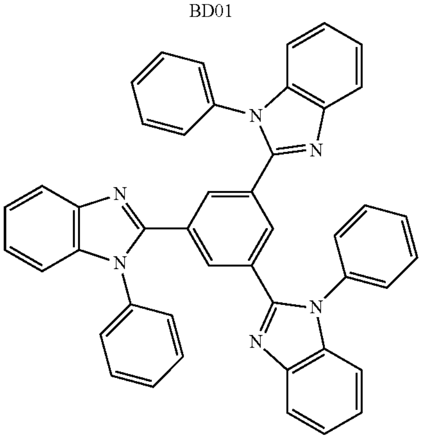

TPBI

At least one of the hole injection layer 210, the hole transporting layer 220, the electron blocking layer 230, the emitting material layer 240, the hole blocking layer 250, the electron transporting layer 260 and the electron injection layer 270 may include the compound of the present disclosure.

For example, the emitting material layer 240 may include the compound of the present disclosure. The emitting material layer 240 may include only the compound. Alternatively, the emitting material layer 240 may further include a known compound as a host or a dopant. In this case, the compound of the present disclosure is used as a dopant or a host.

For example, when the compound of the present disclosure is used as a dopant, the emitting material layer 240 further includes a host. In this instance, the excited singlet energy level of the host is higher (greater) than that of the compound of the present disclosure, or the excited triplet energy level of the host is higher than that of the compound of the present disclosure. In addition, the compound of the present disclosure may have a weight % of about 1 to 40 with respect to the host.

In the emitting material layer 240, the compound of the present disclosure may be used as a first dopant (assistance dopant), and a second dopant may be further included. In this case, the emitting material layer 240 may provide dark blue emission.

On the other hand, in the emitting material layer 240, the compound of the present disclosure may be used as a host, and a dopant may be further included. The dopant has a weight % of about 1 to 40 with respect to the compound of the present disclosure as the host. In this case, the dopant may be at least one of a delayed fluorescent dopant (delayed fluorescent compound), a fluorescent dopant (fluorescent compound) and a phosphorescent dopant (phosphorescent compound).

For example, when the emitting material layer 240 includes a host, which is the compound of the present disclosure, and a delayed fluorescent dopant, a difference ($|HOMO_{Host}-HOMO_{Dopant}|$) between the HOMO level ($HOMO_{Host}$) of the host and the HOMO level ($HOMO_{Dopant}$) of the delayed fluorescent dopant or a difference ($|LUMO_{Host}-LUMO_{Dopant}|$) between the LUMO level ($LUMO_{Host}$) of the host and the LUMO level ($LUMO_{Dopant}$) of the dopant is 0.5 eV. As a result, the charge transfer efficiency from the host to the delayed fluorescent dopant is improved.

The energy level of triplet state of the delayed fluorescent dopant is smaller (lower) than the energy level of triplet state of the host, and a difference between the energy level of singlet state of the delayed fluorescent dopant and the energy level of triplet state of the delayed fluorescent dopant is equal to less than 0.3 eV. ($\Delta E_{ST}$50.3 eV) As the difference "$\Delta E_{ST}$" is smaller, the emitting efficiency is higher. In addition, even if the difference "$\Delta E_{ST}$" between the energy level of singlet state of the delayed fluorescent dopant and the energy level of triplet state of the delayed fluorescent dopant is about 0.3 eV, which is relatively large, the excitons in the singlet state and the excitons in the triplet state can be transited into the intermediate state.

On the other hand, the emitting material layer 240 may include the compound of the present disclosure as a host, a delayed fluorescent dopant (first dopant) and a fluorescent dopant (second dopant). The sum of the first and second dopants may be about 1 to 40 wt % with respect to the host.

In this case, the energy level of singlet state of the first dopant is greater than that of the second dopant. In addition, the energy level of triplet state of the first dopant is smaller than that of the host and greater than that of the second dopant.

When the emitting material layer 240 includes the host and the first and second dopant, the emission efficiency and the color sense may be further improved. Namely, since the energy transfer occurs from the host to the first dopant, the singlet energy and triplet energy of the first dopant are transferred to the second dopant, the light emission occurs in the second dopant. As a result, the quantum efficiency of the organic light emitting device D is increased, and the full width at half maximum (FWHM) is narrowed.

The first dopant with delayed fluorescence property has high quantum efficiency. However, since the first dopant has wide FWHM, the first dopant provides poor color purity. The second dopant with fluorescence property has narrow FWHM and an advantage in the color purity. However, the triplet exciton of the second dopant is not involved in the light emission such that the second dopant has low quantum efficiency.

However, when the emitting material layer 240 includes the first dopant, which is a delayed fluorescent material, and the second dopant, which is a fluorescent material, there are advantages in both emitting efficiency and color purity.

[Synthesis]

In one embodiment of the present disclosure, the intermediate SubC may be synthesized as follows, but it is not limited thereto.

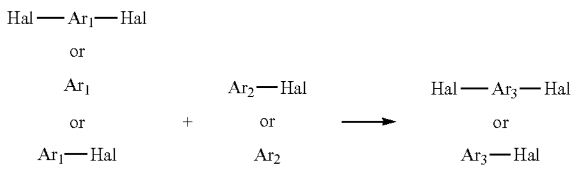

<subA> <subB> <subC>

Synthesis of the Compound "subC1"

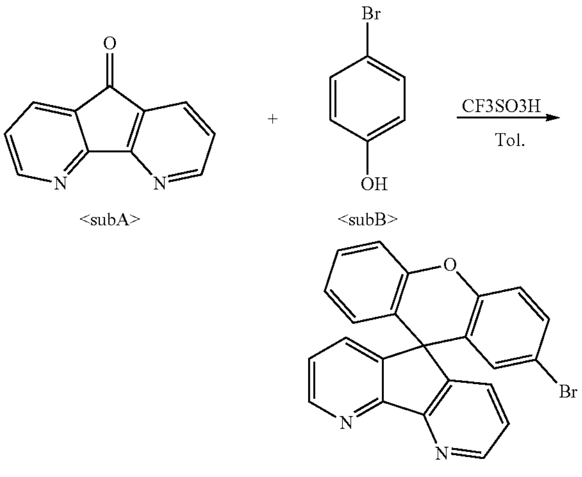

<subA> <subB>

<subC1>

In the rounded-bottom flask, 4,5-diazafluorenone (subA, 5 g), 4-Bromophenol (subB, 7.3 g) and trifluoromethanesulfonic acid (5.5 g) were dissolved in toluene (50 ml), and the mixture was refluxed and stirred. The reaction was confirmed by thin layer chromatography (TLC), and the reaction was terminated after adding water. The organic layer was extracted with methylene chloride (MC) was filtered under reduced pressure. The column purification process and the recrystallization process were performed to the mixture the compound "subC1" (2'-bromospiro[cyclopenta[1,2-b:5,4-b']dipyridine-5,9'-xanthene], 6.4 g, 50% yield) was obtained.

Compounds "SubC2" to "SubC10" were synthesized by varying starting materials "SubA" and "SubB" as shown in Table 1 with synthesis of the compound "SubC". (Y=yield)

TABLE 1
| | Sub A | Sub B | Sub C | Y (%) |
|---|---|---|---|---|
| Sub C1 | 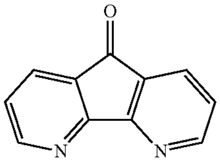 [SMILES: O=C1c2cccnc2-c2ncccc21] | 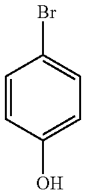 | 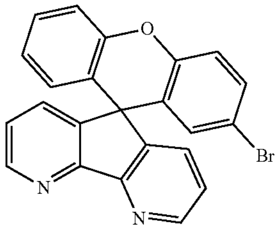 [SMILES: Brc1ccc2c(c1)C1(c3ccccc3O2)c2cccnc2-c2ncccc21] | 50 |
| Sub C2 | 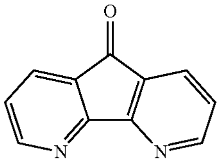 [SMILES: O=C1c2cccnc2-c2ncccc21] | 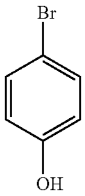 | 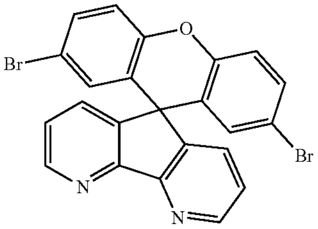 [SMILES: Brc1ccc2c(c1)C1(c3cc(Br)ccc3O2)c2cccnc2-c2ncccc21] | 52 |
| Sub C3 | 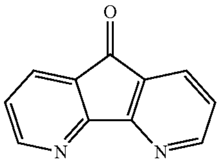 | 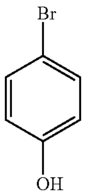 | 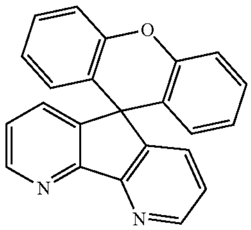 [SMILES: c1ccc2c(c1)Oc1ccccc1C21c2cccnc2-c2ncccc21] | 55 |
| Sub C4 | 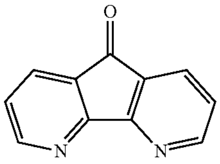 [SMILES: O=C1c2cccnc2-c2ncccc21] | 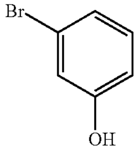 | 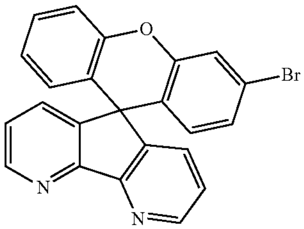 [SMILES: Brc1ccc2c(c1)Oc1ccccc1C21c2cccnc2-c2ncccc21] | 49 |
| Sub C5 | 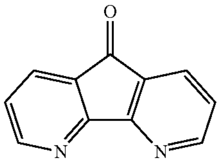 [SMILES: O=C1c2cccnc2-c2ncccc21] | 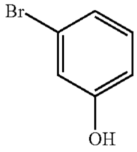 | 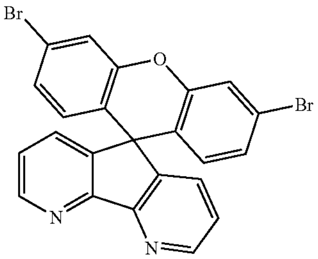 [SMILES: Brc1ccc2c(c1)Oc1cc(Br)ccc1C21c2cccnc2-c2ncccc21] | 44 |
| Sub C6 | 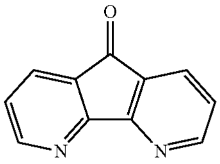 [SMILES: O=C1c2cccnc2-c2ncccc21] | 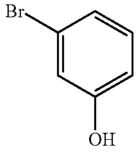 | 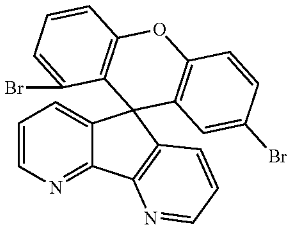 [SMILES: Brc1ccc2c(c1)C1(c3cccnc3-c3ncccc31)c1c(Br)cccc1O2] | 60 |

TABLE 1-continued

| | Sub A | Sub B | Sub C | Y (%) |
|---|---|---|---|---|
| Sub C7 | 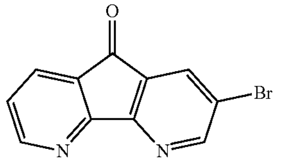 [SMILES: O=C1c2cccnc2-c2ncc(Br)cc21] | 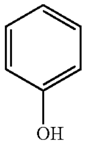 | 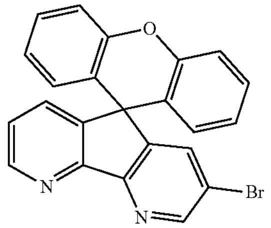 [SMILES: Brc1cnc2c(c1)C1(c3ccccc3Oc3ccccc31)c1cccnc1-2] | 48 |
| Sub C8 | 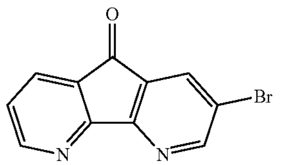 [SMILES: O=C1c2cccnc2-c2ncc(Br)cc21] | 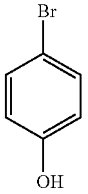 | 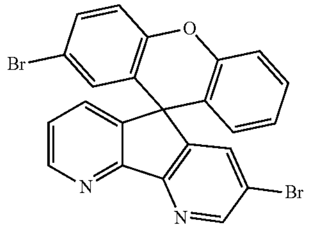 [SMILES: Brc1ccc2c(c1)C1(c3ccccc3O2)c2cccnc2-c2ncc(Br)cc21] | 54 |
| Sub C9 | 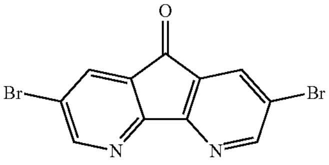 [SMILES: O=C1c2cc(Br)cnc2-c2ncc(Br)cc21] | 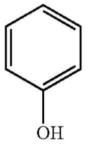 | 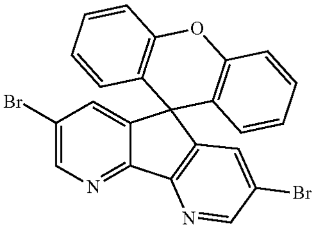 [SMILES: Brc1cnc2c(c1)C1(c3ccccc3Oc3ccccc31)c1cc(Br)cnc1-2] | 45 |
| Sub C10 | 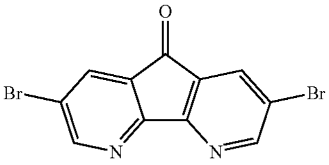 [SMILES: O=C1c2cc(Br)cnc2-c2ncc(Br)cc21] | 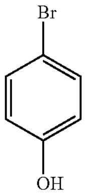 | 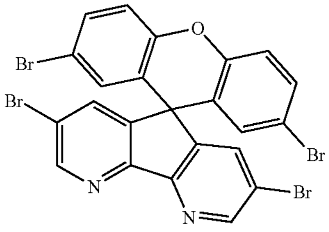 [SMILES: Brc1ccc2c(c1)C1(c3cc(Br)ccc3O2)c2cc(Br)cnc2-c2ncc(Br)cc21] | 43 |

The compounds of the present disclosure may be synthesized as follows, but it is not limited thereto.

Hal—Ar3—Hal or Ar3—Hal <subC> + HN—Ar4 or (HO)2B—Ar3 <subD> Ar3—Ar4 <Product A>

Synthesis of the Compound "A"

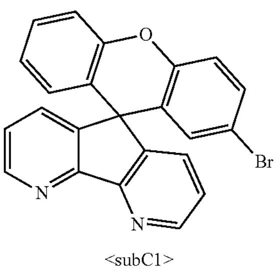

<subC1>

+

-continued

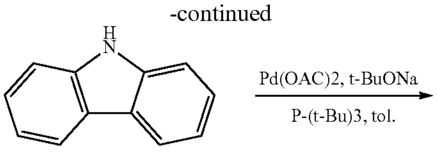

<subD>

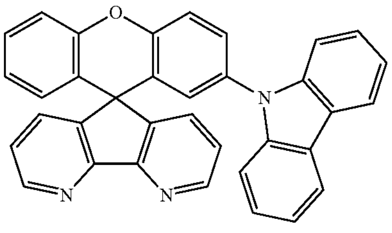

<Product A>

In the rounded-bottom flask, 2'-bromospiro[cyclopenta[1,2-b:5,4-b']dipyridine-5,9'-xanthene] (SubC1, 5 g), carbazole (SubD, 3 g), t-BuONa (2.3 g) and Pd(OAc)$_2$ (0.2 g) were dissolved in toluene (50 ml), and the mixture was refluxed and stirred. The reaction was confirmed by thin layer chromatography (TLC), and the reaction was terminated after adding water. The organic layer was extracted with methylene chloride (MC) and was filtered under reduced pressure. The column purification process and the recrystallization process were performed to the mixture such that the compound "A" (2'-(9H-carbazol-9-yl)-[cyclopenta[1,2-b:5,4-b']dipyridine-5,9'-xanthene], 6.4 g, 54% yield) was obtained.

Molecular Weight: 499.56; m/z: 499.17 (100.0%), 500.17 (39.2%), 501.18 (7.1%)

Synthesis of the Compound "B"

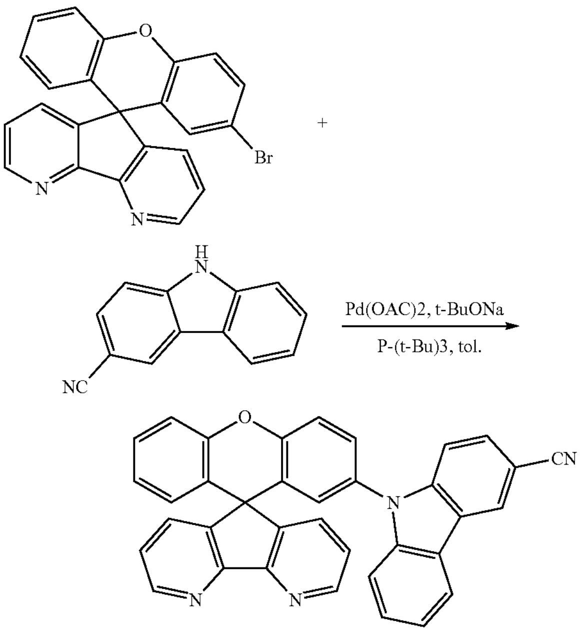

In compound "B" was obtained by the above reaction with the same synthesis conditions of the compound "A." (59% yield)

Molecular Weight: 524.57; m/z: 524.16 (100.0%), 525.17 (39.2%), 526.17 (7.7%), 525.16 (1.5%), 527.17 (1.1%)

Synthesis of the Compound "C"

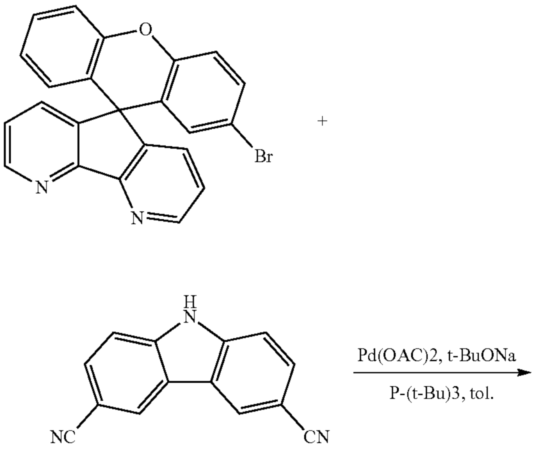

-continued

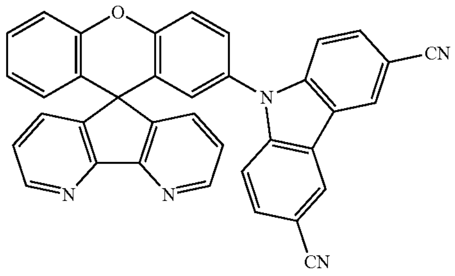

In compound "C" was obtained by the above reaction with the same synthesis conditions of the compound "A." (62% yield)

Molecular Weight: 549.58; m/z: 549.16 (100.0%), 550.16 (41.9%), 551.17 (7.9%), 552.17 (1.1%)

Synthesis of the Compound "D"

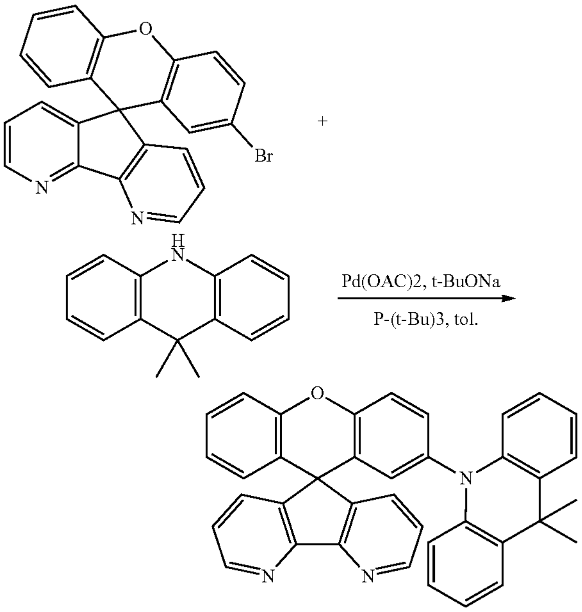

? indicates text missing or illegible when filed

In compound "D" was obtained by the above reaction with the same synthesis conditions of the compound "A." (62% yield)

Molecular Weight: 541.64; m/z: 541.22 (100.0%), 542.22 (41.4%), 543.22 (8.9%), 542.21 (1.1%), 544.23 (1.1%)

Synthesis of the Compound "E"

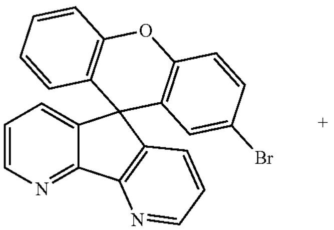

-continued

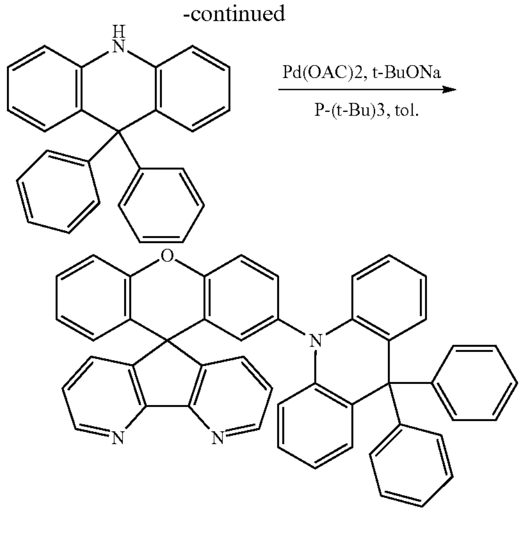

In compound “E” was obtained by the above reaction with the same synthesis conditions of the compound “A.” (60% yield)

Molecular Weight: 665.78; m/z: 665.25 (100.0%), 666.25 (52.3%), 667.25 (14.0%), 668.26 (2.2%), 666.24 (1.1%)

Synthesis of the Compound “F”

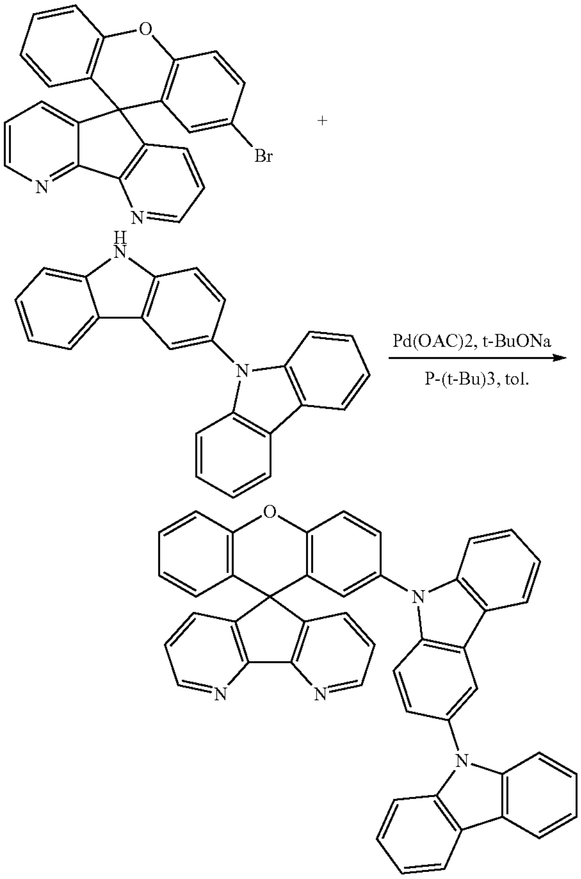

In compound “F” was obtained by the above reaction with the same synthesis conditions of the compound “A.” (65% yield)

Molecular Weight: 664.75; m/z: 664.23 (100.0%), 665.23 (51.2%), 666.23 (13.6%), 667.24 (2.1%), 665.22 (1.5%)

Synthesis of the Compound “G”

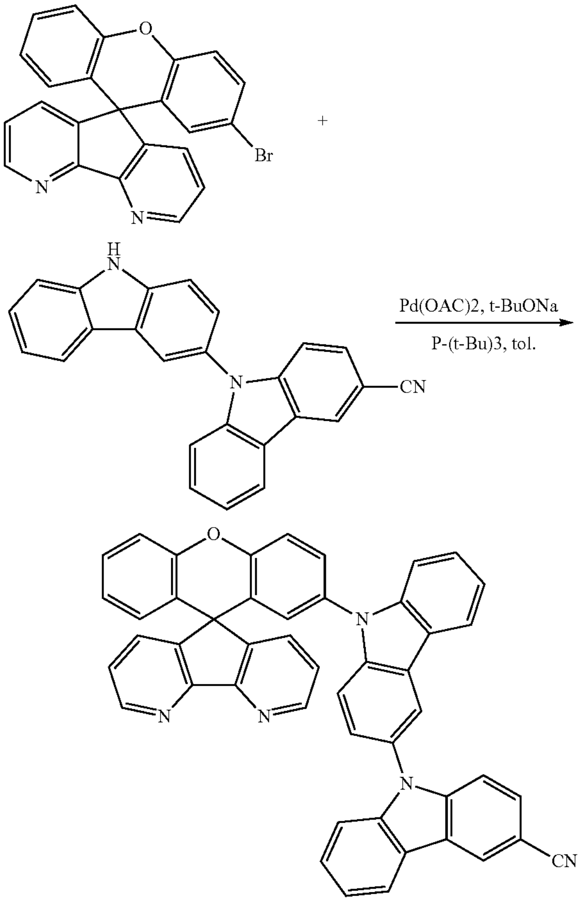

In compound “G” was obtained by the above reaction with the same synthesis conditions of the compound “A.” (66% yield)

Molecular Weight: 689.76; m/z: 689.22 (100.0%), 690.22 (53.8%), 691.23 (13.6%), 692.23 (2.6%)

Synthesis of the Compound “H”

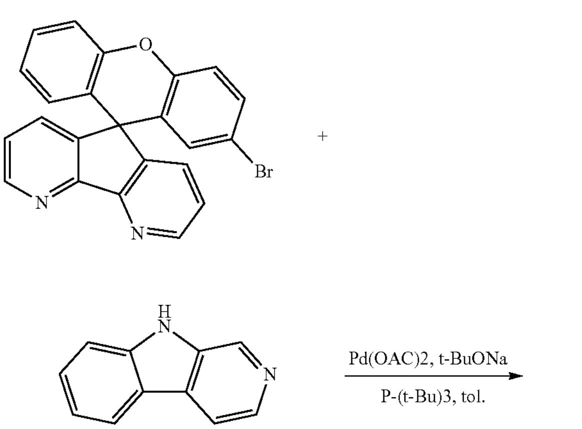

-continued

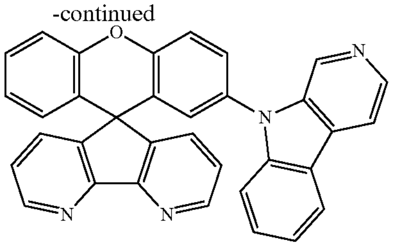

In compound "H" was obtained by the above reaction with the same synthesis conditions of the compound "A." (66% yield)

Molecular Weight: 500.55; m/z: 500.16 (100.0%), 501.17 (37.0%), 502.17 (6.9%), 501.16 (1.5%)

Synthesis of the Compound "I"

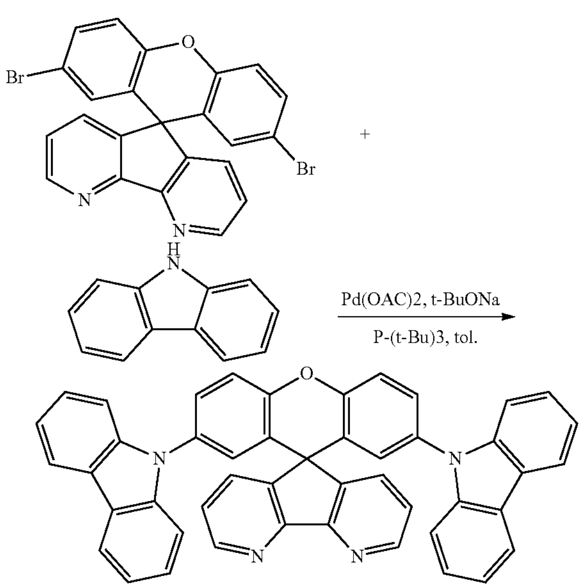

(?) indicates text missing or illegible when filed

In compound "I" was obtained by the above reaction with the same synthesis conditions of the compound "A." (62% yield)

m/z: 918.32 (100.0%), 919.32 (64.3%), 920.32 (21.0%), 921.33 (4.2%), 919.31 (1.5%)

Synthesis of the Compound "J"

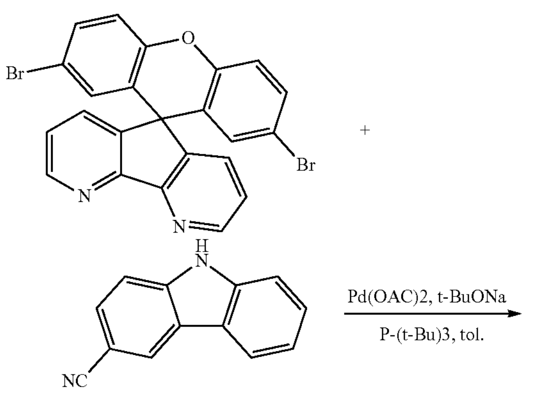

-continued

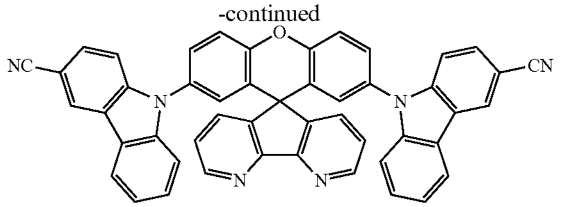

In compound "J" was obtained by the above reaction with the same synthesis conditions of the compound "A." (63% yield)

Molecular Weight: 714.77; m/z: 714.22 (100.0%), 715.22 (53.3%), 716.22 (15.2%), 717.23 (2.4%), 715.21 (2.2%)

Synthesis of the Compound "K"

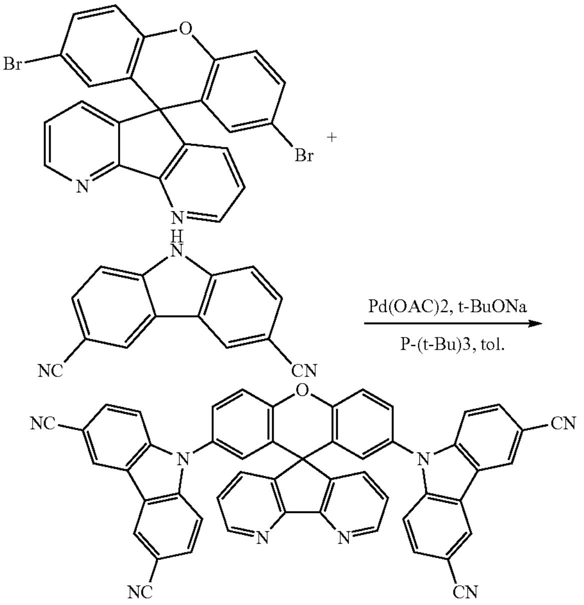

In compound "K" was obtained by the above reaction with the same synthesis conditions of the compound "A." (59% yield)

Molecular Weight: 764.79; m/z: 764.21 (100.0%), 765.21 (55.5%), 766.21 (16.8%), 765.20 (3.0%), 767.22 (2.7%)

Synthesis of the Compound "L"

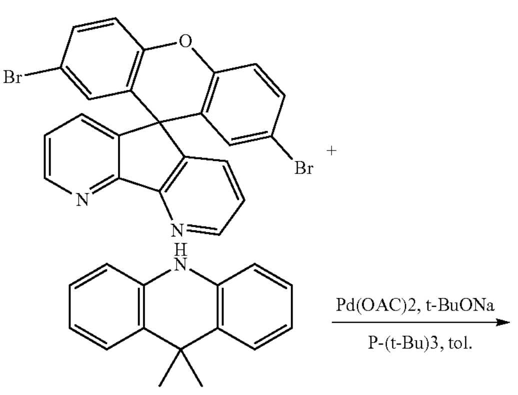

-continued

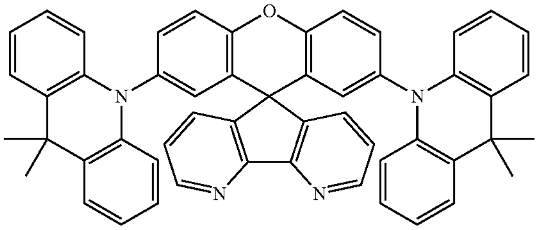

In compound "L" was obtained by the above reaction with the same synthesis conditions of the compound "A." (65% yield)

Molecular Weight: 748.91; m/z: 748.32 (100.0%), 749.32 (58.8%), 750.33 (16.4%), 751.33 (3.2%), 750.32 (1.1%)

Synthesis of the Compound "M"

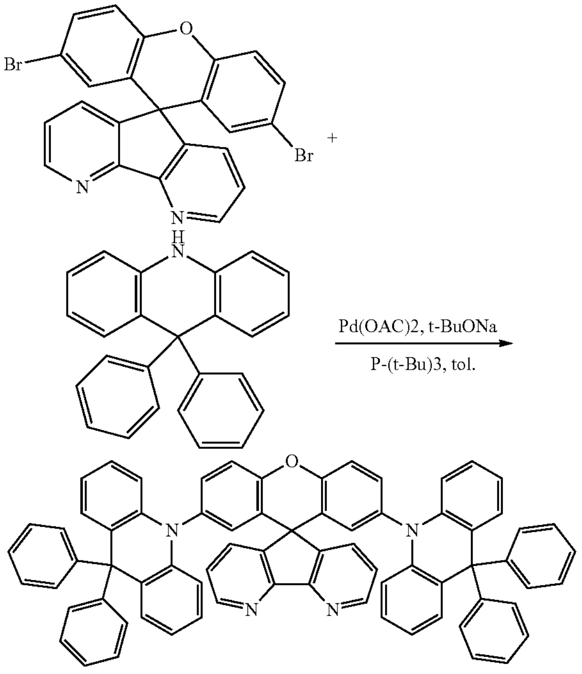

In compound "M" was obtained by the above reaction with the same synthesis conditions of the compound "A." (61% yield)

Molecular Weight: 997.19; m/z: 996.38 (100.0%), 997.39 (79.5%), 998.39 (31.4%), 999.39 (8.5%), 1000.40 (1.5%), 997.38 (1.5%), 998.38 (1.2%)

Synthesis of the Compound "N"

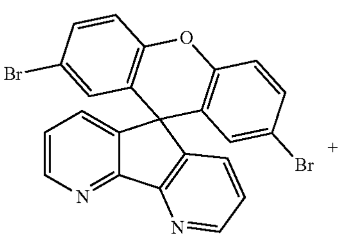

-continued

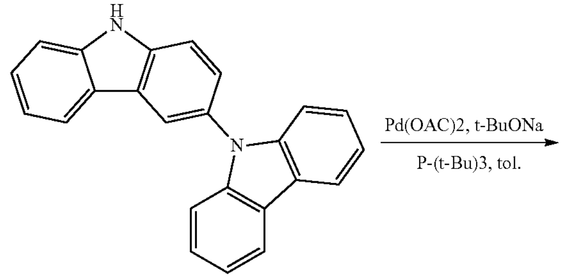

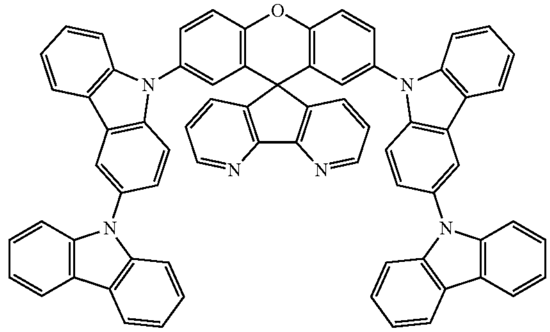

In compound "N" was obtained by the above reaction with the same synthesis conditions of the compound "A." (58% yield)

Molecular Weight: 995.13; m/z: 994.34 (100.0%), 995.35 (77.3%), 996.35 (29.7%), 997.35 (8.2%), 995.34 (2.2%), 996.34 (1.7%), 998.36 (1.4%)

Synthesis of the Compound "O"

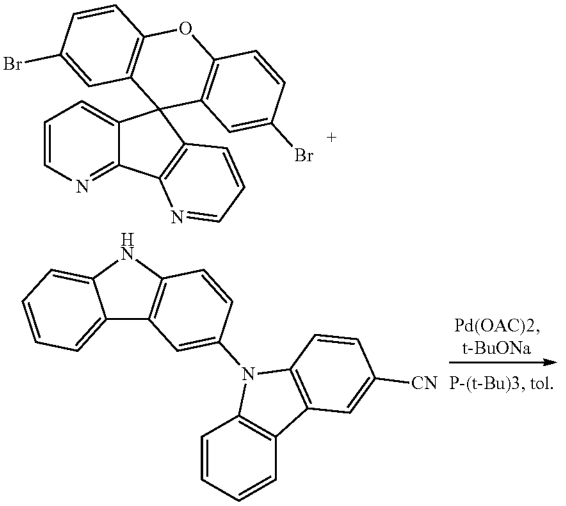

-continued

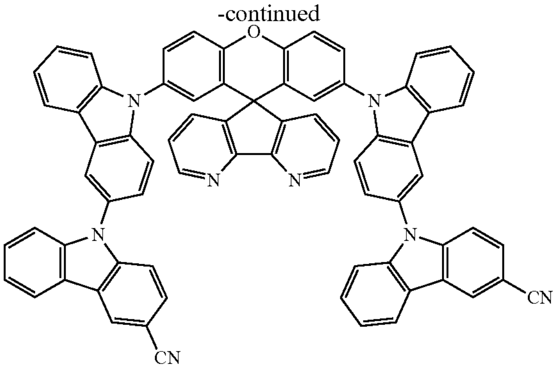

In compound “O” was obtained by the above reaction with the same synthesis conditions of the compound “A.” (59% yield)

Molecular Weight: 1045.15; m/z: 1044.33 (100.0%), 1045.34 (79.5%), 1046.34 (31.4%), 1047.34 (9.0%), 1045.33 (3.0%), 1046.33 (2.4%), 1048.35 (1.5%)

Synthesis of the Compound “P”

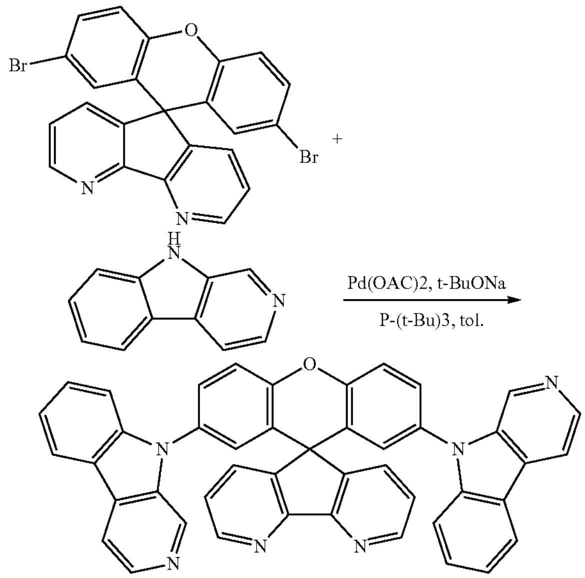

In compound “P” was obtained by the above reaction with the same synthesis conditions of the compound “A.” (56% yield)

Molecular Weight: 666.73; m/z: 666.22 (100.0%), 667.22 (49.0%), 668.22 (12.9%), 667.21 (2.2%), 669.23

Synthesis of the Compound “Q”

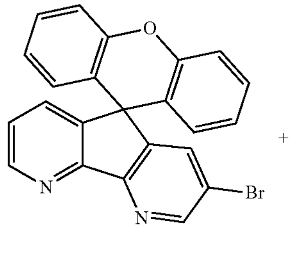

-continued

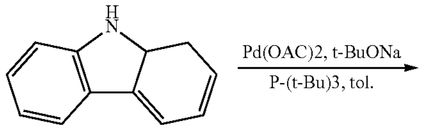

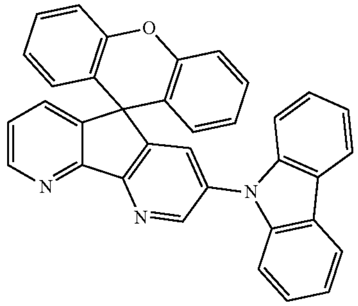

In compound “Q” was obtained by the above reaction with the same synthesis conditions of the compound “A.” (57% yield)

Molecular Weight: 499.56; m/z: 499.17 (100.0%), 500.17 (39.2%), 501.18 (7.1%)

Synthesis of the Compound “R”

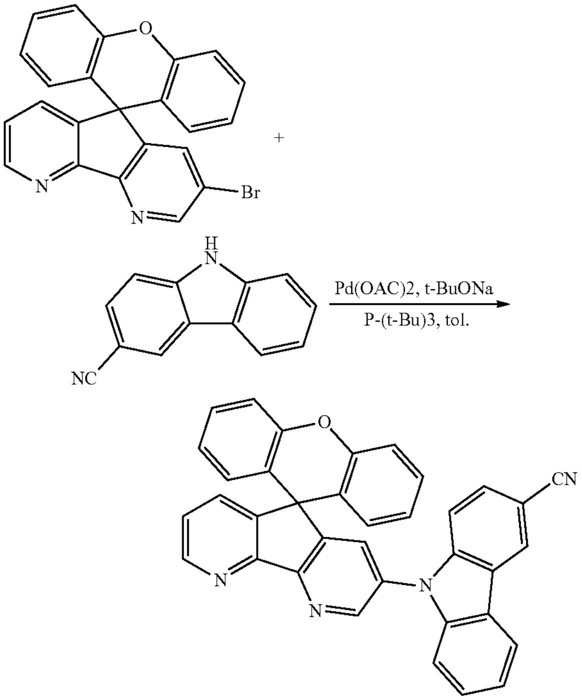

In compound “R” was obtained by the above reaction with the same synthesis conditions of the compound “A.” (75% yield)

Molecular Weight: 524.57; m/z: 524.16 (100.0%), 525.17 (39.2%), 526.17 (7.7%), 525.16 (1.5%), 527.17 (1.1%)

Synthesis of the Compound "S"

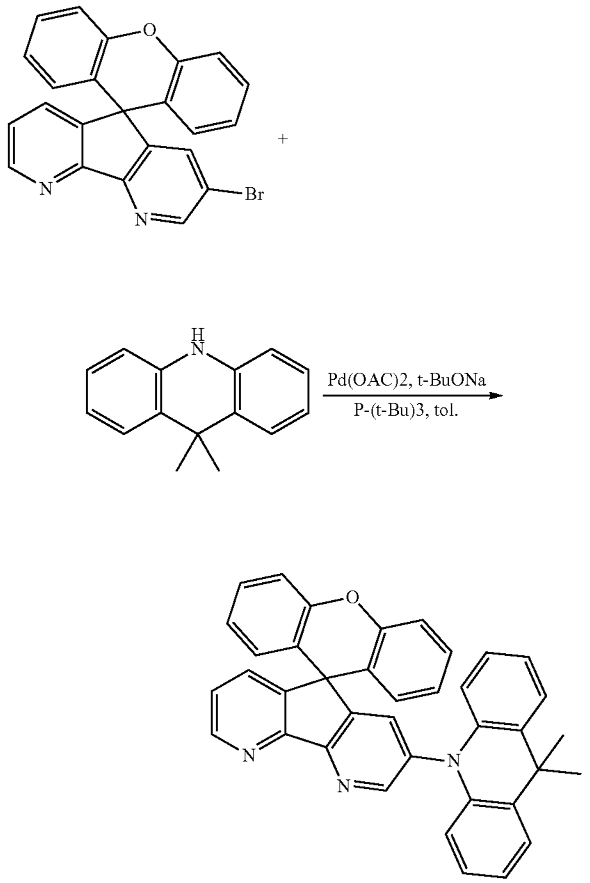

In compound "S" was obtained by the above reaction with the same synthesis conditions of the compound "A." (74% yield)

Molecular Weight: 541.64; m/z: 541.22 (100.0%), 542.22 (41.4%), 543.22 (8.9%), 542.21 (1.1%), 544.23 (1.1%)

Synthesis of the Compound "T"

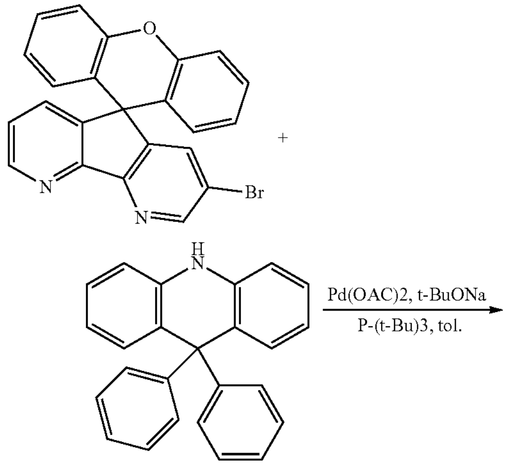

-continued

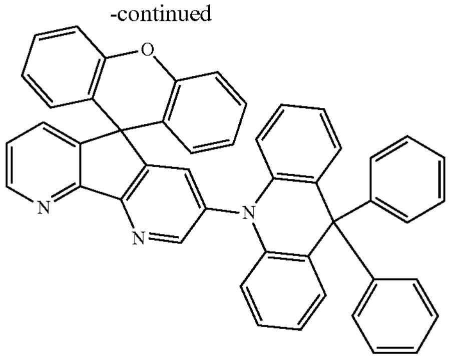

In compound "T" was obtained by the above reaction with the same synthesis conditions of the compound "A." (70% yield)

Molecular Weight: 665.78; m/z: 665.25 (100.0%), 666.25 (52.3%), 667.25 (14.0%), 668.26 (2.2%), 666.24 (1.1%)

Synthesis of the Compound "U"

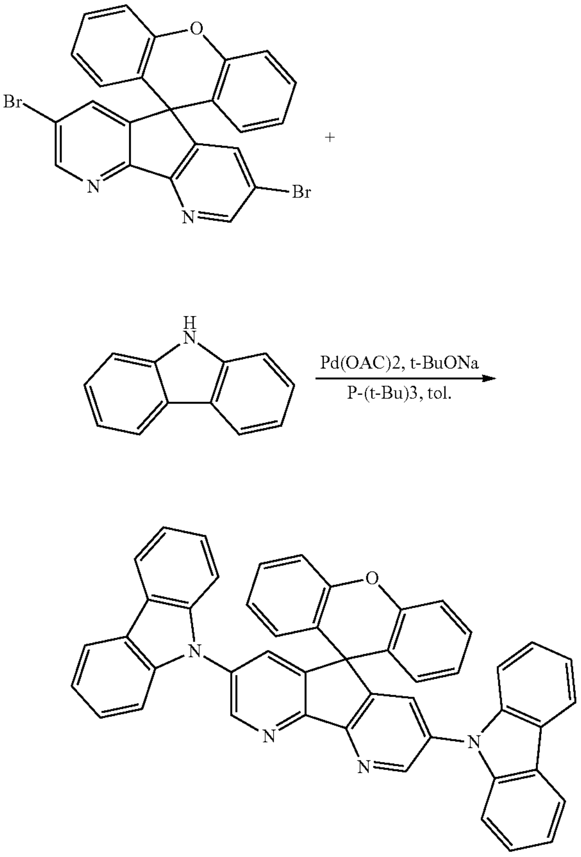

In compound "U" was obtained by the above reaction with the same synthesis conditions of the compound "A." (47% yield)

Molecular Weight: 664.75; m/z: 664.23 (100.0%), 665.23 (51.2%), 666.23 (13.6%), 667.24 (2.1%), 665.22 (1.5%)

Synthesis of the Compound "V"

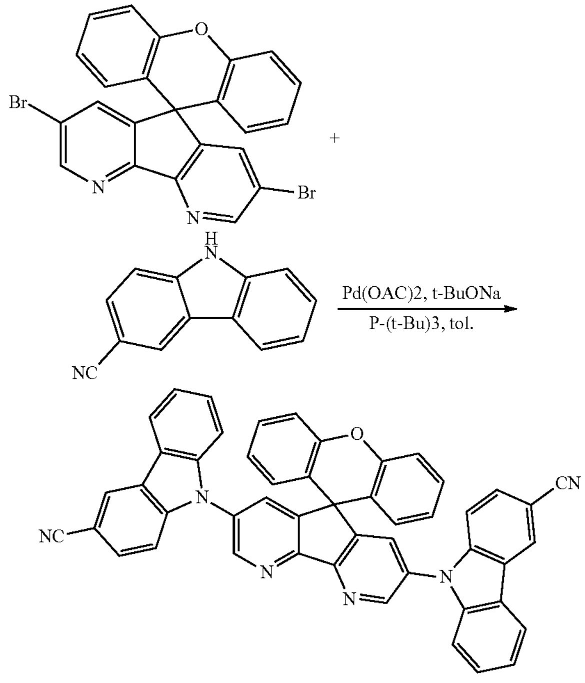

In compound "V" was obtained by the above reaction with the same synthesis conditions of the compound "A." (54% yield)

Molecular Weight: 714.77; m/z: 714.22 (100.0%), 715.22 (53.3%), 716.22 (15.2%), 717.23 (2.4%), 715.21 (2.2%)

Synthesis of the Compound "W"

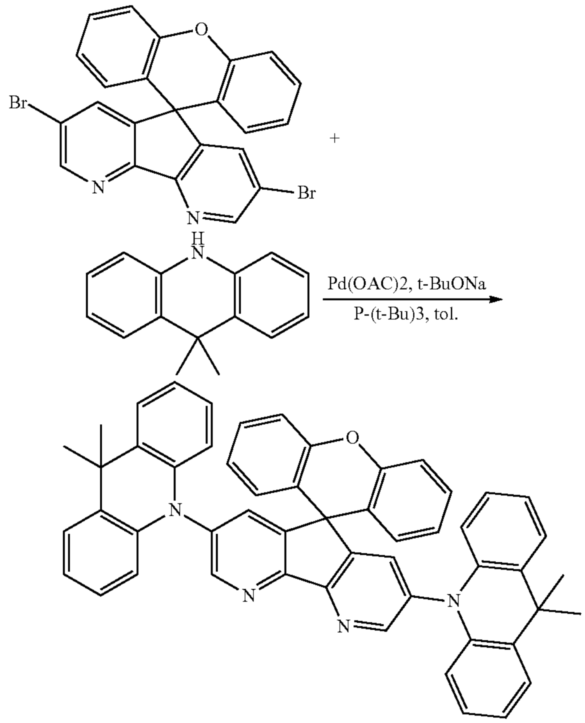

In compound "W" was obtained by the above reaction with the same synthesis conditions of the compound "A." (54% yield)

Molecular Weight: 748.91; m/z: 748.32 (100.0%), 749.32 (58.8%), 750.33 (16.4%), 751.33 (3.2%), 750.32 (1.1%)

Synthesis of the Compound "X"

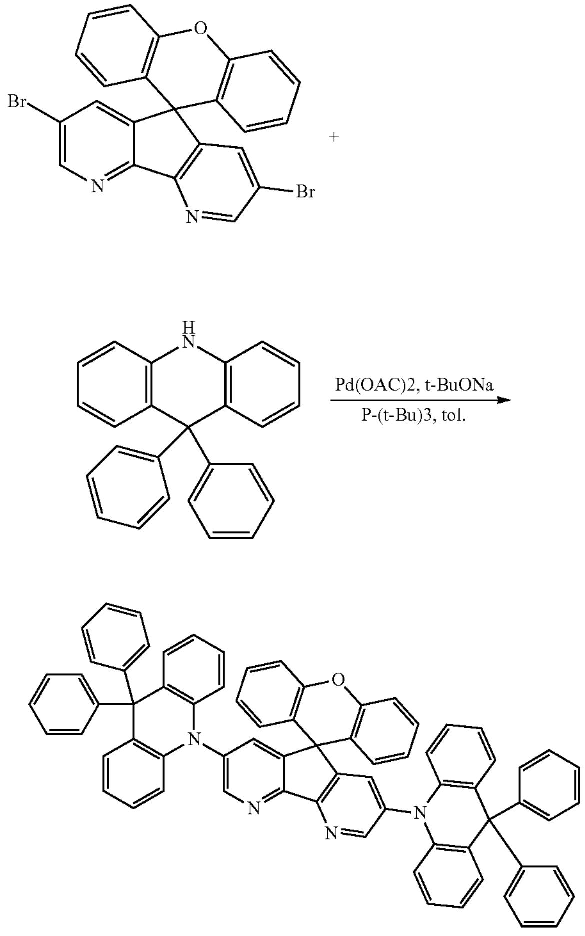

In compound "X" was obtained by the above reaction with the same synthesis conditions of the compound "A." (54% yield)

Molecular Weight: 997.19; m/z: 996.38 (100.0%), 997.39 (79.5%), 998.39 (31.4%), 999.39 (8.5%), 1000.40 (1.5%), 997.38 (1.5%), 998.38 (1.2%)

Synthesis of the Compound "Y"

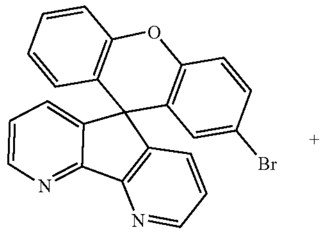

<SubC1>

-continued

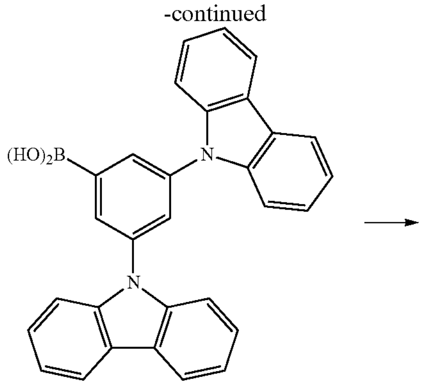

<SubD25>

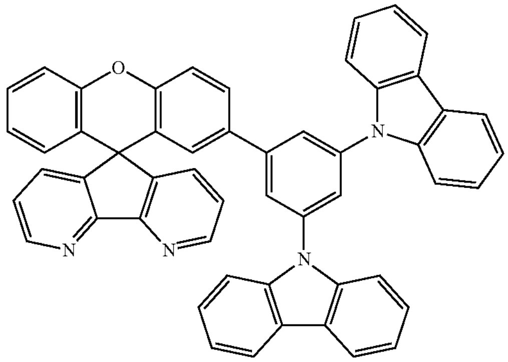

<Product Y>

After the compound "SubC1" was dissolved in tetrahydrofuran/toluene (volume ratio=5:1), the compound "SubD25" (1.2 equivalent) was added. Potassium carbonate (4.4 equivalent) and Pd(0) (0.05 equivalent) dissolved in distilled water (DI water) were added. The reaction mixture was refluxed under the temperature of 80° C. and stirred for 24 hrs. The reaction was confirmed by TLC, and the reaction was terminated. The organic layer was extracted with ethylene acetate (EA) and was filtered under reduced pressure. The column purification process and the recrystallization process were performed to the mixture such that the compound "Y" (51% yield) was obtained.

Molecular Weight: 740.85; m/z: 740.26 (100.0%), 741.26 (57.7%), 742.26 (17.2%), 743.27 (3.1%), 741.25 (1.5%)

Delayed Fluorescent Type OLED (1) Example 1 (Ex1)

A glass substrate (ITO substrate) coated with indium-tin-oxide (ITO) with a thickness of 150 nm was washed by distilled water. After washing by the distilled water, the ITO substrate was ultrasonically washed with a solvent such as isopropyl alcohol, acetone or methanol and dried. The ITO substrate was transferred into a plasma cleaner, and then the ITO substrate was cleaned for 5 minutes using oxygen plasma. The hole injection layer with a thickness of 60 nm was formed on the ITO substrate by spin-coating PEDOT:PSS. The hole transporting layer (TAPC, 20 nm) and the electron blocking layer (mCP, 10 nm) were sequentially formed on the hole injection layer by using the thermal evaporator. The emitting material layer (EML) (mCP (host) and the compound "A" (delayed fluorescent dopant, 5% doping), 25 nm) was formed on the electron blocking layer. The electron transporting layer (TPBi, 30 nm), the electron injection layer (LiF, 1 nm) and the cathode (Al, 100 nm) were sequentially formed on the emitting material layer. The laminating structure was encapsulated in the glove box such that the OLED was manufactured.

(2) Examples 2 to 19 (Ex2 to 19)

The compounds "B" to "S" were used instead of the compound "A" in Example 1 such that the OLEDs of Examples 2 to 19 were manufactured, respectively.

(3) Comparative Examples 1 to 9 (CE1 to 9)

The compounds "Ref1" to "Ref9" were used instead of the compound "A" in Example 1 such that the OLEDs of Comparative Examples 1 to 9 were manufactured.

Ref 1

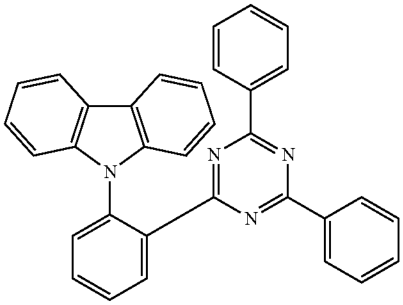

Ref 2

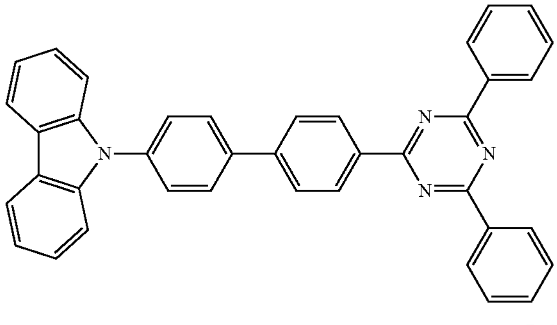

Ref 3

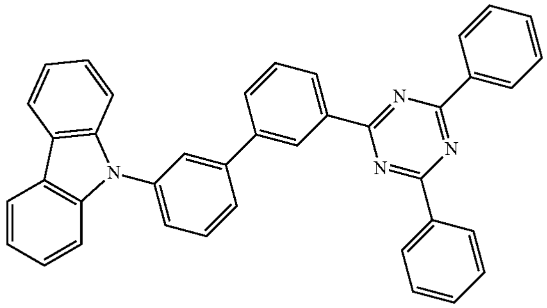

-continued

Ref 4

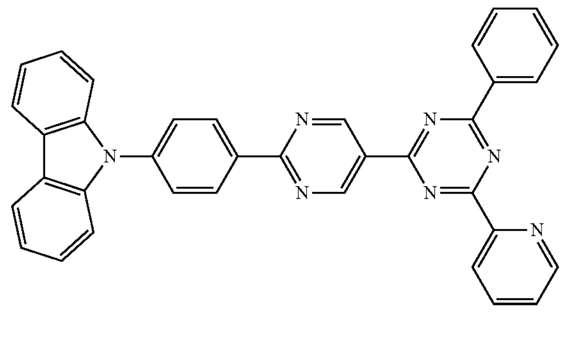

Ref 5

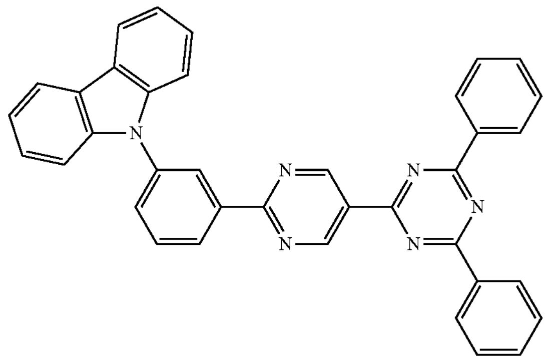

Ref 6

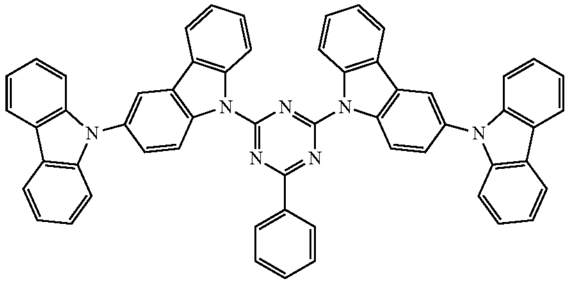

Ref.7

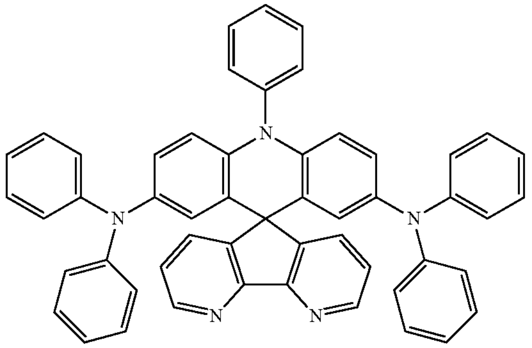

-continued

Ref.8

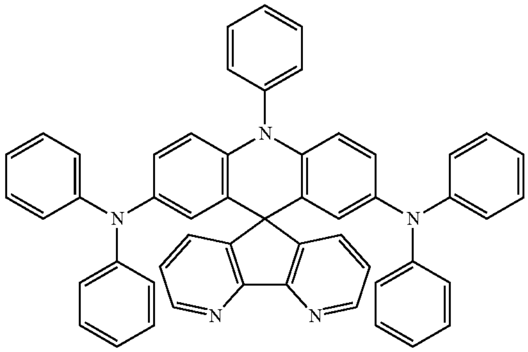

Ref.9

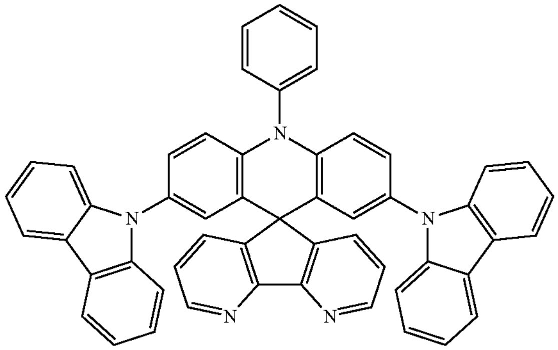

(4) Example 20 (Ex20)

A glass substrate (ITO substrate) coated with indium-tin-oxide (ITO) with a thickness of 150 nm was washed by distilled water. After washing by the distilled water, the ITO substrate was ultrasonically washed with a solvent such as isopropyl alcohol, acetone or methanol and dried. The ITO substrate was transferred into a plasma cleaner, and then the ITO substrate was cleaned for 5 minutes using oxygen plasma. The hole injection layer with a thickness of 60 nm was formed on the ITO substrate by spin-coating PEDOT:PSS. The hole transporting layer (TAPC, 20 nm) and the electron blocking layer (mCP, 10 nm) were sequentially formed on the hole injection layer by using the thermal evaporator. The emitting material layer (mCP (host), and the compound “A” (assist dopant, 20% doping) and BD01 (dopant, 5% doping), 25 nm) was formed on the electron blocking layer. The electron transporting layer (TPBi, 30 nm), the electron injection layer (LiF, 1 nm) and the cathode (Al, 100 nm) were sequentially formed on the emitting material layer. The laminating structure was encapsulated in the glove box such that the OLED was manufactured.

(5) Examples 21 to 24 (Ex26 to 24)

The compounds “B”, “F”, “G” and “H” were used instead of the compound “A” in Example 1 such that the OLEDs of Examples 21 to 24 were manufactured, respectively.

The electron and the hole were injected into the OLED by using the Keithley 2400 source measurement, and the luminance is measured using the Konica Minolta spectrophotometer (CS-2000). The performance of the OLED of Examples and Comparative Examples was measured under atmospheric pressure and listed in Table 2. (H: host, D1:

assist dopant (first dopant), D2: dopant (second dopant), V: driving voltage [V], EQE: external quantum efficiency [%])

TABLE 2

| | EML | | | | | | CIE | |
|---|---|---|---|---|---|---|---|---|
| | H | D1 | D2 | V | EQE | Cd/A | X | y |
| CE1 | mCP | — | Ref 1 | 6 | 9.3 | 14.6 | 0.15 | 0.22 |
| CE2 | mCP | — | Ref 2 | 6 | 6.8 | 9.8 | 0.15 | 0.20 |
| CE3 | mCP | — | Ref 3 | 6 | 8.5 | 13.8 | 0.15 | 0.20 |
| CE4 | mCP | — | Ref 4 | 6 | 7.1 | 10.2 | 0.16 | 0.22 |
| CE5 | mCP | — | Ref 5 | 6 | 9.1 | 14.3 | 0.16 | 0.23 |
| CE6 | mCP | — | Ref 6 | 6 | 11 | 29.1 | 0.20 | 0.44 |
| CE7 | mCP | | Ref 7 | 6.1 | 12.2 | 18.7 | 0.22 | 0.25 |
| CE8 | mCP | | Ref 8 | 5.9 | 9.2 | 20.8 | 0.22 | 0.30 |
| CE9 | mCP | | Ref 9 | 5.8 | 10.8 | 22.1 | 0.22 | 0.33 |
| Ex1 | mCP | — | A | 5.5 | 14.2 | 30.9 | 0.15 | 0.20 |
| Ex2 | mCP | — | B | 5.4 | 14.7 | 31.3 | 0.15 | 0.20 |
| Ex3 | mCP | — | C | 5.5 | 15.3 | 31.6 | 0.15 | 0.20 |
| Ex4 | mCP | — | D | 5.6 | 14.8 | 30.3 | 0.15 | 0.20 |
| Ex5 | mCP | — | E | 5.4 | 13.9 | 30.1 | 0.15 | 0.20 |
| Ex6 | mCP | — | F | 5.5 | 14.9 | 30.5 | 0.15 | 0.20 |
| Ex7 | mCP | — | G | 5.5 | 15.1 | 31.5 | 0.15 | 0.20 |
| Ex8 | mCP | — | H | 5.6 | 14.3 | 30.9 | 0.15 | 0.20 |
| Ex9 | mCP | — | I | 5.5 | 14.3 | 30.7 | 0.15 | 0.20 |
| Ex10 | mCP | — | J | 5.5 | 14.8 | 31.2 | 0.15 | 0.20 |
| Ex11 | mCP | — | K | 5.6 | 15.2 | 31.8 | 0.15 | 0.20 |
| Ex12 | mCP | — | L | 5.6 | 15.1 | 31.5 | 0.15 | 0.22 |
| Ex13 | mCP | — | M | 5.6 | 15.7 | 31.9 | 0.15 | 0.22 |
| Ex14 | mCP | — | N | 5.7 | 15.3 | 31.8 | 0.15 | 0.22 |
| Ex15 | mCP | — | O | 5.6 | 14.8 | 31.3 | 0.15 | 0.22 |
| Ex16 | mCP | — | P | 5.6 | 14.9 | 31.5 | 0.15 | 0.22 |
| Ex17 | mCP | — | Q | 5.6 | 15.2 | 31.7 | 0.15 | 0.22 |
| Ex18 | mCP | — | R | 5.7 | 15.1 | 31.8 | 0.15 | 0.22 |
| Ex19 | mCP | — | S | 5.7 | 14.6 | 31.1 | 0.15 | 0.23 |
| Ex20 | mCP | A | BD01 | 5.5 | 16.8 | 44.2 | 0.14 | 0.11 |
| Ex21 | mCP | B | BD01 | 5.6 | 15.9 | 40.1 | 0.14 | 0.11 |
| Ex22 | mCP | F | BD01 | 5.6 | 16.5 | 42.3 | 0.14 | 0.12 |
| Ex23 | mCP | G | BD01 | 5.6 | 16.1 | 42.1 | 0.14 | 0.12 |
| Ex24 | mCP | H | BD01 | 5.5 | 15.8 | 41.5 | 0.14 | 0.12 |

As illustrated above, the emitting layer was formed using a thermally active delayed fluorescent compound, and the results of the performance evaluation are shown in Table 2. As shown in Table 2, all of the OLED of Examples using the compound of the present disclosure has the quantum efficiency over 5% (when the light extraction efficiency is 20%) which is the maximum external quantum efficiency that can be obtained from the general fluorescent device.

This shows that the compound of the present disclosure is capable of efficient transition of triplet energy to singlet energy through thermally active delayed fluorescence. In addition, the OLED of Examples using the compound of the present disclosure has a lower driving voltage and higher efficiency and EQE compared to Comparative Examples 1 to 9. Moreover, referring to Examples 20 to 24 using the compound of the present disclosure as the assist dopant, the OLED provides the dark blue emission and has excellent performance.

The compound of the present disclosure, which can solve the problem of the external quantum efficiency of the conventional fluorescent material, can be used as a TADF material as well as a fluorescent material. Since the electron donor unit and the electron acceptor unit co-exist in the molecule such that exciplex can be provided, the OLED using the compound of the present disclosure has properties of high efficiency, long lifespan and low driving voltage.

[OLED]

The hole injection layer (HATCN, 50 Å), the hole transporting layer (NPB, 500 Å), the electron blocking layer (MCP, 100 Å), the emitting material layer (host and dopant (30 wt %), 250 Å), the electron transporting layer (TPBi, 300 Å), the electron injection layer (LiF, 10 Å) and the cathode (Al, 1000 Å) are sequentially formed on the ITO substrate to form the OLED. The compound in Formula 24 is used as the dopant.

Formula 24

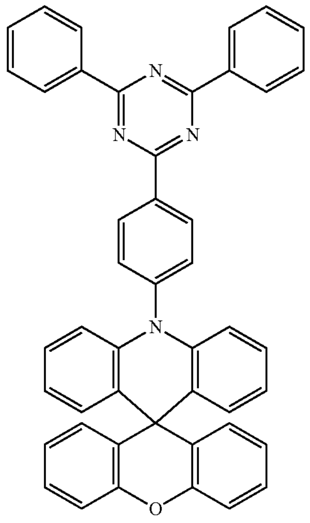

(1) Example 25 (Ex25)

The compound "A" is used as the host.

(2) Example 26 (Ex26)

The compound "I" is used as the host.

(3) Example 27 (Ex27)

The compound "Y" is used as the host.

(4) Comparative Example 10 (CE10)

The compound in Formula 25 is used as the host.

(5) Comparative Example 11 (CE11)

The compound "Ref9" is used as the host.

Formula 25

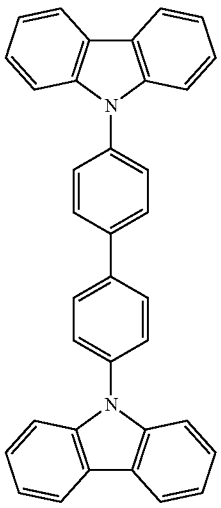

Properties, i.e., driving voltage, external quantum efficiency (EQE), efficiency (cd/A) and color coordinate, of the OLED manufactured in Examples 25 to 27 and Comparative Examples 10 and 11 were measured using a current source (KEITHLEY) and a photometer (PR650) and listed in Table 3.

TABLE 3

| | voltage [V] | EQE (%) | cd/A | CIE (x, y) |
|---|---|---|---|---|
| CE10 | 5.4 | 8.1 | 15.1 | (0.18, 0.37) |
| CE11 | 4.2 | 9.6 | 17.5 | (0.17, 0.36) |
| EX25 | 3.8 | 16.9 | 35.0 | (0.17, 0.34) |
| Ex26 | 3.8 | 16.2 | 34.6 | (0.17, 0.37) |
| Ex27 | 3.7 | 16.2 | 32.6 | (0.17, 0.35) |

As shown in Table 3, when the compound of the present disclosure is used as a host of the emitting material layer, the driving voltage is reduced and the quantum efficiency and luminance are improved. Moreover, the compound of the present disclosure as the host has properties suitable for a delayed fluorescent dopant.

Figure 3:
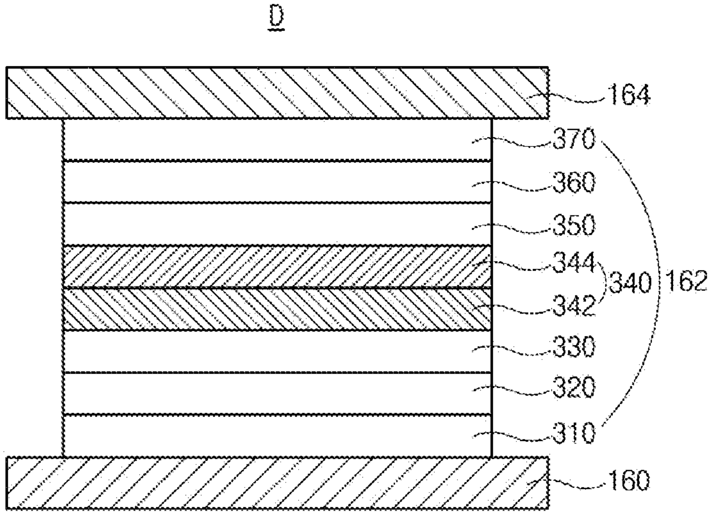
FIG. 3 is a schematic cross-sectional view of an OLED according to a second embodiment of the present disclosure.

FIG. 3 is a schematic cross-sectional view of an OLED according to a second embodiment of the present disclosure.

As shown in FIG. 3, an OLED D includes the first electrode 160 and the second electrode 164, which face each other, and the organic emitting layer 162 therebetween. The organic emitting layer 162 includes an EML 340, which includes first and second layers 342 and 344 and is positioned between the first and second electrodes 160 and 164, an HTL 320 between the first electrode 160 and the EML 340 and an ETL 360 between the second electrode 164 and the EML 340.

In addition, the organic emitting layer 162 may further include a HIL 310 between the first electrode 160 and the HTL 320 and an EIL 370 between the second electrode 164 and the ETL 360.

Moreover, the organic emitting layer 162 may further include an EBL 330 between the HTL 320 and the EML 340 and a HBL 350 between the EML 340 and the ETL 360.

For example, in the EML 340, the first layer 342 (e.g., a first emitting material layer) may include the compound of the present disclosure as a first host and may further include a delayed fluorescent dopant (first dopant), and the second layer 344 (e.g., a second emitting material layer) may include a second host and a fluorescent dopant (second dopant). Alternatively, the second layer 344 may include the compound of the present disclosure as a first host and may further include a delayed fluorescent dopant (first dopant), and the first layer 342 may include a second host and a fluorescent dopant (second dopant). In this instance, the second host may be the compound of the present disclosure. The energy level of singlet state of the delayed fluorescent dopant is higher than that of the fluorescent dopant.

The OLED, where the first layer 342 includes the delayed fluorescent dopant and the second layer 344 includes the fluorescent dopant, will be explained.

In the OLED D, the energy level of singlet state and the energy level of triplet state of the delayed fluorescent dopant are transferred into the fluorescent dopant such that the light emission is provided from the fluorescent dopant. As a result, the quantum efficiency of the OLED D is increased, and the FWHM of the OLED D is narrowed.

The delayed fluorescent dopant has high quantum efficiency. However, since the light emitted from the delayed fluorescent dopant has wide FWHM, the light from the delayed fluorescent dopant has poor color purity. On the other hand, the fluorescence dopant has narrow FWHM and high color purity. However, since the energy level of triplet state of the fluorescence dopant is not involved in the emission, the fluorescence dopant has low quantum efficiency.

Since the EML 340 of the OLED D in the present disclosure includes the first layer 342, which includes the delayed fluorescent dopant, and the second layer 344, which includes the fluorescence dopant, the OLED D has advantages in both the emitting efficiency and the color purity.

The energy level of triplet state of the delayed fluorescent dopant is converted into the energy level of singlet state of the delayed fluorescent dopant by the reverse intersystem crossing (RISC) effect, and the energy level of singlet state of the delayed fluorescent dopant is transferred into the energy level of singlet state of the fluorescence dopant. Namely, the difference between the energy level of triplet state of the delayed fluorescent dopant and the energy level of singlet state of the delayed fluorescent dopant is not greater than 0.3 eV such that the energy level of triplet state of the delayed fluorescent dopant is converted into the energy level of singlet state of the delayed fluorescent dopant by the RISC effect.

As a result, the delayed fluorescent dopant has an energy transfer function, and the first layer 342 including the delayed fluorescent dopant is not engaged in the light emission. The light emission is generated in the second layer 344 including the fluorescence dopant.

The energy level of triplet state of the delayed fluorescent dopant is converted into the energy level of singlet state of the delayed fluorescent dopant by the RISC effect. In addition, since the energy level of singlet state of the delayed fluorescent dopant is higher than that of the fluorescence dopant, the energy level of singlet state of the delayed fluorescent dopant is transferred into the energy level of singlet state of the fluorescence dopant. As a result, the fluorescence dopant emits the light using the energy level of singlet state and the energy level of triplet state such that the quantum efficiency (emitting efficiency) of the OLED D is improved.

In other words, the OLED D and the organic light emitting display device 100 (of FIG. 1) including the OLED D has advantages in both the emitting efficiency (quantum efficiency) and the color purity (FWHM).

In each of the first and second layers 342 and 344, the first and second hosts may have a percentage by weight being larger than the delayed fluorescent dopant and the fluorescence dopant, respectively. In addition, the percentage by weight of the delayed fluorescent dopant in the first layer 342 may be greater than that of the fluorescence dopant in the second layer 344. As a result, the energy transfer from the delayed fluorescent dopant into the fluorescence dopant is sufficiently generated.

The energy level of singlet state of the first host is greater than that of the delayed fluorescent dopant, and the energy level of triplet state of the first host is greater than that of the delayed fluorescent dopant. In addition, the energy level of singlet state of the second host is greater than that of the fluorescence dopant.

When not satisfying this condition, a quenching happens at the first and second dopants or an energy transfer from the host to the dopant does not happen, and thus the quantum efficiency of the OLED D is reduced.

As mentioned above, the compound of the present disclosure has high energy level of triplet state, the energy transfer efficiency to the delayed fluorescent dopant is increased such that the quantum efficiency of the OLED D is improved.

For example, the second host, which is included in the second layer 344 with the fluorescence dopant, may be same as a material of the HBL 350. In this instance, the second layer 344 may have a hole blocking function with an emission function. Namely, the second layer 344 may serve as a buffer layer for blocking the hole. When the HBL 350 is omitted, the second layer 344 serves as an emitting material layer and a hole blocking layer.

When the first layer 342 includes the fluorescence dopant and the second layer 344 includes the delayed fluorescent dopant, the first host of the first layer 342 may be same as a material of the EBL 330. In this instance, the first layer 342 may have an electron blocking function with an emission function. Namely, the first layer 342 may serve as a buffer layer for blocking the electron. When the EBL 330 is omitted, the first layer 342 serves as an emitting material layer and an electron blocking layer.

On the other hand, the compound of the present disclosure may have a delayed fluorescent property to use as a delayed fluorescent dopant. In this instance, one of the first and second layers 342 and 344 of the EML 340 may include the compound of the present disclosure as a first dopant (delayed fluorescent dopant), and the other one of the first and second layers 342 and 344 may include a fluorescent dopant or a phosphorescent dopant as a second dopant.

Figure 4:
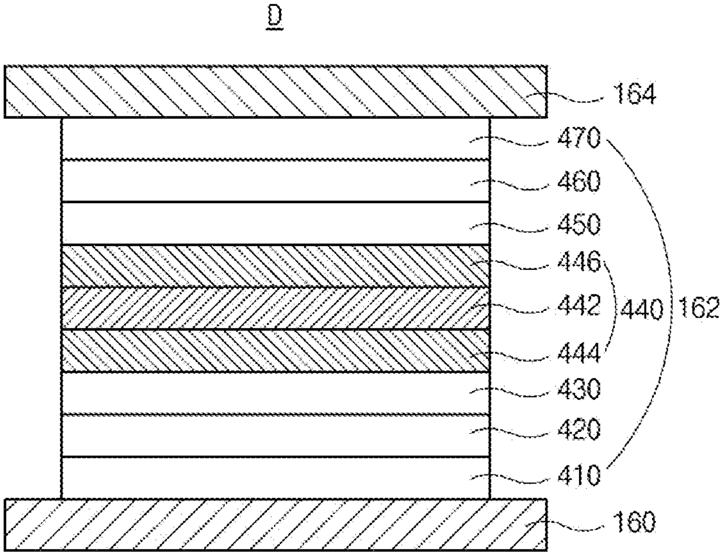
FIG. 4 is a schematic cross-sectional view of an OLED according to a third embodiment of the present disclosure.

FIG. 4 is a schematic cross-sectional view of an OLED according to a third embodiment of the present disclosure.

As shown in FIG. 4, an OLED D includes the first and second electrodes 160 and 164, which face each other, and the organic emitting layer 162 therebetween. The organic emitting layer 162 includes an EML 440, which includes first to third layers 442, 444, and 446 and is positioned between the first and second electrodes 160 and 164, a HTL 420 between the first electrode 160 and the EML 440 and an ETL 460 between the second electrode 164 and the EML 440.

In addition, the organic emitting layer 162 may further include a HIL 410 between the first electrode 160 and the HTL 420 and an EIL 470 between the second electrode 164 and the ETL 460.

Moreover, the organic emitting layer 162 may further include an EBL 430 between the HTL 420 and the EML 440 and a HBL 450 between the EML 440 and the ETL 460.

In the EML 440, the first layer 442 is positioned between the second layer 444 and the third layer 446. Namely, the second layer 444 is positioned between the EBL 430 and the first layer 442, and the third layer 446 is positioned between the first layer 442 and the HBL 450.

The first layer 442 (e.g., a first emitting material layer) includes the compound of the present disclosure as a first host and further includes a delayed fluorescent dopant (first dopant). The second layer 444 includes a second host and a fluorescent dopant (second dopant), and the third layer 446 includes a third host and a fluorescent dopant (third dopant). The fluorescent dopants in the second and third layers 444 and 446 may be same or different. In addition, the second host and the third host may be the compound of the present disclosure. The delayed fluorescent dopant has an energy level of singlet state being larger than the fluorescent dopant.

In the OLED D, the energy level of singlet state and the energy level of triplet state of the delayed fluorescent dopant in the first layer 442 are transferred into the fluorescence dopant in the second layer 444 and/or the third layer 446 such that the emission is generated from the fluorescence dopant. As a result, the quantum efficiency of the OLED D is increased, and the FWHM of the OLED D is narrowed.

In each of the first to third layers 442, 444 and 446, the first to third hosts may have a percentage by weight being larger than the delayed fluorescent dopant and the fluorescence dopant, respectively. In addition, the percentage by weight of the delayed fluorescent dopant (i.e., the first dopant) in the first layer 442 may be greater than that of each of the fluorescence dopant (i.e., the second dopant) in the second layer 444 and the fluorescence dopant (i.e., the third dopant) in the third layer 446.

The energy level of singlet state of the first host is greater than that of the delayed fluorescent dopant, and the energy level of triplet state of the first host is greater than that of the delayed fluorescent dopant. In addition, the energy level of singlet state of the second host is greater than that of the fluorescent dopant in the second layer 444, and the energy level of singlet state of the third host is greater than that of the fluorescent dopant in the third layer 446.

As mentioned above, the compound of the present disclosure has high energy level of triplet state, the energy transfer efficiency to the delayed fluorescent dopant is increased such that the quantum efficiency of the OLED D is improved.

For example, the second host in the second layer 444 may be same as a material of the EBL 430. In this instance, the second layer 444 may have an electron blocking function with an emission function. Namely, the second layer 444 may serve as a buffer layer for blocking the electron. When the EBL 430 is omitted, the second layer 444 serves as an emitting material layer and an electron blocking layer.

The third host in the third layer 446 may be same as a material of the HBL 450. In this instance, the third layer 446 may have a hole blocking function with an emission function. Namely, the third layer 446 may serve as a buffer layer for blocking the hole. When the HBL 450 is omitted, the third layer 446 serves as an emitting material layer and a hole blocking layer.

The second host in the second layer 444 may be same as a material of the EBL 430, and the third host in the third layer 446 may be same as a material of the HBL 450. In this instance, the second layer 444 may have an electron blocking function with an emission function, and the third layer 446 may have a hole blocking function with an emission function. Namely, the second layer 444 may serve as a buffer layer for blocking the electron, and the third layer 446 may serve as a buffer layer for blocking the hole. When the EBL 430 and the HBL 450 are omitted, the second layer 444 serves as an emitting material layer and an electron blocking layer and the third layer 446 serves as an emitting material layer and a hole blocking layer.

On the other hand, the compound of the present disclosure may have a delayed fluorescent property to use as a delayed fluorescent dopant. In this instance, the first layer 442 of the EML 440 may include the compound of the present disclosure as a first dopant (delayed fluorescent dopant), and each of the second and third layers 444 and 446 may include a fluorescent dopant or a phosphorescent dopant.

It will be apparent to those skilled in the art that various modifications and variations can be made in the present disclosure without departing from the spirit or scope of the present disclosure. Thus, it is intended that the present disclosure cover the modifications and variations of the present disclosure provided they come within the scope of the appended claims and their equivalents.

What is claimed is:

1. An organic light emitting device, comprising:

a first electrode;

a second electrode facing the first electrode; and a first emitting material layer between the first electrode and the second electrode, the first emitting material layer including a compound, wherein the compound is represented by Formula 1:

Formula 1

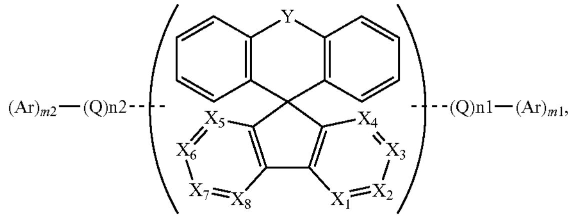

wherein Y is $CR_1R_2$, or O, and each of $R_1$ and $R_2$ is independently selected from the group consisting of hydrogen, substituted or non-substituted $C_6$-$C_{24}$ aryl group and substituted or non-substituted $C_5$-$C_{24}$ heteroaryl group, wherein each of $X_1$ to $X_8$ is independently selected from C or N, and wherein $X_1$ and $X_8$ are each N, wherein n1, n2, m1 and m2 is one of 0, 1 and 2, and at least one of n1 and n2 is 1 or more, wherein when each of m1 and m2 is 0, Q is independently selected from the group consisting of substituted or non-substituted $C_6$-$C_{60}$ aryl group, substituted or non-substituted $C_5$-$C_{60}$ heteroaryl group, CN and $NR_3R_4$, and each of $R_3$ and $R_4$ is independently selected from the group consisting of hydrogen, substituted or non-substituted $C_6$-$C_{60}$ aryl group and substituted or non-substituted $C_5$-$C_{60}$ heteroaryl group, wherein when each of m1 and m2 is 1 or 2, Q is independently selected from the group consisting of substituted or non-substituted $C_6$-$C_{60}$ aryl group and substituted or non-substituted $C_5$-$C_{60}$ heteroaryl group, wherein Ar is independently selected from the group consisting of substituted or non-substituted $C_1$-$C_{20}$ alkyl group, substituted or non-substituted $C_6$-$C_{24}$ aryl group, substituted or non-substituted $C_5$-$C_{24}$ heteroaryl group, CN and $NR_5R_6$, and each of $R_5$ and $R_6$ is independently selected from the group consisting of hydrogen, substituted or non-substituted $C_6$-$C_{24}$ aryl group and substituted or non-substituted $C_5$-$C_{24}$ heteroaryl group, wherein each of n1 and n2 is 1 or 2, a plurality of Qs are same, wherein the first emitting material layer further includes a first dopant, and the compound is used as a first host, and wherein a difference between an energy level of a highest occupied molecular orbital (HOMO) of the first host and an energy level of a HOMO of the first dopant or a difference between an energy level of a lowest unoccupied molecular orbital (LUMO) of the first host and an energy level of a LUMO of the first dopant is less than about 0.5 eV.

2. An organic light emitting device, comprising:

a first electrode;

a second electrode facing the first electrode; and a first emitting material layer between the first electrode and the second electrode, the first emitting material layer including a compound of Formula 1:

Formula 1

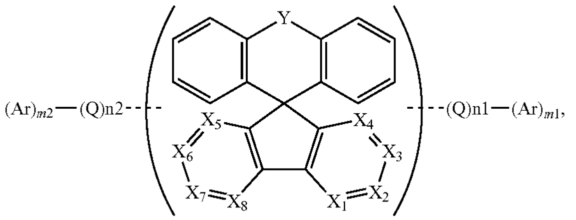

wherein Y is $CR_1R_2$, or O, and each of $R_1$ and $R_2$ is independently selected from the group consisting of hydrogen, substituted or non-substituted $C_6$-$C_{24}$ aryl group and substituted or non-substituted $C_5$-$C_{24}$ heteroaryl group, wherein each of $X_1$ to $X_8$ is independently selected from C or N, and at least one of $X_1$ to $X_8$ is N, wherein n1, n2, m1 and m2 is one of 0, 1 and 2, and at least one of n1 and n2 is 1 or more, wherein when each of m1 and m2 is 0, Q is independently selected from the group consisting of substituted or non-substituted $C_6$-$C_{60}$ aryl group, substituted or non-substituted $C_5$-$C_{60}$ heteroaryl group, CN and $NR_3R_4$, and each of $R_3$ and $R_4$ is independently selected from the group consisting of hydrogen, substituted or non-substituted $C_6$-$C_{60}$ aryl group and substituted or non-substituted $C_5$-$C_{60}$ heteroaryl group, wherein when each of m1 and m2 is 1 or 2, Q is independently selected from the group consisting of substituted or non-substituted $C_6$-$C_{60}$ aryl group and substituted or non-substituted $C_5$-$C_{60}$ heteroaryl group, and wherein Ar is independently selected from the group consisting of substituted or non-substituted $C_1$-$C_{20}$ alkyl group, substituted or non-substituted $C_6$-$C_{24}$ aryl group, substituted or non-substituted $C_5$-$C_{24}$ heteroaryl group, CN and $NR_5R_6$, and each of $R_5$ and $R_6$ is independently selected from the group consisting of hydrogen, substituted or non-substituted $C_6$-$C_{24}$ aryl group and substituted or non-substituted $C_5$-$C_{24}$ heteroaryl group, wherein the first emitting material layer further includes a first host, and the compound is used as a first dopant, wherein when each of n1 and n2 is 1 or 2, a plurality of Qs are same, and wherein an energy level of a singlet state of the first host is greater than a singlet state of the compound, or an energy level of a triplet state of the first host is greater than a triplet state of the compound.

3. The organic light emitting device according to claim 2, wherein the first emitting material layer further includes a fluorescent compound or a phosphorescent compound as a second dopant.

4. The organic light emitting device according to claim 2, further comprising:

a second emitting material layer positioned between the first electrode and the first emitting material layer or between the first emitting material layer and the second electrode, wherein the second emitting material layer includes a second host and one of a fluorescent compound or a phosphorescent compound as a second dopant.

5. The organic light emitting device according to claim 1, wherein the first emitting material layer further includes a second dopant being one of a fluorescent compound or a phosphorescent compound, and wherein an energy level of a singlet state of the first dopant is greater than a singlet state of the second dopant.

6. The organic light emitting device according to claim 1, further comprising:

a second emitting material layer including a second host and a second dopant being one of a fluorescent compound or a phosphorescent compound and positioned between the first electrode and the first emitting material layer.

7. The organic light emitting device according to claim 6, further comprising:

a third emitting material layer including a third host and a third dopant being one of a fluorescent compound or a phosphorescent compound and positioned between the second electrode and the first emitting material layer.

8. An organic light emitting display device, comprising:

a substrate;

an organic light emitting device of claim 1 disposed on the substrate; and an encapsulation film covering the organic light emitting device.

* * * * *